(12) United States Patent
Pasteris et al.

(10) Patent No.: US 9,604,962 B2
(45) Date of Patent: Mar. 28, 2017

(54) FUNGICIDAL AZOCYCLIC AMIDES

(71) Applicant: E I DU PONT DE NEMOURS AND COMPANY, Wilmington, DE (US)

(72) Inventors: Robert James Pasteris, Newark, DE (US); Rafael Shapiro, Wilmington, DE (US)

(73) Assignee: E I DU PONT DE NEMOURS AND COMPANY, Wilmington, DE (US)

(*) Notice: Subject to any disclaimer, the term of this patent is extended or adjusted under 35 U.S.C. 154(b) by 0 days.

(21) Appl. No.: 14/748,372

(22) Filed: Jun. 24, 2015

(65) Prior Publication Data
US 2015/0291556 A1 Oct. 15, 2015

Related U.S. Application Data

(60) Division of application No. 14/087,481, filed on Nov. 22, 2013, now Pat. No. 9,090,604, which is a division of application No. 12/303,256, filed as application No. PCT/US2007/016875 on Jul. 27, 2007, now Pat. No. 8,642,634, which is a continuation-in-part of application No. PCT/US2007/014647, filed on Jun. 22, 2007.

(60) Provisional application No. 60/833,824, filed on Jul. 27, 2006, provisional application No. 60/897,173, filed on Jan. 24, 2007.

(51) Int. Cl.
| C07D 401/06 | (2006.01) |
| C07D 211/62 | (2006.01) |
| C07D 417/14 | (2006.01) |
| C07D 413/14 | (2006.01) |
| C07D 231/12 | (2006.01) |
| C07D 261/04 | (2006.01) |
| C07D 261/08 | (2006.01) |
| A01N 43/78 | (2006.01) |
| A01N 43/80 | (2006.01) |

(52) U.S. Cl.
CPC .......... *C07D 401/06* (2013.01); *A01N 43/78* (2013.01); *A01N 43/80* (2013.01); *C07D 211/62* (2013.01); *C07D 231/12* (2013.01); *C07D 261/04* (2013.01); *C07D 261/08* (2013.01); *C07D 413/14* (2013.01); *C07D 417/14* (2013.01)

(58) Field of Classification Search
None
See application file for complete search history.

(56) References Cited

U.S. PATENT DOCUMENTS

| 3,950,427 A | 4/1976 | Engel et al. |
| 5,001,115 A | 3/1991 | Sloan |

(Continued)

FOREIGN PATENT DOCUMENTS

| AU | 63760 B | 10/1994 |
| FR | 2254320 A | 7/2004 |

(Continued)

OTHER PUBLICATIONS

FR2254320—Abstract—Jun. 28, 2005.

(Continued)

*Primary Examiner* — Kamal Saeed
(74) *Attorney, Agent, or Firm* — Charlene Gross Sternberg

(57) ABSTRACT

Disclosed are compounds of Formulae 1, 1A, 1B and 1C including all geometric and stereoisomers, N-oxides, and salts thereof,

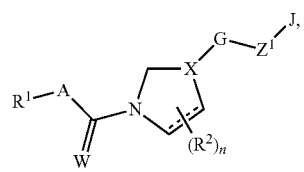

1

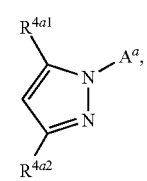

1A

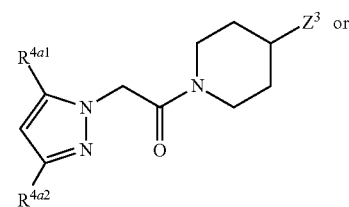

1B

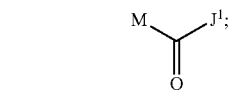

1C wherein
$R^1$, $R^2$, $R^{4a1}$, $R^{4a2}$, A, $A^a$, G, M, W, $Z^1$, $Z^3$, X, J, $J^1$ and n are as defined in the disclosure.
Also disclosed are compositions containing the compounds of Formula 1 and methods for controlling plant disease caused by a fungal pathogen comprising applying an effective amount of a compound or a composition of the invention.

4 Claims, No Drawings

(56) References Cited

U.S. PATENT DOCUMENTS

| | | |
|---|---|---|
| 5,126,338 A | 6/1992 | Worthington et al. |
| 5,922,717 A | 7/1999 | Pieper et al. |
| 6,514,977 B1 | 2/2003 | Anantanarayan et al. |
| 7,151,075 B2 | 12/2006 | Baumann et al. |
| 7,851,473 B2* | 12/2010 | Matsumoto .......... A61K 31/495 514/252.02 |
| 8,449,898 B2* | 5/2013 | Gregory ................ A01N 43/40 424/405 |
| 8,722,678 B2* | 5/2014 | Hanagan .............. C07D 403/14 514/252.05 |
| 2004/0167197 A1 | 8/2004 | Rudolph et al. |
| 2007/0004750 A1 | 1/2007 | Lorsbach et al. |
| 2010/0004288 A1 | 1/2010 | Pasteris et al. |
| 2011/0269712 A1 | 11/2011 | Bisaha et al. |

FOREIGN PATENT DOCUMENTS

| | | |
|---|---|---|
| WO | 93/18016 A1 | 9/1993 |
| WO | 00/25768 A1 | 5/2000 |
| WO | 01/34150 A1 | 5/2001 |
| WO | 2004/058723 A1 | 7/2004 |
| WO | 2004/058751 A1 | 7/2004 |
| WO | 2005/003128 A1 | 1/2005 |
| WO | 2005/063754 A1 | 7/2005 |
| WO | 2005/074934 A1 | 8/2005 |
| WO | 2005/087765 A1 | 9/2005 |
| WO | 2005/116002 A2 | 12/2005 |
| WO | 2005/116653 A2 | 12/2005 |
| WO | 2006/032322 A1 | 3/2006 |
| WO | 2006/034279 A1 | 3/2006 |
| WO | 2006/054652 A1 | 5/2006 |
| WO | 2006/066924 A2 | 6/2006 |
| WO | 2006/067401 A1 | 6/2006 |
| WO | 2007/014290 A2 | 2/2007 |
| WO | 2007/070433 A2 | 6/2007 |
| WO | 2007/654553 A2 | 6/2007 |
| WO | 2008/013622 A2 | 1/2008 |
| WO | 2008/091580 A2 | 7/2008 |
| WO | 2008/091594 A2 | 7/2008 |
| WO | 2009/055514 A2 | 4/2009 |
| WO | 2009/094407 A2 | 7/2009 |
| WO | 2009/094445 A2 | 7/2009 |

OTHER PUBLICATIONS

Wade, Peter et al., J. Org. Chem. vol. 49, 1984, pp. 4595-4601.
CAS RN 340185-56-0, STN Entry Date Jun. 8, 2001.
CAS RN 340185-68-4, STN Entry Date Jun. 8, 2001.
CAS RN 340186-38-1, STN Entry Date Jun. 8, 2001.
CAS RN 340186-41-6, STN Entry Date Jun. 8, 2001.
Database Registry [Online]: Chemical Abstracts Service, Columbus, Ohio, USA. Retrieved from STN, Registry No. 891373-94-7 (Entered STN: Jul. 10, 2006).
Database Registry [Online]: Chemical Abstracts Service, Columbus, Ohio, USA. Retrieved from STN, Registry No. 606088-96-4 (Entered STN: Oct. 17, 2003).
Database Registry [Online]: Chemical Abstracts Service, Columbus, Ohio, USA. Retrieved from STN, Registry No. 606088-95-3 (Entered STN: Oct. 17, 2003).
Michaelis et al., Berichte der Deutschen Chernischen Gesellschaft, vol. 43, Jan. 1, 1910, pp. 2116-2120.
Chambers et al., International IUPAC Congress of Pesticide Chemistry, Pesticide Chemistry Proceedings, vol. 5, 1972, pp. 209-230.
Boa et al., Organic Papers, vol. E60, 2004, pp. 966-967.
Tensmeyer et al., Journal of Organic Chemisty, vol. 31, No. 6, 1966, pp. 1878-1883.

* cited by examiner

FUNGICIDAL AZOCYCLIC AMIDES

FIELD OF THE INVENTION

This invention relates to certain carboxamides, their N-oxides, salts and compositions, and methods of their use as fungicides.

BACKGROUND OF THE INVENTION

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different sites of action.

World Patent Publication WO 05/003128 discloses thiazolylpiperidine derivatives of Formula i as MTP (Microsomal Triglyceride transfer Protein) inhibitors.

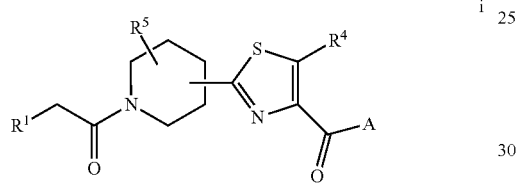

wherein
A is a radical selected from the radicals a1 and a2 below

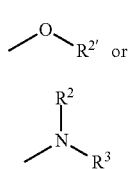

and $R^1$, $R^2$, $R^{2'}$, $R^3$, $R^4$ and $R^5$ are as defined in the disclosure.

World Patent Publication WO 04/058751 discloses piperidinyl-thiazole carboxamide derivatives for altering vascular tone.

SUMMARY OF THE INVENTION

This invention relates to compounds of Formula 1 including all geometric and stereoisomers, N-oxides, and salts thereof, agricultural compositions containing them and their use as fungicides:

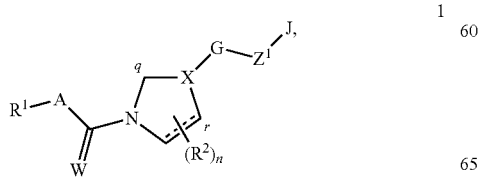

wherein
$R^1$ is an optionally substituted phenyl, naphthalenyl or 5- or 6-membered heteroaromatic ring;
A is $CHR^{15}$ or $NR^{16}$;
$R^{15}$ is H, halogen, cyano, hydroxy, —CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_3$-$C_5$ alkoxycarbonylalkyl, $C_2$-$C_5$ alkylaminocarbonyl, $C_3$-$C_5$ dialkylaminocarbonyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl or $C_1$-$C_4$ haloalkylsulfonyl;
$R^{16}$ is H, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_3$-$C_5$ alkoxycarbonylalkyl, $C_2$-$C_5$ alkylaminocarbonyl, $C_3$-$C_5$ dialkylaminocarbonyl, $C_1$-$C_4$ alkylsulfonyl or $C_1$-$C_4$ haloalkylsulfonyl;
W is O or S;
X is a radical selected from

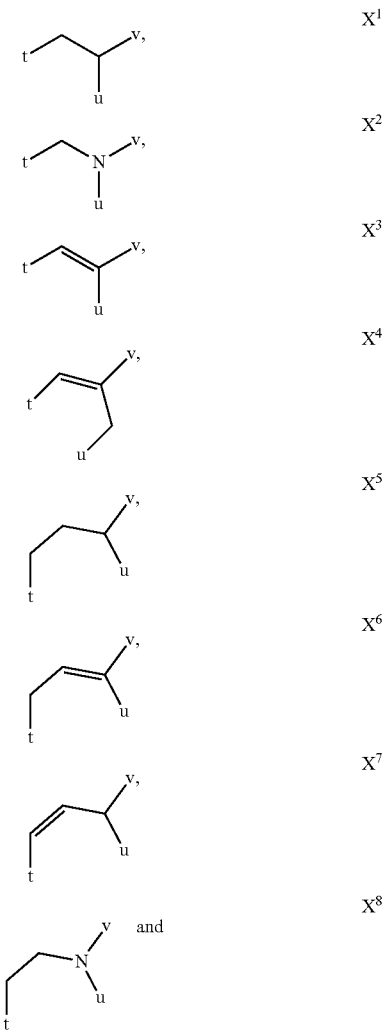

-continued

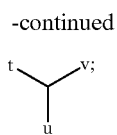

wherein the bond of $X^1$, $X^2$, $X^3$, $X^4$, $X^5$, $X^6$, $X^7$, $X^8$ or $X^9$ which is identified with "t" is connected to the carbon atom identified with "q" of Formula 1, the bond which is identified with "u" is connected to the carbon atom identified with "r" of Formula 1, and the bond which is identified with "v" is connected to G;

each $R^2$ is independently $C_1$-$C_4$ alkyl, $C_2$-$C_4$ alkenyl, $C_1$-$C_4$ haloalkyl, $C_1$-$C_4$ alkoxy, halogen, cyano or hydroxy; or two $R^2$ are taken together as $C_1$-$C_4$ alkylene or $C_2$-$C_4$ alkenylene to form a bridged bicyclic or fused bicyclic ring system; or two $R^2$ attached to adjacent ring carbon atoms joined by a double bond are taken together as —CH=CH—CH=CH— optionally substituted with 1 to 3 substituents selected from $C_1$-$C_4$ alkyl, $C_1$-$C_4$ haloalkyl, $C_1$-$C_4$ alkoxy, $C_1$-$C_4$ haloalkoxy, halogen, hydroxy, amino, cyano and nitro;

G is an optionally substituted 5-membered heteroaromatic ring or 5-membered saturated or partially saturated heterocyclic ring;

J is a 5-, 6- or 7-membered ring, a 8- to 11-membered bicyclic ring system or a 7- to 11-membered spirocyclic ring system, each ring or ring system containing ring members selected from carbon and optionally 1 to 4 heteroatoms selected from up to 2 O, up to 2 S and up to 4 N, and optionally including 1 to 3 ring members selected from the group consisting of C(=O), C(=S), S(O), S(O)$_2$ and SiR$^{17}$R$^{18}$, each ring or ring system optionally substituted with 1 to 5 substituents independently selected from R$^5$;

each $R^5$ is independently H, halogen, cyano, hydroxy, amino, nitro, —CHO, —C(=O)OH, —C(=O)NH$_2$, —NR$^{25}$R$^{26}$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{10}$ alkylcycloalkylalkyl, $C_3$-$C_8$ cycloalkenyl, $C_3$-$C_8$ halocycloalkenyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylaminoalkyl, $C_3$-$C_8$ dialkylaminoalkyl, $C_2$-$C_6$ haloalkylaminoalkyl, $C_4$-$C_{10}$ cycloalkylaminoalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_4$-$C_8$ cycloalkoxycarbonyl, $C_5$-$C_{10}$ cycloalkylalkoxycarbonyl, $C_2$-$C_6$ alkylaminocarbonyl, $C_3$-$C_8$ dialkylaminocarbonyl, $C_4$-$C_8$ cycloalkylaminocarbonyl, $C_2$-$C_6$ haloalkoxyalkyl, $C_1$-$C_6$ hydroxyalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_{10}$ trialkylsilyl, $C_1$-$C_6$ alkylsulfonylamino, $C_1$-$C_6$ haloalkylsulfonylamino or —Z$^2$Q;

each $R^{25}$ is independently H, $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl;

each $R^{26}$ is independently $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl, $C_2$-$C_6$ haloalkoxycarbonyl or —Z$^4$Q;

each $R^{17}$ and $R^{18}$ is independently $C_1$-$C_5$ alkyl, $C_2$-$C_5$ alkenyl, $C_2$-$C_5$ alkynyl, $C_3$-$C_5$ cycloalkyl, $C_3$-$C_6$ halocycloalkyl, $C_4$-$C_{10}$ cycloalkylalkyl, $C_4$-$C_7$ alkylcycloalkyl, $C_5$-$C_7$ alkylcycloalkylalkyl, $C_1$-$C_5$ haloalkyl, $C_1$-$C_5$ alkoxy or $C_1$-$C_5$ haloalkoxy;

each Q is independently phenyl, benzyl, naphthalenyl, a 5- or 6-membered heteroaromatic ring or an 8- to 11-membered heteroaromatic bicyclic ring system, each optionally substituted with 1 to 5 substituents independently selected from R$^7$ on carbon atom ring members and R$^{12}$ on nitrogen atom ring members; or each Q is independently a 3- to 7-membered nonaromatic carbocyclic ring, a 5-, 6- or 7-membered nonaromatic heterocyclic ring or an 8- to 11-membered nonaromatic bicyclic ring system, each optionally including ring members selected from the group consisting of C(=O), C(=S), S(O), S(O)$_2$ and SiR$^{17}$R$^{18}$, and optionally substituted with 1 to 5 substituents independently selected from R$^7$ on carbon atom ring members and R$^{12}$ on nitrogen atom ring members;

each $R^7$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; or $R^5$ and $R^7$ are taken together with the atoms linking $R^5$ and $R^7$ to form an optionally substituted 5- to 7-membered ring containing ring members selected from carbon and optionally 1 to 3 heteroatoms selected from up to 1 O, up to 1 S and up to 1 N and optionally including 1 to 3 ring members selected from the group consisting of C(=O), C(=S), S(O), S(O)$_2$ and SiR$^{17}$R$^{18}$;

each $R^{12}$ is independently H, $C_1$-$C_3$ alkyl, $C_2$-$C_3$ alkylcarbonyl, $C_1$-$C_3$ alkoxy or $C_2$-$C_3$ alkoxycarbonyl;

each $Z^1$ and $Z^2$ is independently a direct bond, O, C(=O), S(O)$_m$, CHR$^{20}$ or NR$^{21}$;

each $Z^4$ is independently O, C(=O), S(O)$_m$ or CHR$^{20}$;

each $R^{20}$ is independently H, $C_1$-$C_4$ alkyl or $C_1$-$C_4$ haloalkyl;

each $R^{21}$ is independently H, $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl;

each m is independently 0, 1 or 2; and n is 0, 1 or 2;

provided that:

(a) when $R^1$ is unsubstituted thienyl, X is $X^1$ and the ring containing X is saturated, G is an unsubstituted thiazole ring connected at its 2-position to X and at its 4-position to $Z^1$ in Formula 1, A is $CHR^{15}$, $R^{15}$ is H, and J is an isoxazole ring connected at its 4-position to $Z^1$ and substituted at its 5-position with methyl and at its 3-position with meta-substituted phenyl, then $Z^1$ is O, C(=O), $S(O)_m$, $CHR^{20}$ or $NR^{21}$.

More particularly, this invention pertains to compounds of Formula 1 including all geometric and stereoisomers, N-oxides, and salts thereof; provided that (b) when A is $NR^{16}$, X is $X^1$ or $X^2$, $Z^1$ is a direct bond, and J is phenyl, then J is substituted with at least one $R^5$ other than H, F, Cl, CN, $OCH_3$, $CF_3$ and $CH_3$, and (c) when A is $CHR^{15}$, $R^{15}$ is H, W is O, X is $X^1$, n is 0, G is a thiazole ring connected at its 2-position to X, and at its 4-position to $Z^1$ in Formula 1, and bonded at its 5-position to H, F, Cl or Br, $Z^1$ is a direct bond, and $R^1$ is

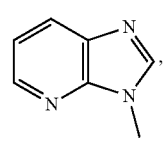
R¹-1

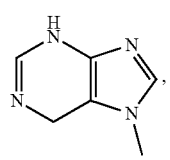
R¹-2

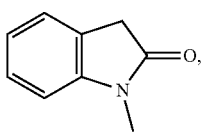
R¹-3

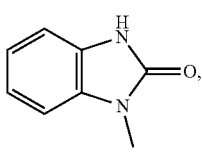
R¹-4

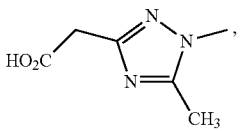
R¹-5

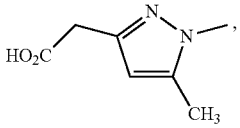
R¹-6

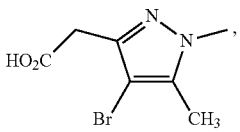
R¹-7

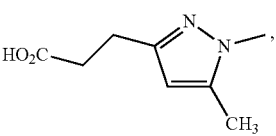
R¹-8

-continued

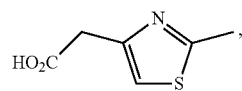
R¹-9

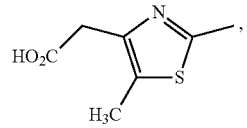
R¹-10

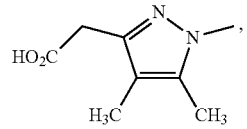
R¹-11

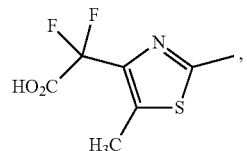
R¹-12

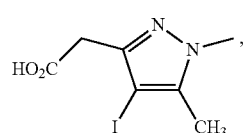
R¹-13

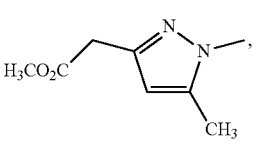
R¹-14

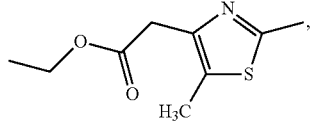
R¹-15

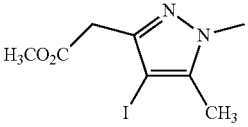
R¹-16

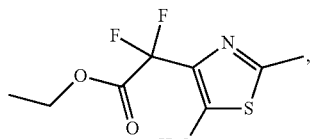
R¹-17

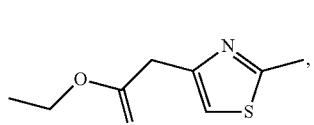
R¹-18

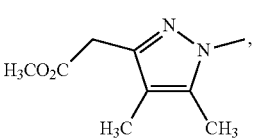
R¹-19

-continued

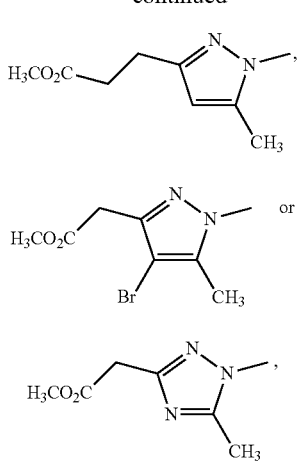

then when J is a substituted phenyl or substituted pyrimidin-4-yl, it is substituted with at least one $R^5$ other than H, $SCF_3$, $OCF_3$, $C(CH_3)_3$, $S(O)_2CF_3$, $OCH_3$, $CF_3$, Br, cyclopropyl, 1-methylcyclopropyl, OH or $CF_2CH_3$, and when J is a 2,3-dihydro-1H-inden-4-yl or 5,6,7,8-tetrahydronaphthalen-2-yl, it is substituted with at least one $R^5$ other than H, $CH_3$ or $C(CH_3)_3$.

This invention also relates to a compound of Formula 1A

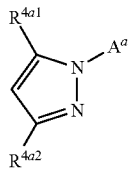

1A wherein
each $R^{4a1}$ and $R^{4a2}$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy, $C_1$-$C_2$ haloalkoxy, $C_1$-$C_2$ alkylthio, $C_1$-$C_2$ haloalkylthio, $C_2$-$C_3$ alkoxyalkyl, $C_2$-$C_3$ alkylcarbonyl, $C_2$-$C_3$ alkoxycarbonyl, $C_2$-$C_3$ alkylaminocarbonyl or $C_3$-$C_4$ dialkylaminocarbonyl;
$A^a$ is H, $CH_2CO_2H$, $CH_2CO_2R^{30}$ or $CH_2C(=O)Cl$; and
$R^{30}$ is $C_1$-$C_3$ alkyl.

This invention also relates to a compound of Formula 1B

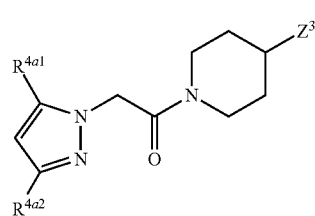

1B wherein
each $R^{4a1}$ and $R^{4a2}$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy, $C_1$-$C_2$ haloalkoxy, $C_1$-$C_2$ alkylthio, $C_1$-$C_2$ haloalkylthio, $C_2$-$C_3$ alkoxyalkyl, $C_1$-$C_3$ alkylcarbonyl, $C_2$-$C_3$ alkoxycarbonyl, $C_2$-$C_3$ alkylaminocarbonyl or $C_3$-$C_4$ dialkylaminocarbonyl; and
$Z^3$ is CN or $C(=S)NH_2$.

This invention further relates to a compound of Formula 1C

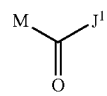

1C wherein
M is $C_1$-$C_3$ alkyl, $C_1$-$C_3$ haloalkyl, hydroxy, $C_1$-$C_4$ alkoxy, $C_1$-$C_2$ haloalkoxy, $C_1$-$C_4$ alkylamino, $C_2$-$C_8$ dialkylamino, 1-piperidinyl, 1-pyrrolidinyl or 4-morpholinyl; and
$J^1$ is J-29-1 through J-29-58 depicted in Exhibit A as described below.

More particularly, this invention pertains to compounds of Formulae 1A, 1B and 1C, including all geometric and stereoisomers, an N-oxide or salt thereof (except that the compounds of Formula 1C of this invention are limited to those stereoisomer embodiments depicted for $J^1$ in the Summary of Invention above).

This invention also relates to a fungicidal composition comprising a fungicidally effective amount of a compound of Formula 1 and at least one additional component selected from the group consisting of surfactants, solid diluents and liquid diluents.

This invention also relates to a fungicidal composition comprising a mixture of a compound of Formula 1 (including all geometric and stereoisomers, N-oxides, and salts thereof) and at least one other fungicide (e.g., at least one other fungicide having a different site of action).

This invention further relates to a method for controlling plant diseases caused by fungal plant pathogens comprising applying to the plant or portion thereof, or to the plant seed, a fungicidally effective amount of Formula 1 (including all geometric and stereoisomers, N-oxides, and salts thereof) (e.g., as a composition described herein).

This invention additionally relates to fungicidal compositions and methods of controlling plant diseases as described above, except that proviso (a) is removed from the definition of the scope of Formula 1.

DETAILS OF THE INVENTION

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and Both A and B are true (or present).

Also, use of "a" or "an" are employed to describe elements and components of the invention. This is done merely for convenience and to give a general sense of the invention.

This description should be read to include one or at least one and the singular also includes the plural unless it is obvious that it is meant otherwise.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath of the surface of the growing medium (e.g., soil), such as roots, tubers, bulbs and corms, and also members growing above the growing medium, such as foliage (including stems and leaves), flowers, fruits and seeds.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkylene" denotes a straight-chain or branched alkanediyl. Examples of "alkylene" include $CH_2$, $CH_2CH_2$, $CH(CH_3)$, $CH_2CH_2CH_2$, $CH_2CH(CH_3)$ and the different butylene isomers. "Alkenylene" denotes a straight-chain or branched alkenediyl containing one olefinic bond. Examples of "alkenylene" include $CH=CH$, $CH_2CH=CH$, $CH=C(CH_3)$, $CH_2CH=CH$ and $CH_2CH=CHCH_2$. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. Examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. Examples of "alkylaminocarbonyl" include $CH_3NHC(=O)$—, $CH_3CH_2NHC(=O)$—, $CH_3CH_2CH_2NHC(=O)$—, $(CH_3)_2CHNHC(=O)$— and the different butylamino- or pentylaminocarbonyl isomers. Examples of "dialkylaminocarbonyl" include $(CH_3)_2NC(=O)$—, $(CH_3CH_2)_2NC(=O)$—, $CH_3CH_2(CH_3)NC(=O)$—, $(CH_3)_2CHN(CH_3)C(=O)$— and $CH_3CH_2CH_2(CH_3)NC(=O)$—. "Alkylamino", "dialkylamino" and the like, are defined analogously to the above examples. "Trialkylsilyl" includes 3 branched and/or straight-chain alkyl radicals attached to and linked through a silicon atom, such as trimethylsilyl, triethylsilyl and tert-butyldimethylsilyl. "Cycloalkyl" includes, for example, cyclopropyl, cyclobutyl, cyclopentyl, and cyclohexyl. Examples of "cycloalkylalkyl" include cyclopropylmethyl, cyclopentylethyl, and other cycloalkyl moieties bonded to straight-chain or branched alkyl groups. "Alkylcycloalkyl" denotes alkyl substitution on a cycloalkyl moiety. Examples include 4-methylcyclohexyl and 3-ethylcyclopentyl.

Unless otherwise indicated, a "ring" or "ring system" as a component of Formula 1 (e.g., substituent J and Q) is carbocyclic or heterocyclic. The term "ring system" denotes two or more connected rings. The term "spirocyclic ring system" denotes a ring system consisting of two rings connected at a single atom (so the rings have a single atom in commonality). Illustrative of a $J^1$ moiety that is a spirocyclic ring system is J-29-28 depicted in the definition of Formula 1C. The term "bicyclic ring system" denotes a ring system consisting of two rings sharing two or more common atoms. In a "fused bicyclic ring system" the common atoms are adjacent, and therefore the rings share two adjacent atoms and bond connecting them. In a "bridged bicyclic ring system" the common atoms are not adjacent (i.e. there is no bond between the bridgehead atoms). A "bridged bicyclic ring system" is conceptually formed by bonding a segment of one or more atoms to nonadjacent ring members of a ring.

A ring, a bicyclic ring system or spirocyclic ring system can be part of an extended ring system containing more than two rings wherein substituents on the ring, bicyclic ring system or spirocyclic are taken together to form the additional rings, which may be in bicyclic and/or spirocyclic relationships with other rings in the extended ring system. For example, the particular $J^1$ moiety J-29-26 depicted in the definition of Formula 1C consists of a dihydro isoxazoline ring having one $R^5$ substituent as $Z^2Q$, which is a cyclobutyl ring substituted with two methyl groups as $R^7$ and also one $R^7$ group taken together with another $R^5$ substituent on the dihydro isoxazoline ring as —$CH_2CH_2$— to form the additional six-membered ring component in the ring system.

The term "ring member" refers to an atom (e.g., C, O, N or S) or other moiety (e.g., C(=O), C(=S), S(O) or $S(O)_2$) forming the backbone of a ring or ring system. The term "carbocyclic ring" denotes a ring wherein the atoms forming the ring backbone are selected only from carbon. The term "carbocyclic ring system" denotes two or more fused rings wherein the atoms forming the backbone of the rings are selected only from carbon. The term "heterocyclic ring" denotes a ring wherein at least one of the atoms forming the ring backbone is other than carbon. The term "heterocyclic ring system" denotes two or more fused rings wherein at least one of the atoms forming the backbone of the rings is other than carbon. "Aromatic" indicates that each of ring atoms is essentially in the same plane and has a p-orbital perpendicular to the ring plane, and in which (4n+2) π electrons, where n is a positive integer, are associated with the ring to comply with Hückel's rule. The term "heteroaromatic ring" refers to a heterocyclic ring that is aromatic. The term "saturated heterocyclic ring" denotes a heterocyclic ring containing only single bonds between ring members. The term "partially saturated heterocyclic ring" denotes a heterocyclic ring containing at least one double bond but which is not aromatic.

The dotted line in Formula 1 and in other rings depicted in the present description (e.g., J-44, J-45, J-48 and J-49 in Exhibit 3) represents that the bond indicated can be a single bond or double bond. Unless otherwise indicated, heterocyclic rings and ring systems are attached to the remainder of Formula 1 through any available carbon or nitrogen by replacement of a hydrogen on said carbon or nitrogen, and all substituents on the heterocyclic rings and ring systems are attached through any available carbon or nitrogen by replacement of a hydrogen on said carbon or nitrogen.

As already described, J is a 5-, 6- or 7-membered ring, a 8- to 11-membered bicyclic ring system or a 7- to 11-membered spirocyclic ring system, each ring or ring system containing ring members selected from carbon and optionally 1 to 4 heteroatoms selected from up to 2 O, up to 2 S and up to 4 N, and optionally including 1 to 3 ring members selected from the group consisting of C(=O), C(=S), S(O), S(O)$_2$ and SiR$^{17}$R$^{18}$, each ring or ring system optionally substituted with 1 to 5 substituents independently selected from R$^5$. As the heteroatoms are optional, 0 to 4 heteroatoms may be present. In this description the heteroatoms selected from up to 2 S are atoms and not the moieties S(O) or S(O)$_2$. The heteroatoms selected from up to 4 N may be oxidized as N-oxides, because the present invention also relates to N-oxide derivatives of the compounds of Formula 1. Therefore the optional 1 to 3 ring members selected from the group consisting of C(=O), C(=S), S(O), S(O)$_2$ and SiR$^{17}$R$^{18}$ are in addition to the optional 1 to 4 heteroatoms selected from up to 2 O, up to 2 S and up to 4 N. Of note is when the total number of unoxidized sulfur atoms (i.e. S) and oxidized sulfur moieties (i.e. S(O) and S(O)$_2$) does not exceed 2, so that at most two ring members selected from S, S(O) and S(O)$_2$ are present in the ring or ring system. When none of the optional heteroatoms and none of the optional ring members selected from S(O), S(O)$_2$ and SiR$^{17}$R$^{18}$ are present, the ring or ring system is carbocyclic. The R$^5$ substituents may be attached to carbon atom ring members and to nitrogen atom ring members having an available point of attachment. The carbon-based ring members C(=O) and C(=S) do not have available points of attachment. Furthermore in SiR$^{17}$R$^{18}$ ring members, the substituents R$^{17}$ and R$^{18}$ are otherwise separately defined, and these ring members cannot be further substituted with R$^5$. As the R$^5$ substituents are optional, 0 to 5 substituents may be present, limited by the number of available points of attachment.

Similarly, R$^5$ and R$^7$ may be taken together with the atoms linking R$^5$ and R$^7$ to form an optionally substituted 5- to 7-membered ring containing ring members selected from carbon and optionally 1 to 3 heteroatoms selected from up to 1 O, up to 1 S and up to 1 N and optionally including 1 to 3 ring members selected from the group consisting of C(=O), C(=S), S(O), S(O)$_2$ and SiR$^{17}$R$^{18}$. As the heteroatoms are optional, 0 to 3 heteroatoms may be present. In this description the heteroatom selected from up to 1 S is an atom and not the moieties S(O) or S(O)$_2$. The heteroatom selected from up to 1 N may be oxidized as an N-oxide, because the present invention also relates to N-oxide derivatives of the compounds of Formula 1. Therefore the optional 1 to 3 ring members selected from the group consisting of C(=O), C(=S), S(O), S(O)$_2$ and SiR$^{17}$R$^{18}$ are in addition to the optional 1 to 3 heteroatoms selected from up to 1 O, up to 1 S and up to 1 N. Of note is when the total number of unoxidized sulfur atoms (i.e. S) and oxidized sulfur moieties (i.e. S(O) and S(O)$_2$) does not exceed 1, so that at most one ring member selected from S, S(O) and S(O)$_2$ is present in the ring. When none of the optional heteroatoms and none of the optional ring members selected from S(O), S(O)$_2$ and SiR$^{17}$R$^{18}$ are present, the ring is carbocyclic. The 5- to 7-membered ring is optionally substituted. The substituents on the atoms linking R$^5$ and R$^7$ are described in the definition of the components linking R$^5$ and R$^7$. For example, when linking component Z$^2$ is CHR$^{20}$, the substituent R$^{20}$ is defined to be H, C$_1$-C$_4$ alkyl or C$_1$-C$_4$ haloalkyl. Regarding optional substituents attached to the portion of the ring consisting of R$^5$ and R$^7$ taken together, an optional substituent is a non-hydrogen substituent that does not extinguish fungicidal activity. Optional substituents may be attached to carbon atom ring members and to nitrogen atom ring members having an available point of attachment. The carbon-based ring members C(=O) and C(=S) do not have available points of attachment. Furthermore in SiR$^{17}$R$^{18}$ ring members, the substituents R$^{17}$ and R$^{18}$ are otherwise separately defined, and these ring members cannot be further substituted.

The term "halogen", either alone or in compound words such as "haloalkyl", includes fluorine, chlorine, bromine or iodine. Furthermore, when used in compound words such as "haloalkyl", said alkyl may be partially or fully substituted with halogen atoms which may be the same or different. Examples of "haloalkyl" include F$_3$C, ClCH$_2$, CF$_3$CH$_2$ and CF$_3$CCl$_2$. The terms "haloalkenyl", "haloalkynyl", "halocycloalkyl", "haloalkoxy", "haloalkylthio", and the like, are defined analogously to the term "haloalkyl". Examples of "haloalkenyl" include (Cl)$_2$C=CHCH$_2$ and CF$_3$CH$_2$CH=CHCH$_2$. Examples of "haloalkynyl" include HC≡CCHCl, CF$_3$C≡C, CCl$_3$C≡C and FCH$_2$C≡CCH$_2$. Examples of "haloalkoxy" include CF$_3$O, CCl$_3$CH$_2$O, HCF$_2$CH$_2$CH$_2$O and CF$_3$CH$_2$O. Examples of "haloalkylthio" include CCl$_3$S, CF$_3$S, CCl$_3$CH$_2$S and ClCH$_2$CH$_2$CH$_2$S. Examples of "haloalkylsulfinyl" include CF$_3$S(O), CCl$_3$S(O), CF$_3$CH$_2$S(O) and CF$_3$CF$_2$S(O). Examples of "haloalkylsulfonyl" include CF$_3$S(O)$_2$, CCl$_3$S(O)$_2$, CF$_3$CH$_2$S(O)$_2$ and CF$_3$CF$_2$S(O)$_2$.

The total number of carbon atoms in a substituent group is indicated by the "C$_i$-C$_j$" prefix where i and j are numbers from 1 to 10. For example, C$_1$-C$_4$ alkylsulfonyl designates methylsulfonyl through butylsulfonyl; C$_2$ alkoxyalkyl designates CH$_3$OCH$_2$; C$_3$ alkoxyalkyl designates, for example, CH$_3$CH(OCH$_3$), CH$_3$OCH$_2$CH$_2$ or CH$_3$CH$_2$OCH$_2$; and C$_4$ alkoxyalkyl designates the various isomers of an alkyl group substituted with an alkoxy group containing a total of four carbon atoms, examples including CH$_3$CH$_2$CH$_2$OCH$_2$ and CH$_3$CH$_2$OCH$_2$CH$_2$.

When a compound is substituted with a substituent bearing a subscript that indicates the number of said substituents can vary, then when the number of said substituents is greater than 1, said substituents are independently selected from the group of defined substituents. Furthermore when a range is indicated (e.g., i-j substituents), then the number of substituents may be selected from the integers between i and j inclusive. When a group (e.g., J) contains a substituent (e.g., R$^5$) which can be hydrogen, then when this substituent is taken as hydrogen, it is recognized that this is equivalent to said group being unsubstituted. When a variable group is shown to be optionally attached to a position, for example (R$^2$)$_n$ wherein n may be 0, or as a further example (R$^4$)$_k$ wherein k may be 0 in Exhibit 1, then hydrogen may be at the position even if not recited in the definition of the variable group (e.g., R$^2$ and R$^4$). When a position on a group is said to be "not substituted" or "unsubstituted", then hydrogen atoms are attached to take up any free valency. The term "optionally substituted" in connection with groups listed for R$^1$, R$^2$, R$^5$, R$^7$, G, J and Q refers to groups that are unsubstituted or have at least 1 non-hydrogen substituent. Unless otherwise indicated, these groups may be substituted with as many optional substituents as can be accommodated by replacing a hydrogen atom with a non-hydrogen substituent on any available carbon or nitrogen atom. Commonly, the number of optional substituents (when present) ranges from 1 to 3. When a range specified for the number of substituents (e.g., x being an integer from 0 to 5 in Exhibit 3) exceeds the number of positions available for substituents on a ring (e.g., 2 positions available for $(R^5)_x$ on J-1 in Exhibit 3), the actual higher end of the range is recognized to be the number of available positions. The term "optionally substituted" means that the number of substituents can be zero. For example, the phrase "optionally substituted with up to 2 substituents selected from $R^3$ on carbon ring members and selected from $R^{11}$ on nitrogen ring members" means that 0, 1 or 2 substituents can be present (if number of potential connection points allows), and thus the number of $R^3$ and $R^{11}$ substituents can be zero. Similarly, the phrase "optionally substituted with 1 to 5 substituents" means that 0, 1, 2, 3, 4 or 5 substituents can be present if the number of available connection points allows. The term "unsubstituted" in connection with a group such as a ring or ring system means the group does not have any substituents other than its one or more attachments to the remainder of Formula 1. The term "meta-substituted phenyl" means a phenyl ring substituted with a non-hydrogen substituent at a meta position relative to attachment of the phenyl ring to the remainder of Formula 1.

As noted above, $R^1$ is an optionally substituted phenyl, naphthalenyl or 5- or 6-membered heteroaromatic ring; G is an optionally substituted 5-membered heteroaromatic ring or 5-membered saturated or partially saturated heterocyclic ring; and $R^5$ and $R^7$ may be taken together with the atoms linking $R^5$ and $R^7$ to form an optionally substituted 5- to 7-membered ring containing ring members selected from carbon and optionally 1 to 3 heteroatoms selected from up to 1 O, up to 1 S and up to 1 N and optionally including 1 to 3 ring members selected from the group consisting of C(=O), C(=S), S(O), S(O)$_2$ and SiR$^{17}$R$^{18}$. The term "substituted" in connection with the definitions of $R^1$, G, $R^5$ and $R^7$ refers to groups that have at least one non-hydrogen substituent that does not extinguish fungicidal activity. Since these groups are optionally substituted, they need not have any non-hydrogen substituents. As these groups are "optionally substituted" without the number of substituents indicated, these groups may be substituted with as many optional substituents as can be accommodated by replacing a hydrogen atom with a non-hydrogen substituent on any available carbon or nitrogen atom.

Naming of substituents in the present disclosure uses recognized terminology providing conciseness in precisely conveying to those skilled in the art the chemical structure. For sake of conciseness, locant descriptors may be omitted; "pyrazol-1-yl" means "1H-pyrazol-1-yl" according to the Chemical Abstracts system of nomenclature. The term "pyridyl" is synonymous with "pyridinyl". The order of listing substituents may be different from the Chemical Abstracts system if the difference does not affect the meaning.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers, or as an optically active form. For example, when J is J-29 (see Exhibit 3) bonded at the 3-position to the remainder of Formula 1 and J-29 has one $R^5$ substituent other than H at the 5-position, then Formula 1 possesses a chiral center at the carbon atom to which $R^5$ is bonded. The two enantiomers are depicted as Formula 1' and Formula 1" with the chiral center identified with an asterisk (*).

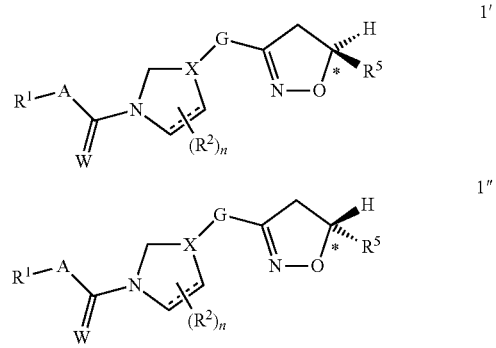

This invention comprises racemic mixtures, for example, equal amounts of the enantiomers of Formulae 1' and 1". In addition, this invention includes compounds that are enriched compared to the racemic mixture in an enantiomer of Formula 1. Also included are the essentially pure enantiomers of compounds of Formula 1, for example, Formula 1' and Formula 1".

When enantiomerically enriched, one enantiomer is present in greater amounts than the other, and the extent of enrichment can be defined by an expression of enantiomeric excess ("ee"), which is defined as (2x−1)·100%, where x is the mole fraction of the dominant enantiomer in the mixture (e.g., an ee of 20% corresponds to a 60:40 ratio of enantiomers).

Preferably the compositions of this invention have at least a 50%/0 enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Compounds of Formula 1 can comprise additional chiral centers. For example, substituents and other molecular constituents such as $R^4$, $R^5$, $R^7$, G, J, Q and $X^1$ through $X^9$ may themselves contain chiral centers. This invention comprises racemic mixtures as well as enriched and essentially pure stereoconfigurations at these additional chiral centers.

Compounds of this invention can exist as one or more conformational isomers due to restricted rotation about the amide bond (e.g., C(W)—N) in Formula 1. This invention comprises mixtures of conformational isomers. In addition, this invention includes compounds that are enriched in one conformer relative to others.

Some of the unsaturated rings and ring systems depicted in Exhibits 1, 2, 3 and 4 can have an arrangement of single and double bonds between ring members different from that depicted. Such differing arrangements of bonds for a particular arrangement of ring atoms correspond to different tautomers. For these unsaturated rings and ring systems, the particular tautomer depicted is to be considered representative of all the tautomers possible for the arrangement of ring atoms shown. The tables listing particular compounds incorporating the ring and ring systems depicted in the Exhibits may involve a tautomer different from the tautomer depicted in the Exhibits.

The compounds of the invention include N-oxide derivatives. One skilled in the art will appreciate that not all nitrogen-containing heterocycles can form N-oxides since the nitrogen requires an available lone pair of electrons for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as tert-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

The present compounds of Formula 1 can be in the form of agriculturally suitable salts. One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 are useful for control of plant diseases caused by fungal plant pathogens (i.e. are agriculturally suitable). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formulae 1, 1A, 1B and 1C, N-oxides and salts thereof.

Embodiments of the present invention include:

Embodiment 1. A compound of Formula 1 wherein A is CHR$^{15}$.

Embodiment 1a. A compound of Embodiment 1 wherein R$^{15}$ is H, halogen, cyano, hydroxy, —CHO, $C_1$-$C_4$ alkyl, $C_1$-$C_4$ haloalkyl or $C_2$-$C_5$ alkoxycarbonyl.

Embodiment 1b. A compound of Embodiment 1a wherein R$^{15}$ is H, cyano, hydroxy, methyl or methoxycarbonyl.

Embodiment 1c. A compound of Embodiment 1b wherein R$^{15}$ is H.

Embodiment 2. A compound of Formula 1 wherein A is NR$^{16}$.

Embodiment 2a. A compound of Embodiment 2 wherein R$^{16}$ is H, $C_1$-$C_4$ alkyl, $C_1$-$C_4$ haloalkyl, $C_2$-$C_4$ alkylcarbonyl, $C_2$-$C_4$ haloalkylcarbonyl or $C_2$-$C_4$ alkoxycarbonyl.

Embodiment 2b. A compound of Embodiment 2a wherein R$^{16}$ is H, methyl, methylcarbonyl or methoxycarbonyl.

Embodiment 2c. A compound of Embodiment 2b wherein R$^{16}$ is H.

Embodiment 3. A compound of Formula 1 wherein W is O.

Embodiment 4. A compound of Formula 1 wherein W is S.

Embodiment 5. A compound of Formula 1 wherein each R$^2$ is independently $C_1$-$C_2$ alkyl, $C_1$-$C_2$ haloalkyl, $C_1$-$C_2$ alkoxy, halogen, cyano or hydroxy.

Embodiment 5a. A compound of Embodiment 5 wherein each R$^2$ is independently methyl, methoxy, cyano or hydroxy.

Embodiment 5b. A compound of Embodiment 5a wherein each R$^2$ is methyl.

Embodiment 6. A compound of Formula 1 wherein n is 0 or 1.

Embodiment 7. A compound of Embodiment 6 wherein n is 0.

Embodiment 7a. A compound of Embodiment 6 wherein n is 1.

Embodiment 8. A compound of Formula 1 wherein X is X$^1$, X$^2$ or X$^3$.

Embodiment 9. A compound of Embodiment 8 wherein X is X$^1$ or X$^2$.

Embodiment 10. A compound of Embodiment 9 wherein X is X$^1$.

Embodiment 11. A compound of Formula 1 wherein the ring comprising X is saturated (i.e. contains only single bonds).

Embodiment 12. A compound of Formula 1 wherein R$^1$ is a phenyl or 5- or 6-membered heteroaromatic ring optionally substituted with substituents that do not link together to make R$^1$ a fused ring system.

Embodiment 12a. A compound of Embodiment 12 wherein R$^1$ is a phenyl or 5- or 6-membered heteroaromatic ring optionally substituted with 1-3 substituents independently selected from R$^{4a}$ on carbon ring members and R$^{4b}$ on nitrogen ring members;

each R$^{4a}$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; and each R$^{4b}$ is independently $C_1$-$C_6$ alkyl, $C_3$-$C_6$ alkenyl, $C_3$-$C_6$ alkynyl, $C_3$-$C_6$ cycloalkyl, $C_1$-$C_6$ haloalkyl, $C_3$-$C_6$ haloalkenyl, $C_3$-$C_6$ haloalkynyl, $C_3$-$C_6$ halocycloalkyl or $C_2$-$C_4$ alkoxyalkyl.

Embodiment 12b. A compound of Embodiment 12a wherein R$^1$ is a phenyl or 5- or 6-membered heteroaromatic ring optionally substituted with 1-2 substituents independently selected from R$^{4a}$ on carbon ring members and R$^{4b}$ on nitrogen ring members.

Embodiment 13. A compound of Embodiment 12b wherein R$^1$ is one of U-1 through U-50 depicted in Exhibit 1;

Exhibit 1
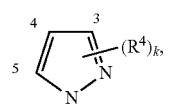 U-1
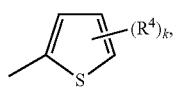 U-2
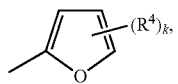 U-3
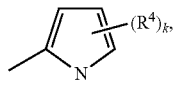 U-4
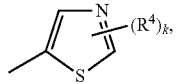 U-5
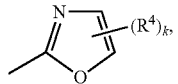 U-6
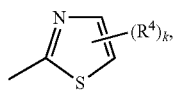 U-7
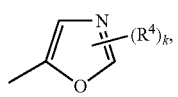 U-8
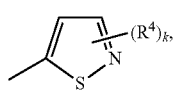 U-9
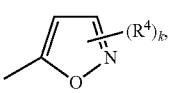 U-10
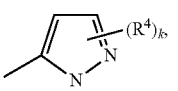 U-11
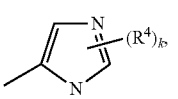 U-12
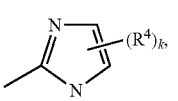 U-13
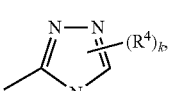 U-14
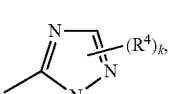 U-15
-continued
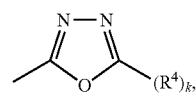 U-16
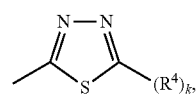 U-17
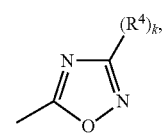 U-18
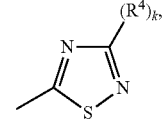 U-19
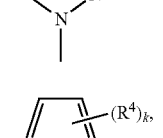 U-20
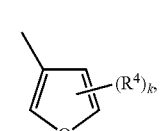 U-21
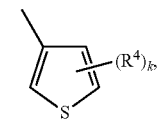 U-22
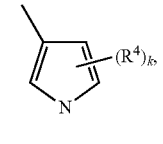 U-23
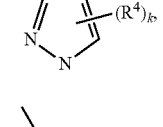 U-24
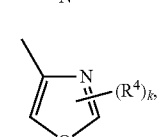 U-25
U-26
U-27

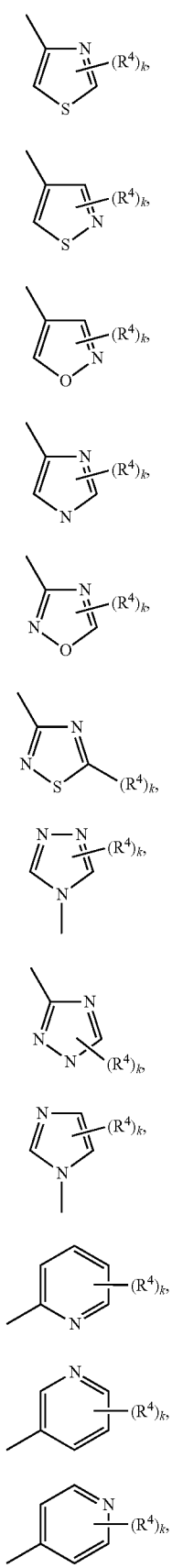
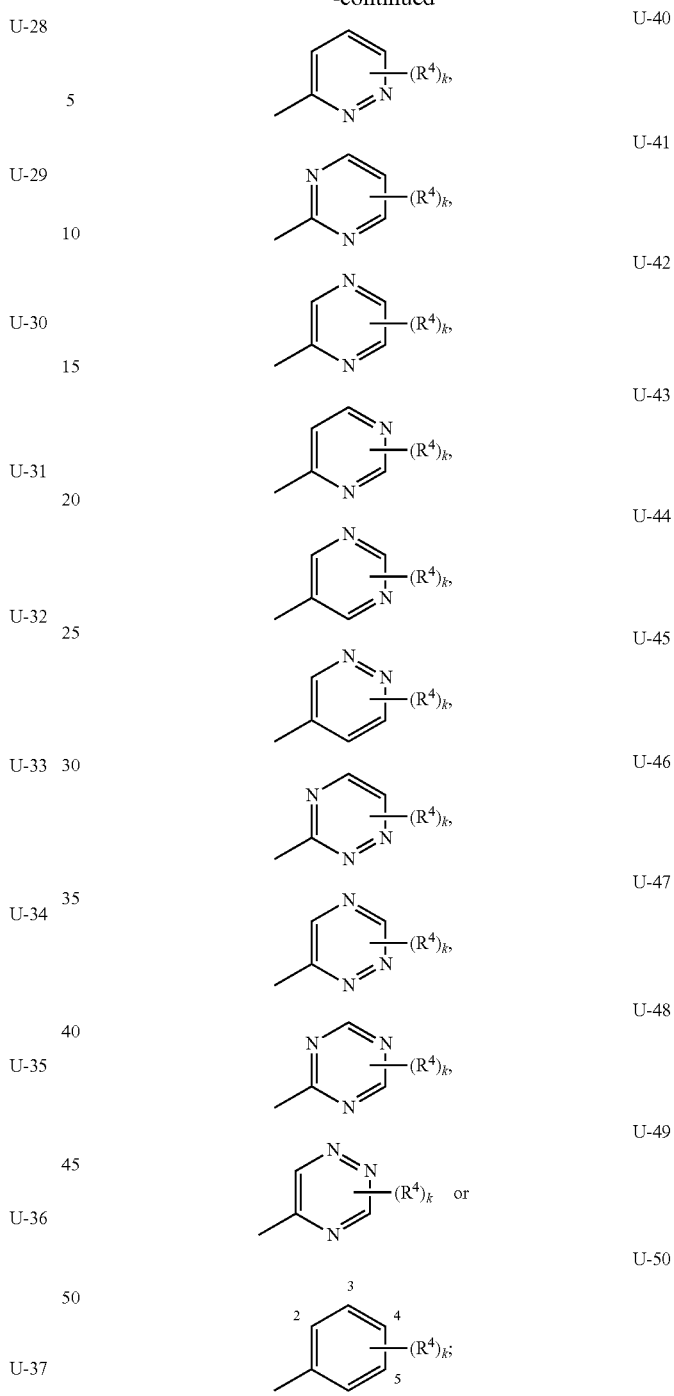
wherein
when $R^4$ is attached to a carbon ring member, said $R^4$ is selected from $R^{4a}$, and when $R^4$ is attached to a nitrogen ring member (e.g., in U-4, U-11 through U-15, U-24 through U-26, U-31 or U-35), said $R^4$ is selected from $R^{4b}$; and
k is 0, 1 or 2.
Embodiment 14. A compound of Embodiment 13 wherein $R^1$ is selected from U-1 through U-5, U-8, U-11, U-13, U-15, U-20 through U-28, U-31, U-36 through U-39 and U-50.

Embodiment 15. A compound of Embodiment 14 wherein $R^1$ is selected from U-1 through U-3, U-5, U-8, U-11, U-13, U-20, U-22, U-23, U-25 through U-28, U-36 through U-39 and U-50.

Embodiment 16. A compound of Embodiment 15 wherein $R^1$ is selected from U-1 through U-3, U-11, U-13, U-20, U-22, U-23, U-36 through U-39 and U-50.

Embodiment 17. A compound of Embodiment 16 wherein $R^1$ is U-1 or U-50.

Embodiment 18. A compound of Embodiment 17 wherein $R^1$ is U-1.

Embodiment 19. A compound of Embodiment 17 wherein $R^1$ is U-50.

Embodiment 20. A compound of any one of Embodiments 12 and 13 wherein each $R^{4a}$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy, $C_1$-$C_2$ haloalkoxy, $C_1$-$C_2$ alkylthio, $C_1$-$C_2$ haloalkylthio, $C_1$-$C_3$ alkoxyalkyl, $C_2$-$C_3$ alkylcarbonyl, $C_2$-$C_3$ alkoxycarbonyl, $C_2$-$C_3$ alkylaminocarbonyl or $C_3$-$C_4$ dialkylaminocarbonyl.

Embodiment 21. A compound of Embodiment 20 wherein each $R^{4a}$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_1$-$C_3$ haloalkynyl, halocyclopropyl, halogen, cyano, nitro, $C_1$-$C_2$ alkoxy or $C_1$-$C_2$ haloalkoxy.

Embodiment 22. A compound of Embodiment 21 wherein each $R^{4a}$ is independently halogen, $C_1$-$C_3$ alkyl, $C_1$-$C_3$ haloalkyl, $C_1$-$C_2$ alkoxy or $C_1$-$C_2$ haloalkoxy.

Embodiment 23. A compound of Embodiment 21 wherein each $R^{4a}$ is independently halogen, $C_1$-$C_2$, alkyl, $C_1$-$C_2$ haloalkyl or $C_1$-$C_2$ alkoxy.

Embodiment 24. A compound of Embodiment 23 wherein each $R^{4a}$ is independently $C_1$-$C_2$ alkyl, trifluoromethyl, Cl, Br, I or methoxy.

Embodiment 25. A compound of Embodiment 24 wherein each $R^{4a}$ is independently $C_1$-$C_2$ alkyl, trifluoromethyl, Cl or Br.

Embodiment 26. A compound of any one of Embodiments 12 and 13 wherein each $R^{4b}$ is independently $C_1$-$C_3$ alkyl, $C_3$ alkenyl (e.g., allyl), $C_3$ alkynyl (e.g., propargyl), cyclopropyl, $C_1$-$C_3$ haloalkyl, $C_3$ haloalkenyl, $C_3$ haloalkynyl, halocyclopropyl or $C_2$-$C_3$ alkoxyalkyl.

Embodiment 27. A compound of Embodiment 26 wherein each $R^{4b}$ is independently $C_1$-$C_3$ alkyl, $C_3$ alkenyl, $C_3$ alkynyl, cyclopropyl, $C_1$-$C_3$ haloalkyl, $C_3$ haloalkenyl or halocyclopropyl.

Embodiment 28. A compound of Embodiment 27 wherein each $R^{4b}$ is independently $C_1$-$C_2$ alkyl or $C_1$-$C_2$ haloalkyl.

Embodiment 29. A compound of Embodiment 28 wherein each $R^{4b}$ is independently $C_1$-$C_2$ alkyl or trifluoromethyl.

Embodiment 30. A compound of Embodiment 29 wherein each $R^{4b}$ is independently $C_1$-$C_2$ alkyl.

Embodiment 31. A compound of Embodiment 13 wherein k is 1 or 2 and at least one $R^4$ is Cl.

Embodiment 32. A compound of Embodiment 13 wherein k is 1 or 2 and at least one $R^4$ is Br.

Embodiment 33. A compound of Embodiment 13 wherein k is 1 or 2 and at least one $R^4$ is methyl.

Embodiment 34. A compound of Embodiment 13 wherein k is 1 or 2 and at least one $R^4$ is ethyl.

Embodiment 35. A compound of Embodiment 13 wherein k is 1 or 2 and at least one $R^4$ is trifluoromethyl.

Embodiment 36. A compound of Embodiment 13 wherein k is 1 or 2 and at least one $R^4$ is methoxy.

Embodiment 37. A compound of Embodiment 18 wherein k is 1 and $R^4$ is connected to the 3- or 5-position of U-1.

Embodiment 38. A compound of Embodiment 18 wherein k is 2 and one $R^4$ is connected to the 3-position and the other $R^4$ is connected to the 5-position of U-1.

Embodiment 39. A compound of Embodiment 19 wherein k is 1 and $R^4$ is connected to the 2- or 3-position of U-50.

Embodiment 40. A compound of Embodiment 19 wherein k is 2 and one $R^4$ is connected to the 2-position and the other $R^4$ is connected to the 5-position of U-50.

Embodiment 41. A compound of Formula 1 wherein G is a 5-membered heteroaromatic ring or 5-membered saturated or partially saturated heterocyclic ring, each ring optionally substituted with up to 2 substituents selected from $R^3$ on carbon ring members and selected from $R^{11}$ on nitrogen ring members;

each $R^3$ is independently $C_1$-$C_3$ alkyl, $C_1$-$C_3$ haloalkyl or halogen; and each $R^{11}$ is independently $C_1$-$C_3$ alkyl.

Embodiment 42. A compound of Embodiment 41 wherein G is one of G-1 through G-59 depicted in Exhibit 2:

Exhibit 2

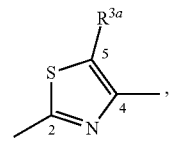
G-1

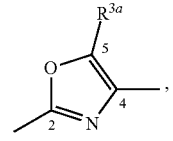
G-2

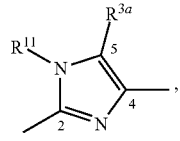
G-3

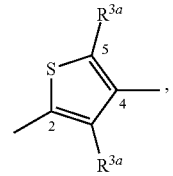
G-4

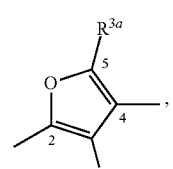
G-5

-continued
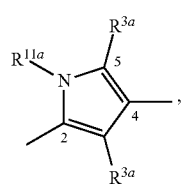 G-6
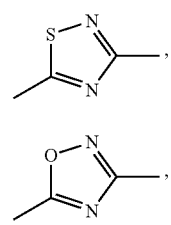 G-7
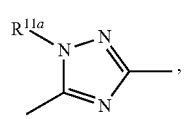 G-8
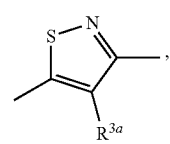 G-9
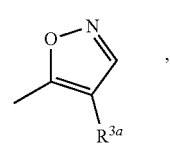 G-10
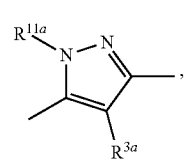 G-11
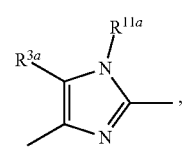 G-12
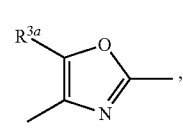 G-13
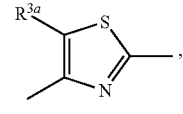 G-14
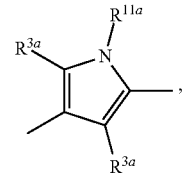 G-15
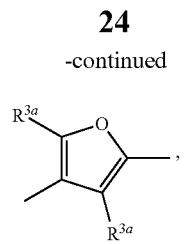 G-16
-continued
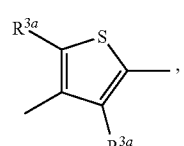 G-17
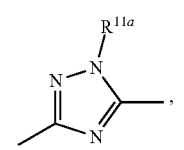 G-18
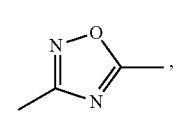 G-19
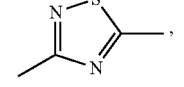 G-20
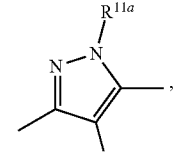 G-21
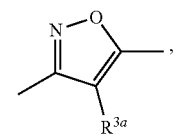 G-22
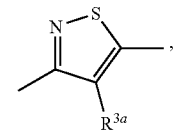 G-23
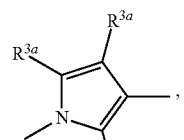 G-24
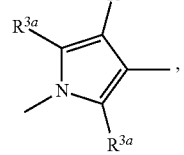 G-25
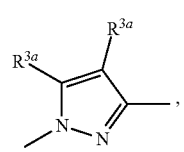 G-26

-continued
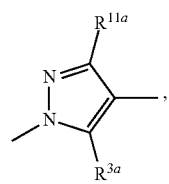 G-27
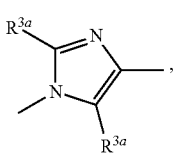 G-28
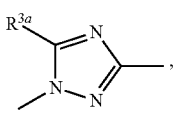 G-29
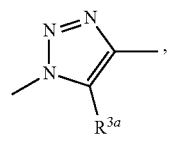 G-30
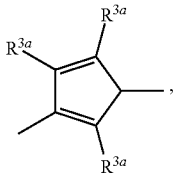 G-31
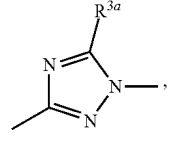 G-32
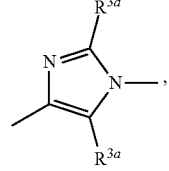 G-33
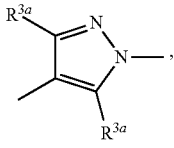 G-34
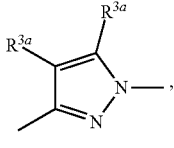 G-35
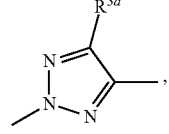 G-36
-continued
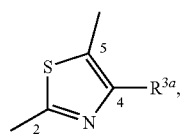 G-37
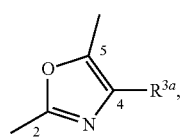 G-38
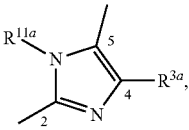 G-39
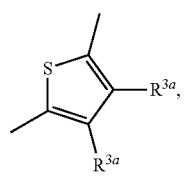 G-40
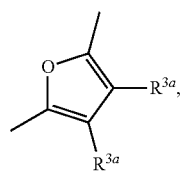 G-41
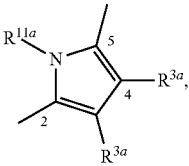 G-42
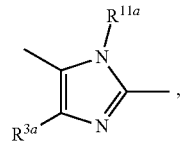 G-43
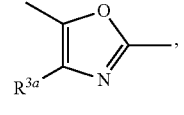 G-44
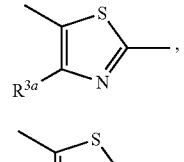 G-45
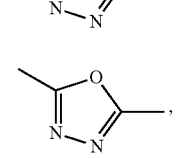 G-46
G-47

G-48 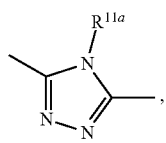

G-49 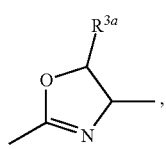

G-50 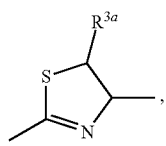

G-51 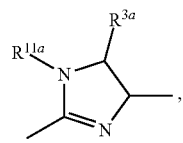

G-52 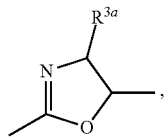

G-53 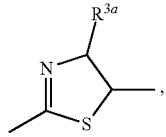

G-54 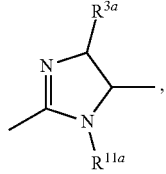

G-55 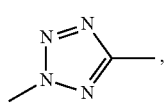

G-56 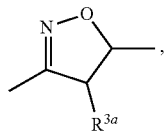

G-57 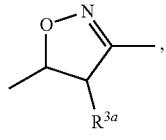

G-58 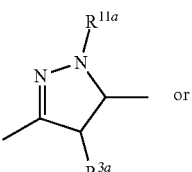 or

G-59 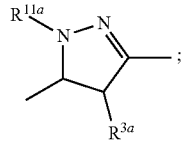;

wherein the bond projecting to the left is bonded to X, and the bond projecting to the right is bonded to $Z^1$; each $R^{3a}$ is independently selected from H or $R^3$; and $R^{11a}$ is selected from H and $R^{11}$;

provided that:

when G is G-6, G-16 or G-42, and each $R^{3a}$ is other than H, then $R^{11a}$ is H;

when G is G-25 or G-31, then at least one $R^{3a}$ is H; and when G is one of G-31 through G-35, then $Z^1$ is a direct bond or $CHR^{20}$.

Embodiment 43. A compound of Embodiment 42 wherein G is selected from G-1 through G-3, G-7, G-8, G-10, G-11, G-14, G-15, G-23, G-24, G-26 through G-28, G-30, G-36 through G-38 and G-49 through G-55.

Embodiment 44. A compound of Embodiment 43 wherein G is selected from G-1, G-2, G-7, G-8, G-14, G-15, G-23, G-24, G-26, G-27, G-36, G-37, G-38, G-49, G-50 and G-55.

Embodiment 45. A compound of Embodiment 44 wherein G is selected from G-1, G-2, G-15. G-26, G-27, G-36, G-37 and G-38.

Embodiment 46. A compound of Embodiment 45 wherein G is selected from G-1, G-2, G-15, G-26 and G-36.

Embodiment 47. A compound of Embodiment 46 wherein G is G-1. Of note are embodiments of these compounds within Embodiments 1 through 40, Embodiments 52 through 83, and Embodiments A1 through A5.

Embodiment 48. A compound of Embodiment 46 wherein G is G-2. Of note are embodiments of these compounds within Embodiments 1 through 40, Embodiments 52 through 83, and Embodiments A1 through A5.

Embodiment 49. A compound of Embodiment 46 wherein G is G-15. Of note are embodiments of these compounds within Embodiments 1 through 40, Embodiments 52 through 83, and Embodiments A1 through A5.

Embodiment 50. A compound of Embodiment 46 wherein G is G-26. Of note are embodiments of these compounds within Embodiments 1 through 40, Embodiments 52 through 83, and Embodiments A1 through A5.

Embodiment 51. A compound of Embodiment 46 wherein G is G-36. Of note are embodiments of these compounds within Embodiments 1 through 40, Embodiments 52 through 83, and Embodiments A1 through A5.

Embodiment 52. A compound of any one of Embodiments 41 through 51 wherein $R^{3a}$ is H, $C_1$-$C_3$ alkyl or halogen.

Embodiment 53. A compound of Embodiment 52 wherein $R^{3a}$ is H or methyl.
Embodiment 54. A compound of any one of Embodiments 41 through 51 wherein $R^{3a}$ is H and $R^{11a}$ is H or methyl.
Embodiment 55. A compound of any one of Formula 1 and Embodiments 41 through 51 wherein G is unsubstituted.
Embodiment 56. A compound of Formula 1 wherein J is one of J-1 through J-82 depicted in Exhibit 3;
Exhibit 3
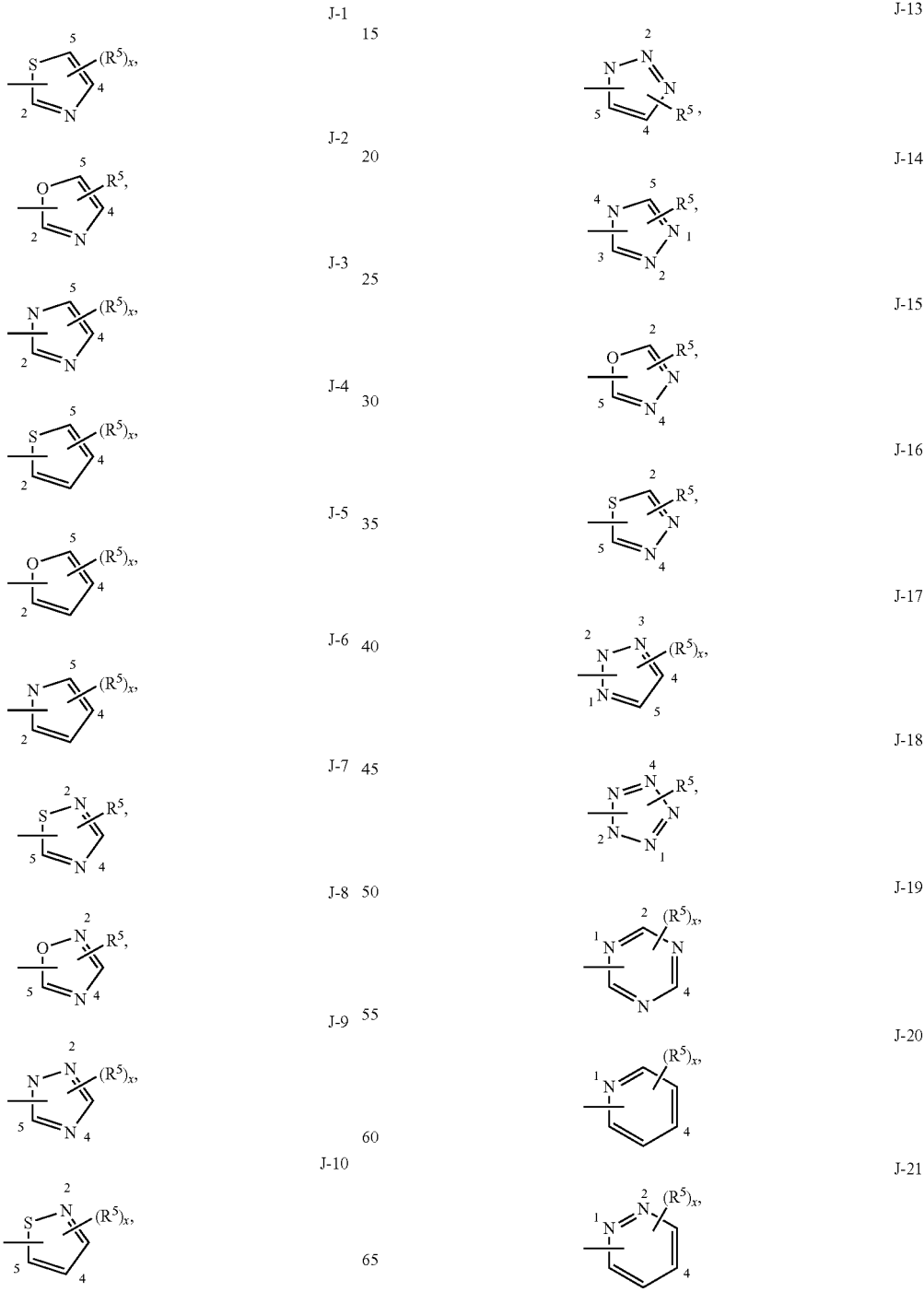

-continued
J-22
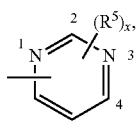
J-23
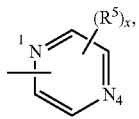
J-24
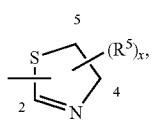
J-25
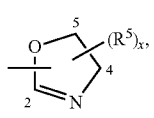
J-26
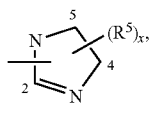
J-27
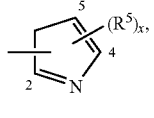
J-28
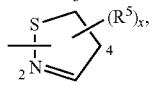
J-29
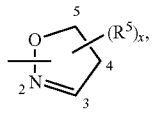
J-30
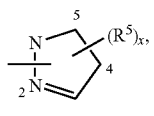
J-31
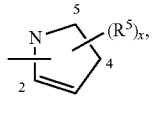
J-32
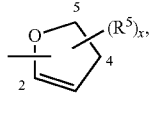
J-33
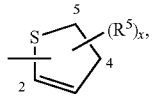
-continued
J-34
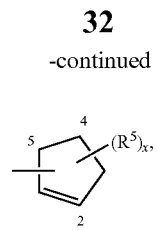
J-35
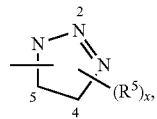
J-36
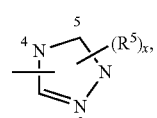
J-37
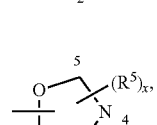
J-38
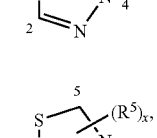
J-39
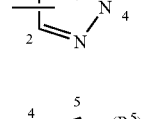
J-40
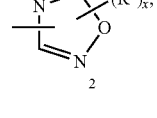
J-41
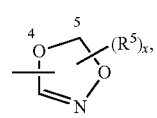
J-42
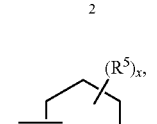
J-43
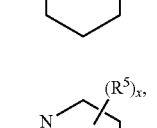
J-44
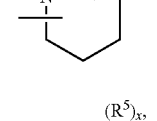

J-45 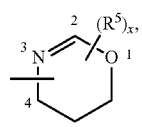
J-46 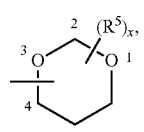
J-47 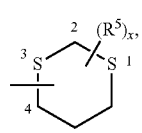
J-48 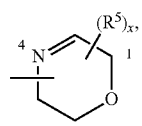
J-49 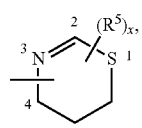
J-50 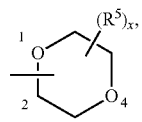
J-51 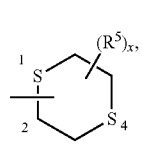
J-52 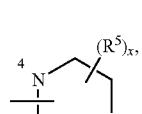
J-53 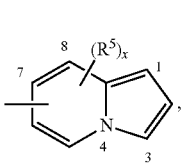
J-54 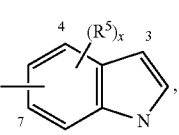
J-55 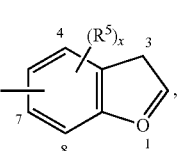
J-56 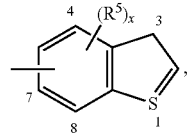
J-57 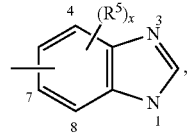
J-58 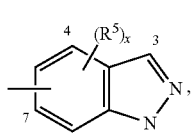
J-59 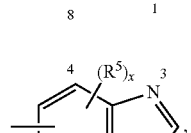
J-60 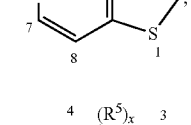
J-61 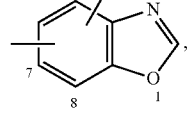
J-62 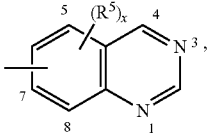
J-63 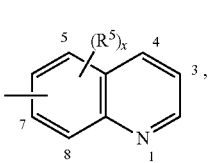
J-64 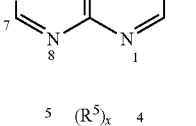
J-65 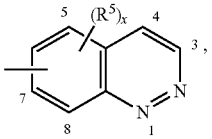

-continued
J-66 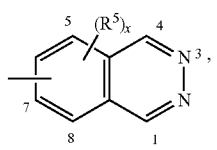
J-67 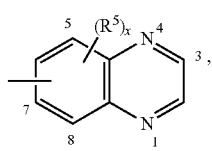
J-68 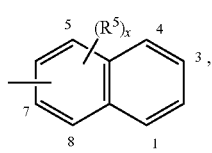
J-69 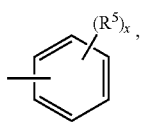
J-70 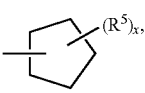
J-71 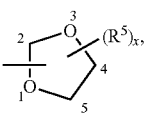
J-72 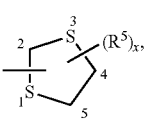
J-73 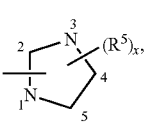
J-74 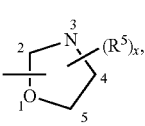
J-75 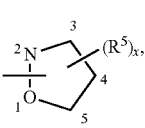
J-76 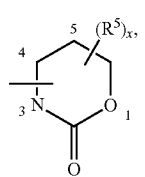
-continued
J-77 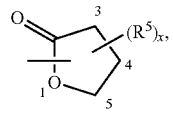
J-78 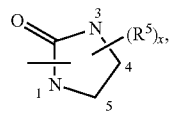
J-79 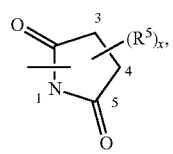
J-80 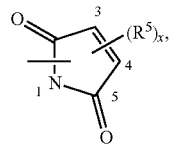
J-81 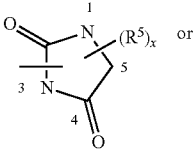 or
J-82 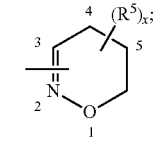
wherein the bond shown projecting to the left is bonded to $Z^1$; and x is an integer from 0 to 5.
Embodiment 56a. A compound of Embodiment 56 wherein J is one of J-29-1 through J-29-58 depicted in Exhibit A:
Exhibit A
J-29-1 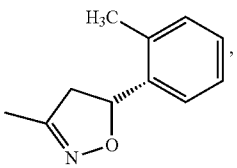
J-29-2 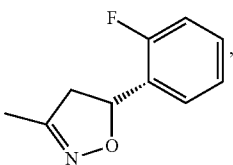

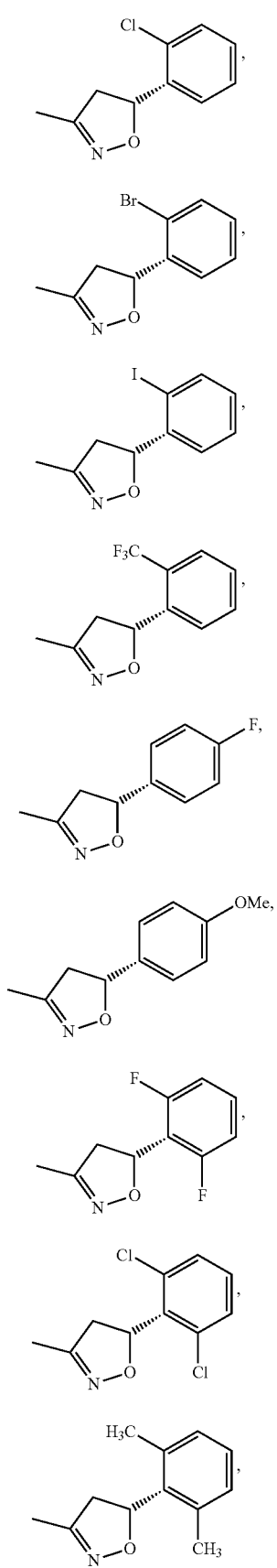
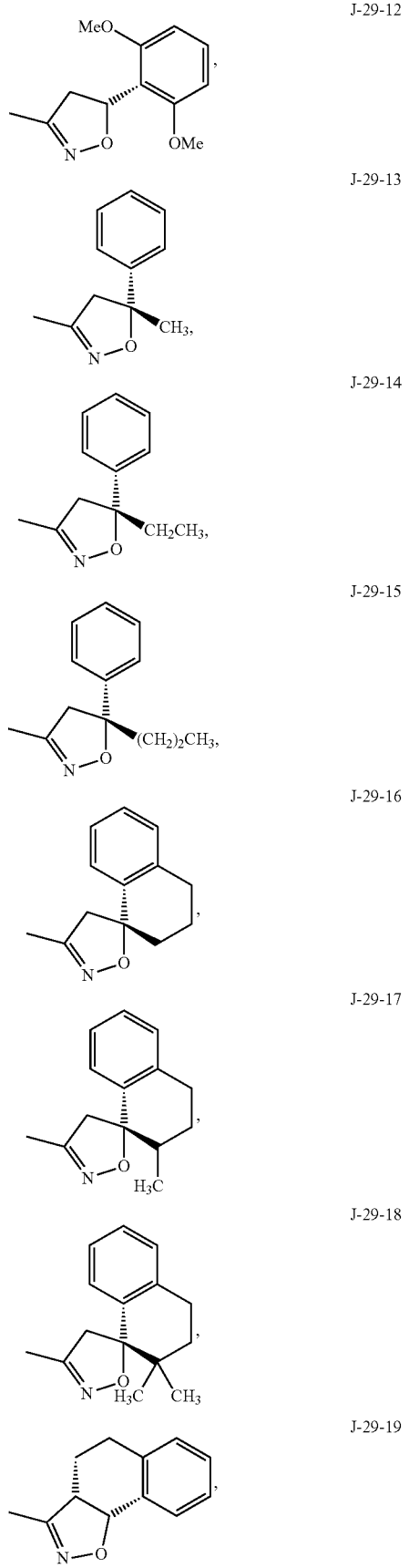

-continued
J-29-20 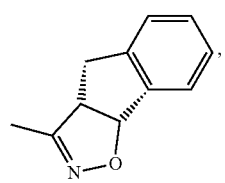
J-29-21 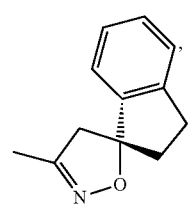
J-29-22 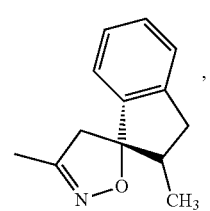
J-29-23 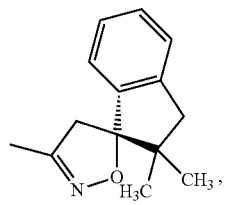
J-29-24 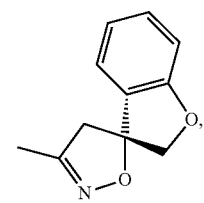
J-29-25 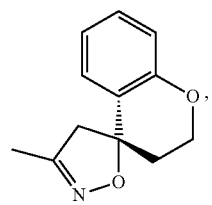
J-29-26 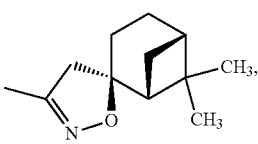
J-29-27 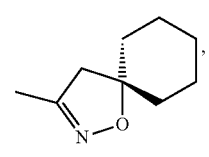
-continued
J-29-28 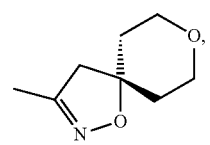
J-29-29 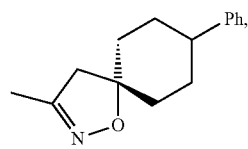
J-29-30 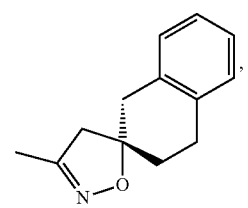
J-29-31 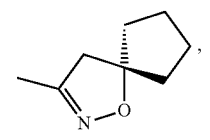
J-29-32 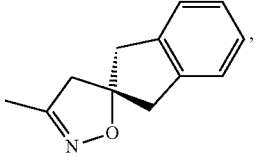
J-29-33 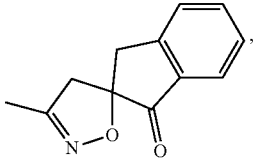
J-29-34 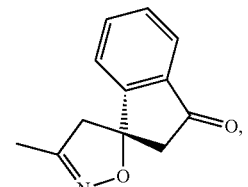
J-29-35 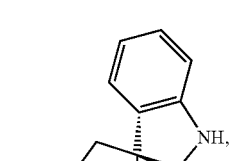
J-29-36 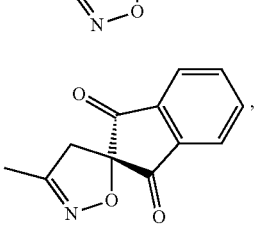

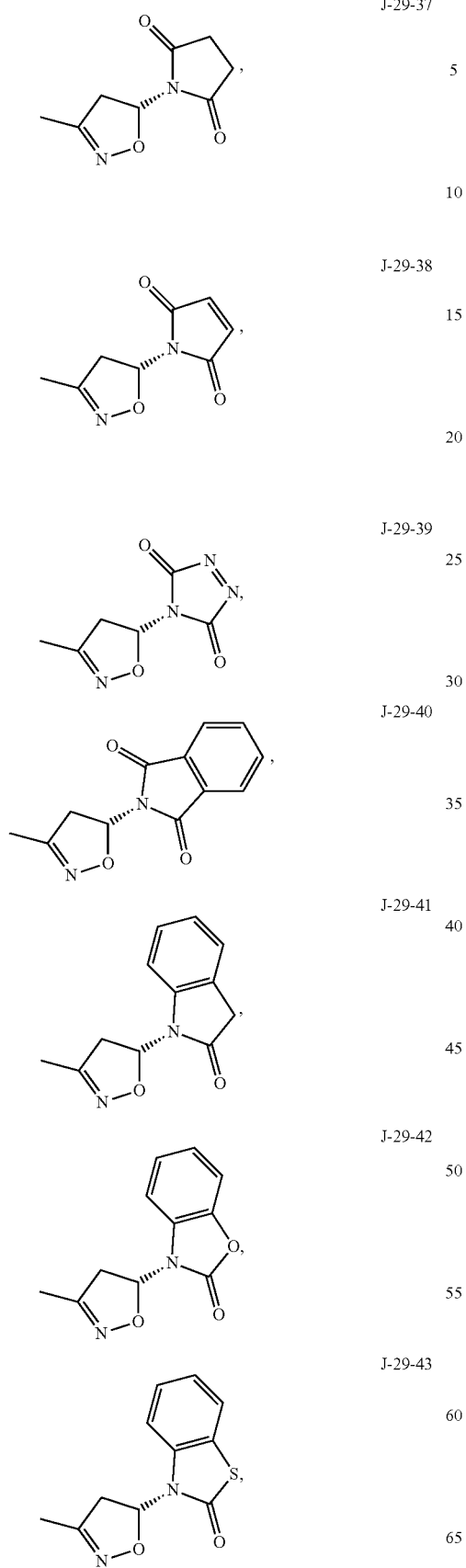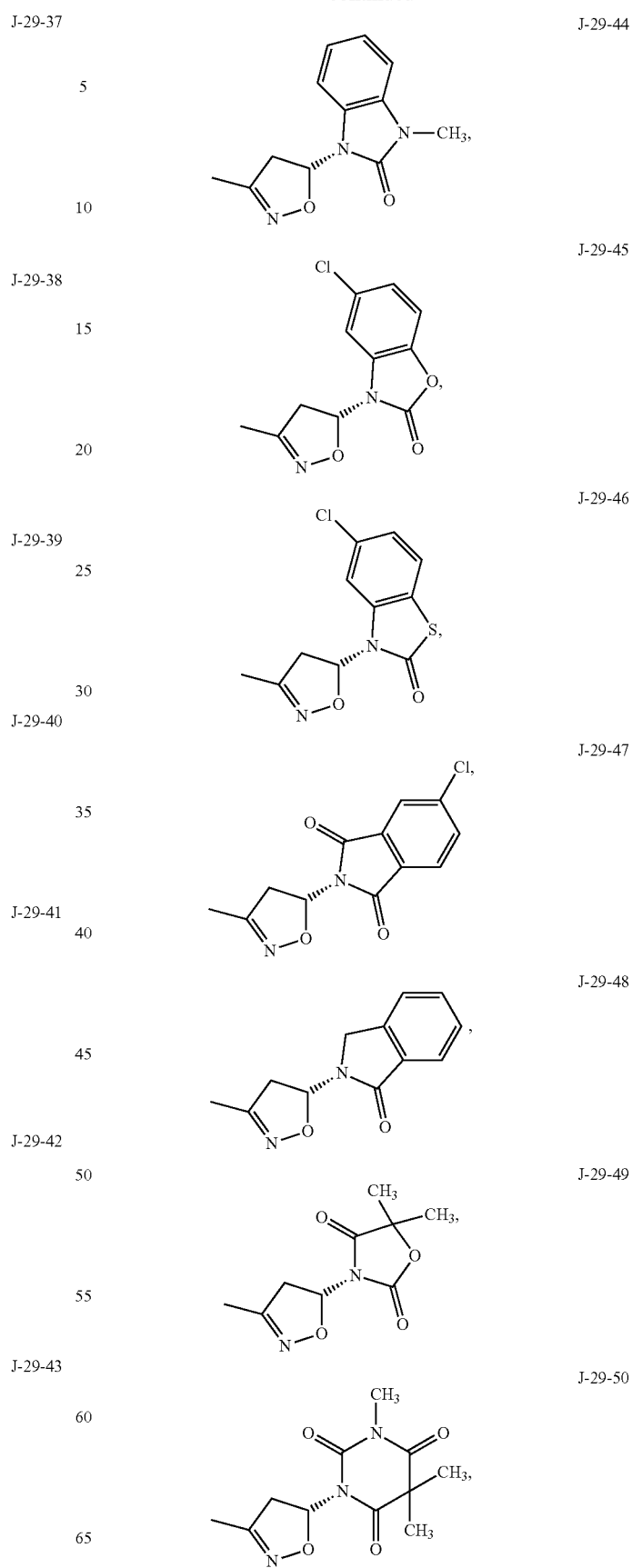

-continued

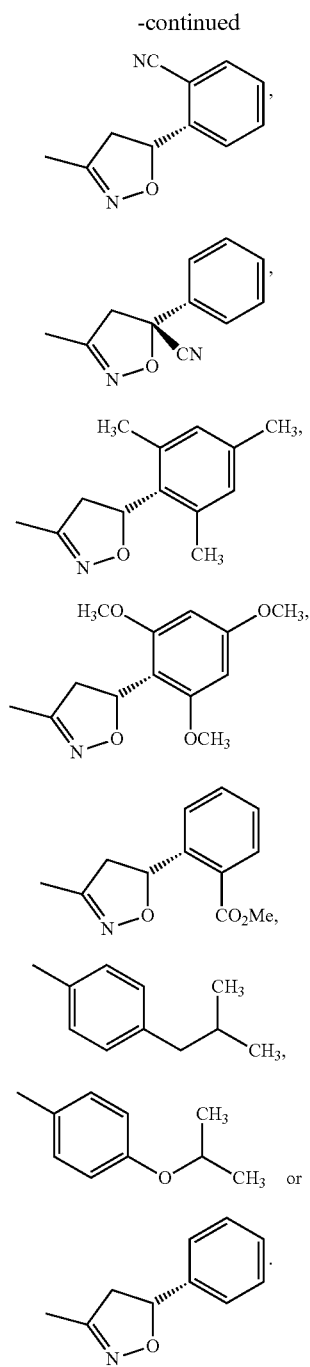

J-29-51

J-29-52

J-29-53

J-29-54

J-29-55

J-29-56

J-29-57

J-29-58

Embodiment 57. A compound of embodiment 56 wherein J is selected from J-1, J-2, J-3, J-4, J-5, J-7, J-8, J-9, J-10, J-11, J-12, J-14, J-15, J-16, J-20, J-24, J-25, J-26, J-29, J-30, J-37, J-38, J-45 and J-69.

Embodiment 58. A compound of Embodiment 57 wherein J is selected from J-4, J-5, J-8, J-11, J-15, J-16, J-20, J-29, J-30, J-37, J-38, and J-69.

Embodiment 59. A compound of Embodiment 58 wherein J is selected from J-4, J-5, J-11, J-20, J-29, J-37, J-38, and J-69.

Embodiment 60. A compound of Embodiment 59 wherein J is J-11.

Embodiment 61. A compound of Embodiment 59 wherein J is J-29.

Embodiment 61a. A compound of Embodiment 61 wherein J is any one of J-29-1 to J-29-58 (depicted in Exhibit A).

Embodiment 62. A compound of Embodiment 59 wherein J is J-69.

Embodiment 63. A compound of Embodiment 60 wherein the 3-position of J-11 is connected to $Z^1$ and the 5-position of J-11 is connected to $R^5$ other than H.

Embodiment 63a. A compound of Embodiment 63 wherein the 3-position of J-11 is connected to $Z^1$ and the 5-position of J-11 is connected to $Z^2Q$.

Embodiment 64. A compound of Embodiment 61 wherein the 3-position of J-29 is connected to $Z^1$ and the 5-position of J-29 is connected to $R^5$ other than H.

Embodiment 64a. A compound of Embodiment 65 wherein the 3-position of J-29 is connected to $Z^1$ and the 5-position of J-29 is connected to $Z^2Q$.

Embodiment 65. A compound of Formula 1 or Embodiment 56 wherein each $R^5$ is independently H, cyano, $C_1$-$C_6$ alkyl, $C_2$-$C_6$ alkenyl, $C_2$-$C_6$ alkynyl. $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkoxycarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_3$-$C_{10}$ trialkylsilyl, —$NR^{25}R^{26}$ or $Z^2Q$.

Embodiment 66. A compound of Embodiment 65 wherein each $R^5$ is independently H, cyano, $C_1$-$C_6$ alkyl, $C_1$-$C_6$ haloalkyl, $C_3$-$C_8$ cycloalkyl, $C_3$-$C_8$ halocycloalkyl, $C_2$-$C_6$ alkoxyalkyl, $C_1$-$C_6$ alkoxy, $C_1$-$C_6$ haloalkoxy, $C_3$-$C_8$ cycloalkoxy, $C_2$-$C_6$ alkenyloxy, $C_2$-$C_6$ haloalkenyloxy, $C_2$-$C_6$ alkynyloxy, $C_2$-$C_6$ alkoxyalkoxy, $C_2$-$C_6$ alkylcarbonyloxy, $C_2$-$C_6$ haloalkylcarbonyloxy, $C_1$-$C_6$ alkylthio, $C_1$-$C_6$ haloalkylthio, $C_3$-$C_{10}$ trialkylsilyl, —$NR^{25}R^{26}$ or $Z^2Q$.

Embodiment 67. A compound of Embodiment 66 wherein each $R^5$ is independently H, cyano, $C_1$-$C_6$ alkyl, $C_1$-$C_6$ haloalkyl, $C_1$-$C_6$ alkoxy, $C_1$-$C_6$ haloalkoxy, —$NR^{25}R^{26}$ or $Z^2Q$.

Embodiment 68. A compound of Formula 1 or Embodiment 56 wherein one instance of $R^5$ is $Z^2Q$ and other instances of $R^5$ are independently selected from H, cyano, $C_1$-$C_4$ alkyl, $C_1$-$C_4$ haloalkyl, $C_2$-$C_4$ alkylcarbonyl and halogen.

Embodiment 69. A compound of Embodiment 68 wherein the other instances of $R^5$ are independently selected from H and $C_1$-$C_3$ alkyl.

Embodiment 70. A compound of Embodiment 56 wherein x is 1 or 2.

Embodiment 71. A compound of Embodiment 70 wherein x is 1.

Embodiment 72. A compound of Embodiment 71 wherein $R^5$ is $Z^2Q$.

Embodiment 73. A compound of Formula 1 wherein $Z^1$ is direct bond.

Embodiment 74. A compound of Formula 1 wherein $Z^2$ is direct bond.

Embodiment 75. A compound of Formula 1 wherein Q is one of Q-1 through Q-102 depicted in Exhibit 4;

Exhibit 4
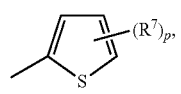 Q-1
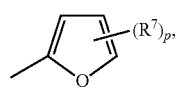 Q-2
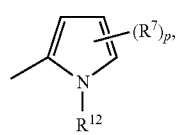 Q-3
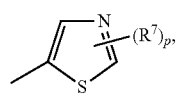 Q-4
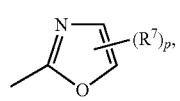 Q-5
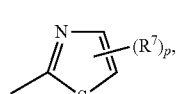 Q-6
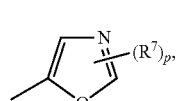 Q-7
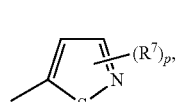 Q-8
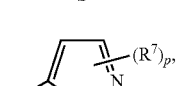 Q-9
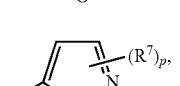 Q-10
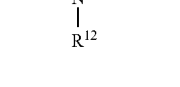 Q-11
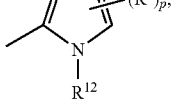 Q-12
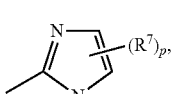 Q-13
-continued
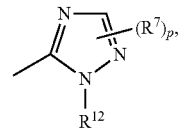 Q-14
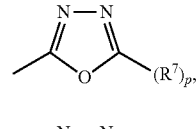 Q-15
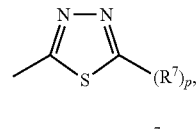 Q-16
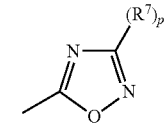 Q-17
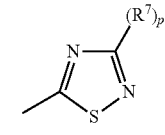 Q-18
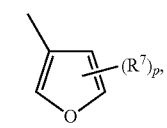 Q-19
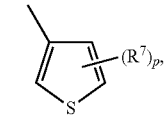 Q-20
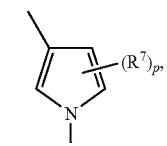 Q-21
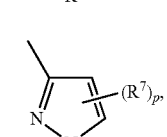 Q-22
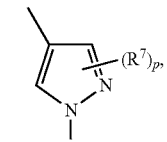 Q-23
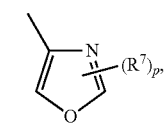 Q-24

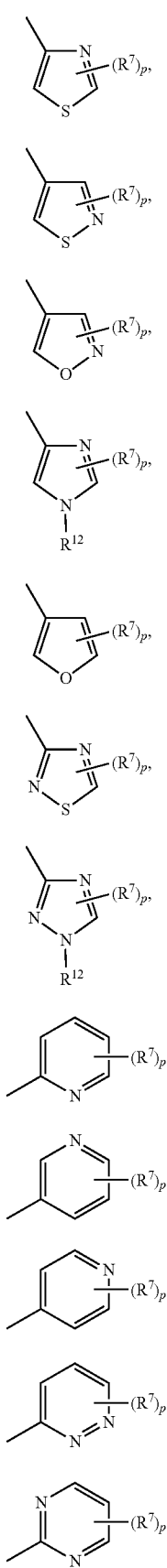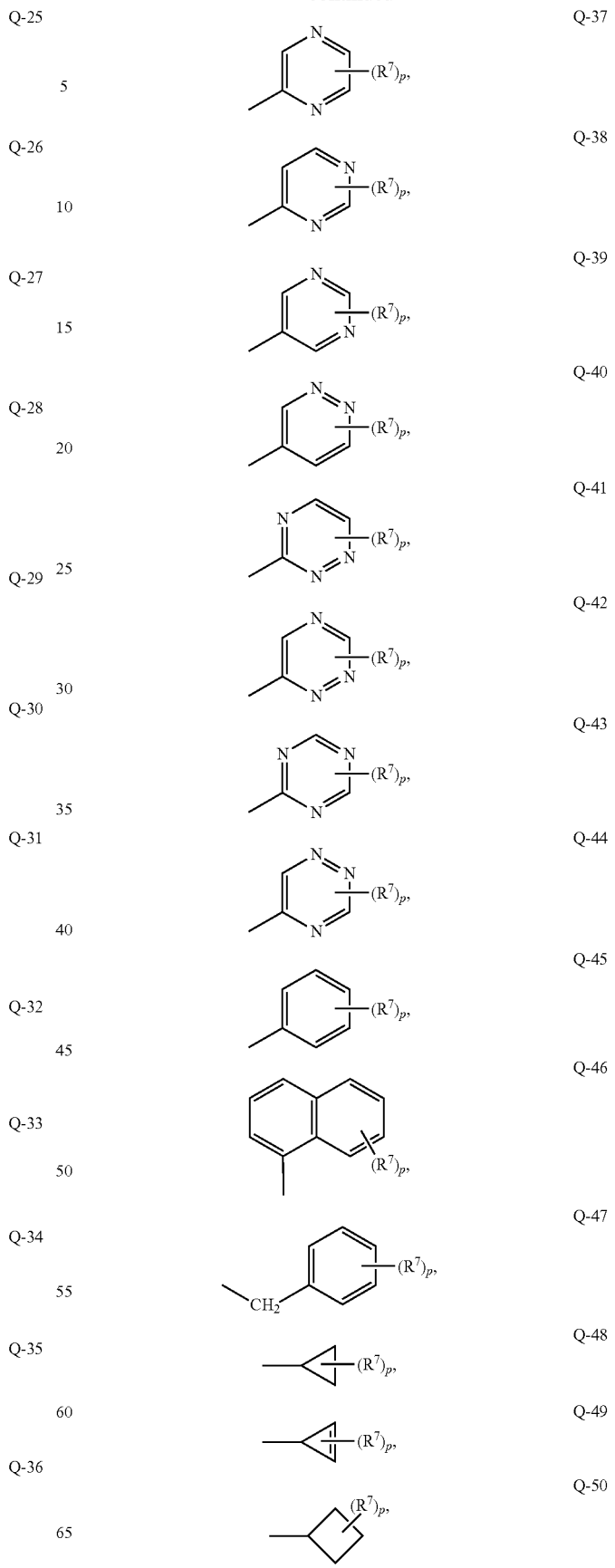

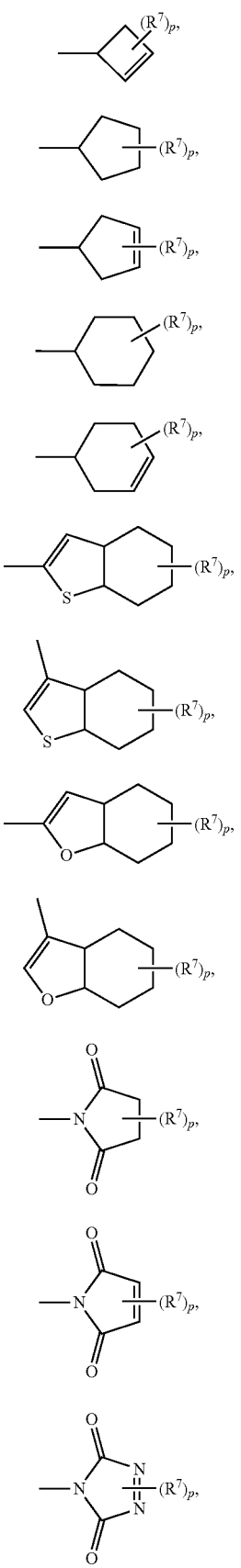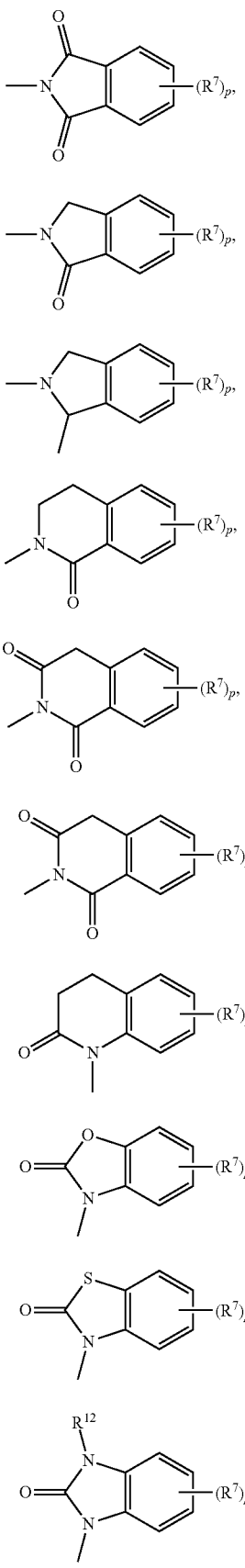

-continued

Q-73, Q-74, Q-75, Q-76, Q-77, Q-78, Q-79, Q-80, Q-81, Q-82, Q-83, Q-84, Q-85, Q-86, Q-87, Q-88, Q-89, Q-90, Q-91

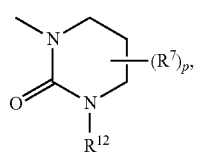 Q-92

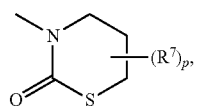 Q-93

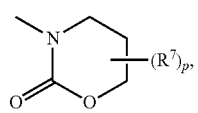 Q-94

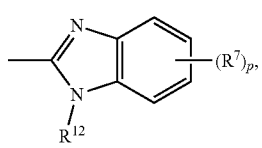 Q-95

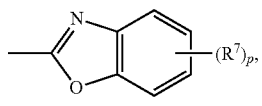 Q-96

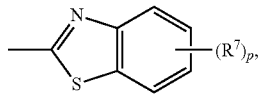 Q-97

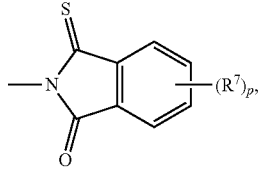 Q-98

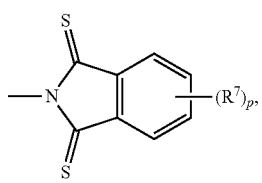 Q-99

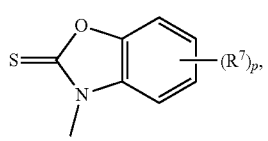 Q-100

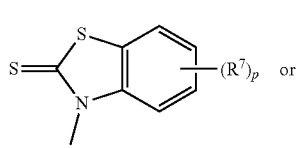 Q-101

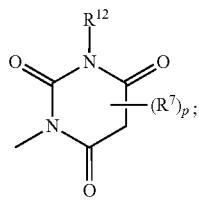 Q-102 wherein p is 0, 1, 2, 3, 4 or 5.

Embodiment 76. A compound of Embodiment 75 wherein Q is selected from Q-1, Q-20, Q-32 through Q-34, Q-45 through Q-47, Q-60 through Q-73, Q-76 through Q-79, Q-84 through Q-94 and Q-98 through Q-102.

Embodiment 77. A compound of Embodiment 76 wherein Q is Q-1, Q-45, Q-63, Q-64, Q-65, Q-68, Q-69, Q-70, Q-71, Q-72, Q-73, Q-76, Q-78, Q-79, Q-84, Q-85, Q-98. Q-99. Q-100. Q-101 or Q-102.

Embodiment 78. A compound of Embodiment 77 wherein Q is Q-45, Q-63, Q-64, Q-65, Q-68, Q-69, Q-70, Q-71, Q-72 or Q-85.

Embodiment 78a. A compound of Embodiment 78 wherein Q is Q-45, Q-63, Q-65, Q-70, Q-71, Q-72 or Q-85.

Embodiment 78b. A compound of Embodiment 78 wherein Q is Q-45, Q-63, Q-65 or Q-70.

Embodiment 79. A compound of Formula 1 or Embodiment 75 wherein each $R^7$ is independently $C_1$-$C_3$ alkyl, $C_1$-$C_3$ haloalkyl, halogen, hydroxy, amino, cyano, nitro, $C_1$-$C_2$ alkoxy or $C_1$-$C_2$ haloalkoxy.

Embodiment 80. A compound of Embodiment 79 wherein each $R^7$ is independently $C_1$-$C_3$ alkyl, halogen, hydroxy, cyano or $C_1$-$C_2$ alkoxy.

Embodiment 81. A compound of Embodiment 80 wherein each $R^7$ is independently methyl, F, Cl, Br, hydroxy, cyano or methoxy.

Embodiment 82. A compound of Formula 1 wherein when $R^5$ and $R^7$ are taken together with the atoms linking $R^5$ and $R^7$ to form an optionally substituted 5- to 7-membered ring, the ring members are selected from carbon and optionally 1 to 3 heteroatoms selected from up to 1 O, up to 1 S and up to 1 N and optionally include 1 to 3 ring members selected from the group consisting of C(=O), C(=S), S(O), S(O)$_2$ and SiR$^{17}$R$^{18}$.

Embodiment 82a. A compound of Embodiment 82 wherein when $R^5$ and $R^7$ are taken together with the atoms linking $R^5$ and $R^7$ to form an optionally substituted 5- to 7-membered ring, then $R^5$ and $R^7$ are taken together with the atoms linking $R^5$ and $R^7$ to form a 5- to 7-membered ring containing as ring members carbon atoms and optionally 1 to 3 heteroatoms selected from up to 1 O, up to 1 S and up to 1 N, and optionally including 1 to 3 ring members selected from the group consisting of C(=O), C(=S), S(O), S(O)$_2$ and SiR$^{17}$R$^{18}$, optionally substituted with up to 2 substituents selected from $R^8$; and each $R^8$ is independently $C_1$-$C_3$ alkyl.

Embodiment 82b. A compound of Formula 1 wherein when $R^5$ and $R^7$ are taken together with the atoms linking $R^5$ and $R^7$ to form an optionally substituted 5- to 7-membered ring, then $R^5$ and $R^7$ are taken together with the atoms linking $R^5$ and $R^7$ to form a 5- to 7-membered ring containing ring members selected from carbon and optionally 1 to 3 heteroatoms selected from up to 1 O, up to 1 S and up to 1 N, and optionally including 1 to 3 ring members selected from the group consisting of C(=O), C(=S), S(O), S(O)$_2$ and SiR$^{17}$R$^{18}$, the ring optionally substituted on ring members other than the atoms linking R$^5$ and R$^7$ with substituents selected from R$^8$; and each R$^8$ is independently C$_1$-C$_6$ alkyl, C$_2$-C$_6$ alkenyl, C$_2$-C$_6$ alkynyl, C$_3$-C$_6$ cycloalkyl, C$_4$-C$_{10}$ cycloalkylalkyl, C$_4$-C$_{10}$ alkylcycloalkyl, C$_5$-C$_{10}$ alkylcycloalkylalkyl, C$_1$-C$_6$ haloalkyl, C$_2$-C$_6$ haloalkenyl, C$_2$-C$_6$ haloalkynyl, C$_3$-C$_6$ halocycloalkyl, halogen, hydroxy, amino, cyano, nitro, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ haloalkylthio, C$_1$-C$_4$ haloalkylsulfinyl, C$_1$-C$_4$ haloalkylsulfonyl, C$_1$-C$_4$ alkylamino, C$_2$-C$_8$ dialkylamino, C$_3$-C$_6$ cycloalkylamino, C$_2$-C$_4$ alkoxyalkyl, C$_1$-C$_4$ hydroxyalkyl, C$_2$-C$_4$ alkylcarbonyl, C$_1$-C$_6$ alkoxycarbonyl, C$_2$-C$_6$ alkylcarbonyloxy, C$_2$-C$_6$ alkylcarbonylthio, C$_2$-C$_6$ alkylaminocarbonyl, C$_3$-C$_8$ dialkylaminocarbonyl or C$_3$-C$_6$ trialkylsilyl.

Embodiment 82c. A compound of Formula 1 wherein when R$^5$ and R$^7$ are taken together with the atoms linking R$^5$ and R$^7$ to form an optionally substituted 5- to 7-membered ring, then R$^5$ and R$^7$ are taken together with the atoms linking R$^5$ and R$^7$ to form a 5- to 7-membered ring containing as ring members 2 to 7 carbon atoms and optionally 1 to 3 heteroatoms selected from up to 1 O, up to 1 S and up to 1 N and optionally including 1 ring member selected from SiR$^{17}$R$^{18}$, the ring optionally substituted on ring members other than the atoms linking R$^5$ and R$^7$ with substituents selected from R$^8$; and each R$^8$ is independently C$_1$-C$_6$ alkyl, C$_1$-C$_6$ alkenyl, C$_2$-C$_6$ alkynyl, C$_3$-C$_6$ cycloalkyl, C$_4$-C$_{10}$ cycloalkylalkyl, C$_4$-C$_{10}$ alkylcycloalkyl, C$_5$-C$_{10}$ alkylcycloalkylalkyl, C$_1$-C$_6$ haloalkyl, C$_2$-C$_6$ haloalkenyl, C$_2$-C$_6$ haloalkynyl, C$_3$-C$_6$ halocycloalkyl, halogen, hydroxy, amino, cyano, nitro, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ haloalkylthio, C$_1$-C$_4$ haloalkylsulfinyl, C$_1$-C$_4$ haloalkylsulfonyl, C$_1$-C$_4$ alkylamino, C$_2$-C$_8$ dialkylamino, C$_3$-C$_6$ cycloalkylamino, C$_2$-C$_4$ alkoxyalkyl, C$_1$-C$_4$ hydroxyalkyl, C$_2$-C$_4$ alkylcarbonyl, C$_2$-C$_6$ alkoxycarbonyl, C$_2$-C$_6$ alkylcarbonyloxy, C$_2$-C$_6$ alkylcarbonylthio, C$_2$-C$_6$ alkylaminocarbonyl, C$_3$-C$_8$ dialkylaminocarbonyl or C$_3$-C$_6$ trialkylsilyl.

Embodiment 82d. A compound of Embodiment 82b or 82c wherein the ring is optionally substituted on ring members other than the atoms linking R$^5$ and R$^7$ with up to 4 substituents selected from R$^8$.

Embodiment 82e. A compound of Embodiment 82d wherein the ring is optionally substituted on ring members other than the atoms linking R$^5$ and R$^7$ with up to 2 substituents selected from R$^8$.

Embodiment 82f. A compound of Embodiment 82b or 82c wherein each R$^8$ is independently C$_1$-C$_3$ alkyl.

Embodiment 82g. A compound of Embodiment 82b wherein when R$^5$ and R$^7$ are taken together with the atoms linking R$^5$ and R$^7$ to form an optionally substituted 5- to 7-membered ring, then R$^5$ and R$^7$ are taken together with the atoms linking R$^5$ and R$^7$ to form a 5- to 7-membered ring containing ring members selected from carbon and optionally 1 to 3 heteroatoms selected from up to 1 O, up to 1 S and up to 1 N, and optionally including 1 to 3 ring members selected from the group consisting of C(=O), C(=S), S(O), S(O)$_2$ and SiR$^{17}$R$^{18}$, optionally substituted with up to 2 substituents selected from R$^8$; and each R$^8$ is C$_1$-C$_3$ alkyl.

Embodiment 82h. A compound of Embodiment 82c wherein when R$^5$ and R$^7$ are taken together with the atoms linking R$^5$ and R$^7$ to form an optionally substituted 5- to 7-membered ring, then R$^5$ and R$^7$ are taken together with the atoms linking R$^5$ and R$^7$ to form a 5- to 7-membered ring containing as ring members 2 to 7 carbon atoms and optionally 1 to 3 heteroatoms selected from up to 1 O up to 1 S and up to 1 N, optionally substituted with up to 2 substituents selected from R$^8$; and each R$^8$ is C$_1$-C$_3$ alkyl.

Embodiment 83. A compound of Formula 1 or Embodiment 75 wherein p is 0, 1, 2 or 3.

Embodiment 84. A compound of Formula 1 wherein R$^1$ is an optionally substituted phenyl or 5- or 6-membered heteroaromatic ring.

Embodiment 85. A compound of Formula 1 wherein A is CH$_2$ or NH.

Embodiment 86. A compound of Formula 1 wherein X is selected from X$^1$, X$^2$, X$^3$, X$^4$. X$^5$, X$^6$, X$^7$ and X$^8$.

Embodiment 87. A compound of Formula 1 wherein J is a 5- or 6-membered ring, a 8- to 11-membered bicyclic ring system or a 7- to 11-membered spirocyclic ring system, each ring or ring system containing ring members selected from carbon and optionally 1 to 3 heteroatoms selected from up to 1 O, up to 1 S and up to 3 N, and optionally including 1 to 3 ring members selected from the group consisting of C(=O), C(=S), S(O) and S(O)$_2$, each ring or ring system optionally substituted with 1 to 5 substituents independently selected from R$^5$.

Embodiment 88. A compound of Formula 1 wherein J is a phenyl or 5- or 6-membered heteroaromatic ring, or a naphthalenyl or 8- to 11-membered heteroaromatic bicyclic ring system, each ring or ring system optionally substituted with 1 to 5 substituents independently selected from R$^5$; or J is a 5-, 6- or 7-membered nonaromatic ring, an 8- to 11-membered nonaromatic bicyclic or a 7- to 11-membered spirocyclic ring system, each ring or ring system optionally including 1 to 3 ring members selected from the group consisting of C(=O), C(=S), S(O), S(O)$_2$ and SiR$^{17}$R$^{18}$, and optionally substituted with 1 to 5 substituents independently selected from R$^5$.

Embodiment 89. A compound of Formula 1 wherein each R$^5$ is independently H, C$_1$-C$_6$ alkyl, C$_1$-C$_6$ alkenyl, C$_2$-C$_6$ alkynyl, C$_3$-C$_6$ cycloalkyl, C$_4$-C$_{10}$ cycloalkylalkyl, C$_4$-C$_{10}$ alkylcycloalkyl, C$_5$-C$_{10}$ alkylcycloalkylalkyl, C$_1$-C$_6$ haloalkyl, C$_2$-C$_6$ haloalkenyl, C$_2$-C$_6$ haloalkynyl, C$_3$-C$_6$ halocycloalkyl, halogen, hydroxy, amino, cyano, nitro, C$_1$-C$_6$ alkoxy, C$_1$-C$_6$ haloalkoxy, C$_1$-C$_6$ alkylthio, C$_1$-C$_6$ alkylsulfinyl, C$_1$-C$_6$ alkylsulfonyl, C$_1$-C$_6$ haloalkylthio, C$_1$-C$_6$ haloalkylsulfinyl, C$_1$-C$_6$ haloalkylsulfonyl, C$_2$-C$_6$ alkoxyalkyl, C$_2$-C$_6$ haloalkoxyalkyl, C$_1$-C$_6$ hydroxyalkyl, C$_2$-C$_6$ alkylcarbonyl, C$_2$-C$_6$ alkoxycarbonyl, C$_2$-C$_6$ alkylcarbonyloxy, C$_2$-C$_6$ alkylaminocarbonyl, C$_3$-C$_8$ dialkylaminocarbonyl, C$_3$-C$_6$ trialkylsilyl or —Z$^2$Q; each R$^7$ is independently C$_1$-C$_6$ alkyl, C$_2$-C$_6$ alkenyl, C$_2$-C$_6$ alkynyl, C$_3$-C$_6$ cycloalkyl, C$_4$-C$_{10}$ cycloalkylalkyl, C$_4$-C$_{10}$ alkylcycloalkyl, C$_5$-C$_{10}$ alkylcycloalkylalkyl, C$_1$-C$_6$ haloalkyl, C$_2$-C$_6$ haloalkenyl, C$_2$-C$_6$ haloalkynyl, C$_3$-C$_6$ halocycloalkyl, halogen, hydroxy, amino, cyano, nitro, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ haloalkylthio, C$_1$-C$_4$ haloalkylsulfonyl, C$_1$-C$_4$ alkylamino, C$_2$-C$_8$ dialkylamino, C$_3$-C$_6$ cycloalkylamino, C$_2$-C$_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; or $R^5$ and $R^7$ are taken together with the atoms linking $R^5$ and $R^7$ to form an optionally substituted 5- to 7-membered ring containing as ring members 2 to 7 carbon atoms and optionally 1 to 3 heteroatoms selected from up to 1 O, up to 1 S and up to 1 N.

Embodiment 90. A compound of Formula 1 wherein each Q is independently an optionally substituted phenyl, benzyl, naphthalenyl, $C_3$-$C_6$ cycloalkyl, $C_3$-$C_6$ cycloalkenyl or 5- or 6-membered heteroaromatic ring, each optionally substituted with 1 to 3 substituents selected from $R^7$ on carbon ring members and $R^{12}$ on nitrogen ring members.

Embodiment 90a. A compound of Formula 1 wherein each Q is independently a 3- to 7-membered nonaromatic carbocyclic ring, a 5-, 6- or 7-membered nonaromatic heterocyclic ring or an 8- to 11-membered nonaromatic bicyclic ring system, each optionally including ring members selected from the group consisting of C(=O), C(=S), S(O), S(O)$_2$ and SiR$^{17}$R$^{18}$, and optionally substituted with 1 to 5 substituents independently selected from $R^7$ on carbon atom ring members and $R^{12}$ on nitrogen atom ring members;

Embodiment 91. A compound of Formula 1 wherein each $Z^1$ and $Z^2$ is independently a direct bond, O, C(=O), S(O)$_m$, CHR$^{20}$ or NR$^{21}$;

Embodiment 92. A compound of Formula 1 wherein $R^{21}$ is H, $C_1$-$C_3$ alkyl, $C_2$-$C_3$ alkylcarbonyl or $C_2$-$C_3$ alkoxycarbonyl.

Embodiment 93. A compound of Formula 1 wherein when G is an optionally substituted thiazole ring connected at its 2-position to X and at its 4-position to $Z^1$ in Formula 1, A is CHR$^{15}$, and J is an optionally substituted isoxazole ring connected at its 4-position to $Z^1$, then $Z^1$ is O, C(=O), S(O)$_m$, CHR$^{20}$ or NR$^{21}$.

Embodiment 94. A compound of Formula 1 wherein when G is an optionally substituted thiazole ring connected at its 2-position to X and at its 4-position to $Z^1$ in Formula 1, and J is an optionally substituted isoxazole ring connected at its 4-position to $Z^1$, then $Z^1$ is O, C(=O), S(O)$_m$, CHR$^{20}$ or NR$^{21}$.

Embodiment 95. A compound of Formula 1 wherein when G is an optionally substituted thiazole ring connected at its 2-position to X and at its 4-position to $Z^1$ in Formula 1. A is CHR$^{15}$, $Z^1$ is a direct bond, and J is an optionally substituted isoxazole ring, then J is connected to the remainder of the Formula 1 at the 3- or 5-position of the isoxazole ring.

Embodiment 96. A compound of Formula 1 wherein when G is an optionally substituted thiazole ring connected at its 2-position to X and at its 4-position to $Z^1$ in Formula 1, A is CHR$^{15}$, $Z^1$ is a direct bond, and J is an optionally substituted isoxazole ring, then J is connected to the remainder of the Formula 1 at the 3-position of the isoxazole ring.

Embodiment 97. A compound of Formula 1 wherein when G is an optionally substituted thiazole ring connected at its 2-position to X and at its 4-position to $Z^1$ in Formula 1, $Z^1$ is a direct bond, and J is an optionally substituted isoxazole ring, then J is connected to the remainder of the Formula 1 at the 3-position of the isoxazole ring.

Embodiment 98. A compound of Formula 1 wherein when X is $X^2$ and the ring containing X is saturated, A is CHR$^{15}$, G is an optionally substituted 5-membered heteroaromatic ring, $Z^1$ is a direct bond, and J is a phenyl or 5- or 6-membered heteroaromatic ring or a naphthalenyl or 8- to 11-membered heteroaromatic bicyclic ring system, then the J ring or ring system is substituted with at least one $R^5$ that is other than H.

Embodiment 99. A compound of Formula 1 wherein when X is $X^2$ and the ring containing X is saturated, A is CHR$^{15}$, G is an optionally substituted 5-membered heteroaromatic ring, $Z^1$ is a direct bond, and J is a phenyl or 5- or 6-membered heteroaromatic ring or a naphthalenyl or 8- to 11-membered heteroaromatic bicyclic ring system, then the J ring or ring system is substituted with at least one $R^5$ that is $Z^2$Q.

Embodiment 100. A compound of Formula 1 wherein when X is $X^1$ and the ring containing X is saturated, A is NH, G is an optionally substituted thiazole ring connected at its 2-position to X and at its 4-position to $Z^1$ in Formula 1, and J is an optionally substituted imidazole ring connected at its 2-position to the remainder of Formula 1, then $Z^1$ is O, C(=O), S(O)$_m$, CHR$^{20}$ or NR$^{21}$.

Embodiment 101. A compound of Formula 1 wherein when X is $X^1$ and the ring containing X is saturated, A is NR$^{16}$, G is an optionally substituted thiazole ring connected at its 2-position to X and at its 4-position to $Z^1$ in Formula 1, and J is an optionally substituted imidazole ring connected at its 2-position to the remainder of Formula 1, then $Z^1$ is O, C(=O), S(O)$_m$, CHR$^{20}$ or NR$^{21}$.

Embodiment 102. A compound of Formula 1 wherein when G is an optionally substituted thiazole ring connected at its 2-position to X and at its 4-position to $Z^1$ in Formula 1, then J is other than optionally substituted imidazolyl.

Embodiment 103. A compound of Formula 1 wherein each $Z^4$ is independently C(=O) or S(O)$_2$.

Embodiment 104. A compound of Embodiment 103 wherein each $Z^4$ is C(=O).

Embodiment 105. A compound of Formula 1 wherein each $R^2$ is independently $C_1$-$C_4$ alkyl, $C_1$-$C_4$ alkenyl, $C_2$-$C_4$ haloalkyl, $C_1$-$C_4$ alkoxy, halogen, cyano or hydroxy; or
two $R^2$ are taken together as $C_1$-$C_3$ alkylene or $C_2$-$C_3$ alkenylene to form a bridged bicyclic ring system; or
two $R^2$ attached to adjacent ring carbon atoms joined by a double bond are taken together as —CH=CH—CH=CH— optionally substituted with 1 to 3 substituents selected from $C_1$-$C_4$ alkyl, $C_1$-$C_4$ haloalkyl, $C_1$-$C_4$ alkoxy, $C_1$-$C_4$ haloalkoxy, halogen, hydroxy, amino, cyano and nitro.

Combinations of Embodiments 1-105 are illustrated by:

Embodiment A1. A compound of Formula 1 wherein
G is a 5-membered heteroaromatic ring or 5-membered saturated or partially saturated heterocyclic ring, each ring optionally substituted with up to 2 substituents selected from $R^3$ on carbon ring members and selected from $R^{11}$ on nitrogen ring members;
$R^1$ is a phenyl or 5- or 6-membered heteroaromatic ring optionally substituted with 1 to 2 substituents independently selected from $R^{4a}$ on carbon ring members and $R^{4b}$ on nitrogen ring members;
each $R^2$ is independently $C_1$-$C_2$ alkyl, $C_1$-$C_2$ haloalkyl, $C_1$-$C_2$ alkoxy, halogen, cyano or hydroxy;
each $R^3$ is independently $C_1$-$C_3$ alkyl, $C_1$-$C_3$ haloalkyl or halogen;
each $R^{4a}$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_1$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl;
each $R^{4b}$ is independently $C_1$-$C_6$ alkyl, $C_3$-$C_6$ alkenyl, $C_3$-$C_6$ alkynyl, $C_3$-$C_6$ cycloalkyl, $C_1$-$C_6$ haloalkyl, $C_3$-$C_6$ haloalkenyl, $C_3$-$C_6$ haloalkynyl, $C_3$-$C_6$ halocycloalkyl or $C_2$-$C_4$ alkoxyalkyl;
each $R^{11}$ is independently $C_1$-$C_3$ alkyl;
$R^{15}$ is H, halogen, cyano, hydroxy, —CHO, $C_1$-$C_4$ alkyl, $C_1$-$C_4$ haloalkyl or $C_2$-$C_5$ alkoxycarbonyl;
$R^{16}$ is H, $C_1$-$C_4$ alkyl, $C_1$-$C_4$ haloalkyl, $C_2$-$C_4$ alkylcarbonyl, $C_2$-$C_4$ haloalkylcarbonyl or $C_1$-$C_4$ alkoxycarbonyl;
when $R^5$ and $R^7$ are taken together with the atoms linking $R^5$ and $R^7$ to form an optionally substituted 5- to 7-membered ring, then $R^5$ and $R^7$ are taken together with the atoms linking $R^5$ and $R^7$ to form a 5- to 7-membered ring containing ring members selected from carbon and optionally 1 to 3 heteroatoms selected from up to 1 O, up to 1 S and up to 1 N, and optionally including 1 to 3 ring members selected from the group consisting of C(=O), C(=S), S(O), S(O)$_2$ and SiR$^{17}$R$^{18}$, the ring optionally substituted on ring members other than the atoms linking $R^5$ and $R^7$ with up to 4 substituents selected from $R^8$;
each $R^8$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio. $C_2$-$C_6$ alkylaminocarbonyl, $C_3$-$C_8$ dialkylaminocarbonyl or $C_3$-$C_6$ trialkylsilyl; and
each $Z^4$ is independently C(=O) or S(O)$_2$.

Embodiment A2. A compound of Embodiment A1 wherein
G is one of G-1 through G-59 (as depicted in Exhibit 2) wherein the bond projecting to the left is bonded to X, and bond projecting to the right is bonded to $Z^1$;
J is one of J-1 through J-82 (as depicted in Exhibit 3) wherein the bond shown projecting to the left is bonded to $Z^1$;
Q is one of Q-1 through Q-102 (as depicted in Exhibit 4);
$R^1$ is one of U-1 through U-50 (as depicted in Exhibit 1);
each $R^2$ is independently methyl, methoxy, cyano or hydroxy;
each $R^{3a}$ is independently selected from H and $R^3$;

each $R^5$ is independently H, cyano, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_1$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkoxycarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_3$-$C_{10}$ trialkylsilyl, —NR$^{25}$R$^{26}$ or $Z^2$Q;
$R^{11a}$ is selected from H and $R^{11}$;
$R^{15}$ is H, cyano, hydroxy, methyl or methoxycarbonyl;
$R^{16}$ is H, methyl, methylcarbonyl or methoxycarbonyl;
each $Z^4$ is C(=O);
k is 0, 1 or 2;
p is 0, 1, 2 or 3; and
x is an integer from 0 to 5;
provided that:
(a) when $R^4$ is attached to a carbon ring member, said $R^4$ is selected from $R^{4a}$;
(b) when $R^4$ is attached to a nitrogen ring member (e.g., in U-4, U-11 through U-15, U-24 through U-26, U-31 or U-35), said $R^4$ is selected from $R^{4b}$;
(c) when G is G-6, G-16 or G-42, and each $R^{3a}$ is other than H, then $R^{11a}$ is H;
(d) when G is G-25 or G-31, then at least one $R^{3a}$ is H; and
(e) when G is one of G-31 through G-35, then $Z^1$ is a direct bond or CHR$^{20}$.

Embodiment A3. A compound of Embodiment A2 wherein
G is selected from G-1, G-2, G-7, G-8, G-14, G-15, G-23, G-24, G-26, G-27, G-36, G-37, G-38, G-49, G-50 and G-55;
J is selected from J-1, J-2, J-3, J-4, J-5, J-7, J-8, J-9, J-10. J-11, J-12, J-14, J-15, J-16, J-20, J-24, J-25, J-26, J-29, J-30, J-37, J-38, J-45 and J-69;
each Q is independently Q-1, Q-20, Q-32 through Q-34, Q-45 through Q-47, Q-60 through Q-73, Q-76 through Q-79, Q-84 through Q-94 or Q-98 through Q-102;
A is CH$_2$ or NH;
W is O;
X is $X^1$, $X^2$ or $X^3$;
each $R^5$ is independently H, cyano, $C_1$-$C_6$ alkyl, $C_1$-$C_6$ haloalkyl, $C_3$-$C_8$ cycloalkyl, $C_3$-$C_8$ halocycloalkyl, $C_2$-$C_6$ alkoxyalkyl, $C_1$-$C_6$ alkoxy, $C_1$-$C_6$ haloalkoxy, $C_3$-$C_8$ cycloalkoxy, $C_2$-$C_6$ alkenyloxy, $C_2$-$C_6$ haloalkenyloxy, $C_2$-$C_6$ alkynyloxy, $C_2$-$C_6$ alkoxyalkoxy, $C_2$-$C_6$ alkylcarbonyloxy, $C_2$-$C_6$ haloalkylcarbonyloxy, $C_1$-$C_6$ alkylthio, $C_1$-$C_6$ haloalkylthio, $C_3$-$C_{10}$ trialkylsilyl, —NR$^{25}$R$^{26}$ or $Z^2$Q;
$Z^1$ is a direct bond;
each $Z^2$ is independently a direct bond or NR$^{21}$;
$R^1$ is selected from U-1 through U-3, U-11, U-13, U-20, U-22, U-23, U-36 through U-39 and U-50;
each $R^3$ is independently methyl or halogen;
each $R^{4a}$ is independently $C_1$-$C_2$ alkyl, $C_1$-$C_2$ haloalkyl, halogen, $C_1$-$C_2$ alkoxy or $C_1$-$C_2$ haloalkoxy;
each $R^{4b}$ is independently $C_1$-$C_2$ alkyl or $C_1$-$C_2$ haloalkyl;

each $R^7$ is independently halogen, cyano, $C_1$-$C_3$ alkyl, $C_1$-$C_3$ haloalkyl, hydroxy, $C_1$-$C_2$ alkoxy or $C_1$-$C_2$ haloalkoxy;

k is 1 or 2; and n is 0.

Of note are Embodiment A3 compounds wherein one $R^5$ is $Z^2Q$ and any other $R^5$ substituents are independently selected from H, $C_1$-$C_6$ alkyl, $C_1$-$C_6$ haloalkyl, $C_3$-$C_8$ cycloalkyl, $C_3$-$C_8$ halocycloalkyl, $C_2$-$C_6$ alkoxyalkyl, $C_1$-$C_6$ alkoxy, $C_1$-$C_6$ haloalkoxy, $C_3$-$C_8$ cycloalkoxy, $C_2$-$C_6$ alkenyloxy, $C_2$-$C_6$ haloalkenyloxy, $C_2$-$C_6$ alkynyloxy, $C_2$-$C_6$ alkoxyalkoxy, $C_2$-$C_6$ alkylcarbonyloxy, $C_2$-$C_6$ haloalkylcarbonyloxy, $C_1$-$C_6$ alkylthio, $C_1$-$C_6$ haloalkylthio, $C_3$-$C_{10}$ trialkylsilyl and —$NR^{25}R^{26}$. Also of note are Embodiment A3 compounds wherein all $R^5$ substituents are other than $Z^2Q$ (e.g., each $R^5$ is independently selected from H, $C_1$-$C_6$ alkyl, $C_1$-$C_6$ haloalkyl, $C_3$-$C_8$ cycloalkyl, $C_3$-$C_8$ halocycloalkyl, $C_2$-$C_6$ alkoxyalkyl, $C_1$-$C_6$ alkoxy, $C_1$-$C_6$ haloalkoxy, $C_3$-$C_8$ cycloalkoxy, $C_2$-$C_6$ alkenyloxy, $C_2$-$C_6$ haloalkenyloxy, $C_2$-$C_6$ alkynyloxy, $C_2$-$C_6$ alkoxyalkoxy, $C_2$-$C_6$ alkylcarbonyloxy, $C_2$-$C_6$ haloalkylcarbonyloxy, $C_1$-$C_6$ alkylthio, $C_1$-$C_6$ haloalkylthio, $C_3$-$C_{10}$ trialkylsilyl and —$NR^{25}R^{26}$).

Embodiment A4. A compound of Embodiment A3 wherein

A is $CH_2$;

G is selected from G-1, G-2, G-15, G-26, G-27, G-36, G-37 and G-38; and G is unsubstituted;

J is selected from J-4, J-5, J-8, J-11, J-15, J-16, J-20, J-29, J-30, J-37, J-38, and J-69;

Q is selected from Q-1, Q-45, Q-63, Q-64, Q-65, Q-68, Q-69, Q-70, Q-71, Q-72, Q-73, Q-76, Q-78, Q-79, Q-84, Q-85, Q-98, Q-99, Q-100, Q-101 and Q-102;

X is $X^1$ or $X^2$; and the ring comprising X is saturated;

$R^1$ is U-1 or U-50;

each $R^{4a}$ is independently $C_1$-$C_2$ alkyl, trifluoromethyl, Cl, Br, I or methoxy; and each $R^5$ is independently H, cyano, $C_1$-$C_6$ alkyl, $C_1$-$C_6$ haloalkyl, $C_1$-$C_6$ alkoxy, $C_1$-$C_6$ haloalkoxy, —$NR^{25}R^{26}$ or $Z^2Q$.

Embodiment A5. A compound of Embodiment A4 wherein

G is selected from G-1, G-2, G-15, G-26 and G-36;

J is selected from J-4, J-5, J-11, J-20, J-29, J-37, J-38, and J-69;

Q is selected from Q-45, Q-63, Q-64, Q-65, Q-68, Q-69, Q-70, Q-71, Q-72 and Q-85; and X is $X^1$.

Embodiment A6. A compound of Formula 1 wherein $R^1$ is an optionally substituted phenyl or 5- or 6-membered heteroaromatic ring;

A is $CH_2$ or NH;

X is $X^1$, $X^2$, $X^3$, $X^4$, $X^5$, $X^6$, $X^7$ or $X^8$;

each $R^2$ is independently $C_1$-$C_4$ alkyl, $C_2$-$C_4$ alkenyl, $C_1$-$C_4$ haloalkyl, $C_1$-$C_4$ alkoxy, halogen, cyano or hydroxy; or two $R^2$ are taken together as $C_1$-$C_3$ alkylene or $C_2$-$C_3$ alkenylene to form a bridged bicyclic ring system; or two $R^2$ attached to adjacent ring carbon atoms joined by a double bond are taken together as —CH=CH—CH=CH— optionally substituted with 1 to 3 substituents selected from $C_1$-$C_4$ alkyl, $C_1$-$C_4$ haloalkyl, $C_1$-$C_4$ alkoxy, $C_1$-$C_4$ haloalkoxy, halogen, hydroxy, amino, cyano and nitro;

J is a 5- or 6-membered ring or a 8- to 11-membered bicyclic ring system, each ring or ring system containing ring members selected from carbon and optionally 1 to 3 heteroatoms selected from up to 1 O, up to 1 S and up to 3 N, and optionally including 1 to 3 ring members selected from the group consisting of C(=O), C(=S), S(O), or S(O)$_2$, each ring or ring system optionally substituted with 1 to 5 substituents independently selected from $R^5$;

each $R^5$ is independently H, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_6$ alkoxy, $C_1$-$C_6$ haloalkoxy, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_2$-$C_6$ alkoxyalkyl, $C_2$-$C_6$ haloalkoxyalkyl, $C_1$-$C_6$ hydroxyalkyl, $C_2$-$C_6$ alkylcarbonyl, $C_2$-$C_6$ alkoxycarbonyl, $C_2$-$C_6$ alkylcarbonyloxy, $C_2$-$C_6$ alkylaminocarbonyl, $C_3$-$C_8$ dialkylaminocarbonyl, $C_3$-$C_6$ trialkylsilyl or —$Z^2Q$;

each Q is independently an optionally substituted phenyl, benzyl, naphthalenyl, $C_3$-$C_6$ cycloalkyl, $C_3$-$C_6$ cycloalkenyl or 5- or 6-membered heteroaromatic ring, each optionally substituted with 1 to 3 substituents selected from $R^7$ on carbon ring members and $R^{12}$ on nitrogen ring members;

each $R^7$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_1$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; or $R^5$ and $R^7$ are taken together with the atoms linking $R^5$ and $R^7$ to form an optionally substituted 5- to 7-membered ring containing as ring members 2 to 7 carbon atoms and optionally 1 to 3 heteroatoms selected from up to 1 O, up to 1 S and up to 1 N;

each $R^{12}$ is independently $C_1$-$C_3$ alkyl;

each $Z^1$ and $Z^2$ are independently a direct bond, O, S(O)$_m$, CHR$^{20}$ or NR$^{21}$; and $R^{21}$ is H or $C_1$-$C_3$ alkyl.

Embodiment A7. A compound of Embodiment A6 wherein

G is a 5-membered heteroaromatic ring or 5-membered saturated or partially saturated heterocyclic ring, each ring optionally substituted with up to 2 substituents selected from $R^3$ on carbon ring members and selected from $R^{11}$ on nitrogen ring members;

$R^1$ is a phenyl or 5- or 6-membered heteroaromatic ring optionally substituted with 1 to 2 substituents independently selected from $R^{4a}$ on carbon ring members and $R^{4b}$ on nitrogen ring members;

each $R^3$ is independently $C_1$-$C_3$ alkyl, $C_1$-$C_3$ haloalkyl or halogen;

each $R^{4a}$ is independently $C_1$-$C_6$ alkyl, $C_2$-$C_6$ alkenyl, $C_1$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl;

each $R^{4b}$ is independently $C_1$-$C_6$ alkyl, $C_3$-$C_6$ alkenyl, $C_3$-$C_6$ alkynyl, $C_3$-$C_6$ cycloalkyl, $C_1$-$C_6$ haloalkyl, $C_3$-$C_6$ haloalkenyl, $C_3$-$C_6$ haloalkynyl, $C_3$-$C_6$ halocycloalkyl or $C_2$-$C_4$ alkoxyalkyl;

each $R^{11}$ is independently $C_1$-$C_3$ alkyl; and when $R^5$ and $R^7$ are taken together with the atoms linking $R^5$ and $R^7$ to form an optionally substituted 5- to 7-membered ring, then $R^5$ and $R^7$ are taken together with the atoms linking $R^5$ and $R^7$ to form a 5- to 7-membered ring containing as ring members 2 to 7 carbon atoms and optionally 1 to 3 heteroatoms selected from up to 1 O, up to 1 S and up to 1 N, optionally substituted with up to 2 substituents selected from $R^8$; and each $R^8$ is independently $C_1$-$C_3$ alkyl.

Embodiment A8. A compound of Embodiment A7 wherein
G is one of G-1 through G-55 (as depicted in Exhibit 2) wherein the bond projecting to the left is bonded to X, and bond projecting to the right is bonded to $Z^1$;
J is one of J-1 through J-82 (as depicted in Exhibit 3) wherein the bond shown projecting to the left is bonded to $Z^1$;
Q is one of Q-1 through Q-55 (as depicted in Exhibit 4);
$R^1$ is one of U-1 through U-50 (as depicted in Exhibit 1);
each $R^{3a}$ is independently selected from H and $R^3$;
$R^{11a}$ is selected from H and $R^{11}$;
k is 0, 1 or 2;
p is 0, 1 or 2; and
x is an integer from 0 to 5;
provided that:
(a) when $R^4$ is attached to a carbon ring member, said $R^4$ is selected from $R^{4a}$;
(b) when $R^4$ is attached to a nitrogen ring member (e.g., in U-4, U-11 through U-15, U-24 through U-26, U-31 or U-35), said $R^4$ is selected from $R^{4b}$;
(c) when G is G-6, G-16 or G-42, and each $R^{3a}$ is other than H, then $R^{11a}$ is H;
(d) when G is G-25 or G-31, then at least one $R^{3a}$ is H; and
(e) when G is one of G-31 through G-35, then $Z^1$ is a direct bond or $CHR^{20}$.

Embodiment A9. A compound of Embodiment A8 wherein
G is selected from G-1, G-2, G-15, G-26, G-27, G-36, G-37 and G-38;
J is selected from J-1, J-2, J-3, J-4, J-5, J-7, J-8, J-9, J-10, J-11, J-12, J-14, J-15, J-16, J-20, J-24, J-25, J-26, J-29, J-30, J-45 and J-69;
each Q is independently Q-1, Q-20, Q-32 to 34, Q-45 Q-46 or Q-47;
W is O;
X is $X^1$, $X^2$ or $X^3$;
each $Z^1$ and $Z^2$ is a direct bond;
$R^1$ is selected from U-1 through U-3, U-11, U-13, U-20, U-22, U-23, U-36 through U-39 and U-50;
each $R^3$ is independently methyl or halogen;
each $R^{4a}$ is independently $C_1$-$C_2$ alkyl, $C_1$-$C_2$ haloalkyl, halogen or $C_1$-$C_2$ alkoxy;
each $R^{4b}$ is independently $C_1$-$C_2$ alkyl or $C_1$-$C_2$ haloalkyl;
one instance of $R^5$ is $Z^2Q$ and other instances of $R^5$ are independently selected from H, $C_1$-$C_4$ alkyl, $C_1$-$C_4$ haloalkyl and halogen;
each $R^7$ is independently halogen, $C_1$-$C_3$ alkyl, $C_1$-$C_3$ haloalkyl, hydroxy, $C_1$-$C_2$ alkoxy or $C_1$-$C_2$ haloalkoxy;
k is 1 or 2; and
n is 0.

Embodiment A10. A compound of Embodiment A9 wherein
A is $CH_2$;
G is selected from G-1, G-2, G-15, G-26, and G-36; and G is unsubstituted;
J is selected from J-11, J-25, J-26, J-29 and J-30;
Q is selected from Q-1 and Q-45;
X is $X^1$ or $X^2$; and the ring comprising X is saturated;
$R^1$ is U-1 or U-50; and
each $R^{4a}$ is independently $C_1$-$C_2$ alkyl, trifluoromethyl, Cl, Br, I or methoxy.

Embodiment A11. A compound of Embodiment A10 wherein
J is selected from J-11 and J-29;
X is $X^1$; and
each $R^{4a}$ is independently $C_1$-$C_2$ alkyl, trifluoromethyl or Cl.

Embodiment A12. A compound of Formula 1 wherein
$R^1$ is U-1 or U-50 (as depicted in Exhibit 1) wherein when $R^4$ is attached to a carbon ring member, said $R^4$ is selected from $R^{4a}$;
each $R^{4a}$ is independently $C_1$-$C_2$ alkyl, trifluoromethyl, Cl, Br, I or methoxy;
A is $CH_2$;
W is O;
X is $X^1$ or $X^2$ and ring comprising X is saturated;
each $R^2$ is independently ethyl, methoxy, cyano or hydroxy;
G is selected from G-1, G-2, G-15, G-26 and G-36 (as depicted in Exhibit 2) wherein the bond projecting to the left is bonded to X, and the bond projecting to the right is bonded to $Z^1$;
each $R^{3a}$ is independently selected from H and $R^3$;
each $R^3$ is independently methyl or halogen;
J is selected from J-11, J-25, J-26, J-29 and J-30 (as depicted in Exhibit 3); wherein the bond shown projecting to the left is bonded to $Z^1$;
each $R^5$ is independently H, halogen, cyano, hydroxy, amino, nitro, —CHO, —C(=O)OH, —C(=O)NH$_2$, —NR$^{25}$R$^{26}$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{10}$ alkylcycloalkylalkyl, $C_3$-$C_8$ cycloalkenyl, $C_3$-$C_8$ halocycloalkenyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkylsulfinylalkyl, $C_1$-$C_6$ alkylsulfonylalkyl, $C_2$-$C_6$ alkylaminoalkyl, $C_3$-$C_8$ dialkylaminoalkyl, $C_2$-$C_6$ haloalkylaminoalkyl, $C_4$-$C_{10}$ cycloalkylaminoalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_4$-$C_8$ cycloalkoxycarbonyl, $C_5$-$C_{10}$ cycloalkylalkoxycarbonyl, $C_2$-$C_6$ alkylaminocarbonyl, $C_3$-$C_8$ dialkylaminocarbonyl, $C_4$-$C_8$ cycloalkylaminocarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_1$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy. $C_3$-$C_6$ alkylcarbonylalkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_{10}$ trialkylsilyl, $C_1$-$C_6$ alkylsulfonylamino, $C_1$-$C_6$ haloalkylsulfonylamino or —$Z^2Q$;

each Q is independently selected from Q-1, Q-45 and Q-63 (as depicted in Exhibit 4);

each $R^7$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio. $C_2$-$C_6$ alkylaminocarbonyl, $C_3$-$C_8$ dialkylaminocarbonyl or $C_3$-$C_6$ trialkylsilyl; or $R^5$ and $R^7$ are taken together with the atoms linking $R^5$ and $R^7$ to form a 5- to 7-membered ring containing as ring members 2 to 7 carbon atoms and optionally 1 to 3 heteroatoms selected from up to 1 O, up to 1 S, and up to 1 N and optionally including 1 ring member selected from $SiR^{17}R^{18}$, the ring optionally substituted on ring members other than the atoms linking $R^5$ and $R^7$ with up to 4 substituents selected from $R^8$;

each $R^8$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl;

each $Z^1$ and $Z^2$ is a direct bond;

each $Z^4$ is independently C(=O) or S(O)$_2$;

n is 0, 1 or 2;

k is 0, 1 or 2;

p is 0, 1 or 2; and x is an integer from 0 to 5.

Embodiments of the present invention also include:

Embodiment B1. A compound of Formula 1A wherein each $R^{4a1}$ and $R^{4a2}$ is independently $C_1$-$C_3$ alkyl, $C_2$-$C_3$ alkenyl, $C_2$-$C_3$ alkynyl, cyclopropyl, $C_1$-$C_3$ haloalkyl, halocyclopropyl, halogen, cyano, nitro, $C_1$-$C_2$ alkoxy or $C_1$-$C_2$ haloalkoxy.

Embodiment B2. A compound of Embodiment B1 wherein each $R^{4a1}$ and $R^{4a2}$ is independently $C_1$-$C_3$ alkyl, $C_1$-$C_3$ haloalkyl, halogen, cyano, $C_1$-$C_2$ alkoxy or $C_1$-$C_2$ haloalkoxy.

Embodiment B3. A compound of Embodiment B2 wherein each $R^{4a1}$ and $R^{4a2}$ is independently $C_1$-$C_3$ alkyl, $C_1$-$C_3$ haloalkyl or halogen.

Embodiment B4. A compound of Formula 1A wherein $A^a$ is H.

Embodiment B5. A compound of Formula 1A wherein $A^a$ is CH$_2$CO$_2$H.

Embodiment B6. A compound of Formula 1A wherein $A^a$ is CH$_2$CO$_2$R$^{30}$.

Embodiment B7. A compound of Formula 1A wherein $A^a$ is CH$_2$C(=O)Cl.

Embodiment B8. A compound of Formula 1B wherein each $R^{4a1}$ and $R^{4a2}$ is independently $C_1$-$C_3$ alkyl, $C_2$-$C_3$ alkenyl, $C_2$-$C_3$ alkynyl, cyclopropyl, $C_1$-$C_3$ haloalkyl, halocyclopropyl, halogen, cyano, nitro, $C_1$-$C_2$ alkoxy or $C_1$-$C_2$ haloalkoxy.

Embodiment B9. A compound of Embodiment B8 wherein each $R^{4a1}$ and $R^{4a2}$ is independently $C_1$-$C_3$ alkyl, $C_1$-$C_3$ haloalkyl, halogen, cyano, $C_1$-$C_2$ alkoxy or $C_1$-$C_2$ haloalkoxy.

Embodiment B10. A compound of Embodiment B9 wherein each $R^{4a1}$ and $R^{4a2}$ is independently $C_1$-$C_3$ alkyl, $C_1$-$C_3$ haloalkyl or halogen.

Embodiment B11. A compound of Formula 1B wherein $Z^3$ is CN.

Embodiment B12. A compound of Formula 1B wherein $Z^3$ is C(=S)NH$_2$.

With regards to the compounds of Formula 1C of this invention, it is noted that various embodiments of J-29 can be present in two or more enantiomeric forms. The enantiomeric forms of J-29 embodiments for compounds of Formula 1C of this invention are those depicted about in the Exhibit A above. All J-29 enantiomers are included in the Formula 1C compounds in this invention for embodiments where no specific J-29 enantiomeric form is depicted (e.g., J-29-33 enantiomers and J-29-22 enantiomers based on the methyl group position).

Embodiment B13. A compound of Formula 1C wherein M is $C_1$-$C_2$ alkyl, $C_1$-$C_2$ haloalkyl, hydroxy, $C_1$-$C_4$ alkoxy, $C_1$-$C_2$ haloalkoxy, $C_1$-$C_3$ alkylamino, $C_2$-$C_6$ dialkylamino, 1-piperidinyl, 1-pyrrolidinyl or 4-morpholinyl.

Specific embodiments include compounds of Formula 1 selected from the group consisting of:

4-[4-[(5R)-4,5-dihydro-5-phenyl-3-isoxazolyl]-2-thiazolyl]-1-[[5-methyl-3-(trifluoromethyl)-1H-pyrazol-1-yl]acetyl]piperidine and its enantiomer (Compound 1), 1-[[5-methyl-3-(trifluoromethyl)-1H-pyrazol-1-yl]acetyl]-4-[4-(5-phenyl-3-isoxazolyl)-2-thiazolyl]piperidine (Compound 2), 1-[4-[4-[(5R)-4,5-dihydro-5-methyl-5-phenyl-3-isoxazolyl]-2-thiazolyl]-1-piperidinyl]-2-[5-methyl-3-(trifluoromethyl)-1H-pyrazol-1-yl]ethanone and its enantiomer (Compound 15), 2-[5-methyl-3-(trifluoromethyl)-1H-pyrazol-1-yl]-1-[4-[4-[(3aS,9bR),3a,4,5,9b-tetrahydronaphth[2,1-d]isoxazol-3-yl]-2-thiazolyl]-1-piperidinyl]ethanone and its enantiomer (Compound 16), 1-[4-[4-[(5R)-4,5-dihydro-5-phenyl-3-isoxazolyl]-2-thiazolyl]-1-piperidinyl]-2-[5-ethyl-3-(trifluoromethyl)-1-pyrazol-1-yl]ethanone and its enantiomer (Compound 19), 2-[3,5-bis(trifluoromethyl)-1H-pyrazol-1-yl]-1-[4-[4-[(5R)-4,5-dihydro-5-phenyl-3-isoxazolyl]-2-thiazolyl]-1-piperidinyl]ethanone and its enantiomer (Compound 22), 1-[4-[4-[(5R)-3',4'-dihydrospiro[isoxazole-5(4H),1',(2'H)-naphthalen]-3-yl]-2-thiazolyl]-1-piperidinyl]-2-[5-methyl-3-(trifluoromethyl)-1H-pyrazol-1-yl]ethanone and its enantiomer (Compound 37), 1-[4-[4-[(5R)-2,3-dihydrospiro[1H-indene-1,5'(4'H)-isoxazol]-3'-yl]-2-thiazolyl]-1-piperidinyl]-2-[5-methyl-3-(trifluoromethyl)-1H-pyrazol-1-yl]ethanone and its enantiomer (Compound 44), 2-[5-chloro-3-(trifluoromethyl)-1H-pyrazol-1-yl]-1-[4-[4-[(5R)-4,5-dihydro-5-phenyl-3-isoxazoly]-2-thiazolyl]-1-piperidinyl]ethanone and its enantiomer (Compound 107), 2-[(5R)-4,5-dihydro-3-[2-[1-[2-[5-methyl-3-(trifluoromethyl)-1H-pyrazol-1-yl]acetyl]-4-piperidinyl]-4-thiazolyl-5-isoxazolyl]-1H-isoindole-1,3(2H)-dione and its enantiomer (Compound 129), 2-[5-chloro-3-(trifluoromethyl)-1H-pyrazol-1-yl]-1-[4-[4-[(1R)-2,3-dihydrospiro[1H-indene-1,5'(4'H)-isoxazol]-3'-yl]-2-thiazolyl]-1-piperidinyl]ethanone and its enantiomer (Compound 232), 2-[5-chloro-3-(trifluoromethyl)-1H-pyrazol-1-yl]-1-[4-[4-[(1'R)-3',4'-dihydrospiro[isoxazole-5(4H),1'(2'H)-naphthalen]-3-yl]-2-thiazolyl]-1-piperidinyl]ethanone and its enantiomer (Compound 230), 2-[5-methyl-3-(trifluoromethyl)-1H-pyrazol-1-yl]-1-[4-[4-(3R)-spiro[benzofuran-3(2H),5'(4'H)-isoxazol]-3'-yl-2-thiazolyl]-1-piperidinyl]ethanone and its enantiomer (Compound 185), 1-[4-[4-[(1R)-2,3-dihydrospiro[1H-indene-1,5'(4'H)-isoxazol]-3'-yl]-2-thiazolyl]-1-piperidinyl]-2-(3,5-dimethyl-1H-pyrazol-1-yl)ethanone and its enantiomer (Compound 165), 2-[3,5-bis(trifluoromethyl)-1H-pyrazol-1-yl]-1-[4-[4-[(1'R)-3',4'-dihydrospiro[isoxazole-5(4H),1'(2'H)-naphthalen]-3-yl]-2-thiazolyl]-1-piperidinyl]ethanone and its enantiomer (Compound 229), 2-[3,5-bis(trifluoromethyl)-1H-pyrazol-1-yl]-1-[4-[4-[(1R)-2,3-dihydrospiro[1H-indene-1,5'(4'H)-isoxazol]-3'-yl]-2-thiazolyl]-1-piperidinyl]ethanone and its enantiomer (Compound 231), 1-[4-[4-[(5R)-5-(2,6-dichlorophenyl)-4,5-dihydro-3-isoxazolyl]-2-thiazolyl]-1-piperidinyl]-2-[5-methyl-3-(trifluoromethyl)-1H-pyrazol-1-yl]ethanone and its enantiomer (Compound 135), 1-[4-[4-[(5R)-4,5-dihydro-5-(2-fluorophenyl-3-isoxazolyl]-2-thiazolyl]-1-piperidinyl]-2-[5-methyl-3-(trifluoromethyl)-1H-pyrazol-1-yl]ethanone and its enantiomer (Compound 79), 1-[4-[4-[(5R)-4,5-dihydro-5-(2-methylphenyl)-3-isoxazolyl]-2-thiazolyl]-1-piperidinyl]-2-[5-methyl-3-(trifluoromethyl)-1H-pyrazol-1-yl]ethanone and its enantiomer (Compound 161), 1-[4-[4-[(5R)-5-(2,6-dimethylphenyl)-4,5-dihydro-3-isoxazolyl]-2-thiazolyl]-1-piperidinyl]-2-[5-methyl-3-(trifluoromethyl)-1H-pyrazol-1-yl]ethanone and its enantiomer (Compound 178), 1-[4-[4-[(5R)-4,5-dihydro-5-(2,4,6-trimethylphenyl)-3-isoxazolyl]-2-thiazolyl]-1-piperidinyl]-2-[5-methyl-3-(trifluoromethyl)-1H-pyrazol-1-yl]ethanone and its enantiomer (Compound 179), 1-[4-[4-[(1'R)-3',4'-dihydrospiro[isoxazole-5(4H),1'(2'H)-naphthalen]-3-yl]-2-thiazolyl]-1-piperidinyl]-2-(3,5-dimethyl-1H-pyrazol-1-yl)ethanone and its enantiomer (Compound 164), 1-[4-[4-[(5R)-4,5-dihydro-5-(2,4,6-trimethoxyphenyl)-3-isoxazolyl]-2-thiazolyl]-1-piperidinyl]-2-[5-methyl-3-(trifluoromethyl)-1H-pyrazol-1-yl]ethanone and its enantiomer (Compound 155), 3-[(5R)-4,5-dihydro-3-[2-[1-[2-[5-methyl-3-(trifluoromethyl)-1H-pyrazol-1-yl]acetyl]-4-piperidinyl]-4-thiazolyl]-5-isoxazolyl]-2(3H)-benzoxazolone and its enantiomer (Compound 225), 1-[4-[4-[(5R)-5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone and its enantiomer (Compound 214), 2-[(5R)-4,5-dihydro-3-[2-[1-[2-[5-methyl-3-(trifluoromethyl)-1H-pyrazol-1-yl]acetyl]-4-piperidinyl]-4-thiazolyl]-5-isoxazolyl]benzonitrile and its enantiomer (Compound 220), 2-[5-chloro-3-(trifluoromethyl)-1H-pyrazol-1-yl]-1-[4-[4-[(5R)-4,5-dihydro-5-methyl-5-phenyl-3-isoxazolyl]-2-thiazolyl]-1-piperidinyl]ethanone and its enantiomer (Compound 261), 2-[3,5-bis(trifluoromethyl)-1H-pyrazol-1-yl]-1-[4-[4-[(5R)-4,5-dihydro-5-methyl-5-phenyl-3-isoxazolyl]-2-thiazolyl]-1-piperidinyl]ethanone and its enantiomer (Compound 260), 1-[4-[4-[(5R)-5-(2-chlorophenyl)-4,5-dihydro-3-isoxazolyl]-2-thiazolyl]-1-piperidinyl]-2-[5-methyl-3-(trifluoromethyl)-1H-pyrazol-1-yl]ethanone and its enantiomer (Compound 8), 1-[4-[4-[(5R)-4,5-dihydro-5-phenyl-3-isoxazolyl]-2-thiazolyl]-1-piperidinyl]-2-[3-methyl-5-(trifluoromethyl)-1H-pyrazol-1-yl]ethanone and its enantiomer (Compound 128), 1-[4-[4-[(4S)-2,3-dihydrospiro[4H-1-benzopyran-4,5'(4'H)-isoxazol]-3'-yl)-2-thiazolyl]-1-piperidinyl]-2-[5-methyl-3-(trifluoromethyl)-1H-pyrazol-1-yl]ethanone and its enantiomer (Compound 137), and (5R)-4,5-dihydro-3-[2-[1-[2-[5-methyl-3-(trifluoromethyl)-1H-pyrazol-1-yl]acetyl]-4-piperidinyl]-4-thiazolyl]-5-phenyl-5-isoxazolecarbonitrile and its enantiomer (Compound 265).

Specific embodiments also include compounds of Formula 1B selected from the group consisting of:

1-[2-[5-methyl-3-(trifluoromethyl)-1H-pyrazol-1-yl]acetyl]-4-piperidinecarbothioamide, 1-[2-[3,5-bis(trifluoromethyl)-1H-pyrazol-1-yl]acetyl]-4-piperidinecarbothioamide, 1-[2-[5-methyl-3-(trifluoromethyl)-1H-pyrazol-1-yl]acetyl]-4-piperidinecarbonitrile, and 1-[2-[3,5-bis(trifluoromethyl)-1H-pyrazol-1-yl]acetyl]-4-piperidinecarbonitrile.

Of note are compounds of Formula 1, including all geometric and stereoisomers, N-oxides, and agriculturally suitable salts thereof, agricultural compositions containing them and their use as fungicides wherein $R^1$ is an optionally substituted phenyl or 5- or 6-membered heteroaromatic ring;

A is $CH_2$ or NH;

X is $X^1$, $X^2$, $X^3$, $X^4$, $X^5$, $X^6$, $X^7$ or $X^8$;

each $R^2$ is independently $C_1$-$C_4$ alkyl, $C_1$-$C_4$ alkenyl, $C_1$-$C_4$ haloalkyl, $C_1$-$C_4$ alkoxy, halogen, cyano or hydroxy; or two $R^2$ are taken together as $C_1$-$C_3$ alkylene or $C_2$-$C_3$ alkenylene to form a bridged bicyclic ring system; or two $R^2$ attached to adjacent ring carbon atoms joined by a double bond are taken together as —CH═CH—CH═CH— optionally substituted with 1 to 3 substituents selected from $C_1$-$C_4$ alkyl, $C_1$-$C_4$ haloalkyl, $C_1$-$C_4$ alkoxy, $C_1$-$C_4$ haloalkoxy, halogen, hydroxy, amino, cyano and nitro;

J is a 5- or 6-membered ring or a 8- to 11-membered bicyclic ring system, each ring or ring system containing ring members selected from carbon and optionally 1 to 3 heteroatoms selected from up to 1 O, up to 1 S and up to 3 N, and optionally including 1 to 3 ring members selected from the group consisting of C(=O), C(=S), S(O), or S(O)$_2$, each ring or ring system optionally substituted with 1 to 5 substituents independently selected from $R^5$;

each $R^5$ is independently H, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_6$ alkoxy, $C_1$-$C_6$ haloalkoxy, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylamino, $C_2$-$C_8$ dialkylamino, $C_3$-$C_6$ cycloalkylamino, $C_2$-$C_6$ alkoxyalkyl, $C_2$-$C_6$ haloalkoxyalkyl, $C_1$-$C_6$ hydroxyalkyl, $C_2$-$C_6$ alkylcarbonyl, $C_2$-$C_6$ alkoxycarbonyl, $C_2$-$C_6$ alkylcarbonyloxy, $C_1$-$C_6$ alkylcarbonylthio, $C_2$-$C_6$ alkylaminocarbonyl, $C_3$-$C_8$ dialkylaminocarbonyl, $C_3$-$C_6$ trialkylsilyl, or —$Z^2$Q;

each Q is independently an optionally substituted phenyl, benzyl, naphthalenyl, $C_3$-$C_6$ cycloalkyl, $C_3$-$C_6$ cycloalkenyl or 5- or 6-membered heteroaromatic ring, each optionally substituted with 1 to 3 substituents selected from $R^7$ on carbon ring members and $R^{12}$ on nitrogen ring members;

each $R^7$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; or $R^5$ and $R^7$ are taken together with the atoms linking $R^5$ and $R^7$ to form an optionally substituted 5- to 7-membered ring containing as ring members 2 to 7 carbon atoms and optionally 1 to 3 heteroatoms selected from up to 1 O, up to 1 S and up to 1 N;

$R^{12}$ is $C_1$-$C_3$ alkyl;

each $Z^1$ and $Z^2$ is independently a direct bond, 0. S(O)$_m$, CHR$^{20}$ or NR$^{21}$;

m is 0, 1 or 2 (which is understood to mean that each m is independently 0, 1 or 2); and $R^{21}$ is H or $C_1$-$C_3$ alkyl (subject to proviso (b) and/or proviso (c) as applicable).

Also of note are compounds of Formula 1, including all geometric and stereoisomers, N-oxides, and salts thereof, agricultural compositions containing them and their use as fungicides wherein each $R^5$ is independently H, halogen, cyano, hydroxy, amino, nitro, —CHO, —C(=O)OH, —C(=O)NH$_2$, —NR$^{25}$R$^{26}$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{10}$ alkylcycloalkylalkyl, $C_3$-$C_8$ cycloalkenyl, $C_3$-$C_8$ halocycloalkenyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylaminoalkyl, $C_3$-$C_8$ dialkylaminoalkyl, $C_2$-$C_6$ haloalkylaminoalkyl, $C_4$-$C_{10}$ cycloalkylaminoalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_4$-$C_8$ cycloalkoxycarbonyl, $C_5$-$C_{10}$ cycloalkylalkoxycarbonyl, $C_2$-$C_6$ alkylaminocarbonyl, $C_3$-$C_8$ dialkylaminocarbonyl, $C_4$-$C_8$ cycloalkylaminocarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_1$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_{10}$ trialkylsilyl, $C_1$-$C_6$ alkylsulfonylamino, $C_1$-$C_6$ haloalkylsulfonylamino or —$Z^2$Q;

each $R^7$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl. $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; or $R^5$ and $R^7$ are taken together with the atoms linking $R^5$ and $R^7$ to form an optionally substituted 5- to 7-membered ring containing as ring members 2 to 7 carbon atoms and optionally 1 to 3 heteroatoms selected from up to 1 O, up to 1 S, up to 1 Si and up to 1 N; and $R^{12}$ is $C_1$-$C_3$ alkyl (subject to proviso (b) and/or proviso (c) as applicable).

This invention provides a fungicidal composition comprising a compound of Formula 1 (including all geometric and stereoisomers. N-oxides, and salts thereof), and at least one other fungicide. Of note as embodiments of such compositions are compositions comprising a compound corresponding to any of the compound embodiments described above.

This invention provides a fungicidal composition comprising a fungicidally effective amount of a compound of Formula 1 (including all geometric and stereoisomers, N-oxides, and agriculturally suitable salts thereof), and at least one additional component selected from the group consisting of surfactants, solid diluents and liquid diluents. Of note as embodiments of such compositions are compositions comprising a compound corresponding to any of the compound embodiments described above.

This invention provides a method for controlling plant diseases caused by fungal plant pathogens comprising applying to the plant or portion thereof, or to the plant seed, a fungicidally effective amount of a compound of Formula 1 (including all geometric and stereoisomers, N-oxides, and agriculturally suitable salts thereof). Of note as embodiment of such methods are methods comprising applying a fungicidally effective amount of a compound corresponding to any of the compound embodiments describe above. Of particular notes are embodiments where the compounds are applied as compositions of this invention.

The compounds of Formulae 1, 1A, 1B and 1C can be prepared by one or more of the following methods and variations as described in Schemes 1-20. The definitions of A, G, J, W, X, Q, $Z^1$, $R^1$, $R^2$, $R^{15}$, $R^{16}$ and n in the compounds of Formulae 1-38 below are as defined above in the Summary of the Invention unless otherwise noted. Formulae 1a-1e and Formulae 1Ba and 1Bb are various subsets of Formula 1 and 1B respectively.

As shown in Scheme 1, compounds of Formula 1a (Formula 1 wherein A is $CHR^{15}$) wherein W is O can be prepared by coupling of an acid chloride of Formula 2 with an amine of Formula 3 in the presence of an acid scavenger. Typical acid scavengers include amine bases such as triethylamine, N,N-diisopropylethylamine and pyridine. Other scavengers include hydroxides such as sodium and potassium hydroxide and carbonates such as sodium carbonate and potassium carbonate. In certain instances it is useful to use polymer-supported acid scavengers such as polymer-bound N,N-diisopropylethylamine and polymer-bound 4-(dimethylamino)pyridine. Acid salts of the Formula 3 amines can also be used in this reaction, provided that at least 2 equivalents of the acid scavenger is present. Typical acids used to form salts with amines include hydrochloric acid, oxalic acid and trifluoroacetic acid. In a subsequent step, amides of Formula 1a wherein W is O can be converted to thioamides of Formula 1a wherein W is S using a variety of standard thiating reagents such as phosphorus pentasulfide or 2,4-bis (4-methoxyphenyl)-1,3-dithia-2,4-diphosphetane-2,4-disulfide (Lawesson's reagent).

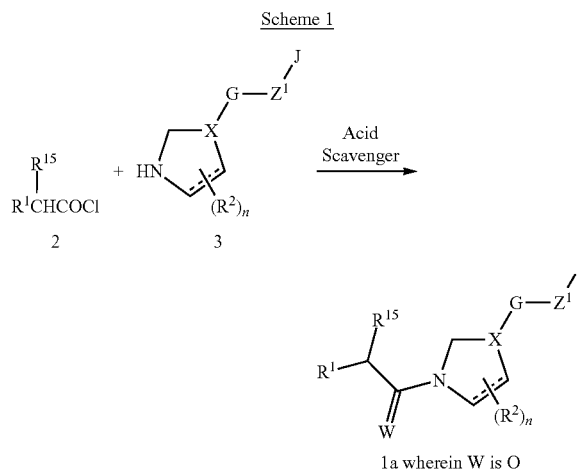

An alternate procedure for the preparation of compounds of Formula 1a wherein W is O is depicted in Scheme 2 and involves coupling of an acid of Formula 4 with an amine of Formula 3 (or its acid salt) in the presence of a dehydrative coupling reagent such as dicyclohexylcarbodiimide (DCC), 1-(3-dimethylaminopropyl)-3-ethylcarbodiimide hydrochloride (EDC) or O-benzotriazol-1-yl-N,N,N'N'-tetramethyluronium hexafluoro-phosphate (HBTU). Polymer-supported reagents are again useful here, such as polymer-bound cyclohexylcarbodiimide. These reactions are typically run at 0-40° C. in a solvent such as dichloromethane or acetonitrile in the presence of a base such as triethylamine or N,N-diisopropylethylamine. The acids of Formula 4 are known or can be prepared by methods known to one skilled in the art. For example, $R^1CH_2COOH$ where $R^1$ is a heteroaromatic ring linked through nitrogen can be prepared by reacting the corresponding $R^1H$ compound with a haloacetic acid or ester in the presence of base; see, for example, U.S. Pat. No. 4,084,955. $R^1CH_2COOH$ wherein $R^1$ is a phenyl or a heteroaromatic ring linked through carbon can be prepared from the corresponding $R^1CH_2$-halogen compounds by displacement of the halogen with cyanide followed by hydrolysis; see, for example, K. Adachi, *Yuki Gosei Kagaku Kvokaishi* 1969, 27, 875-876; from $R^1C(=O)CH_3$ by the Willgerodt-Kindler reaction; see, for example, H. R. Darabi et al., *Tetrahedron Letters* 1999, 40, 7549-7552 and M. M. Alam and S. R. Adapa, *Synthetic Communications* 2003, 33, 59-63 and references cited therein; or from $R^1Br$ or $R^1I$ by palladium-catalyzed coupling with tert-butyl acetate or diethyl malonate followed by ester hydrolysis; see, for example, W. A. Moradi and S. L. Buchwald, *J. Am. Chem. Soc.* 2001, 123, 7996-8002 and J. F. Hartwig et al., *J. Am. Chem. Soc.* 2002, 124, 12557-12565.

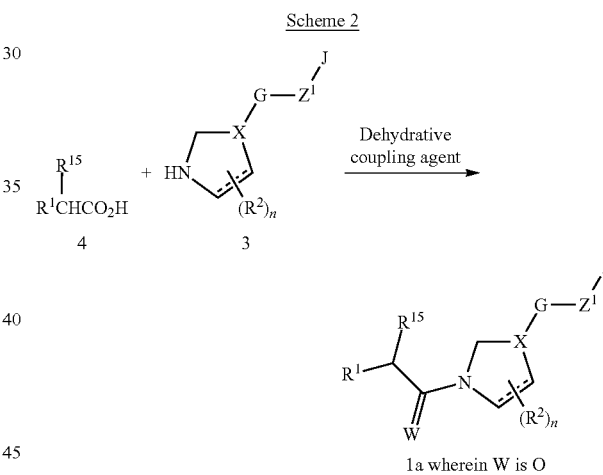

As the synthetic literature includes many amide-forming methods, the synthetic procedures of Schemes 1 and 2 are simply representative examples of an wide variety of methods useful for the preparation of Formula 1 compounds. One skilled in the art also realizes that acid chlorides of Formula 2 can be prepared from acids of Formula 4 by numerous well-known methods.

Certain compounds of Formula 1b (Formula 1 wherein A is $CHR^{15}$ and W is O) wherein $R^1$ is a 5-membered nitrogen-containing heteroaromatic ring linked through the nitrogen atom can be prepared by reaction of the parent heterocycle of Formula 5 and a haloacetamide of Formula 6 as shown in Scheme 3. The reaction is carried out in the presence of a base such as sodium hydride or potassium carbonate in a solvent such as tetrahydrofuran, N,N-dimethylformamide or acetonitrile at 0 to 80° C. The haloacetamide of Formula 6 can be prepared by the reaction of an amine of Formula 3 with an α-halo carboxylic acid halide or an α-halo carboxylic acid or its anhydride, analogous to the amide-forming reactions described in Schemes 1 and 2, respectively.

Scheme 3

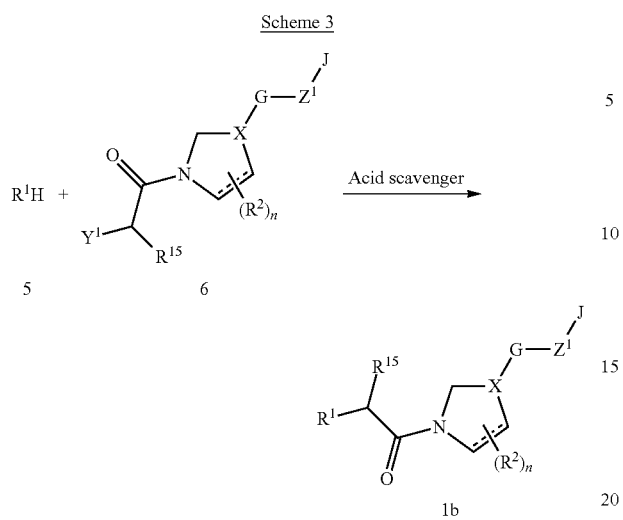

wherein R¹ is a 5-membered nitrogen-containing heteroaromatic ring unsubstituted on N; and Y¹ is Cl, Br or I.

Compounds of Formulae 1c (Formula 1 wherein A is NH), wherein R¹ is phenyl, naphthalenyl or a 5- or 6-membered heteroaromatic ring, and W is O or S, can be prepared by reaction of an amine of Formula 3 with an isocyanate or isothiocyanate, respectively, of Formula 7 as depicted in Scheme 4. This reaction is typically carried out at an ambient temperature in an aprotic solvent such as dichloromethane or acetonitrile.

Scheme 4

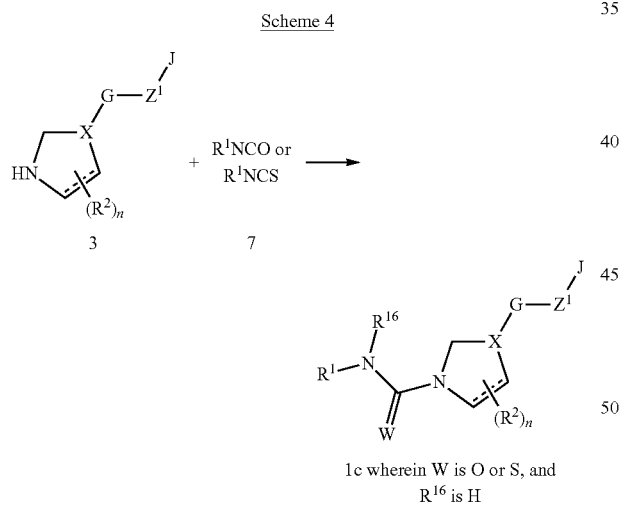

1c wherein W is O or S, and R¹⁶ is H

Compounds of Formulae 1c can also be prepared by the reaction of an amine of Formula 8 with a carbamoyl or thiocarbamoyl chloride or imidazole of Formula 9 as shown in Scheme 5. When Y is chlorine, the reaction is typically carried out in the presence of an acid scavenger. Typical acid scavengers include amine bases such as triethylamine, N,N-diisopropylethylamine and pyridine. Other scavengers include hydroxides such as sodium and potassium hydroxide and carbonates such as sodium carbonate and potassium carbonate. The carbamoyl or thiocarbamoyl chlorides of Formula 9 (wherein Y is Cl) can be prepared from amines of Formula 3 by treatment with phosgene or thiophosgene, respectively, or their equivalents, while carbamoyl or thiocarbamoyl imidazoles of Formula 9 (wherein Y is imidazol-1-yl) can be prepared from amines of Formula 3 by treatment with 1,1'-carbonyldiimidazole or 1,1'-thiocarbonyldiimidazole, respectively, according to general methods known to one skilled in the art.

Scheme 5

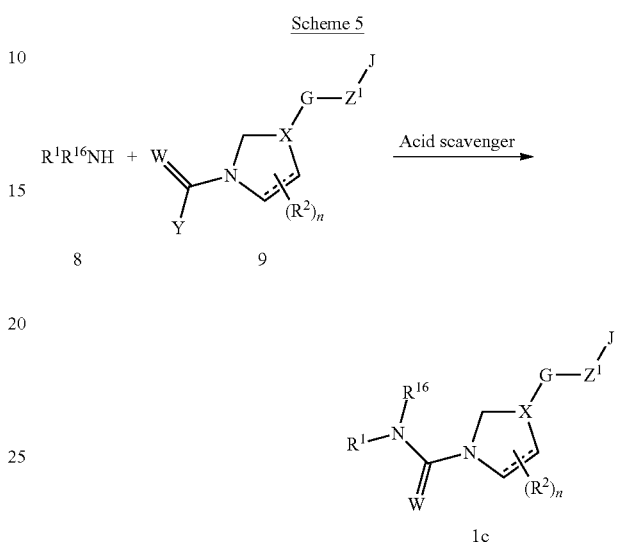

wherein W is O or S; and Y is Cl or imidazol-1-yl.

Certain compounds of Formula 1d (i.e. Formula 1 in which the ring containing X is saturated) can be prepared from compounds of Formula 1e where the ring containing X is unsaturated by catalytic hydrogenation as shown in Scheme 6. Typical conditions involve exposing a compound of Formula 1e to hydrogen gas at a pressure of 70 to 700 kPa, preferably 270 to 350 kPa, in the presence of a metal catalyst such as palladium supported on an inert carrier such as activated carbon, in a weight ratio of 5 to 20% of metal to carrier, suspended in a solvent such as ethanol at an ambient temperature. This type of reduction is very well known; see, for example, *Catalytic Hydrogenation*, L. Cerveny, Ed., Elsevier Science, Amsterdam, 1986. One skilled in the art will recognize that other certain functionalities that may be present in compounds of Formula 1e can also be reduced under catalytic hydrogenation conditions, thus requiring a suitable choice of catalyst and conditions.

Scheme 6

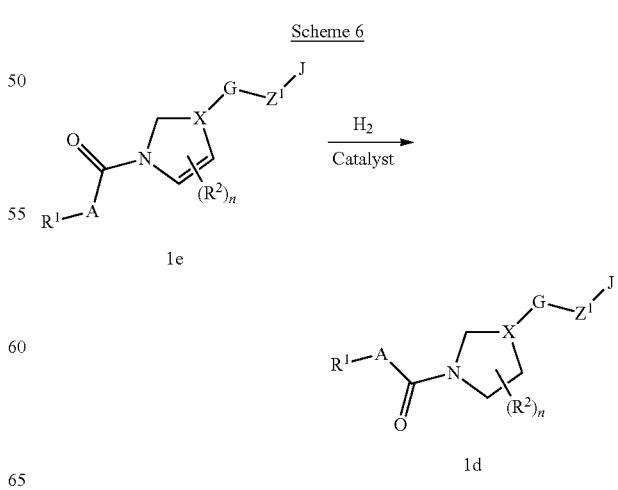

wherein X is X¹, X², X⁵, X⁸ or X⁹.

Certain compounds of Formula 1 wherein X is $X^1$, $X^5$, $X^7$ or $X^9$, and G is linked to the ring containing X via a nitrogen atom, can be prepared by displacement of an appropriate leaving group $Y^2$ on the ring containing the X of Formula 10 with a nitrogen-containing heterocycle of Formula 11 in the presence of a base as depicted in Scheme 7. Suitable bases include sodium hydride or potassium carbonate, and the reaction is carried out in a solvent such as N,N-dimethylformamide or acetonitrile at 0 to 80° C. Suitable leaving groups in the compounds of Formula 10 include bromide, iodide, mesylate ($OS(O)_2CH_3$), triflate ($OS(O)_2CF_3$) and the like, and compounds of Formula 10 can be prepared from the corresponding compounds wherein $Y^2$ is OH, using general methods known in the art.

Scheme 7

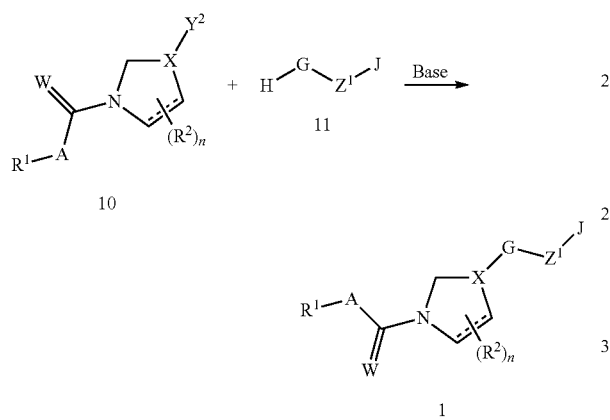

wherein W is O or S; X is $X^1$, $X^5$, $X^7$ or $X^9$; and $Y^2$ is a leaving group such as Br, I, $OS(O)_2Me$ or $OS(O)_2CF_3$.

Compounds of Formula 1 wherein X is $X^2$ or $X^8$ can be prepared by reaction of a compound of Formula 12 with a heterocyclic halide or triflate ($OS(O)_2CF_3$) of Formula 13 as shown in Scheme 8. The reaction is carried out in the presence of a base such as potassium carbonate in a solvent such as dimethylsulfoxide, N,N-dimethylformamide or acetonitrile at 0 to 80° C. Compounds of Formula 13 wherein $Y^2$ is triflate can be prepared from corresponding compounds wherein $Y^2$ is OH by methods known to one skilled in the art.

Scheme 8

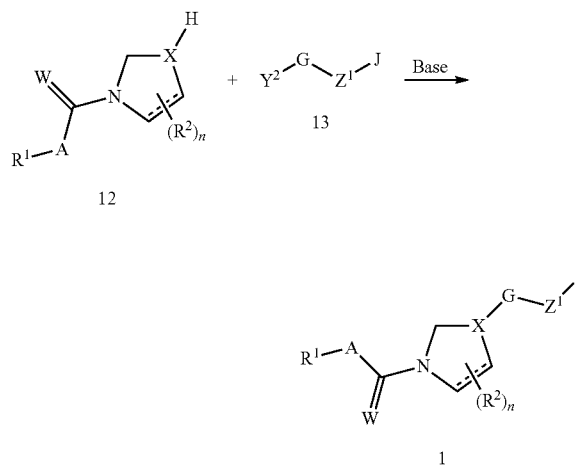

wherein W is O or S; X is $X^2$ or $X^8$; and $Y^2$ is a leaving group such as Br, I, $OS(O)_2Me$ or $OS(O)_2CF_3$.

The amine compounds of Formula 3 can be prepared from the protected amine compounds of Formula 14 where $Y^3$ is an amine-protecting group as shown in Scheme 9. A wide array of amine-protecting groups are available (see, for example, T. W. Greene and P. G. M. Wuts, *Protective Groups in Organic Synthesis.* 2nd ed.; Wiley: New York, 1991), and the use and choice of the appropriate protecting groups will be apparent to one skilled in chemical synthesis. The protecting group can be removed and the amine isolated as its acid salt or the free amine by general methods known in the art. One skilled in the art will also recognize that the protected amines of Formula 14 can be prepared by methods analogous to those described in Schemes 6, 7, and 8 above where the group $R^1AC(=W)$ is replaced by $Y^3$ to give useful intermediates of Formula 14 for the preparation of compounds of Formula 1.

Scheme 9

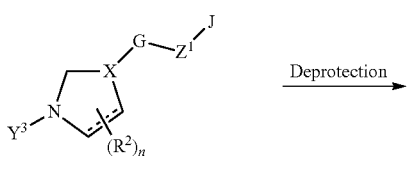

wherein $Y^3$ is an amine protecting group

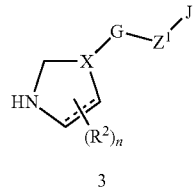

The compounds of Formula 14 can also be prepared by reaction of a suitably functionalized compound of Formula 15 with a suitably functionalized compound of Formula 16 as shown in Scheme 10. The functional groups $Y^4$ and $Y^5$ are selected from, but not limited to, moieties such as aldehydes, ketones, esters, acids, amides, thioamides, nitriles, amines, alcohols, thiols, hydrazines, oximes, amidines, amideoximes, olefins, acetylenes, halides, alkyl halides, methanesulfonates, trifluoromethanesulfonates, boronic acids, boronates, and the like, which under the appropriate reaction conditions, will allow the construction of the various heterocyclic rings G. As an example, reaction of a compound of Formula 15 where $Y^4$ is a thioamide group with a compound of Formula 16 where $Y^5$ is a bromoacetyl group will give a compound of Formula 14 where G is a thiazole ring. The synthetic literature describes many general methods for forming 5-membered heteroaromatic rings and 5-membered partially saturated heterocyclic rings (e.g., G-1 through G-59); see, for example, *Comprehensive Heterocyclic Chemistry*, Vol. 4-6, A. R. Katritzky and C. W. Rees editors, Pergamon Press, New York, 1984; *Comprehensive Heterocyclic Chemistry II*, Vol. 2-4, A. R. Katritzky, C. W. Rees, and E. F. Scriven editors, Pergamon Press, New York, 1996; and the series, *The Chemistry of Heterocyclic Compounds*, E. C. Taylor, editor, Wiley, New York. The use of intermediates of Formula 15 where X is $X^1$ and $Y^4$ is Br, I, methanesulfonate or trifluoromethanesulfonate to prepare organozinc reagents for use in cross-coupling reactions with aromatic rings has been described; see, for example, S. Bellotte. *Synlett* 1998, 379-380, and M. Nakamura et al., *Synlett* 2005, 1794-1798. One skilled in the art knows how to select the appropriate functional groups to construct the desired heterocyclic rings such as G. Compounds of Formula 15 and 16 are known or can be prepared by one skilled in the art.

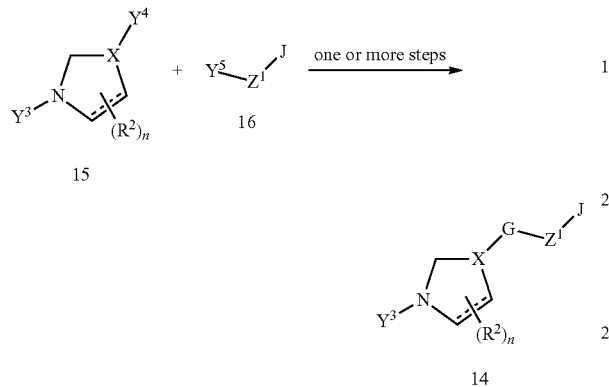

Scheme 10 wherein $Y^4$ and $Y^5$ are functional groups suitable for construction of the desired heterocycle G.

Certain compounds of Formula 14 where $Z^1$ is O, S, or $NR^{21}$ can be prepared by displacement of an appropriate leaving group $Y^2$ on G of Formula 17 with a compound of Formula 18 in the presence of a base as depicted in Scheme 11. Suitable bases include sodium hydride or potassium carbonate, and the reaction is carried out in a solvent such as N,N-dimethylformamide or acetonitrile at 0 to 80° C. Suitable leaving groups in the compounds of Formula 17 include bromide, iodide, mesylate $(OS(O)_2CH_3)$, triflate $(OS(O)_2CF_3)$ and the like. Compounds of Formula 17 can be prepared from corresponding compounds wherein $Y^2$ is OH by general methods known in the art. Many of the compounds of Formula 18 are known or can be prepared by general methods known in the art.

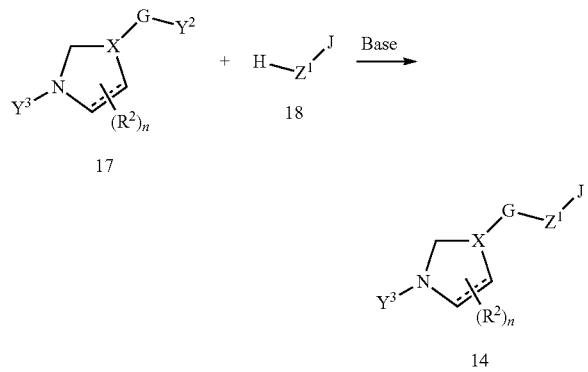

Scheme 11 wherein $Y^2$ is a leaving group such as Br, I, $OS(O)_2Me$ or $OS(O)_2CF_3$; and $Z^1$ is O, S or $NR^{21}$.

Certain compounds of Formula 14 where $Z^1$ is O, S, or $NR^{21}$ can also be prepared by displacement of an appropriate leaving group $Y^2$ on J of Formula 20 with a compound of Formula 19 in the presence of a base as depicted in Scheme 12. Suitable bases include sodium hydride or potassium carbonate, and the reaction is carried out in a solvent such as N,N-dimethylformamide or acetonitrile at 0 to 80° C. Suitable leaving groups in the compounds of Formula 20 include bromide, iodide, mesylate $(OS(O)_2CH_3)$, triflate $(OS(O)_2CF_3)$ and the like. Compounds of Formula 20 can be prepared from corresponding compounds wherein $Y^2$ is OH using general methods known in the art.

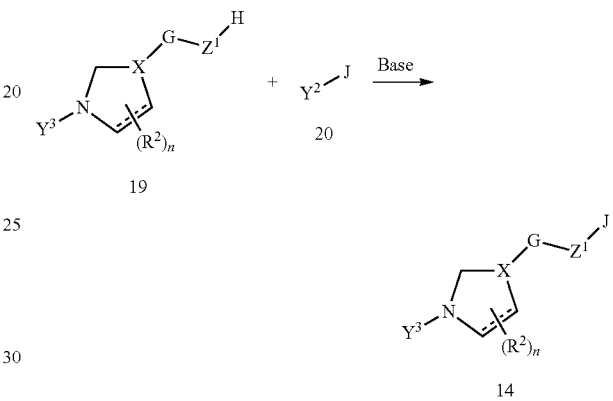

Scheme 12 wherein $Y^2$ is a leaving group such as Br, I, $OS(O)_2Me$ or $OS(O)_2CF_3$; and $Z^1$ is O, S or $NR^{21}$.

Compounds of Formula 14 can also be prepared by reaction of a suitably functionalized compound of Formula 21 with a suitably functionalized compound of Formula 22 as shown in Scheme 13. The functional groups $Y^6$ and $Y^7$ are selected from, but not limited to, moieties such as aldehydes, ketones, esters, acids, amides, thioamides, nitriles, amines, alcohols, thiols, hydrazines, oximes, amidines, amide oximes, olefins, acetylenes, halides, alkyl halides, methanesulfonates, trifluoromethanesulfonates, boronic acids, boronates, and the like, which, under the appropriate reaction conditions will allow the construction of the various heterocyclic rings J. As an example, reaction of a compound of Formula 21 where $Y^6$ is a chloro oxime moiety with a compound of Formula 22 where $Y^7$ is a vinyl or acetylene group in the presence of base will give a compound of Formula 14 where J is an isoxazoline or isoxazole, respectively. The synthetic literature includes many general methods for the formation of carbocyclic and heterocyclic rings and ring systems (for example, J-1 through J-82); see, for example, *Comprehensive Heterocyclic Chemistry*, Vol. 4-6, A. R. Katritzky and C. W. Rees editors, Pergamon Press, New York, 1984; *Comprehensive Heterocyclic Chemistry II*, Vol. 2-4, A. R. Katritzky, C. W. Rees, and E. F. Scriven editors, Pergamon Press, New York, 1996; the series, *The Chemistry of Heterocyclic Compounds*, E. C. Taylor, editor, Wiley, New York, and *Rodd's Chemistry of Carbon Compounds*, Vol. 2-4, Elsevier, New York. General procedures for cycloaddition of nitrile oxides with olefins are well documented in the chemical literature. For relevant references see Lee, *Synthesis* 1982, 6, 508-509 and Kanemasa et al., *Tetrahedron* 2000, 56, 1057-1064 as well as references cited within. One skilled in the art knows how to select the appropriate functional groups to construct the desired heterocyclic ring J. Compounds of Formula 22 are known or can be prepared by general methods known in the art.

wherein $Y^6$ and $Y^7$ are functional groups suitable for construction of the desired heterocycle J.

An alternate preparation for the compounds of Formula 14 where $Z^1$ is a bond includes the well known Suzuki reaction involving Pd-catalyzed cross-coupling of an iodide or bromide of Formula 23 or 26 with a boronic acid of Formula 24 or 25, respectively, as shown in Scheme 14. Many catalysts are useful for this type of transformation; a typical catalyst is tetrakis(triphenylphosphine)palladium. Solvents such as tetrahydrofuran, acetonitrile, diethyl ether and dioxane are suitable. The Suzuki reaction and related coupling procedures offer many alternatives for creation of the G-J bond. For leading references see for example C. A. Zificsak and D. J. Hlasta, *Tetrahedron* 2004, 60, 8991-9016. For a thorough review of palladium chemistry applicable to the synthesis of G-J bonds see J. J. Li and G. W. Gribble, editors, *Palladium in Heterocyclic Chemistry: A Guide for the Synthetic Chemist*, Elsevier: Oxford, UK, 2000. Many variations of catalyst type, base and reaction conditions are known in the art for this general method.

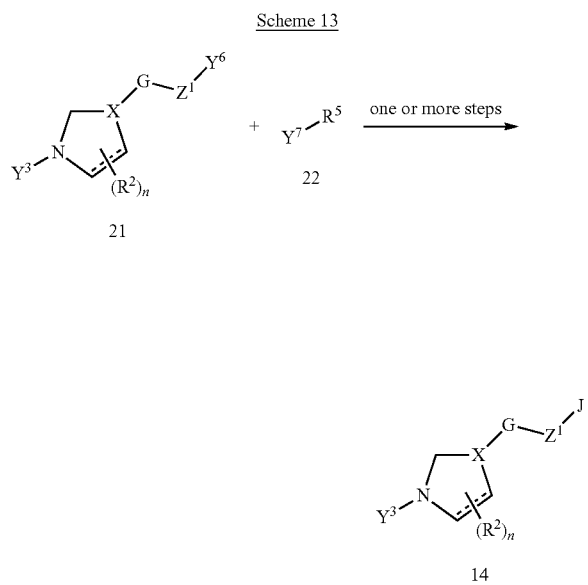

Scheme 13

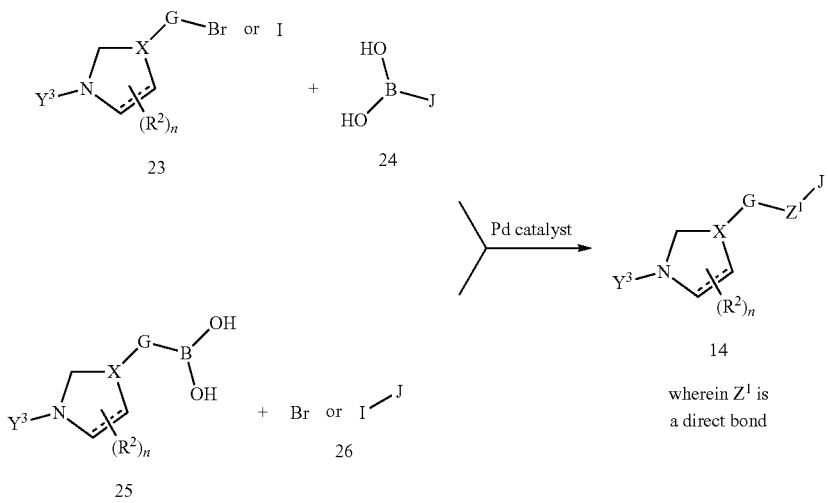

Scheme 14

One skilled in the art will recognize that many compounds of Formula 1 can be prepared directly by methods analogous to those described in Schemes 10 through 14 above where the group Y³ is replaced by R¹AC(=W). Thus, compounds corresponding to Formulae 15, 17, 19, 21, 23 and 25 in which Y³ is replaced by R¹AC(=W) are useful intermediates for the preparation of compounds of Formula 1.

Thioamides of Formula 1Bb are particularly useful intermediates for preparing compounds of Formula 1 wherein X is X¹. A thioamide of Formula 1Bb can be prepared by the addition of hydrogen sulfide to the corresponding nitrile of Formula 1Ba as shown in Scheme 15.

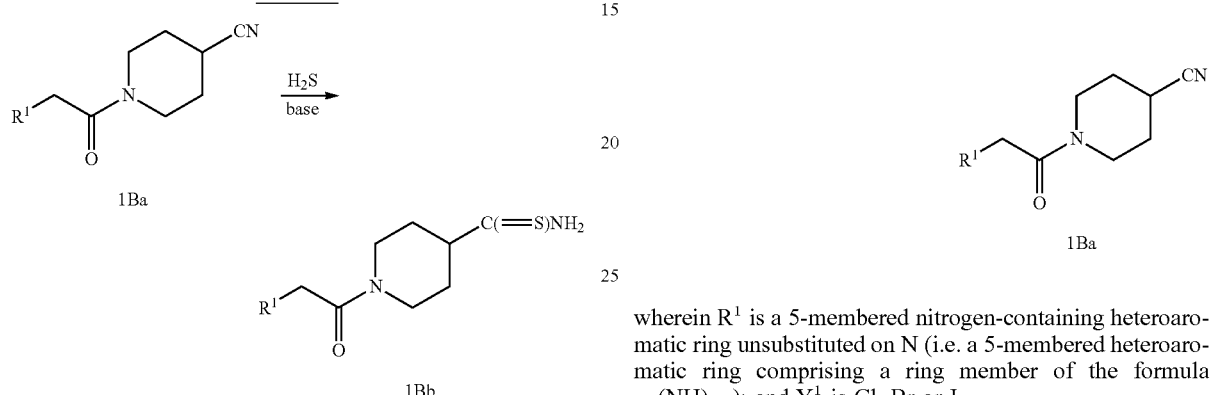

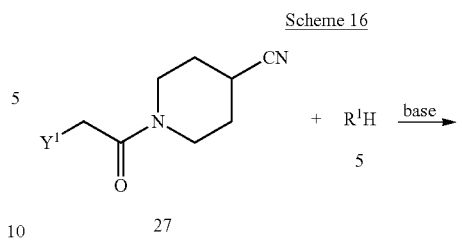

wherein R¹ is a 5-membered nitrogen-containing heteroaromatic ring unsubstituted on N (i.e. a 5-membered heteroaromatic ring comprising a ring member of the formula —(NH)—); and Y¹ is Cl, Br or I.

The haloacetamides of Formula 27 can be prepared by the two methods shown in Scheme 17.

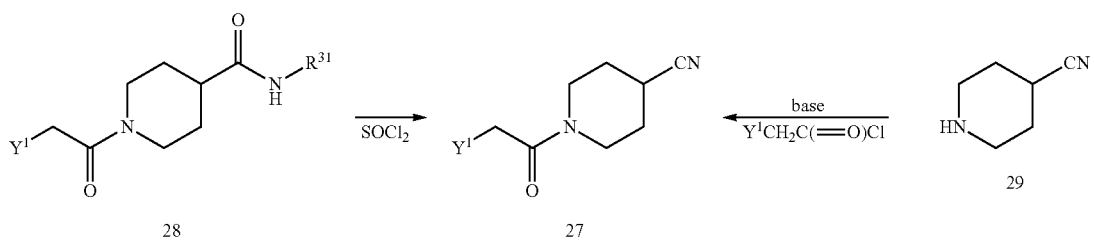

The method of Scheme 15 can be carried out by contacting a compound of Formula 1Ba with hydrogen sulfide in the presence of an amine such as pyridine, diethylamine or diethanolamine. Alternatively, hydrogen sulfide can be used in the form of its bisulfide salt with an alkali metal or ammonia. This type of reaction is well documented in the literature (e.g., A. Jackson et al., EP 696,581 (1996)).

Certain compounds of Formula 1Ba wherein R¹ is a 5-membered nitrogen-containing heteroaromatic ring linked through a nitrogen atom can be prepared by reaction of the parent heterocycle of Formula 5 and a haloacetamide of Formula 27 as shown in Scheme 16. The reaction is carried out in the presence of a base such as sodium hydride or potassium carbonate in a solvent such as tetrahydrofuran, N,N-dimethylformamide or acetonitrile at 0 to 80° C.

wherein Y¹ is Cl, Br, or I; and R³¹ is a tertiary alkyl group such as —C(Me)₃.

In one method, 4-cyanopiperidine of Formula 29 is haloacetylated by contact with the appropriate haloacetyl chloride typically in the presence of a base according to standard methods. Preferred conditions involve use of an aqueous solution of an inorganic base such as an alkali metal or alkaline-earth carbonate, bicarbonate, or phosphate, and a non-water-miscible organic solvent such as toluene, ethyl acetate or 1,2-dichloroethane. In the second method depicted in Scheme 17, a 1-(haloacetyl)-N-substituted isonipecotamide derivative of Formula 28, wherein R³¹ is tertiary alkyl such as C(Me)₃, is dehydrated using a standard amide dehydrating agent such as thionyl chloride or phosphorus oxychloride in a suitable solvent. A particularly preferred solvent for this transformation is an N,N-dialkylamide such as N,N-dimethylformamide. The reaction is typically carried out by adding 0.9 to 2 equivalents, preferably 1.1 equivalents, of phosphorus oxychloride or thionyl chloride, to a mixture of a compound of Formula 28 and 0.5 to 10 parts by weight of solvent, at a temperature at which the reaction rapidly proceeds during the addition. The addition time for this reaction is typically around 20 to 90 minutes at typical temperatures of around 35 to 55° C.

As shown in Scheme 18, the compounds of Formula 28 can be prepared from the compound of Formula 30 by analogy with the haloacetylation reaction described for Scheme 17.

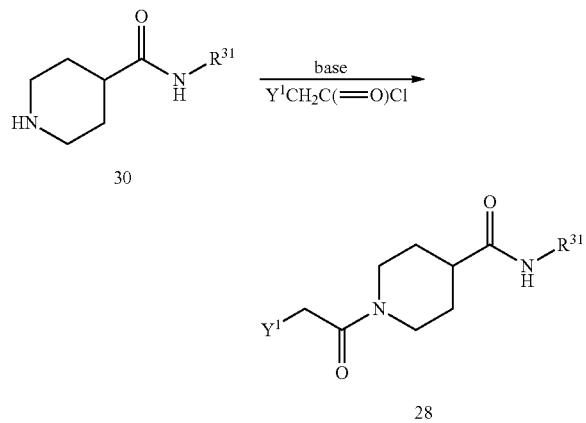

The compounds of Formula 30 are known or can be prepared from 4-cyanopyridine or isonicotinic acid using methods well-known in the art; see, for example, G. Marzolph, et al., DE 3,537,762 (1986) for preparation of N-t-butyl pyridinecarboxamides from cyanopyridines and t-butanol and S. F. Nelsen, et al., J. Org. Chem., 1990, 55, 3825 for hydrogenation of N-methylisonicotinamide with a platinum catalyst.

Halomethyl isoxazole ketones of Formula 35 are particularly useful intermediates for preparing certain chiral compounds of Formula 1 wherein J is, for example, selected from J-29-1 through J-29-12 as depicted in Exhibit A.

Halomethyl isoxazole ketones of Formula 35 can be prepared by the multi-step reaction sequences shown in Scheme 19.

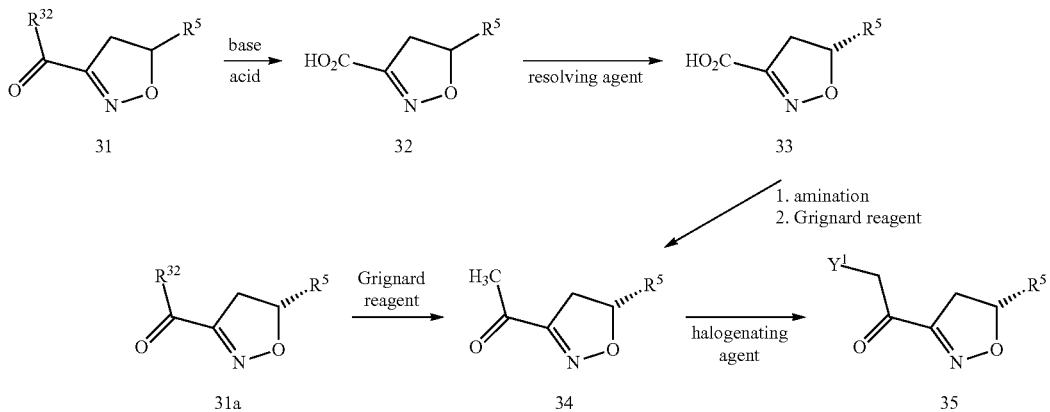

wherein $R^{32}$ is $C_2$-$C_8$ dialkylamino, $C_2$-$C_6$ haloalkylamino, 1-piperidinyl, 1-pyrrolidinyl or 4-morpholinyl; and $R^5$ are as defined above in the Summary of the Invention.

The preparation of the racemic carboxylic acids of Formula 32 can be accomplished according to the well-known methods of basic or acidic hydrolysis of the corresponding compounds of Formula 31, preferably using a slight excess of sodium hydroxide in a water-miscible co-solvent such as methanol or tetrahydrofuran at about 25 to 45° C. The product can be isolated by adjusting pH to about 1 to 3 and then filtration or extraction, optionally after removal of the organic solvent by evaporation. The racemic carboxylic acids of Formula 32 can be resolved by classical fractional crystallization of diastereomeric salts of suitable chiral amine bases such as cinchonine, dihydrocinchonine or a mixture thereof. A cinchonine-dihydrocinchonine mixture in about a 85:15 ratio is particularly useful, as it provides, for example, the (R)-configured carboxylic acids of Formula 33, wherein $R^5$ is a substituted phenyl group, as the less soluble salt. Furthermore, these chiral amine bases are readily available on a commercial scale. The (R)-configured halomethyl ketone intermediates of Formula 35 afford the more fungicidally active final products of Formula 1 after coupling with thioamides of Formula 1Bb. The halomethyl ketones of Formula 35 can be prepared by first reacting the corresponding amides of Formula 31, either as pure enantiomers (i.e. Formula 31a) or in enantiomerically enriched or racemic mixtures, with one molar equivalent of a methylmagnesium halide (Grignard reagent) in a suitable solvent or solvent mixture such as tetrahydrofuran and toluene at about 0 to 20° C., and the crude ketone products of Formula 34 can be isolated by quenching with aqueous acid, extraction, and concentration. Then the crude ketones of Formula 34 are halogenated with a reagent such as sulfuryl chloride to afford the chloromethyl ketones of Formula 35 wherein $Y^1$ is Cl or molecular bromine to afford the corresponding bromomethyl ketones of Formula 35 wherein $Y^1$ is Br. The halomethyl ketones of Formula 35 can be purified by crystallization from a solvent such as hexanes or methanol, or can be used without further purification in the condensation reaction with thioamides.

The isoxazole carboxamides of Formula 31 can be prepared by cycloaddition of the corresponding hydroxamoyl chlorides of Formula 36 with olefin derivatives of Formula 37, as shown in Scheme 20.

Scheme 20

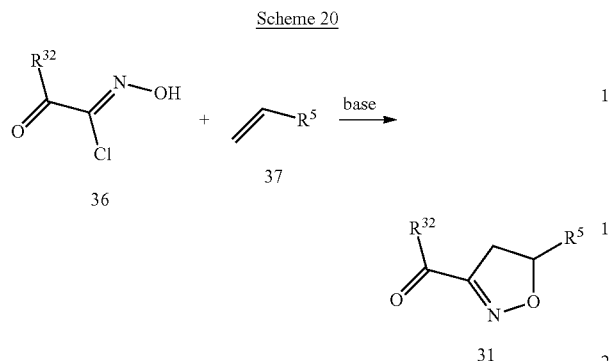

In this method, all three reacting components (the compounds of Formulae 36 and 37, and the base) are contacted so as to minimize hydrolysis or dimerization of the hydroxamoyl chloride of Formula 36. In one typical procedure, the base, which can either be a tertiary amine base such as triethylamine or an inorganic base such as an alkali metal or alkaline-earth carbonate, bicarbonate or phosphate, is mixed with the olefin derivative of Formula 37, and the hydroxamoyl chloride of Formula 36 is added gradually at a temperature at which the cycloaddition proceeds at a relatively rapid rate, typically between 5 and 25° C. Alternatively, the base can be added gradually to the other two components (the compounds of Formulae 36 and 37). This alternative procedure is preferable when the hydroxamoyl chloride of Formula 36 is substantially insoluble in the reaction medium. The solvent in the reaction medium can be water or an inert organic solvent such as toluene, hexane or even the olefin derivative used in excess. The product can be separated from the salt co-product by filtration or washing with water, followed by evaporation of the solvent. The crude product can be purified by crystallization, or the crude product can be used directly in the methods of Scheme 19. Compounds of Formula 31 are useful precursors to the corresponding methyl ketones of Formula 34 and halomethyl ketones of Formula 35, and are also useful for preparing the resolved enantiomers of the compounds of Formulae 34 and 35 by hydrolysis, resolution, methyl ketone synthesis and halogenation, as shown in Scheme 19.

It is recognized that some reagents and reaction conditions described above for preparing compounds of Formulae 1, 1A, 1B and 1C may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, T. W. Greene and P. G. M. Wuts, *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formulae 1, 1A, 1B and 1C. One skilled in the art will also recognize that it may be necessary to perform a combination of the steps illustrated in the above schemes in an order other than that implied by the particular sequence presented to prepare the compounds of Formulae 1, 1A, 1B and 1C.

One skilled in the art will also recognize that compounds of Formulae 1, 1A, 1B and 1C and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "m" means multiplet, "q" means quartet, "dd" means doublet of doublet, "br s" means broad singlet, "br d" means broad doublet. "br t" means broad triplet, "br m" means broad multiplet.

EXAMPLE 1

Preparation of 4-[4-[4,5-dihydro-5-phenyl-3-isoxazolyl]-2-thiazolyl]-1-[[5-methyl-3-(trifluoromethyl)-1H-pyrazol-1-yl]acetyl]piperidine (Compound 1)

Step A: Preparation of 1,1-dimethylethyl 4-[4-(4,5-dihydro-5-phenyl-3-isoxazolyl)-2-thiazolyl]-1-piperidinecarboxylate To a suspension of 1,1-dimethylethyl 4-(4-formyl-2-thiazolyl)-1-piperidinecarboxylate (1.0 g, 3.4 mmol) in ethanol (5 mL) was added an aqueous solution of hydroxylamine (50 wt. %, 0.25 mL, 4.0 mmol). The reaction mixture was heated at 60° C. for 1 h, during which time the reaction mixture became homogeneous. The resulting solution was cooled to room temperature and diluted with tetrahydrofuran (10 mL). To the reaction mixture was added styrene (0.57 mL, 5 mmol), followed by portionwise addition of Clorox® aqueous sodium hypochlorite solution (10.5 mL) over 3 h. The reaction mixture was stirred overnight at room temperature, and the resulting solid was filtered, washed with water and diethyl ether, and air dried to give the title compound as a white powder (610 mg). The filtrate was diluted with saturated aqueous sodium bicarbonate solution and extracted with diethyl ether. The extract was dried (MgSO$_4$) and concentrated under reduced pressure to give 850 mg of the title compound as a yellow oil. The oil was diluted with diethyl ether (4 mL) and allowed to stand to give additional 233 mg of the product as a white solid.

$^1$H NMR (CDCl$_3$) δ 1.47 (s, 9H), 1.7 (m, 2H), 2.1 (m, 2H), 2.85 (m, 2H), 3.2 (m, 1H), 3.45 (m, 1H), 3.84 (m, 1H) 4.2 (br s, 2H), 5.75 (m, 1H), 7.25-7.40 (m, 5H), 7.61 (s, 1H).

Step B: Preparation of 4-[4-[4,5-dihydro-5-phenyl-3-isoxazolyl]-2-thiazolyl]-1-[[5-methyl-3-(trifluoromethyl)-1H-pyrazol-1-yl]acetyl]piperidine To a solution of 1,1-dimethylethyl 4-[4-(4,5-dihydro-5-phenyl-3-isoxazolyl)-2-thiazolyl]-1-piperidinecarboxylate (i.e. the product of Example 1, Step A) (0.815 g, 1.97 mmol) in dichloromethane (50 mL) was added a solution of hydrogen chloride in diethyl ether (2 M, 10 mL, 20 mmol). The reaction mixture was stirred at room temperature for 1 h to give a gummy precipitate. Methanol was added to dissolve the precipitate, and the reaction mixture was stirred for an additional 1 h. The reaction mixture was concentrated under reduced pressure and partitioned between ethyl acetate and saturated aqueous sodium bicarbonate solution, and the organic layer was dried ($MgSO_4$) and concentrated to give the free amine as a clear oil (0.31 g), which solidified on standing. A mixture of the resulting free amine (0.31 g, 1.0 mmol), 5-methyl-3-(trifluoromethyl)-1H-pyrazole-1-acetic acid (0.208 g, 1.0 mmol), 1-[3-(dimethylamino)propyl]-3-ethylcarbodiimide hydrochloride (0.25 g, 1.3 mmol), triethylamine (150 μL, 1.08 mmol) and a catalytic amount of 1-hydroxybenzotriazole hydrate (~1 mg) in dichloromethane (5 mL) was swirled to form a vortex and held at room temperature for 16 h. The reaction mixture was diluted with dichloromethane (10 mL), and washed with 1 N aqueous hydrochloric acid and saturated aqueous sodium bicarbonate solution. The organic layer was dried ($MgSO_4$) and concentrated under reduced pressure to give 0.47 g of the title product, a compound of present invention, as a white foam.

$^1$H NMR ($CDCl_3$) δ 1.8 (m, 2H), 2.2 (m, 2H), 2.32 (s, 3H), 2.9 (m, 1H), 3.3 (m, 2H), 3.42 (m, 1H), 3.85 (m, 1H) 4.05 (m, 1H), 4.55 (m, 1H), 4.98 (m, 2H), 5.75 (m, 1H), 6.33 (s, 1H), 7.25-7.42 (m, 5H), 7.63 (s, 1H).

The following compounds were prepared by procedures analogous to Step B of Example 1:

1-[4-[4-(4,5-dihydro-5-phenyl-3-isoxazolyl)-2-thiazolyl]-1-piperidinyl]-2-[3-methyl-5-(trifluoromethyl)-1H-pyrazol-1-yl]ethanone (Compound 128); $^1$H NMR ($CDCl_3$) δ 1.7-1.9 (m, 2H), 2.16 (m, 1H), 2.24 (m, 1H), 2.29 (s, 3H), 2.84-2.92 (br t, 1H), 3.30 (m, 2H), 3.43 (m, 1H), 3.86 (m, 2H), 4.59 (br d, 1H), 5.04 (s, 2H), 5.75 (m, 1H), 6.47 (s, 1H), 7.29-7.39 (m, 5H), 7.64 (s, 1H).

1-[4-[4-(4,5-dihydro-5-phenyl-3-isoxazolyl)-2-thiazolyl]-1-piperidinyl]-2-[5-ethyl-3-(trifluoromethyl)-1H-pyrazol-1-yl]ethanone (Compound 19); m.p. 128-133° C. (crystallized from methyl acetate/petroleum ether); $^1$H NMR ($CDCl_3$) δ 1.28 (t, 3H), 1.8 (m, 2H), 2.2 (m, 2H), 2.62 (q, 2H), 2.9 (m, 1H), 3.3 (m, 2H), 3.42 (m, 1H), 3.85 (m, 1H) 4.05 (m, 1H), 4.55 (m, 1H), 4.98 (m, 2H), 5.75 (m, 1H), 6.33 (s, 1H), 7.25-7.42 (m, 5H), 7.63 (s, 1H).

2-[3,5-bis(trifluoromethyl)-1H-pyrazol-1-yl]-1-[4-[4-(4,5-dihydro-5-phenyl-3-isoxazolyl)-2-thiazolyl]-1-piperidinyl]ethanone (Compound 22) m.p. 130-133° C. (crystallized from methyl acetate/petroleum ether); $^1$H NMR ($CDCl_3$) δ 1.8 (m, 2H), 2.2 (m, 2H), 2.9 (m, 1H), 3.3 (m, 2H), 3.42 (m, 1H), 3.85 (m, 2H), 4.55 (m, 1H), 5.10 (s, 2H), 5.77 (m, 1H), 6.95 (s, 1H), 7.25-7.42 (m, 5H), 7.64 (s, 1H).

1-[4-[4-(2,3-dihydrospiro[4H-1-benzopyran-4,5'(4'H)-isoxazol]-3'-yl]-2-thiazolyl]-1-piperidinyl]-2-[5-methyl-3-(trifluoromethyl)-1H-pyrazol-1-yl]ethanone (Compound 137); $^1$H NMR ($CDCl_3$) δ 1.83 (m, 2H), 2.18 (m, 3H), 2.33 (s, 3H), 2.42 (m, 1H), 2.90 (m, 1H), 3.31 (m, 2H), 3.47 (d, 1H), 3.83 (d, 1H), 4.05 (m, 1H), 4.27 (m, 1H), 4.40 (m, 1H), 4.58 (d, 1H), 4.97 (m, 2H), 6.33 (s, 1H), 6.87 (d, 1H), 6.95 (dd, 1H), 7.21 (dd, 1H), 7.38 (d, 1H), 7.67 (s, 1H).

1-[4-[4-(2,3-dihydrospiro[4H-1-benzothiopyran-4,5'(4'H)-isoxazol]-3'-yl)-2-thiazolyl]-1-piperidinyl]-2-[5-methyl-3-(trifluoromethyl)-1H-pyrazol-1-yl]ethanone (Compound 102); $^1$H NMR ($CDCl_3$) δ 1.82 (m, 2H), 2.23 (m, 2H), 2.31 (s, 3H), 2.37 (m, 1H), 2.50 (m, 1H), 2.90 (m, 1H), 3.14 (m, 1H), 3.17 (m, 1H), 3.27 (m, 2H), 3.48 (d, 1H), 3.66 (d, 1H), 4.05 (m, 1H), 4.57 (d, 1H), 4.97 (m, 2H), 6.33 (s, 1H), 7.06 (m, 3H), 7.45 (d, 1H), 7.65 (s, 1H).

EXAMPLE 2

Preparation of 1-[[5-methyl-3-(trifluoromethyl)-1H-pyrazol-1-yl]acetyl]-4-[4-(5-phenyl-3-isoxazolyl)-2-thiazolyl]piperidine (Compound 2)

Step A: Preparation of 2-(4-piperidinyl)-4-thiazolecarboxaldehyde monohydrochloride To a solution of 1,1-dimethylethyl 4-(4-formyl-2-thiazolyl)-1-piperidinecarboxylate (1.0 g, 3.4 mmol) in dichloromethane (20 mL) was added a solution of hydrogen chloride in diethyl ether (2.0 mL, 15 ml, 30 mmol). The reaction mixture was stirred under nitrogen at room temperature for 2 h and then evaporated under reduced pressure to give 1.2 g of the title compound as a white solid.

$^1$H NMR ($CDCl_3$) δ 2.31-2.38 (m, 2H), 2.44-2.50 (m, 2H), 3.11-3.20 (m, 2H), 3.36-3.44 (m, 1H), 3.57-3.65 (m, 2H), 8.14 (s, 1H), 10.01 (s, 1H).

Step B: Preparation of 4-(4-formyl-2-thiazolyl)-1-[[5-methyl-3-(trifluoromethyl)-1H-pyrazol-1-yl]acetyl]piperidine To a solution of 5-methyl-3-(trifluoromethyl)-1H-pyrazole-1-acetic acid (0.8 g, 3.8 mmol) in dichloromethane (10 mL) was added oxalyl chloride (2.4 g, 19.2 mmol) and two drops of N,N-dimethylformamide, resulting in slight exothermicity. The reaction mixture was then heated at reflux for 15 minutes. The reaction mixture was concentrated in vacuo, and the residue was suspended in tetrahydrofuran (10 mL) and treated with a solution of 2-(4-piperidinyl)-4-thiazolecarboxaldehyde monohydrochloride (i.e. the product of Example 2, Step A) (1.1 g, 5.1 mmol) in tetrahydrofuran (10 mL), followed by dropwise addition of triethylamine (1.2 g, 11.9 mmol). The reaction mixture was stirred overnight at room temperature and then partitioned between 1 N aqueous hydrochloric acid and ethyl acetate. The organic layer was separated, and the aqueous layer was extracted with additional ethyl acetate (2×30 mL). The combined organic layers were washed with 1 N aqueous hydrochloric acid, saturated aqueous sodium bicarbonate solution, and brine. The organic layer was dried ($MgSO_4$) and evaporated under reduced pressure to give 0.8 g of the title compound as a yellow oil.

$^1$H NMR ($CDCl_3$) δ 1.79-1.90 (m, 2H), 2.18-2.29 (m, 2H), 2.33 (s, 3H), 2.87-2.94 (m, 1H), 3.28-3.40 (m, 2H), 4.05-4.15 (m, 1H), 4.56-4.64 (m, 1H), 4.99-5.02 (m, 2H), 6.35 (s, 1H), 8.12 (s, 1H), 10.01 (s, 1H).

Step C: Preparation of 4-[4-[(hydroxyimino)methyl]-2-thiazolyl]-1-[[5-methyl-3-(trifluoromethyl)-1H-pyrazol-1-yl]acetyl]piperidine To a solution of 4-(4-formyl-2-thiazolyl)-1-[[5-methyl-3-(trifluoromethyl)-1H-pyrazol-1-yl]acetyl]piperidine (i.e. the product of Example 2, Step B) (0.8 g, 2.07 mmol) in ethyl alcohol (15 mL) was added hydroxylamine (50% aqueous solution, 0.136 g, 4.1 mmol), and the reaction mixture was stirred at room temperature for 10 minutes. The reaction mixture was concentrated under reduced pressure to give a yellow oil, which was purified by flash column chromatography on silica gel using 50% ethyl acetate in hexanes as eluant to give 0.7 g of the title compound as a white solid.

$^1$H NMR (CDCl$_3$) δ 1.72-1.85 (m, 2H), 2.17-2.27 (m, 2H), 2.32 (s, 3H), 2.82-2.91 (m, 1H), 3.25-3.37 (m, 2H), 4.02-4.09 (m, 1H), 4.58-4.63 (m, 1H), 4.95-5.03 (m, 2H), 6.35 (s, 1H), 7.43 (s, 1H), 7.71 (s, 1H), 8.19 (s, 1H).

Step D: Preparation of 1-[[5-methyl-3-(trifluoromethyl)-1H-pyrazol-1-yl]acetyl]-4-[4-(5-phenyl-3-isoxazolyl)-2-thiazolyl]piperidine 4-[4-[(Hydroxyimino)methyl]-2-thiazolyl]-1-[[5-methyl-3-(trifluoromethyl)-1H-pyrazol-1-yl]acetyl]piperidine (i.e. the product of Example 2, Step C) (0.2 g, 0.5 mmol) was suspended in tetrahydrofuran (20 mL), and phenylacetylene (1.1 mL, 1 mmol) was added, followed by a slow dropwise addition of Clorox® bleach solution (6.15 wt. % sodium hypochlorite, 10 mL) over 1 h. The reaction mixture was partitioned between saturated aqueous sodium bicarbonate solution and ethyl acetate. The organic layer was separated, and the aqueous layer was extracted with ethyl acetate (3×30 mL). The combined organic layers were washed with brine, dried (MgSO$_4$) and concentrated under reduced pressure to give an oil, which was purified by flash column chromatography on silica gel using 10% methanol in ethyl acetate as eluant to give 70 mg of the title product, a compound of present invention, as a clear yellow oil.

$^1$H NMR (CDCl$_3$) δ 1.80-1.92 (m, 2H), 2.22-2.32 (m, 2H), 2.34 (s, 3H), 2.90-2.98 (m, 1H), 3.31-3.41 (m, 2H), 4.05-4.11 (m, 1H), 4.58-4.65 (m, 1H), 4.97-5.07 (m, 2H), 6.36 (s, 1H), 6.98 (s, 1H), 7.47-7.53 (m, 3H), 7.84 (s, 2H), 7.88 (m, 1H).

EXAMPLE 3

Preparation of 4-[4-(4,5-dihydro-1-methyl-5-phenyl-1H-imidazol-2-yl)-2-thiazolyl]-1-[[5-methyl-3-(trifluoromethyl)-1H-pyrazol-1-yl]acetyl]piperidine (Compound 7)

To a solution of 4-(4-formyl-2-thiazolyl)-1-[[5-methyl-3-(trifluoromethyl)-1H-pyrazol-1-yl]acetyl]piperidine (i.e. the product of Example 2, Step B) (0.8 g, 2.07 mmol) in tert-butanol (5 mL) was added NI-methyl-1-phenyl-1,2-ethanediamine (43.57 mg, 0.29 mmol). The reaction mixture was stirred at room temperature under a nitrogen atmosphere for 30 minutes, and then potassium carbonate (107.8 mg, 0.78 mmol) and iodine (43.57 mg, 0.33 mmol) were added. The reaction mixture was stirred at 70° C. for 3 h and then quenched by addition of saturated aqueous sodium sulfite solution until the iodine color almost disappeared. The reaction mixture was extracted with chloroform, and the organic layer was washed with saturated aqueous sodium bicarbonate solution and brine, dried (Na$_2$SO$_4$), filtered and concentrated. The residue was purified by preparative thin-layer chromatography on silica gel using a mixture of 94% ethyl acetate, 5% methanol and 1% triethylamine as eluant to give 64 mg of the title product, a compound of the present invention, as an oil.

$^1$H NMR (CDCl$_3$) δ 1.72-1.87 (m, 2H), 2.15-2.28 (m, 2H), 2.31 (s, 3H), 2.86-2.92 (m, 1H), 2.97 (s, 3H), 3.26-3.37 (m, 2H), 3.62-4.39 (m, 2H), 4.0-4.6 (m, 2H), 4.93-5.05 (m, 2H), 6.31 (s, 1H), 7.30-7.41 (m, 5H), 7.88 (s, 1H).

EXAMPLE 4

Preparation of 4-[4-(4,5-dihydro-3-phenyl-5-isoxazolyl)-2-thiazolyl]-1-[(5-methyl-3-(trifluoromethyl)-1H-pyrazol-1-yl)acetyl]piperidine (Compound 6)

Step A: Preparation of 1,1-dimethylethyl 4-(4-ethenyl-2-thiazolyl)-1-piperidinecarboxylate To a cold (−50° C.) suspension of methyltriphenylphosphonium bromide (1.2 g, 3.3 mmol) in tetrahydrofuran (5 mL) was added a solution of sodium bis(trimethylsilyl)amide (3.4 mL, 3.4 mmol), and the resulting mixture was stirred for 1 h at room temperature. The resulting cloudy yellow solution was re-cooled to −30° C., and 1,1-dimethylethyl 4-(4-formyl-2-thiazolyl)-1-piperidinecarboxylate (0.5 g, 1.68 mmol) was added. The resulting slightly yellow solution was stirred at room temperature for 3 h, then diluted with water, and extracted with ethyl acetate. The organic layer was washed with brine, dried (MgSO$_4$), filtered, and purified by column chromatography on silica gel using 15-30% ethyl acetate in hexanes as eluant to give 471 mg of the title compound as a colorless oil.

$^1$H NMR (CDCl$_3$) δ 1.47 (s, 9H), 1.68 (m, 2H), 2.10 (m, 2H), 2.88 (m, 2H), 3.15 (m, 1H), 4.18 (m, 2H), 5.34 (d, 1H), 6.02 (d, 1H), 6.68 (dd, 1H), 6.99 (s, 1H).

Step B: Preparation of 4-(4-ethenyl-2-thiazolyl)piperidine

To a solution of 1,1-dimethylethyl 4-(4-ethenyl-2-thiazolyl)-1-piperidinecarboxylate (i.e. the product of Example 4, Step A) (471 mg, 1.6 mmol) in dichloromethane (5 mL) was added a solution of hydrogen chloride in diethyl ether (2.0 M, 7 mL, 14 mmol). The reaction mixture was stirred under nitrogen at room temperature for 4 h, and then 1 N aqueous sodium hydroxide solution was added until pH of the reaction mixture increased to about 10. The resulting mixture was extracted with dichloromethane (2×). The organic layers were combined, washed with brine, dried (MgSO$_4$), filtered and concentrated in vacuo to give 302 mg of the title compound as an oil.

$^1$H NMR (CDCl$_3$) δ 1.70 (m, 2H), 1.82 (br s, 1H), 2.12 (br d, 2H), 2.76 (br t, 2H), 3.11 (m, 1H), 3.18 (m, 2H), 5.32 (d, 1H), 6.02 (d, 1H), 6.70 (dd, 1H), 6.99 (s, 1H).

Step C: Preparation of 4-(4-ethenyl-2-thiazolyl)-1-[[5-methyl-3-(trifluoromethyl)-1H-pyrazol-1-yl]acetyl]piperidine To a solution of 5-methyl-3-(trifluoromethyl)-1H-pyrazole-1-acetic acid (0.5 g, 2.4 mmol) in dichloromethane (4 mL) was added oxalyl chloride (0.3 mL, 3.6 mmol) and one drop of N,N-dimethylformamide, resulting in slight exothermicity. The reaction mixture was then heated at reflux for 15 minutes. The reaction mixture was evaporated, and the resulting residue was suspended in dichloromethane (4 mL) and treated with a solution of 4-(4-ethenyl-2-thiazolyl)piperidine (i.e. the product of Example 4. Step B) (302 mg, 1.5 mmol) in dichloromethane (2 mL), followed by addition of triethylamine (0.32 mL, 2.3 mmol). The reaction mixture was stirred overnight at room temperature, then concentrated, and purified by column chromatography on silica gel using 30-40% ethyl acetate in hexanes as eluant to give 414 mg of the title compound as a white solid.

¹H NMR (CDCl₃) δ 1.78 (m, 2H), 2.18 (m, 2H), 2.32 (s, 3H), 2.90 (br t, 1H), 3.30 (m, 2H), 4.03 (d, 1H), 4.55 (d, 1H), 5.00 (m, 2H), 5.35 (d, 1H), 6.02 (d, 1H), 6.33 (s, 1H), 6.68 (dd, 1H), 7.01 (s, 1H).

Step D: Preparation of 4-[4-(4,5-dihydro-3-phenyl-5-isoxazolyl)-2-thiazolyl]-1-[(5-methyl-3-(trifluoromethyl)-1H-pyrazol-1-yl)acetyl]piperidine To a solution of benzaldehyde oxime (49 mg, 0.4 mmol) in N,N-dimethylformamide (3 mL) was added N-chlorosuccinimide (54 mg, 0.4 mmol), followed by addition of 4-(4-ethenyl-2-thiazolyl)-1-[[5-methyl-3-(trifluoromethyl)-1H-pyrazol-1-yl]acetyl]piperidine (i.e. the product of Example 4, Step C) (103 mg, 0.27 mmol) and triethylamine (41 mg, 0.4 mmol). The resulting mixture was stirred at room temperature for 5 h, then diluted with water, extracted with dichloromethane (2×). The organic layers were combined and dried (MgSO₄), and filtered. The filtrate was concentrated, and the residue was purified by column chromatography on silica gel using 55-70% ethyl acetate in hexanes as eluant to give 90 mg of the title product, a compound of the present invention as a white solid.

¹H NMR (CDCl₃) δ 1.76 (m, 2H), 2.17 (m, 2H), 2.31 (s, 3H), 2.88 (br t, 1H), 3.25 (m, 2H), 3.65 (m, 1H), 3.78 (m, 1H), 4.02 (br d, 1H), 4.56 (br d, 1H), 4.99 (m, 2H), 5.84 (dd, 1H), 6.32 (s, 1H), 7.28 (s, 1H), 7.40-7.42 (m, 3H), 7.69-7.71 (m, 2H).

EXAMPLE 5

Preparation of 1-[4-[4-[5-(2-chlorophenyl)-4,5-dihydro-3-isoxazolyl]-2-thiazolyl]-1-piperidinyl]-2-[5-methyl-3-(trifluoromethyl)-1H-pyrazol-1-yl]ethanone (Compound 8)

To a solution of 1-chloro-2-ethenylbenzene (0.035 g, 0.25 mmol), triethylamine (2.5 mg, 0.025 mmol) and Clorox® aqueous sodium hypochlorite solution (1 mL, 16.1 mmol) in dichloromethane (5 mL) was added 4-[4-[(hydroxyimino)methyl]-2-thiazolyl]-1-[[5-methyl-3-(trifluoromethyl)-1H-pyrazol-1-yl]acetyl]piperidine (i.e. the product of Example 2, Step C) (0.10 g, 0.25 mmol) in dichloromethane (5 mL) dropwise over 1 h at 0° C. The reaction mixture was allowed to stir for 1h, then filtered through Celite® diatomaceous filter aid, and concentrated under reduced pressure to give an oil, which was purified by column chromatography on silica gel using 50% ethyl acetate in hexane as eluant to give 73 mg of the title compound as a white foam, melting at 115-122° C. (crystallized from methyl acetate/petroleum ether).

¹H NMR (CDCl₃) δ 1.74-1.80 (m, 2H), 2.14-2.22 (m, 2H), 2.32 (s, 3H), 2.85-2.91 (m, 1H), 3.26-3.30 (m, 2H), 3.31-3.32 (m, 1H), 4.05-4.07 (m, 1H), 4.55-4.58 (m, 1H), 4.93-5.03 (q, 2H), 6.01-6.06 (m, 1H), 6.331 (s, 1H), 7.25-7.29 (m, 2H), 7.38-7.40 (m, 1H), 7.56-7.58 (m, 1H), 7.62 (s, 1H).

EXAMPLE 6

Preparation of 1-[4-[4-(4,5-dihydro-5-phenyl-3-isoxazolyl)-2-thiazolyl]-1-piperidinyl]-2-[5-methyl-3-(trifluoromethyl)-1H-pyrazol-1-yl]ethanethione (Compound 130)

A solution of 4-[4-[4,5-dihydro-5-phenyl-3-isoxazolyl]-2-thiazolyl]-1-[[5-methyl-3-(trifluoromethyl)-1H-pyrazol-1-yl]acetyl]piperidine (i.e. the product of Example 1, Step B) (235 mg, 0.47 mmol) and phosphorus pentasulfide (104.5 mg, 0.235 mmol) in pyridine (5 ml) was heated under reflux for 2 h. The reaction mixture was then concentrated under reduced pressure, and the residue was distributed between dichloromethane (10 mL) and water (10 mL). The organic layer was washed with 1 N hydrochloric acid, water, saturated aqueous sodium bicarbonate solution and brine, dried (MgSO₄), and concentrated under reduced pressure to give 240 mg of the title product, a compound of the present invention, as a white foam.

¹H NMR (CDCl₃) δ 1.80-2.00 (m, 2H), 2.20-2.28 (m, 2H), 2.45 (s, 3H), 3.35-3.46 (3H, m), 3.50-3.61 (m, 1H), 3.80-3.88 (m, 1H), 4.70-4.80 (m, 1H), 5.30-5.33 (m, 2H), 5.35-5.40 (m, 1H), 5.74-5.80 (nm, 1H), 6.32 (s, 1H), 7.30-7.40 (m, 5H), 7.65 (s, 1H).

EXAMPLE 7

Preparation of 1-[4-[4-(4,5-dihydro-5-phenyl-3-isoxazolyl)-2-thiazolyl]-1-piperazinyl]-2-[5-methyl-3-(trifluoromethyl)-1H-pyrazol-1-yl]ethanone (Compound 154)

Step A: Preparation of 1,1-dimethylethyl 4-(aminothioxomethyl)-1-piperazinecarboxylate To a solution of thiocarbonyldiimidazole (2.1 g, 11.8 mmol) in tetrahydrofuran (30 mL) at room temperature, was added 1,1-dimethylethyl 1-piperazinecarboxylate (2 g, 10.75 mmol). The reaction mixture was stirred at room temperature for 2 h and then heated to 55° C. for additional 2 h. The reaction mixture was cooled to room temperature, and concentrated under reduced pressure until approximately 20 mL of tetrahydrofuran remained. The residue was then treated with a 2 M solution of ammonia in methanol (10 mL) and stirred at room temperature for 24 h. The reaction mixture was concentrated under reduced pressure, and the residue was triturated with diethyl ether (25 mL) to give a white precipitate. The precipitate was filtered and dried to give 1.5 g of the title compound as a white solid.

¹H NMR (CDCl₃) δ 1.39 (s, 9H), 3.32 (m, 4H), 3.73 (m, 4H), 7.49 (br s, 2H).

Step B: Preparation of 3-chloro-N-hydroxy-2-oxo-propanimidoyl chloride

To a solution of 1,3-dichloroacetone (100 g, 0.79 mol) in 2 M solution of hydrogen chloride in diethyl ether (400 mL) at 15° C. was added t-butyl nitrite (55 g, 0.534 mol) over 10 minutes. The reaction progress was monitored by ¹H NMR to obtain ~85% conversion with no more than 3% of the bis-nitrosation side product. The reaction mixture was concentrated under reduced pressure to leave a semi-solid, which was then thoroughly rinsed with n-BuCl. The resulting solid was collected under filtration to give a 77 g of the title compound as a white solid. The filtrate was further concentrated under reduced pressure to give a semi-solid residue, which was rinsed with additional n-BuCl. The resulting solid was collected under filtration to give additional 15 g of the title compound as a white solid.

¹H NMR (DMSO-d₆) δ 4.96 (s, 2H), 13.76 (s, 1H).

Step C: Preparation of 2-chloro-1-(4,5-dihydro-5-phenyl-3-isoxazolyl)ethanone

To a mixture of styrene (6.79 g, 65.3 mmol) and sodium bicarbonate (32.1 g, powder) in acetonitrile (100 mL), 3-chloro-N-hydroxy-2-oxo-propanimidoyl chloride (i.e. the product of Example 7, Step B) (10 g, 64.1 mmol) was added in 10 portions over 20 minutes. The reaction mixture was then stirred for additional 1 h and filtered. The filtered solid was rinsed with acetonitrile, and the combined filtrates were concentrated under reduced pressure to leave an oil, which was triturated first with hexanes and then with 1-chlorobutane to give 13.6 g of the title compound as a white solid.

$^1$H NMR (CDCl$_3$) δ 3.13 (m, 1H), 3.66 (m, 1H), 4.96 (s, 2H), 5.83 (m, 1H), 7.34-7.44 (m, 5H).

Step D: Preparation of 1,1-dimethylethyl 4-[4-(4,5-dihydro-5-phenyl-3-isoxazolyl)-2-thiazolyl]-1-piperazineacetate To a solution of 2-chloro-1-(4,5-dihydro-5-phenyl-3-isoxazolyl)ethanone (i.e. the product of Example 7, Step C) (0.450 g, 2.018 mmol) and 1,1-dimethylethyl 4-(aminothioxomethyl)-1-piperazinecarboxylate (i.e. the product of Example 7, Step A) (0.5 g, 2.04 mmol) in ethanol (10 mL) was added triethylamine (0.204 g, 2.013 mmol), and the reaction mixture was stirred at room temperature for 12 h. The reaction mixture was concentrated under reduced pressure, and the residue was partitioned between ethyl acetate (30 mL) and water (30 mL). The organic layer was separated and washed with brine (25 mL), dried (Na$_2$SO$_4$), and concentrated under reduced pressure. The crude residue was purified by column chromatography using 20% ethyl acetate in petroleum ether as eluant to give 700 mg of the title compound as a white solid.

$^1$H NMR (CDCl$_3$) δ 1.48 (s, 9H), 3.30 (m, 1H), 3.54 (m, 8H), 3.74 (m, 1H), 5.71 (m, 1H), 6.91 (s, 1H), 7.40-7.29 (m, 5H).

Step E: Preparation of 1-[4-(4,5-dihydro-5-phenyl-3-isoxazolyl)-2-thiazolyl]-piperazine hydrochloride To a solution of 1,1-dimethylethyl 4-[4-(4,5-dihydro-5-phenyl-3-isoxazolyl)-2-thiazolyl]-1-piperazineacetate (i.e. the product of Example 7, Step D) (0.7 g, 1.686 mmol) in diethyl ether (10 mL) was added a 2 M solution of hydrogen chloride in methanol (10 mL) at room temperature. The reaction mixture was stirred at room temperature for 8 h. The resulting white precipitate was filtered, and dried to give 500 mg of the title compound as a white solid.

$^1$H NMR (CDCl$_3$) δ 3.21 (m, 4H), 3.27 (m, 1H), 3.68 (m, 4H), 3.79 (m, 1H), 5.68 (m, 1H), 7.41-7.29 (m, 6H), 9.49 (br s, 2H).

Step F: Preparation of 1-[4-[4-(4,5-dihydro-5-phenyl-3-isoxazolyl)-2-thiazolyl]-1-piperazinyl]-2-[5-methyl-3-(trifluoromethyl)-1H-pyrazol-1-yl]ethanone To a solution of 1-[4-(4,5-dihydro-5-phenyl-3-isoxazolyl)-2-thiazolyl]piperazine hydrochloride (i.e. the product of Example 7, Step E) (200 mg, 0.57 mmol) and 5-methyl-3-(trifluoromethyl)-1H-pyrazole-1-acetic acid (0.120 g, 0.57 mmol) in dichloromethane (10 mL) at room temperature was added 1-[3-(dimethylamino)propyl]-3-ethylcarbodiimide hydrochloride (0.110 g, 0.57 mmol), triethylamine (0.086 g, 0.85 mmol) and 1-hydroxybenzotriazole hydrate (0.020 g, 0.14 mmol). The reaction mixture was stirred at room temperature for 24 h. The reaction mixture was diluted with dichloromethane (30 mL), and washed with water (20 mL) and brine (20 mL). The organic layer was dried (Na$_2$SO$_4$) and concentrated under reduced pressure. The crude residue was purified by column chromatography using 3% methanol in chloroform as eluant to give 180 mg of the title product, a compound of the present invention as a white solid.

$^1$H NMR (CDCl$_3$) δ 2.32 (s, 3H), 3.29 (m, 1H), 3.52 (m, 2H), 3.61 (m, 2H), 3.79-3.72 (m, 5H), 4.98 (m, 2H), 5.69 (m, 1H), 6.33 (s, 1H), 6.93 (s, 1H), 7.38-7.28 (m, 5H).

Mass spectrum at 505.5 (M+1).

EXAMPLE 8

Preparation of 1-[4-[4-(3',4'-dihydrospiro[isoxazole-5(4H),1',(2'H)-naphthalen]-3-yl)-2-thiazolyl]-1-piperidinyl]-2-[5-methyl-3-(trifluoromethyl)-1H-pyrazol-1-yl]ethanone (Compound 37)

Step A: Preparation of 1-(2-chloroacetyl)-4-piperidinecarbonitrile

A mixture of 4-piperidinecarbonitrile (200 g, 1.80 mol) and 40% aqueous potassium carbonate solution (342 g, 0.99 mol) in dichloromethane (1 L) was cooled to −10° C., and a solution of chloroacetyl chloride (210 g, 1.86 mol) in dichloromethane (300 mL) was added over about 75 minutes while maintaining the reaction mixture at −10 to 0° C. After the addition was complete, the reaction mixture was separated, the upper aqueous phase was extracted with dichloromethane (2×300 mL), and the combined organic phases were concentrated under reduced pressure to give 312 g of the title compound as a liquid which slowly crystallized on standing. This compound was of sufficient purity to use in subsequent reactions.

$^1$H NMR (CDCl$_3$) δ 1.8-2.1 (m, 4H), 2.95 (m, 1H), 3.5-3.8 (m, 4H), 4.08 (q, 2H).

Step A1: Alternative preparation of 1-(2-chloroacetyl)-4-piperidinecarbonitrile A solution of N-(1,1-dimethylethyl)-4-piperidinecarboxamide (201 g, 1.0 mol) in dichloromethane (1 L) was cooled under nitrogen to −5° C., and chloroacetyl chloride (124 g, 1.1 mol) in 300 mL of dichloromethane was added dropwise over 30 minutes while maintaining the reaction mixture at 0 to 5° C. Then 20% aqueous potassium carbonate solution (450 g, 0.65 mol) was added dropwise over 30 minutes while keeping reaction temperature between 0 and 5° C. The reaction mixture was stirred for an additional 30 minutes at 0° C., and then allowed to warm to room temperature. The layers were separated, and the aqueous layer was extracted with dichloromethane (200 mL). The combined dichloromethane layers were concentrated under reduced pressure to yield a solid, which was triturated with 400 mL of hexanes. The slurry was filtered, and the filter cake was washed with 100 mL of hexanes and dried in a vacuum oven overnight at 50° C. to give 185.5 g of 1-(2-chloroacetyl)-N-(1,1-dimethylethyl)-4-piperidinecarboxamide as a solid, melting at 140.5-141.5° C.

$^1$H NMR (CDCl$_3$) δ 1.35 (s, 9H), 1.6-2.0 (m, 4H), 2.25 (m, 1H), 2.8 (t, 1H), 3.2 (t, 1H), 3.9 (d, 1H), 4.07 (s, 2H), 4.5 (d, 1H), 5.3 (br s, 1H).

To a solution of 1-(2-chloroacetyl)-N-(1,1-dimethylethyl)-4-piperidinecarboxamide (26.1 g, 0.10 mol) in N,N-dimethylformamide (35 mL) was added phosphorus oxychloride (18.8 g, 0.123 mol) dropwise over 30 minutes while allowing the temperature of the reaction mixture to rise to 37° C. The reaction mixture was heated at 55° C. for 1 h and then was slowly added to water (about 150 g) cooled with ice to maintain a temperature of about 10° C. The pH of the reaction mixture was adjusted to 5.5 with 50% NaOH aqueous solution. The mixture was extracted with dichloromethane (4×100 mL), and the combined extract was concentrated under reduced pressure to give 18.1 g of the title compound as a solid. This compound was of sufficient purity to use in subsequent reactions.

Step B: Preparation of 1-[2-[5-methyl-3-(trifluoromethyl)-1H-pyrazol-1-yl]acetyl]-4-piperidinecarbonitrile A solution of 3-methyl-5-trifluoromethylpyrazole (9.3 g, 62 mmol) and 45% aqueous potassium hydroxide solution (7.79 g, 62 mmol) in N,N-dimethylformamide (25 mL) was cooled to 5° C., and 1-(2-chloroacetyl)-4-piperidinecarbonitrile (i.e. the product of Example 8, Step A or A1) (11.2 g, 60 mmol) was added. The reaction mixture was stirred for 8 h at 5-10° C., then diluted with water (100 mL), and filtered. The filter cake was washed with water and dried at 50° C. in a vacuum-oven to give 15 g of the title compound as a solid containing 3% of its regioisomer, i.e. 1-[2-[3-methyl-5-(trifluoromethyl)-1H-pyrazol-1-yl]acetyl]-4-piperidinecarbonitrile.

$^1$H NMR (CDCl$_3$) δ 1.88 (m, 4H), 2.32 (s, 3H), 2.95 (m, 1H), 3.7 (m, 4H), 5.0 (q, 2H), 6.34 (s, 1H).

Step C: Preparation of 1-[2-[5-methyl-3-(trifluoromethyl)-1H-pyrazol-1-yl]acetyl]-4-piperidinecarbothioamide Hydrogen sulfide gas was passed into a solution of 1-[2-[5-methyl-3-(trifluoromethyl)-1H-pyrazol-1-yl] acetyl]-4-piperidinecarbonitrile (i.e. the product of Example 8, Step B) (9.0 g, 30 mmol) and diethanolamine (3.15 g, 30 mmol) in N,N-dimethylformamide (15 mL) at 50° C. in a flask equipped with dry-ice condenser. The hydrogen sulfide feed was stopped when the reaction mixture became saturated with hydrogen sulfide, as indicated by condensation on the cold-finger. The reaction mixture was stirred for an additional 30 minutes at 50° C. Then excess hydrogen sulfide gas was sparged into the scrubber by a subsurface nitrogen flow, and water (70 mL) was gradually added. The reaction mixture was cooled to 5° C., filtered, and washed with water (2×30 mL). The filter cake was dried at 50° C. in a vacuum-oven to give 8.0 g of the title compound as a solid, melting at 185-186° C.

$^1$H NMR (CDCl$_3$) δ 1.7 (m, 2H), 2.0 (m, 2H), 2.29 (m, 3H), 2.65 (t, 1H), 3.0 (m, 3H), 3.2 (t, 1H), 4.0 (d, 1H), 4.6 (d, 1H), 4.96 (d, 1H), 5.4 (d, 1H), 6.35 (s, 1H), 7.4 (br s, 1H), 7.5 (br s, 1H).

Step D: Preparation of 1-[4-[4-(3',4'-dihydrospiro [isoxazole-5(4H),1',(2'H)-naphthalen]-3-yl)-2-thiazolyl]-1-piperidinyl]-2-[5-methyl-3-(trifluoromethyl)-1H-pyrazol-1-yl]ethanone A solution of 1-[2-[5-methyl-3-(trifluoromethyl)-1H-pyrazol-1-yl]acetyl]-4-piperidinecarbothioamide (i.e. the product of Example 8, Step C) (0.5 g, 1.5 mmol), 2-chloro-1-(3',4'-dihydrospiro[isoxazole-5(4H),1',(2'H)-naphthalen]-3-yl)ethanone (prepared by a method analogous to Example 7, Step C) (0.4 g, 1.5 mmol) and tetrabutylammonium bromide (0.030 g, 0.10 mmol) in tetrahydrofuran (15 mL) was stirred overnight at room temperature, and then heated at 55-60° C. for 3 h. The reaction mixture was diluted with water and extracted with dichloromethane. The extract was washed with brine, dried (MgSO$_4$), and concentrated under reduced pressure. The crude product was further purified by medium-pressure liquid chromatography using 50% ethyl acetate in hexanes as eluant to give 260 mg of the title product, a compound of the present invention, as an off-white solid, melting at 81-84° C.

$^1$H NMR (CDCl$_3$) δ 1.76-1.86 (m, 3H), 2.04-2.08 (m, 2H), 2.16-2.26 (m, 2H), 2.32 (s, 3H), 2.83-2.87 (m, 2H), 2.88-2.93 (m, 1H), 3.27-3.35 (m, 2H), 3.48-3.65 (m, 2H), 4.02-4.06 (m, 1H), 4.55-4.59 (m, 1H), 4.94-5.04 (q, 2H), 6.33 (s, 1H), 7.10-7.12 (m, 1H), 7.19-7.21 (m, 2H), 7.40-7.43 (m, 1H), 7.62 (s, 1H).

The following compounds were prepared by procedures analogous to Step D of Example 8:

1-[4-[4-(4,5-dihydro-5-methyl-5-phenyl-3-isoxazolyl)-2-thiazolyl]-1-piperidinyl]-2-[5-methyl-3-(trifluoromethyl)-1H-pyrazol-1-yl]ethanone (Compound 15); m.p. 97-100° C. (crystallized from methyl acetate/petroleum ether); $^1$H NMR (CDCl$_3$) δ 1.74-1.80 (m, 1H), 1.81 (s, 3H), 2.14-2.20 (m, 2H), 2.32 (s, 3H), 2.85-2.91 (m, 1H), 3.26-3.32 (m, 2H), 3.52-3.62 (m, 2H), 4.01-4.05 (m, 1H), 4.54-4.58 (m, 1H), 4.94-5.04 (q, 2H), 6.33 (s, 1H), 7.26-7.29 (m, 1H), 7.35-7.38 (m, 2H), 7.48-7.50 (m, 2H), 7.58 (s, 1H).

2-[5-methyl-3-(trifluoromethyl)-1H-pyrazol-1-yl]-1-[4-[4-(3a,4,5,9b-tetrahydro-naphth[2,1-d]isoxazol-3-yl)-2-thiazolyl]-1-piperidinyl]ethanone (Compound 16); m.p. 162-165° C. (crystallized from methyl acetate/petroleum ether); $^1$H NMR (CDCl$_3$) δ 1.79-1.85 (m, 2H), 2.00-2.05 (m, 2H), 2.20-2.26 (m, 2H), 2.33 (s, 3H), 2.68-2.72 (m, 2H), 2.88-2.94 (m, 1H), 3.30-3.35 (m, 2H), 3.92-3.98 (m, 1H), 4.06-4.10 (m, 1H), 4.58-4.60 (m, 1H), 4.94-5.06 (m, 2H), 5.58-5.60 (d, 1H), 6.34 (s, 1H), 7.17-7.20 (m, 1H), 7.28-7.30 (m, 2H), 7.47-7.49 (m, 1H), 7.72 (s, 1H).

1-[4-[4-(2,3-dihydrospiro[1H-indene-1,5'(4'H)-isoxazol]-3'-yl)-2-thiazolyl]-1-piperidinyl]-2-[5-methyl-3-(trifluoromethyl)-1H-pyrazol-1-yl]ethanone (Compound 44); $^1$H NMR (CDCl$_3$) δ 1.77-1.84 (m, 2H), 2.17-2.25 (m, 2H), 2.33 (s, 3H), 2.61-2.68 (m, 1H), 2.90-2.96 (m, 2H), 3.12-3.20 (m, 1H), 3.31-3.35 (m, 2H), 3.54-3.75 (m, 2H), 4.04-4.10 (m, 1H), 4.56-4.60 (m, 1H), 4.94-5.04 (q, 2H), 6.34 (s, 1H), 7.28-7.30 (m, 3H), 7.37-7.38 (m, 1H), 7.64 (s, 1H).

1-[4-[4-[4,5-dihydro-5-(4-methoxyphenyl)-3-isoxazolyl]-2-thiazolyl]-1-piperidinyl]-2-[5-methyl-3-(trifluoromethyl)-1H-pyrazol-1-yl]ethanone (Compound 18); m.p.t 119-124° C. (crystallized from methyl acetate/petroleum ether); $^1$H NMR (CDCl$_3$) δ 1.76-1.82 (m, 2H), 2.16-2.24 (m, 2H), 2.32 (s, 3H), 2.86-2.92 (m, 1H), 3.28-3.34 (m, 2H), 3.37-3.43 (m, 1H), 3.76-3.83 (m, 1H), 3.81 (s, 3H), 4.03-4.06 (m, 1H), 4.56-459 (m, 1H), 4.94-5.04 (q, 2H), 5.67-5.72 (m, 1H), 6.33 (s, 1H), 6.89-6.91 (d, 2H), 7.31-7.33 (d, 2H), 7.62 (s, 1H).

EXAMPLE 9

Preparation of 1-[4-[4-(4,5-dihydro-5-(2-pyridinyl)-3-isoxazolyl)-2-thiazolyl]-1-piperidinyl]-2-[5-methyl-3-(trifluoromethyl)-1H-pyrazol-1-yl]ethanone (Compound 98)

To a solution of 1-[2-[5-methyl-3-(trifluoromethyl)-1H-pyrazol-1-yl]acetyl]-4-piperidinecarbothioamide (i.e. the product of Example 8, Step C) (200 mg, 0.6 mmol) in tetrahydrofuran (8 mL) was added 3-chloro-N-hydroxy-2-oxopropanimidoyl chloride (i.e. the product of Example 7, Step B) (93 mg, 0.6 mmol), followed by tetrabutylammonium bromide (15 mg, 0.05 mmol). The reaction mixture was heated at 50° C. for 4 h. The reaction mixture was cooled and concentrated under reduced pressure. To the resulting residue, acetonitrile (8 mL) and finely powdered sodium bicarbonate (151 mg, 1.0 mmol) were added followed by 2-ethenylpyridine (63 mg, 0.6 mmol), and the resulting mixture was stirred at room temperature overnight. The reaction mixture was concentrated under reduced pressure and purified by flash chromatography on a silica gel (20 g), Varian Bond Elute SI® column using 0 to 75% ethyl acetate in hexanes as eluant to give 80 mg of the title product, a compound of the present invention, as a yellow semi-solid.

$^1$H NMR (CDCl$_3$) δ 1.47-1.62 (m, 1H), 1.70-1.85 (m, 1H), 2.01-2.18 (m, 2H), 2.49 (s, 3H), 2.82 (t, 1H), 3.20-3.42 (m, 2H), 3.73 (dd, 1H), 3.82 (dd, 1H), 3.98 (d, 1H), 4.38 (d, 1H), 5.26 (m, 2H), 5.80 (dd, 1H), 6.50 (s, 1H), 7.38 (dd, 1H), 7.50 (d, 1H), 7.82 (t, 1H), 8.05 (s, 1H), 8.60 (d, 1H).

EXAMPLE 10

Preparation of 2-[5-chloro-3-(trifluoromethyl)-1H-pyrazol-1-yl]-1-[4-[4-(4,5-dihydro-5-phenyl-3-isoxazolyl)-2-thiazolyl]-1-piperidinyl]ethanone (Compound 107)

Step A: Preparation of N,N-dimethyl-3-(trifluoromethyl)-1H-pyrazole-1-sulfonamide To a solution of 3-trifluoromethylpyrazole (5.0 g, 36 mmol), triethylamine (7.0 mL, 50 mmol) in dichloromethane (40 mL) was added dimethylsulfamoyl chloride (5.5 mL, 51 mmol), and the reaction mixture was heated at reflux for 2 days. The resulting mixture was cooled to ambient temperature and filtered through a pad of silica gel using dichloromethane as eluent. The filtrate was then concentrated under reduced pressure to give an amber residue. The resulting residue was dissolved in diethyl ether. The ether solution was washed with water, dried (MgSO$_4$), and concentrated under reduced pressure to give 8.71 g of the title compound.

$^1$H NMR (CDCl$_3$) δ 3.01 (s, 6H), 6.65 (s, 1H), 8.03 (s, 1H).

Step B: Preparation of 5-chloro-N,N-dimethyl-3-(trifluoromethyl)-1H-pyrazole-1-sulfonamide A stirred solution of N,N-dimethyl-3-(trifluoromethyl)-1H-pyrazole-1-sulfonamide (i.e. the product of Example 10, Step A) (4.0 g, 16 mmol) in tetrahydrofuran (25 mL) was cooled to −78° C., and then treated dropwise with 2 M n-butyllithium in cyclohexane (8.6 mL, 17.2 mmol). The reaction mixture was stirred for a further 30 minutes, and then a solution of hexachloroethane (4.2 g, 18 mmol) in tetrahydrofuran (15 mL) was added dropwise. The reaction mixture was stirred for 1 h, warmed to room temperature, and quenched with water (50 mL). The resulting solution was extracted with dichloromethane, dried (MgSO$_4$), and concentrated under reduced pressure to give 4.38 g of title compound. This compound was of sufficient purity to use in subsequent reactions.

$^1$H NMR (CDCl$_3$) δ 3.15 (s, 6H), 6.58 (s, 1H).

Step C: Preparation 5-chloro-3-(trifluoromethyl)-1H-pyrazole

A solution of 5-chloro-N,N-dimethyl-3-(trifluoromethyl)-1H-pyrazole-1-sulfonamide (i.e. the product of Example 10, Step B) (4.38 g, 15.8 mmol) and trifluoroacetic acid (2.7 mL, 35 mmol) was stirred at 0° C. for 1.5 h. The reaction mixture was diluted with water (15 mL), and sodium carbonate was added to raise the pH to 12. The solution was extracted with diethyl ether, dried (MgSO$_4$), and concentrated under reduced pressure to give 2.1 g of the title compound. This compound was of sufficient purity to use in subsequent reactions.

$^1$H NMR (CDCl$_3$) δ 6.57 (m, 1H).

Step D: Preparation of ethyl 5-chloro-3-(trifluoromethyl)-1H-pyrazole-1-acetate

To a suspension of 5-chloro-3-(trifluoromethyl)-1H-pyrazole (i.e. the product of Example 10, Step C) (2.1 g, 12.3 mmol) and potassium carbonate (3.6 g, 26.0 mmol) in 20 mL of N,N-dimethylformamide was added ethyl bromoacetate (2.1 mL, 18.8 mmol), and the resulting mixture was stirred at room temperature for 12 h. The resulting mixture was diluted with ethyl acetate, washed with water, and dried (MgSO$_4$). The reaction mixture was concentrated in vacuo and further purified by medium-pressure liquid chromatography using 0-50% of ethyl acetate in hexanes as eluant to give 940 mg of the title compound as an oil.

$^1$H NMR (CDCl$_3$) δ 1.29 (m, 3H), 4.27 (q, 2H), 4.96 (m, 2H), 6.55 (s, 1H).

Step D1: Alternative preparation of ethyl 5-chloro-3-(trifluoromethyl)-1H-pyrazole-1-acetate To a solution of aluminum chloride (3.0 g, 22.5 mmol) in dichloromethane (100 mL) was added dropwise a solution of trifluoroacetyl chloride (3 g, 22.6 mmol) in dichloromethane (5 mL) while keeping the temperature of the reaction mixture below −30° C. The reaction mixture was stirred for 15 minutes at −50° C. Then a solution of vinylidene chloride (2.2 g, 22.7 mmol) in dichloromethane (10 mL) was added dropwise over 2 h to the reaction mixture. The reaction mixture was stirred an additional 2 h at −50° C. and then warmed gradually to room temperature. The reaction mixture was diluted with water, and the aqueous layer was extracted with dichloromethane. The organic layers were combined, dried (MgSO$_4$), and concentrated under reduced pressure to give 4,4-dichloro-1,1,1-trifluoro-3-buten-2-one as an oil which was used for the next step without further purification.

$^1$H NMR (CDCl$_3$) δ 5.30 (s, 1H).
$^{19}$F NMR (CDCl$_3$) δ −63.6.

To a mixture of ethyl hydrazinoacetate hydrochloride (2.8 g, 18.1 mmol) and triethylamine (9.2 g, 91 mmol) in a solution of ethanol (20 mL) and N,N-dimethylformamide (1 mL), a solution of crude 4,4-dichloro-1,1,1-trifluoro-3-buten-2-one in dichloromethane (20 mL) was added dropwise while keeping the temperature of the reaction mixture below 10° C. After stirring a further 2 h at below 10° C., the reaction mixture was concentrated under reduced pressure. The residue was diluted with diethyl ether, and the mixture was filtered. The resulting filtrate was concentrated to give 4.34 g of the title compound as a solid. This compound was of sufficient purity to use in subsequent reactions.

$^1$H NMR (CDCl$_3$) δ 1.29 (t, 3H), 4.27 (q, 2H), 4.97 (s, 1H), 6.55 (s, 1H).
$^{19}$F NMR (CDCl$_3$) δ −63.4.

Step E: Preparation of 5-chloro-3-(trifluoromethyl)-1H-pyrazole-1-acetic acid

A solution of ethyl 5-chloro-3-(trifluoromethyl)-1H-pyrazole-1-acetate (i.e. the product of Example 10, Step D or D1)

(218 mg, 0.85 mmol) in tetrahydrofuran (1 mL) was treated with a 50 wt. % aqueous solution of sodium hydroxide (0.2 mL) in water (0.6 mL). The reaction mixture was stirred at room temperature for 4 h. The reaction mixture was treated with concentrated aqueous hydrochloric acid to lower the pH to 1, and then extracted with ethyl acetate. The extract was dried (MgSO$_4$) and concentrated under pressure to give 140 mg of the title compound. This compound was of sufficient purity to use in subsequent reactions.

$^1$H NMR (DMSO-d$_6$) δ 5.41 (s, 2H), 7.09 (s, 1H).

Step F: Preparation of 2-[5-chloro-3-(trifluoromethyl)-1H-pyrazol-1-yl]-1-[4-[4-(4,5-dihydro-5-phenyl-3-isoxazolyl)-2-thiazolyl]-1-piperidinyl]ethanone To a solution of 1,1-dimethylethyl 4-[4-(4,5-dihydro-5-phenyl-3-isoxazolyl)-2-thiazolyl]-1-piperidinecarboxylate (i.e. the product of Example 1, Step A) (1.026 g, 2.48 mmol) in ethanol (10 mL) was added a 2 M solution of hydrogen chloride in diethyl ether (4.2 mL, 12.6 mmol). The reaction mixture was stirred at room temperature overnight. Then the reaction mixture was heated at 60° C. for 2 h. The reaction mixture was cooled to room temperature and concentrated under reduced pressure to give 0.710 g of 4-[4-(4,5-dihydro-5-phenyl-3-isoxazolyl)-2-thiazolyl]-1-piperidine, hydrochloride as a white solid.

To 5-chloro-3-(trifluoromethyl)-1H-pyrazole-1-acetic acid (i.e. the product of Example 10, Step E) (0.14 g, 0.61 mmol) in dichloromethane (5 mL) was added N,N-dimethylformamide (1 drop) followed by oxalyl chloride (0.07 mL, 0.80 mmol) at room temperature. The reaction mixture was stirred at room temperature for 1 h, and then concentrated under reduced pressure. The resulting crude 5-chloro-3-(trifluoromethyl)-1H-pyrazole-1-acetyl chloride was taken up in 5 mL of dichloromethane, and the resulting solution was added dropwise to a mixture of 4-[4-(4,5-dihydro-5-phenyl-3-isoxazolyl)-2-thiazolyl]-1-piperidine, hydrochloride (0.20 g, 0.57 mmol) prepared above and triethylamine (0.40 mL, 2.85 mmol) in 10 mL of dichloromethane at 0° C. The reaction mixture was stirred overnight at room temperature, and then diluted with 1.0 N aqueous hydrochloric acid solution. The organic layer was separated, washed with water, dried (MgSO$_4$), and concentrated under reduced pressure and purified by medium-pressure liquid chromatography using ethyl acetate in hexanes as eluant to give 40 mg of the title product, a compound of the present invention, as a solid, melting at 128-131° C.

$^1$H NMR (CDCl$_3$) δ 1.81 (nm, 2H), 2.20 (m, 2H), 2.89 (m, 1H), 3.31 (m, 2H), 3.46 (m, 1H), 3.87 (m, 2H), 4.55 (m, 1H), 5.08 (m, 2H), 5.75 (m, 1H), 6.54 (s, 1H), 7.25-7.42 (m, 5H), 7.63 (s, 1H).

EXAMPLE 11

Preparation of 2-[5-bromo-3-(trifluoromethyl)-1H-pyrazol-1-yl]-1-[4-[4-(4,5-dihydro-5-phenyl-3-isoxazoly)-2-thiazolyl]-1-piperidinyl]ethanone (Compound 126)

Step A: Preparation of 5-bromo-N,N-dimethyl-3-(trifluoromethyl)-1H-pyrazole-1-sulfonamide A stirred solution of N,N-dimethyl-3-(trifluoromethyl)-H-pyrazole-1-sulfonamide (i.e. the product of Example 10, Step A) (4.25 g, 17.5 mmol) in tetrahydrofuran (50 mL) was cooled to −78° C., and then 2 M n-butyllithium in cyclohexane (10.0 mL, 20.0 mmol) was added dropwise. The reaction mixture was stirred a further 30 minutes, and then bromine (1.0 mL, 3.1 g, 18.7 mmol) was added dropwise. The reaction mixture was stirred for 10 minutes, warmed to room temperature, and quenched with brine (50 mL). The resulting solution was extracted with diethyl ether, dried (MgSO$_4$), and concentrated under reduced pressure to give 6.77 g of title compound as a light yellow oil. This compound was of sufficient purity to use in subsequent reactions.

$^1$H NMR (CDCl$_3$) δ 3.15 (s, 6H), 6.69 (s, 1H).

Step B: Preparation 5-bromo-3-(trifluoromethyl)-1H-pyrazole

A solution of 5-bromo-N,N-dimethyl-3-(trifluoromethyl)-1H-pyrazole-1-sulfonamide (i.e. the product of Example 11, Step A) (4.50 g, 14.0 mmol) and trifluoroacetic acid (2.0 mL, 26 mmol) was stirred at 25° C. for 4 h. The reaction mixture was diluted with water (20 mL), and sodium hydroxide was added to raise the pH to 12. The solution was extracted with chloroform, dried (MgSO$_4$), and concentrated under reduced pressure to give 2.73 g of the title compound as a yellow light oil. This compound was of sufficient purity to use in subsequent reactions.

$^1$H NMR (CDCl$_3$) δ 6.63 (m, 1H).

Step C: Preparation of ethyl 5-bromo-3-(trifluoromethyl)-1-pyrazole-1-acetate

A suspension of 5-bromo-3-(trifluoromethyl)-1H-pyrazole (i.e. the product of Example 11, Step B) (2.73 g, 12.7 mmol) and potassium carbonate (2.0 g, 14.5 mmol) in N,N-dimethylformamide (20 mL) was treated with ethyl iodoacetate (3.0 ml, 25.3 mmol), and the resulting mixture was stirred at 95° C. for 3 h. The resulting mixture was diluted with ethyl acetate, washed with water, and dried (MgSO$_4$). The reaction mixture was concentrated in vacuo and further purified by medium-pressure liquid chromatography using 0-50% of ethyl acetate in hexanes as eluant to give 2.84 g of the title compound as a brown oil.

$^1$H NMR (CDCl$_3$) δ 1.29 (m, 3H), 4.26 (q, 2H), 5.00 (m, 2H), 6.64 (s, 1H).

Step D: Preparation of 5-bromo-3-(trifluoromethyl)-1H-pyrazole-1-acetic acid

A solution of ethyl 5-bromo-3-(trifluoromethyl)-1H-pyrazole-1-acetate (i.e. the product of Example 11, Step C) (2.84 g, 9.4 mmol) in tetrahydrofuran (10 mL) was treated with a 50 wt. % aqueous solution of sodium hydroxide solution (1.0 mL). The reaction mixture was stirred at room temperature for 2 h. The reaction mixture was treated with concentrated aqueous hydrochloric acid to lower the pH to 1, and then extracted with ethyl acetate. The extract was dried (MgSO$_4$) and concentrated under pressure to give 2.26 g of the title compound as a light brown solid. Recrystallization from 1-chlorobutane (20 mL) gave 0.68 g of the title compound as lustrous light pink plates.

$^1$H NMR (CDCl$_3$) δ 5.08 (s, 2H), 6.65 (s, 1H).

Step E: Preparation of 2-[5-bromo-3-(trifluoromethyl)-1H-pyrazol-1-yl]-1-[4-[4-(4,5-dihydro-5-phenyl-3-isoxazoly)-2-thiazolyl]-1-piperidinyl]ethanone To a solution of 5-bromo-3-(trifluoromethyl)-1H-pyrazole-1-acetic acid (i.e. the product of Example 11, Step D)

(0.12 g, 0.61 mmol) in dichloromethane (5 mL) was added N,N-dimethylformamide (1 drop) followed by oxalyl chloride (0.25 mL, 2.86 mmol). The reaction mixture was stirred at room temperature for 1 h and then concentrated under reduced pressure. The residue containing crude acid chloride was taken up in dichloromethane (5 mL), and the solution was added dropwise to a mixture of 4-[4-(4,5-dihydro-5-phenyl-3-isoxazolyl)-2-thiazolyl]-1-piperidine hydrochloride (i.e. the intermediate product of Example 10, Step F) (0.15 g, 0.43 mmol) and triethylamine (0.25 mL, 1.8 mmol) in dichloromethane (5 mL) at 0° C. The reaction mixture was allowed to warm to room temperature, and then stirred overnight at room temperature. The mixture was then partitioned between 1.0 N aqueous hydrochloric acid solution and dichloromethane. The organic layer was washed with water, dried (MgSO$_4$), concentrated under reduced pressure, and purified by medium-pressure liquid chromatography using ethyl acetate in hexanes as eluant to give 90 mg of the title product, a compound of the present invention, as an amorphous solid.

$^1$H NMR (CDCl$_3$) δ 1.84 (m, 2H), 2.20 (m, 2H), 2.89 (m, 1H), 3.31 (m, 2H), 3.46 (m, 1H), 3.89 (m, 2H), 4.58 (m, 1H), 5.11 (m, 2H), 5.75 (m, 1H), 6.63 (s, 1H), 7.25-7.42 (m, 5H), 7.66 (s, 1H).

EXAMPLE 12

Preparation of 1-[4-[4-[(5R)-4,5-dihydro-5-phenyl-3-isoxazolyl]-2-thiazolyl]-1-piperidinyl]-2-[5-methyl-3-(trifluoromethyl)-1H-pyrazol-1-yl]ethanone (Compound 3)

Step A: Preparation of 4,5-dihydro-N,N-dimethyl-5-phenyl-3-isoxazolecarboxamide

To a solution of 2-(dimethylamino)-N-hydroxy-2-oxoethanimidoyl chloride (prepared according to the procedure of E. Raleigh. U.S. Pat. No. 3,557,089) (6.0 g, 40 mmol), styrene (6.0 g, 60 mmol) in toluene (15 mL) was added a solution of potassium hydrogen carbonate (5.0 g, 50 mmol) in water (25 mL) over 1 h, while keeping the reaction temperature between 7 and 10° C. The reaction mixture was diluted with 10 mL of toluene, and stirred for an additional 10 minutes. The organic layer was separated and washed with water. The organic layer was concentrated under reduced pressure until no styrene remained to give 8.7 g of the title compound as a light yellow oil. This compound was of sufficient purity to use in subsequent reactions.

$^1$H NMR (CDCl$_3$) δ 3.08 (s, 3H), 3.32 (s, 3H), 3.35 (dd, 1H), 3.71 (dd, 1H), 5.65 (dd, 1H), 7.35 (m, 5H).

Step B: Preparation of 4,5-dihydro-5-phenyl-3-isoxazolecarboxylic acid

To a solution of 4,5-dihydro-N,N-dimethyl-5-phenyl-3-isoxazolecarboxamide (i.e. the product of Example 12, Step A) (60.0 g, 275 mmol) in methanol (300 mL) was added an aqueous sodium hydroxide solution (44 g of 50 wt. % aqueous NaOH in 50 mL of water) dropwise over 30 minutes while maintaining the temperature of the reaction mixture at 45° C. The reaction mixture was allowed to cool to room temperature and stirred overnight. The resulting mixture was concentrated under reduced pressure, and treated with 200 mL of water. The pH of the reaction mixture was adjusted using concentrated hydrochloric acid to about 1.0. The crude product was extracted into ethyl acetate (200 mL). The ethyl acetate solution was concentrated under reduced pressure, and the residue was triturated with hexanes. The resulting precipitate was filtered, washed with hexanes (2×20 mL), and dried under vacuum to give 46.5 g of the title compound as a solid.

$^1$H NMR (CDCl$_3$) δ 3.25 (dd, 1H), 3.75 (dd, 1H), 5.85 (dd, 1H), 7.35 (m, 5H), 8.1 (br s, 1H).

Step C: Preparation of the cinchonine salt of (5R)-4,5-dihydro-5-phenyl-3-isoxazolecarboxylic acid A mixture of racemic 4,5-dihydro-5-phenyl-3-isoxazolecarboxylic acid (i.e. the product of Example 12, Step B) (9.5 g, 50 mmol) in methanol (70 mL) was heated to 55° C., and cinchonine (containing about 15% dihydrocinchonine, 14.5 g, 50 mmol) was added over 20 minutes while keeping the temperature of the reaction mixture between 53 and 57° C. The reaction mixture was allowed to cool to room temperature over 60 minutes, and then water (35 mL) was added dropwise over 30 minutes. The resulting slurry was cooled to 10° C. and filtered. The filter cake was washed twice with 10 mL of 25% methanol in water, and air dried to give 8.52 g of the title compound as a solid. The diastereomeric ratio of the product was determined using chiral high performance liquid chromatography (HPLC) analysis on a Daicel Chiralcel®, OD HPLC column to be about 99:1.

$^1$H NMR (CDCl$_3$) δ 3.25 (dd, 1H), 3.75 (dd, 1H), 5.85 (dd, 1H), 7.35 (m, 5H), 8.1 (br s, 1H).

Step D: Preparation of (5R)-4,5-dihydro-N,N-dimethyl-5-phenyl-3-isoxazole-carboxamide The cinchonine salt of (5R)-4,5-dihydro-5-phenyl-3-isoxazolecarboxylic acid (i.e. the product of Example 12, Step C) (98% diastereomeric excess, 16.5 g, 34.3 mmol) was slurried in a mixture of 1 N hydrochloric acid (90 mL), cyclohexane (100 mL) and ethyl acetate (40 mL). After all the solids dissolved, the phases were separated, and the organic layer was washed with brine (20 mL) and concentrated under reduced pressure to give 5.6 g of white solid. To a solution of the resulting free acid (5.0 g, 26.2 mmol) in ethyl acetate (100 mL) at room temperature was added N,N-dimethylformamide (1 drop) followed by thionyl chloride (4.25 g, 35.7 mmol). The reaction mixture was then heated under reflux for 3 h. The resulting mixture was cooled and concentrated under reduced pressure. The residue containing crude acid chloride was dissolved in ethyl acetate (25 mL), and this solution was added in portions to a pre-cooled (5° C.) mixture of dimethylamine in tetrahydrofuran (29 mL of a 2.0 M solution), while maintaining the temperature of the mixture at 5-10° C. When the addition was complete, the reaction mixture was concentrated under reduced pressure, and diluted with water (50 mL). The resulting precipitate was filtered, washed with water and suction-dried overnight to give 4.1 g of the title compound as a light tan solid, melting at 59-61° C. This compound was of sufficient purity to use in subsequent reactions.

Step E: Preparation of 2-bromo-1-[(5R)-4,5-dihydro-5-phenyl-3-isoxazolyl]ethanone A solution of (5R)-4,5-dihydro-N,N-dimethyl-5-phenyl-3-isoxazole-carboxamide (i.e. the product of Example 12, Step D) (3.5 g, 16.0 mmol) in a mixture of tetrahydrofuran (5 mL) and toluene (10 mL) was cooled to −15° C., and methyl magnesium bromide (3.0 M solution in tetrahydrofuran, 8.8 mL, 26.4 mmol) was added over 1 h at −15° C.

Then the reaction mixture was poured over a mixture of 20 g of concentrated hydrochloric acid and 80 g of ice, and the organic phase was separated. The aqueous phase was extracted with ethyl acetate (100 mL), and the combined extract was washed with brine (40 mL) and concentrated under reduced pressure to give 3.2 g of 1-[(5R)-4,5-dihydro-5-phenyl-3-isoxazoyl]ethanone.

$^1$H NMR (CDCl$_3$) δ 2.55 (s, 3H), 3.17 (dd, 1H), 3.54 (dd, 1H), 5.75 (dd, 1H), 7.35 (m, 5H).

1-[(5R)-4,5-dihydro-5-phenyl-3-isoxazoyl]ethanone (3.2 g, 16.7 mmol) was dissolved in 1,2-dichloroethane (15 mL), and a solution of bromine (2.13 g, 13.3 mmol) in dichloroethane (5 mL) was added over 30 minutes while maintaining the temperature of the reaction mixture at about 30° C. The reaction mixture was diluted with water (10 mL), and the organic layer was concentrated under reduced pressure and purified by medium-pressure liquid chromatography using 35% of dichloromethane in hexanes as eluant to give 2.6 g of the title compound as a white solid, melting at 31-33° C.

$^1$H NMR (CDCl$_3$) δ 3.20 (dd, 1H), 3.60 (dd, 1H), 4.49 (s, 2H), 5.80 (dd, 1H), 7.35 (m, 5H).

Step E1: Alternative preparation of 2-bromo-1-(4,5-dihydro-5-phenyl-3-isoxazolyl)-ethanone To a solution of 4,5-dihydro-N,N-dimethyl-5-phenyl-3-isoxazolecarboxamide (i.e. the product of Example 12, Step A) (17 g, 78.0 mmol) in a mixture of tetrahydrofuran (20 mL) and toluene (80 mL) was added methyl magnesium bromide (3.0 M solution in tetrahydrofuran, 28 mL, 84 mmol) over 1 h, while keeping the reaction temperature between −10 and −15° C. The reaction mixture was poured over a mixture of concentrated hydrochloric acid (20 g) and ice (80 g), and the organic phase was separated. The aqueous phase was extracted with ethyl acetate (100 mL), and the combined organic extracts were washed with brine (40 mL) and concentrated under reduced pressure to give 14.4 g of 1-(4,5-dihydro-5-phenyl-3-isoxazoyl)ethanone as a light yellow oil.

$^1$H NMR (CDCl$_3$) δ 2.55 (s, 3H), 3.17 (dd, 1H), 3.54 (dd, 1H), 5.75 (dd, 1H), 7.35 (m, 5H).

1-(4,5-Dihydro-5-phenyl-3-isoxazoyl)ethanone (11.5 g, 60 mmol) was dissolved in ethyl acetate (45 mL), and a solution of bromine (9.6 g, 60.0 mmol) in ethyl acetate (30 mL) was added over 30 minutes while maintaining the temperature of the reaction mixture at about 30° C. After 1 h, the reaction mixture was diluted with water (10 mL) and the organic layer was concentrated under reduced pressure to give 16.7 g of reddish oil which contained about 10% starting methyl ketone and ~10% dibrominated ketone.

$^1$H NMR (CDCl$_3$) δ 3.20 (dd, 1H), 3.60 (dd, 1H), 4.49 (s, 2H), 5.80 (dd, 1H), 7.35 (m, 5H).

Step F: Preparation of 1-[4-[4-[(5R)-4,5-dihydro-5-phenyl-3-isoxazolyl]-2-thiazolyl]-1-piperidinyl]-2-[5-methyl-3-(trifluoromethyl)-1H-pyrazol-1-yl]ethanone A mixture of 1-[2-[5-methyl-3-(trifluoromethyl)-1H-pyrazol-1-yl]acetyl]-4-piperidinecarbothioamide (i.e. the product of Example 8, Step C) (1.7 g, 5.0 mmol) and 2-bromo-1-[(5R)-4,5-dihydro-5-phenyl-3-isoxazolyl]ethanone (i.e. the product of Example 12, Step E or E1) (1.35 g, 5 mmol) in ethanol (15 mL) was heated at 50° C. for 30 minutes. The reaction mixture was diluted with water and extracted with dichloromethane. The extract was washed with brine, dried (MgSO$_4$), and concentrated under reduced pressure to give the title product, a compound of the present invention, as a pale-yellow gum. High performance liquid chromatography (HPLC) analysis showed that the title product was about 95% pure and contained the (R)-enantiomer in about 98% enantiomeric excess.

$^1$H NMR (CDCl$_3$) δ 1.8 (m, 2H), 2.2 (m, 2H), 2.32 (s, 3H), 2.9 (m, 1H), 3.3 (m, 2H), 3.42 (dd, 1H), 3.82 (dd, 1H), 4.05 (m, 1H), 4.6 (m, 1H), 5.0 (q, 2H), 5.78 (dd, 1H), 6.35 (s, 1H), 7.4 (m, 5H), 7.62 (s, 1H).

EXAMPLE 13

Preparation of 1-[4-[4-(4,5-dihydro-5-phenyl-3-isoxazolyl)-2-thiazolyl]-3,6-dihydro-1(2H)-pyridinyl]-2-[5-methyl-3-(trifluoromethyl)-1H-pyrazol-1-yl]ethanone (Compound 217)

Step A: Preparation of 4-[4-(4,5-dihydro-5-phenyl-3-isoxazolyl)-2-thiazolyl]pyridine To a solution of thioisonicotinamide (0.5 g, 3.6 mmol) in 1-methyl-2-pyrrolidinone (25 mL) was added 2-chloro-1-(4,5-dihydro-5-phenyl-3-isoxazolyl)ethanone (0.807 g, 3.6 mmol), at room temperature. The reaction mixture was then heated to 100° C. for 3 h. Then the reaction mixture was cooled to room temperature, quenched with water (100 mL), extracted with ethyl acetate (50 mL×2). The reaction mixture was diluted with water (50 mL) and brine (50 mL), and the organic layer was concentrated under reduced pressure and purified by medium-pressure liquid chromatography using 2% of methanol in chloroform as eluant to give 0.7 g of the title compound as a brown solid.

$^1$H NMR (CDCl$_3$) δ 3.5 (m, 1H), 3.9 (m, 1H), 5.8 (m, 1H), 7.35 (m, 5H), 8.16 (s, 1H), 8.3 (d, 2H), 8.8 (d, 2H).

Step B: Preparation of 4-[4-(4,5-dihydro-5-phenyl-3-isoxazolyl)-2-thiazolyl]-1,2,3,6-tetrahydro-1-(phenylmethyl)pyridine To a solution of 4-[4-(4,5-dihydro-5-phenyl-3-isoxazolyl)-2-thiazolyl]pyridine (i.e. the product of Example 13, Step A) (0.60 g, 1.95 mmol) in toluene (10 mL) was added benzyl bromide (0.670 g, 3.90 mmol), and the reaction mixture was heated to 100° C. for 12 h. Then the reaction mixture was cooled to room temperature. The solid that precipitated out was filtered and dried. The solid was dissolved in methanol (10 mL), and sodium borohydride (0.072 g, 1.95 mmol) was added in portions. The reaction mixture was stirred at room temperature for 2 h, diluted with water (50 mL), neutralized with 1.5 N aqueous hydrochloric acid solution, and extracted with ethyl acetate (50 mL). The organic layer was separated, washed with brine (25 mL), and concentrated under reduced pressure. The residue was purified by medium-pressure liquid chromatography using 3% of methanol in chloroform as eluant to give 0.4 g of the title compound as a white solid.

$^1$H NMR (CDCl$_3$) δ 3.03-3.1 (m, 2H), 3.4-3.6 (m, 4H), 3.8-4.0 (m, 2H), 4.25-4.32 (m, 2H), 5.76-5.79 (m, 1H), 6.47 (s, 1H), 7.34-7.48 (m, 10H), 7.72 (s, 1H).

Step C: Preparation of 4-[4-(4,5-dihydro-5-phenyl-3-isoxazolyl)-2-thiazolyl]-1,2,3,6-tetrahydropyridine hydrochloride To a solution of 4-[4-(4,5-dihydro-5-phenyl-3-isoxazolyl)-2-thiazolyl]-1,2,3,6-tetrahydro-1-(phenylmethyl)pyridine (i.e. the product of Example 13, Step B) (0.400 g, 0.99 mmol) in dichloroethane (10 mL) was added 1-chloroethyl chloroformate (0.286 g, 1.99 mmol), and the reaction mixture was heated to 80° C. for 5 h. The reaction mixture was cooled to room temperature and concentrated under reduced pressure. Methanol (10 mL) was added to the residue, and the resulting mixture was heated to 60° C. for 1 h, cooled to room temperature, and concentrated under reduced pressure. The residue was triturated with 50% of petroleum ether in ethyl acetate, and the solid formed was filtered and dried to give 0.25 g of the title compound as a white solid.

$^1$H NMR (DMSO-$d_6$) δ 2.50-2.55 (m, 2H), 3.31-3.39 (m, 3H), 3.86-3.91 (m, 3H), 5.73-5.78 (m, 1H), 6.67 (s, 1H), 7.34-7.39 (m, 5H), 7.68 (s, 1H), 9.47 (s, 2H).

Step D: Preparation of 1-[4-[4-(4,5-dihydro-5-phenyl-3-isoxazolyl)-2-thiazolyl]-3,6-dihydro-1(2H)-pyridinyl]-2-[5-methyl-3-(trifluoromethyl)-1H-pyrazol-1yl]ethanone To a solution of 4-[4-(4,5-dihydro-5-phenyl-3-isoxazolyl)-2-thiazolyl]-1,2,3,6-tetrahydropyridine hydrochloride (i.e. the product of Example 13, Step C) (0.250 g, 0.720 mmol) and 5-methyl-3-(trifluoromethyl)-H-pyrazole-1-acetic acid (0.150 g, 0.720 mmol) in dichloromethane (10 mL) was added N-(3-dimethylaminopropyl)-N'-ethylcarbodiimide (0.138 g, 0.720 mmol), 1-hydroxybenzotriazole (0.024 g, 0.177 mmol), and triethylamine (0.145 g, 1.44 mmol) at room temperature. The reaction mixture was stirred at room temperature for 24 h. The reaction mixture was diluted with dichloromethane (30 mL) and washed with water (20 mL) and brine (20 mL). The organic layer was separated, washed with water, dried (Na$_2$SO$_4$), and concentrated under reduced pressure and purified by medium-pressure liquid chromatography using 3% methanol in chloroform as eluant to give 200 mg of the title product, a compound of the present invention, as a white solid.

$^1$H NMR (CDCl$_3$) δ 2.3 (s, 3H), 2.71-2.75 (m, 2H), 3.42-3.46 (m, 1H), 3.74-3.88 (m, 3H), 4.24-4.27 (m, 2H), 5.02 (s, 2H), 5.71-5.76 (m, 1H), 6.32 (s, 1H), 6.57 (s, 1H), 7.3-7.38 (m, 5H), 7.64 (s, 1H).

By the procedures described herein, together with methods known in the art, the following compounds of Tables 1A to 8 can be prepared. The following abbreviations are used in the Tables which follow: t means tertiary, s means secondary, n means normal, i means iso, c means cyclo, Ac means acetyl, Me means methyl, Et means ethyl, Pr means propyl (i.e. n-propyl), i-Pr means isopropyl, c-Pr means cyclopropyl, Bu means butyl, Pen means pentyl, Hex means hexyl, Am means amyl, CN means cyano. A dash (-) indicates no substituents.

The invention includes but is not limited to the following exemplary species.

TABLE 1A

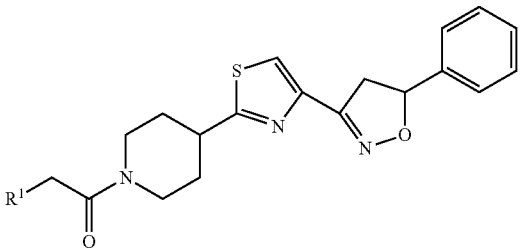

| $R^1$ |
|---|
| phenyl |
| 2-methylphenyl |
| 2-methoxyphenyl |
| 2-chlorophenyl |
| 2-bromophenyl |
| 2-ethylphenyl |
| 2-ethoxyphenyl |
| 2-(methylthio)phenyl |
| 2-(ethylthio)phenyl |
| 2-(trifluoromethoxy)phenyl |
| 3-chlorophenyl |
| 3-bromophenyl |
| 3-iodophenyl |
| 3-methylphenyl |
| 2-chloro-5-(trifluoromethyl)phenyl |
| 2-chloro-5-(2,2,2-trifluoroethyl)phenyl |
| 2-chloro-5-(pentafluoroethyl)phenyl |
| 2-chloro-5-cyanophenyl |
| 2-chloro-5-nitrophenyl |
| 2-bromo-5-chlorophenyl |
| 2,5-dibromophenyl |
| 2-bromo-5-iodophenyl |
| 2-bromo-5-methylphenyl |
| 2-bromo-5-ethylphenyl |
| 2-bromo-5-propylphenyl |
| 2-bromo-5-isopropylphenyl |
| 2-bromo-5-(trifluoromethyl)phenyl |
| 2-bromo-5-(2,2,2-trifluoroethyl)phenyl |
| 2-bromo-5-(pentafluoroethyl)phenyl |
| 2-bromo-5-cyanophenyl |
| 2-bromo-5-nitrophenyl |
| 5-chloro-2-methylphenyl |
| 5-bromo-2-methylphenyl |
| 5-iodo-2-methylphenyl |
| 2,5-dimethylphenyl |
| 5-ethyl-2-methylphenyl |
| 2-methyl-5-propylphenyl |
| 5-isopropyl-2-methylphenyl |
| 2-methyl-5-(trifluoromethyl)phenyl |
| 2-methyl-5-(2,2,2-trifluoroethyl)phenyl |
| 2-methyl-5-(pentafluoroethyl)phenyl |
| 5-cyano-2-methylphenyl |
| 2-methyl-5-nitrophenyl |
| 5-chloro-2-methoxyphenyl |
| 5-bromo-2-methoxyphenyl |
| 5-iodo-2-methoxyphenyl |
| 2-methoxy-5-methylphenyl |
| 3-iodo-5-methylpyrazol-1-yl |
| 3-ethyl-5-methylpyrazol-1-yl |
| 5-methyl-3-propylpyrazol-1-yl |
| 3-isopropyl-5-methylpyrazol-1-yl |
| 5-methyl-3-(trifluoromethyl)pyrazol-1-yl |
| 5-methyl-3-(2,2,2-trifluoroethyl)pyrazol-1-yl |
| 5-methyl-3-(pentafluoroethyl)pyrazol-1-yl |
| 3-cyano-5-methylpyrazol-1-yl |
| 5-methyl-3-nitropyrazol-1-yl |
| 5-chloro-3-methylpyrazol-1-yl |
| 3,5-dichloropyrazol-1-yl |
| 5-chloro-3-bromopyrazol-1-yl |
| 5-chloro-3-iodopyrazol-1-yl |
| 5-chloro-3-ethylpyrazol-1-yl |

TABLE 1A-continued

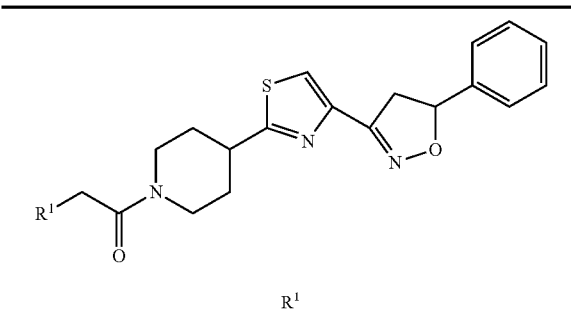

R[1]

5-chloro-3-propylpyrazol-1-yl
5-chloro-3-isopropylpyrazol-1-yl
5-chloro-3-(trifluoromethyl)pyrazol-1-yl
5-chloro-3-(2,2,2-trifluoroethyl)pyrazol-1-yl
5-chloro-3-(pentafluoroethyl)pyrazol-1-yl
5-chloro-3-cyanopyrazol-1-yl
5-chloro-3-nitropyrazol-1-yl
5-bromo-3-methylpyrazol-1-yl
5-bromo-3-chloropyrazol-1-yl
3,5-dibromopyrazol-1-yl
5-bromo-3-iodopyrazol-1-yl
5-bromo-3-ethylpyrazol-1-yl
5-bromo-3-propylpyrazol-1-yl
5-bromo-3-isopropylpyrazol-1-yl
5-bromo-3-(trifluoromethyl)pyrazol-1-yl
5-bromo-3-(2,2,2-trifluoroethyl)pyrazol-1-yl
5-bromo-3-(pentafluoroethyl)pyrazol-1-yl
5-bromo-3-cyanopyrazol-1-yl
5-bromo-3-nitropyrazol-1-yl
2-chloro-5-(dimethylamino)phenyl
2-chloro-5-(diethylamino)phenyl
2-chloro-5-(cyclopropylamino)phenyl
3-(methoxymethyl)phenyl
2-chloro-5-(ethoxymethyl)phenyl
2-chloro-5-(hyroxymethyl)phenyl
2-chloro-5-(methoxycarbonyl)phenyl
2-chloro-5-(ethylcarbonyl)phenyl
2-chloro-5-(methylcarbonyloxy)phenyl
2-chloro-5-(dimethylaminocarbonyl)phenyl
2-chloro-5-(dimethylaminocarbonyl)phenyl
2-methyl-5-(trimethylsilyl)phenyl
3,5-dimethyl-2-thienyl
3,5-dichloro-2-thienyl
3,5-dimethyl-2-furyl
1-methyl-2-pyrrolyl
4-methyl-2-(trifluoromethyl)-5-thiazolyl
4-(trifluoromethyl)-2-thiazolyl
4-(trifluoromethyl)-2-oxazolyl
4-methyl-2-(trifluoromethyl)-5-oxazolyl
4-bromo-5-isothiazolyl
4-bromo-5-isoxazolyl
1-methyl-5-pyrazolyl
1-methyl-5-imidazolyl
1-methyl-4-(trifluoromethyl)-2-imidazolyl
4-methyl-3-(1,3,4-triazolyl)
2-methyl-3-(1,2,4-triazolyl)
5-(trifluoromethyl)-2-(1,3,4-thiadiazolyl)
5-(trifluoromethyl)-2-(1,3,4-oxadiazolyl)
3-(trifluoromethyl)-5-(1,2,4-thiadiazolyl)
3-(trifluoromethyl)-5-(1,2,4-oxadiazolyl)
3-(trifluoromethyl)-1-(1,2,4-triazolyl)
2,5-dimethyl-1-pyrrolyl
1-methyl-3-(trifluoromethyl)pyrazol-5-yl
3-bromo-5-(trifluoromethyl)pyrazol-1-yl
3-iodo-5-(trifluoromethyl)pyrazol-1-yl
3-ethyl-5-(trifluoromethyl)-pyrazol-1-yl
3-propyl-5-(trifluoromethyl)-pyrazol-1-yl
3-isopropyl-5-(trifluoromethyl)pyrazol-1-yl
3-methyl-5-(trifluoromethyl)-pyrazol-1-yl
3-methoxy-5-(trifluoromethyl)-pyrazol-1-yl
5-difluoromethoxy-3-methylpyrazol-1-yl
5-difluoromethoxy-3-chloropyrazol-1-yl
3,5-dibromopyrazol-1-yl
5-difluoromethoxy-3-iodopyrazol-1-yl
5-difluoromethoxy-3-ethylpyrazol-1-yl TABLE 1A-continued

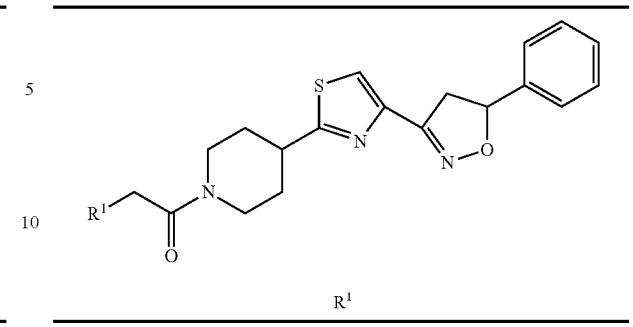

R[1]

5-difluoromethoxy-3-propylpyrazol-1-yl
5-difluoromethoxy-3-isopropylpyrazol-1-yl
5-difluoromethoxy-3-(trifluoromethyl)pyrazol-1-yl
5-difluoromethoxy-3-(2,2,2-trifluoroethyl)pyrazol-1-yl
5-difluoromethoxy-3-(pentafluoroethyl)pyrazol-1-yl
5-difluoromethoxy-3-cyanopyrazol-1-yl
5-difluoromethoxy-3-nitropyrazol-1-yl
3-carbomethoxy-5-(trifluoromethyl)pyrazol-1-yl
5-methoxy-3-methylpyrazol-1-yl
5-methoxy-3-bromopyrazol-1-yl
5-methoxy-3-iodopyrazol-1-yl
5-methoxy-3-ethylpyrazol-1-yl
5-methoxy-3-propylpyrazol-1-yl
5-methoxy-3-isopropylpyrazol-1-yl
5-methoxy-3-(trifluoromethyl)pyrazol-1-yl
5-methoxy-3-(2,2,2-trifluoroethyl)pyrazol-1-yl
5-methoxy-3-(pentafluoroethyl)pyrazol-1-yl
5-methoxy-3-cyanopyrazol-1-yl
5-methoxy-3-nitropyrazol-1-yl
3-ethylphenyl
3-propylphenyl
3-isopropylphenyl
3-(trifluoromethyl)phenyl
3-(2,2,2-trifluoroethyl)phenyl
3-(pentafluoroethyl)phenyl
3-cyanophenyl
3-nitrophenyl
2,5-dichlorophenyl
5-bromo-2-chlorophenyl
2-chloro-5-iodophenyl
2-chloro-5-methylphenyl
2-chloro-5-ethylphenyl
2-chloro-5-propylphenyl
2-chloro-5-isopropylphenyl
5-ethyl-2-methoxyphenyl
2-methoxy-5-propylphenyl
5-isopropyl-2-methoxyphenyl
2-methoxy-5-(trifluoromethyl)phenyl
2-methoxy-5-(2,2,2-trifluoroethyl)phenyl
2-methoxy-5-(pentafluoroethyl)phenyl
5-cyano-2-methoxyphenyl
2-methoxy-5-nitrophenyl
5-chloro-2-ethylphenyl
5-bromo-2-ethylphenyl
2-ethyl-5-iodophenyl
2-ethyl-5-methylphenyl
2,5-diethylphenyl
2-ethyl-5-propylphenyl
2-ethyl-5-isopropylphenyl
2-ethyl-5-(trifluoromethyl)phenyl
2-ethyl-5-(2,2,2-trifluomethyl)phenyl
2-ethyl-5-(pentafluoroethyl)phenyl
5-cyano-2-ethylphenyl
2-ethyl-5-nitrophenyl
3-methylpyrazol-1-yl
3-chloropyrazol-1-yl
3-bromopyrazol-1-yl
3-iodopyrazol-1-yl
3-ethylpyrazol-1-yl
3-(trifluoromethyl)pyrazol-1-yl
3-(2,2,2-trifluoroethyl)pyrazol-1-yl
3-(pentafluoroethyl)pyrazol-1-yl
3-cyanopyrazol-1-yl
3-nitropyrazol-1-yl

TABLE 1A-continued

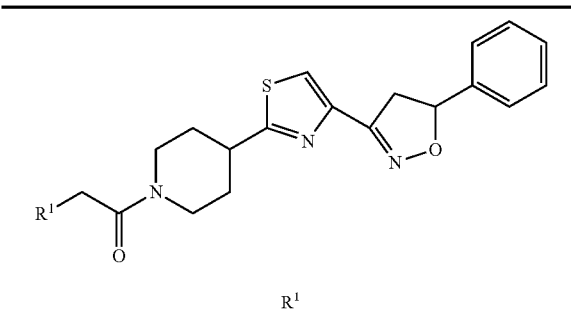

R¹

- 3,5-dimethylpyrazol-1-yl
- 3-chloro-5-methylpyrazol-1-yl
- 3-bromo-5-methylpyrazol-1-yl
- 5-methoxy-3-methylpyrazol-1-yl
- 3-chloro-5-methoxypyrazol-1-yl
- 5-ethyl-3-methylpyrazol-1-yl
- 3-chloro-5-ethylpyrazol-1-yl
- 3-bromo-5-ethylpyrazol-1-yl
- 5-ethyl-3-iodopyrazol-1-yl
- 3,5-diethylpyrazol-1-yl
- 5-ethyl-3-propylpyrazol-1-yl
- 5-ethyl-3-isopropylpyrazol-1-yl
- 5-ethyl-3-(trifluoromethyl)pyrazol-1-yl
- 5-ethyl-3-(2,2,2-trifluoroethyl)pyrazol-1-yl
- 5-ethyl-3-(pentafluomethyl)pyrazol-1-yl
- 3-cyano-5-ethylpyrazol-1-yl
- 5-ethyl-3-nitropyrazol-1-yl
- 5-butyl-2-methylphenyl
- 5-hexyl-2-methylphenyl
- 5-allyl-2-methylphenyl
- 2-methyl-5-(4-methyl-3-pentenyl)phenyl
- 2-methyl-5-propargylphenyl
- 2-methyl-5-(3-methylpropargyl)phenyl
- 5-cyclopropyl-2-methylphenyl
- 5-cyclohexyl-2-methylphenyl
- 2-methyl-5-(pentafluoroisopropyl)phenyl
- 5-(3,3-dichloro-2-propen-1-yl)-2-methylphenyl
- 2-methyl-5-(4,4,4-trifluoro-2-butyn-1-yl)phenyl
- 5-(2,2-dichlorocyclopropan-1-yl)-2-methylphenyl
- 2-methyl-5-(trifluoromethoxy)phenyl
- 2-chloro-5-(isobutylthio)phenyl
- 2-chloro-5-(ethylsulfonyl)phenyl
- 2-chloro-5-(trifluoromethylthio)phenyl
- 2-chloro-5-(trifluoromethylsulfonyl)phenyl
- 2-chloro-5-(methylamino)phenyl
- 2-chloro-5-(tert-butylamino)phenyl
- 2,5-dimethyl-3-furyl
- 2,5-dimethyl-3-thienyl
- 2,5-dichloro-3-thienyl
- 1,4-dimethyl-3-pyrrolyl
- 1,4-dimethyl-3-pyrazolyl
- 1,3-dimethyl-4-pyrazolyl
- 2,5-dimethyl-4-oxazolyl
- 2,5-dimethyl-4-thiazolyl
- 3-bromo-4-isothiazolyl
- 3-bromo-4-isooxazolyl
- 1-methyl-4-imidazolyl
- 5-(trifluoromethyl)-3-(1,2,4-oxadiazolyl)
- 5-(trifluoromethyl)-3-(1,2,4-tiadiazolyl)
- 2-bromo-1-(1,3,4-triazolyl)
- 5-(trifluoromethyl)-3-(1,2,4-triazolyl)
- 2-bromo-1-imidazolyl
- 3,6-dimethyl-2-pyridyl
- 2,5-dimethyl-3-pyridyl
- 2,5-dimethyl-4-pyridyl
- 3,6-dichloro-2-pyridyl
- 2,5-dichloro-3-pyridyl
- 2,5-dichloro-4-pyridyl
- 4-bromo-3-pyridazinyl
- 4-(trifluoromethyl)-2-pyrimidinyl
- 3,6-dimethyl-2-pyrazinyl
- 2,5-dimethyl-4-pyrimidinyl
- 4-methoxy-5-pyrimidinyl
- 3,6-dimethyl-4-pyridazinyl

TABLE 1A-continued

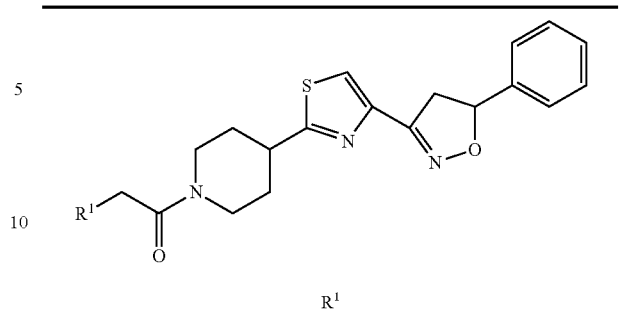

R¹

- 5-(trifluoromethyl)-3-(1,2,4-triazinyl)
- 5-methoxy-6-(1,2,4-triazinyl)
- 4-(trifluoromethyl)-2-(1,3,5-triazinyl)
- 3,6-dimethyl-5-(1,2,4-triazinyl)
- 1-methyl-4-(trifluoromethyl)imidazol-2-yl
- 3,5-bis-(trifluoromethyl)pyrazol-1-yl
- 3-(2,2,2-trifluoroethyl)-5-(trifluoromethyl)pyrazol-1-yl
- 3-(pentafluoroethyl)-5-(trifluoromethyl)pyrazol-1-yl
- 3-cyano-5-(trifluoromethyl)pyrazol-1-yl
- 3-nitro-5-(trifluoromethyl)pyrazol-1-yl
- 3-chloro-5-(trifluoromethyl)-pyrazol-1-yl
- 3,5-bis-(trichloromethyl)pyrazol-1-yl
- 3-difluoromethoxy-5-methylpyrazol-1-yl
- 3-difluoromethoxy-5-chloropyrazol-1-yl
- 3-difluoromethoxy-5-bromopyrazol-1-yl
- 3-difluoromethoxy-5-iodopyrazol-1-yl
- 3-difluoromethoxy-5-ethylpyrazol-1-yl
- 3-difluoromethoxy-5-(trifluoromethyl)pyrazol-1-yl
- 3-difluoromethoxy-5-(2,2,2-trifluoroethyl)pyrazol-1-yl
- 3-difluoromethoxy-5-(pentafluoroethyl)pyrazol-1-yl
- 3-difluoromethoxy-5-cyanopyrazol-1-yl
- 3-difluoromethoxy-5-nitropyrazol-1-yl
- 3,5-bis-(difluoromethoxy)pyrazol-1-yl
- 5-carbomethoxy-3-(trifluoromethyl)pyrazol-1-yl
- 3,5-dimethoxypyrazol-1-yl
- 5-ethoxy-3-methylpyrazol-1-yl
- 5-ethoxy-3-bromopyrazol-1-yl
- 5-ethoxy-3-iodopyrazol-1-yl
- 5-ethoxy-3-ethylpyrazol-1-yl
- 5-ethoxy-3-propylpyrazol-1-yl
- 5-ethoxy-3-isopropylpyrazol-1-yl
- 5-ethoxy-3-(trifluoromethyl)pyrazol-1-yl
- 5-ethoxy-3-(2,2,2-trifluoroethyl)pyrazol-1-yl
- 5-ethoxy-3-(pentafluoroethyl)pyrazol-1-yl
- 5-ethoxy-3-cyanopyrazol-1-yl
- 5-ethoxy-3-nitropyrazol-1-yl

TABLE 1B

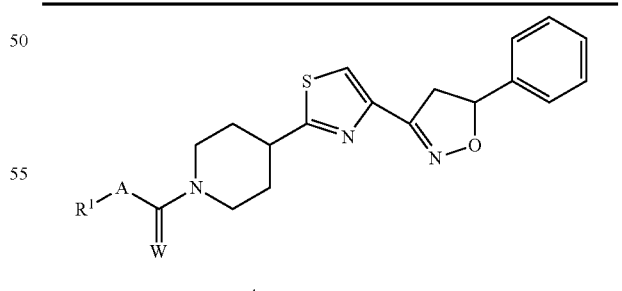

| R¹ | A | W |
|---|---|---|
| 2-methoxyphenyl | NH | O |
| 2,5-dichlorophenyl | NH | O |
| 5-bromo-2-chlorophenol | NH | O |
| 2-chloro-5-methylphenyl | NH | O |
| 2-chloro-5-(trifluoromethyl)phenyl | NH | O |
| 2,5-dibromophenyl | NH | O |
| 2-bromo-5-methylphenyl | NH | O |

TABLE 1B-continued

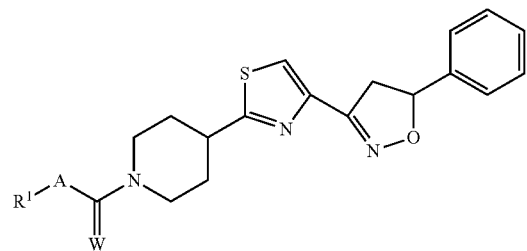

| R¹ | A | W |
|---|---|---|
| 2-bromo-5-(trifluoromethyl)phenyl | NH | O |
| 5-chloro-2-methylphenyl | NH | O |
| 5-bromo-2-methylphenyl | NH | O |
| 2,5-dimethylphenyl | NH | O |
| 5-ethyl-2-methylphenyl | NH | O |
| 2-methyl-5-(trifluoromethyl)phenyl | NH | O |
| 5-bromo-2-methoxyphenyl | NH | O |
| 2-methoxy-5-methylphenyl | NH | O |
| 2-methoxy-5-(trifluoromethyl)phenyl | NH | O |
| 3-ethyl-5-methylpyrazol-1-yl | CH₂ | S |
| 5-methyl-3-(trifluoromethyl)pyrazol-1-yl | CH₂ | S |
| 3,5-dichloropyrazol-1-yl | CH₂ | S |
| 5-chloro-3-(trifluoromethyl)pyrazol-1-yl | CH₂ | S |
| 3,5-bis-(trifluoromethyl)pyrazol-1-yl | CH₂ | S |
| 3,5-dimethylpyrazol-1-yl | CH₂ | S |
| 3,5-dibromoryrazol-1-yl | CH₂ | S |
| 5-bromo-3-(trifluoromethyl)pyrazol-1-yl | CH₂ | S |
| 3,5-diethylpyrazol-1-yl | CH₂ | S |
| 5-ethyl-3-(trifluoromethyl)pyrazol-1-yl | CH₂ | S |
| 2-methoxyphenyl | NH | S |
| 2,5-dichlorophenyl | NH | S |
| 5-bromo-2-chlorophenyl | NH | S |
| 2-chloro-5-methylphenyl | NH | S |
| 2-chloro-5-(trifluoromethyl)phenyl | NH | S |
| 2,5-dibromophenyl | NH | S |
| 2-bromo-5-methylphenyl | NH | S |
| 2-bromo-5-(trifluoromethyl)phenyl | NH | S |
| 5-chloro-2-methylphenyl | NH | S |
| 5-bromo-2-methylphenyl | NH | S |

TABLE 1B-continued

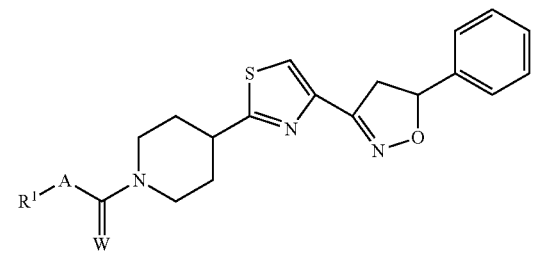

| R¹ | A | W |
|---|---|---|
| 2,5-dimethylphenyl | NH | S |
| 5-ethyl-2-methylphenyl | NH | S |
| 2-methyl-5-(trifluoromethyl)phenyl | NH | S |
| 5-bromo-2-methoxyphenyl | NH | S |
| 2-methoxy-5-methylphenyl | NH | S |
| 2-methoxy-5-(trifluoromethyl)phenyl | NH | S |
| 5-methyl-3-(trifluoromethyl)pyrazol-1-yl | NCH₃ | O |
| 5-methyl-3-(trifluoromethyl)pyrazol-1-yl | NAc | O |
| 3-methyl-5-(trifluoromethyl)pyrazol-1-yl | CH₂ | S |
| 5-methyl-3-(trifluoromethyl)pyrazol-1-yl | CHCH₃ | O |
| 5-methyl-3-(trifluoromethyl)pyrazol-1-yl | CHCOOCH₃ | O |
| 5-methyl-3-(trifluoromethyl)pyrazol-1-yl | CHCl | O |
| 5-methyl-3-(trifluoromethyl)pyrazol-1-yl | NCOOCH₃ | O |
| 5-methyl-3-(trifluoromethyl)pyrazol-1-yl | NH | S |
| 3,5-dimethylpyrazol-1-yl | NH | O |
| 3,5-dichloropyrazol-1-yl | NH | O |
| 3,5-dibromopyrazol-1-yl | NH | O |
| 5-methyl-3-(trifluoromethyl)pyrazol-1-yl | NH | O |
| 5-chloro-3-(trifluoromethyl)pyrazol-1-yl | NH | O |
| 5-bromo-3-(trifluoromethyl)pyrazol-1-yl | NH | O |
| 5-ethyl-3-(trifluoromethyl)pyrazol-1-yl | NH | O |
| 3,5-bis-(trifluoromethyl)pyrazol-1-yl | NH | O |
| 3-methyl-5-(triftuoromethyl)pyrazol-1-yl | NH | O |
| 3-chloro-5-(trifluoromethyl)pyrazol-1-yl | NH | O |
| 3-bromo-5-(trifluoromethyl)pyrazol-1-yl | NH | O |
| 5-methoxy-3-(trifluoromethyl)pyrazol-1-yl | NH | O |
| 5-difluoromethoxy-3-(trifluoromethyl)pyrazol-1-yl | NH | O |

TABLE 2*

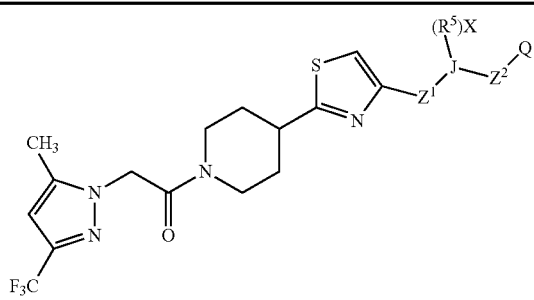

| Z¹ | J | (R⁵)ₓ | Z² | Q | (R⁷)ₚ | R¹² | J-orientation** |
|---|---|---|---|---|---|---|---|
| bond | J-1 | — | bond | Q-45 | — | — | 2/4 |
| bond | J-1 | — | bond | Q-45 | — | — | 2/5 |
| bond | J-1 | — | bond | Q-45 | — | — | 4/2 |
| bond | J-1 | — | bond | Q-45 | — | — | 5/2 |
| bond | J-2 | — | bond | Q-45 | — | — | 2/4 |
| bond | J-2 | — | bond | Q-45 | — | — | 2/5 |
| bond | J-2 | — | bond | Q-45 | — | — | 4/2 |
| bond | J-2 | — | bond | Q-45 | — | — | 5/2 |
| bond | J-3 | 1-Me | bond | Q-45 | — | — | 2/4 |
| bond | J-3 | 1-Me | bond | Q-45 | — | — | 2/5 |
| bond | J-3 | 1-Me | bond | Q-45 | — | — | 4/2 |
| bond | J-3 | 1-Me | bond | Q-45 | — | — | 5/2 |
| CH₂ | J-3 | — | bond | Q-45 | — | — | 1/4 |
| bond | J-3 | — | bond | Q-45 | — | — | 4/1 |
| bond | J-4 | — | bond | Q-45 | — | — | 2/4 |

TABLE 2*-continued

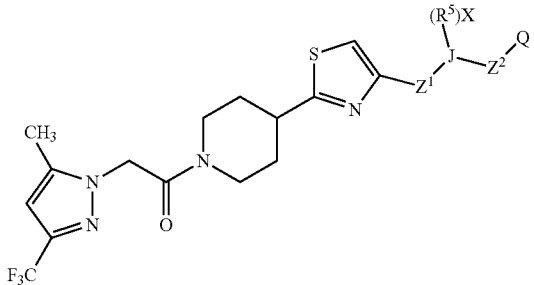

| $Z^1$ | J | $(R^5)_x$ | $Z^2$ | Q | $(R^7)_p$ | $R^{12}$ | J-orientation** |
|---|---|---|---|---|---|---|---|
| bond | J-4 | — | bond | Q-45 | — | — | 2/5 |
| bond | J-4 | — | bond | Q-45 | — | — | 4/2 |
| bond | J-4 | — | bond | Q-45 | — | — | 5/2 |
| bond | J-4 | — | bond | Q-45 | — | — | 3/5 |
| bond | J-4 | — | bond | Q-45 | — | — | 5/3 |
| bond | J-5 | — | bond | Q-45 | — | — | 2/4 |
| bond | J-5 | — | bond | Q-45 | — | — | 2/5 |
| bond | J-5 | — | bond | Q-45 | — | — | 4/2 |
| bond | J-5 | — | bond | Q-45 | — | — | 5/2 |
| bond | J-5 | — | bond | Q-45 | — | — | 3/5 |
| bond | J-5 | — | bond | Q-45 | — | — | 5/3 |
| bond | J-6 | — | bond | Q-45 | — | — | 2/4 |
| bond | J-6 | — | bond | Q-45 | — | — | 2/5 |
| bond | J-6 | — | bond | Q-45 | — | — | 4/2 |
| bond | J-6 | — | bond | Q-45 | — | — | 5/2 |
| bond | J-6 | — | bond | Q-45 | — | — | 3/5 |
| bond | J-6 | — | bond | Q-45 | — | — | 5/3 |
| $CH_2$ | J-6 | — | bond | Q-45 | — | — | 1/3 |
| bond | J-6 | — | bond | Q-45 | — | — | 3/1 |
| bond | J-7 | — | bond | Q-45 | — | — | 5/3 |
| bond | J-7 | — | bond | Q-45 | — | — | 3/5 |
| bond | J-8 | — | bond | Q-45 | — | — | 5/3 |
| bond | J-8 | — | bond | Q-45 | — | — | 3/5 |
| bond | J-9 | 1-Me | bond | Q-45 | — | — | 5/3 |
| bond | J-9 | 1-Me | bond | Q-45 | — | — | 3/5 |
| $CH_2$ | J-9 | — | bond | Q-45 | — | — | 1/4 |
| bond | J-9 | — | bond | Q-45 | — | — | 4/1 |
| bond | J-10 | — | bond | Q-45 | — | — | 3/5 |
| bond | J-10 | — | bond | Q-45 | — | — | 5/3 |
| bond | J-11 | — | bond | Q-45 | — | — | 3/5 |
| bond | J-11 | — | bond | Q-45 | — | — | 5/3 |
| bond | J-12 | 1-Me | bond | Q-45 | — | — | 3/5 |
| bond | J-12 | 1-Me | bond | Q-45 | — | — | 5/3 |
| $CH_2$ | J-12 | — | bond | Q-45 | — | — | 1/3 |
| bond | J-12 | — | bond | Q-45 | — | — | 3/1 |
| bond | J-13 | — | bond | Q-45 | — | — | 1/4 |
| bond | J-13 | — | bond | Q-45 | — | — | 4/1 |
| bond | J-14 | 1-Me | bond | Q-45 | — | — | 3/5 |
| bond | J-14 | — | bond | Q-45 | — | — | 5/3 |
| bond | J-15 | — | bond | Q-45 | — | — | 2/5 |
| bond | J-16 | — | bond | Q-45 | — | — | 2/5 |
| $CH_2$ | J-17 | — | bond | Q-45 | — | — | 2/4 |
| bond | J-17 | — | bond | Q-45 | — | — | 4/2 |
| $CH_2$ | J-18 | — | bond | Q-45 | — | — | 2/5 |
| bond | J-18 | — | bond | Q-45 | — | — | 5/2 |
| bond | J-19 | — | bond | Q-45 | — | — | 2/4 |
| bond | J-19 | — | bond | Q-45 | — | — | 4/2 |
| bond | J-20 | — | bond | Q-45 | — | — | 2/4 |
| bond | J-20 | — | bond | Q-45 | — | — | 2/5 |
| bond | J-20 | — | bond | Q-45 | — | — | 2/6 |
| bond | J-20 | — | bond | Q-45 | — | — | 3/5 |
| bond | J-20 | — | bond | Q-45 | — | — | 4/2 |
| bond | J-20 | — | bond | Q-45 | — | — | 5/2 |
| bond | J-21 | — | bond | Q-45 | — | — | 3/5 |
| bond | J-21 | — | bond | Q-45 | — | — | 3/6 |
| bond | J-21 | — | bond | Q-45 | — | — | 5/3 |
| bond | J-22 | — | bond | Q-45 | — | — | 2/4 |
| bond | J-22 | — | bond | Q-45 | — | — | 2/5 |
| bond | J-22 | — | bond | Q-45 | — | — | 4/6 |
| bond | J-22 | — | bond | Q-45 | — | — | 4/2 |
| bond | J-22 | — | bond | Q-45 | — | — | 5/2 |
| bond | J-23 | — | bond | Q-45 | — | — | 2/5 |
| bond | J-23 | — | bond | Q-45 | — | — | 2/6 |

TABLE 2*-continued

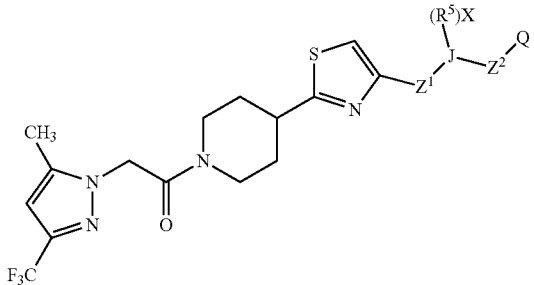

| $Z^1$ | J | $(R^5)_x$ | $Z^2$ | Q | $(R^7)_p$ | $R^{12}$ | J-orientation** |
|---|---|---|---|---|---|---|---|
| bond | J-24 | — | bond | Q-45 | — | — | 2/4 |
| bond | J-24 | — | bond | Q-45 | — | — | 2/5 |
| bond | J-24 | — | bond | Q-45 | — | — | 4/2 |
| bond | J-24 | — | bond | Q-45 | — | — | 5/2 |
| bond | J-25 | — | bond | Q-45 | — | — | 2/4 |
| bond | J-25 | — | bond | Q-45 | — | — | 2/5 |
| bond | J-25 | — | bond | Q-45 | — | — | 4/2 |
| bond | J-25 | — | bond | Q-45 | — | — | 5/2 |
| bond | J-26 | — | bond | Q-45 | — | — | 2/4 |
| bond | J-26 | — | bond | Q-45 | — | — | 2/5 |
| bond | J-26 | — | bond | Q-45 | — | — | 4/2 |
| bond | J-26 | — | bond | Q-45 | — | — | 5/2 |
| $CH_2$ | J-26 | — | bond | Q-45 | — | — | 1/4 |
| bond | J-26 | — | bond | Q-45 | — | — | 4/1 |
| bond | J-27 | — | bond | Q-45 | — | — | 2/4 |
| bond | J-27 | — | bond | Q-45 | — | — | 2/5 |
| bond | J-27 | — | bond | Q-45 | — | — | 3/5 |
| bond | J-27 | — | bond | Q-45 | — | — | 4/2 |
| bond | J-27 | — | bond | Q-45 | — | — | 5/2 |
| bond | J-27 | — | bond | Q-45 | — | — | 5/3 |
| bond | J-28 | — | bond | Q-45 | — | — | 3/5 |
| bond | J-28 | — | bond | Q-45 | — | — | 5/3 |
| bond | J-29 | — | bond | Q-45 | — | — | 3/5 |
| bond | J-29 | — | bond | Q-45 | — | — | 5/3 |
| bond | J-30 | — | bond | Q-45 | — | — | 3/5 |
| bond | J-30 | — | bond | Q-45 | — | — | 5/3 |
| $CH_2$ | J-30 | — | bond | Q-45 | — | — | 1/3 |
| bond | J-30 | — | bond | Q-45 | — | — | 3/1 |
| $CH_2$ | J-30 | — | bond | Q-45 | — | — | 1/4 |
| bond | J-30 | — | bond | Q-45 | — | — | 4/1 |
| $CH_2$ | J-31 | — | bond | Q-45 | — | — | 1/3 |
| $CH_2$ | J-31 | — | bond | Q-45 | — | — | 1/4 |
| bond | J-31 | — | bond | Q-45 | — | — | 2/4 |
| bond | J-31 | — | bond | Q-45 | — | — | 2/5 |
| bond | J-31 | — | bond | Q-45 | — | — | 3/5 |
| bond | J-31 | — | bond | Q-45 | — | — | 3/1 |
| bond | J-31 | — | bond | Q-45 | — | — | 4/1 |
| bond | J-31 | — | bond | Q-45 | — | — | 4/2 |
| bond | J-31 | — | bond | Q-45 | — | — | 5/2 |
| bond | J-32 | — | bond | Q-45 | — | — | 2/4 |
| bond | J-32 | — | bond | Q-45 | — | — | 2/5 |
| bond | J-32 | — | bond | Q-45 | — | — | 3/5 |
| bond | J-32 | — | bond | Q-45 | — | — | 5/3 |
| bond | J-32 | — | bond | Q-45 | — | — | 5/2 |
| bond | J-32 | — | bond | Q-45 | — | — | 4/2 |
| bond | J-33 | — | bond | Q-45 | — | — | 2/4 |
| bond | J-33 | — | bond | Q-45 | — | — | 2/5 |
| bond | J-33 | — | bond | Q-45 | — | — | 3/5 |
| bond | J-33 | — | bond | Q-45 | — | — | 5/3 |
| bond | J-33 | — | bond | Q-45 | — | — | 5/2 |
| bond | J-33 | — | bond | Q-45 | — | — | 4/2 |
| bond | J-34 | — | bond | Q-45 | — | — | 1/3 |
| bond | J-34 | — | bond | Q-45 | — | — | 1/4 |
| bond | J-34 | — | bond | Q-45 | — | — | 3/5 |
| bond | J-34 | — | bond | Q-45 | — | — | 3/1 |
| bond | J-34 | — | bond | Q-45 | — | — | 4/1 |
| $CH_2$ | J-35 | — | bond | Q-45 | — | — | 1/4 |
| bond | J-35 | — | bond | Q-45 | — | — | 4/1 |
| $CH_2$ | J-36 | — | bond | Q-45 | — | — | 1/3 |
| bond | J-36 | — | bond | Q-45 | — | — | 3/1 |
| bond | J-36 | — | bond | Q-45 | — | — | 3/5 |
| bond | J-36 | — | bond | Q-45 | — | — | 5/3 |
| bond | J-37 | — | bond | Q-45 | — | — | 2/5 |

TABLE 2*-continued

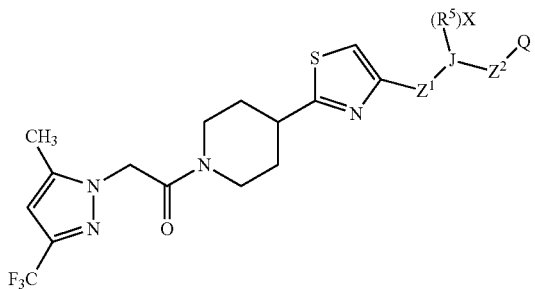

| Z¹ | J | (R⁵)ₓ | Z² | Q | (R⁷)ₚ | R¹² | J-orientation** |
|---|---|---|---|---|---|---|---|
| bond | J-37 | — | bond | Q-45 | — | — | 5/2 |
| bond | J-37 | — | bond | Q-45 | — | — | 2/4 |
| bond | J-37 | — | bond | Q-45 | — | — | 4/2 |
| bond | J-38 | — | bond | Q-45 | — | — | 2/5 |
| bond | J-38 | — | bond | Q-45 | — | — | 5/2 |
| bond | J-38 | — | bond | Q-45 | — | — | 2/4 |
| bond | J-38 | — | bond | Q-45 | — | — | 4/2 |
| bond | J-39 | 4-Me | bond | Q-45 | — | — | 3/5 |
| bond | J-39 | 4-Me | bond | Q-45 | — | — | 5/3 |
| bond | J-40 | — | bond | Q-45 | — | — | 3/5 |
| bond | J-40 | — | bond | Q-45 | — | — | 5/3 |
| bond | J-41 | — | bond | Q-45 | — | — | 1/3 |
| bond | J-41 | — | bond | Q-45 | — | — | 1/4 |
| CH₂ | J-42 | — | bond | Q-45 | — | — | 1/3 |
| CH₂ | J-42 | — | bond | Q-45 | — | — | 1/4 |
| CH₂ | J-43 | — | bond | Q-45 | — | — | 1/4 |
| bond | J-44 | — | bond | Q-45 | — | — | 1/3 |
| bond | J-44 | — | bond | Q-45 | — | — | 2/4 |
| bond | J-44 | — | bond | Q-45 | — | — | 2/5 |
| bond | J-44 | — | bond | Q-45 | — | — | 2/6 |
| bond | J-45 | — | bond | Q-45 | — | — | 2/4 |
| bond | J-45 | — | bond | Q-45 | — | — | 2/5 |
| bond | J-45 | — | bond | Q-45 | — | — | 2/6 |
| bond | J-46 | — | bond | Q-45 | — | — | 2/4 |
| bond | J-46 | — | bond | Q-45 | — | — | 2/5 |
| bond | J-46 | — | bond | Q-45 | — | — | 4/2 |
| bond | J-46 | — | bond | Q-45 | — | — | 5/2 |
| bond | J-47 | — | bond | Q-45 | — | — | 2/4 |
| bond | J-47 | — | bond | Q-45 | — | — | 2/5 |
| bond | J-47 | — | bond | Q-45 | — | — | 4/2 |
| bond | J-47 | — | bond | Q-45 | — | — | 5/2 |
| bond | J-48 | — | bond | Q-45 | — | — | 3/5 |
| bond | J-49 | — | bond | Q-45 | — | — | 2/4 |
| bond | J-49 | — | bond | Q-45 | — | — | 2/5 |
| bond | J-49 | — | bond | Q-45 | — | — | 4/2 |
| bond | J-49 | — | bond | Q-45 | — | — | 5/2 |
| bond | J-50 | — | bond | Q-45 | — | — | 2/6 |
| bond | J-51 | — | bond | Q-45 | — | — | 2/6 |
| bond | J-52 | — | bond | Q-45 | — | — | 2/6 |
| bond | J-53 | — | — | — | — | — | 2/3 |
| bond | J-54 | — | — | — | — | — | 2/3 |
| bond | J-55 | — | — | — | — | — | 2/3 |
| bond | J-56 | — | — | — | — | — | 2/3 |
| bond | J-57 | 1-Me | — | — | — | — | 2/4 |
| bond | J-58 | 1-Me | — | — | — | — | 3/4 |
| bond | J-59 | — | — | — | — | — | 2/4 |
| bond | J-60 | — | — | — | — | — | 2/4 |
| bond | J-61 | — | — | — | — | — | 2/4 |
| bond | J-62 | — | — | — | — | — | 2/4 |
| bond | J-63 | — | — | — | — | — | 3/4 |
| bond | J-64 | — | — | — | — | — | 2/3 |
| bond | J-65 | — | — | — | — | — | 3/4 |
| bond | J-66 | — | — | — | — | — | 6/7 |
| bond | J-67 | — | — | — | — | — | 2/3 |
| bond | J-68 | — | — | — | — | — | 2/3 |
| bond | J-69 | — | bond | Q-45 | — | — | 1/3 |
| bond | J-69 | — | bond | Q-45 | — | — | 1/4 |
| bond | J-70 | — | bond | Q-45 | — | — | 1/3 |
| bond | J-71 | — | bond | Q-45 | — | — | 2/4 |
| bond | J-71 | — | bond | Q-45 | — | — | 4/2 |
| bond | J-72 | — | bond | Q-45 | — | — | 2/4 |
| bond | J-72 | — | bond | Q-45 | — | — | 4/2 |
| bond | J-73 | — | bond | Q-45 | — | — | 2/4 |

TABLE 2*-continued

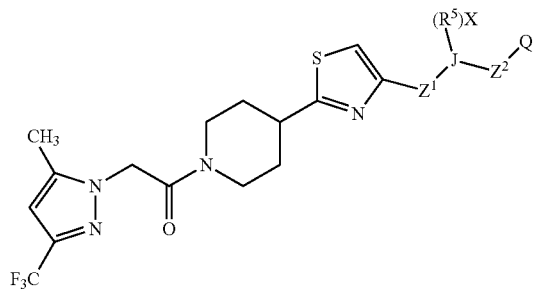

| $Z^1$ | J | $(R^5)_x$ | $Z^2$ | Q | $(R^7)_p$ | $R^{12}$ | J-orientation** |
|---|---|---|---|---|---|---|---|
| bond | J-73 | — | bond | Q-45 | — | — | 4/2 |
| bond | J-73 | — | bond | Q-45 | — | — | 1/3 |
| bond | J-73 | — | bond | Q-45 | — | — | 1/4 |
| bond | J-73 | — | bond | Q-45 | — | — | 4/1 |
| bond | J-74 | 3-Me | bond | Q-45 | — | — | 2/4 |
| bond | J-74 | 3-Me | bond | Q-45 | — | — | 2/5 |
| bond | J-74 | 3-Me | bond | Q-45 | — | — | 4/2 |
| bond | J-74 | 3-Me | bond | Q-45 | — | — | 5/2 |
| bond | J-74 | — | bond | Q-45 | — | — | 3/5 |
| bond | J-74 | — | bond | Q-45 | — | — | 5/3 |
| bond | J-75 | — | bond | Q-45 | — | — | 3/5 |
| bond | J-75 | — | bond | Q-45 | — | — | 5/3 |
| bond | J-75 | — | bond | Q-45 | — | — | 2/4 |
| bond | J-75 | — | bond | Q-45 | — | — | 2/5 |
| bond | J-75 | 2-Me | bond | Q-45 | — | — | 3/5 |
| bond | J-75 | 2-Me | bond | Q-45 | — | — | 5/3 |
| bond | J-76 | — | bond | Q-45 | — | — | 3/6 |
| bond | J-76 | — | bond | Q-45 | — | — | 6/3 |
| bond | J-77 | — | bond | Q-45 | — | — | 3/5 |
| bond | J-77 | — | bond | Q-45 | — | — | 5/3 |
| bond | J-78 | — | bond | Q-45 | — | — | 1/3 |
| bond | J-79 | — | bond | Q-45 | — | — | 1/3 |
| bond | J-79 | — | bond | Q-45 | — | — | 3/1 |
| bond | J-80 | — | bond | Q-45 | — | — | 1/3 |
| bond | J-80 | — | bond | Q-45 | — | — | 3/1 |
| bond | J-81 | — | bond | Q-45 | — | — | 3/5 |
| bond | J-81 | — | bond | Q-45 | — | — | 5/3 |
| bond | J-82 | — | bond | Q-45 | — | — | 3/5 |
| bond | J-82 | — | bond | Q-45 | — | — | 3/6 |
| bond | J-82 | — | bond | Q-45 | — | — | 5/3 |
| bond | J-82 | — | bond | Q-45 | — | — | 6/3 |
| $CH_2$ | J-83 | — | — | — | — | — | 2/6 |
| O | J-29 | — | bond | Q-45 | — | — | 3/5 |
| S | J-29 | — | bond | Q-45 | — | — | 3/5 |
| SO | J-29 | — | bond | Q-45 | — | — | 3/5 |
| $SO_2$ | J-29 | — | bond | Q-45 | — | — | 3/5 |
| NH | J-29 | — | bond | Q-45 | — | — | 3/5 |
| NMe | J-29 | — | bond | Q-45 | — | — | 3/5 |
| NPr | J-29 | — | bond | Q-45 | — | — | 3/5 |
| $CH_2$ | J-29 | — | bond | Q-45 | — | — | 3/5 |
| CH-i-Bu | J-29 | — | bond | Q-45 | — | — | 3/5 |
| bond | J-29 | 4-Me | bond | Q-45 | — | — | 3/5 |
| bond | J-29 | 5-Me | bond | Q-45 | — | — | 3/5 |
| bond | J-29 | 4,5-di-Me | bond | Q-45 | — | — | 3/5 |
| bond | J-29 | 4,4-di-Me | bond | Q-45 | — | — | 3/5 |
| bond | J-29 | [Note 1] | bond | Q-45 | 6-Me, [Note 1] | — | 3/5 |
| bond | J-29 | [Note 2] | bond | Q-45 | 6-Me, [Note 2] | — | 3/5 |
| bond | J-29 | 5-Et | bond | Q-45 | — | — | 3/5 |
| bond | J-29 | 5-t-Bu | — | — | — | — | 3/5 |
| bond | J-29 | 5-t-amyl | — | — | — | — | 3/5 |
| bond | J-29 | 5-(4-Me-3-penten-1-yl) | — | — | — | — | 3/5 |
| bond | J-29 | 5-(3,3-di-Me-1-butyn-1-yl) | — | — | — | — | 3/5 |
| bond | J-29 | 5-c-Pr | bond | Q-45 | — | — | 3/5 |
| bond | J-29 | 5-(4-Me-cyclohexyl) | — | — | — | — | 3/5 |
| bond | J-29 | 5-$CF_3$ | bond | Q-45 | — | — | 3/5 |
| bond | J-29 | 5-perfluoropropyl | — | — | — | — | 3/5 |
| bond | J-29 | 5-(3,3-di-Cl-2-propen-1-yl) | — | — | — | — | 3/5 |
| bond | J-29 | 5-OMe | bond | Q-45 | — | — | 3/5 |
| bond | J-29 | 5-$SiMe_3$ | — | — | — | — | 3/5 |
| bond | J-69 | 4-F | bond | Q-45 | — | — | 1/3 |
| bond | J-69 | 4-Cl | bond | Q-45 | — | — | 1/3 |
| bond | J-69 | 4-OH | bond | Q-45 | — | — | 1/3 |

TABLE 2*-continued

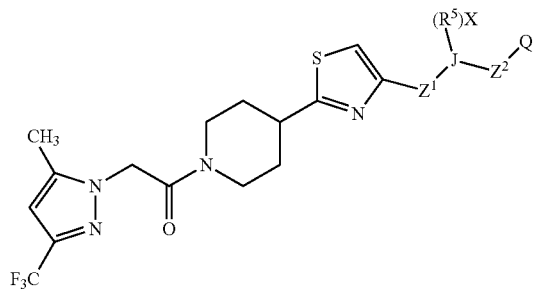

| $Z^1$ | J | $(R^5)_x$ | $Z^2$ | Q | $(R^7)_p$ | $R^{12}$ | J-orientation** |
|---|---|---|---|---|---|---|---|
| bond | J-69 | 4-NH$_2$ | bond | Q-45 | — | — | 1/3 |
| bond | J-69 | 4-CN | O | Q-45 | — | — | 1/3 |
| bond | J-69 | 4-NO$_2$ | NH | Q-45 | — | — | 1/3 |
| bond | J-69 | 4-CF$_3$ | S | Q-45 | — | — | 1/3 |
| bond | J-69 | — | O | Q-45 | — | — | 1/3 |
| bond | J-69 | — | S | Q-45 | — | — | 1/3 |
| bond | J-69 | — | SO | Q-45 | — | — | 1/3 |
| bond | J-69 | — | SO$_2$ | Q-45 | — | — | 1/3 |
| bond | J-69 | — | NH | Q-45 | — | — | 1/3 |
| bond | J-69 | — | N—Me | Q-45 | — | — | 1/3 |
| bond | J-69 | — | CH$_2$ | Q-45 | — | — | 1/3 |
| bond | J-69 | 4-OEt | bond | Q-45 | — | — | 1/3 |
| bond | J-69 | 4-OCF$_3$ | bond | Q-45 | — | — | 1/3 |
| bond | J-69 | 4-SMe | bond | Q-45 | — | — | 1/3 |
| bond | J-69 | 4-SOMe | bond | Q-45 | — | — | 1/3 |
| bond | J-69 | 4-SO$_2$Me | bond | Q-45 | — | — | 1/3 |
| bond | J-69 | 4-SO$_2$—t-Bu | — | — | — | — | 1/3 |
| bond | J-69 | 4-SCF$_3$ | bond | Q-45 | — | — | 1/3 |
| bond | J-69 | 4-SO$_2$CH$_2$CF$_3$ | — | — | — | — | 1/4 |
| bond | J-22 | 4-NH—i-Bu | — | — | — | — | 2/4 |
| bond | J-22 | 4-di-EtN | — | — | — | — | 2/4 |
| bond | J-22 | 4-NH-cyclohexyl | — | — | — | — | 2/4 |
| bond | J-69 | 4-CH$_2$O—i-Pr | — | — | — | — | 1/4 |
| bond | J-69 | 4-CH$_2$OCHF$_2$ | bond | Q-45 | — | — | 1/3 |
| bond | J-69 | 4-CH$_2$OH | bond | Q-45 | — | — | 1/3 |
| bond | J-74 | 3-acetyl | bond | Q-45 | — | — | 2/5 |
| bond | J-69 | 4-CO$_2$—i-Pr | — | — | — | — | 1/4 |
| bond | J-69 | 4-O-acetyl | bond | Q-45 | — | — | 1/3 |
| bond | J-69 | 4-S-acetyl | bond | Q-45 | — | — | 1/3 |
| bond | J-69 | 4-CONHMe | bond | Q-45 | — | — | 1/3 |
| bond | J-69 | 4-CONEt$_2$ | — | — | — | — | 1/4 |
| bond | J-69 | — | O | Q-45 | — | — | 1/4 |
| bond | J-29 | — | bond | Q-1 | — | — | 3/5 |
| bond | J-29 | — | bond | Q-2 | — | — | 3/5 |
| bond | J-29 | — | bond | Q-3 | — | Me | 3/5 |
| bond | J-29 | — | bond | Q-4 | — | — | 3/5 |
| bond | J-29 | — | bond | Q-5 | — | — | 3/5 |
| bond | J-29 | — | bond | Q-6 | — | — | 3/5 |
| bond | J-29 | — | bond | Q-7 | — | — | 3/5 |
| bond | J-29 | — | bond | Q-8 | — | — | 3/5 |
| bond | J-29 | — | bond | Q-9 | — | — | 3/5 |
| bond | J-29 | — | bond | Q-10 | — | Me | 3/5 |
| bond | J-29 | — | bond | Q-11 | — | Me | 3/5 |
| bond | J-29 | — | bond | Q-12 | — | Me | 3/5 |
| bond | J-29 | — | bond | Q-13 | — | Me | 3/5 |
| bond | J-29 | — | bond | Q-14 | — | Me | 3/5 |
| bond | J-29 | — | bond | Q-15 | — | — | 3/5 |
| bond | J-29 | — | bond | Q-16 | — | — | 3/5 |
| bond | J-29 | — | bond | Q-17 | — | — | 3/5 |
| bond | J-29 | — | bond | Q-18 | — | — | 3/5 |
| bond | J-29 | — | bond | Q-19 | — | — | 3/5 |
| bond | J-29 | — | bond | Q-20 | — | — | 3/5 |
| bond | J-29 | — | bond | Q-21 | — | Me | 3/5 |
| bond | J-29 | — | bond | Q-22 | — | Me | 3/5 |
| bond | J-29 | — | bond | Q-23 | — | Me | 3/5 |
| bond | J-29 | — | bond | Q-24 | — | — | 3/5 |
| bond | J-29 | — | bond | Q-25 | — | — | 3/5 |
| bond | J-29 | — | bond | Q-26 | — | — | 3/5 |
| bond | J-29 | — | bond | Q-27 | — | — | 3/5 |
| bond | J-29 | — | bond | Q-28 | — | Me | 3/5 |
| bond | J-29 | — | bond | Q-29 | — | — | 3/5 |
| bond | J-29 | — | bond | Q-30 | — | — | 3/5 |
| bond | J-29 | — | bond | Q-31 | — | Me | 3/5 |

TABLE 2*-continued

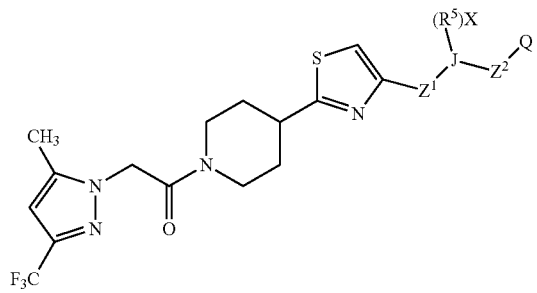

| $Z^1$ | J | $(R^5)_x$ | $Z^2$ | Q | $(R^7)_p$ | $R^{12}$ | J-orientation** |
|---|---|---|---|---|---|---|---|
| bond | J-29 | — | bond | Q-32 | — | — | 3/5 |
| bond | J-29 | — | bond | Q-33 | — | — | 3/5 |
| bond | J-29 | — | bond | Q-34 | — | — | 3/5 |
| bond | J-29 | — | bond | Q-35 | — | — | 3/5 |
| bond | J-29 | — | bond | Q-36 | — | — | 3/5 |
| bond | J-29 | — | bond | Q-37 | — | — | 3/5 |
| bond | J-29 | — | bond | Q-38 | — | — | 3/5 |
| bond | J-29 | — | bond | Q-39 | — | — | 3/5 |
| bond | J-29 | — | bond | Q-40 | — | — | 3/5 |
| bond | J-29 | — | bond | Q-41 | — | — | 3/5 |
| bond | J-29 | — | bond | Q-42 | — | — | 3/5 |
| bond | J-29 | — | bond | Q-43 | — | — | 3/5 |
| bond | J-29 | — | bond | Q-44 | — | — | 3/5 |
| bond | J-29 | — | bond | Q-46 | — | — | 3/5 |
| bond | J-29 | — | $CH_2$ | Q-47 | — | — | 3/5 |
| bond | J-29 | — | bond | Q-48 | — | — | 3/5 |
| bond | J-29 | — | bond | Q-49 | — | — | 3/5 |
| bond | J-29 | — | bond | Q-50 | — | — | 3/5 |
| bond | J-29 | — | bond | Q-51 | — | — | 3/5 |
| bond | J-29 | — | bond | Q-52 | — | — | 3/5 |
| bond | J-29 | — | bond | Q-53 | — | — | 3/5 |
| bond | J-29 | — | bond | Q-54 | — | — | 3/5 |
| bond | J-29 | — | bond | Q-55 | — | — | 3/5 |
| bond | J-29 | — | bond | Q-56 | — | — | 3/5 |
| bond | J-29 | — | bond | Q-57 | — | — | 3/5 |
| bond | J-29 | — | bond | Q-58 | — | — | 3/5 |
| bond | J-29 | — | bond | Q-59 | — | — | 3/5 |
| bond | J-29 | — | bond | Q-60 | — | — | 3/5 |
| bond | J-29 | — | bond | Q-61 | — | — | 3/5 |
| bond | J-29 | — | bond | Q-62 | — | — | 3/5 |
| bond | J-29 | — | bond | Q-63 | — | — | 3/5 |
| bond | J-29 | — | bond | Q-64 | — | — | 3/5 |
| bond | J-29 | — | bond | Q-65 | — | — | 3/5 |
| bond | J-29 | — | bond | Q-66 | — | — | 3/5 |
| bond | J-29 | — | bond | Q-67 | — | — | 3/5 |
| bond | J-29 | — | bond | Q-68 | — | — | 3/5 |
| bond | J-29 | — | bond | Q-69 | — | — | 3/5 |
| bond | J-29 | — | bond | Q-45 | 2-Me | — | 3/5 |
| bond | J-29 | — | bond | Q-45 | 3-Me | — | 3/5 |
| bond | J-29 | — | bond | Q-45 | 4-Me | — | 3/5 |
| bond | J-29 | — | bond | Q-45 | 2-Cl | — | 3/5 |
| bond | J-29 | — | bond | Q-45 | 3-Cl | — | 3/5 |
| bond | J-29 | — | bond | Q-45 | 4-Cl | — | 3/5 |
| bond | J-29 | — | bond | Q-45 | 2-OMe | — | 3/5 |
| bond | J-29 | — | bond | Q-45 | 3-OMe | — | 3/5 |
| bond | J-29 | — | bond | Q-45 | 4-OMe | — | 3/5 |
| bond | J-29 | — | bond | Q-45 | 2-Et | — | 3/5 |
| bond | J-29 | — | bond | Q-45 | 3-i-Pr | — | 3/5 |
| bond | J-29 | — | bond | Q-45 | 2,6-di-Me | — | 3/5 |
| bond | J-29 | — | bond | Q-45 | 4-vinyl | — | 3/5 |
| bond | J-29 | — | bond | Q-45 | 4-ethynyl | — | 3/5 |
| bond | J-29 | — | bond | Q-45 | 4-c-Pr | — | 3/5 |
| bond | J-29 | — | bond | Q-45 | 3-$CF_3$ | — | 3/5 |
| bond | J-29 | — | bond | Q-45 | 3-$OCF_3$ | — | 3/5 |
| bond | J-29 | — | bond | Q-45 | 4-Br | — | 3/5 |
| bond | J-29 | — | bond | Q-45 | 3-OH | — | 3/5 |
| bond | J-29 | — | bond | Q-45 | 3-$NH_2$ | — | 3/5 |
| bond | J-29 | — | bond | Q-45 | 2-CN | — | 3/5 |
| bond | J-29 | — | bond | Q-45 | 2-$NO_2$ | — | 3/5 |
| bond | J-29 | — | bond | Q-45 | 4-O—t-Bu | — | 3/5 |
| bond | J-29 | — | bond | Q-45 | 4-SMe | — | 3/5 |
| bond | J-29 | — | bond | Q-45 | 4-$SCF_3$ | — | 3/5 |
| bond | J-29 | — | bond | Q-45 | 3-$SO_2Me$ | — | 3/5 |

TABLE 2*-continued

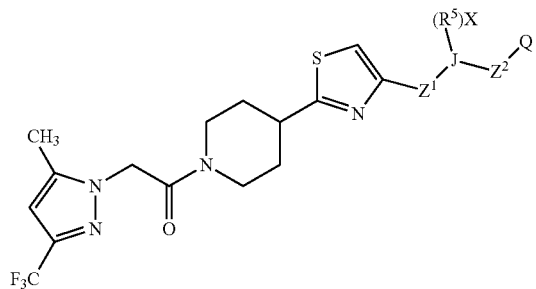

| $Z^1$ | J | $(R^5)_x$ | $Z^2$ | Q | $(R^7)_p$ | $R^{12}$ | J-orientation** |
|---|---|---|---|---|---|---|---|
| bond | J-29 | — | bond | Q-45 | 3-NHMe | — | 3/5 |
| bond | J-29 | — | bond | Q-45 | 4-NMe$_2$ | — | 3/5 |
| bond | J-29 | — | bond | Q-45 | 2-CH$_2$OMe | — | 3/5 |
| bond | J-29 | — | bond | Q-45 | 3-COMe | — | 3/5 |
| bond | J-29 | — | bond | Q-45 | 3-CO$_2$Me | — | 3/5 |
| bond | J-29 | — | bond | Q-45 | 3-CONHMe | — | 3/5 |
| bond | J-29 | — | bond | Q-45 | 4-OCOMe | — | 3/5 |
| bond | J-29 | — | bond | Q-45 | 4-SCOMe | — | 3/5 |
| bond | J-29 | — | bond | Q-45 | 3-CONMe$_2$ | — | 3/5 |
| bond | J-29 | — | bond | Q-45 | 4-SiMe$_3$ | — | 3/5 |
| bond | J-29 | — | bond | Q-45 | 2,6-di-F | — | 3/5 |
| bond | J-29 | — | bond | Q-45 | 2,6-di-Cl | — | 3/5 |
| bond | J-29 | — | bond | Q-45 | 2-OH | — | 3/5 |
| bond | J-29 | — | bond | Q-45 | 4-OCHF$_2$ | — | 3/5 |
| bond | J-26 | 1-Me | bond | Q-45 | — | — | 2/5 |
| bond | J-26 | [Note 3] | bond | Q-45 | [Note 3] | — | 2/5 |
| bond | J-26 | 1-Me, [Note 3] | bond | Q-45 | [Note 3] | — | 2/5 |
| bond | J-26 | — | bond | Q-45 | 4-OH | — | 2/5 |
| bond | J-26 | — | bond | Q-45 | 4-OMe | — | 2/5 |
| bond | J-26 | — | CH$_2$ | Q-45 | 4-OH | — | 2/5 |
| bond | J-26 | — | CH$_2$ | Q-45 | 4-OMe | — | 2/5 |
| bond | J-26 | — | bond | Q-45 | 4-OH | — | 2/4 |
| bond | J-26 | — | bond | Q-45 | 4-OMe | — | 2/4 |
| bond | J-26 | — | CH$_2$ | Q-45 | 4-OH | — | 2/4 |
| bond | J-26 | — | CH$_2$ | Q-45 | 4-OMe | — | 2/4 |
| bond | J-25 | — | bond | Q-45 | 4-OH | — | 2/4 |
| bond | J-25 | — | bond | Q-45 | 4-OMe | — | 2/4 |
| bond | J-25 | — | CH$_2$ | Q-45 | 4-OH | — | 2/4 |
| bond | J-25 | — | CH$_2$ | Q-45 | 4-OMe | — | 2/4 |
| bond | J-1 | 5-Me | bond | Q-45 | — | — | 2/4 |
| bond | J-3 | — | bond | Q-45 | — | — | 2/4 |
| bond | J-3 | [Note 4] | CH$_2$ | Q-45 | [Note 4] | — | 2/5 |
| bond | J-29 | 5-CO$_2$Me | CH$_2$ | Q-45 | — | — | 3/5 |
| bond | J-29 | 5-CO$_2$Et | bond | Q-45 | — | — | 3/5 |
| bond | J-29 | 4,4-di-Me-5-CO$_2$Me | bond | Q-45 | — | — | 3/5 |
| bond | J-29 | 5-CONEt$_2$ | bond | Q-45 | — | — | 3/5 |
| bond | J-29 | — | NH | Q-45 | — | — | 3/5 |
| bond | J-29 | — | NMe | Q-45 | — | — | 3/5 |
| bond | J-29 | — | NEt | Q-45 | — | — | 3/5 |
| bond | J-29 | — | NPr | Q-45 | — | — | 3/5 |
| bond | J-29 | 5-NHAc | — | — | — | — | 3/5 |
| bond | J-29 | 5-NAc$_2$ | — | — | — | — | 3/5 |
| bond | J-29 | 5-N(Me)Ac | — | — | — | — | 3/5 |
| bond | J-29 | 5-N(Me)C(=O)Ph | — | — | — | — | 3/5 |
| bond | J-29 | 5-N(Et)Ac | — | — | — | — | 3/5 |
| bond | J-29 | 5-N(Et)C(=O)Ph | — | — | — | — | 3/5 |
| bond | J-29 | 5-NHC(=O)OMe | — | — | — | — | 3/5 |
| bond | J-29 | 5-N(Me)C(=O)OMe | — | — | — | — | 3/5 |
| bond | J-29 | 5-NHC(=O)OEt | — | — | — | — | 3/5 |
| bond | J-29 | 5-N(Me)C(=O)OEt | — | — | — | — | 3/5 |
| bond | J-69 | 3-Cl | — | — | — | — | 1/3 |
| bond | J-69 | 3-Br | — | — | — | — | 1/3 |
| bond | J-69 | 3-I | — | — | — | — | 1/3 |
| bond | J-69 | 3-Me | — | — | — | — | 1/3 |
| bond | J-69 | 3-Et | — | — | — | — | 1/3 |
| bond | J-69 | 3-Pr | — | — | — | — | 1/3 |
| bond | J-69 | 3-i-Pr | — | — | — | — | 1/3 |
| bond | J-69 | 3-Bu | — | — | — | — | 1/3 |
| bond | J-69 | 3-i-Bu | — | — | — | — | 1/3 |
| bond | J-69 | 3-s-Bu | — | — | — | — | 1/3 |
| bond | J-69 | 3-t-Bu | — | — | — | — | 1/3 |
| bond | J-69 | 3-Am | — | — | — | — | 1/3 |
| bond | J-69 | 3-i-Am | — | — | — | — | 1/3 |

TABLE 2*-continued

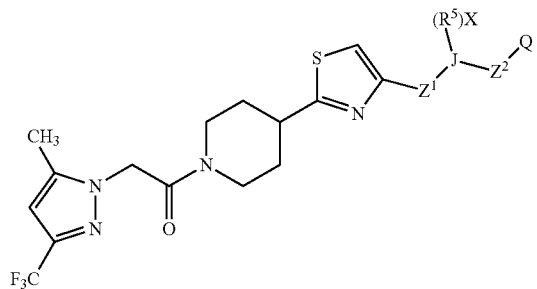

| $Z^1$ | J | $(R^5)_x$ | $Z^2$ | Q | $(R^7)_p$ | $R^{12}$ | J-orientation** |
|---|---|---|---|---|---|---|---|
| bond | J-69 | 3-t-Am | — | — | — | — | 1/3 |
| bond | J-69 | 3-cyclopropyl | — | — | — | — | 1/3 |
| bond | J-69 | 3-cyclobutyl | — | — | — | — | 1/3 |
| bond | J-69 | 3-cyclopentyl | — | — | — | — | 1/3 |
| bond | J-69 | 3-cyclohexyl | — | — | — | — | 1/3 |
| bond | J-69 | 3-trifluorometoxy | — | — | — | — | 1/3 |
| bond | J-69 | 3-isopropyoxy | — | — | — | — | 1/3 |
| bond | J-69 | 3-isobutoxy | — | — | — | — | 1/3 |
| bond | J-69 | 4-Cl | — | — | — | — | 1/4 |
| bond | J-69 | 4-Br | — | — | — | — | 1/4 |
| bond | J-69 | 4-I | — | — | — | — | 1/4 |
| bond | J-69 | 4-Me | — | — | — | — | 1/4 |
| bond | J-69 | 4-Et | — | — | — | — | 1/4 |
| bond | J-69 | 4-Pr | — | — | — | — | 1/4 |
| bond | J-69 | 4-i-Pr | — | — | — | — | 1/4 |
| bond | J-69 | 4-Bu | — | — | — | — | 1/4 |
| bond | J-69 | 4-i-Bu | — | — | — | — | 1/4 |
| bond | J-69 | 4-s-Bu | — | — | — | — | 1/4 |
| bond | J-69 | 4-t-Bu | — | — | — | — | 1/4 |
| bond | J-69 | 4-Am | — | — | — | — | 1/4 |
| bond | J-69 | 4-i-Am | — | — | — | — | 1/4 |
| bond | J-69 | 4-t-Am | — | — | — | — | 1/4 |
| bond | J-69 | 4-cyclopropyl | — | — | — | — | 1/4 |
| bond | J-69 | 4-cyclobutyl | — | — | — | — | 1/4 |
| bond | J-69 | 4-cyclopentyl | — | — | — | — | 1/4 |
| bond | J-69 | 4-cyclohexyl | — | — | — | — | 1/4 |
| bond | J-69 | 4-trifluorometoxy | — | — | — | — | 1/4 |
| bond | J-69 | 4-isopropyoxy | — | — | — | — | 1/4 |
| bond | J-69 | 4-isobutoxy | — | — | — | — | 1/4 |
| bond | J-69 | 3,4-di-Cl | — | — | — | — | 1/4 |
| bond | J-69 | 3,4-di-Br | — | — | — | — | 1/4 |
| bond | J-69 | 3,4-di-Me | — | — | — | — | 1/4 |
| bond | J-69 | 3,4-di-Et | — | — | — | — | 1/4 |
| bond | J-69 | 3,4-di-OMe | — | — | — | — | 1/4 |
| bond | J-69 | 3,4-di-OEt | — | — | — | — | 1/4 |
| bond | J-69 | 3-OMe-4-O-propargyl | — | — | — | — | 1/4 |
| bond | J-4 | 5-i-Bu | — | — | — | — | 2/5 |
| bond | J-4 | 5-i-Am | — | — | — | — | 2/5 |
| bond | J-5 | 5-i-Bu | — | — | — | — | 2/5 |
| bond | J-5 | 5-i-Am | — | — | — | — | 2/5 |
| bond | J-11 | 5-i-Bu | — | — | — | — | 3/5 |
| bond | J-11 | 5-i-Am | — | — | — | — | 3/5 |
| bond | J-29 | — | bond | Q-70 | — | — | 3/5 |
| bond | J-29 | — | bond | Q-71 | — | — | 3/5 |
| bond | J-29 | — | bond | Q-72 | — | Me | 3/5 |
| bond | J-29 | — | bond | Q-73 | — | — | 3/5 |
| bond | J-29 | — | bond | Q-74 | — | — | 3/5 |
| bond | J-29 | — | bond | Q-75 | — | Me | 3/5 |
| bond | J-29 | — | bond | Q-76 | — | — | 3/5 |
| bond | J-29 | — | bond | Q-77 | — | — | 3/5 |
| bond | J-29 | — | bond | Q-78 | — | Me | 3/5 |
| bond | J-29 | — | bond | Q-79 | — | Me | 3/5 |
| bond | J-29 | — | bond | Q-80 | — | — | 3/5 |
| bond | J-29 | — | bond | Q-81 | — | — | 3/5 |
| bond | J-29 | — | bond | Q-82 | — | — | 3/5 |
| bond | J-29 | — | bond | Q-83 | — | — | 3/5 |
| bond | J-29 | — | bond | Q-84 | — | — | 3/5 |
| bond | J-29 | — | bond | Q-85 | — | — | 3/5 |
| bond | J-29 | — | bond | Q-86 | — | Me | 3/5 |
| bond | J-29 | — | bond | Q-87 | — | — | 3/5 |
| bond | J-29 | — | bond | Q-88 | — | Me | 3/5 |
| bond | J-29 | — | bond | Q-89 | — | — | 3/5 |
| bond | J-29 | — | bond | Q-90 | — | — | 3/5 |

TABLE 2*-continued

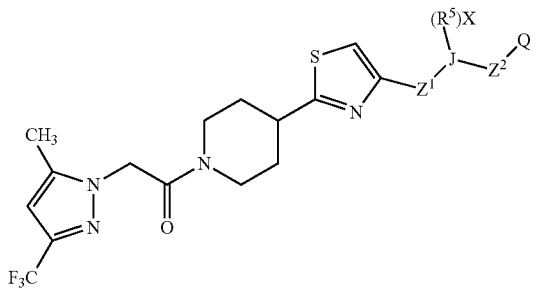

| $Z^1$ | J | $(R^5)_x$ | $Z^2$ | Q | $(R^7)_p$ | $R^{12}$ | J-orientation** |
|---|---|---|---|---|---|---|---|
| bond | J-29 | — | bond | Q-91 | — | — | 3/5 |
| bond | J-29 | — | bond | Q-92 | — | Me | 3/5 |
| bond | J-29 | — | bond | Q-93 | — | — | 3/5 |
| bond | J-29 | — | bond | Q-94 | — | — | 3/5 |
| bond | J-29 | — | bond | Q-95 | — | Me | 3/5 |
| bond | J-29 | — | bond | Q-96 | — | — | 3/5 |
| bond | J-29 | — | bond | Q-97 | — | — | 3/5 |
| bond | J-29 | — | bond | Q-98 | — | — | 3/5 |
| bond | J-29 | — | bond | Q-99 | — | — | 3/5 |
| bond | J-29 | — | bond | Q-100 | — | — | 3/5 |
| bond | J-29 | — | bond | Q-101 | — | — | 3/5 |
| bond | J-29 | — | bond | Q-102 | — | Me | 3/5 |
| bond | J-29 | — | bond | Q-87 | 4-phenyl | — | 3/5 |
| bond | J-29 | — | bond | Q-72 | — | acetyl | 3/5 |
| bond | J-29 | — | bond | Q-72 | — | methoxycarbonyl | 3/5 |
| bond | J-29 | — | bond | Q-72 | — | methoxy | 3/5 |
| bond | J-29 | — | bond | Q-71 | 4-Cl | — | 3/5 |
| bond | J-29 | — | bond | Q-71 | 5-Cl | — | 3/5 |
| bond | J-29 | — | bond | Q-71 | 6-Cl | — | 3/5 |
| bond | J-29 | — | bond | Q-71 | 7-Cl | — | 3/5 |
| bond | J-29 | — | bond | Q-71 | 4-Me | — | 3/5 |
| bond | J-29 | — | bond | Q-71 | 5-Me | — | 3/5 |
| bond | J-29 | — | bond | Q-71 | 6-Me | — | 3/5 |
| bond | J-29 | — | bond | Q-71 | 5-$CF_3$ | — | 3/5 |
| bond | J-29 | — | bond | Q-71 | 5-$NO_2$ | — | 3/5 |
| bond | J-29 | — | bond | Q-71 | 6-Br | — | 3/5 |
| bond | J-29 | — | bond | Q-71 | 6-$NO_2$ | — | 3/5 |
| bond | J-29 | — | bond | Q-71 | 6-$NH_2$ | — | 3/5 |
| bond | J-29 | — | bond | Q-71 | 6-OMe | — | 3/5 |
| bond | J-29 | — | bond | Q-71 | 5,6-di-OMe | — | 3/5 |
| bond | J-29 | — | bond | Q-71 | 5,6-di-Cl | — | 3/5 |
| bond | J-29 | — | bond | Q-70 | 5-Cl | — | 3/5 |
| bond | J-29 | — | bond | Q-70 | 5-Me | — | 3/5 |
| bond | J-29 | — | bond | Q-70 | 5-$NO_2$ | — | 3/5 |
| bond | J-29 | — | bond | Q-70 | 5-$NH_2$ | — | 3/5 |
| bond | J-29 | — | bond | Q-70 | 6-Cl | — | 3/5 |
| bond | J-29 | — | bond | Q-70 | 6-Me | — | 3/5 |
| bond | J-29 | — | bond | Q-70 | 6-$NO_2$ | — | 3/5 |
| bond | J-29 | — | bond | Q-70 | 6-$NH_2$ | — | 3/5 |
| bond | J-29 | — | bond | Q-70 | 5,6-di-Cl | — | 3/5 |
| bond | J-29 | — | bond | Q-70 | 5-Cl-6-OH | — | 3/5 |
| bond | J-29 | — | bond | Q-72 | 5-Cl | Me | 3/5 |
| bond | J-29 | — | bond | Q-72 | 5-Me | Me | 3/5 |
| bond | J-29 | — | bond | Q-72 | 5-$NO_2$ | Me | 3/5 |
| bond | J-29 | — | bond | Q-72 | 5-$NH_2$ | Me | 3/5 |
| bond | J-29 | — | bond | Q-72 | 6-Cl | Me | 3/5 |
| bond | J-29 | — | bond | Q-72 | 6-Me | Me | 3/5 |
| bond | J-29 | — | bond | Q-72 | 6-$NO_2$ | Me | 3/5 |
| bond | J-29 | — | bond | Q-72 | 6-$NH_2$ | Me | 3/5 |
| bond | J-29 | — | bond | Q-72 | 5,6-di-Cl | Me | 3/5 |
| bond | J-29 | — | bond | Q-63 | 4-Me | — | 3/5 |
| bond | J-29 | — | bond | Q-63 | 4-$NO_2$ | — | 3/5 |
| bond | J-29 | — | bond | Q-63 | 4-$NH_2$ | — | 3/5 |
| bond | J-29 | — | bond | Q-63 | 5-Cl | — | 3/5 |
| bond | J-29 | — | bond | Q-63 | 5-Me | — | 3/5 |
| bond | J-29 | — | bond | Q-63 | 5-CN | — | 3/5 |
| bond | J-29 | — | bond | Q-63 | 5-$NO_2$ | — | 3/5 |
| bond | J-29 | — | bond | Q-63 | 5-$NH_2$ | — | 3/5 |
| bond | J-29 | — | bond | Q-63 | 5-COOMe | — | 3/5 |

TABLE 2*-continued

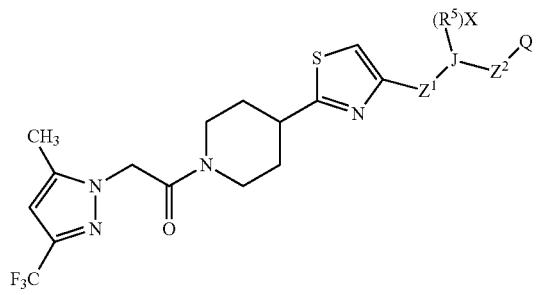

| $Z^1$ | J | $(R^5)_x$ | $Z^2$ | Q | $(R^7)_p$ | $R^{12}$ | J-orientation** |
|---|---|---|---|---|---|---|---|
| bond | J-29 | — | bond | Q-63 | 5-di-Cl | — | 3/5 |
| bond | J-29 | 5-N(Ac)C(=O)Ph | bond | — | — | — | 3/5 |
| bond | J-29 | 5-N(Ac)C(=O)(2-carbomethoxy-Ph) | bond | — | — | — | 3/5 |

*The definitions of J, $R^5$, Q, $R^7$ and $R^{12}$ in the compounds of this table are as defined in Exhibits 3 and 4 in the above Embodiments. A dash "—" in the $(R^5)_x$ column indicates no substitution on J. A dash in each of the $Z^2$ and Q columns indicates that no $Z^2Q$ substituent is attached as $R^5$ to J. A dash in the $(R^7)_p$ and/or $R^{12}$ columns indicates no substitution on Q.

**J-orientation refers to the attachment points for $Z^1$ and $Z^2$ (or another $R^5$ when $Z^2$ is not present) on ring J. The first number refers to the ring position on J where $Z^1$ is attached, and the second number refers to the ring position on J where $Z^2$ is attached or, when $Z^2$ is not present, the ring position on J where the substituent listed under $(R^5)_x$ is attached.

[Note 1]:
$R^5$ and $R^7$ taken together to form a $CH_2CH_2$ bridge between position 4 of J-29 and position 2 of Q-45.

[Note 2]:
$R^5$ and $R^7$ take together form a $CH_2$ bridge between position 4 of J-29 and position 2 of Q-45.

[Note 3]:
$R^5$ and $R^7$ taken together to form a $CH_2CH_2$ bridge between position 4 of J-26 and position 2 of Q-45.

[Note 4]:
$R^5$ and $R^7$ taken together to form a $CH_2CH_2$ bridge between position 1 of J-3 and position 2 of Q-45.

TABLE 3*

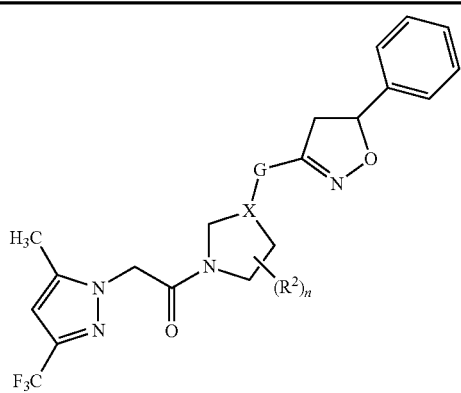

TABLE 3*-continued

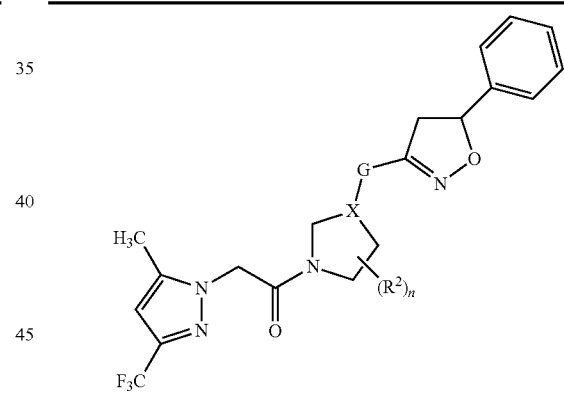

| X | $(R^2)_n$ | G | $R^{3a}$ | $R^{11a}$ | X | $(R^2)_n$ | G | $R^{3a}$ | $R^{11a}$ |
|---|---|---|---|---|---|---|---|---|---|
| $X^1$ | — | G-1 | H | — | $X^1$ | — | G-21 | H | — |
| $X^1$ | — | G-2 | H | — | $X^1$ | — | G-22 | H | H |
| $X^1$ | — | G-3 | H | H | $X^1$ | — | G-23 | H | — |
| $X^1$ | — | G-4 | H | — | $X^1$ | — | G-24 | H | — |
| $X^1$ | — | G-5 | H | — | $X^1$ | — | G-25 | H | — |
| $X^1$ | — | G-6 | H | H | $X^1$ | — | G-26 | H | — |
| $X^1$ | — | G-7 | H | — | $X^1$ | — | G-27 | H | — |
| $X^1$ | — | G-8 | H | — | $X^1$ | — | G-28 | H | — |
| $X^1$ | — | G-9 | H | H | $X^1$ | — | G-29 | H | — |
| $X^1$ | — | G-10 | H | — | $X^1$ | — | G-30 | H | — |
| $X^1$ | — | G-11 | H | — | $X^1$ | — | G-31 | H | — |
| $X^1$ | — | G-12 | H | H | $X^1$ | — | G-32 | H | — |
| $X^1$ | — | G-13 | H | H | $X^1$ | — | G-33 | H | — |
| $X^1$ | — | G-14 | H | — | $X^1$ | — | G-34 | H | — |
| $X^1$ | — | G-15 | H | — | $X^1$ | — | G-35 | H | — |
| $X^1$ | — | G-16 | H | H | $X^1$ | — | G-36 | H | — |
| $X^1$ | — | G-17 | H | — | $X^1$ | — | G-37 | H | — |
| $X^1$ | — | G-18 | H | — | $X^1$ | — | G-38 | H | — |
| $X^1$ | — | G-19 | H | H | $X^1$ | — | G-39 | H | H |
| $X^1$ | — | G-20 | H | — | $X^1$ | — | G-40 | H | — |

TABLE 3*-continued

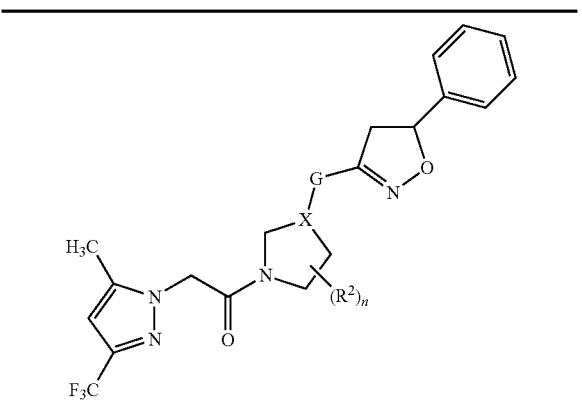

| X | (R²)ₙ | G | R³ᵃ | R¹¹ᵃ |
|---|---|---|---|---|
| X¹ | — | G-41 | H | — |
| X¹ | — | G-42 | H | H |
| X¹ | — | G-43 | H | H |
| X¹ | — | G-44 | H | — |
| X¹ | — | G-45 | H | — |
| X¹ | — | G-46 | H | — |
| X¹ | — | G-47 | H | — |
| X¹ | — | G-48 | H | H |
| X¹ | — | G-49 | H | — |
| X¹ | — | G-50 | H | — |
| X¹ | — | G-51 | H | H |
| X¹ | — | G-52 | H | — |
| X¹ | — | G-53 | H | — |
| X¹ | — | G-54 | H | H |
| X¹ | — | G-55 | H | — |
| X¹ | — | G-56 | H | — |
| X¹ | — | G-57 | H | — |
| X¹ | — | G-58 | H | H |
| X¹ | — | G-59 | H | H |
| X¹ | — | G-2 | Me | — |
| X¹ | — | G-2 | Cl | — |
| X¹ | — | G-2 | F | — |
| X¹ | — | G-2 | CF₃ | — |
| X¹ | — | G-14 | n-Pr | — |
| X¹ | — | G-3 | H | Me |
| X¹ | — | G-3 | H | n-Pr |
| X¹ | — | G-26 | 5-Me | — |
| X¹ | 2-Me | G-1 | H | — |
| X¹ | 3-Me | G-1 | H | — |
| X¹ | 2,6-di-Me | G-1 | H | — |
| X¹ | 3,5-di-Me | G-1 | H | — |
| X¹ | 3-n-Bu | G-1 | H | — |
| X¹ | 4-MeO | G-1 | H | — |
| X¹ | 4-OH | G-1 | H | — |
| X¹ | 4-Cl | G-1 | H | — |
| X¹ | 4-Br | G-1 | H | — |
| X¹ | 4-CN | G-1 | H | — |
| X² | — | G-1 | H | — |
| X² | — | G-2 | H | — |
| X² | — | G-3 | H | H |
| X² | — | G-4 | H | — |
| X² | — | G-5 | H | — |
| X² | — | G-6 | H | H |
| X² | — | G-7 | H | — |
| X² | — | G-8 | H | — |
| X² | — | G-9 | H | H |
| X² | — | G-10 | H | — |
| X² | — | G-11 | H | — |
| X² | — | G-12 | H | H |
| X² | — | G-13 | H | H |
| X² | — | G-14 | H | — |
| X² | — | G-15 | H | — |
| X² | — | G-16 | H | H |
| X² | — | G-17 | H | — |
| X² | — | G-18 | H | — |
| X² | — | G-19 | H | H |
| X² | — | G-20 | H | — |
| X² | — | G-21 | H | — |
| X² | — | G-22 | H | H |

TABLE 3*-continued

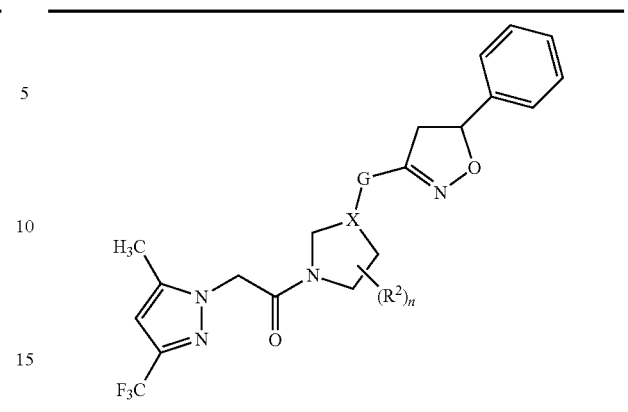

| X | (R²)ₙ | G | R³ᵃ | R¹¹ᵃ |
|---|---|---|---|---|
| X² | — | G-23 | H | — |
| X² | — | G-24 | H | — |
| X² | — | G-31 | H | — |
| X² | — | G-32 | H | — |
| X² | — | G-33 | H | — |
| X² | — | G-34 | H | — |
| X² | — | G-35 | H | — |
| X² | — | G-37 | H | — |
| X² | — | G-38 | H | — |
| X² | — | G-39 | H | H |
| X² | — | G-40 | H | — |
| X² | — | G-41 | H | — |
| X² | — | G-42 | H | H |
| X² | — | G-43 | H | H |
| X² | — | G-44 | H | — |
| X² | — | G-45 | H | — |
| X² | — | G-46 | H | — |
| X² | — | G-47 | H | — |
| X² | — | G-48 | H | H |
| X² | — | G-49 | H | — |
| X² | — | G-50 | H | — |
| X² | — | G-51 | H | H |
| X² | — | G-52 | H | — |
| X² | — | G-53 | H | — |
| X² | — | G-54 | H | H |
| X² | — | G-2 | Me | — |
| X² | — | G-2 | Cl | — |
| X² | — | G-2 | F | — |
| X² | — | G-2 | CF₃ | — |
| X² | — | G-14 | n-Pr | — |
| X² | — | G-3 | H | Me |
| X² | — | G-3 | H | n-Pr |
| X² | 2-Me | G-1 | H | — |
| X² | 3-Me | G-1 | H | — |
| X² | 2,6-di-Me | G-1 | H | — |
| X² | 3,5-di-Me | G-1 | H | — |
| X² | 3-n-Bu | G-1 | H | — |
| X³ | — | G-1 | H | — |
| X³ | — | G-2 | H | — |
| X³ | — | G-3 | H | H |
| X³ | — | G-4 | H | — |
| X³ | — | G-5 | H | — |
| X³ | — | G-6 | H | H |
| X³ | — | G-7 | H | — |
| X³ | — | G-8 | H | — |
| X³ | — | G-9 | H | H |
| X³ | — | G-10 | H | — |
| X³ | — | G-11 | H | — |
| X³ | — | G-12 | H | H |
| X³ | — | G-13 | H | H |
| X³ | — | G-14 | H | — |
| X³ | — | G-15 | H | — |
| X³ | — | G-16 | H | H |
| X³ | — | G-17 | H | — |
| X³ | — | G-18 | H | — |
| X³ | — | G-19 | H | H |
| X³ | — | G-20 | H | — |
| X³ | — | G-21 | H | — |
| X³ | — | G-22 | H | H |

TABLE 3*-continued

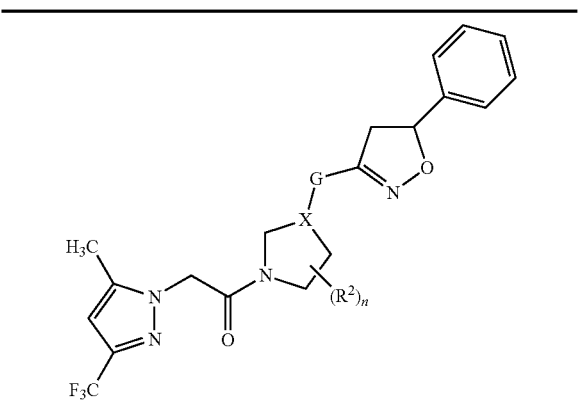

| X | $(R^2)_n$ | G | $R^{3a}$ | $R^{11a}$ |
|---|---|---|---|---|
| $X^3$ | — | G-23 | H | — |
| $X^3$ | — | G-24 | H | — |
| $X^3$ | — | G-31 | H | — |
| $X^3$ | — | G-32 | H | — |
| $X^3$ | — | G-33 | H | — |
| $X^3$ | — | G-34 | H | — |
| $X^3$ | — | G-35 | H | — |
| $X^3$ | — | G-37 | H | — |
| $X^3$ | — | G-38 | H | — |
| $X^3$ | — | G-39 | H | H |
| $X^3$ | — | G-40 | H | — |
| $X^3$ | — | G-41 | H | — |
| $X^3$ | — | G-42 | H | H |
| $X^3$ | — | G-43 | H | H |
| $X^3$ | — | G-44 | H | — |
| $X^3$ | — | G-45 | H | — |
| $X^3$ | — | G-46 | H | — |
| $X^3$ | — | G-47 | H | — |
| $X^3$ | — | G-48 | H | H |
| $X^3$ | — | G-49 | H | — |
| $X^3$ | — | G-50 | H | — |
| $X^3$ | — | G-51 | H | H |
| $X^3$ | — | G-52 | H | — |
| $X^3$ | — | G-53 | H | — |
| $X^3$ | — | G-54 | H | H |

TABLE 3*-continued

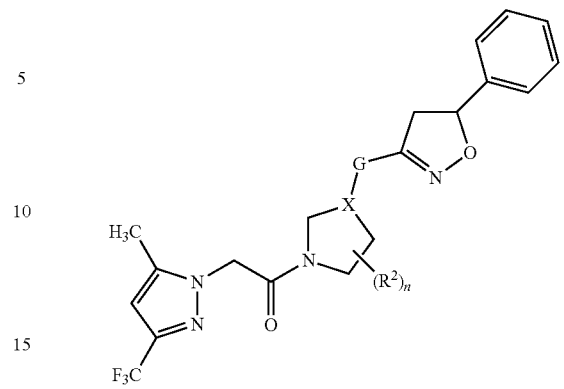

| X | $(R^2)_n$ | G | $R^{3a}$ | $R^{11a}$ |
|---|---|---|---|---|
| $X^3$ | — | G-2 | Me | — |
| $X^3$ | — | G-2 | Cl | — |
| $X^3$ | — | G-2 | F | — |
| $X^3$ | — | G-2 | $CF_3$ | — |
| $X^3$ | — | G-14 | n-Pr | — |
| $X^3$ | — | G-3 | H | Me |
| $X^3$ | — | G-3 | H | n-Pr |
| $X^3$ | 2-Me | G-1 | H | — |
| $X^3$ | 3-Me | G-1 | H | — |
| $X^3$ | 2,6-di-Me | G-1 | H | — |
| $X^3$ | 3,5-di-Me | G-1 | H | — |
| $X^3$ | 3-n-Bu | G-1 | H | — |
| $X^3$ | 5-Me | G-1 | H | — |
| $X^3$ | 6-Me | G-1 | H | — |
| $X^4$ | — | G-1 | H | — |
| $X^5$ | — | G-1 | H | — |
| $X^6$ | — | G-1 | H | — |
| $X^7$ | — | G-1 | H | — |
| $X^8$ | — | G-1 | H | — |
| $X^9$ | — | G-1 | H | — |

*The definitions of X, G, $R^{3a}$ and $R^{11a}$ in the compounds of this table are as defined in the Summary of the Invention and Exhibit 2 in the above Embodiments.
A dash "—" in the $(R^2)_n$ column indicates no substituents.

TABLE 4*

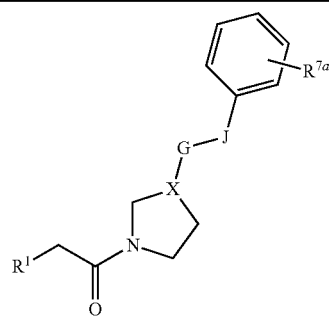

| $R^1$ | X | G | J* | $(R^5)_y$ | $R^{7a}$ |
|---|---|---|---|---|---|
| 2,5-dichlorophenyl | $X^1$ | G-1 | J-1 (2/4) | — | H |
| 2-chloro-5-(trifluoromethyl)phenyl | $X^1$ | G-1 | J-1 (2/4) | — | H |
| 2,5-dimethylphenyl | $X^1$ | G-1 | J-1 (2/4) | — | H |
| 2-methyl-5-(trifluoromethyl)phenyl | $X^1$ | G-1 | J-1 (2/4) | — | H |
| 3,5-dimethylpyrazol-1-yl | $X^1$ | G-1 | J-1 (2/4) | — | H |
| 5-methyl-3-(trifluoromethyl)pyrazol-1-yl | $X^1$ | G-1 | J-1 (2/4) | — | H |
| 5-chloro-3-(trifluoromethyl)pyrazol-1-yl | $X^1$ | G-1 | J-1 (2/4) | — | H |
| 5-bromo-3-(trifluoromethyl)pyrazol-1-yl | $X^1$ | G-1 | J-1 (2/4) | — | H |
| 5-ethyl-3-(trifluoromethyl)pyrazol-1-yl | $X^1$ | G-1 | J-1 (2/4) | — | H |
| 3,5-bis-(trifluoromethyl)pyrazol-1-yl | $X^1$ | G-1 | J-1 (2/4) | — | H |
| 1-methyl-3-(trifluoromethyl)pyrazol-5-yl | $X^1$ | G-1 | J-1 (2/4) | — | H |
| 1-methyl-4-(trifluoromethyl)imidazol-2-yl | $X^1$ | G-1 | J-1 (2/4) | — | H |

TABLE 4*-continued

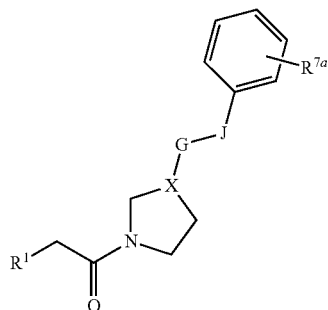

| R¹ | X | G  | J * | (R⁵)ᵧ | R⁷ᵃ |
|---|---|---|---|---|---|
| 2,5-dichlorophenyl | X¹ | G-1 | J-2 (2/4) | — | H |
| 2-chloro-5-(trifluoromethyl)phenyl | X¹ | G-1 | J-2 (2/4) | — | H |
| 2,5-dimethylphenyl | X¹ | G-1 | J-2 (2/4) | — | H |
| 2-methyl-5-(trifluoromethyl)phenyl | X¹ | G-1 | J-2 (2/4) | — | H |
| 3,5-dimethylpyrazol-1-yl | X¹ | G-1 | J-2 (2/4) | — | H |
| 5-methyl-3-(trifluoromethyl)pyrazol-1-yl | X¹ | G-1 | J-2 (2/4) | — | H |
| 5-chloro-3-(trifluoromethyl)pyrazol-1-yl | X¹ | G-1 | J-2 (2/4) | — | H |
| 5-bromo-3-(trifluoromethyl)pyrazol-1-yl | X¹ | G-1 | J-2 (2/4) | — | H |
| 5-ethyl-3-(trifluoromethyl)pyrazol-1-yl | X¹ | G-1 | J-2 (2/4) | — | H |
| 3,5-bis-(trifluoromethyl)pyrazol-1-yl | X¹ | G-1 | J-2 (2/4) | — | H |
| 1-methyl-3-(trifluoromethyl)pyrazol-5-yl | X¹ | G-1 | J-2 (2/4) | — | H |
| 1-methyl-4-(trifluoromethyl)imidazol-2-yl | X¹ | G-1 | J-2 (2/4) | — | H |
| 2,5-dichlorophenyl | X¹ | G-1 | J-3 (2/4) | 1-Me | H |
| 2-chloro-5-(trifluoromethyl)phenyl | X¹ | G-1 | J-3 (2/4) | 1-Me | H |
| 2,5-dimethylphenyl | X¹ | G-1 | J-3 (2/4) | 1-Me | H |
| 2-methyl-5-(trifluoromethyl)phenyl | X¹ | G-1 | J-3 (2/4) | 1-Me | H |
| 3,5-dimethylpyrazol-1-yl | X¹ | G-1 | J-3 (2/4) | 1-Me | H |
| 5-methyl-3-(trifluoromethyl)pyrazol-1-yl | X¹ | G-1 | J-3 (7/4) | 1-Me | H |
| 5-chloro-3-(trifluoromethyl)pyrazol-1-yl | X¹ | G-1 | J-3 (2/4) | 1-Me | H |
| 5-bromo-3-(trifluoromethyl)pyrazol-1-yl | X¹ | G-1 | J-3 (2/4) | 1-Me | H |
| 5-ethyl-3-(trifluoromethyl)pyrazol-1-yl | X¹ | G-1 | J-3 (2/4) | 1-Me | H |
| 3,5-bis-(trifluoromethyl)pyrazol-1-yl | X¹ | G-1 | J-3 (2/4) | 1-Me | H |
| 1-methyl-3-(trifluoromethyl)pyrazol-5-yl | X¹ | G-1 | J-3 (2/4) | 1-Me | H |
| 1-methyl-4-(trifluoromethyl)imidazol-2-yl | X¹ | G-1 | J-3 (2/4) | 1-Me | H |
| 2,5-dichlorophenyl | X¹ | G-1 | J-4 (2/5) | — | H |
| 2-chloro-5-(trifluoromethyl)phenyl | X¹ | G-1 | J-4 (2/5) | — | H |
| 2,5-dimethylphenyl | X¹ | G-1 | J-4 (2/5) | — | H |
| 2-methyl-5-(trifluoromethyl)phenyl | X¹ | G-1 | J-4 (2/5) | — | H |
| 3,5-dimethylpyrazol-1-yl | X¹ | G-1 | J-4 (2/5) | — | H |
| 5-methyl-3-(trifluoromethyl)pyrazol-1-yl | X¹ | G-1 | J-4 (2/5) | — | H |
| 5-chloro-3-(trifluoromethyl)pyrazol-1-yl | X¹ | G-1 | J-4 (2/5) | — | H |
| 5-bromo-3-(trifluoromethyl)pyrazol-1-yl | X¹ | G-1 | J-4 (2/5) | — | H |
| 5-ethyl-3-(trifluoromethyl)pyrazol-1-yl | X¹ | G-1 | J-4 (2/5) | — | H |
| 3,5-bis-(trifluoromethyl)pyrazol-1-yl | X¹ | G-1 | J-4 (2/5) | — | H |
| 1-methyl-3-(trifluoromethyl)pyrazol-5-yl | X¹ | G-1 | J-4 (2/5) | — | H |
| 1-methyl-4-(trifluoromethyl)imidazol-2-yl | X¹ | G-1 | J-4 (2/5) | — | H |
| 2,5-dichlorophenyl | X¹ | G-1 | J-8 (5/3) | — | H |
| 2-chloro-5-(trifluoromethyl)phenyl | X¹ | G-1 | J-8 (5/3) | — | H |
| 2,5-dimethylphenyl | X¹ | G-1 | J-8 (5/3) | — | H |
| 2-methyl-5-(trifluoromethyl)phenyl | X¹ | G-1 | J-8 (5/3) | — | H |
| 3,5-dimethylpyrazol-1-yl | X¹ | G-1 | J-8 (5/3) | — | H |
| 5-methyl-3-(trifluoromethyl)pyrazol-1-yl | X¹ | G-1 | J-8 (5/3) | — | H |
| 5-chloro-3-(trifluoromethyl)pyrazol-1-yl | X¹ | G-1 | J-8 (5/3) | — | H |
| 5-bromo-3-(trifluoromethyl)pyrazol-1-yl | X¹ | G-1 | J-8 (5/3) | — | H |
| 5-ethyl-3-(trifluoromethyl)pyrazol-1-yl | X¹ | G-1 | J-8 (5/3) | — | H |
| 3,5-bis-(trifluoromethyl)pyrazol-1-yl | X¹ | G-1 | J-8 (5/3) | — | H |
| 1-methyl-3-(trifluoromethyl)pyrazol-5-yl | X¹ | G-1 | J-8 (5/3) | — | H |
| 1-methyl-4-(trifluoromethyl)imidazol-2-yl | X¹ | G-1 | J-8 (5/3) | — | H |
| 2,5-dichlorophenyl | X¹ | G-1 | J-9 (5/3) | — | H |
| 2-chloro-5-(trifluoromethyl)phenyl | X¹ | G-1 | J-9 (5/3) | — | H |
| 2,5-dimethylphenyl | X¹ | G-1 | J-9 (5/3) | — | H |
| 2-methyl-5-(trifluoromethyl)phenyl | X¹ | G-1 | J-9 (5/3) | — | H |
| 3,5-dimethylpyrazol-1-yl | X¹ | G-1 | J-9 (5/3) | — | H |
| 5-methyl-3-(trifluoromethyl)pyrazol-1-yl | X¹ | G-1 | J-9 (5/3) | — | H |
| 5-chloro-3-(trifluoromethyl)pyrazol-1-yl | X¹ | G-1 | J-9 (5/3) | — | H |
| 5-bromo-3-(trifluoromethyl)pyrazol-1-yl | X¹ | G-1 | J-9 (5/3) | — | H |
| 5-ethyl-3-(trifluoromethyl)pyrazol-1-yl | X¹ | G-1 | J-9 (5/3) | — | H |
| 3,5-bis-(trifluoromethyl)pyrazol-4-yl | X¹ | G-1 | J-9 (5/3) | — | H |
| 1-methyl-3-(trifluoromethyl)pyrazol-5-yl | X¹ | G-1 | J-9 (5/3) | — | H |
| 1-methyl-4-(trifluoromethyl)imidazol-2-yl | X¹ | G-1 | J-9 (5/3) | — | H |
| 2,5-dichlorophenyl | X¹ | G-1 | J-11 (3/5) | — | H |
| 2-chloro-5-(trifluoromethyl)phenyl | X¹ | G-1 | J-11 (3/5) | — | H |

TABLE 4*-continued

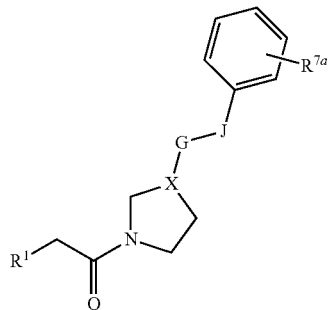

| R¹ | X | G  | J * | (R⁵)ᵧ | R⁷ᵃ |
|---|---|---|---|---|---|
| 2,5-dimethylphenyl | X¹ | G-1 | J-11 (3/5) | — | H |
| 2-methyl-5-(trifluoromethyl)phenyl | X¹ | G-1 | J-11 (3/5) | — | H |
| 3,5-dimethylpyrazol-1-yl | X¹ | G-1 | J-11 (3/5) | — | H |
| 5-methyl-3-(trifluoromethyl)pyrazol-1-yl | X¹ | G-1 | J-11 (3/5) | — | H |
| 5-chloro-3-(trifluoromethyl)pyrazol-1-yl | X¹ | G-1 | J-11 (3/5) | — | H |
| 5-bromo-3-(trifluoromethyl)pyrazol-1-yl | X¹ | G-1 | J-11 (3/5) | — | H |
| 5-ethyl-3-(trifluoromethyl)pyrazol-1-yl | X¹ | G-1 | J-11 (3/5) | — | H |
| 3,5-bis-(trifluoromethyl)pyrazol-1-yl | X¹ | G-1 | J-11 (3/5) | — | H |
| 1-methyl-3-(trifluoromethyl)pyrazol-5-yl | X¹ | G-1 | J-11 (3/5) | — | H |
| 1-methyl-4-(trifluoromethyl)imidazol-2-yl | X¹ | G-1 | J-11 (3/5) | — | H |
| 2,5-dichlorophenyl | X¹ | G-1 | J-12 (3/5) | — | H |
| 2-chloro-5-(trifluoromethyl)phenyl | X¹ | G-1 | J-12 (3/5) | — | H |
| 2,5-dimethylphenyl | X¹ | G-1 | J-12 (3/5) | — | H |
| 2-methyl-5-(trifluoromethyl)phenyl | X¹ | G-1 | J-12 (3/5) | — | H |
| 3,5-dimethylpyrazol-1-yl | X¹ | G-1 | J-12 (3/5) | — | H |
| 5-methyl-3-(trifluoromethyl)pyrazol-1-yl | X¹ | G-1 | J-12 (3/5) | — | H |
| 5-chloro-3-(trifluoromethyl)pyrazol-1-yl | X¹ | G-1 | J-12 (3/5) | — | H |
| 5-bromo-3-(trifluoromethyl)pyrazol-1-yl | X¹ | G-1 | J-12 (3/5) | — | H |
| 5-ethyl-3-(trifluoromethyl)pyrazol-1-yl | X¹ | G-1 | J-12 (3/5) | — | H |
| 3,-bis-(trifluoromethyl)pyrazol-1-yl | X¹ | G-1 | J-12 (3/5) | — | H |
| 1-methyl-3-(trifluoromethyl)pyrazol-5-yl | X¹ | G-1 | J-12 (3/5) | — | H |
| 1-methyl-4-(trifluoromethyl)imidazol-2-yl | X¹ | G-1 | J-12 (3/5) | — | H |
| 2,5-dichlorophenyl | X¹ | G-1 | J-12 (3/5) | 1-Me | H |
| 2-chloro-5-(trifluoromethyl)phenyl | X¹ | G-1 | J-12 (3/5) | 1-Me | H |
| 2,5-dimethylphenyl | X¹ | G-1 | J-12 (3/5) | 1-Me | H |
| 2-methyl-5-(trifluoromethyl)phenyl | X¹ | G-1 | J-12 (3/5) | 1-Me | H |
| 3,5-dimethylpyrazol-1-yl | X¹ | G-1 | J-12 (3/5) | 1-Me | H |
| 5-methyl-3-(trifluoromethyl)pyrazol-1-yl | X¹ | G-1 | J-12 (3/5) | 1-Me | H |
| 5-chloro-3-(trifluoromethyl)pyrazol-1-yl | X¹ | G-1 | J-12 (3/5) | 1-Me | H |
| 5-bromo-3-(trifluoromethyl)pyrazol-1-yl | X¹ | G-1 | J-12 (3/5) | 1-Me | H |
| 5-ethyl-3-(trifluoromethyl)pyrazol-1-yl | X¹ | G-1 | J-12 (3/5) | 1-Me | H |
| 3,5-bis-(trifluoromethyl)pyrazol-1-yl | X¹ | G-1 | J-12 (3/5) | 1-Me | H |
| 1-methyl-3-(trifluoromethyl)pyrazol-5-yl | X¹ | G-1 | J-12 (3/5) | 1-Me | H |
| 1-methyl-4-(trifluoromethyl)imidazol-2-yl | X¹ | G-1 | J-12 (3/5) | 1-Me | H |
| 2,5-dichlorophenyl | X¹ | G-1 | J-14 (3/5) | — | H |
| 2-chloro-5-(trifluoromethyl)phenyl | X¹ | G-1 | J-14 (3/5) | — | H |
| 2,5-dimethylphenyl | X¹ | G-1 | J-14 (3/5) | — | H |
| 2-methyl-5-(trifluoromethyl)phenyl | X¹ | G-1 | J-14 (3/5) | — | H |
| 3,5-dimethylpyrazol-1-yl | X¹ | G-1 | J-14 (3/5) | — | H |
| 5-methyl-3-(trifluoromethyl)pyrazol-1-yl | X¹ | G-1 | J-14 (3/5) | — | H |
| 5-chloro-3-(trifluoromethyl)pyrazol-1-yl | X¹ | G-1 | J-14 (3/5) | — | H |
| 5-bromo-3-(trifluoromethyl)pyrazol-1-yl | X¹ | G-1 | J-14 (3/5) | — | H |
| 5-ethyl-3-(trifluoromethyl)pyrazol-1-yl | X¹ | G-1 | J-14 (3/5) | — | H |
| 3,5-bis-(trifluoromethyl)pyrazol-1-yl | X¹ | G-1 | J-14 (3/5) | — | H |
| 1-methyl-3-(trifluoromethyl)pyrazol-5-yl | X¹ | G-1 | J-14 (3/5) | — | H |
| 1-methyl-4-(trifluoromethyl)imidazol-2-yl | X¹ | G-1 | J-14 (3/5) | — | H |
| 2,5-dichlorophenyl | X¹ | G-1 | J-15 (2/5) | — | H |
| 2-chloro-5-(trifluoromethyl)phenyl | X¹ | G-1 | J-15 (2/5) | — | H |
| 2,5-dimethylphenyl | X¹ | G-1 | J-15 (2/5) | — | H |
| 2-methyl-5-(trifluoromethyl)phenyl | X¹ | G-1 | J-15 (2/5) | — | H |
| 3,5-dimethylpyrazol-1-yl | X¹ | G-1 | J-15 (2/5) | — | H |
| 5-methyl-3-(trifluoromethyl)pyrazol-1-yl | X¹ | G-1 | J-15 (2/5) | — | H |
| 5-chloro-3-(trifluoromethy)pyrazol-1-yl | X¹ | G-1 | J-15 (2/5) | — | H |
| 5-bromo-3-(trifluoromethyl)pyrazol-1-yl | X¹ | G-1 | J-15 (2/5) | — | H |
| 5-ethyl-3-(trifluoromethyl)pyrazol-1-yl | X¹ | G-1 | J-15 (2/5) | — | H |
| 3,5-bis-(trifluoromethyl)pyrazol-1-yl | X¹ | G-1 | J-15 (2/5) | — | H |
| 1-methyl-3-(trifluoromethyl)pyrazol-5-yl | X¹ | G-1 | J-15 (2/5) | — | H |
| 1-methyl-4-(trifluoromethyl)imidazol-2-yl | X¹ | G-1 | J-15 (2/5) | — | H |
| 2,5-dichlorophenyl | X¹ | G-1 | J-16 (2/5) | — | H |
| 2-chloro-5-(trifluoromethyl)phenyl | X¹ | G-1 | J-16 (2/5) | — | H |
| 2,5-dimethylphenyl | X¹ | G-1 | J-16 (2/5) | — | H |
| 2-methyl-5-(trifluoromethyl)phenyl | X¹ | G-1 | J-16 (2/5) | — | H |

TABLE 4*-continued

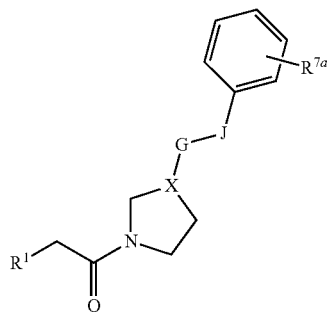

| R¹ | X | G  | J * | (R⁵)ᵧ | R⁷ᵃ |
|---|---|---|---|---|---|
| 3,5-dimethylpyrazol-1-yl | X¹ | G-1 | J-16 (2/5) | — | H |
| 5-methyl-3-(trifluoromethyl)pyrazol-1-yl | X¹ | G-1 | J-16 (2/5) | — | H |
| 5-chloro-3-(trifluoromethyl)pyrazol-1-yl | X¹ | G-1 | J-16 (2/5) | — | H |
| 5-bromo-3-(trifluoromethyl)pyrazol-1-yl | X¹ | G-1 | J-16 (2/5) | — | H |
| 5-ethyl-3-(trifluoromethyl)pyrazol-1-yl | X¹ | G-1 | J-16 (2/5) | — | H |
| 3,5-bis-(trifluoromethyl)pyrazol-1-yl | X¹ | G-1 | J-16 (2/5) | — | H |
| 1-methyl-3-(trifluoromethyl)pyrazol-5-yl | X¹ | G-1 | J-16 (2/5) | — | H |
| 1-methyl-4-(trifluoromethyl)imidazol-2-yl | X¹ | G-1 | J-16 (2/5) | — | H |
| 2,5-dichlorophenyl | X¹ | G-1 | J-22 (2/4) | — | H |
| 2-chloro-5-(trifluoromethyl)phenyl | X¹ | G-1 | J-22 (2/4) | — | H |
| 2,5-dimethylphenyl | X¹ | G-1 | J-22 (2/4) | — | H |
| 2-methyl-5-(trifluoromethyl)phenyl | X¹ | G-1 | J-22 (2/4) | — | H |
| 3,5-dimethylpyrazol-1-yl | X¹ | G-1 | J-22 (2/4) | — | H |
| 5-methyl-3-(trifluoromethyl)pyrazol-1-yl | X¹ | G-1 | J-22 (2/4) | — | H |
| 5-chloro-3-(trifluoromethyl)pyrazol-1-yl | X¹ | G-1 | J-22 (2/4) | — | H |
| 5-bromo-3-(trifluoromethyl)pyrazol-1-yl | X¹ | G-1 | J-22 (2/4) | — | H |
| 5-ethyl-3-(trifluoromethyl)pyrazol-1-yl | X¹ | G-1 | J-22 (2/4) | — | H |
| 3,5-bis-(trifluoromethyl)pyrazol-1-yl | X¹ | G-1 | J-22 (2/4) | — | H |
| 1-methyl-3-(trifluoromethyl)pyrazol-5-yl | X¹ | G-1 | J-22 (2/4) | — | H |
| 1-methyl-4-(trifluoromethyl)imidazol-2-yl | X¹ | G-1 | J-22 (2/4) | — | H |
| 2,5-dichlorophenyl | X¹ | G-1 | J-24 (2/4) | — | H |
| 2-chloro-5-(trifluoromethyl)phenyl | X¹ | G-1 | J-24 (2/4) | — | H |
| 2,5-dimethylphenyl | X¹ | G-1 | J-24 (2/4) | — | H |
| 2-methyl-5-(trifluoromethyl)phenyl | X¹ | G-1 | J-24 (2/4) | — | H |
| 3,5-dimethylpyrazol-1-yl | X¹ | G-1 | J-24 (2/4) | — | H |
| 5-methyl-3-(trifluoromethyl)pyrazol-1-yl | X¹ | G-1 | J-24 (2/4) | — | H |
| 5-chloro-3-(trifluoromethyl)pyrazol-1-yl | X¹ | G-1 | J-24 (2/4) | — | H |
| 5-bromo-3-(trifluoromethyl)pyrazol-1-yl | X¹ | G-1 | J-24 (2/4) | — | H |
| 5-ethyl-3-(trifluoromethyl)pyrazol-1-yl | X¹ | G-1 | J-24 (2/4) | — | H |
| 3,5-bis-(trifluoromethyl)pyrazol-1-yl | X¹ | G-1 | J-24 (2/4) | — | H |
| 1-methyl-3-(trifluoromethyl)pyrazol-5-yl | X¹ | G-1 | J-24 (2/4) | — | H |
| 1-methyl-4-(trifluoromethyl)imidazol-2-yl | X¹ | G-1 | J-24 (2/4) | — | H |
| 2,5-dichlorophenyl | X¹ | G-1 | J-25 (2/4) | — | H |
| 2-chloro-5-(trifluoromethyl)phenyl | X¹ | G-1 | J-25 (2/4) | — | H |
| 2,5-dimethylphenyl | X¹ | G-1 | J-25 (2/4) | — | H |
| 2-methyl-5-(trifluoromethyl)phenyl | X¹ | G-1 | J-25 (2/4) | — | H |
| 3,5-dimethylpyrazol-1-yl | X¹ | G-1 | J-25 (2/4) | — | H |
| 5-methyl-3-(trifluoromethyl)pyrazol-1-yl | X¹ | G-1 | J-25 (2/4) | — | H |
| 5-chloro-3-(trifluoromethyl)pyrazol-1-yl | X¹ | G-1 | J-25 (2/4) | — | H |
| 5-bromo-3-(trifluoromethyl)pyrazol-1-yl | X¹ | G-1 | J-25 (2/4) | — | H |
| 5-ethyl-3-(trifluoromethyl)pyrazol-1-yl | X¹ | G-1 | J-25 (2/4) | — | H |
| 3,5-bis-(trifluoromethyl)pyrazol-1-yl | X¹ | G-1 | J-25 (2/4) | — | H |
| 1-methyl-3-(trifluoromethyl)pyrazol-5-yl | X¹ | G-1 | J-25 (2/4) | — | H |
| 1-methyl-4-(trifluoromethyl)imidazol-2-yl | X¹ | G-1 | J-25 (2/4) | — | H |
| 2,5-dichlorophenyl | X¹ | G-1 | J-26 (2/4) | — | H |
| 2-chloro-5-(trifluoromethyl)phenyl | X¹ | G-1 | J-26 (2/4) | — | H |
| 2,5-dimethylphenyl | X¹ | G-1 | J-26 (2/4) | — | H |
| 2-methyl-5-(trifluoromethyl)phenyl | X¹ | G-1 | J-26 (2/4) | — | H |
| 3,5-dimethylpyrazol-1-yl | X¹ | G-1 | J-26 (2/4) | — | H |
| 5-methyl-3-(trifluoromethyl)pyrazol-1-yl | X¹ | G-1 | J-26 (2/4) | — | H |
| 5-chloro-3-(trifluoromethyl)pyrazol-1-yl | X¹ | G-1 | J-26 (2/4) | — | H |
| 5-bromo-3-(trifluoromethyl)pyrazol-1-yl | X¹ | G-1 | J-26 (2/4) | — | H |
| 5-ethyl-3-(trifluoromethyl)pyrazol-1-yl | X¹ | G-1 | J-26 (2/4) | — | H |
| 3,5-bis-(trifluoromethyl)pyrazol-1-yl | X¹ | G-1 | J-26 (2/4) | — | H |
| 1-methyl-3-(trifluoromethyl)pyrazol-5-yl | X¹ | G-1 | J-26 (2/4) | — | H |
| 1-methyl-4-(trifluoromethyl)imidazol-2-yl | X¹ | G-1 | J-26 (2/4) | — | H |
| 2,5-dichlorophenyl | X¹ | G-1 | J-26 (2/4) | 1-Me | H |
| 2-chloro-5-(trifluoromethyl)phenyl | X¹ | G-1 | J-26 (2/4) | 1-Me | H |
| 2,5-dimethylphenyl | X¹ | G-1 | J-26 (2/4) | 1-Me | H |
| 2-methyl-5-(trifluoromethyl)phenyl | X¹ | G-1 | J-26 (2/4) | 1-Me | H |
| 3,5-dimethylpyrazol-1-yl | X¹ | G-1 | J-26 (2/4) | 1-Me | H |
| 5-methyl-3-(trifluoromethyl)pyrazol-1-yl | X¹ | G-1 | J-26 (2/4) | 1-Me | H |

TABLE 4*-continued

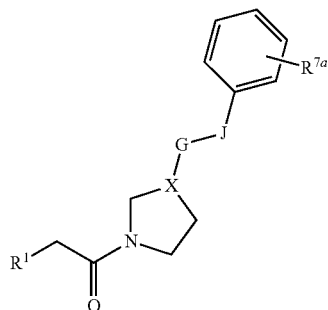

| R¹ | X | G  | J * | (R⁵)_y | R⁷ᵃ |
|---|---|---|---|---|---|
| 5-chloro-3-(trifluoromethyl)pyrazol-1-yl | X¹ | G-1 | J-26 (2/4) | 1-Me | H |
| 5-bromo-3-(trifluoromethyl)pyrazol-1-yl | X¹ | G-1 | J-26 (2/4) | 1-Me | H |
| 5-ethyl-3-(trifluoromethyl)pyrazol-1-yl | X¹ | G-1 | J-26 (2/4) | 1-Me | H |
| 3,5-bis-(trifluoromethyl)pyrazol-1-yl | X¹ | G-1 | J-26 (2/4) | 1-Me | H |
| 1-methyl-3-(trifluoromethyl)pyrazol-5-yl | X¹ | G-1 | J-26 (2/4) | 1-Me | H |
| 1-methyl-4-(trifluoromethyl)imidazol-2-yl | X¹ | G-1 | J-26 (2/4) | 1-Me | H |
| 2,5-dichlorophenyl | X¹ | G-1 | J-26 (2/5) | 1-Me | H |
| 2-chloro-5-(trifluoromethyl)phenyl | X¹ | G-1 | J-26 (2/5) | 1-Me | H |
| 2,5-dimethylphenyl | X¹ | G-1 | J-26 (2/5) | 1-Me | H |
| 2-methyl-5-(trifluoromethyl)phenyl | X¹ | G-1 | J-26 (2/5) | 1-Me | H |
| 3,5-dimethylpyrazol-1-yl | X¹ | G-1 | J-26 (2/5) | 1-Me | H |
| 5-methyl-3-(trifluoromethyl)pyrazol-1-yl | X¹ | G-1 | J-26 (2/5) | 1-Me | H |
| 5-chloro-3-(trifluoromethyl)pyrazol-1-yl | X¹ | G-1 | J-26 (2/5) | 1-Me | H |
| 5-bromo-3-(trifluoromethyl)pyrazol-1-yl | X¹ | G-1 | J-26 (2/5) | 1-Me | H |
| 5-ethyl-3-(trifluoromethyl)pyrazol-1-yl | X¹ | G-1 | J-26 (2/5) | 1-Me | H |
| 3,5-bis-(trifluoromethyl)pyrazol-1-yl | X¹ | G-1 | J-26 (2/5) | 1-Me | H |
| 1-methyl-3-(trifluoromethyl)pyrazol-5-yl | X¹ | G-1 | J-26 (2/5) | 1-Me | H |
| 1-methyl-4-(trifluoromethyl)imidazol-2-yl | X¹ | G-1 | J-26 (2/5) | 1-Me | H |
| 2,5-dichlorophenyl | X¹ | G-1 | J-28 (3/5) | — | H |
| 2-chloro-5-(trifluoromethyl)phenyl | X¹ | G-1 | J-28 (3/5) | — | H |
| 2,5-dimethylphenyl | X¹ | G-1 | J-28 (3/5) | — | H |
| 2-methyl-5-(trifluoromethyl)phenyl | X¹ | G-1 | J-28 (3/5) | — | H |
| 3,5-dimethylpyrazol-1-yl | X¹ | G-1 | J-28 (3/5) | — | H |
| 5-methyl-3-(trifluoromethyl)pyrazol-1-yl | X¹ | G-1 | J-28 (3/5) | — | H |
| 5-chloro-3-(trifluoromethyl)pyrazol-1-yl | X¹ | G-1 | J-28 (3/5) | — | H |
| 5-bromo-3-(trifluoromethyl)pyrazol-1-yl | X¹ | G-1 | J-28 (3/5) | — | H |
| 5-ethyl-3-(trifluoromethyl)pyrazol-1-yl | X¹ | G-1 | J-28 (3/5) | — | H |
| 3,5-bis-(trifluoromethyl)pyrazol-1-yl | X¹ | G-1 | J-28 (3/5) | — | H |
| 1-methyl-3-(trifluoromethyl)pyrazol-5-yl | X¹ | G-1 | J-28 (3/5) | — | H |
| 1-methyl-4-(trifluoromethyl)imidazol-2-yl | X¹ | G-1 | J-28 (3/5) | — | H |
| 2,5-dichlorophenyl | X¹ | G-1 | J-30 (3/5) | — | H |
| 2-chloro-5-(trifluoromethyl)phenyl | X¹ | G-1 | J-30 (3/5) | — | H |
| 2,5-dimethylphenyl | X¹ | G-1 | J-30 (3/5) | — | H |
| 2-methyl-5-(trifluoromethyl)phenyl | X¹ | G-1 | J-30 (3/5) | — | H |
| 3,5-dimethylpyrazol-1-yl | X¹ | G-1 | J-30 (3/5) | — | H |
| 5-methyl-3-(trifluoromethyl)pyrazol-1-yl | X¹ | G-1 | J-30 (3/5) | — | H |
| 5-chloro-3-(trifluoromethyl)pyrazol-1-yl | X¹ | G-1 | J-30 (3/5) | — | H |
| 5-bromo-3-(trifluoromethyl)pyrazol-1-yl | X¹ | G-1 | J-30 (3/5) | — | H |
| 5-ethyl-3-(trifluoromethyl)pyrazol-1-yl | X¹ | G-1 | J-30 (3/5) | — | H |
| 3,5-bis-(trifluoromethyl)pyrazol-1-yl | X¹ | G-1 | J-30 (3/5) | — | H |
| 1-methyl-3-(trifluoromethyl)pyrazol-5-yl | X¹ | G-1 | J-30 (3/5) | — | H |
| 1-methyl-4-(trifluoromethyl)imidazol-2-yl | X¹ | G-1 | J-30 (3/5) | — | H |
| 2,5-dichlorophenyl | X¹ | G-1 | J-30 (3/5) | 1-Me | H |
| 2-chloro-5-(trifluoromethyl)phenyl | X¹ | G-1 | J-30 (3/5) | 1-Me | H |
| 2,5-dimethylphenyl | X¹ | G-1 | J-30 (3/5) | 1-Me | H |
| 2-methyl-5-(trifluoromethyl)phenyl | X¹ | G-1 | J-30 (3/5) | 1-Me | H |
| 3,5-dimethylpyrazol-1-yl | X¹ | G-1 | J-30 (3/5) | 1-Me | H |
| 5-methyl-3-(trifluoromethyl)pyrazol-1-yl | X¹ | G-1 | J-30 (3/5) | 1-Me | H |
| 5-chloro-3-(trifluoromethyl)pyrazol-1-yl | X¹ | G-1 | J-30 (3/5) | 1-Me | H |
| 5-bromo-3-(trifluoromethyl)pyrazol-1-yl | X¹ | G-1 | J-30 (3/5) | 1-Me | H |
| 5-ethyl-3-(trifluoromethyl)pyrazol-1-yl | X¹ | G-1 | J-30 (3/5) | 1-Me | H |
| 3,5-bis-(trifluoromethyl)pyrazol-1-yl | X¹ | G-1 | J-30 (3/5) | 1-Me | H |
| 1-methyl-3-(trifluoromethyl)pyrazol-5-yl | X¹ | G-1 | J-30 (3/5) | 1-Me | H |
| 1-methyl-4-(trifluoromethyl)imidazol-2-yl | X¹ | G-1 | J-30 (3/5) | 1-Me | H |
| 2,5-dichlorophenyl | X¹ | G-1 | J-36 (3/5) | 1-Me | H |
| 2-chloro-5-(trifluoromethyl)phenyl | X¹ | G-1 | J-36 (3/5) | 1-Me | H |
| 2,5-dimethylphenyl | X¹ | G-1 | J-36 (3/5) | 1-Me | H |
| 2-methyl-5-(trifluoromethyl)phenyl | X¹ | G-1 | J-36 (3/5) | 1-Me | H |
| 3,5-dimethylpyrazol-1-yl | X¹ | G-1 | J-36 (3/5) | 1-Me | H |
| 5-methyl-3-(trifluoromethyl)pyrazol-1-yl | X¹ | G-1 | J-36 (3/5) | 1-Me | H |
| 5-chloro-3-(trifluoromethyl)pyrazol-1-yl | X¹ | G-1 | J-36 (3/5) | 1-Me | H |
| 5-bromo-3-(trifluoromethyl)pyrazol-1-yl | X¹ | G-1 | J-36 (3/5) | 1-Me | H |

TABLE 4*-continued

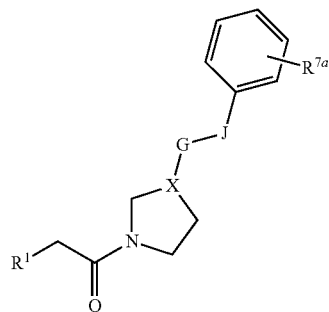

| R¹ | X | G  | J * | (R⁵)_y | R⁷ᵃ |
|---|---|---|---|---|---|
| 5-ethyl-3-(trifluoromethyl)pyrazol-1-yl | X¹ | G-1 | J-36 (3/5) | 1-Me | H |
| 3,5-bis-(trifluoromethyl)pyrazol-1-yl | X¹ | G-1 | J-36 (3/5) | 1-Me | H |
| 1-methyl-3-(trifluoromethyl)pyrazol-5-yl | X¹ | G-1 | J-36 (3/5) | 1-Me | H |
| 1-methyl-4-(trifluoromethyl)imidazol-2-yl | X¹ | G-1 | J-36 (3/5) | 1-Me | H |
| 2,5-dichlorophenyl | X¹ | G-1 | J-37 (2/5) | — | H |
| 2-chloro-5-(trifluoromethyl)phenyl | X¹ | G-1 | J-37 (2/5) | — | H |
| 2,5-dimethylphenyl | X¹ | G-1 | J-37 (2/5) | — | H |
| 2-methyl-5-(trifluoromethyl)phenyl | X¹ | G-1 | J-37 (2/5) | — | H |
| 3,5-dimethylpyrazol-1-yl | X¹ | G-1 | J-37 (2/5) | — | H |
| 5-methyl-3-(trifluoromethyl)pyrazol-1-yl | X¹ | G-1 | J-37 (2/5) | — | H |
| 5-chloro-3-(trifluoromethyl)pyrazol-1-yl | X¹ | G-1 | J-37 (2/5) | — | H |
| 5-bromo-3-(trifluoromethyl)pyrazol-1-yl | X¹ | G-1 | J-37 (2/5) | — | H |
| 5-ethyl-3-(trifluoromethyl)pyrazol-1-yl | X¹ | G-1 | J-37 (2/5) | — | H |
| 3,5-bis-(trifluoromethyl)pyrazol-1-yl | X¹ | G-1 | J-37 (2/5) | — | H |
| 1-methyl-3-(trifluoromethyl)pyrazol-5-yl | X¹ | G-1 | J-37 (2/5) | — | H |
| 1-methyl-4-(trifluoromethyl)imidazol-2-yl | X¹ | G-1 | J-37 (2/5) | — | H |
| 2,5-dichlorophenyl | X¹ | G-1 | J-38 (2/5) | — | H |
| 2-chloro-5-(trifluoromethyl)phenyl | X¹ | G-1 | J-38 (2/5) | — | H |
| 2,5-dimethylphenyl | X¹ | G-1 | J-38 (2/5) | — | H |
| 2-methyl-5-(trifluoromethyl)phenyl | X¹ | G-1 | J-38 (2/5) | — | H |
| 3,5-dimethylpyrazol-1-yl | X¹ | G-1 | J-38 (2/5) | — | H |
| 5-methyl-3-(trifluoromethyl)pyrazol-1-yl | X¹ | G-1 | J-38 (2/5) | — | H |
| 5-chloro-3-(trifluoromethyl)pyrazol-1-yl | X¹ | G-1 | J-38 (2/5) | — | H |
| 5-bromo-3-(trifluoromethyl)pyrazol-1-yl | X¹ | G-1 | J-38 (2/5) | — | H |
| 5-ethyl-3-(trifluoromethyl)pyrazol-1-yl | X¹ | G-1 | J-38 (2/5) | — | H |
| 3,5-bis-(trifluoromethyl)pyrazol-1-yl | X¹ | G-1 | J-38 (2/5) | — | H |
| 1-methyl-3-(trifluoromethyl)pyrazol-5-yl | X¹ | G-1 | J-38 (2/5) | — | H |
| 1-methyl-4-(trifluoromethyl)imidazol-2-yl | X¹ | G-1 | J-38 (2/5) | — | H |
| 2,5-dichlorophenyl | X¹ | G-1 | J-39 (3/5) | — | H |
| 2-chloro-5-(trifluoromethyl)phenyl | X¹ | G-1 | J-39 (3/5) | — | H |
| 2,5-dimethylphenyl | X¹ | G-1 | J-39 (3/5) | — | H |
| 2-methyl-5-(trifluoromethyl)phenyl | X¹ | G-1 | J-39 (3/5) | — | H |
| 3,5-dimethylpyrazol-1-yl | X¹ | G-1 | J-39 (3/5) | — | H |
| 5-methyl-3-(trifluoromethyl)pyrazol-1-yl | X¹ | G-1 | J-39 (3/5) | — | H |
| 5-chloro-3-(trifluoromethyl)pyrazol-1-yl | X¹ | G-1 | J-39 (3/5) | — | H |
| 5-bromo-3-(trifluoromethyl)pyrazol-1-yl | X¹ | G-1 | J-39 (3/5) | — | H |
| 5-ethyl-3-(trifluoromethyl)pyrazol-1-yl | X¹ | G-1 | J-39 (3/5) | — | H |
| 3,5-bis-(trifluoromethyl)pyrazol-1-yl | X¹ | G-1 | J-39 (3/5) | — | H |
| 1-methyl-3-(trifluoromethyl)pyrazol-5-yl | X¹ | G-1 | J-39 (3/5) | — | H |
| 1-methyl-4-(trifluoromethyl)imidazol-2-yl | X¹ | G-1 | J-39 (3/5) | — | H |
| 2,5-dichlorophenyl | X¹ | G-1 | J-40 (3/5) | — | H |
| 2-chloro-5-(trifluoromethyl)phenyl | X¹ | G-1 | J-40 (3/5) | — | H |
| 2,5-dimethylphenyl | X¹ | G-1 | J-40 (3/5) | — | H |
| 2-methyl-5-(trifluoromethyl)phenyl | X¹ | G-1 | J-40 (3/5) | — | H |
| 3,5-dimethylpyrazol-1-yl | X¹ | G-1 | J-40 (3/5) | — | H |
| 5-methyl-3-(trifluoromethyl)pyrazol-1-yl | X¹ | G-1 | J-40 (3/5) | — | H |
| 5-chloro-3-(trifluoromethyl)pyrazol-1-yl | X¹ | G-1 | J-40 (3/5) | — | H |
| 5-bromo-3-(trifluoromethyl)pyrazol-1-yl | X¹ | G-1 | J-40 (3/5) | — | H |
| 5-ethyl-3-(trifluoromethyl)pyrazol-1-yl | X¹ | G-1 | J-40 (3/5) | — | H |
| 3,5-bis-(trifluoromethyl)pyrazol-1-yl | X¹ | G-1 | J-40 (3/5) | — | H |
| 1-methyl-3-(trifluoromethyl)pyrazol-5-yl | X¹ | G-1 | J-40 (3/5) | — | H |
| 1-methyl-4-(trifluoromethyl)imidazol-2-yl | X¹ | G-1 | J-40 (3/5) | — | H |
| 2,5-dichlorophenyl | X¹ | G-1 | J-69 (1/3) | — | H |
| 2-chloro-5-(trifluoromethyl)phenyl | X¹ | G-1 | J-69 (1/3) | — | H |
| 2,5-dimethylphenyl | X¹ | G-1 | J-69 (1/3) | — | H |
| 2-methyl-5-(trifluoromethyl)phenyl | X¹ | G-1 | J-69 (1/3) | — | H |
| 3,5-dimethylpyrazol-1-yl | X¹ | G-1 | J-69 (1/3) | — | H |
| 5-methyl-3-(trifluoromethyl)pyrazol-1-yl | X¹ | G-1 | J-69 (1/3) | — | H |
| 5-chloro-3-(trifluoromethyl)pyrazol-1-yl | X¹ | G-1 | J-69 (1/3) | — | H |
| 5-bromo-3-(trifluoromethyl)pyrazol-1-yl | X¹ | G-1 | J-69 (1/3) | — | H |
| 5-ethyl-3-(trifluoromethyl)pyrazol-1-yl | X¹ | G-1 | J-69 (1/3) | — | H |
| 3,5-bis-(trifluoromethyl)pyrazol-1-yl | X¹ | G-1 | J-69 (1/3) | — | H |

TABLE 4*-continued

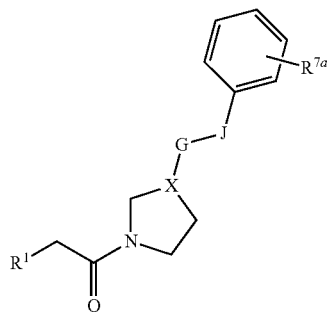

| R¹ | X | G  | J * | (R⁵)_y | R^{7a} |
|---|---|---|---|---|---|
| 1-methyl-3-(trifluoromethyl)pyrazol-5-yl | X¹ | G-1 | J-69 (1/3) | — | H |
| 1-methyl-4-(trifluoromethyl)imidazol-2-yl | X¹ | G-1 | J-69 (1/3) | — | H |
| 2,5-dichlorophenyl | X¹ | G-1 | J-69 (1/4) | — | H |
| 2-chloro-5-(trifluoromethyl)phenyl | X¹ | G-1 | J-69 (1/4) | — | H |
| 2,5-dimethylphenyl | X¹ | G-1 | J-69 (1/4) | — | H |
| 2-methyl-5-(trifluoromethyl)phenyl | X¹ | G-1 | J-69 (1/4) | — | H |
| 3,5-dimethylpyrazol-1-yl | X¹ | G-1 | J-69 (1/4) | — | H |
| 5-methyl-3-(trifluoromethyl)pyrazol-1-yl | X¹ | G-1 | J-69 (1/4) | — | H |
| 5-chloro-3-(trifluoromethyl)pyrazol-1-yl | X¹ | G-1 | J-69 (1/4) | — | H |
| 5-bromo-3-(trifluoromethyl)pyrazol-1-yl | X¹ | G-1 | J-69 (1/4) | — | H |
| 5-ethyl-3-(trifluoromethyl)pyrazol-1-yl | X¹ | G-1 | J-69 (1/4) | — | H |
| 3,5-bis-(trifluoromethyl)pyrazol-1-yl | X¹ | G-1 | J-69 (1/4) | — | H |
| 1-methyl-3-(trifluoromethyl)pyrazol-5-yl | X¹ | G-1 | J-69 (1/4) | — | H |
| 1-methyl-4-(trifluoromethyl)imidazol-2-yl | X¹ | G-1 | J-69 (1/4) | — | H |
| 2,5-dichlorophenyl | X¹ | G-1 | J-11 (3/5) | — | 2-Me |
| 2-chloro-5-(trifluoromethyl)phenyl | X¹ | G-1 | J-11 (3/5) | — | 2-Me |
| 2,5-dimethylphenyl | X¹ | G-1 | J-11 (3/5) | — | 2-Me |
| 2-methyl-5-(trifluoromethyl)phenyl | X¹ | G-1 | J-11 (3/5) | — | 2-Me |
| 3,5-dimethylpyrazol-1-yl | X¹ | G-1 | J-11 (3/5) | — | 2-Me |
| 5-methyl-3-(trifluoromethyl)pyrazol-1-yl | X¹ | G-1 | J-11 (3/5) | — | 2-Me |
| 5-chloro-3-(trifluoromethyl)pyrazol-1-yl | X¹ | G-1 | J-11 (3/5) | — | 2-Me |
| 5-bromo-3-(trifluoromethyl)pyrazol-1-yl | X¹ | G-1 | J-11 (3/5) | — | 2-Me |
| 5-ethyl-3-(trifluoromethyl)pyrazol-1-yl | X¹ | G-1 | J-11 (3/5) | — | 2-Me |
| 3,5-bis-(trifluoromethyl)pyrazol-1-yl | X¹ | G-1 | J-11 (3/5) | — | 2-Me |
| 1-methyl-3-(trifluoromethyl)pyrazol-5-yl | X¹ | G-1 | J-11 (3/5) | — | 2-Me |
| 1-methyl-4-(trifluoromethyl)imidazol-2-yl | X¹ | G-1 | J-11 (3/5) | — | 2-Me |
| 2,5-dichlorophenyl | X¹ | G-1 | J-11 (3/5) | — | 3-Me |
| 2-chloro-5-(trifluoromethyl)phenyl | X¹ | G-1 | J-11 (3/5) | — | 3-Me |
| 2,5-dimethylphenyl | X¹ | G-1 | J-11 (3/5) | — | 3-Me |
| 2-methyl-5-(trifluoromethyl)phenyl | X¹ | G-1 | J-11 (3/5) | — | 3-Me |
| 3,5-dimethylpyrazol-1-yl | X¹ | G-1 | J-11 (3/5) | — | 3-Me |
| 5-methyl-3-(trifluoromethyl)pyrazol-1-yl | X¹ | G-1 | J-11 (3/5) | — | 3-Me |
| 5-chloro-3-(trifluoromethyl)pyrazol-1-yl | X¹ | G-1 | J-11 (3/5) | — | 3-Me |
| 5-bromo-3-(trifluoromethyl)pyrazol-1-yl | X¹ | G-1 | J-11 (3/5) | — | 3-Me |
| 5-ethyl-3-(trifluoromethyl)pyrazol-1-yl | X¹ | G-1 | J-11 (3/5) | — | 3-Me |
| 3,5-bis-(trifluoromethyl)pyrazol-1-yl | X¹ | G-1 | J-11 (3/5) | — | 3-Me |
| 1-methyl-3-(trifluoromethyl)pyrazol-5-yl | X¹ | G-1 | J-11 (3/5) | — | 3-Me |
| 1-methyl-4-(trifluoromethyl)imidazol-2-yl | X¹ | G-1 | J-11 (3/5) | — | 3-Me |
| 2,5-dichlorophenyl | X¹ | G-1 | J-11 (3/5) | — | 4-Me |
| 2-chloro-5-(trifluoromethyl)phenyl | X¹ | G-1 | J-11 (3/5) | — | 4-Me |
| 2,5-dimethylphenyl | X¹ | G-1 | J-11 (3/5) | — | 4-Me |
| 2-methyl-5-(trifluoromethyl)phenyl | X¹ | G-1 | J-11 (3/5) | — | 4-Me |
| 3,5-dimethylpyrazol-1-yl | X¹ | G-1 | J-11 (3/5) | — | 4-Me |
| 5-methyl-3-(trifluoromethyl)pyrazol-1-yl | X¹ | G-1 | J-11 (3/5) | — | 4-Me |
| 5-chloro-3-(trifluoromethyl)pyrazol-1-yl | X¹ | G-1 | J-11 (3/5) | — | 4-Me |
| 5-bromo-3-(trifluoromethyl)pyrazol-1-yl | X¹ | G-1 | J-11 (3/5) | — | 4-Me |
| 5-ethyl-3-(trifluoromethyl)pyrazol-1-yl | X¹ | G-1 | J-11 (3/5) | — | 4-Me |
| 3,5-bis-(trifluoromethyl)pyrazol-1-yl | X¹ | G-1 | J-11 (3/5) | — | 4-Me |
| 1-methyl-3-(trifluoromethyl)pyrazol-5-yl | X¹ | G-1 | J-11 (3/5) | — | 4-Me |
| 1-methyl-4-(trifluoromethyl)imidazol-2-yl | X¹ | G-1 | J-11 (3/5) | — | 4-Me |
| 2,5-dichlorophenyl | X¹ | G-1 | J-11 (3/5) | — | 2-Cl |
| 2-chloro-5-(trifluoromethyl)phenyl | X¹ | G-1 | J-11 (3/5) | — | 2-Cl |
| 2,5-dimethylphenyl | X¹ | G-1 | J-11 (3/5) | — | 2-Cl |
| 2-methyl-5-(trifluoromethyl)phenyl | X¹ | G-1 | J-11 (3/5) | — | 2-Cl |
| 3,5-dimethylpyrazol-1-yl | X¹ | G-1 | J-11 (3/5) | — | 2-Cl |
| 5-methyl-3-(trifluoromethyl)pyrazol-1-yl | X¹ | G-1 | J-11 (3/5) | — | 2-Cl |
| 5-chloro-3-(trifluoromethyl)pyrazol-1-yl | X¹ | G-1 | J-11 (3/5) | — | 2-Cl |
| 5-bromo-3-(trifluoromethyl)pyrazol-1-yl | X¹ | G-1 | J-11 (3/5) | — | 2-Cl |
| 5-ethyl-3-(trifluoromethyl)pyrazol-1-yl | X¹ | G-1 | J-11 (3/5) | — | 2-Cl |
| 3,5-bis-(trifluoromethyl)pyrazol-1-yl | X¹ | G-1 | J-11 (3/5) | — | 2-Cl |
| 1-methyl-3-(trifluoromethyl)pyrazol-5-yl | X¹ | G-1 | J-11 (3/5) | — | 2-Cl |
| 1-methyl-4-(trifluoromethyl)imidazol-2-yl | X¹ | G-1 | J-11 (3/5) | — | 2-Cl |

TABLE 4*-continued

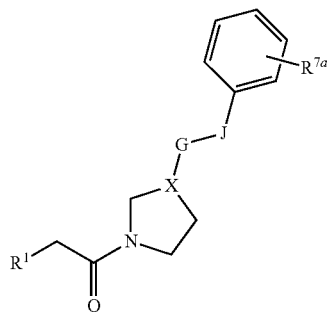

| R¹ | X | G  | J * | (R⁵)ᵧ | R⁷ᵃ |
|---|---|---|---|---|---|
| 2,5-dichlorophenyl | X¹ | G-1 | J-11 (3/5) | — | 4-Cl |
| 2-chloro-5-(trifluoromethyl)phenyl | X¹ | G-1 | J-11 (3/5) | — | 4-Cl |
| 2,5-dimethylphenyl | X¹ | G-1 | J-11 (3/5) | — | 4-Cl |
| 2-methyl-5-(trifluoromethyl)phenyl | X¹ | G-1 | J-11 (3/5) | — | 4-Cl |
| 3,5-dimethylpyrazol-1-yl | X¹ | G-1 | J-11 (3/5) | — | 4-Cl |
| 5-methyl-3-(trifluoromethyl)pyrazol-1-yl | X¹ | G-1 | J-11 (3/5) | — | 4-Cl |
| 5-chloro-3-(trifluoromethyl)pyrazol-1-yl | X¹ | G-1 | J-11 (3/5) | — | 4-Cl |
| 5-bromo-3-(trifluoromethyl)pyrazol-1-yl | X¹ | G-1 | J-11 (3/5) | — | 4-Cl |
| 5-ethyl-3-(trifluoromethyl)pyrazol-1-yl | X¹ | G-1 | J-11 (3/5) | — | 4-Cl |
| 3,5-bis-(trifluoromethyl)pyrazol-1-yl | X¹ | G-1 | J-11 (3/5) | — | 4-Cl |
| 1-methyl-3-(trifluoromethyl)pyrazol-5-yl | X¹ | G-1 | J-11 (3/5) | — | 4-Cl |
| 1-methyl-4-(trifluoromethyl)imidazol-2-yl | X¹ | G-1 | J-11 (3/5) | — | 4-Cl |
| 2,5-dichlorophenyl | X¹ | G-1 | J-29 (3/5) | 5-Me | 2-Me |
| 2-chloro-5-(trifluoromethyl)phenyl | X¹ | G-1 | J-29 (3/5) | 5-Me | 2-Me |
| 2,5-dimethylphenyl | X¹ | G-1 | J-29 (3/5) | 5-Me | 2-Me |
| 2-methyl-5-(trifluoromethyl)phenyl | X¹ | G-1 | J-29 (3/5) | 5-Me | 2-Me |
| 3,5-dimethylpyrazol-1-yl | X¹ | G-1 | J-29 (3/5) | 5-Me | 2-Me |
| 5-methyl-3-(trifluoromethyl)pyrazol-1-yl | X¹ | G-1 | J-29 (3/5) | 5-Me | 2-Me |
| 5-chloro-3-(trifluoromethyl)pyrazol-1-yl | X¹ | G-1 | J-29 (3/5) | 5-Me | 2-Me |
| 5-bromo-3-(trifluoromethyl)pyrazol-1-yl | X¹ | G-1 | J-29 (3/5) | 5-Me | 2-Me |
| 5-ethyl-3-(trifluoromethyl)pyrazol-1-yl | X¹ | G-1 | J-29 (3/5) | 5-Me | 2-Me |
| 3,5-bis-(trifluoromethyl)pyrazol-1-yl | X¹ | G-1 | J-29 (3/5) | 5-Me | 2-Me |
| 1-methyl-3-(trifluoromethyl)pyrazol-5-yl | X¹ | G-1 | J-29 (3/5) | 5-Me | 2-Me |
| 1-methyl-4-(trifluoromethyl)imidazol-2-yl | X¹ | G-1 | J-29 (3/5) | 5-Me | 2-Me |
| 2,5-dichlorophenyl | X¹ | G-1 | J-29 (3/5) | — | 3-Me |
| 2-chloro-5-(trifluoromethyl)phenyl | X¹ | G-1 | J-29 (3/5) | — | 3-Me |
| 2,5-dimethylphenyl | X¹ | G-1 | J-29 (3/5) | — | 3-Me |
| 2-methyl-5-(trifluoromethyl)phenyl | X¹ | G-1 | J-29 (3/5) | — | 3-Me |
| 3,5-dimethylpyrazol-1-yl | X¹ | G-1 | J-29 (3/5) | — | 3-Me |
| 5-methyl-3-(trifluoromethyl)pyrazol-1-yl | X¹ | G-1 | J-29 (3/5) | — | 3-Me |
| 5-chloro-3-(trifluoromethyl)pyrazol-1-yl | X¹ | G-1 | J-29 (3/5) | — | 3-Me |
| 5-bromo-3-(trifluoromethyl)pyrazol-1-yl | X¹ | G-1 | J-29 (3/5) | — | 3-Me |
| 5-ethyl-3-(trifluoromethyl)pyrazol-1-yl | X¹ | G-1 | J-29 (3/5) | — | 3-Me |
| 3,5-bis-(trifluoromethyl)pyrazol-1-yl | X¹ | G-1 | J-29 (3/5) | — | 3-Me |
| 1-methyl-3-(trifluoromethyl)pyrazol-5-yl | X¹ | G-1 | J-29 (3/5) | — | 3-Me |
| 1-methyl-4-(trifluoromethyl)imidazol-2-yl | X¹ | G-1 | J-29 (3/5) | — | 3-Me |
| 2,5-dichlorophenyl | X¹ | G-1 | J-29 (3/5) | — | 4-Me |
| 2-chloro-5-(trifluoromethyl)phenyl | X¹ | G-1 | J-29 (3/5) | — | 4-Me |
| 2,5-dimethylphenyl | X¹ | G-1 | J-29 (3/5) | — | 4-Me |
| 2-methyl-5-(trifluoromethyl)phenyl | X¹ | G-1 | J-29 (3/5) | — | 4-Me |
| 3,5-dimethylpyrazol-1-yl | X¹ | G-1 | J-29 (3/5) | — | 4-Me |
| 5-methyl-3-(trifluoromethyl)pyrazol-1-yl | X¹ | G-1 | J-29 (3/5) | — | 4-Me |
| 5-chloro-3-(trifluoromethyl)pyrazol-1-yl | X¹ | G-1 | J-29 (3/5) | — | 4-Me |
| 5-bromo-3-(trifluoromethyl)pyrazol-1-yl | X¹ | G-1 | J-29 (3/5) | — | 4-Me |
| 5-ethyl-3-(trifluoromethyl)pyrazol-1-yl | X¹ | G-1 | J-29 (3/5) | — | 4-Me |
| 3,5-bis-(trifluoromethyl)pyrazol-1-yl | X¹ | G-1 | J-29 (3/5) | — | 4-Me |
| 1-methyl-3-(trifluoromethyl)pyrazol-5-yl | X¹ | G-1 | J-29 (3/5) | — | 4-Me |
| 1-methyl-4-(trifluoromethyl)imidazol-2-yl | X¹ | G-1 | J-29 (3/5) | — | 4-Me |
| 2,5-dichlorophenyl | X¹ | G-1 | J-29 (3/5) | 5-Me | 2-Cl |
| 2-chloro-5-(trifluoromethyl)phenyl | X¹ | G-1 | J-29 (3/5) | 5-Me | 2-Cl |
| 2,5-dimethylphenyl | X¹ | G-1 | J-29 (3/5) | 5-Me | 2-Cl |
| 2-methyl-5-(trifluoromethyl)phenyl | X¹ | G-1 | J-29 (3/5) | 5-Me | 2-Cl |
| 3,5-dimethylpyrazol-1-yl | X¹ | G-1 | J-29 (3/5) | 5-Me | 2-Cl |
| 5-methyl-3-(trifluoromethyl)pyrazol-1-yl | X¹ | G-1 | J-29 (3/5) | 5-Me | 2-Cl |
| 5-chloro-3-(trifluoromethyl)pyrazol-1-yl | X¹ | G-1 | J-29 (3/5) | 5-Me | 2-Cl |
| 5-bromo-3-(trifluoromethyl)pyrazol-1-yl | X¹ | G-1 | J-29 (3/5) | 5-Me | 2-Cl |
| 5-ethyl-3-(trifluoromethyl)pyrazol-1-yl | X¹ | G-1 | J-29 (3/5) | 5-Me | 2-Cl |
| 3,5-bis-(trifluoromethyl)pyrazol-1-yl | X¹ | G-1 | J-29 (3/5) | 5-Me | 2-Cl |
| 1-methyl-3-(trifluoromethyl)pyrazol-5-yl | X¹ | G-1 | J-29 (3/5) | 5-Me | 2-Cl |
| 1-methyl-4-(trifluoromethyl)imidazol-2-yl | X¹ | G-1 | J-29 (3/5) | 5-Me | 2-Cl |
| 2,5-dichlorophenyl | X¹ | G-1 | J-29 (3/5) | — | 4-Cl |
| 2-chloro-5-(trifluoromethyl)phenyl | X¹ | G-1 | J-29 (3/5) | — | 4-Cl |

TABLE 4*-continued

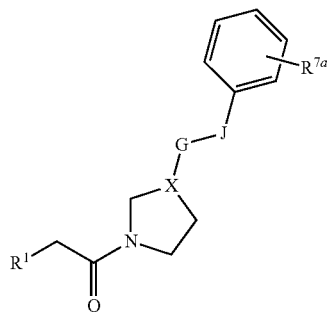

| R¹ | X | G  | J * | (R⁵)ᵧ | R⁷ᵃ |
|---|---|---|---|---|---|
| 2,5-dimethylphenyl | X¹ | G-1 | J-29 (3/5) | — | 4-Cl |
| 2-methyl-5-(trifluoromethyl)phenyl | X¹ | G-1 | J-29 (3/5) | — | 4-Cl |
| 3,5-dimethylpyrazol-1-yl | X¹ | G-1 | J-29 (3/5) | — | 4-Cl |
| 5-methyl-3-(trifluoromethyl)pyrazol-1-yl | X¹ | G-1 | J-29 (3/5) | — | 4-Cl |
| 5-chloro-3-(trifluoromethyl)pyrazol-1-yl | X¹ | G-1 | J-29 (3/5) | — | 4-Cl |
| 5-bromo-3-(trifluoromethyl)pyrazol-1-yl | X¹ | G-1 | J-29 (3/5) | — | 4-Cl |
| 5-ethyl-3-(trifluoromethyl)pyrazol-1-yl | X¹ | G-1 | J-29 (3/5) | — | 4-Cl |
| 3,5-bis-(trifluoromethyl)pyrazol-1-yl | X¹ | G-1 | J-29 (3/5) | — | 4-Cl |
| 1-methyl-3-(trifluoromethyl)pyrazol-5-yl | X¹ | G-1 | J-29 (3/5) | — | 4-Cl |
| 1-methyl-4-(trifluoromethyl)imidazol-2-yl | X¹ | G-1 | J-29 (3/5) | — | 4-Cl |
| 2,5-dichlorophenyl | X¹ | G-1 | J-29 (3/5) | 5-Me | H |
| 2-chloro-5-(trifluoromethyl)phenyl | X¹ | G-1 | J-29 (3/5) | 5-Me | H |
| 2,5-dimethylphenyl | X¹ | G-1 | J-29 (3/5) | 5-Me | H |
| 2-methyl-5-(trifluoromethyl)phenyl | X¹ | G-1 | J-29 (3/5) | 5-Me | H |
| 3,5-dimethylpyrazol-1-yl | X¹ | G-1 | J-29 (3/5) | 5-Me | H |
| 5-methyl-3-(trifluoromethyl)pyrazol-1-yl | X¹ | G-1 | J-29 (3/5) | 5-Me | H |
| 5-chloro-3-(trifluoromethyl)pyrazol-1-yl | X¹ | G-1 | J-29 (3/5) | 5-Me | H |
| 5-bromo-3-(trifluoromethyl)pyrazol-1-yl | X¹ | G-1 | J-29 (3/5) | 5-Me | H |
| 5-ethyl-3-(trifluoromethyl)pyrazol-1-yl | X¹ | G-1 | J-29 (3/5) | 5-Me | H |
| 3,5-bis-(trifluoromethyl)pyrazol-1-yl | X¹ | G-1 | J-29 (3/5) | 5-Me | H |
| 1-methyl-3-(trifluoromethyl)pyrazol-5-yl | X¹ | G-1 | J-29 (3/5) | 5-Me | H |
| 1-methyl-4-(trifluoromethyl)imidazol-2-yl | X¹ | G-1 | J-29 (3/5) | 5-Me | H |
| 2,5-dichlorophenyl | X¹ | G-1 | J-29 (3/5) | 4-Me | H |
| 2-chloro-5-(trifluoromethyl)phenyl | X¹ | G-1 | J-29 (3/5) | 4-Me | H |
| 2,5-dimethylphenyl | X¹ | G-1 | J-29 (3/5) | 4-Me | H |
| 2-methyl-5-(trifluoromethyl)phenyl | X¹ | G-1 | J-29 (3/5) | 4-Me | H |
| 3,5-dimethylpyrazol-1-yl | X¹ | G-1 | J-29 (3/5) | 4-Me | H |
| 5-methyl-3-(trifluoromethyl)pyrazol-1-yl | X¹ | G-1 | J-29 (3/5) | 4-Me | H |
| 5-chloro-3-(trifluoromethyl)pyrazol-1-yl | X¹ | G-1 | J-29 (3/5) | 4-Me | H |
| 5-bromo-3-(trifluoromethyl)pyrazol-1-yl | X¹ | G-1 | J-29 (3/5) | 4-Me | H |
| 5-ethyl-3-(trifluoromethyl)pyrazol-1-yl | X¹ | G-1 | J-29 (3/5) | 4-Me | H |
| 3,5-bis-(trifluoromethyl)pyrazol-1-yl | X¹ | G-1 | J-29 (3/5) | 4-Me | H |
| 1-methyl-3-(trifluoromethyl)pyrazol-5-yl | X¹ | G-1 | J-29 (3/5) | 4-Me | H |
| 1-methyl-4-(trifluoromethyl)imidazol-2-yl | X¹ | G-1 | J-29 (3/5) | 4-Me | H |
| 2,5-dichlorophenyl | X¹ | G-1 | J-29 (3/5) | 4,4-di-Me | H |
| 2-chloro-5-(trifluoromethyl)phenyl | X¹ | G-1 | J-29 (3/5) | 4,4-di-Me | H |
| 2,5-dimethylphenyl | X¹ | G-1 | J-29 (3/5) | 4,4-di-Me | H |
| 2-methyl-5-(trifluoromethyl)phenyl | X¹ | G-1 | J-29 (3/5) | 4,4-di-Me | H |
| 3,5-dimethylpyrazol-1-yl | X¹ | G-1 | J-29 (3/5) | 4,4-di-Me | H |
| 5-methyl-3-(trifluoromethyl)pyrazol-1-yl | X¹ | G-1 | J-29 (3/5) | 4,4-di-Me | H |
| 5-chloro-3-(trifluoromethyl)pyrazol-1-yl | X¹ | G-1 | J-29 (3/5) | 4,4-di-Me | H |
| 5-bromo-3-(trifluoromethyl)pyrazol-1-yl | X¹ | G-1 | J-29 (3/5) | 4,4-di-Me | H |
| 5-ethyl-3-(trifluoromethyl)pyrazol-1-yl | X¹ | G-1 | J-29 (3/5) | 4,4-di-Me | H |
| 3,5-bis-(trifluoromethyl)pyrazol-1-yl | X¹ | G-1 | J-29 (3/5) | 4,4-di-Me | H |
| 1-methyl-3-(trifluoromethyl)pyrazol-5-yl | X¹ | G-1 | J-29 (3/5) | 4,4-di-Me | H |
| 1-methyl-4-(trifluoromethyl)imidazol-2-yl | X¹ | G-1 | J-29 (3/5) | 4,4-di-Me | H |
| 2,5-dichlorophenyl | X¹ | G-2 | J-1 (2/4) | — | H |
| 2-chloro-5-(trifluoromethyl)phenyl | X¹ | G-2 | J-1 (2/4) | — | H |
| 2,5-dimethylphenyl | X¹ | G-2 | J-1 (2/4) | — | H |
| 2-methyl-5-(trifluoromethyl)phenyl | X¹ | G-2 | J-1 (2/4) | — | H |
| 3,5-dimethylpyrazol-1-yl | X¹ | G-2 | J-1 (2/4) | — | H |
| 5-methyl-3-(trifluoromethyl)pyrazol-1-yl | X¹ | G-2 | J-1 (2/4) | — | H |
| 5-chloro-3-(trifluoromethyl)pyrazol-1-yl | X¹ | G-2 | J-1 (2/4) | — | H |
| 5-bromo-3-(trifluoromethyl)pyrazol-1-yl | X¹ | G-2 | J-1 (2/4) | — | H |
| 5-ethyl-3-(trifluoromethyl)pyrazol-1-yl | X¹ | G-2 | J-1 (2/4) | — | H |
| 3,5-bis-(trifluoromethyl)pyrazol-1-yl | X¹ | G-2 | J-1 (2/4) | — | H |
| 1-methyl-3-(trifluoromethyl)pyrazol-5-yl | X¹ | G-2 | J-1 (2/4) | — | H |
| 1-methyl-4-(trifluoromethyl)imidazol-2-yl | X¹ | G-2 | J-1 (2/4) | — | H |
| 2,5-dichlorophenyl | X¹ | G-2 | J-2 (2/4) | — | H |
| 2-chloro-5-(trifluoromethyl)phenyl | X¹ | G-2 | J-2 (2/4) | — | H |
| 2,5-dimethylphenyl | X¹ | G-2 | J-2 (2/4) | — | H |
| 2-methyl-5-(trifluoromethyl)phenyl | X¹ | G-2 | J-2 (2/4) | — | H |

TABLE 4*-continued

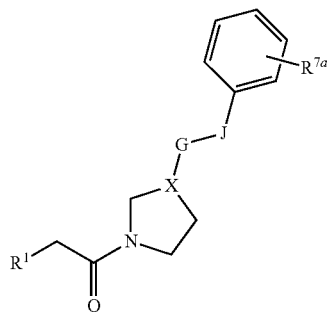

| R¹ | X | G  | J * | (R⁵)_y | R^{7a} |
|---|---|---|---|---|---|
| 3,5-dimethylpyrazol-1-yl | X¹ | G-2 | J-2 (2/4) | — | H |
| 5-methyl-3-(trifluoromethyl)pyrazol-1-yl | X¹ | G-2 | J-2 (2/4) | — | H |
| 5-chloro-3-(trifluoromethyl)pyrazol-1-yl | X¹ | G-2 | J-2 (2/4) | — | H |
| 5-bromo-3-(trifluoromethyl)pyrazol-1-yl | X¹ | G-2 | J-2 (2/4) | — | H |
| 5-ethyl-3-(trifluoromethyl)pyrazol-1-yl | X¹ | G-2 | J-2 (2/4) | — | H |
| 3,5-bis-(trifluoromethyl)pyrazol-1-yl | X¹ | G-2 | J-2 (2/4) | — | H |
| 1-methyl-3-(trifluoromethyl)pyrazol-5-yl | X¹ | G-2 | J-2 (2/4) | — | H |
| 1-methyl-4-(trifluoromethyl)imidazol-2-yl | X¹ | G-2 | J-2 (2/4) | — | H |
| 2,5-dichlorophenyl | X¹ | G-2 | J-3 (2/4) | 1-Me | H |
| 2-chloro-5-(trifluoromethyl)phenyl | X¹ | G-2 | J-3 (2/4) | 1-Me | H |
| 2,5-dimethylphenyl | X¹ | G-2 | J-3 (2/4) | 1-Me | H |
| 2-methyl-5-(trifluoromethyl)phenyl | X¹ | G-2 | J-3 (2/4) | 1-Me | H |
| 3,5-dimethylpyrazol-1-yl | X¹ | G-2 | J-3 (2/4) | 1-Me | H |
| 5-methyl-3-(trifluoromethyl)pyrazol-1-yl | X¹ | G-2 | J-3 (2/4) | 1-Me | H |
| 5-chloro-1-(trifluoromethyl)pyrazol-1-yl | X¹ | G-2 | J-3 (2/4) | 1-Me | H |
| 5-bromo-3-(trifluoromethyl)pyrazol-1-yl | X¹ | G-2 | J-3 (2/4) | 1-Me | H |
| 5-ethyl-3-(trifluoromethyl)pyrazol-1-yl | X¹ | G-2 | J-3 (2/4) | 1-Me | H |
| 3,5-bis-(trifluoromethyl)pyrazol-1-yl | X¹ | G-2 | J-3 (2/4) | 1-Me | H |
| 1-methyl-3-(trifluoromethyl)pyrazol-5-yl | X¹ | G-2 | J-3 (2/4) | 1-Me | H |
| 1-methyl-4-(trifluoromethyl)imidazol-2-yl | X¹ | G-2 | J-3 (2/4) | 1-Me | H |
| 2,5-dichlorophenyl | X¹ | G-2 | J-4 (2/5) | — | H |
| 2-chloro-5-(trifluoromethyl)phenyl | X¹ | G-2 | J-4 (2/5) | — | H |
| 2,5-dimethylphenyl | X¹ | G-2 | J-4 (2/5) | — | H |
| 2-methyl-5-(trifluoromethyl)phenyl | X¹ | G-2 | J-4 (2/5) | — | H |
| 3,5-dimethylpyrazol-1-yl | X¹ | G-2 | J-4 (2/5) | — | H |
| 5-methyl-3-(trifluoromethyl)pyrazol-1-yl | X¹ | G-2 | J-4 (2/5) | — | H |
| 5-chloro-3-(trifluoromethyl)pyrazol-1-yl | X¹ | G-2 | J-4 (2/5) | — | H |
| 5-bromo-3-(trifluoromethyl)pyrazol-1-yl | X¹ | G-2 | J-4 (2/5) | — | H |
| 5-ethyl-3-(trifluoromethyl)pyrazol-1-yl | X¹ | G-2 | J-4 (2/5) | — | H |
| 3,5-bis-(trifluoromethyl)pyrazol-1-yl | X¹ | G-2 | J-4 (2/5) | — | H |
| 1-methyl-3-(trifluoromethyl)pyrazol-5-yl | X¹ | G-2 | J-4 (2/5) | — | H |
| 1-methyl-4-(trifluoromethyl)imidazol-2-yl | X¹ | G-2 | J-4 (2/5) | — | H |
| 2,5-dichlorophenyl | X¹ | G-2 | J-8 (5/3) | — | H |
| 2-chloro-5-(trifluoromethyl)phenyl | X¹ | G-2 | J-8 (5/3) | — | H |
| 2,5-dimethylphenyl | X¹ | G-2 | J-8 (5/3) | — | H |
| 2-methyl-5-(trifluoromethyl)phenyl | X¹ | G-2 | J-8 (5/3) | — | H |
| 3,5-dimethylpyrazol-1-yl | X¹ | G-2 | J-8 (5/3) | — | H |
| 5-methyl-3-(trifluoromethyl)pyrazol-1-yl | X¹ | G-2 | J-8 (5/3) | — | H |
| 5-chloro-3-(trifluoromethyl)pyrazol-1-yl | X¹ | G-2 | J-8 (5/3) | — | H |
| 5-bromo-3-(trifluoromethyl)pyrazol-1-yl | X¹ | G-2 | J-8 (5/3) | — | H |
| 5-ethyl-3-(trifluoromethyl)pyrazol-1-yl | X¹ | G-2 | J-8 (5/3) | — | H |
| 3,5-bis-(trifluoromethyl)pyrazol-1-yl | X¹ | G-2 | J-8 (5/3) | — | H |
| 1-methyl-3-(trifluoromethyl)pyrazol-5-yl | X¹ | G-2 | J-8 (5/3) | — | H |
| 1-methyl-4-(trifluoromethyl)imidazol-2-yl | X¹ | G-2 | J-8 (5/3) | — | H |
| 2,5-dichlorophenyl | X¹ | G-2 | J-9 (5/3) | — | H |
| 2-chloro-5-(trifluoromethyl)phenyl | X¹ | G-2 | J-9 (5/3) | — | H |
| 2,5-dimethylphenyl | X¹ | G-2 | J-9 (5/3) | — | H |
| 2-methyl-5-(trifluoromethyl)phenyl | X¹ | G-2 | J-9 (5/3) | — | H |
| 3,5-dimethylpyrazol-1-yl | X¹ | G-2 | J-9 (5/3) | — | H |
| 5-methyl-3-(trifluoromethyl)pyrazol-1-yl | X¹ | G-2 | J-9 (5/3) | — | H |
| 5-chloro-3-(trifluoromethyl)pyrazol-1-yl | X¹ | G-2 | J-9 (5/3) | — | H |
| 5-bromo-3-(trifluoromethyl)pyrazol-1-yl | X¹ | G-2 | J-9 (5/3) | — | H |
| 5-ethyl-3-(trifluoromethyl)pyrazol-1-yl | X¹ | G-2 | J-9 (5/3) | — | H |
| 3,5-bis-(trifluoromethyl)pyrazol-1-yl | X¹ | G-2 | J-9 (5/3) | — | H |
| 1-methyl-3-(trifluoromethyl)pyrazol-5-yl | X¹ | G-2 | J-9 (5/3) | — | H |
| 1-methyl-4-(trifluoromethyl)imidazol-2-yl | X¹ | G-2 | J-9 (5/3) | — | H |
| 2,5-dichlorophenyl | X¹ | G-2 | J-11 (3/5) | — | H |
| 2-chloro-5-(trifluoromethyl)phenyl | X¹ | G-2 | J-11 (3/5) | — | H |
| 2,5-dimethylphenyl | X¹ | G-2 | J-11 (3/5) | — | H |
| 2-methyl-5-(trifluoromethyl)phenyl | X¹ | G-2 | J-11 (3/5) | — | H |
| 3,5-dimethylpyrazol-1-yl | X¹ | G-2 | J-11 (3/5) | — | H |
| 5-methyl-3-(trifluoromethyl)pyrazol-1-yl | X¹ | G-2 | J-11 (3/5) | — | H |

TABLE 4*-continued

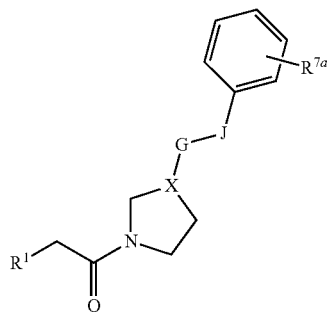

| R¹ | X | G  | J * | (R⁵)ᵧ | R⁷ᵃ |
|---|---|---|---|---|---|
| 5-chloro-3-(trifluoromethyl)pyrazol-1-yl | X¹ | G-2 | J-11 (3/5) | — | H |
| 5-bromo-3-(trifluoromethyl)pyrazol-1-yl | X¹ | G-2 | J-11 (3/5) | — | H |
| 5-ethyl-3-(trifluoromethyl)pyrazol-1-yl | X¹ | G-2 | J-11 (3/5) | — | H |
| 3,5-bis-(trifluoromethyl)pyrazol-1-yl | X¹ | G-2 | J-11 (3/5) | — | H |
| 1-methyl-3-(trifluoromethyl)pyrazol-5-yl | X¹ | G-2 | J-11 (3/5) | — | H |
| 1-methyl-4-(trifluoromethyl)imidazol-2-yl | X¹ | G-2 | J-11 (3/5) | — | H |
| 2,5-dichlorophenyl | X¹ | G-2 | J-12 (3/5) | — | H |
| 2-chloro-5-(trifluoromethyl)phenyl | X¹ | G-2 | J-12 (3/5) | — | H |
| 2,5-dimethylphenyl | X¹ | G-2 | J-12 (3/5) | — | H |
| 2-methyl-5-(trifluoromethyl)phenyl | X¹ | G-2 | J-12 (3/5) | — | H |
| 3,5-dimethylpyrazol-1-yl | X¹ | G-2 | J-12 (3/5) | — | H |
| 5-methyl-3-(trifluoromethyl)pyrazol-1-yl | X¹ | G-2 | J-12 (3/5) | — | H |
| 5-chloro-3-(trifluoromethyl)pyrazol-1-yl | X¹ | G-2 | J-12 (3/5) | — | H |
| 5-bromo-3-(trifluoromethyl)pyrazol-1-yl | X¹ | G-2 | J-12 (3/5) | — | H |
| 5-ethyl-3-(trifluoromethyl)pyrazol-1-yl | X¹ | G-2 | J-12 (3/5) | — | H |
| 3,5-bis-(trifluoromethyl)pyrazol-1-yl | X¹ | G-2 | J-12 (3/5) | — | H |
| 1-methyl-3-(trifluoromethyl)pyrazol-5-yl | X¹ | G-2 | J-12 (3/5) | — | H |
| 1-methyl-4-(trifluoromethyl)imidazol-2-yl | X¹ | G-2 | J-12 (3/5) | — | H |
| 2,5-dichlorophenyl | X¹ | G-2 | J-12 (3/5) | 1-Me | H |
| 2-chloro-5-(trifluoromethyl)phenyl | X¹ | G-2 | J-12 (3/5) | 1-Me | H |
| 2,5-dimethylphenyl | X¹ | G-2 | J-12 (3/5) | 1-Me | H |
| 2-methyl-5-(trifluoromethyl)phenyl | X¹ | G-2 | J-12 (3/5) | 1-Me | H |
| 3,5-dimethylpyrazol-1-yl | X¹ | G-2 | J-12 (3/5) | 1-Me | H |
| 5-methyl-3-(trifluoromethyl)pyrazol-1-yl | X¹ | G-2 | J-12 (3/5) | 1-Me | H |
| 5-chloro-3-(trifluoromethyl)pyrazol-1-yl | X¹ | G-2 | J-12 (3/5) | 1-Me | H |
| 5-bromo-3-(trifluoromethyl)pyrazol-1-yl | X¹ | G-2 | J-12 (3/5) | 1-Me | H |
| 5-ethyl-3-(trifluoromethyl)pyrazol-1-yl | X¹ | G-2 | J-12 (3/5) | 1-Me | H |
| 3,5-bis-(trifluoromethyl)pyrazol-1-yl | X¹ | G-2 | J-12 (3/5) | 1-Me | H |
| 1-methyl-3-(trifluoromethyl)pyrazol-5-yl | X¹ | G-2 | J-12 (3/5) | 1-Me | H |
| 1-methyl-4-(trifluoromethyl)imidazol-2-yl | X¹ | G-2 | J-12 (3/5) | 1-Me | H |
| 2,5-dichlorophenyl | X¹ | G-2 | J-14 (3/5) | — | H |
| 2-chloro-5-(trifluoromethyl)phenyl | X¹ | G-2 | J-14 (3/5) | — | H |
| 2,5-dimethylphenyl | X¹ | G-2 | J-14 (3/5) | — | H |
| 2-methyl-5-(trifluoromethyl)phenyl | X¹ | G-2 | J-14 (3/5) | — | H |
| 3,5-dimethylpyrazol-1-yl | X¹ | G-2 | J-14 (3/5) | — | H |
| 5-methyl-3-(trifluoromethyl)pyrazol-1-yl | X¹ | G-2 | J-14 (3/5) | — | H |
| 5-chloro-3-(trifluoromethyl)pyrazol-1-yl | X¹ | G-2 | J-14 (3/5) | — | H |
| 5-bromo-3-(trifluoromethyl)pyrazol-1-yl | X¹ | G-2 | J-14 (3/5) | — | H |
| 5-ethyl-3-(trifluoromethyl)pyrazol-1-yl | X¹ | G-2 | J-14 (3/5) | — | H |
| 3,5-bis-(trifluoromethyl)pyrazol-1-yl | X¹ | G-2 | J-14 (3/5) | — | H |
| 1-methyl-3-(trifluoromethyl)pyrazol-5-yl | X¹ | G-2 | J-14 (3/5) | — | H |
| 1-methyl-4-(trifluoromethyl)imidazol-2-yl | X¹ | G-2 | J-14 (3/5) | — | H |
| 2,5-dichlorophenyl | X¹ | G-2 | J-15 (2/5) | — | H |
| 2-chloro-5-(trifluoromethyl)phenyl | X¹ | G-2 | J-15 (2/5) | — | H |
| 2,5-dimethylphenyl | X¹ | G-2 | J-15 (2/5) | — | H |
| 2-methyl-5-(trifluoromethyl)phenyl | X¹ | G-2 | J-15 (2/5) | — | H |
| 3,5-dimethylpyrazol-1-yl | X¹ | G-2 | J-15 (2/5) | — | H |
| 5-methyl-3-(trifluoromethyl)pyrazol-1-yl | X¹ | G-2 | J-15 (2/5) | — | H |
| 5-chloro-3-(trifluoromethyl)pyrazol-1-yl | X¹ | G-2 | J-15 (2/5) | — | H |
| 5-bromo-3-(trifluoromethyl)pyrazol-1-yl | X¹ | G-2 | J-15 (2/5) | — | H |
| 5-ethyl-3-(trifluoromethyl)pyrazol-1-yl | X¹ | G-2 | J-15 (2/5) | — | H |
| 3,5-bis-(trifluoromethyl)pyrazol-1-yl | X¹ | G-2 | J-15 (2/5) | — | H |
| 1-methyl-3-(trifluoromethyl)pyrazol-5-yl | X¹ | G-2 | J-15 (2/5) | — | H |
| 1-methyl-4-(trifluoromethyl)imidazol-2-yl | X¹ | G-2 | J-15 (2/5) | — | H |
| 2,5-dichlorophenyl | X¹ | G-2 | J-16 (2/5) | — | H |
| 2-chloro-5-(trifluoromethyl)phenyl | X¹ | G-2 | J-16 (2/5) | — | H |
| 2,5-dimethylphenyl | X¹ | G-2 | J-16 (2/5) | — | H |
| 2-methyl-5-(trifluoromethyl)phenyl | X¹ | G-2 | J-16 (2/5) | — | H |
| 3,5-dimethylpyrazol-1-yl | X¹ | G-2 | J-16 (2/5) | — | H |
| 5-methyl-3-(trifluoromethyl)pyrazol-1-yl | X¹ | G-2 | J-16 (2/5) | — | H |
| 5-chloro-3-(trifluoromethyl)pyrazol-1-yl | X¹ | G-2 | J-16 (2/5) | — | H |
| 5-bromo-3-(trifluoromethyl)pyrazol-1-yl | X¹ | G-2 | J-16 (2/5) | — | H |

TABLE 4*-continued

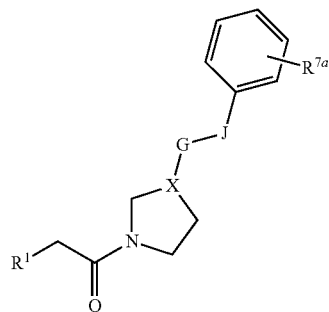

| R¹ | X | G  | J * | (R⁵)ᵧ | R⁷ᵃ |
|---|---|---|---|---|---|
| 5-ethyl-3-(trifluoromethyl)pyrazol-1-yl | X¹ | G-2 | J-16 (2/5) | — | H |
| 3,5-bis-(trifluoromethyl)pyrazol-1-yl | X¹ | G-2 | J-16 (2/5) | — | H |
| 1-methyl-3-(trifluoromethyl)pyrazol-5-yl | X¹ | G-2 | J-16 (2/5) | — | H |
| 1-methyl-4-(trifluoromethyl)imidazol-2-yl | X¹ | G-2 | J-16 (2/5) | — | H |
| 2,5-dichlorophenyl | X¹ | G-2 | J-22 (2/4) | — | H |
| 2-chloro-5-(trifluoromethyl)phenyl | X¹ | G-2 | J-22 (2/4) | — | H |
| 2,5-dimethylphenyl | X¹ | G-2 | J-22 (2/4) | — | H |
| 2-methyl-5-(trifluoromethyl)phenyl | X¹ | G-2 | J-22 (2/4) | — | H |
| 3,5-dimethylpyrazol-1-yl | X¹ | G-2 | J-22 (2/4) | — | H |
| 5-methyl-3-(trifluoromethyl)pyrazol-1-yl | X¹ | G-2 | J-22 (2/4) | — | H |
| 5-chloro-3-(trifluoromethyl)pyrazol-1-yl | X¹ | G-2 | J-22 (2/4) | — | H |
| 5-bromo-3-(trifluoromethyl)pyrazol-1-yl | X¹ | G-2 | J-22 (2/4) | — | H |
| 5-ethyl-3-(trifluoromethyl)pyrazol-1-yl | X¹ | G-2 | J-22 (2/4) | — | H |
| 3,5-bis-(trifluoromethyl)pyrazol-1-yl | X¹ | G-2 | J-22 (2/4) | — | H |
| 1-methyl-3-(trifluoromethyl)pyrazol-5-yl | X¹ | G-2 | J-22 (2/4) | — | H |
| 1-methyl-4-(trifluoromethyl)imidazol-2-yl | X¹ | G-2 | J-22 (2/4) | — | H |
| 2,5-dichlorophenyl | X¹ | G-2 | J-24 (2/4) | — | H |
| 2-chloro-5-(trifluoromethyl)phenyl | X¹ | G-2 | J-24 (2/4) | — | H |
| 2,5-dimethylphenyl | X¹ | G-2 | J-24 (2/4) | — | H |
| 2-methyl-5-(trifluoromethyl)phenyl | X¹ | G-2 | J-24 (2/4) | — | H |
| 3,5-dimethylpyrazol-1-yl | X¹ | G-2 | J-24 (2/4) | — | H |
| 5-methyl-3-(trifluoromethyl)pyrazol-1-yl | X¹ | G-2 | J-24 (2/4) | — | H |
| 5-chloro-3-(trifluoromethy)pyrazol-1-yl | X¹ | G-2 | J-24 (2/4) | — | H |
| 5-bromo-3-(trifluoromethyl)pyrazol-1-yl | X¹ | G-2 | J-24 (2/4) | — | H |
| 5-ethyl-3-(trifluoromethyl)pyrazol-1-yl | X¹ | G-2 | J-24 (2/4) | — | H |
| 3,5-bis-(trifluoromethyl)pyrazol-1-yl | X¹ | G-2 | J-24 (2/4) | — | H |
| 1-methyl-3-(trifluoromethyl)pyrazol-5-yl | X¹ | G-2 | J-24 (2/4) | — | H |
| 1-methyl-4-(trifluoromethyl)imidazol-2-yl | X¹ | G-2 | J-24 (2/4) | — | H |
| 2,5-dichlorophenyl | X¹ | G-2 | J-25 (2/4) | — | H |
| 2-chloro-5-(trifluoromethyl)phenyl | X¹ | G-2 | J-25 (2/4) | — | H |
| 2,5-dimethylphenyl | X¹ | G-2 | J-25 (2/4) | — | H |
| 2-methyl-5-(trifluoromethyl)phenyl | X¹ | G-2 | J-25 (2/4) | — | H |
| 3,5-dimethylpyrazol-1-yl | X¹ | G-2 | J-25 (2/4) | — | H |
| 5-methyl-3-(trifluoromethyl)pyrazol-1-yl | X¹ | G-2 | J-25 (2/4) | — | H |
| 5-chloro-3-(trifluoromethyl)pyrazol-1-yl | X¹ | G-2 | J-25 (2/4) | — | H |
| 5-bromo-3-(trifluoromethyl)pyrazol-1-yl | X¹ | G-2 | J-25 (2/4) | — | H |
| 5-ethyl-3-(trifluoromethyl)pyrazol-1-yl | X¹ | G-2 | J-25 (2/4) | — | H |
| 3,5-bis-(trifluoromethyl)pyrazol-1-yl | X¹ | G-2 | J-25 (2/4) | — | H |
| 1-methyl-3-(trifluoromethyl)pyrazol-5-yl | X¹ | G-2 | J-25 (2/4) | — | H |
| 1-methyl-4-(trifluoromethyl)imidazol-2-yl | X¹ | G-2 | J-25 (2/4) | — | H |
| 2,5-dichlorophenyl | X¹ | G-2 | J-26 (2/4) | — | H |
| 2-chloro-5-(trifluoromethyl)phenyl | X¹ | G-2 | J-26 (2/4) | — | H |
| 2,5-dimethylphenyl | X¹ | G-2 | J-26 (2/4) | — | H |
| 2-methyl-5-(trifluoromethyl)phenyl | X¹ | G-2 | J-26 (2/4) | — | H |
| 3,5-dimethylpyrazol-1-yl | X¹ | G-2 | J-26 (2/4) | — | H |
| 5-methyl-3-(trifluoromethyl)pyrazol-1-yl | X¹ | G-2 | J-26 (2/4) | — | H |
| 5-chloro-3-(trifluoromethyl)pyrazol-1-yl | X¹ | G-2 | J-26 (2/4) | — | H |
| 5-bromo-3-(trifluoromethyl)pyrazol-1-yl | X¹ | G-2 | J-26 (2/4) | — | H |
| 5-ethyl-3-(trifluoromethyl)pyrazol-1-yl | X¹ | G-2 | J-26 (2/4) | — | H |
| 3,5-bis-(trifluoromethyl)pyrazol-1-yl | X¹ | G-2 | J-26 (2/4) | — | H |
| 1-methyl-3-(trifluoromethyl)pyrazol-5-yl | X¹ | G-2 | J-26 (2/4) | — | H |
| 1-methyl-4-(trifluoromethyl)imidazol-2-yl | X¹ | G-2 | J-26 (2/4) | — | H |
| 2,5-dichlorophenyl | X¹ | G-2 | J-26 (2/4) | 1-Me | H |
| 2-chloro-5-(trifluoromethyl)phenyl | X¹ | G-2 | J-26 (2/4) | 1-Me | H |
| 2,5-dimethylphenyl | X¹ | G-2 | J-26 (2/4) | 1-Me | H |
| 2-methyl-5-(trifluoromethyl)phenyl | X¹ | G-2 | J-26 (2/4) | 1-Me | H |
| 3,5-dimethylpyrazol-1-yl | X¹ | G-2 | J-26 (2/4) | 1-Me | H |
| 5-methyl-3-(trifluoromethyl)pyrazol-1-yl | X¹ | G-2 | J-26 (2/4) | 1-Me | H |
| 5-chloro-3-(trifluoromethyl)pyrazol-1-yl | X¹ | G-2 | J-26 (2/4) | 1-Me | H |
| 5-bromo-3-(trifluoromethyl)pyrazol-1-yl | X¹ | G-2 | J-26 (2/4) | 1-Me | H |
| 5-ethyl-3-(trifluoromethy)pyrazol-1-yl | X¹ | G-2 | J-26 (2/4) | 1-Me | H |
| 3,5-bis-(trifluoromethyl)pyrazol-1-yl | X¹ | G-2 | J-26 (2/4) | 1-Me | H |

TABLE 4*-continued

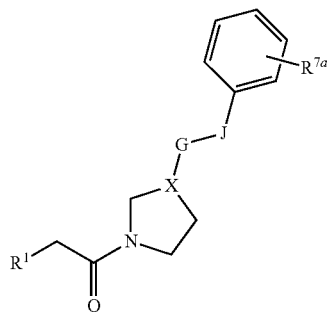

| R¹ | X | G  | J * | (R⁵)_y | R⁷ᵃ |
|---|---|---|---|---|---|
| 1-methyl-3-(trifluoromethyl)pyrazol-5-yl | X¹ | G-2 | J-26 (2/4) | 1-Me | H |
| 1-methyl-4-(trifluoromethyl)imidazol-2-yl | X¹ | G-2 | J-26 (2/4) | 1-Me | H |
| 2,5-dichlorophenyl | X¹ | G-2 | J-26 (2/5) | 1-Me | H |
| 2-chloro-5-(trifluoromethyl)phenyl | X¹ | G-2 | J-26 (2/5) | 1-Me | H |
| 2,5-dimethylphenyl | X¹ | G-2 | J-26 (2/5) | 1-Me | H |
| 2-methyl-5-(trifluoromethyl)phenyl | X¹ | G-2 | J-26 (2/5) | 1-Me | H |
| 3,5-dimethylpyrazol-1-yl | X¹ | G-2 | J-26 (2/5) | 1-Me | H |
| 5-methyl-3-(trifluoromethyl)pyrazol-1-yl | X¹ | G-2 | J-26 (2/5) | 1-Me | H |
| 5-chloro-3-(trifluoromethyl)pyrazol-1-yl | X¹ | G-2 | J-26 (2/5) | 1-Me | H |
| 5-bromo-3-(trifluoromethyl)pyrazol-1-yl | X¹ | G-2 | J-26 (2/5) | 1-Me | H |
| 5-ethyl-3-(trifluoromethyl)pyrazol-1-yl | X¹ | G-2 | J-26 (2/5) | 1-Me | H |
| 3,5-bis-(trifluoromethyl)pyrazol-1-yl | X¹ | G-2 | J-26 (2/5) | 1-Me | H |
| 1-methyl-3-(trifluoromethyl)pyrazol-5-yl | X¹ | G-2 | J-26 (2/5) | 1-Me | H |
| 1-methyl-4-(trifluoromethyl)imidazol-2-yl | X¹ | G-2 | J-26 (2/5) | 1-Me | H |
| 2,5-dichlorophenyl | X¹ | G-2 | J-28 (3/5) | — | H |
| 2-chloro-5-(trifluoromethyl)phenyl | X¹ | G-2 | J-28 (3/5) | — | H |
| 2,5-dimethylphenyl | X¹ | G-2 | J-28 (3/5) | — | H |
| 2-methyl-5-(trifluoromethyl)phenyl | X¹ | G-2 | J-28 (3/5) | — | H |
| 3,5-dimethylpyrazol-1-yl | X¹ | G-2 | J-28 (3/5) | — | H |
| 5-methyl-3-(trifluoromethyl)pyrazol-1-yl | X¹ | G-2 | J-28 (3/5) | — | H |
| 5-chloro-3-(trifluoromethyl)pyrazol-1-yl | X¹ | G-2 | J-28 (3/5) | — | H |
| 5-bromo-3-(trifluoromethyl)pyrazol-1-yl | X¹ | G-2 | J-28 (3/5) | — | H |
| 5-ethyl-3-(trifluoromethyl)pyrazol-1-yl | X¹ | G-2 | J-28 (3/5) | — | H |
| 3,5-bis-(trifluoromethyl)pyrazol-1-yl | X¹ | G-2 | J-28 (3/5) | — | H |
| 1-methyl-3-(trifluoromethyl)pyrazol-5-yl | X¹ | G-2 | J-28 (3/5) | — | H |
| 1-methyl-4-(trifluoromethyl)imidazol-2-yl | X¹ | G-2 | J-28 (3/5) | — | H |
| 2,5-dichlorophenyl | X¹ | G-2 | J-30 (3/5) | — | H |
| 2-chloro-5-(trifluoromethyl)phenyl | X¹ | G-2 | J-30 (3/5) | — | H |
| 2,5-dimethylphenyl | X¹ | G-2 | J-30 (3/5) | — | H |
| 2-methyl-5-(trifluoromethyl)phenyl | X¹ | G-2 | J-30 (3/5) | — | H |
| 3,5-dimethylpyrazol-1-yl | X¹ | G-2 | J-30 (3/5) | — | H |
| 5-methyl-3-(trifluoromethyl)pyrazol-1-yl | X¹ | G-2 | J-30 (3/5) | — | H |
| 5-chloro-3-(trifluoromethyl)pyrazol-1-yl | X¹ | G-2 | J-30 (3/5) | — | H |
| 5-bromo-3-(trifluoromethyl)pyrazol-1-yl | X¹ | G-2 | J-30 (3/5) | — | H |
| 5-ethyl-3-(trifluoromethyl)pyrazol-1-yl | X¹ | G-2 | J-30 (3/5) | — | H |
| 3,5-bis-(trifluoromethyl)pyrazol-1-yl | X¹ | G-2 | J-30 (3/5) | — | H |
| 1-methyl-3-(trifluoromethyl)pyrazol-5-yl | X¹ | G-2 | J-30 (3/5) | — | H |
| 1-methyl-4-(trifluoromethyl)imidazol-2-yl | X¹ | G-2 | J-30 (3/5) | — | H |
| 2,5-dichlorophenyl | X¹ | G-2 | J-30 (3/5) | 1-Me | H |
| 2-chloro-5-(trifluoromethyl)phenyl | X¹ | G-2 | J-30 (3/5) | 1-Me | H |
| 2,5-dimethylphenyl | X¹ | G-2 | J-30 (3/5) | 1-Me | H |
| 2-methyl-5-(trifluoromethyl)phenyl | X¹ | G-2 | J-30 (3,5) | 1-Me | H |
| 3,5-dimethylpyrazol-1-yl | X¹ | G-2 | J-30 (3/5) | 1-Me | H |
| 5-methyl-3-(trifluoromethyl)pyrazol-1-yl | X¹ | G-2 | J-30 (3/5) | 1-Me | H |
| 5-chloro-3-(trifluoromethyl)pyrazol-1-yl | X¹ | G-2 | J-30 (3/5) | 1-Me | H |
| 5-bromo-3-(trifluoromethyl)pyrazol-1-yl | X¹ | G-2 | J-30 (3/5) | 1-Me | H |
| 5-ethyl-3-(trifluoromethyl)pyrazol-1-yl | X¹ | G-2 | J-30 (3/5) | 1-Me | H |
| 3,5-bis-(trifluoromethyl)pyrazol-1-yl | X¹ | G-2 | J-30 (3/5) | 1-Me | H |
| 1-methyl-3-(trifluoromethyl)pyrazol-5-yl | X¹ | G-2 | J-30 (3/5) | 1-Me | H |
| 1-methyl-4-(trifluoromethyl)imidazol-2-yl | X¹ | G-2 | J-30 (3/5) | 1-Me | H |
| 2,5-dichlorophenyl | X¹ | G-2 | J-36 (3/5) | 1-Me | H |
| 2-chloro-5-(trifluoromethyl)phenyl | X¹ | G-2 | J-36 (3/5) | 1-Me | H |
| 2,5-dimethylphenyl | X¹ | G-2 | J-36 (3/5) | 1-Me | H |
| 2-methyl-5-(trifluoromethyl)phenyl | X¹ | G-2 | J-36 (3/5) | 1-Me | H |
| 3,5-dimethylpyrazol-1-yl | X¹ | G-2 | J-36 (3/5) | 1-Me | H |
| 5-methyl-3-(trifluoromethyl)pyrazol-1-yl | X¹ | G-2 | J-36 (3/5) | 1-Me | H |
| 5-chloro-3-(trifluoromethyl)pyrazol-1-yl | X¹ | G-2 | J-36 (3/5) | 1-Me | H |
| 5-bromo-3-(trifluoromethyl)pyrazol-1-yl | X¹ | G-2 | J-36 (3/5) | 1-Me | H |
| 5-ethyl-3-(trifluoromethyl)pyrazol-1-yl | X¹ | G-2 | J-36 (3/5) | 1-Me | H |
| 3,5-bis-(trifluoromethyl)pyrazol-1-yl | X¹ | G-2 | J-36 (3/5) | 1-Me | H |
| 1-methyl-3-(trifluoromethyl)pyrazol-5-yl | X¹ | G-2 | J-36 (3/5) | 1-Me | H |
| 1-methyl-4-(trifluoromethyl)imidazol-2-yl | X¹ | G-2 | J-36 (3/5) | 1-Me | H |

TABLE 4*-continued

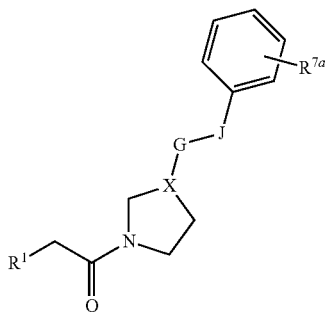

| R¹ | X | G  | J * | (R⁵)_y | R⁷ᵃ |
|---|---|---|---|---|---|
| 2,5-dichlorophenyl | X¹ | G-2 | J-37 (2/5) | — | H |
| 2-chloro-5-(trifluoromethyl)phenyl | X¹ | G-2 | J-37 (2/5) | — | H |
| 2,5-dimethylphenyl | X¹ | G-2 | J-37 (2/5) | — | H |
| 2-methyl-5-(trifluoromethyl)phenyl | X¹ | G-2 | J-37 (2/5) | — | H |
| 3,5-dimethylpyrazol-1-yl | X¹ | G-2 | J-37 (2/5) | — | H |
| 5-methyl-3-(trifluoromethyl)pyrazol-1-yl | X¹ | G-2 | J-37 (2/5) | — | H |
| 5-chloro-3-(trifluoromethyl)pyrazol-1-yl | X¹ | G-2 | J-37 (2/5) | — | H |
| 5-bromo-3-(trifluoromethyl)pyrazol-1-yl | X¹ | G-2 | J-37 (2/5) | — | H |
| 5-ethyl-3-(trifluoromethyl)pyrazol-1-yl | X¹ | G-2 | J-37 (2/5) | — | H |
| 3,5-bis-(trifluoromethyl)pyrazol-1-yl | X¹ | G-2 | J-37 (2/5) | — | H |
| 1-methyl-3-(trifluoromethyl)pyrazol-5-yl | X¹ | G-2 | J-37 (2/5) | — | H |
| 1-methyl-4-(trifluoromethyl)imidazol-2-yl | X¹ | G-2 | J-37 (2/5) | — | H |
| 2,5-dichlorophenyl | X¹ | G-2 | J-38 (2/5) | — | H |
| 2-chloro-5-(trifluoromethyl)phenyl | X¹ | G-2 | J-38 (2/5) | — | H |
| 2,5-dimethylphenyl | X¹ | G-2 | J-38 (2/5) | — | H |
| 2-methyl-5-(trifluoromethyl)phenyl | X¹ | G-2 | J-38 (2/5) | — | H |
| 3,5-dimethylpyrazol-1-yl | X¹ | G-2 | J-38 (2/5) | — | H |
| 5-methyl-3-(trifluoromethyl)pyrazol-1-yl | X¹ | G-2 | J-38 (2/5) | — | H |
| 5-chloro-3-(trifluoromethyl)pyrazol-1-yl | X¹ | G-2 | J-38 (2/5) | — | H |
| 5-bromo-3-(trifluoromethyl)pyrazol-1-yl | X¹ | G-2 | J-38 (2/5) | — | H |
| 5-ethyl-3-(trifluoromethyl)pyrazol-1-yl | X¹ | G-2 | J-38 (2/5) | — | H |
| 3,5-bis-(trifluoromethyl)pyrazol-1-yl | X¹ | G-2 | J-38 (2/5) | — | H |
| 1-methyl-3-(trifluoromethyl)pyrazol-5-yl | X¹ | G-2 | J-38 (2/5) | — | H |
| 1-methyl-4-(trifluoromethyl)imidazol-2-yl | X¹ | G-2 | J-38 (2/5) | — | H |
| 2,5-dichlorophenyl | X¹ | G-2 | J-39 (3/5) | — | H |
| 2-chloro-5-(trifluoromethyl)phenyl | X¹ | G-2 | J-39 (3/5) | — | H |
| 2,5-dimethylphenyl | X¹ | G-2 | J-39 (3/5) | — | H |
| 2-methyl-5-(trifluoromethyl)phenyl | X¹ | G-2 | J-39 (3/5) | — | H |
| 3,5-dimethylpyrazol-1-yl | X¹ | G-2 | J-39 (3/5) | — | H |
| 5-methyl-3-(trifluoromethyl)pyrazol-1-yl | X¹ | G-2 | J-39 (3/5) | — | H |
| 5-chloro-3-(trifluoromethyl)pyrazol-1-yl | X¹ | G-2 | J-39 (3/5) | — | H |
| 5-bromo-3-(trifluoromethyl)pyrazol-1-yl | X¹ | G-2 | J-39 (3/5) | — | H |
| 5-ethyl-3-(trifluoromethy)pyrazol-1-yl | X¹ | G-2 | J-39 (3/5) | — | H |
| 3,5-bis-(trifluoromethyl)pyrazol-1-yl | X¹ | G-2 | J-39 (3/5) | — | H |
| 1-methyl-3-(trifluoromethyl)pyrazol-5-yl | X¹ | G-2 | J-39 (3/5) | — | H |
| 1-methyl-4-(trifluoromethyl)imidazol-2-yl | X¹ | G-2 | J-39 (3/5) | — | H |
| 2,5-dichlorophenyl | X¹ | G-2 | J-40 (3/5) | — | H |
| 2-chloro-5-(trifluoromethyl)phenyl | X¹ | G-2 | J-40 (3/5) | — | H |
| 2,5-dimethylphenyl | X¹ | G-2 | J-40 (3/5) | — | H |
| 2-methyl-5-(trifluoromethyl)phenyl | X¹ | G-2 | J-40 (3/5) | — | H |
| 3,5-dimethylpyrazol-1-yl | X¹ | G-2 | J-40 (3/5) | — | H |
| 5-methyl-3-(trifluoromethyl)pyrazol-1-yl | X¹ | G-2 | J-40 (3/5) | — | H |
| 5-chloro-3-(trifluoromethyl)pyrazol-1-yl | X¹ | G-2 | J-40 (3/5) | — | H |
| 5-bromo-3-(trifluoromethyl)pyrazol-1-yl | X¹ | G-2 | J-40 (3/5) | — | H |
| 5-ethyl-3-(trifluoromethyl)pyrazol-1-yl | X¹ | G-2 | J-40 (3/5) | — | H |
| 3,5-bis-(trifluoromethyl)pyrazol-1-yl | X¹ | G-2 | J-40 (3/5) | — | H |
| 1-methyl-3-(trifluoromethyl)pyrazol-5-yl | X¹ | G-2 | J-40 (3/5) | — | H |
| 1-methyl-4-(trifluoromethyl)imidazol-2-yl | X¹ | G-2 | J-40 (3/5) | — | H |
| 2,5-dichlorophenyl | X¹ | G-2 | J-69 (1/3) | — | H |
| 2-chloro-5-(trifluoromethyl)phenyl | X¹ | G-2 | J-69 (1/3) | — | H |
| 2,5-dimethylphenyl | X¹ | G-2 | J-69 (1/3) | — | H |
| 2-methyl-5-(trifluoromethyl)phenyl | X¹ | G-2 | J-69 (1/3) | — | H |
| 3,5-dimethylpyrazol-1-yl | X¹ | G-2 | J-69 (1/3) | — | H |
| 5-methyl-3-(trifluoromethyl)pyrazol-1-yl | X¹ | G-2 | J-69 (1/3) | — | H |
| 5-chloro-3-(trifluoromethyl)pyrazol-1-yl | X¹ | G-2 | J-69 (1/3) | — | H |
| 5-bromo-3-(trifluoromethyl)pyrazol-1-yl | X¹ | G-2 | J-69 (1/3) | — | H |
| 5-ethyl-3-(trifluoromethyl)pyrazol-1-yl | X¹ | G-2 | J-69 (1/3) | — | H |
| 3,5-bis-(trifluoromethyl)pyrazol-1-yl | X¹ | G-2 | J-69 (1/3) | — | H |
| 1-methyl-3-(trifluoromethyl)pyrazol-5-yl | X¹ | G-2 | J-69 (1/3) | — | H |
| 1-methyl-4-(tritiuoromethyl)imidazol-2-yl | X¹ | G-2 | J-69 (1/3) | — | H |
| 2,5-dichlorophenyl | X¹ | G-2 | J-69 (1/4) | — | H |
| 2-chloro-5-(trifluoromethyl)phenyl | X¹ | G-2 | J-69 (1/4) | — | H |

TABLE 4*-continued

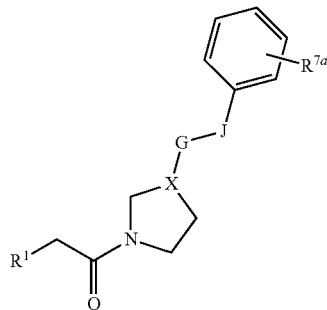

| R¹ | X | G  | J * | (R⁵)ᵧ | R⁷ᵃ |
|---|---|---|---|---|---|
| 2,5-dimethylphenyl | X¹ | G-2 | J-69 (1/4) | — | H |
| 2-methyl-5-(trifluoromethyl)phenyl | X¹ | G-2 | J-69 (1/4) | — | H |
| 3,5-dimethylpyrazol-1-yl | X¹ | G-2 | J-69 (1/4) | — | H |
| 5-methyl-3-(trifluoromethyl)pyrazol-1-yl | X¹ | G-2 | J-69 (1/4) | — | H |
| 5-chloro-3-(trifluoromethyl)pyrazol-1-yl | X¹ | G-2 | J-69 (1/4) | — | H |
| 5-bromo-3-(trifluoromethyl)pyrazol-1-yl | X¹ | G-2 | J-69 (1/4) | — | H |
| 5-ethyl-3-(trifluoromethyl)pyrazol-1-yl | X¹ | G-2 | J-69 (1/4) | — | H |
| 3,5-bis-(trifluoromethyl)pyrazol-1-yl | X¹ | G-2 | J-69 (1/4) | — | H |
| 1-methyl-3-(trifluoromethyl)pyrazol-5-yl | X¹ | G-2 | J-69 (1/4) | — | H |
| 1-methyl-4-(trifluoromethyl)imidazol-2-yl | X¹ | G-2 | J-69 (1/4) | — | H |
| 2,5-dichlorophenyl | X¹ | G-2 | J-11 (3/5) | — | 2-Me |
| 2-chloro-5-(trifluoromethyl)phenyl | X¹ | G-2 | J-11 (3/5) | — | 2-Me |
| 2,5-dimethylphenyl | X¹ | G-2 | J-11 (3/5) | — | 2-Me |
| 2-methyl-5-(trifluoromethyl)phenyl | X¹ | G-2 | J-11 (3/5) | — | 2-Me |
| 3,5-dimethylpyrazol-1-yl | X¹ | G-2 | J-11 (3/5) | — | 2-Me |
| 5-methyl-3-4 trifluoromethyl)pyrazol-1-yl | X¹ | G-2 | J-11 (3/5) | — | 2-Me |
| 5-chloro-3-(trifluoromethyl)pyrazol-1-yl | X¹ | G-2 | J-11 (3/5) | — | 2-Me |
| 5-bromo-3-(trifluoromethyl)pyrazol-1-yl | X¹ | G-2 | J-11 (3/5) | — | 2-Me |
| 5-ethyl-3-(trifluoromethyl)pyrazol-1-yl | X¹ | G-2 | J-11 (3/5) | — | 2-Me |
| 3,5-bis-(trifluoromethyl)pyrazol-1-yl | X¹ | G-2 | J-11 (3/5) | — | 2-Me |
| 1-methyl-3-(trifluoromethyl)pyrazol-5-yl | X¹ | G-2 | J-11 (3/5) | — | 2-Me |
| 1-methyl-4-(trifluoromethyl)imidazol-2-yl | X¹ | G-2 | J-11 (3/5) | — | 2-Me |
| 2,5-dichlorophenyl | X¹ | G-2 | J-11 (3/5) | — | 3-Me |
| 2-chloro-5-(trifluoromethyl)phenyl | X¹ | G-2 | J-11 (3/5) | — | 3-Me |
| 2,5-dimethylphenyl | X¹ | G-2 | J-11 (3/5) | — | 3-Me |
| 2-methyl-5-(trifluoromethyl)phenyl | X¹ | G-2 | J-11 (3/5) | — | 3-Me |
| 3,5-dimethylpyrazol-1-yl | X¹ | G-2 | J-11 (3/5) | — | 3-Me |
| 5-methyl-3-(trifluoromethyl)pyrazol-1-yl | X¹ | G-2 | J-11 (3/5) | — | 3-Me |
| 5-chloro-3-(trifluoromethyl)pyrazol-1-yl | X¹ | G-2 | J-11 (3/5) | — | 3-Me |
| 5-bromo-3-(trifluoromethyl)pyrazol-1-yl | X¹ | G-2 | J-11 (3/5) | — | 3-Me |
| 5-ethyl-3-(trifluoromethyl)pyrazol-1-yl | X¹ | G-2 | J-11 (3/5) | — | 3-Me |
| 3,5-bis-(trifluoromethyl)pyrazol-1-yl | X¹ | G-2 | J-11 (3/5) | — | 3-Me |
| 1-methyl-3-(trifluoromethyl)pyrazol-5-yl | X¹ | G-2 | J-11 (3/5) | — | 3-Me |
| 1-methyl-4-(trifluoromethyl)imidazol-2-yl | X¹ | G-2 | J-11 (3/5) | — | 3-Me |
| 2,5-dichlorophenyl | X¹ | G-2 | J-11 (3/5) | — | 4-Me |
| 2-chloro-5-(trifluoromethyl)phenyl | X¹ | G-2 | J-11 (3/5) | — | 4-Me |
| 2,5-dimethylphenyl | X¹ | G-2 | J-11 (3/5) | — | 4-Me |
| 2-methyl-5-(trifluoromethyl)phenyl | X¹ | G-2 | J-11 (3/5) | — | 4-Me |
| 3,5-dimethylpyrazol-1-yl | X¹ | G-2 | J-11 (3/5) | — | 4-Me |
| 5-methyl-3-(trifluoromethyl)pyrazol-1-yl | X¹ | G-2 | J-11 (3/5) | — | 4-Me |
| 5-chloro-3-(trifluoromethyl)pyrazol-1-yl | X¹ | G-2 | J-11 (3/5) | — | 4-Me |
| 5-bromo-3-(trifluoromethyl)pyrazol-1-yl | X¹ | G-2 | J-11 (3/5) | — | 4-Me |
| 5-ethyl-3-(trifluoromethyl)pyrazol-1-yl | X¹ | G-2 | J-11 (3/5) | — | 4-Me |
| 3,5-bis-(trifluoromethyl)pyrazol-1-yl | X¹ | G-2 | J-11 (3/5) | — | 4-Me |
| 1-methyl-3-(trifluoromethyl)pyrazol-5-yl | X¹ | G-2 | J-11 (3/5) | — | 4-Me |
| 1-methyl-4-(trifluoromethyl)imidazol-2-yl | X¹ | G-2 | J-11 (3/5) | — | 4-Me |
| 2,5-dichlorophenyl | X¹ | G-2 | J-11 (3/5) | — | 2-Cl |
| 2-chloro-5-(trifluoromethyl)phenyl | X¹ | G-2 | J-11 (3/5) | — | 2-Cl |
| 2,5-dimethylphenyl | X¹ | G-2 | J-11 (3/5) | — | 2-Cl |
| 2-methyl-5-(trifluoroethyl)phenyl | X¹ | G-2 | J-11 (3/5) | — | 2-Cl |
| 3,5-dimethylpyrazol-1-yl | X¹ | G-2 | J-11 (3/5) | — | 2-Cl |
| 5-methyl-3-(trifluoromethyl)pyrazol-1-yl | X¹ | G-2 | J-11 (3/5) | — | 2-Cl |
| 5-chloro-3-(trifluoromethyl)pyrazol-1-yl | X¹ | G-2 | J-11 (3/5) | — | 2-Cl |
| 5-bromo-3-(trifluoromethyl)pyrazol-1-yl | X¹ | G-2 | J-11 (3/5) | — | 2-Cl |
| 5-ethyl-3-(trifluoromethyl)pyrazol-1-yl | X¹ | G-2 | J-11 (3/5) | — | 2-Cl |
| 3,5-bis-(trifluoromethyl)pyrazol-1-yl | X¹ | G-2 | J-11 (3/5) | — | 2-Cl |
| 1-methyl-3-(trifluoromethyl)pyrazol-5-yl | X¹ | G-2 | J-11 (3/5) | — | 2-Cl |
| 1-methyl-4-(trifluoromethyl)imidazol-2-yl | X¹ | G-2 | J-11 (3/5) | — | 2-Cl |
| 2,5-dichlorophenyl | X¹ | G-2 | J-11 (3/5) | — | 4-Cl |
| 2-chloro-5-(trifluoromethyl)phenyl | X¹ | G-2 | J-11 (3/5) | — | 4-Cl |
| 2,5-dimethylphenyl | X¹ | G-2 | J-11 (3/5) | — | 4-Cl |
| 2-methyl-5-(trifluoromethyl)phenyl | X¹ | G-2 | J-11 (3/5) | — | 4-Cl |

TABLE 4*-continued

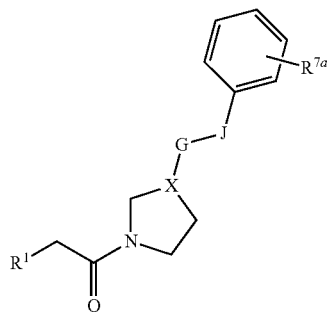

| R¹ | X | G  | J * | (R⁵)ᵧ | R⁷ᵃ |
|---|---|---|---|---|---|
| 3,5-dimethylpyrazol-1-yl | X¹ | G-2 | J-11 (3/5) | — | 4-Cl |
| 5-methyl-3-(trifluoromethyl)pyrazol-1-yl | X¹ | G-2 | J-11 (3/5) | — | 4-Cl |
| 5-chloro-3-(trifluoromethyl)pyrazol-1-yl | X¹ | G-2 | J-11 (3/5) | — | 4-Cl |
| 5-bromo-3-(trifluoromethyl)pyrazol-1-yl | X¹ | G-2 | J-11 (3/5) | — | 4-Cl |
| 5-ethyl-3-(trifluoromethyl)pyrazol-1-yl | X¹ | G-2 | J-11 (3/5) | — | 4-Cl |
| 3,5-bis-(trifluoromethyl)pyrazol-1-yl | X¹ | G-2 | J-11 (3/5) | — | 4-Cl |
| 1-methyl-3-(trifluoromethyl)pyrazol-5-yl | X¹ | G-2 | J-11 (3/5) | — | 4-Cl |
| 1-methyl-4-(trifluoromethyl)imidazol-2-yl | X¹ | G-2 | J-11 (3/5) | — | 4-Cl |
| 2,5-dichlorophenyl | X¹ | G-2 | J-29 (3/5) | — | 2-Me |
| 2-chloro-5-(trifluoromethyl)phenyl | X¹ | G-2 | J-29 (3/5) | — | 2-Me |
| 2,5-dimethylphenyl | X¹ | G-2 | J-29 (3/5) | — | 2-Me |
| 2-methyl-5-(trifluoromethyl)phenyl | X¹ | G-2 | J-29 (3/5) | — | 2-Me |
| 3,5-dimethylpyrazol-1-yl | X¹ | G-2 | J-29 (3/5) | — | 2-Me |
| 5-methyl-3-(trifluoromethyl)pyrazol-1-yl | X¹ | G-2 | J-29 (3/5) | — | 2-Me |
| 5-chloro-3-(trifluoromethyl)pyrazol-1-yl | X¹ | G-2 | J-29 (3/5) | — | 2-Me |
| 5-bromo-3-(trifluoromethyl)pyrazol-1-yl | X¹ | G-2 | J-29 (3/5) | — | 2-Me |
| 5-ethyl-3-(trifluoromethyl)pyrazol-1-yl | X¹ | G-2 | J-29 (3/5) | — | 2-Me |
| 3,5-bis-(trifluoromethyl)pyrazol-1-yl | X¹ | G-2 | J-29 (3/5) | — | 2-Me |
| 1-methyl-3-(trifluoromethyl)pyrazol-5-yl | X¹ | G-2 | J-29 (3/5) | — | 2-Me |
| 1-methyl-4-(trifluoromethyl)imidazol-2-yl | X¹ | G-2 | J-29 (3/5) | — | 2-Me |
| 2,5-dichlorophenyl | X¹ | G-2 | J-29 (3/5) | — | 3-Me |
| 2-chloro-5-(trifluoromethyl)phenyl | X¹ | G-2 | J-29 (3/5) | — | 3-Me |
| 2,5-dimethylphenyl | X¹ | G-2 | J-29 (3/5) | — | 3-Me |
| 2-methyl-5-(trifluoromethyl)phenyl | X¹ | G-2 | J-29 (3/5) | — | 3-Me |
| 3,5-dimethylpyrazol-1-yl | X¹ | G-2 | J-29 (3/5) | — | 3-Me |
| 5-methyl-3-(trifluoromethyl)pyrazol-1-yl | X¹ | G-2 | J-29 (3/5) | — | 3-Me |
| 5-chloro-3-(trifluoromethyl)pyrazol-1-yl | X¹ | G-2 | J-29 (3/5) | — | 3-Me |
| 5-bromo-3-(trifluoromethyl)pyrazol-1-yl | X¹ | G-2 | J-29 (3/5) | — | 3-Me |
| 5-ethyl-3-(trifluoromethyl)pyrazol-1-yl | X¹ | G-2 | J-29 (3/5) | — | 3-Me |
| 3,5-bis-(trifluoromethyl)pyrazol-1-yl | X¹ | G-2 | J-29 (3/5) | — | 3-Me |
| 1-methyl-3-(trifluoromethyl)pyrazol-5-yl | X¹ | G-2 | J-29 (3/5) | — | 3-Me |
| 1-methyl-4-(trifluoromethyl)imidazol-2-yl | X¹ | G-2 | J-29 (3/5) | — | 3-Me |
| 2,5-dichlorophenyl | X¹ | G-2 | J-29 (3/5) | — | 4-Me |
| 2-chloro-5-(trifluoromethyl)phenyl | X¹ | G-2 | J-29 (3/5) | — | 4-Me |
| 2,5-dimethylphenyl | X¹ | G-2 | J-29 (3/5) | — | 4-Me |
| 2-methyl-5-(trifluoromethyl)phenyl | X¹ | G-2 | J-29 (3/5) | — | 4-Me |
| 3,5-dimethylpyrazol-1-yl | X¹ | G-2 | J-29 (3/5) | — | 4-Me |
| 5-methyl-3-(trifluoromethyl)pyrazol-1-yl | X¹ | G-2 | J-29 (3/5) | — | 4-Me |
| 5-chloro-3-(trifluoromethyl)pyrazol-1-yl | X¹ | G-2 | J-29 (3/5) | — | 4-Me |
| 5-bromo-3-(trifluoromethyl)pyrazol-1-yl | X¹ | G-2 | J-29 (3/5) | — | 4-Me |
| 5-ethyl-3-(trifluoromethyl)pyrazol-1-yl | X¹ | G-2 | J-29 (3/5) | — | 4-Me |
| 3,5-bis-(trifluoromethyl)pyrazol-1-yl | X¹ | G-2 | J-29 (3/5) | — | 4-Me |
| 1-methyl-3-(trifluoromethyl)pyrazol-5-yl | X¹ | G-2 | J-29 (3/5) | — | 4-Me |
| 1-methyl-4-(trifluoromethyl)imidazol-2-yl | X¹ | G-2 | J-29 (3/5) | — | 4-Me |
| 2,5-dichlorophenyl | X¹ | G-2 | J-29 (3/5) | — | 2-Cl |
| 2-chloro-5-(trifluoromethyl)phenyl | X¹ | G-2 | J-29 (3/5) | — | 2-Cl |
| 2,5-dimethylphenyl | X¹ | G-2 | J-29 (3/5) | — | 2-Cl |
| 2-methyl-5-(trifluoromethyl)phenyl | X¹ | G-2 | J-29 (3/5) | — | 2-Cl |
| 3,5-dimethylpyrazol-1-yl | X¹ | G-2 | J-29 (3/5) | — | 2-Cl |
| 5-methyl-3-(trifluoromethyl)pyrazol-1-yl | X¹ | G-2 | J-29 (3/5) | — | 2-Cl |
| 5-chloro-3-(trifluoromethyl)pyrazol-1-yl | X¹ | G-2 | J-29 (3/5) | — | 2-Cl |
| 5-bromo-3-(trifluoromethyl)pyrazol-1-yl | X¹ | G-2 | J-29 (3/5) | — | 2-Cl |
| 5-ethyl-3-(trifluoromethyl)pyrazol-1-yl | X¹ | G-2 | J-29 (3/5) | — | 2-Cl |
| 3,5-bis-(trifluoromethyl)pyrazol-1-yl | X¹ | G-2 | J-29 (3/5) | — | 2-Cl |
| 1-methyl-3-(trifluoromethyl)pyrazol-5-yl | X¹ | G-2 | J-29 (3/5) | — | 2-Cl |
| 1-methyl-4-(trifluoromethyl)imidazol-2-yl | X¹ | G-2 | J-29 (3/5) | — | 2-Cl |
| 2,5-dichlorophenyl | X¹ | G-2 | J-29 (3/5) | — | 4-Cl |
| 2-chloro-5-(trifluoromethyl)phenyl | X¹ | G-2 | J-29 (3/5) | — | 4-Cl |
| 2,5-dimethylphenyl | X¹ | G-2 | J-29 (3/5) | — | 4-Cl |
| 2-methyl-5-(trifluoromethyl)phenyl | X¹ | G-2 | J-29 (3/5) | — | 4-Cl |
| 3,5-dimethylpyrazol-1-yl | X¹ | G-2 | J-29 (3/5) | — | 4-Cl |
| 5-methyl-3-(trifluoromethyl)pyrazol-1-yl | X¹ | G-2 | J-29 (3/5) | — | 4-Cl |

TABLE 4*-continued

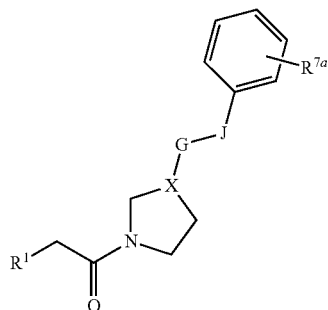

| R¹ | X | G  | J * | (R⁵)ᵧ | R⁷ᵃ |
|---|---|---|---|---|---|
| 5-chloro-3-(trifluoromethyl)pyrazol-1-yl | X¹ | G-2 | J-29 (3/5) | — | 4-Cl |
| 5-bromo-3-(trifluoromethyl)pyrazol-1-yl | X¹ | G-2 | J-29 (3/5) | — | 4-Cl |
| 5-ethyl-3-(trifluoromethyl)pyrazol-1-yl | X¹ | G-2 | J-29 (3/5) | — | 4-Cl |
| 3,5-bis-(trifluoromethyl)pyrazol-1-yl | X¹ | G-2 | J-29 (3/5) | — | 4-Cl |
| 1-methyl-3-(trifluoromethyl)pyrazol-5-yl | X¹ | G-2 | J-29 (3/5) | — | 4-Cl |
| 1-methyl-4-(trifluoromethyl)imidazol-2-yl | X¹ | G-2 | J-29 (3/5) | — | 4-Cl |
| 2,5-dichlorophenyl | X¹ | G-2 | J-29 (3/5) | 5-Me | H |
| 2-chloro-5-(trifluoromethyl)phenyl | X¹ | G-2 | J-29 (3/5) | 5-Me | H |
| 2,5-dimethylphenyl | X¹ | G-2 | J-29 (3/5) | 5-Me | H |
| 2-methyl-5-(trifluoromethyl)phenyl | X¹ | G-2 | J-29 (3/5) | 5-Me | H |
| 3,5-dimethylpyrazol-1-yl | X¹ | G-2 | J-29 (3/5) | 5-Me | H |
| 5-methyl-3-(trifluoromethyl)pyrazol-1-yl | X¹ | G-2 | J-29 (3/5) | 5-Me | H |
| 5-chloro-3-(trifluoromethyl)pyrazol-1-yl | X¹ | G-2 | J-29 (3/5) | 5-Me | H |
| 5-bromo-3-(trifluormethyl)pyrazol-1-yl | X¹ | G-2 | J-29 (3/5) | 5-Me | H |
| 5-ethyl-3-(trifluoromethyl)pyrazol-1-yl | X¹ | G-2 | J-29 (3/5) | 5-Me | H |
| 3,5-bis-(trifluoromethyl)pyrazol-1-yl | X¹ | G-2 | J-29 (3/5) | 5-Me | H |
| 1-methyl-3-(trifluoromethyl)pyrazol-5-yl | X¹ | G-2 | J-29 (3/5) | 5-Me | H |
| 1-methyl-4-(trifluoromethyl)imidazol-2-yl | X¹ | G-2 | J-29 (3/5) | 5-Me | H |
| 2,5-dichlorophenyl | X¹ | G-2 | J-29 (3/5) | 4-Me | H |
| 2-chloro-5-(trifluoromethyl)phenyl | X¹ | G-2 | J-29 (3/5) | 4-Me | H |
| 2,5-dimethylphenyl | X¹ | G-2 | J-29 (3/5) | 4-Me | H |
| 2-methyl-5-(trifluoromethyl)phenyl | X¹ | G-2 | J-29 (3/5) | 4-Me | H |
| 3,5-dimethylpyrazol-1-yl | X¹ | G-2 | J-29 (3/5) | 4-Me | H |
| 5-methyl-3-(trifluoromethyl)pyrazol-1-yl | X¹ | G-2 | J-29 (3/5) | 4-Me | H |
| 5-chloro-3-(trifluoromethyl)pyrazol-1-yl | X¹ | G-2 | J-29 (3/5) | 4-Me | H |
| 5-bromo-3-(trifluoromethyl)pyrazol-1-yl | X¹ | G-2 | J-29 (3/5) | 4-Me | H |
| 5-ethyl-3-(trifluoromethyl)pyrazol-1-yl | X¹ | G-2 | J-29 (3/5) | 4-Me | H |
| 3,5-bis-(trifluoromethyl)pyrazol-1-yl | X¹ | G-2 | J-29 (3/5) | 4-Me | H |
| 1-methyl-3-(trifluoromethyl)pyrazol-5-yl | X¹ | G-2 | J-29 (3/5) | 4-Me | H |
| 1-methyl-4-(trifluoromethyl)imidazol-2-yl | X¹ | G-2 | J-29 (3/5) | 4-Me | H |
| 2,5-dichlorophenyl | X¹ | G-2 | J-29 (3/5) | 4,4-di-Me | H |
| 2-chloro-5-(trifluoromethyl)phenyl | X¹ | G-2 | J-29 (3/5) | 4,4-di-Me | H |
| 2,5-dimethylphenyl | X¹ | G-2 | J-29 (3/5) | 4,4-di-Me | H |
| 2-methyl-5-(trifluoromethyl)phenyl | X¹ | G-2 | J-29 (3/5) | 4,4-di-Me | H |
| 3,5-dimethylpyrazol-1-yl | X¹ | G-2 | J-29 (3/5) | 4,4-di-Me | H |
| 5-methyl-3-(trifluoromethyl)pyrazol-1-yl | X¹ | G-2 | J-29 (3/5) | 4,4-di-Me | H |
| 5-chloro-3-(trifluoromethyl)pyrazol-1-yl | X¹ | G-2 | J-29 (3/5) | 4,4-di-Me | H |
| 5-bromo-3-(trifluoromethyl)pyrazol-1-yl | X¹ | G-2 | J-29 (3/5) | 4,4-di-Me | H |
| 5-ethyl-3-(trifluoromethyl)pyrazol-1-yl | X¹ | G-2 | J-29 (3/5) | 4,4-di-Me | H |
| 3,5-bis-(trifluoromethyl)pyrazol-1-yl | X¹ | G-2 | J-29 (3/5) | 4,4-di-Me | H |
| 1-methyl-3-(trifluoromethyl)pyrazol-5-yl | X¹ | G-2 | J-29 (3/5) | 4,4-di-Me | H |
| 1-methyl-4-(trifluoromethyl)imidazol-2-yl | X¹ | G-2 | J-29 (3/5) | 4,4-di-Me | H |
| 2,5-dichlorophenyl | X² | G-1 | J-1 (2/4) | — | H |
| 2-chloro-5-(trifluoromethyl)phenyl | X² | G-1 | J-1 (2/4) | — | H |
| 2,5-dimethylphenyl | X² | G-1 | J-1 (2/4) | — | H |
| 2-methyl-5-(trifluoromethyl)phenyl | X² | G-1 | J-1 (2/4) | — | H |
| 3,5-dimethylpyrazol-1-yl | X² | G-1 | J-1 (2/4) | — | H |
| 5-methyl-3-(trifluoromethyl)pyrazol-1-yl | X² | G-1 | J-1 (2/4) | — | H |
| 5-chloro-3-(trifluoromethyl)pyrazol-1-yl | X² | G-1 | J-1 (2/4) | — | H |
| 5-bromo-3-(trifluoromethyl)pyrazol-1-yl | X² | G-1 | J-1 (2/4) | — | H |
| 5-ethyl-3-(trifluoromethyl)pyrazol-1-yl | X² | G-1 | J-1 (2/4) | — | H |
| 3,5-bis-(trifluoromethyl)pyrazol-1-yl | X² | G-1 | J-1 (2/4) | — | H |
| 1-methyl-3-(trifluoromethyl)pyrazol-5-yl | X² | G-1 | J-1 (2/4) | — | H |
| 1-methyl-4-(trifluoromethyl)imidazol-2-yl | X² | G-1 | J-1 (2/4) | — | H |
| 2,5-dichlorophenyl | X² | G-1 | J-2 (2/4) | — | H |
| 2-chloro-5-(trifluoromethyl)phenyl | X² | G-1 | J-2 (2/4) | — | H |
| 2,5-dimethylphenyl | X² | G-1 | J-2 (2/4) | — | H |
| 2-methyl-5-(trifluoromethyl)phenyl | X² | G-1 | J-2 (2/4) | — | H |
| 3,5-dimethylpyrazol-1-yl | X² | G-1 | J-2 (2/4) | — | H |
| 5-methyl-3-(trifluoromethyl)pyrazol-1-yl | X² | G-1 | J-2 (2/4) | — | H |
| 5-chloro-3-(trifluoromethyl)pyrazol-1-yl | X² | G-1 | J-2 (2/4) | — | H |
| 5-bromo-3-(trifluoromethyl)pyrazol-1-yl | X² | G-1 | J-2 (2/4) | — | H |

TABLE 4*-continued

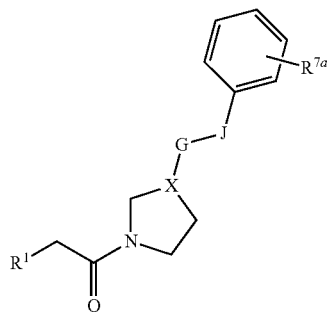

| R¹ | X | G  | J * | (R⁵)ᵧ | R⁷ᵃ |
|---|---|---|---|---|---|
| 5-ethyl-3-(trifluoromethyl)pyrazol-1-yl | X² | G-1 | J-2 (2/4) | — | H |
| 3,5-bis-(trifluoromethyl)pyrazol-1-yl | X² | G-1 | J-2 (2/4) | — | H |
| 1-methyl-3-(trifluoromethyl)pyrazol-5-yl | X² | G-1 | J-2 (2/4) | — | H |
| 1-methyl-4-(trifluoromethyl)imidazol-2-yl | X² | G-1 | J-2 (2/4) | — | H |
| 2,5-dichlorophenyl | X² | G-1 | J-3 (2/4) | 1-Me | H |
| 2-chloro-5-(trifluoromethyl)phenyl | X² | G-1 | J-3 (2/4) | 1-Me | H |
| 2,5-dimethylphenyl | X² | G-1 | J-3 (2/4) | 1-Me | H |
| 2-methyl-5-(trifluoromethyl)phenyl | X² | G-1 | J-3 (2/4) | 1-Me | H |
| 3,5-dimethylpyrazol-1-yl | X² | G-1 | J-3 (2/4) | 1-Me | H |
| 5-methyl-3-(trifluoromethyl)pyrazol-1-yl | X² | G-1 | J-3 (2/4) | 1-Me | H |
| 5-chloro-3-(trifluoromethyl)pyrazol-1-yl | X² | G-1 | J-3 (2/4) | 1-Me | H |
| 5-bromo-3-(trifluoromethyl)pyrazol-1-yl | X² | G-1 | J-3 (2/4) | 1-Me | H |
| 5-ethyl-3-(trifluoromethyl)pyrazol-1-yl | X² | G-1 | J-3 (2/4) | 1-Me | H |
| 3,5-bis-(trifluoromethyl)pyrazol-1-yl | X² | G-1 | J-3 (2/4) | 1-Me | H |
| 1-methyl-3-(trifluoromethyl)pyrazol-5-yl | X² | G-1 | J-3 (2/4) | 1-Me | H |
| 1-methyl-4-(trifluoromethyl)imidazol-2-yl | X² | G-1 | J-3 (2/4) | 1-Me | H |
| 2,5-dichlorophenyl | X² | G-1 | J-4 (2/5) | — | H |
| 2-chloro-5-(trifluoromethyl)phenyl | X² | G-1 | J-4 (2/5) | — | H |
| 2,5-dimethylphenyl | X² | G-1 | J-4 (2/5) | — | H |
| 2-methyl-5-(trifluoromethyl)phenyl | X² | G-1 | J-4 (2/5) | — | H |
| 3,5-dimethylpyrazol-1-yl | X² | G-1 | J-4 (2/5) | — | H |
| 5-methyl-3-(trifluoromethyl)pyrazol-1-yl | X² | G-1 | J-4 (2/5) | — | H |
| 5-chloro-3-(trifluoromethyHpyrazol-1-yl | X² | G-1 | J-4 (2/5) | — | H |
| 5-bromo-3-(trifluoromethyl)pyrazol-1-yl | X² | G-1 | J-4 (2/5) | — | H |
| 5-ethyl-3-(trifluoromethyl)pyrazol-1-yl | X² | G-1 | J-4 (2/5) | — | H |
| 3,5-bis-(trifluoromethyl)pyrazol-1-yl | X² | G-1 | J-4 (2/5) | — | H |
| 1-methyl-3-(trifluoromethyl)pyrazol-5-yl | X² | G-1 | J-4 (2/5) | — | H |
| 1-methyl-4-(trifluoromethyl)imidazol-2-yl | X² | G-1 | J-4 (2/5) | — | H |
| 2,5-dichlorophenyl | X² | G-1 | J-8 (5/3) | — | H |
| 2-chloro-5-(trifluoromethyl)phenyl | X² | G-1 | J-8 (5/3) | — | H |
| 2,5-dimethylphenyl | X² | G-1 | J-8 (5/3) | — | H |
| 2-methyl-5-(trifluoromethyl)phenyl | X² | G-1 | J-8 (5/3) | — | H |
| 3,5-dimethylpyrazol-1-yl | X² | G-1 | J-8 (5/3) | — | H |
| 5-methyl-3-(trifluoromethyl)pyrazol-1-yl | X² | G-1 | J-8 (5/3) | — | H |
| 5-chloro-3-(trifluoromethyl)pyrazol-1-yl | X² | G-1 | J-8 (5/3) | — | H |
| 5-bromo-3-(trifluoromethyltpyrazol-1-yl | X² | G-1 | J-8 (5/3) | — | H |
| 5-ethyl-3-(trifluoromethyl)pyrazol-1-yl | X² | G-1 | J-8 (5/3) | — | H |
| 3,5-bis-(trifluoromethyl)pyrazol-1-yl | X² | G-1 | J-8 (5/3) | — | H |
| 1-methyl-3-(trifluoromethyl)pyrazol-5-yl | X² | G-1 | J-8 (5/3) | — | H |
| 1-methyl-4-(trifluoromethyl)imidazol-2-yl | X² | G-1 | J-8 (5/3) | — | H |
| 2,5-dichlorophenyl | X² | G-1 | J-9 (5/3) | — | H |
| 2-chloro-5-(trifluoromethyl)phenyl | X² | G-1 | J-9 (5/3) | — | H |
| 2,5-dimethylphenyl | X² | G-1 | J-9 (5/3) | — | H |
| 2-methyl-5-(trifluoromethyl)phenyl | X² | G-1 | J-9 (5/3) | — | H |
| 3,5-dimethylpyrazol-1-yl | X² | G-1 | J-9 (5/3) | — | H |
| 5-methyl-3-(trifluoromethyl)pyrazol-1-yl | X² | G-1 | J-9 (5/3) | — | H |
| 5-chloro-3-(trifluoromethyl)pyrazol-1-yl | X² | G-1 | J-9 (5/3) | — | H |
| 5-bromo-3-(trifluoromethyl)pyrazol-1-yl | X² | G-1 | J-9 (5/3) | — | H |
| 5-ethyl-3-(trifluoromethyl)pyrazol-1-yl | X² | G-1 | J-9 (5/3) | — | H |
| 3,5-bis-(trifluoroethyl)pyrazol-1-yl | X² | G-1 | J-9 (5/3) | — | H |
| 1-methyl-3-(trifluoromethyl)pyrazol-5-yl | X² | G-1 | J-9 (5/3) | — | H |
| 1-methyl-4-(trifluoromethyl)imidazol-2-yl | X² | G-1 | J-9 (5/3) | — | H |
| 2,5-dichlorophenyl | X² | G-1 | J-11 (3/5) | — | H |
| 2-chloro-5-(trifluoromethyl)phenyl | X² | G-1 | J-11 (3/5) | — | H |
| 2,5-dimethylphenyl | X² | G-1 | J-11 (3/5) | — | H |
| 2-methyl-5-(trifluoromethyl)phenyl | X² | G-1 | J-11 (3/5) | — | H |
| 3,5-dimethylpyrazol-1-yl | X² | G-1 | J-11 (3/5) | — | H |
| 5-methyl-3-(trifluoromethyl)pyrazol-1-yl | X² | G-1 | J-11 (3/5) | — | H |
| 5-chloro-3-(trinuoromethyl)pyrazol-1-yl | X² | G-1 | J-11 (3/5) | — | H |
| 5-bromo-3-(trifluoromethyl)pyrazol-1-yl | X² | G-1 | J-11 (3/5) | — | H |
| 5-ethyl-3-(trifluoromethyl)pyrazol-1-yl | X² | G-1 | J-11 (3/5) | — | H |
| 3,5-bis-(trifluoromethyl)pyrazol-1-yl | X² | G-1 | J-11 (3/5) | — | H |

TABLE 4*-continued

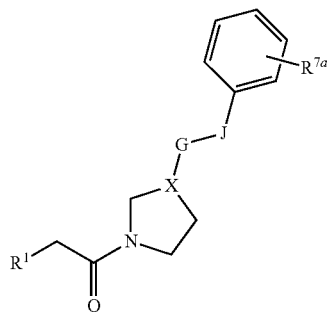

| R¹ | X | G  | J * | (R⁵)_y | R^{7a} |
|---|---|---|---|---|---|
| 1-methyl-3-(trifluoromethyl)pyrazol-5-yl | X² | G-1 | J-11 (3/5) | — | H |
| 1-methyl-4-(trifluoromethyl)imidazol-2-yl | X² | G-1 | J-11 (3/5) | — | H |
| 2,5-dichlorophenyl | X² | G-1 | J-12 (3/5) | — | H |
| 2-chloro-5-(trifluoromethyl)phenyl | X² | G-1 | J-12 (3/5) | — | H |
| 2,5-dimethylphenyl | X² | G-1 | J-12 (3/5) | — | H |
| 2-methyl-5-(trifluoromethyl)phenyl | X² | G-1 | J-12 (3/5) | — | H |
| 3,5-dimethylpyrazol-1-yl | X² | G-1 | J-12 (3/5) | — | H |
| 5-methyl-3-(trifluoromethyl)pyrazol-1-yl | X² | G-1 | J-12 (3/5) | — | H |
| 5-chloro-3-(trifluoromethyl)pyrazol-1-yl | X² | G-1 | J-12 (3/5) | — | H |
| 5-bromo-3-(trifluoromethyl)pyrazol-1-yl | X² | G-1 | J-12 (3/5) | — | H |
| 5-ethyl-3-(trifluoromethyl)pyrazol-1-yl | X² | G-1 | J-12 (3/5) | — | H |
| 3,5-bis-(trifluoromethyl)pyrazol-1-yl | X² | G-1 | J-12 (3/5) | — | H |
| 1-methyl-3-(trifluoromethyl)pyrazol-5-yl | X² | G-1 | J-12 (3/5) | — | H |
| 1-methyl-4-(trifluoromethyl)imidazol-2-yl | X² | G-1 | J-12 (3/5) | — | H |
| 2,5-dichlorophenyl | X² | G-1 | J-12 (3/5) | 1-Me | H |
| 2-chloro-5-(trifluoromethyl)phenyl | X² | G-1 | J-12 (3/5) | 1-Me | H |
| 2,5-dimethylphenyl | X² | G-1 | J-12 (3/5) | 1-Me | H |
| 2-methyl-5-(trifluoromethyl)phenyl | X² | G-1 | J-12 (3/5) | 1-Me | H |
| 3,5-dimethylpyrazol-1-yl | X² | G-1 | J-12 (3/5) | 1-Me | H |
| 5-methyl-3-(trifluoromethyl)pyrazol-1-yl | X² | G-1 | J-12 (3/5) | 1-Me | H |
| 5-chloro-3-(trifluoromethyl)pyrazol-1-yl | X² | G-1 | J-12 (3/5) | 1-Me | H |
| 5-bromo-3-(trifluoromethyl)pyrazol-1-yl | X² | G-1 | J-12 (3/5) | 1-Me | H |
| 5-ethyl-3-(trifluoromethyl)pyrazol-1-yl | X² | G-1 | J-12 (3/5) | 1-Me | H |
| 3,5-bis-(trifluoromethyl)pyrazol-1-yl | X² | G-1 | J-12 (3/5) | 1-Me | H |
| 1-methyl-3-(trifluoromethyl)pyrazol-5-yl | X² | G-1 | J-12 (3/5) | 1-Me | H |
| 1-methyl-4-(trifluoromethyl)imidazol-2-yl | X² | G-1 | J-12 (3/5) | 1-Me | H |
| 2,5-dichlorophenyl | X² | G-1 | J-14 (3/5) | — | H |
| 2-chloro-5-(trifluoromethyl)phenyl | X² | G-1 | J-14 (3/5) | — | H |
| 2,5-dimethylphenyl | X² | G-1 | J-14 (3/5) | — | H |
| 2-methyl-5-(trifluoromethyl)phenyl | X² | G-1 | J-14 (3/5) | — | H |
| 3,5-dimethylpyrazol-1-yl | X² | G-1 | J-14 (3/5) | — | H |
| 5-methyl-3-(trifluoromethyl)pyrazol-1-yl | X² | G-1 | J-14 (3/5) | — | H |
| 5-chloro-3-(trifluoromethyl)pyrazol-1-yl | X² | G-1 | J-14 (3/5) | — | H |
| 5-bromo-3-(trifluoromethyl)pyrazol-1-yl | X² | G-1 | J-14 (3/5) | — | H |
| 5-ethyl-3-(trifluoromethyl)pyrazol-1-yl | X² | G-1 | J-14 (3/5) | — | H |
| 3,5-bis-(trifluoromethyl)pyrazol-1-yl | X² | G-1 | J-14 (3/5) | — | H |
| 1-methyl-3-(trifluoromethyl)pyrazol-5-yl | X² | G-1 | J-14 (3/5) | — | H |
| 1-methyl-4-(trifluoromethyl)imidazol-2-yl | X² | G-1 | J-14 (3/5) | — | H |
| 2,5-dichlorophenyl | X² | G-1 | J-15 (2/5) | — | H |
| 2-chloro-5-(trifluoromethyl)phenyl | X² | G-1 | J-15 (2/5) | — | H |
| 2,5-dimethylphenyl | X² | G-1 | J-15 (2/5) | — | H |
| 2-methyl-5-(trifluoromethyl)phenyl | X² | G-1 | J-15 (2/5) | — | H |
| 3,5-dimethylpyrazol-1-yl | X² | G-1 | J-15 (2/5) | — | H |
| 5-methyl-3-(trifluoromethyl)pyrazol-1-yl | X² | G-1 | J-15 (2/5) | — | H |
| 5-chloro-3-(trifluoromethyl)pyrazol-1-yl | X² | G-1 | J-15 (2/5) | — | H |
| 5-bromo-3-(trifluoromethyl)pyrazol-1-yl | X² | G-1 | J-15 (2/5) | — | H |
| 5-ethyl-3-(trifluoromethyl)pyrazol-1-yl | X² | G-1 | J-15 (2/5) | — | H |
| 3,5-bis-(trifluoromethyl)pyrazol-1-yl | X² | G-1 | J-15 (2/5) | — | H |
| 1-methyl-3-(trifluoromethyl)pyrazol-5-yl | X² | G-1 | J-15 (2/5) | — | H |
| 1-methyl-4-(trifluoromethyl)imidazol-2-yl | X² | G-1 | J-15 (2/5) | — | H |
| 2,5-dichlorophenyl | X² | G-1 | J-16 (2/5) | — | H |
| 2-chloro-5-(trifluoromethyl)phenyl | X² | G-1 | J-16 (2/5) | — | H |
| 2,5-dimethylphenyl | X² | G-1 | J-16 (2/5) | — | H |
| 2-methyl-5-(trifluoromethyl)phenyl | X² | G-1 | J-16 (2/5) | — | H |
| 3,5-dimethylpyrazol-1-yl | X² | G-1 | J-16 (2/5) | — | H |
| 5-methyl-3-(trifluoromethyl)pyrazol-1-yl | X² | G-1 | J-16 (2/5) | — | H |
| 5-chloro-3-(trifluoromethyl)pyrazol-1-yl | X² | G-1 | J-16 (2/5) | — | H |
| 5-bromo-3-(trifluoromethyl)pyrazol-1-yl | X² | G-1 | J-16 (2/5) | — | H |
| 5-ethyl-3-(trifluoromethyl)pyrazol-1-yl | X² | G-1 | J-16 (2/5) | — | H |
| 3,5-bis-(trifluoromethyl)pyrazol-1-yl | X² | G-1 | J-16 (2/5) | — | H |
| 1-methyl-3-(trifluoromethyl)pyrazol-5-yl | X² | G-1 | J-16 (2/5) | — | H |
| 1-methyl-4-(trifluoromethyl)imidazol-2-yl | X² | G-1 | J-16 (2/5) | — | H |

TABLE 4*-continued

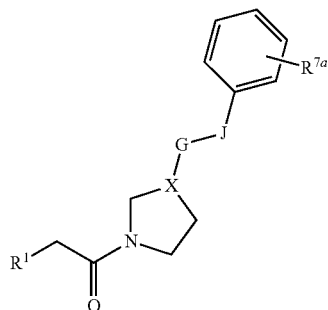

| R¹ | X | G  | J * | (R⁵)_y | R^{7a} |
|---|---|---|---|---|---|
| 2,5-dichlorophenyl | X² | G-1 | J-22 (2/4) | — | H |
| 2-chloro-5-(trifluoromethyl)phenyl | X² | G-1 | J-22 (2/4) | — | H |
| 2,5-dimethylphenyl | X² | G-1 | J-22 (2/4) | — | H |
| 2-methyl-5-(trifluoromethyl)phenyl | X² | G-1 | J-22 (2/4) | — | H |
| 3,5-dimethylpyrazol-1-yl | X² | G-1 | J-22 (2/4) | — | H |
| 5-methyl-3-(trifluoromethyl)pyrazol-1-yl | X² | G-1 | J-22 (2/4) | — | H |
| 5-chloro-3-(trifluoromethyl)pyrazol-1-yl | X² | G-1 | J-22 (2/4) | — | H |
| 5-bromo-3-(trifluoromethyl)pyrazol-1-yl | X² | G-1 | J-22 (2/4) | — | H |
| 5-ethyl-3-(trifluoromethyl)pyrazol-1-yl | X² | G-1 | J-22 (2/4) | — | H |
| 3,5-bis-(trifluoromethyl)pyrazol-1-yl | X² | G-1 | J-22 (2/4) | — | H |
| 1-methyl-3-(trifluoromethyl)pyrazol-5-yl | X² | G-1 | J-22 (2/4) | — | H |
| 1-methyl-4-(trifluoromethyl)imidazol-2-yl | X² | G-1 | J-22 (2/4) | — | H |
| 2,5-dichlorophenyl | X² | G-1 | J-24 (2/4) | — | H |
| 2-chloro-5-(trifluoromethyl)phenyl | X² | G-1 | J-24 (2/4) | — | H |
| 2,5-dimethylphenyl | X² | G-1 | J-24 (2/4) | — | H |
| 2-methyl-5-(trifluoromethyl)phenyl | X² | G-1 | J-24 (2/4) | — | H |
| 3,5-dimethylpyrazol-1-yl | X² | G-1 | J-24 (2/4) | — | H |
| 5-methyl-3-(trifluoromethyl)pyrazol-1-yl | X² | G-1 | J-24 (2/4) | — | H |
| 5-chloro-3-(trifluoromethyl)pyrazol-1-yl | X² | G-1 | J-24 (2/4) | — | H |
| 5-bromo-3-(trifluoromethyl)pyrazol-1-yl | X² | G-1 | J-24 (2/4) | — | H |
| 5-ethyl-3-(trifluoromethyl)pyrazol-1-yl | X² | G-1 | J-24 (2/4) | — | H |
| 3,5-bis-(trifluoromethyl)pyrazol-1-yl | X² | G-1 | J-24 (2/4) | — | H |
| 1-methyl-3-(trifluoromethyl)pyrazol-5-yl | X² | G-1 | J-24 (2/4) | — | H |
| 1-methyl-4-(trifluoromethyl)imidazol-2-yl | X² | G-1 | J-24 (2/4) | — | H |
| 2,5-dichlorophenyl | X² | G-1 | J-25 (2/4) | — | H |
| 2-chloro-5-(trifluoromethyl)phenyl | X² | G-1 | J-25 (2/4) | — | H |
| 2,5-dimethylphenyl | X² | G-1 | J-25 (2/4) | — | H |
| 2-methyl-5-(trifluoromethyl)phenyl | X² | G-1 | J-25 (2/4) | — | H |
| 3,5-dimethylpyrazol-1-yl | X² | G-1 | J-25 (2/4) | — | H |
| 5-methyl-3-(trifluoromethyl)pyrazol-1-yl | X² | G-1 | J-25 (2/4) | — | H |
| 5-chloro-3-(trifluoromethyl)pyrazol-1-yl | X² | G-1 | J-25 (2/4) | — | H |
| 5-bromo-3-(trifluoromethyl)pyrazol-1-yl | X² | G-1 | J-25 (2/4) | — | H |
| 5-ethyl-3-(trifluoromethyl)pyrazol-1-yl | X² | G-1 | J-25 (2/4) | — | H |
| 3,5-bis-(trifluoromethyl)pyrazol-1-yl | X² | G-1 | J-25 (2/4) | — | H |
| 1-methyl-3-(trifluoromethyl)pyrazol-5-yl | X² | G-1 | J-25 (2/4) | — | H |
| 1-methyl-4-(trifluoromethyl)imidazol-2-yl | X² | G-1 | J-25 (2/4) | — | H |
| 2,5-dichlorophenyl | X² | G-1 | J-26 (2/4) | — | H |
| 2-chloro-5-(trifluoromethyl)phenyl | X² | G-1 | J-26 (2/4) | — | H |
| 2,5-dimethylphenyl | X² | G-1 | J-26 (2/4) | — | H |
| 2-methyl-5-(trifluoromethyl)phenyl | X² | G-1 | J-26 (2/4) | — | H |
| 3,5-dimethylpyrazol-1-yl | X² | G-1 | J-26 (2/4) | — | H |
| 5-methyl-3-(trifluoromethyl)pyrazol-1-yl | X² | G-1 | J-26 (2/4) | — | H |
| 5-chloro-3-(trifluoromethy)pyrazol-1-yl | X² | G-1 | J-26 (2/4) | — | H |
| 5-bromo-3-(trifluoromethyl)pyrazol-1-yl | X² | G-1 | J-26 (2/4) | — | H |
| 5-ethyl-3-(trifluoromethyl)pyrazol-1-yl | X² | G-1 | J-26 (2/4) | — | H |
| 3,5-bis-(trifluoromethyl)pyrazol-1-yl | X² | G-1 | J-26 (2/4) | — | H |
| 1-methyl-3-(trifluoromethyl)pyrazol-5-yl | X² | G-1 | J-26 (2/4) | — | H |
| 1-methyl-4-(trifluoromethyl)imidazol-2-yl | X² | G-1 | J-26 (2/4) | — | H |
| 2,5-dichlorophenyl | X² | G-1 | J-26 (2/4) | 1-Me | H |
| 2-chloro-5-(trifluoromethyl)phenyl | X² | G-1 | J-26 (2/4) | 1-Me | H |
| 2,5-dimethylphenyl | X² | G-1 | J-26 (2/4) | 1-Me | H |
| 2-methyl-5-(trifluoromethyl)phenyl | X² | G-1 | J-26 (2/4) | 1-Me | H |
| 3,5-dimethylpyrazol-1-yl | X² | G-1 | J-26 (2/4) | 1-Me | H |
| 5-methyl-3-(trifluoromethyl)pyrazol-1-yl | X² | G-1 | J-26 (2/4) | 1-Me | H |
| 5-chloro-3-(trifluoromethyl)pyrazol-1-yl | X² | G-1 | J-26 (2/4) | 1-Me | H |
| 5-bromo-3-(trifluoromethyl)pyrazol-1-yl | X² | G-1 | J-26 (2/4) | 1-Me | H |
| 5-ethyl-3-(trifluoromethyl)pyrazol-1-yl | X² | G-1 | J-26 (2/4) | 1-Me | H |
| 3,5-bis-(trifluoromethy)pyrazol-1-yl | X² | G-1 | J-26 (2/4) | 1-Me | H |
| 1-methyl-3-(trifluoromethyl)pyrazol-5-yl | X² | G-1 | J-26 (2/4) | 1-Me | H |
| 1-methyl-4-(trifluoromethyl)imidazol-2-yl | X² | G-1 | J-26 (2/4) | 1-Me | H |
| 2,5-dichlorophenyl | X² | G-1 | J-26 (2/5) | 1-Me | H |
| 2-chloro-5-(trifluoromethyl)phenyl | X² | G-1 | J-26 (2/5) | 1-Me | H |

TABLE 4*-continued

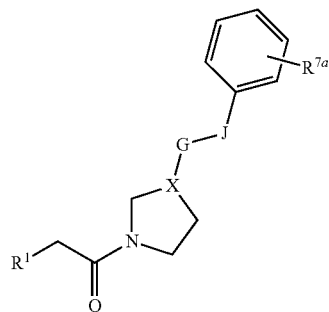

| R¹ | X | G | J* | (R⁵)ᵧ | R⁷ᵃ |
|---|---|---|---|---|---|
| 2,5-dimethylphenyl | X² | G-1 | J-26 (2/5) | 1-Me | H |
| 2-methyl-5-(trifluoromethyl)phenyl | X² | G-1 | J-26 (2/5) | 1-Me | H |
| 3,5-dimethylpyrazol-1-yl | X² | G-1 | J-26 (2/5) | 1-Me | H |
| 5-methyl-3-(trifluoromethyl)pyrazol-1-yl | X² | G-1 | J-26 (2/5) | 1-Me | H |
| 5-chloro-3-(trifluoromethyl)pyrazol-1-yl | X² | G-1 | J-26 (2/5) | 1-Me | H |
| 5-bromo-.-(trifluoromethyl)pyzol-1-yl | X² | G-1 | J-26 (2/5) | 1-Me | H |
| 5-ethyl-3-(trifluoromethyl)pyrazol-1-yl | X² | G-1 | J-26 (2/5) | 1-Me | H |
| 3,5-bis-(trifluoromethyl)pyrazol-1-yl | X² | G-1 | J-26 (2/5) | 1-Me | H |
| 1-methyl-3-(trifluoromethyl)pyrazol-5-yl | X² | G-1 | J-26 (2/5) | 1-Me | H |
| 1-methyl-4-(trifluoromethyl)imidazol-2-yl | X² | G-1 | J-26 (2/5) | 1-Me | H |
| 2,5-dichlorophenyl | X² | G-1 | J-28 (3/5) | — | H |
| 2-chloro-5-(trifluoromethyl)phenyl | X² | G-1 | J-28 (3/5) | — | H |
| 2,5-dimethylphenyl | X² | G-1 | J-28 (3/5) | — | H |
| 2-methyl-5-(trifluoromethyl)phenyl | X² | G-1 | J-28 (3/5) | — | H |
| 3,5-dimethylpyrazol-1-yl | X² | G-1 | J-28 (3/5) | — | H |
| 5-methyl-3-(trifluoromethyl)pyrazol-1-yl | X² | G-1 | J-28 (3/5) | — | H |
| 5-chloro-3-(trifluoromethyl)pyrazol-1-yl | X² | G-1 | J-28 (3/5) | — | H |
| 5-bromo-3-(trifluoromethyl)pyrazol-1-yl | X² | G-1 | J-28 (3/5) | — | H |
| 5-ethyl-3-(trifluoromethyl)pyrazol-1-yl | X² | G-1 | J-28 (3/5) | — | H |
| 3,5-bis-(trifluoromethyl)pyrazol-1-yl | X² | G-1 | J-28 (3/5) | — | H |
| 1-methyl-3-(trifluoromethyl)pyrazol-5-yl | X² | G-1 | J-28 (3/5) | — | H |
| 1-methyl-4-(trifluoromethyl)imidazol-2-yl | X² | G-1 | J-28 (3/5) | — | H |
| 2,5-dichlorophenyl | X² | G-1 | J-30 (3/5) | — | H |
| 2-chloro-5-(trifluoromethyl)phenyl | X² | G-1 | J-30 (3/5) | — | H |
| 2,5-dimethylphenyl | X² | G-1 | J-30 (3/5) | — | H |
| 2-methyl-5-(trifluoromethyl)phenyl | X² | G-1 | J-30 (3/5) | — | H |
| 3,5-dimethylpyrazol-1-yl | X² | G-1 | J-30 (3/5) | — | H |
| 5-methyl-3-(trifluoromethyl)pyrazol-1-yl | X² | G-1 | J-30 (3/5) | — | H |
| 5-chloro-3-(trifluoromethyl)pyrazol-1-yl | X² | G-1 | J-30 (3/5) | — | H |
| 5-bromo-3-(trifluoromethyl)pyrazol-1-yl | X² | G-1 | J-30 (3/5) | — | H |
| 5-ethyl-3-(trifluoromethyl)pyrazol-1-yl | X² | G-1 | J-30 (3/5) | — | H |
| 3,5-bis-(trifluoromethyl)pyrazol-1-yl | X² | G-1 | J-30 (3/5) | — | H |
| 1-methyl-3-(trifluoromethyl)pyrazol-5-yl | X² | G-1 | J-30 (3/5) | — | H |
| 1-methyl-4-(trifluoromethyl)imidazol-2-yl | X² | G-1 | J-30 (3/5) | — | H |
| 2,5-dichlorophenyl | X² | G-1 | J-30 (3/5) | 1-Me | H |
| 2-chloro-5-(trifluoromethyl)phenyl | X² | G-1 | J-30 (3/5) | 1-Me | H |
| 2,5-dimethylphenyl | X² | G-1 | J-30 (3/5) | 1-Me | H |
| 2-methyl-5-(trifluoromethyl)phenyl | X² | G-1 | J-30 (3/5) | 1-Me | H |
| 3,5-dimethylpyrazol-1-yl | X² | G-1 | J-30 (3/5) | 1-Me | H |
| 5-methyl-3-(trifluoromethyl)pyrazol-1-yl | X² | G-1 | J-30 (3/5) | 1-Me | H |
| 5-chloro-3-(trifluoromethyl)pyrazol-1-yl | X² | G-1 | J-30 (3/5) | 1-Me | H |
| 5-bromo-3-(trifluoromethyl)pyrazol-1-yl | X² | G-1 | J-30 (3/5) | 1-Me | H |
| 5-ethyl-3-(trifluoromethyl)pyrazol-1-yl | X² | G-1 | J-30 (3/5) | 1-Me | H |
| 3,5-bis-(trifluoromethyl)pyrazol-1-yl | X² | G-1 | J-30 (3/5) | 1-Me | H |
| 1-methyl-3-(trifluoromethyl)pyrazol-5-yl | X² | G-1 | J-30 (3/5) | 1-Me | H |
| 1-methyl-4-(trifluoromethyl)imidazol-2-yl | X² | G-1 | J-30 (3/5) | 1-Me | H |
| 2,5-dichlorophenyl | X² | G-1 | J-36 (3/5) | 1-Me | H |
| 2-chloro-5-(trifluoromethyl)phenyl | X² | G-1 | J-36 (3/5) | 1-Me | H |
| 2,5-dimethylphenyl | X² | G-1 | J-36 (3/5) | 1-Me | H |
| 2-methyl-5-(trifluoromethyl)phenyl | X² | G-1 | J-36 (3/5) | 1-Me | H |
| 3,5-dimethylpyrazol-1-yl | X² | G-1 | J-36 (3/5) | 1-Me | H |
| 5-methyl-3-(trifluoromethyl)pyrazol-1-yl | X² | G-1 | J-36 (3/5) | 1-Me | H |
| 5-chloro-3-(trifluoromethyl)pyrazol-1-yl | X² | G-1 | J-36 (3/5) | 1-Me | H |
| 5-bromo-3-(trifluoromethyl)pyrazol-1-yl | X² | G-1 | J-36 (3/5) | 1-Me | H |
| 5-ethyl-3-(trifluoromethyl)pyrazol-1-yl | X² | G-1 | J-36 (3/5) | 1-Me | H |
| 3,5-bis-(trifluoromethyl)pyrazol-1-yl | X² | G-1 | J-36 (3/5) | 1-Me | H |
| 1-methyl-3-(trifluoromethyl)pyrazol-5-yl | X² | G-1 | J-36 (3/5) | 1-Me | H |
| 1-methyl-4-(trifluoromethyl)imidazol-2-yl | X² | G-1 | J-36 (3/5) | 1-Me | H |
| 2,5-dichlorophenyl | X² | G-1 | J-37 (2/5) | — | H |
| 2-chloro-5-(trifluoromethyl)phenyl | X² | G-1 | J-37 (2/5) | — | H |
| 2,5-dimethylphenyl | X² | G-1 | J-37 (2/5) | — | H |
| 2-methyl-5-(trifluoromethyl)phenyl | X² | G-1 | J-37 (2/5) | — | H |

TABLE 4*-continued

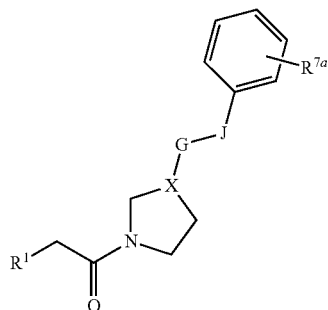

| R¹ | X | G  | J * | (R⁵)_y | R⁷ᵃ |
|---|---|---|---|---|---|
| 3,5-dimethylpyrazol-1-yl | X² | G-1 | J-37 (2/5) | — | H |
| 5-methyl-3-(trifluoromethyl)pyrazol-1-yl | X² | G-1 | J-37 (2/5) | — | H |
| 5-chloro-3-(trifluoromethyl)pyrazol-1-yl | X² | G-1 | J-37 (2/5) | — | H |
| 5-bromo-3-(trifluoromethyl)pyrazol-1-yl | X² | G-1 | J-37 (2/5) | — | H |
| 5-ethyl-3-(trifluoromethyl)pyrazol-1-yl | X² | G-1 | J-37 (2/5) | — | H |
| 3,5-bis-(trifluoromethyl)pyrazol-1-yl | X² | G-1 | J-37 (2/5) | — | H |
| 1-methyl-3-(trifluoromethyl)pyrazol-5-yl | X² | G-1 | J-37 (2/5) | — | H |
| 1-methyl-4-(trifluoromethyl)imidazol-2-yl | X² | G-1 | J-37 (2/5) | — | H |
| 2,5-dichlorophenyl | X² | G-1 | J-38 (2/5) | — | H |
| 2-chloro-5-(trifluoromethyl)phenyl | X² | G-1 | J-38 (2/5) | — | H |
| 2,5-dimethylphenyl | X² | G-1 | J-38 (2/5) | — | H |
| 2-methyl-5-(trifluoromethyl)phenyl | X² | G-1 | J-38 (2/5) | — | H |
| 3,5-dimethylpyrazol-1-yl | X² | G-1 | J-38 (2/5) | — | H |
| 5-methyl-3-(trifluoromethyl)pyrazol-1-yl | X² | G-1 | J-38 (2/5) | — | H |
| 5-chloro-3-(trifluoromethyl)pyrazol-1-yl | X² | G-1 | J-38 (2/5) | — | H |
| 5-bromo-3-(trifluoromethyl)pyrazol-1-yl | X² | G-1 | J-38 (2/5) | — | H |
| 5-ethyl-3-(trifluoromethyl)pyrazol-1-yl | X² | G-1 | J-38 (2/5) | — | H |
| 3,5-bis-(trifluoromethyl)pyrazol-1-yl | X² | G-1 | J-38 (2/5) | — | H |
| 1-methyl-3-(trifluoromethyl)pyrazol-5-yl | X² | G-1 | J-38 (2/5) | — | H |
| 1-methyl-4-(trifluoromethyl)imidazol-2-yl | X² | G-1 | J-38 (2/5) | — | H |
| 2,5-dichlorophenyl | X² | G-1 | J-39 (3/5) | — | H |
| 2-chloro-5-(trifluoromethyl)phenyl | X² | G-1 | J-39 (3/5) | — | H |
| 2,5-dimethylphenyl | X² | G-1 | J-39 (3/5) | — | H |
| 2-methyl-5-(trifluoromethyl)phenyl | X² | G-1 | J-39 (3/5) | — | H |
| 3,5-dimethylpyrazol-1-yl | X² | G-1 | J-39 (3/5) | — | H |
| 5-methyl-3-(trifluoromethyl)pyrazol-1-yl | X² | G-1 | J-39 (3/5) | — | H |
| 5-chloro-3-(trifluoromethyl)pyrazol-1-yl | X² | G-1 | J-39 (3/5) | — | H |
| 5-bromo-3-(trifluoromethyl)pyrazol-1-yl | X² | G-1 | J-39 (3/5) | — | H |
| 5-ethyl-3-(trifluoromethyl)pyrazol-1-yl | X² | G-1 | J-39 (3/5) | — | H |
| 3,5-bis-(trifluoromethyl)pyrazol-1-yl | X² | G-1 | J-39 (3/5) | — | H |
| 1-methyl-3-(trifluoromethyl)pyrazol-5-yl | X² | G-1 | J-39 (3/5) | — | H |
| 1-methyl-4-(trifluoromethyl)imidazol-2-yl | X² | G-1 | J-39 (3/5) | — | H |
| 2,5-dichlorophenyl | X² | G-1 | J-40 (3/5) | — | H |
| 2-chloro-5-(trifluoromethyl)phenyl | X² | G-1 | J-40 (3/5) | — | H |
| 2,5-dimethylphenyl | X² | G-1 | J-40 (3/5) | — | H |
| 2-methyl-5-(trifluoromethyl)phenyl | X² | G-1 | J-40 (3/5) | — | H |
| 3,5-dimethylpyrazol-1-yl | X² | G-1 | J-40 (3/5) | — | H |
| 5-methyl-3-(trifluoromethyl)pyrazol-1-yl | X² | G-1 | J-40 (3/5) | — | H |
| 5-chloro-3-(trifluoromethyl)pyrazol-1-yl | X² | G-1 | J-40 (3/5) | — | H |
| 5-bromo-3-(trifluoromethyl)pyrazol-1-yl | X² | G-1 | J-40 (3/5) | — | H |
| 5-ethyl-3-(trifluoromethyl)pyrazol-1-yl | X² | G-1 | J-40 (3/5) | — | H |
| 3,5-bis-(trifluoromethyl)pyrazol-1-yl | X² | G-1 | J-40 (3/5) | — | H |
| 1-methyl-3-(trifluoromethyl)pyrazol-5-yl | X² | G-1 | J-40 (3/5) | — | H |
| 1-methyl-4-(trifluoromethyl)imidazol-2-yl | X² | G-1 | J-40 (3/5) | — | H |
| 2,5-dichlorophenyl | X² | G-1 | J-69 (1/3) | — | H |
| 2-chloro-5-(trifluoromethyl)phenyl | X² | G-1 | J-69 (1/3) | — | H |
| 2,5-dimethylphenyl | X² | G-1 | J-69 (1/3) | — | H |
| 2-methyl-5-(trifluoromethyl)phenyl | X² | G-1 | J-69 (1/3) | — | H |
| 3,5-dimethylpyrazol-1-yl | X² | G-1 | J-69 (1/3) | — | H |
| 5-methyl-3-(trifluoromethyl)pyrazol-1-yl | X² | G-1 | J-69 (1/3) | — | H |
| 5-chloro-3-(trifluoromethyl)pyrazol-1-yl | X² | G-1 | J-69 (1/3) | — | H |
| 5-bromo-3-(trifluoromethyl)pyrazol-1-yl | X² | G-1 | J-69 (1/3) | — | H |
| 5-ethyl-3-(trifluoromethyl)pyrazol-1-yl | X² | G-1 | J-69 (1/3) | — | H |
| 3,5-bis-(trifluoromethyl)pyrazol-1-yl | X² | G-1 | J-69 (1/3) | — | H |
| 1-methyl-3-(trifluoromethyl)pyrazol-5-yl | X² | G-1 | J-69 (1/3) | — | H |
| 1-methyl-4-(trifluoromethyl)imidazol-2-yl | X² | G-1 | J-69 (1/3) | — | H |
| 2,5-dichlorophenyl | X² | G-1 | J-69 (1/4) | — | H |
| 2-chloro-5-(trifluoromethyl)phenyl | X² | G-1 | J-69 (1/4) | — | H |
| 2,5-dimethylphenyl | X² | G-1 | J-69 (1/4) | — | H |
| 2-methyl-5-(trifluoromethyl)phenyl | X² | G-1 | J-69 (1/4) | — | H |
| 3,5-dimethylpyrazol-1-yl | X² | G-1 | J-69 (1/4) | — | H |
| 5-methyl-3-(trifluoromethyl)pyrazol-1-yl | X² | G-1 | J-69 (1/4) | — | H |

TABLE 4*-continued

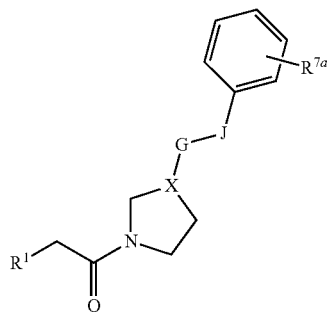

| R¹ | X | G  | J * | (R⁵)_y | R⁷ᵃ |
|---|---|---|---|---|---|
| 5-chloro-3-(trifluoromethyl)pyrazol-1-yl | X² | G-1 | J-69 (1/4) | — | H |
| 5-bromo-3-(trifluoromethyl)pyrazol-1-yl | X² | G-1 | J-69 (1/4) | — | H |
| 5-ethyl-3-(trifluoromethyl)pyrazol-1-yl | X² | G-1 | J-69 (1/4) | — | H |
| 3,5-bis-(trifluoromethyl)pyrazol-1-yl | X² | G-1 | J-69 (1/4) | — | H |
| 1-methyl-3-(trifluoromethyl)pyrazol-5-yl | X² | G-1 | J-69 (1/4) | — | H |
| 1-methyl-4-(trifluoromethyl)imidazol-2-yl | X² | G-1 | J-69 (1/4) | — | H |
| 2,5-dichlorophenyl | X² | G-1 | J-11 (3/5) | — | 2-Me |
| 2-chloro-5-(trifluoromethyl)phenyl | X² | G-1 | J-11 (3/5) | — | 2-Me |
| 2,5-dimethylphenyl | X² | G-1 | J-11 (3/5) | — | 2-Me |
| 2-methyl-5-(trifluoromethyl)phenyl | X² | G-1 | J-11 (3/5) | — | 2-Me |
| 3,5-dimethylpyrazol-1-yl | X² | G-1 | J-11 (3/5) | — | 2-Me |
| 5-methyl-3-(trifluoromethyl)pyrazol-1-yl | X² | G-1 | J-11 (3/5) | — | 2-Me |
| 5-chloro-3-(trifluoromethyl)pyrazol-1-yl | X² | G-1 | J-11 (3/5) | — | 2-Me |
| 5-bromo-3-(trifluoromethyl)pyrazol-1-yl | X² | G-1 | J-11 (3/5) | — | 2-Me |
| 5-ethyl-3-(trifluoromethyl)pyrazol-1-yl | X² | G-1 | J-11 (3/5) | — | 2-Me |
| 3,5-bis-(trifluoromethyl)pyrazol-1-yl | X² | G-1 | J-11 (3/5) | — | 2-Me |
| 1-methyl-3-(trifluoromethyl)pyrazol-5-yl | X² | G-1 | J-11 (3/5) | — | 2-Me |
| 1-methyl-4-(trifluoromethyl)imidazol-2-yl | X² | G-1 | J-11 (3/5) | — | 2-Me |
| 2,5-dichlorophenyl | X² | G-1 | J-11 (3/5) | — | 3-Me |
| 2-chloro-5-(trifluoromethyl)phenyl | X² | G-1 | J-11 (3/5) | — | 3-Me |
| 2,5-dimethylphenyl | X² | G-1 | J-11 (3/5) | — | 3-Me |
| 2-methyl-5-(trifluoromethyl)phenyl | X² | G-1 | J-11 (3/5) | — | 3-Me |
| 3,5-dimethylpyrazol-1-yl | X² | G-1 | J-11 (3/5) | — | 3-Me |
| 5-methyl-3-(trifluoromethyl)pyrazol-1-yl | X² | G-1 | J-11 (3/5) | — | 3-Me |
| 5-chloro-3-(trifluoromethyl)pyrazol-1-yl | X² | G-1 | J-11 (3/5) | — | 3-Me |
| 5-bromo-3-(trifluoromethyl)pyrazol-1-yl | X² | G-1 | J-11 (3/5) | — | 3-Me |
| 5-ethyl-3-(trifluoromethyl)pyrazol-1-yl | X² | G-1 | J-11 (3/5) | — | 3-Me |
| 3,5-bis-(trifluoromethyl)pyrazol-1-yl | X² | G-1 | J-11 (3/5) | — | 3-Me |
| 1-methyl-3-(trifluoromethyl)pyrazol-5-yl | X² | G-1 | J-11 (3/5) | — | 3-Me |
| 1-methyl-4-(trifluoromethyl)imidazol-2-yl | X² | G-1 | J-11 (3/5) | — | 3-Me |
| 2,5-dichlorophenyl | X² | G-1 | J-11 (3/5) | — | 4-Me |
| 2-chloro-5-(trifluoromethyl)phenyl | X² | G-1 | J-11 (3/5) | — | 4-Me |
| 2,5-dimethylphenyl | X² | G-1 | J-11 (3/5) | — | 4-Me |
| 2-methyl-5-(trifluoromethyl)phenyl | X² | G-1 | J-11 (3/5) | — | 4-Me |
| 3,5-dimethylpyrazol-1-yl | X² | G-1 | J-11 (3/5) | — | 4-Me |
| 5-methyl-3-(trifluoromethyl)pyrazol-1-yl | X² | G-1 | J-11 (3/5) | — | 4-Me |
| 5-chloro-3-(trifluoromethyl)pyrazol-1-yl | X² | G-1 | J-11 (3/5) | — | 4-Me |
| 5-bromo-3-(trifluoromethyl)pyrazol-1-yl | X² | G-1 | J-11 (3/5) | — | 4-Me |
| 5-ethyl-3-(trifluoromethyl)pyrazol-1-yl | X² | G-1 | J-11 (3/5) | — | 4-Me |
| 3,5-bis-(trifluoromethyl)pyrazol-1-yl | X² | G-1 | J-11 (3/5) | — | 4-Me |
| 1-methyl-3-(trifluoromethyl)pyrazol-5-yl | X² | G-1 | J-11 (3/5) | — | 4-Me |
| 1-methyl-4-(trifluoromethyl)imidazol-2-yl | X² | G-1 | J-11 (3/5) | — | 4-Me |
| 2,5-dichlorophenyl | X² | G-1 | J-11 (3/5) | — | 2-Cl |
| 2-chloro-5-(trifluoromethyl)phenyl | X² | G-1 | J-11 (3/5) | — | 2-Cl |
| 2,5-dimethylphenyl | X² | G-1 | J-11 (3/5) | — | 2-Cl |
| 2-methyl-5-(trifluoromethyl)phenyl | X² | G-1 | J-11 (3/5) | — | 2-Cl |
| 3,5-dimethylpyrazol-1-yl | X² | G-1 | J-11 (3/5) | — | 2-Cl |
| 5-methyl-3-(trifluoromethyl)pyrazol-1-yl | X² | G-1 | J-11 (3/5) | — | 2-Cl |
| 5-chloro-3-(trifluoromethyl)pyrazol-1-yl | X² | G-1 | J-11 (3/5) | — | 2-Cl |
| 5-bromo-3-(trifluoromethyl)pyrazol-1-yl | X² | G-1 | J-11 (3/5) | — | 2-Cl |
| 5-ethyl-3-(trifluoromethyl)pyrazol-1-yl | X² | G-1 | J-11 (3/5) | — | 2-Cl |
| 3,5-bis-(trifluoromethyl)pyrazol-1-yl | X² | G-1 | J-11 (3/5) | — | 2-Cl |
| 1-methyl-3-(trifluoromethyl)pyrazol-5-yl | X² | G-1 | J-11 (3/5) | — | 2-Cl |
| 1-methyl-4-(trifluoromethyl)imidazol-2-yl | X² | G-1 | J-11 (3/5) | — | 2-Cl |
| 2,5-dichlorophenyl | X² | G-1 | J-11 (3/5) | — | 4-Cl |
| 2-chloro-5-(trifluoromethyl)phenyl | X² | G-1 | J-11 (3/5) | — | 4-Cl |
| 2,5-dimethylphenyl | X² | G-1 | J-11 (3/5) | — | 4-Cl |
| 2-methyl-5-(trifluoromethyl)phenyl | X² | G-1 | J-11 (3/5) | — | 4-Cl |
| 3,5-dimethylpyrazol-1-yl | X² | G-1 | J-11 (3/5) | — | 4-Cl |
| 5-methyl-3-(trifluoromethyl)pyrazol-1-yl | X² | G-1 | J-11 (3/5) | — | 4-Cl |
| 5-chloro-3-(trifluoromethyl)pyrazol-1-yl | X² | G-1 | J-11 (3/5) | — | 4-Cl |
| 5-bromo-3-(trifluoromethyl)pyrazol-1-yl | X² | G-1 | J-11 (3/5) | — | 4-Cl |

TABLE 4*-continued

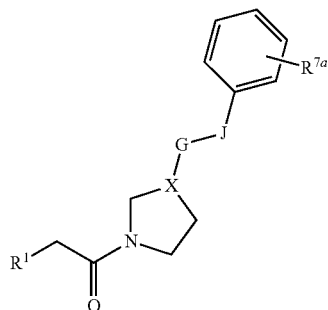

| R¹ | X | G  | J * | (R⁵)_y | R⁷ᵃ |
|---|---|---|---|---|---|
| 5-ethyl-3-(trifluoromethyl)pyrazol-1-yl | X² | G-1 | J-11 (3/5) | — | 4-Cl |
| 3,5-bis-(trifluoromethyl)pyrazol-1-yl | X² | G-1 | J-11 (3/5) | — | 4-Cl |
| 1-methyl-3-(trifluoromethyl)pyrazol-5-yl | X² | G-1 | J-11 (3/5) | — | 4-Cl |
| 1-methyl-4-(trifluoromethyl)imidazol-2-yl | X² | G-1 | J-11 (3/5) | — | 4-Cl |
| 2,5-dichlorophenyl | X² | G-1 | J-29 (3/5) | — | 2-Me |
| 2-chloro-5-(trifluoromethyl)phenyl | X² | G-1 | J-29 (3/5) | — | 2-Me |
| 2,5-dimethylphenyl | X² | G-1 | J-29 (3/5) | — | 2-Me |
| 2-methyl-5-(trifluoromethyl)phenyl | X² | G-1 | J-29 (3/5) | — | 2-Me |
| 3,5-dimethylpyrazol-1-yl | X² | G-1 | J-29 (3/5) | — | 2-Me |
| 5-methyl-3-(trifluoromethyl)pyrazol-1-yl | X² | G-1 | J-29 (3/5) | — | 2-Me |
| 5-chloro-3-(trifluoromethyl)pyrazol-1-yl | X² | G-1 | J-29 (3/5) | — | 2-Me |
| 5-bromo-3-(trifluoromethyl)pyrazol-1-yl | X² | G-1 | J-29 (3/5) | — | 2-Me |
| 5-ethyl-3-(trifluoromethyl)pyrazol-1-yl | X² | G-1 | J-29 (3/5) | — | 2-Me |
| 3,5-bis-(trifluoromethyl)pyrazol-1-yl | X² | G-1 | J-29 (3/5) | — | 2-Me |
| 1-methyl-3-(trifluoromethyl)pyrazol-5-yl | X² | G-1 | J-29 (3/5) | — | 2-Me |
| 1-methyl-4-(trifluoromethyl)imidazol-2-yl | X² | G-1 | J-29 (3/5) | — | 2-Me |
| 2,5-dichlorophenyl | X² | G-1 | J-29 (3/5) | — | 3-Me |
| 2-chloro-5-(trifluoromethyl)phenyl | X² | G-1 | J-29 (3/5) | — | 3-Me |
| 2,5-dimethylphenyl | X² | G-1 | J-29 (3/5) | — | 3-Me |
| 2-methyl-5-(trifluoromethyl)phenyl | X² | G-1 | J-29 (3/5) | — | 3-Me |
| 3,5-dimethylpyrazol-1-yl | X² | G-1 | J-29 (3/5) | — | 3-Me |
| 5-methyl-3-(trifluoromethyl)pyrazol-1-yl | X² | G-1 | J-29 (3/5) | — | 3-Me |
| 5-chloro-3-(trifluoromethyl)pyrazol-1-yl | X² | G-1 | J-29 (3/5) | — | 3-Me |
| 5-bromo-3-(trifluoromethyl)pyrazol-1-yl | X² | G-1 | J-29 (3/5) | — | 3-Me |
| 5-ethyl-3-(trifluoromethyl)pyrazol-1-yl | X² | G-1 | J-29 (3/5) | — | 3-Me |
| 3,5-bis-(trifluoromethyl)pyrazol-1-yl | X² | G-1 | J-29 (3/5) | — | 3-Me |
| 1-methyl-3-(trifluoromethyl)pyrazol-5-yl | X² | G-1 | J-29 (3/5) | — | 3-Me |
| 1-methyl-4-(trifluoromethyl)imidazol-2-yl | X² | G-1 | J-29 (3/5) | — | 3-Me |
| 2,5-dichlorophenyl | X² | G-1 | J-29 (3/5) | — | 4-Me |
| 2-chloro-5-(trifluoromethyl)phenyl | X² | G-1 | J-29 (3/5) | — | 4-Me |
| 2,5-dimethylphenyl | X² | G-1 | J-29 (3/5) | — | 4-Me |
| 2-methyl-5-(trifluoromethyl)phenyl | X² | G-1 | J-29 (3/5) | — | 4-Me |
| 3,5-dimethylpyrazol-1-yl | X² | G-1 | J-29 (3/5) | — | 4-Me |
| 5-methyl-3-(trifluoromethyl)pyrazol-1-yl | X² | G-1 | J-29 (3/5) | — | 4-Me |
| 5-chloro-3-(trifluoromethyl)pyrazol-1-yl | X² | G-1 | J-29 (3/5) | — | 4-Me |
| 5-bromo-3-(trifluoromethyl)pyrazol-1-yl | X² | G-1 | J-29 (3/5) | — | 4-Me |
| 5-ethyl-3-(trifluoromethyl)pyrazol-1-yl | X² | G-1 | J-29 (3/5) | — | 4-Me |
| 3,5-bis-(trifluoromethyl)pyrazol-1-yl | X² | G-1 | J-29 (3/5) | — | 4-Me |
| 1-methyl-3-(trifluoromethyl)pyrazol-5-yl | X² | G-1 | J-29 (3/5) | — | 4-Me |
| 1-methyl-4-(trifluoromethyl)imidazol-2-yl | X² | G-1 | J-29 (3/5) | — | 4-Me |
| 2,5-dichlorophenyl | X² | G-1 | J-29 (3/5) | — | 2-Cl |
| 2-chloro-5-(trifluoromethyl)phenyl | X² | G-1 | J-29 (3/5) | — | 2-Cl |
| 2,5-dimethylphenyl | X² | G-1 | J-29 (3/5) | — | 2-Cl |
| 2-methyl-5-(trifluoromethyl)phenyl | X² | G-1 | J-29 (3/5) | — | 2-Cl |
| 3,5-dimethylpyrazol-1-yl | X² | G-1 | J-29 (3/5) | — | 2-Cl |
| 5-methyl-3-(trifluoromethyl)pyrazol-1-yl | X² | G-1 | J-29 (3/5) | — | 2-Cl |
| 5-chloro-3-(trifluoromethyl)pyrazol-1-yl | X² | G-1 | J-29 (3/5) | — | 2-Cl |
| 5-bromo-3-(trifluoromethyl)pyrazol-1-yl | X² | G-1 | J-29 (3/5) | — | 2-Cl |
| 5-ethyl-3-(trifluoromethyl)pyrazol-1-yl | X² | G-1 | J-29 (3/5) | — | 2-Cl |
| 3,5-bis-(trifluoromethyl)pyrazol-1-yl | X² | G-1 | J-29 (3/5) | — | 2-Cl |
| 1-methyl-3-(trifluoromethyl)pyrazol-5-yl | X² | G-1 | J-29 (3/5) | — | 2-Cl |
| 1-methyl-4-(trifluoromethyl)imidazol-2-yl | X² | G-1 | J-29 (3/5) | — | 2-Cl |
| 2,5-dichlorophenyl | X² | G-1 | J-29 (3/5) | — | 4-Cl |
| 2-chloro-5-(trifluoromethyl)phenyl | X² | G-1 | J-29 (3/5) | — | 4-Cl |
| 2,5-dimethylphenyl | X² | G-1 | J-29 (3/5) | — | 4-Cl |
| 2-methyl-5-(trifluoromethyl)phenyl | X² | G-1 | J-29 (3/5) | — | 4-Cl |
| 3,5-dimethylpyrazol-1-yl | X² | G-1 | J-29 (3/5) | — | 4-Cl |
| 5-methyl-3-(trifluoromethyl)pyrazol-1-yl | X² | G-1 | J-29 (3/5) | — | 4-Cl |
| 5-chloro-3-(trifluoromethyl)pyrazol-1-yl | X² | G-1 | J-29 (3/5) | — | 4-Cl |
| 5-bromo-3-(trifluoromethyl)pyrazol-1- | X² | G-1 | J-29 (3/5) | — | 4-Cl |
| 5-ethyl-3-(trifluoromethyl)pyrazol-1-yl | X² | G-1 | J-29 (3/5) | — | 4-Cl |
| 3,5-bis-(trifluoromethyl)pyrazol-1-yl | X² | G-1 | J-29 (3/5) | — | 4-Cl |

TABLE 4*-continued

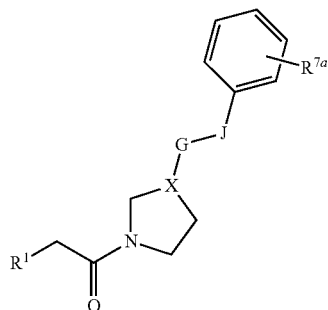

| R¹ | X | G  | J * | (R⁵)_y | R⁷ᵃ |
|---|---|---|---|---|---|
| 1-methyl-3-(trifluoromethyl)pyrazol-5-yl | X² | G-1 | J-29 (3/5) | — | 4-Cl |
| 1-methyl-4-(trifluoromethyl)imidazol-2-yl | X² | G-1 | J-29 (3/5) | — | 4-Cl |
| 2,5-dichlorophenyl | X² | G-1 | J-29 (3/5) | 5-Me | H |
| 2-chloro-5-(trifluoromethyl)phenyl | X² | G-1 | J-29 (3/5) | 5-Me | H |
| 2,5-dimethylphenyl | X² | G-1 | J-29 (3/5) | 5-Me | H |
| 2-methyl-5-(trifluoromethyl)phenyl | X² | G-1 | J-29 (3/5) | 5-Me | H |
| 3,5-dimethylpyrazol-1-yl | X² | G-1 | J-29 (3/5) | 5-Me | H |
| 5-methyl-3-(trifluoromethyl)pyrazol-1-yl | X² | G-1 | J-29 (3/5) | 5-Me | H |
| 5-chloro-3-(trifluoromethyl)pyrazol-1-yl | X² | G-1 | J-29 (3/5) | 5-Me | H |
| 5-bromo-3-(trifluoromethyl)pyrazol-1-yl | X² | G-1 | J-29 (3/5) | 5-Me | H |
| 5-ethyl-3-(trifluoromethyl)pyrazol-1-yl | X² | G-1 | J-29 (3/5) | 5-Me | H |
| 3,5-bis-(trifluoromethyl)pyrazol-1-yl | X² | G-1 | J-29 (3/5) | 5-Me | H |
| 1-methyl-3-(trifluoromethyl)pyrazol-5-yl | X² | G-1 | J-29 (3/5) | 5-Me | H |
| 1-methyl-4-(trifluoromethyl)imidazol-2-yl | X² | G-1 | J-29 (3/5) | 5-Me | H |
| 2,5-dichlorophenyl | X² | G-1 | J-29 (3/5) | 4-Me | H |
| 2-chloro-5-(trifluoromethyl)phenyl | X² | G-1 | J-29 (3/5) | 4-Me | H |
| 2,5-dimethylphenyl | X² | G-1 | J-29 (3/5) | 4-Me | H |
| 2-methyl-5-(trifluoromethyl)phenyl | X² | G-1 | J-29 (3/5) | 4-Me | H |
| 3,5-dimethylpyrazol-1-yl | X² | G-1 | J-29 (3/5) | 4-Me | H |
| 5-methyl-3-(trifluoromethy)pyrazol-1-yl | X² | G-1 | J-29 (3/5) | 4-Me | H |
| 5-chloro-3-(trifluoromethyl)pyrazol-1-yl | X² | G-1 | J-29 (3/5) | 4-Me | H |
| 5-bromo-3-(trifluoromethyl)pyrazol-1-yl | X² | G-1 | J-29 (3/5) | 4-Me | H |
| 5-ethyl-3-(trifluoromethyl)pyrazol-1-yl | X² | G-1 | J-29 (3/5) | 4-Me | H |
| 3,5-bis-(trifluoromethyl)pyrazol-1-yl | X² | G-1 | J-29 (3/5) | 4-Me | H |
| 1-methyl-3-(trifluoromethyl)pyrazol-5-yl | X² | G-1 | J-29 (3/5) | 4-Me | H |
| 1-methyl-4-(trifluoromethyl)imidazol-2-yl | X² | G-1 | J-29 (3/5) | 4-Me | H |
| 2,5-dichlorophenyl | X² | G-1 | J-29 (3/5) | 4,4-di-Me | H |
| 2-chloro-5-(trifluoromethyl)phenyl | X² | G-1 | J-29 (3/5) | 4,4-di-Me | H |
| 2,5-dimethylphenyl | X² | G-1 | J-29 (3/5) | 4,4-di-Me | H |
| 2-methyl-5-(trifluoromethyl)phenyl | X² | G-1 | J-29 (3/5) | 4,4-di-Me | H |
| 3,5-dimethylpyrazol-1-yl | X² | G-1 | J-29 (3/5) | 4,4-di-Me | H |
| 5-methyl-3-(trifluoromethyl)pyrazol-1-yl | X² | G-1 | J-29 (3/5) | 4,4-di-Me | H |
| 5-chloro-3-(trifluoromethyl)pyrazol-1-yl | X² | G-1 | J-29 (3/5) | 4,4-di-Me | H |
| 5-bromo-3-(trifluoromethyl)pyrazol-1-yl | X² | G-1 | J-29 (3/5) | 4,4-di-Me | H |
| 5-ethyl-3-(trifluoromethyl)pyrazol-1-yl | X² | G-1 | J-29 (3/5) | 4,4-di-Me | H |
| 3,5-bis-(trifluoromethyl)pyrazol-1-yl | X² | G-1 | J-29 (3/5) | 4,4-di-Me | H |
| 1-methyl-3-(trifluoromethyl)pyrazol-5-yl | X² | G-1 | J-29 (3/5) | 4,4-di-Me | H |
| 1-methyl-4-(trifluoromethyl)imidazol-2-yl | X² | G-1 | J-29 (3/5) | 4,4-di-Me | H |
| 2,5-dichlorophenyl | X² | G-2 | J-1 (2/4) | — | H |
| 2-chloro-5-(trifluoromethyl)phenyl | X² | G-2 | J-1 (2/4) | — | H |
| 2,5-dimethylphenyl | X² | G-2 | J-1 (2/4) | — | H |
| 2-methyl-5-(trifluoromethyl)phenyl | X² | G-2 | J-1 (2/4) | — | H |
| 3,5-dimethylpyrazol-1-yl | X² | G-2 | J-1 (2/4) | — | H |
| 5-methyl-3-(trifluoromethyl)pyrazol-1-yl | X² | G-2 | J-1 (2/4) | — | H |
| 5-chloro-3-(trifluoromethyl)pyrazol-1-yl | X² | G-2 | J-1 (2/4) | — | H |
| 5-bromo-3-(trifluoromethyl)pyrazol-1-yl | X² | G-2 | J-1 (2/4) | — | H |
| 5-ethyl-3-(trifluoromethyl)pyrazol-1-yl | X² | G-2 | J-1 (2/4) | — | H |
| 3,5-bis-(trifluoromethyl)pyrazol-1-yl | X² | G-2 | J-1 (2/4) | — | H |
| 1-methyl-3-(trifluoromethyl)pyrazol-5-yl | X² | G-2 | J-1 (2/4) | — | H |
| 1-methyl-4-(trifluoromethyl)imidazol-2-yl | X² | G-2 | J-1 (2/4) | — | H |
| 2,5-dichlorophenyl | X² | G-2 | J-2 (2/4) | — | H |
| 2-chloro-5-(trifluoromethyl)phenyl | X² | G-2 | J-2 (2/4) | — | H |
| 2,5-dimethylphenyl | X² | G-2 | J-2 (2/4) | — | H |
| 2-methyl-5-(trifluoromethyl)phenyl | X² | G-2 | J-2 (2/4) | — | H |
| 3,5-dimethylpyrazol-1-yl | X² | G-2 | J-2 (2/4) | — | H |
| 5-methyl-3-(trifluoromethyl)pyrazol-1-yl | X² | G-2 | J-2 (2/4) | — | H |
| 5-chloro-3-(trifluoromethyl)pyrazol-1-yl | X² | G-2 | J-2 (2/4) | — | H |
| 5-bromo-3-(trifluoromethyl)pyrazol-1-yl | X² | G-2 | J-2 (2/4) | — | H |
| 5-ethyl-3-(trifluoromethyl)pyrazol-1-yl | X² | G-2 | J-2 (2/4) | — | H |
| 3,5-bis-(trifluoromethyl)pyrazol-1-yl | X² | G-2 | J-2 (2/4) | — | H |
| 1-methyl-3-(trifluoromethyl)pyrazol-5-yl | X² | G-2 | J-2 (2/4) | — | H |
| 1-methyl-4-(trifluoromethyl)imidazol-2-yl | X² | G-2 | J-2 (2/4) | — | H |

TABLE 4*-continued

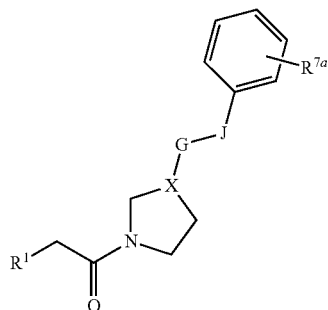

| R¹ | X | G  | J * | (R⁵)_y | R⁷ᵃ |
|---|---|---|---|---|---|
| 2,5-dichlorophenyl | X² | G-2 | J-3 (2/4) | 1-Me | H |
| 2-chloro-5-(trifluoromethyl)phenyl | X² | G-2 | J-3 (2/4) | 1-Me | H |
| 2,5-dimethylphenyl | X² | G-2 | J-3 (2/4) | 1-Me | H |
| 2-ethyl-5-(trifluoromethyl)phenyl | X² | G-2 | J-3 (2/4) | 1-Me | H |
| 3,5-dimethylpyrazol-1-yl | X² | G-2 | J-3 (2/4) | 1-Me | H |
| 5-methyl-3-(trifluoromethyl)pyrazol-1-yl | X² | G-2 | J-3 (2/4) | 1-Me | H |
| 5-chloro-3-(trifluoromethyl)pyrazol-1-yl | X² | G-2 | J-3 (2/4) | 1-Me | H |
| 5-bromo-3-(trifluoromethyl)pyrazol-1-yl | X² | G-2 | J-3 (2/4) | 1-Me | H |
| 5-ethyl-3-(trifluoromethyl)pyrazol-1-yl | X² | G-2 | J-3 (2/4) | 1-Me | H |
| 3,5-bis-(trifluoromethyl)pyrazol-1-yl | X² | G-2 | J-3 (2/4) | 1-Me | H |
| 1-methyl-3-(trifluoromethyl)pyrazol-5-yl | X² | G-2 | J-3 (2/4) | 1-Me | H |
| 1-methyl-4-(trifluoromethyl)imidazol-2-yl | X² | G-2 | J-3 (2/4) | 1-Me | H |
| 2,5-dichlorophenyl | X² | G-2 | J-4 (2/5) | — | H |
| 2-chloro-5-(trifluoromethyl)phenyl | X² | G-2 | J-4 (2/5) | — | H |
| 2,5-dimethylphenyl | X² | G-2 | J-4 (2/5) | — | H |
| 2-methyl-5-(trifluoromethyl)phenyl | X² | G-2 | J-4 (2/5) | — | H |
| 3,5-dimethylpyrazol-1-yl | X² | G-2 | J-4 (2/5) | — | H |
| 5-methyl-3-(trifluoromethyl)pyrazol-1-yl | X² | G-2 | J-4 (2/5) | — | H |
| 5-chloro-3-(trifluoromethyl)pyrazol-1-yl | X² | G-2 | J-4 (2/5) | — | H |
| 5-bromo-3-(trifluoromethyl)pyrazol-1yl | X² | G-2 | J-4 (2/5) | — | H |
| 5-ethyl-3-(trifluoromethyl)pyrazol-1-yl | X² | G-2 | J-4 (2/5) | — | H |
| 3,5-bis-(trifluoromethyl)pyrazol-1-yl | X² | G-2 | J-4 (2/5) | — | H |
| 1-methyl-3-(trifluoromethyl)pyrazol-5-yl | X² | G-2 | J-4 (2/5) | — | H |
| 1-methyl-4-(trifluoromethyl)imidazol-2-yl | X² | G-2 | J-4 (2/5) | — | H |
| 2,5-dichlorophenyl | X² | G-2 | J-8 (5/3) | — | H |
| 2-chloro-5-(trifluoromethyl)phenyl | X² | G-2 | J-8 (5/3) | — | H |
| 2,5-dimethylphenyl | X² | G-2 | J-8 (5/3) | — | H |
| 2-methyl-5-(trifluoromethyl)phenyl | X² | G-2 | J-8 (5/3) | — | H |
| 3,5-dimethylpyrazol-1-yl | X² | G-2 | J-8 (5/3) | — | H |
| 5-methyl-3-(trifluoromethyl)pyrazol-1-yl | X² | G-2 | J-8 (5/3) | — | H |
| 5-chloro-3-(trifluoromethyl)pyrazol-1-yl | X² | G-2 | J-8 (5/3) | — | H |
| 5-bromo-3-(trifluoromethyl)pyrazol-1-yl | X² | G-2 | J-8 (5/3) | — | H |
| 5-ethyl-3-(trifluoromethyl)pyrazol-1-yl | X² | G-2 | J-8 (5/3) | — | H |
| 3,5-bis-(trifluoromethyl)pyrazol-1-yl | X² | G-2 | J-8 (5/3) | — | H |
| 1-methyl-3-(trifluoromethyl)pyrazol-5-yl | X² | G-2 | J-8 (5/3) | — | H |
| 1-methyl-4-(trifluoromethyl)imidazol-2-yl | X² | G-2 | J-8 (5/3) | — | H |
| 2,5-dichlorophenyl | X² | G-2 | J-9 (5/3) | — | H |
| 2-chloro-5-(trifluoromethyl)phenyl | X² | G-2 | J-9 (5/3) | — | H |
| 2,5-dimethylphenyl | X² | G-2 | J-9 (5/3) | — | H |
| 2-methyl-5-(trifluoromethyl)phenyl | X² | G-2 | J-9 (5/3) | — | H |
| 3,5-dimethylpyrazol-1-yl | X² | G-2 | J-9 (5/3) | — | H |
| 5-methyl-3-(trifluoromethyl)pyrazol-1-yl | X² | G-2 | J-9 (5/3) | — | H |
| 5-chloro-3-(trifluoromethyl)pyrazol-1-yl | X² | G-2 | J-9 (5/3) | — | H |
| 5-bromo-3-(trifluoromethyl)pyrazol-1-yl | X² | G-2 | J-9 (5/3) | — | H |
| 5-ethyl-3-(trifluoromethyl)pyrazol-1-yl | X² | G-2 | J-9 (5/3) | — | H |
| 3,5-bis-(trifluoromethyl)pyrazol-1-yl | X² | G-2 | J-9 (5/3) | — | H |
| 1-methyl-3-(trifluoromethyl)pyrazol-5-yl | X² | G-2 | J-9 (5/3) | — | H |
| 1-methyl-4-(trifluoromethyl)imidazol-2-yl | X² | G-2 | J-9 (5/3) | — | H |
| 2,5-dichlorophenyl | X² | G-2 | J-11 (3/5) | — | H |
| 2-chloro-5-(trifluoromethyl)phenyl | X² | G-2 | J-11 (3/5) | — | H |
| 2,5-dimethylphenyl | X² | G-2 | J-11 (3/5) | — | H |
| 2-methyl-5-(trifluoromethyl)phenyl | X² | G-2 | J-11 (3/5) | — | H |
| 3,5-dimethylpyrazol-1-yl | X² | G-2 | J-11 (3/5) | — | H |
| 5-methyl-3-(trifluoromethyl)pyrazol-1-yl | X² | G-2 | J-11 (3/5) | — | H |
| 5-chloro-3-(trifluoromethyl)pyrazol-1-yl | X² | G-2 | J-11 (3/5) | — | H |
| 5-bromo-3-(trifluoromethyl)pyrazol-1-yl | X² | G-2 | J-11 (3/5) | — | H |
| 5-ethyl-3-(trifluoromethyl)pyrazol-1-yl | X² | G-2 | J-11 (3/5) | — | H |
| 3,5-bis-(trifluoromethyl)pyrazol-1-yl | X² | G-2 | J-11 (3/5) | — | H |
| 1-methyl-3-(trifluoromethyl)pyrazol-5-yl | X² | G-2 | J-11 (3/5) | — | H |
| 1-methyl-4-(trifluoromethyl)imidazol-2-yl | X² | G-2 | J-11 (3/5) | — | H |
| 2,5-dichlorophenyl | X² | G-2 | J-12 (3/5) | — | H |
| 2-chloro-5-(trifluoromethyl)phenyl | X² | G-2 | J-12 (3/5) | — | H |

TABLE 4*-continued

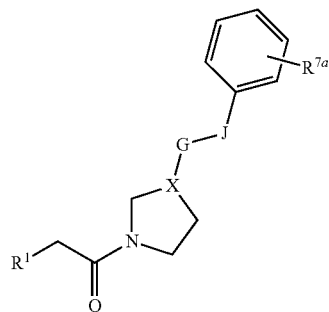

| R¹ | X | G  | J * | (R⁵)ᵧ | R⁷ᵃ |
|---|---|---|---|---|---|
| 2,5-dimethylphenyl | X² | G-2 | J-12 (3/5) | — | H |
| 2-methyl-5-(trifluoromethyl)phenyl | X² | G-2 | J-12 (3/5) | — | H |
| 3,5-dimethylpyrazol-1-yl | X² | G-2 | J-12 (3/5) | — | H |
| 5-methyl-3-(trifluoromethyl)pyrazol-1-yl | X² | G-2 | J-12 (3/5) | — | H |
| 5-chloro-3-(trifluoromethyl)pyrazol-1-yl | X² | G-2 | J-12 (3/5) | — | H |
| 5-bromo-3-(trifluoromethyl)pyrazol-1-yl | X² | G-2 | J-12 (3/5) | — | H |
| 5-ethyl-3-(trifluoromethyl)pyrazol-1-yl | X² | G-2 | J-12 (3/5) | — | H |
| 3,5-bis-(trifluoromethyl)pyrazol-1-yl | X² | G-2 | J-12 (3/5) | — | H |
| 1-methyl-3-(trifluoromethyl)pyrazol-5-yl | X² | G-2 | J-12 (3/5) | — | H |
| 1-methyl-4-(trifluoromethyl)imidazol-2-yl | X² | G-2 | J-12 (3/5) | — | H |
| 2,5-dichlorophenyl | X² | G-2 | J-12 (3/5) | 1-Me | H |
| 2-chloro-5-(trifluoromethyl)phenyl | X² | G-2 | J-12 (3/5) | 1-Me | H |
| 2,5-dimethylphenyl | X² | G-2 | J-12 (3/5) | 1-Me | H |
| 2-methyl-5-(trifluoromethyl)phenyl | X² | G-2 | J-12 (3/5) | 1-Me | H |
| 3,5-dimethylpyrazol-1-yl | X² | G-2 | J-12 (3/5) | 1-Me | H |
| 5-methyl-3-(trifluoromethyl)pyrazol-1-yl | X² | G-2 | J-12 (3/5) | 1-Me | H |
| 5-chloro-3-(trifluoromethyl)pyrazol-1-yl | X² | G-2 | J-12 (3/5) | 1-Me | H |
| 5-bromo-3-(trifluoromethyl)pyrazol-1-yl | X² | G-2 | J-12 (3/5) | 1-Me | H |
| 5-ethyl-3-(trifluoromethyl)pyrazol-1-yl | X² | G-2 | J-12 (3/5) | 1-Me | H |
| 3,5-bis-(trifluoromethy)pyrazol-1-yl | X² | G-2 | J-12 (3/5) | 1-Me | H |
| 1-methyl-3-(trifluoromethyl)pyrazol-5-yl | X² | G-2 | J-12 (3/5) | 1-Me | H |
| 1-methyl-4-(trifluoromethyl)imidazol-2-yl | X² | G-2 | J-12 (3/5) | 1-Me | H |
| 2,5-dichlorophenyl | X² | G-2 | J-14 (3/5) | — | H |
| 2-chloro-5-(trifluoromethyl)phenyl | X² | G-2 | J-14 (3/5) | — | H |
| 2,5-dimethylphenyl | X² | G-2 | J-14 (3/5) | — | H |
| 2-methyl-5-(trifluoromethyl)phenyl | X² | G-2 | J-14 (3/5) | — | H |
| 3,5-dimethylpyrazol-1-yl | X² | G-2 | J-14 (3/5) | — | H |
| 5-methyl-3-(trifluoromethyl)pyrazol-1-yl | X² | G-2 | J-14 (3/5) | — | H |
| 5-chloro-3-(trifluoromethyl)pyrazol-1-yl | X² | G-2 | J-14 (3/5) | — | H |
| 5-bromo-3-(trifluoromethyl)pyrazol-1-yl | X² | G-2 | J-14 (3/5) | — | H |
| 5-ethly-3-(trifluoromethyl)pyrazol-1-yl | X² | G-2 | J-14 (3/5) | — | H |
| 3,5-bis-(trifluoromethyl)pyrazol-1-yl | X² | G-2 | J-14 (3/5) | — | H |
| 1-methyl-3-(trifluoromethyl)pyrazol-5-yl | X² | G-2 | J-14 (3/5) | — | H |
| 1-methyl-4-(trifluoromethyl)imidazol-2-yl | X² | G-2 | J-14 (3/5) | — | H |
| 2,5-dichlorophenyl | X² | G-2 | J-15 (2/5) | — | H |
| 2-chloro-5-(trifluoromethyl)phenyl | X² | G-2 | J-15 (2/5) | — | H |
| 2,5-dimethylphenyl | X² | G-2 | J-15 (2/5) | — | H |
| 2-methyl-5-(trifluoromethyl)phenyl | X² | G-2 | J-15 (2/5) | — | H |
| 3,5-dimethylpyrazol-1-yl | X² | G-2 | J-15 (2/5) | — | H |
| 5-methyl-3-(trifluoromethyl)pyrazol-1-yl | X² | G-2 | J-15 (2/5) | — | H |
| 5-chloro-3-(trifluoromethyl)pyrazol-1-yl | X² | G-2 | J-15 (2/5) | — | H |
| 5-bromo-3-(trifluoromethyl)pyrazol-1-yl | X² | G-2 | J-15 (2/5) | — | H |
| 5-ethyl-3-(trifluoromethyl)pyrazol-1-yl | X² | G-2 | J-15 (2/5) | — | H |
| 3,5-bis-(trifluoromethyl)pyrazol-1-yl | X² | G-2 | J-15 (2/5) | — | H |
| 1-methyl-3-(trifluoromethyl)pyrazol-5-yl | X² | G-2 | J-15 (2/5) | — | H |
| 1-methyl-4-(triftuoromethyl)imidazol-2-yl | X² | G-2 | J-15 (2/5) | — | H |
| 2,5-dichlorophenyl | X² | G-2 | J-16 (2/5) | — | H |
| 2-chloro-5-(trifluoromethyl)phenyl | X² | G-2 | J-16 (2/5) | — | H |
| 2,5-dimethylphenyl | X² | G-2 | J-16 (2/5) | — | H |
| 2-methyl-5-(trifluoromethyl)phenyl | X² | G-2 | J-16 (2/5) | — | H |
| 3,5-dimethylpyrazol-1-yl | X² | G-2 | J-16 (2/5) | — | H |
| 5-methyl-3-(trifluoromethyl)pyrazol-1-yl | X² | G-2 | J-16 (2/5) | — | H |
| 5-chloro-3-(trifluoromethyl)pyrazol-1-yl | X² | G-2 | J-16 (2/5) | — | H |
| 5-bromo-3-(trifluoromethyl)pyrazol-1-yl | X² | G-2 | J-16 (2/5) | — | H |
| 5-ethyl-3-(trifluoromethyl)pyrazol-1-yl | X² | G-2 | J-16 (2/5) | — | H |
| 3,5-bis-(trifluoromethyl)pyrazol-1-yl | X² | G-2 | J-16 (2/5) | — | H |
| 1-methyl-3-(trifluoromethyl)pyrazol-5-yl | X² | G-2 | J-16 (2/5) | — | H |
| 1-methyl-4-(trifluoromethyl)imidazol-2-yl | X² | G-2 | J-16 (2/5) | — | H |
| 2,5-dichlorophenyl | X² | G-2 | J-22 (2/4) | — | H |
| 2-chloro-5-(trifluoromethyl)phenyl | X² | G-2 | J-22 (2/4) | — | H |
| 2,5-dimethylphenyl | X² | G-2 | J-22 (2/4) | — | H |
| 2-methyl-5-(trifluoromethyl)phenyl | X² | G-2 | J-22 (2/4) | — | H |

TABLE 4*-continued

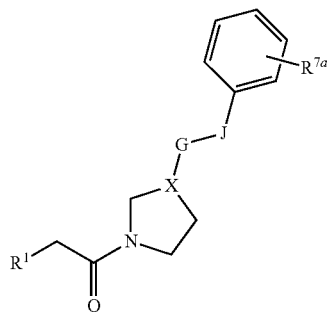

| $R^1$ | X | G  | J * | $(R^5)_y$ | $R^{7a}$ |
|---|---|---|---|---|---|
| 3,5-dimethylpyrazol-1-yl | $X^2$ | G-2 | J-22 (2/4) | — | H |
| 5-methyl-3-(trifluoromethyl)pyrazol-1-yl | $X^2$ | G-2 | J-22 (2/4) | — | H |
| 5-chloro-3-(trifluoromethyl)pyrazol-1-yl | $X^2$ | G-2 | J-22 (2/4) | — | H |
| 5-bromo-3-(trifluoromethyl)pyrazol-1-yl | $X^2$ | G-2 | J-22 (2/4) | — | H |
| 5-ethyl-3-(trifluoromethyl)pyrazol-1-yl | $X^2$ | G-2 | J-22 (2/4) | — | H |
| 3,5-bis-(trifluoromethyl)pyrazol-1-yl | $X^2$ | G-2 | J-22 (2/4) | — | H |
| 1-methyl-3-(trifluoromethyl)pyrazol-5-yl | $X^2$ | G-2 | J-22 (2/4) | — | H |
| 1-methyl-4-(trifluoromethyl)imidazol-2-yl | $X^2$ | G-2 | J-22 (2/4) | — | H |
| 2,5-dichlorophenyl | $X^2$ | G-2 | J-24 (2/4) | — | H |
| 2-chloro-5-(trifluoromethyl)phenyl | $X^2$ | G-2 | J-24 (2/4) | — | H |
| 2,5-dimethylphenyl | $X^2$ | G-2 | J-24 (2/4) | — | H |
| 2-methyl-5-(trifluoromethyl)phenyl | $X^2$ | G-2 | J-24 (2/4) | — | H |
| 3,5-dimethylpyrazol-1-yl | $X^2$ | G-2 | J-24 (2/4) | — | H |
| 5-methyl-3-(trifluoromethyl)pyrazol-1-yl | $X^2$ | G-2 | J-24 (2/4) | — | H |
| 5-chloro-3-(trifluoromethyl)pyrazol-1-yl | $X^2$ | G-2 | J-24 (2/4) | — | H |
| 5-bromo-3-(trifluoromethyl)pyrazol-1-yl | $X^2$ | G-2 | J-24 (2/4) | — | H |
| 5-ethyl-3-(trifluoromethyl)pyrazol-1-yl | $X^2$ | G-2 | J-24 (2/4) | — | H |
| 3,5-bis-(trifluoromethyl)pyrazol-1-yl | $X^2$ | G-2 | J-24 (2/4) | — | H |
| 1-methyl-3-(trifluoromethyl)pyrazol-5-yl | $X^2$ | G-2 | J-24 (2/4) | — | H |
| 1-methyl-4-(trifluoromethyl)imidazol-2-yl | $X^2$ | G-2 | J-24 (2/4) | — | H |
| 2,5-dichlorophenyl | $X^2$ | G-2 | J-25 (2/4) | — | H |
| 2-chloro-5-(trifluoromethyl)phenyl | $X^2$ | G-2 | J-25 (2/4) | — | H |
| 2,5-dimethylphenyl | $X^2$ | G-2 | J-25 (2/4) | — | H |
| 2-methyl-5-(trifluoromethyl)phenyl | $X^2$ | G-2 | J-25 (2/4) | — | H |
| 3,5-dimethylpryrazol-1-yl | $X^2$ | G-2 | J-25 (2/4) | — | H |
| 5-methyl-3-(trifluoromethyl)pyrazol-1-yl | $X^2$ | G-2 | J-25 (2/4) | — | H |
| 5-chloro-3-(trifluoromethy)pyrazol-1-yl | $X^2$ | G-2 | J-25 (2/4) | — | H |
| 5-bromo-3-(trifluoromethyl)pyrazol-1- | $X^2$ | G-2 | J-25 (2/4) | — | H |
| 5-ethyl-3-(trifluoromethyl)pyrazol-1-yl | $X^2$ | G-2 | J-25 (2/4) | — | H |
| 3,5-bis-(trifluoromethyl)pyrazol-1-yl | $X^2$ | G-2 | J-25 (2/4) | — | H |
| 1-methyl-3-(trifluoromethyl)pyrazol-5-yl | $X^2$ | G-2 | J-25 (2/4) | — | H |
| 1-methyl-4-(trifluoromethyl)imidazol-2-yl | $X^2$ | G-2 | J-25 (2/4) | — | H |
| 2,5-dichlorophenyl | $X^2$ | G-2 | J-26 (2/4) | — | H |
| 2-chloro-5-(trifluoromethyl)phenyl | $X^2$ | G-2 | J-26 (2/4) | — | H |
| 2,5-dimethylphenyl | $X^2$ | G-2 | J-26 (2/4) | — | H |
| 2-methyl-5-(trifluoromethyl)phenyl | $X^2$ | G-2 | J-26 (2/4) | — | H |
| 3,5-dimethylpyrazol-1-yl | $X^2$ | G-2 | J-26 (2/4) | — | H |
| 5-methyl-3-(trifluoromethyl)pyrazol-1-yl | $X^2$ | G-2 | J-26 (2/4) | — | H |
| 5-chloro-3-(trifluoromethyl)pyrazol-1-yl | $X^2$ | G-2 | J-26 (2/4) | — | H |
| 5-bromo-3-(trifluoromethyl)pyrazol-1-yl | $X^2$ | G-2 | J-26 (2/4) | — | H |
| 5-ethyl-3-(trifluoromethy)pyrazol-1-yl | $X^2$ | G-2 | J-26 (2/4) | — | H |
| 3,5-bis-(trifluoromethyl)pyrazol-1-yl | $X^2$ | G-2 | J-26 (2/4) | — | H |
| 1-methyl-3-(trifluoromethyl)pyrazol-5-yl | $X^2$ | G-2 | J-26 (2/4) | — | H |
| 1-methyl-4-(trifluoromethyl)imidazol-2-yl | $X^2$ | G-2 | J-26 (2/4) | — | H |
| 2,5-dichlorophenyl | $X^2$ | G-2 | J-26 (2/4) | 1-Me | H |
| 2-chloro-5-(trifluoromethyl)phenyl | $X^2$ | G-2 | J-26 (2/4) | 1-Me | H |
| 2,5-dimethylphenyl | $X^2$ | G-2 | J-26 (2/4) | 1-Me | H |
| 2-methyl-5-(trifluoromethyl)phenyl | $X^2$ | G-2 | J-26 (2/4) | 1-Me | H |
| 3,5-dimethylpyrazol-1-yl | $X^2$ | G-2 | J-26 (2/4) | 1-Me | H |
| 5-methyl-3-(trifluoromethyl)pyrazol 4-yl | $X^2$ | G-2 | J-26 (2/4) | 1-Me | H |
| 5-chloro-3-(trifluoromethyl)pyrazol-1-yl | $X^2$ | G-2 | J-26 (2/4) | 1-Me | H |
| 5-bromo-3-(trifluoromethyl)pyrazol-1-yl | $X^2$ | G-2 | J-26 (2/4) | 1-Me | H |
| 5-ethyl-3-(trifluoromethyl)pyrazol-1-yl | $X^2$ | G-2 | J-26 (2/4) | 1-Me | H |
| 3,5-bis-(trifluoromethyl)pyrazol-1-yl | $X^2$ | G-2 | J-26 (2/4) | 1-Me | H |
| 1-methyl-3-(trifluoromethyl)pyrazol-5-yl | $X^2$ | G-2 | J-26 (2/4) | 1-Me | H |
| 1-methyl-4-(trifluoromethyl)imidazol-2-yl | $X^2$ | G-2 | J-26 (2/4) | 1-Me | H |
| 2,5-dichlorophenyl | $X^2$ | G-2 | J-26 (2/5) | 1-Me | H |
| 2-chloro-5-(trifluoromethyl)phenyl | $X^2$ | G-2 | J-26 (2/5) | 1-Me | H |
| 2,5-dimethylphenyl | $X^2$ | G-2 | J-26 (2/5) | 1-Me | H |
| 2-methyl-5-(trifluoromethyl)phenyl | $X^2$ | G-2 | J-26 (2/5) | 1-Me | H |
| 3,5-dimethylpyrazol-1-yl | $X^2$ | G-2 | J-26 (2/5) | 1-Me | H |
| 5-methyl-3-(trifluoromethyl)pyrazol-1-yl | $X^2$ | G-2 | J-26 (2/5) | 1-Me | H |

TABLE 4*-continued

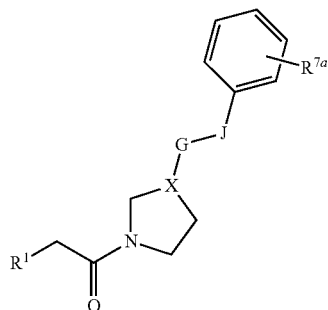

| R¹ | X | G  | J * | (R⁵)ᵧ | R⁷ᵃ |
|---|---|---|---|---|---|
| 5-chloro-3-(trifluoromethyl)pyrazol-1-yl | X² | G-2 | J-26 (2/5) | 1-Me | H |
| 5-bromo-3-(trifluoromethyl)pyrazol-1-yl | X² | G-2 | J-26 (2/5) | 1-Me | H |
| 5-ethyl-3-(trifluoromethyl)pyrazol-1-yl | X² | G-2 | J-26 (2/5) | 1-Me | H |
| 3,5-bis-(trifluoromethyl)pyrazol-1-yl | X² | G-2 | J-26 (2/5) | 1-Me | H |
| 1-methyl-3-(trifluoromethyl)pyrazol-5-yl | X² | G-2 | J-26 (2/5) | 1-Me | H |
| 1-methyl-4-(trifluoromethyl)imidazol-2-yl | X² | G-2 | J-26 (2/5) | 1-Me | H |
| 2,5-dichlorophenyl | X² | G-2 | J-28 (3/5) | — | H |
| 2-chloro-5-(trifluoromethyl)phenyl | X² | G-2 | J-28 (3/5) | — | H |
| 2,5-dimethylphenyl | X² | G-2 | J-28 (3/5) | — | H |
| 2-methyl-5-(trifluoromethyl)phenyl | X² | G-2 | J-28 (3/5) | — | H |
| 3,5-dimethylpyrazol-1-yl | X² | G-2 | J-28 (3/5) | — | H |
| 5-methyl-3-(trifluoromethyl)pyrazol-1-yl | X² | G-2 | J-28 (3/5) | — | H |
| 5-chloro-3-(trifluoromethyl)pyrazol-1-yl | X² | G-2 | J-28 (3/5) | — | H |
| 5-bromo-3-(trifluoromethyl)pyrazol-1-yl | X² | G-2 | J-28 (3/5) | — | H |
| 5-ethyl-3-(trifluoromethyl)pyrazol-1-yl | X² | G-2 | J-28 (3/5) | — | H |
| 3,5-bis-(trifluoromethyl)pyrazol-1-yl | X² | G-2 | J-28 (3/5) | — | H |
| 1-methyl-3-(trifluoromethyl)pyrazol-5-yl | X² | G-2 | J-28 (3/5) | — | H |
| 1-methyl-4-(trifluoromethyl)imidazol-2-yl | X² | G-2 | J-28 (3/5) | — | H |
| 2,5-dichlorophenyl | X² | G-2 | J-30 (3/5) | — | H |
| 2-chloro-5-(trifluoromethyl)phenyl | X² | G-2 | J-30 (3/5) | — | H |
| 2,5-dimethylphenyl | X² | G-2 | J-30 (3/5) | — | H |
| 2-methyl-5-(trifluoromethyl)phenyl | X² | G-2 | J-30 (3/5) | — | H |
| 3,5-dimethylpyrazol-1-yl | X² | G-2 | J-30 (3/5) | — | H |
| 5-methyl-3-(trifluoromethyl)pyrazol-1-yl | X² | G-2 | J-30 (3/5) | — | H |
| 5-chloro-3-(trifluoromethyl)pyrazol-1-yl | X² | G-2 | J-30 (3/5) | — | H |
| 5-bromo-3-(trifluoromethyl)pyrazol-1-yl | X² | G-2 | J-30 (3/5) | — | H |
| 5-ethyl-3-(trifluoromethyl)pyrazol-1-yl | X² | G-2 | J-30 (3/5) | — | H |
| 3,5-bis-(trifluoromethyl)pyrazol-1-yl | X² | G-2 | J-30 (3/5) | — | H |
| 1-methyl-3-(trifluoromethyl)pyrazol-5-yl | X² | G-2 | J-30 (3/5) | — | H |
| 1-methyl-4-(trifluoromethyl)imidazol-2-yl | X² | G-2 | J-30 (3/5) | — | H |
| 2,5-dichlorophenyl | X² | G-2 | J-30 (3/5) | 1-Me | H |
| 2-chloro-5-(trifluoromethyl)phenyl | X² | G-2 | J-30 (3/5) | 1-Me | H |
| 2,5-dimethylphenyl | X² | G-2 | J-30 (3/5) | 1-Me | H |
| 2-methyl-5-(trifluoromethyl)phenyl | X² | G-2 | J-30 (3/5) | 1-Me | H |
| 3,5-dimethylpyrazol-1-yl | X² | G-2 | J-30 (3/5) | 1-Me | H |
| 5-methyl-3-(trifluoromethyl)pyrazol-1-yl | X² | G-2 | J-30 (3/5) | 1-Me | H |
| 5-chloro-3-(trifluoromethyl)pyrazol-1-yl | X² | G-2 | J-30 (3/5) | 1-Me | H |
| 5-bromo-3-(trifluoromethyl)pyrazol-1-yl | X² | G-2 | J-30 (3/5) | 1-Me | H |
| 5-ethyl-3-(trifluoromethyl)pyrazol-1-yl | X² | G-2 | J-30 (3/5) | 1-Me | H |
| 3,5-bis-(trifluoromethyl)pyrazol-1-yl | X² | G-2 | J-30 (3/5) | 1-Me | H |
| 1-methyl-3-(trifluoromethyl)pyrazol-5-yl | X² | G-2 | J-30 (3/5) | 1-Me | H |
| 1-methyl-4-(trifluoromethyl)imidazol-2-yl | X² | G-2 | J-30 (3/5) | 1-Me | H |
| 2,5-dichlorophenyl | X² | G-2 | J-36 (3/5) | 1-Me | H |
| 2-chloro-5-(trifluoromethyl)phenyl | X² | G-2 | J-36 (3/5) | 1-Me | H |
| 2,5-dimethylphenyl | X² | G-2 | J-36 (3/5) | 1-Me | H |
| 2-methyl-5-(trifluoromethyl)phenyl | X² | G-2 | J-36 (3/5) | 1-Me | H |
| 3,5-dimethylpyrazol-1-yl | X² | G-2 | J-36 (3/5) | 1-Me | H |
| 5-methyl-3-(trifluoromethyl)pyrazol-1-yl | X² | G-2 | J-36 (3/5) | 1-Me | H |
| 5-chloro-3-(trifluoromethyl)pyrazol-1-yl | X² | G-2 | J-36 (3/5) | 1-Me | H |
| 5-bromo-3-(trifluoromethyl)pyrazol-1-yl | X² | G-2 | J-36 (3/5) | 1-Me | H |
| 5-ethyl-3-(trifluoromethyl)pyrazol-1-yl | X² | G-2 | J-36 (3/5) | 1-Me | H |
| 3,5-bis-(trifluoromethyl)pyrazol-1-yl | X² | G-2 | J-36 (3/5) | 1-Me | H |
| 1-methyl-3-(trifluoromethyl)pyrazol-5-yl | X² | G-2 | J-36 (3/5) | 1-Me | H |
| 1-methyl-4-(trifluoromethyl)imidazol-2-yl | X² | G-2 | J-36 (3/5) | 1-Me | H |
| 2,5-dichlorophenyl | X² | G-2 | J-37 (2/5) | — | H |
| 2-chloro-5-(trifluoromethyl)phenyl | X² | G-2 | J-37 (2/5) | — | H |
| 2,5-dimethylphenyl | X² | G-2 | J-37 (2/5) | — | H |
| 2-methyl-5-(trifluoromethyl)phenyl | X² | G-2 | J-37 (2/5) | — | H |
| 3,5-dimethylpyrazol-1-yl | X² | G-2 | J-37 (2/5) | — | H |
| 5-methyl-3-(trifluoromethyl)pyrazol-1-yl | X² | G-2 | J-37 (2/5) | — | H |
| 5-chloro-3-(trifluoromethyl)pyrazol-1-yl | X² | G-2 | J-37 (2/5) | — | H |
| 5-bromo-3-(trifluoromethyl)pyrazol-1-yl | X² | G-2 | J-37 (2/5) | — | H |

TABLE 4*-continued

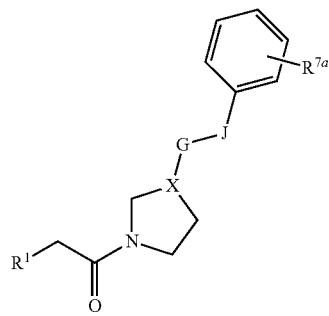

| R¹ | X | G  | J * | (R⁵)ᵧ | R⁷ᵃ |
|---|---|---|---|---|---|
| 5-ethyl-3-(trifluoromethyl)pyrazol-1-yl | X² | G-2 | J-37 (2/5) | — | H |
| 3,5-bis-(trifluoromethyl)pyrazol-1-yl | X² | G-2 | J-37 (2/5) | — | H |
| 1-methyl-3-(trifluoromethyl)pyrazol-5-yl | X² | G-2 | J-37 (2/5) | — | H |
| 1-methyl-4-(trifluoromethyl)imidazol-2-yl | X² | G-2 | J-37 (2/5) | — | H |
| 2,5-dichlorophenyl | X² | G-2 | J-38 (2/5) | — | H |
| 2-chloro-5-(trifluoromethyl)phenyl | X² | G-2 | J-38 (2/5) | — | H |
| 2,5-dimethylphenyl | X² | G-2 | J-38 (2/5) | — | H |
| 2-methyl-5-(trifluoromethyl)phenyl | X² | G-2 | J-38 (2/5) | — | H |
| 3,5-dimethylpyrazol-1-yl | X² | G-2 | J-38 (2/5) | — | H |
| 5-methyl-3-(trifluoromethyl)pyrazol-1-yl | X² | G-2 | J-38 (2/5) | — | H |
| 5-chloro-3-(trifluoromethyl)pyrazol-1-yl | X² | G-2 | J-38 (2/5) | — | H |
| 5-bromo-3-(trifluoromethyl)pyrazol-1-yl | X² | G-2 | J-38 (2/5) | — | H |
| 5-ethyl-3-(trifluoromethyl)pyrazol-1-yl | X² | G-2 | J-38 (2/5) | — | H |
| 3,5-bis-(trifluoromethyl)pyrazol-1-yl | X² | G-2 | J-38 (2/5) | — | H |
| 1-methyl-3-(trifluoromethyl)pyrazol-5-yl | X² | G-2 | J-38 (2/5) | — | H |
| 1-methyl-4-(trifluoromethyl)imidazol-2-yl | X² | G-2 | J-38 (2/5) | — | H |
| 2,5-dichlorophenyl | X² | G-2 | J-39 (3/5) | — | H |
| 2-chloro-5-(trifluoromethyl)phenyl | X² | G-2 | J-39 (3/5) | — | H |
| 2,5-dimethylphenyl | X² | G-2 | J-39 (3/5) | — | H |
| 2-methyl-5-(trifluoromethyl)phenyl | X² | G-2 | J-39 (3/5) | — | H |
| 3,5-dimethylpyrazol-1-yl | X² | G-2 | J-39 (3/5) | — | H |
| 5-methyl-3-(trifluoromethyl)pyrazol-1-yl | X² | G-2 | J-39 (3/5) | — | H |
| 5-chloro-3-(trifluoromethyl)pyrazol-1-yl | X² | G-2 | J-39 (3/5) | — | H |
| 5-bromo-3-(trifluoromethyl)pyrazol-1-yl | X² | G-2 | J-39 (3/5) | — | H |
| 5-ethyl-3-(trifluoromethyl)pyrazol-1-yl | X² | G-2 | J-39 (3/5) | — | H |
| 3,5-bis-(trifluoromethyl)pyrazol-1-yl | X² | G-2 | J-39 (3/5) | — | H |
| 1-methyl-3-(trifluoromethyl)pyrazol-5-yl | X² | G-2 | J-39 (3/5) | — | H |
| 1-methyl-4-(trifluoromethyl)imidazol-2-yl | X² | G-2 | J-39 (3/5) | — | H |
| 2,5-dichlorophenyl | X² | G-2 | J-40 (3/5) | — | H |
| 2-chloro-5-(trifluoromethyl)phenyl | X² | G-2 | J-40 (3/5) | — | H |
| 2,5-dimethylphenyl | X² | G-2 | J-40 (3/5) | — | H |
| 2-methyl-5-(trifluoromethyl)phenyl | X² | G-2 | J-40 (3/5) | — | H |
| 3,5-dimethylpyrazol-1-yl | X² | G-2 | J-40 (3/5) | — | H |
| 5-methyl-3-(trifluoromethyl)pyrazol-1-yl | X² | G-2 | J-40 (3/5) | — | H |
| 5-chloro-3-(trifluoromethyl)pyrazol-1-yl | X² | G-2 | J-40 (3/5) | — | H |
| 5-bromo-3-(trifluoromethyl)pyrazol-1-yl | X² | G-2 | J-40 (3/5) | — | H |
| 5-ethyl-3-(trifluoromethyl)pyrazol-1-yl | X² | G-2 | J-40 (3/5) | — | H |
| 3,5-bis-(trifluoromethyl)pyrazol-1-yl | X² | G-2 | J-40 (3/5) | — | H |
| 1-methyl-3-(trifluoromethyl)pyrazol-5-yl | X² | G-2 | J-40 (3/5) | — | H |
| 1-methyl-4-(trifluoromethyl)imidazol-2-yl | X² | G-2 | J-40 (3/5) | — | H |
| 2,5-dichlorophenyl | X² | G-2 | J-69 (1/3) | — | H |
| 2-chloro-5-(trifluoromethyl)phenyl | X² | G-2 | J-69 (1/3) | — | H |
| 2,5-dimethylphenyl | X² | G-2 | J-69 (1/3) | — | H |
| 2-methyl-5-(trifluoromethyl)phenyl | X² | G-2 | J-69 (1/3) | — | H |
| 3,5-dimethylpyrazol-1-yl | X² | G-2 | J-69 (1/3) | — | H |
| 5-methyl-3-(trifluoromethyl)pyrazol-1-yl | X² | G-2 | J-69 (1/3) | — | H |
| 5-chloro-3-(trifluoromethyl)pyrazol-1-yl | X² | G-2 | J-69 (1/3) | — | H |
| 5-bromo-3-(trifluoromethyl)pyrazol-1-yl | X² | G-2 | J-69 (1/3) | — | H |
| 5-ethyl-3-(trifluoromethyl)pyrazol-1-yl | X² | G-2 | J-69 (1/3) | — | H |
| 3,5-bis-(trifluoromethyl)pyrazol-1-yl | X² | G-2 | J-69 (1/3) | — | H |
| 1-methyl-3-(trifluoromethyl)pyrazol-5-yl | X² | G-2 | J-69 (1/3) | — | H |
| 1-methyl-4-(trifluoromethyl)imidazol-2-yl | X² | G-2 | J-69 (1/3) | — | H |
| 2,5-dichlorophenyl | X² | G-2 | J-69 (1/4) | — | H |
| 2-chloro-5-(trifluoromethyl)phenyl | X² | G-2 | J-69 (1/4) | — | H |
| 2,5-dimethylphenyl | X² | G-2 | J-69 (1/4) | — | H |
| 2-methyl-5-(trifluoromethyl)phenyl | X² | G-2 | J-69 (1/4) | — | H |
| 3,5-dimethylpyrazol-1-yl | X² | G-2 | J-69 (1/4) | — | H |
| 5-methyl-3-(trifluoromethyl)pyrazol-1-yl | X² | G-2 | J-69 (1/4) | — | H |
| 5-chloro-3-(trifluoromethyl)pyrazol-1-yl | X² | G-2 | J-69 (1/4) | — | H |
| 5-bromo-3-(trifluoromethyl)pyrazol-1-yl | X² | G-2 | J-69 (1/4) | — | H |
| 5-ethyl-3-(trifluoromethyl)pyrazol-1-yl | X² | G-2 | J-69 (1/4) | — | H |
| 3,5-bis-(trifluoromethyl)pyrazol-1-yl | X² | G-2 | J-69 (1/4) | — | H |

TABLE 4*-continued

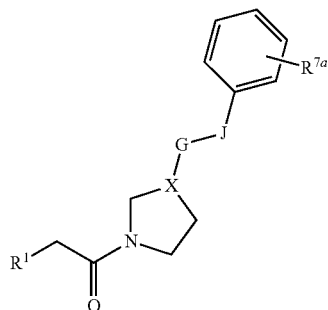

| R¹ | X | G  | J * | (R⁵)y | R⁷ᵃ |
|---|---|---|---|---|---|
| 1-methyl-3-(trifluoromethyl)pyrazol-5-yl | X² | G-2 | J-69 (1/4) | — | H |
| 1-methyl-4-(trifluoromethyl)imidazol-2-yl | X² | G-2 | J-69 (1/4) | — | H |
| 2,5-dichlorophenyl | X² | G-2 | J-11 (3/5) | — | 2-Me |
| 2-chloro-5-(trifluoromethyl)phenyl | X² | G-2 | J-11 (3/5) | — | 2-Me |
| 2,5-dimethylphenyl | X² | G-2 | J-11 (3/5) | — | 2-Me |
| 2-methyl-5-(trifluoromethyl)phenyl | X² | G-2 | J-11 (3/5) | — | 2-Me |
| 3,5-dimethylpyrazol-1-yl | X² | G-2 | J-11 (3/5) | — | 2-Me |
| 5-methyl-3-(trifluoromethyl)pyrazol-1-yl | X² | G-2 | J-11 (3/5) | — | 2-Me |
| 5-chloro-3-(trifluoromethyl)pyrazol-1-yl | X² | G-2 | J-11 (3/5) | — | 2-Me |
| 5-bromo-3-(trifluoromethyl)pyrazol-1-yl | X² | G-2 | J-11 (3/5) | — | 2-Me |
| 5-ethyl-3-(trifluoromethyl)pyrazol-1-yl | X² | G-2 | J-11 (3/5) | — | 2-Me |
| 3,5-bis-(trifluoromethyl)pyrazol-1-yl | X² | G-2 | J-11 (3/5) | — | 2-Me |
| 1-methyl-3-(trifluoromethyl)pyrazol-5-yl | X² | G-2 | J-11 (3/5) | — | 2-Me |
| 1-methyl-4-(trifluoromethyl)imidazol-2-yl | X² | G-2 | J-11 (3/5) | — | 2-Me |
| 2,5-dichlorophenyl | X² | G-2 | J-11 (3/5) | — | 3-Me |
| 2-chloro-5-(trifluoromethyl)phenyl | X² | G-2 | J-11 (3/5) | — | 3-Me |
| 2,5-dimethylphenyl | X² | G-2 | J-11 (3/5) | — | 3-Me |
| 2-methyl-5-(trifluoromethyl)phenyl | X² | G-2 | J-11 (3/5) | — | 3-Me |
| 3,5-dimethylpyrazol-1-yl | X² | G-2 | J-11 (3/5) | — | 3-Me |
| 5-methyl-3-(trifluoromethyl)pyrazol-1-yl | X² | G-2 | J-11 (3/5) | — | 3-Me |
| 5-chloro-3-(trifluoromethyl)pyrazol-1-yl | X² | G-2 | J-11 (3/5) | — | 3-Me |
| 5-bromo-3-(trifluoromethyl)pyrazol-1-yl | X² | G-2 | J-11 (3/5) | — | 3-Me |
| 5-ethyl-3-(trifluoromethyl)pyrazol-1-yl | X² | G-2 | J-11 (3/5) | — | 3-Me |
| 3,5-bis-(trifluoromethyl)pyrazol-1-yl | X² | G-2 | J-11 (3/5) | — | 3-Me |
| 1-methyl-3-(trifluoromethyl)pyrazol-5-yl | X² | G-2 | J-11 (3/5) | — | 3-Me |
| 1-methyl-4-(trifluoromethyl)imidazol-2-yl | X² | G-2 | J-11 (3/5) | — | 3-Me |
| 2,5-dichlorophenyl | X² | G-2 | J-11 (3/5) | — | 4-Me |
| 2-chloro-5-(trifluoromethyl)phenyl | X² | G-2 | J-11 (3/5) | — | 4-Me |
| 2,5-dimethylphenyl | X² | G-2 | J-11 (3/5) | — | 4-Me |
| 2-methyl-5-(trifluoromethyl)phenyl | X² | G-2 | J-11 (3/5) | — | 4-Me |
| 3,5-dimethylpyrazol-1-yl | X² | G-2 | J-11 (3/5) | — | 4-Me |
| 5-methyl-3-(trifluoromethyl)pyrazol-1-yl | X² | G-2 | J-11 (3/5) | — | 4-Me |
| 5-chloro-3-(trifluoromethyl)pyrazol-1-yl | X² | G-2 | J-11 (3/5) | — | 4-Me |
| 5-bromo-3-(trifluoromethyl)pyrazol-1-yl | X² | G-2 | J-11 (3/5) | — | 4-Me |
| 5-ethyl-3-(trifluoromethyl)pyrazol-1-yl | X² | G-2 | J-11 (3/5) | — | 4-Me |
| 3,5-bis-(trifluoromethyl)pyrazol-1-yl | X² | G-2 | J-11 (3/5) | — | 4-Me |
| 1-methyl-3-(trifluoromethyl)pyrazol-5-yl | X² | G-2 | J-11 (3/5) | — | 4-Me |
| 1-methyl-4-(trifluoromethyl)imidazol-2-yl | X² | G-2 | J-11 (3/5) | — | 4-Me |
| 2,5-dichlorophenyl | X² | G-2 | J-11 (3/5) | — | 2-Cl |
| 2-chloro-5-(trifluoromethyl)phenyl | X² | G-2 | J-11 (3/5) | — | 2-Cl |
| 2,5-dimethylphenyl | X² | G-2 | J-11 (3/5) | — | 2-Cl |
| 2-methyl-5-(trifluoromethyl)phenyl | X² | G-2 | J-11 (3/5) | — | 2-Cl |
| 3,5-dimethylpyrazol-1-yl | X² | G-2 | J-11 (3/5) | — | 2-Cl |
| 5-methyl-3-(trifluoromethyl)pyrazol-1-yl | X² | G-2 | J-11 (3/5) | — | 2-Cl |
| 5-chloro-3-(trifluoromethyl)pyrazol-1-yl | X² | G-2 | J-11 (3/5) | — | 2-Cl |
| 5-bromo-3-(rifluoromethyl)pyrazol-1-yl | X² | G-2 | J-11 (3/5) | — | 2-Cl |
| 5-ethyl-3-(trifluoromethyl)pyrazol-1-yl | X² | G-2 | J-11 (3/5) | — | 2-Cl |
| 3,5-bis-(trifluoromethyl)pyrazol-1-yl | X² | G-2 | J-11 (3/5) | — | 2-Cl |
| 1-methyl-3-(trifluoromethyl)pyrazol-5-yl | X² | G-2 | J-11 (3/5) | — | 2-Cl |
| 1-methyl-4-(trifluoromethyl)imidazol-2-yl | X² | G-2 | J-11 (3/5) | — | 2-Cl |
| 2,5-dichlorophenyl | X² | G-2 | J-11 (3/5) | — | 4-Cl |
| 2-chloro-5-(trifluoromethyl)phenyl | X² | G-2 | J-11 (3/5) | — | 4-Cl |
| 2,5-dimethylphenyl | X² | G-2 | J-11 (3/5) | — | 4-Cl |
| 2-methyl-5-(trifluoromethyl)phenyl | X² | G-2 | J-11 (3/5) | — | 4-Cl |
| 3,5-dimethylpyrazol-1-yl | X² | G-2 | J-11 (3/5) | — | 4-Cl |
| 5-methyl-3-(trifluoromethyl)pyrazol-1-yl | X² | G-2 | J-11 (3/5) | — | 4-Cl |
| 5-chloro-3-(trifluoromethyl)pyrazol-1-yl | X² | G-2 | J-11 (3/5) | — | 4-Cl |
| 5-bromo-3-(trifluoromethyl)pyrazol-1-yl | X² | G-2 | J-11 (3/5) | — | 4-Cl |
| 5-ethyl-3-(trifluoromethyl)pyrazol-1-yl | X² | G-2 | J-11 (3/5) | — | 4-Cl |
| 3,5-bis-(trifluoromethyl)pyrazol-1-yl | X² | G-2 | J-11 (3/5) | — | 4-Cl |
| 1-methyl-3-(trifluoromethyl)pyrazol-5-yl | X² | G-2 | J-11 (3/5) | — | 4-Cl |
| 1-methyl-4-(trifluoromethyl)imidazol-2-yl | X² | G-2 | J-11 (3/5) | — | 4-Cl |

TABLE 4*-continued

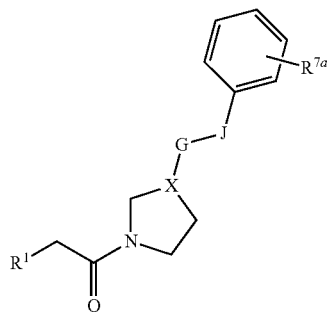

| R¹ | X | G  | J * | (R⁵)_y | R^{7a} |
|---|---|---|---|---|---|
| 2,5-dichlorophenyl | X² | G-2 | J-29 (3/5) | — | 2-Me |
| 2-chloro-5-(trifluoromethyl)phenyl | X² | G-2 | J-29 (3/5) | — | 2-Me |
| 2,5-dimethylphenyl | X² | G-2 | J-29 (3/5) | — | 2-Me |
| 2-methyl-5-(trifluoromethyl)phenyl | X² | G-2 | J-29 (3/5) | — | 2-Me |
| 3,5-dimethylpyrazol-1-yl | X² | G-2 | J-29 (3/5) | — | 2-Me |
| 5-methyl-3-(trifluoromethyl)pyrazol-1-yl | X² | G-2 | J-29 (3/5) | — | 2-Me |
| 5-chloro-3-(trifluoromethyl)pyrazol-1-yl | X² | G-2 | J-29 (3/5) | — | 2-Me |
| 5-bromo-3-(trifluoromethyl)pyrazol-1-yl | X² | G-2 | J-29 (3/5) | — | 2-Me |
| 5-ethyl-3-(trifluoromethyl)pyrazol-1-yl | X² | G-2 | J-29 (3/5) | — | 2-Me |
| 3,5-bis-(trifluoromethyl)pyrazol-1-yl | X² | G-2 | J-29 (3/5) | — | 2-Me |
| 1-methyl-3-(trifluoromethyl)pyrazol-5-yl | X² | G-2 | J-29 (3/5) | — | 2-Me |
| 1-methyl-4-(trifluoromethyl)imidazol-2-yl | X² | G-2 | J-29 (3/5) | — | 2-Me |
| 2,5-dichlorophenyl | X² | G-2 | J-29 (3/5) | — | 3-Me |
| 2-chloro-5-(trifluoromethyl)phenyl | X² | G-2 | J-29 (3/5) | — | 3-Me |
| 2,5-dimethylphenyl | X² | G-2 | J-29 (3/5) | — | 3-Me |
| 2-methyl-5-(trifluoromethyl)phenyl | X² | G-2 | J-29 (3/5) | — | 3-Me |
| 3,5-dimethylpyrazol-1-yl | X² | G-2 | J-29 (3/5) | — | 3-Me |
| 5-methyl-3-(trifluoromethyl)pyrazol-1-yl | X² | G-2 | J-29 (3/5) | — | 3-Me |
| 5-chloro-3-(trifluoromethyl)pyrazol-1-yl | X² | G-2 | J-29 (3/5) | — | 3-Me |
| 5-bromo-3-(trifluoromethyl)pyrazol-1-yl | X² | G-2 | J-29 (3/5) | — | 3-Me |
| 5-ethyl-3-(trifluoromethyl)pyrazol-1-yl | X² | G-2 | J-29 (3/5) | — | 3-Me |
| 3,5-bis-(trifluoromethyl)pyrazol-1-yl | X² | G-2 | J-29 (3/5) | — | 3-Me |
| 1-methyl-3-(trifluoromethyl)pyrazol-5-yl | X² | G-2 | J-29 (3/5) | — | 3-Me |
| 1-methyl-4-(trifluoromethyl)imidazol-2-yl | X² | G-2 | J-29 (3/5) | — | 3-Me |
| 2,5-dichlorophenyl | X² | G-2 | J-29 (3/5) | — | 4-Me |
| 2-chloro-5-(trifluoromethyl)phenyl | X² | G-2 | J-29 (3/5) | — | 4-Me |
| 2,5-dimethylphenyl | X² | G-2 | J-29 (3/5) | — | 4-Me |
| 2-methyl-5-(trifluoromethyl)phenyl | X² | G-2 | J-29 (3/5) | — | 4-Me |
| 3,5-dimethylpyrazol-1-yl | X² | G-2 | J-29 (3/5) | — | 4-Me |
| 5-methyl-3-(trifluoromethyl)pyrazol-1-yl | X² | G-2 | J-29 (3/5) | — | 4-Me |
| 5-chloro-3-(trifluoromethyl)pyrazol-1-yl | X² | G-2 | J-29 (3/5) | — | 4-Me |
| 5-bromo-3-(trifluoromethyl)pyrazol-1-yl | X² | G-2 | J-29 (3/5) | — | 4-Me |
| 5-ethyl-3-(trifluoromethyl)pyrazol-1-yl | X² | G-2 | J-29 (3/5) | — | 4-Me |
| 3,5-bis-(trifluoromethyl)pyrazol-1-yl | X² | G-2 | J-29 (3/5) | — | 4-Me |
| 1-methyl-3-(trifluoromethyl)pyrazol-5-yl | X² | G-2 | J-29 (3/5) | — | 4-Me |
| 1-methyl-4-(trifluoromethyl)imidazol-2-yl | X² | G-2 | J-29 (3/5) | — | 4-Me |
| 2,5-dichlorophenyl | X² | G-2 | J-29 (3/5) | — | 2-Cl |
| 2-chloro-5-(trifluoromethyl)phenyl | X² | G-2 | J-29 (3/5) | — | 2-Cl |
| 2,5-dimethylphenyl | X² | G-2 | J-29 (3/5) | — | 2-Cl |
| 2-methyl-5-(trifluoromethyl)phenyl | X² | G-2 | J-29 (3/5) | — | 2-Cl |
| 3,5-dimethylpyrazol-1-yl | X² | G-2 | J-29 (3/5) | — | 2-Cl |
| 5-methyl-3-(trifluoromethyl)pyrazol-1-yl | X² | G-2 | J-29 (3/5) | — | 2-Cl |
| 5-chloro-3-(trifluoromethyl)pyrazol-1-yl | X² | G-2 | J-29 (3/5) | — | 2-Cl |
| 5-bromo-3-(trifluoromethyl)pyrazol-1-yl | X² | G-2 | J-29 (3/5) | — | 2-Cl |
| 5-ethyl-3-(trifluoromethyl)pyrazol-1-yl | X² | G-2 | J-29 (3/5) | — | 2-Cl |
| 3,5-bis-(trifluoromethyl)pyrazol-1-yl | X² | G-2 | J-29 (3/5) | — | 2-Cl |
| 1-methyl-3-(trifluoromethyl)pyrazol-5-yl | X² | G-2 | J-29 (3/5) | — | 2-Cl |
| 1-methyl-4-(trifluoromethyl)imidazol-2-yl | X² | G-2 | J-29 (3/5) | — | 2-Cl |
| 2,5-dichlorophenyl | X² | G-2 | J-29 (3/5) | — | 4-Cl |
| 2-chloro-5-(trifluoromethyl)phenyl | X² | G-2 | J-29 (3/5) | — | 4-Cl |
| 2,5-dimethylphenyl | X² | G-2 | J-29 (3/5) | — | 4-Cl |
| 2-methyl-5-(trifluoromethyl)phenyl | X² | G-2 | J-29 (3/5) | — | 4-Cl |
| 3,5-dimethylpyrazol-1-yl | X² | G-2 | J-29 (3/5) | — | 4-Cl |
| 5-methyl-3-(trifluoromethyl)pyrazol-1-yl | X² | G-2 | J-29 (3/5) | — | 4-Cl |
| 5-chloro-3-(trifluoromethyl)pyrazol-1-yl | X² | G-2 | J-29 (3/5) | — | 4-Cl |
| 5-bromo-3-(trifluoromethyl)pyrazol-1-yl | X² | G-2 | J-29 (3/5) | — | 4-Cl |
| 5-ethyl-3-(trifluoromethyl)pyrazol-1-yl | X² | G-2 | J-29 (3/5) | — | 4-Cl |
| 3,5-bis-(trifluoromethyl)pyrazol-1-yl | X² | G-2 | J-29 (3/5) | — | 4-Cl |
| 1-methyl-3-(trifluoromethyl)pyrazol-5-yl | X² | G-2 | J-29 (3/5) | — | 4-Cl |
| 1-methyl-4-(trifluoromethyl)imidazol-2-yl | X² | G-2 | J-29 (3/5) | — | 4-Cl |
| 2,5-dichlorophenyl | X² | G-2 | J-29 (3/5) | 5-Me | H |
| 2-chloro-5-(trifluoromethyl)phenyl | X² | G-2 | J-29 (3/5) | 5-Me | H |

TABLE 4*-continued

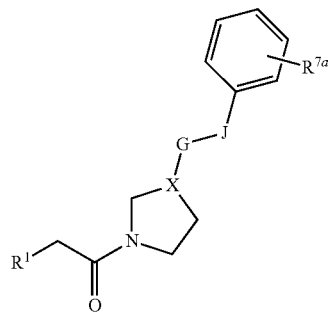

| $R^1$ | X | G  | J * | $(R^5)_y$ | $R^{7a}$ |
|---|---|---|---|---|---|
| 2,5-dimethylphenyl | $X^2$ | G-2 | J-29 (3/5) | 5-Me | H |
| 2-methyl-5-(trifluoromethyl)phenyl | $X^2$ | G-2 | J-29 (3/5) | 5-Me | H |
| 3,5-dimethylpyrazol-1-yl | $X^2$ | G-2 | J-29 (3/5) | 5-Me | H |
| 5-methyl-3-(trifluoromethyl)pyrazol-1-yl | $X^2$ | G-2 | J-29 (3/5) | 5-Me | H |
| 5-chloro-3-(trifluoromethyl)pyrazol-1-yl | $X^2$ | G-2 | J-29 (3/5) | 5-Me | H |
| 5-bromo-3-(trifluoromethyl)pyrazol-1-yl | $X^2$ | G-2 | J-29 (3/5) | 5-Me | H |
| 5-ethyl-3-(trifluoromethyl)pyrazol-1-yl | $X^2$ | G-2 | J-29 (3/5) | 5-Me | H |
| 3,5-bis-(trifluoromethyl)pyrazol-1-yl | $X^2$ | G-2 | J-29 (3/5) | 5-Me | H |
| 1-methyl-3-(trifluoromethyl)pyrazol-5-yl | $X^2$ | G-2 | J-29 (3/5) | 5-Me | H |
| 1-methyl-4-(trifluoromethyl)imidazol-2-yl | $X^2$ | G-2 | J-29 (3/5) | 5-Me | H |
| 2,5-dichlorophenyl | $X^2$ | G-2 | J-29 (3/5) | 4-Me | H |
| 2-chloro-5-(trifluoromethyl)phenyl | $X^2$ | G-2 | J-29 (3/5) | 4-Me | H |
| 2,5-dimethylphenyl | $X^2$ | G-2 | J-29 (3/5) | 4-Me | H |
| 2-methyl-5-(trifluoromethyl)phenyl | $X^2$ | G-2 | J-29 (3/5) | 4-Me | H |
| 3,5-dimethylpyrazol-1-yl | $X^2$ | G-2 | J-29 (3/5) | 4-Me | H |
| 5-methyl-3-(trifluoromethyl)pyrazol-1-yl | $X^2$ | G-2 | J-29 (3/5) | 4-Me | H |
| 5-chloro-3-(trifluoromethyl)pyrazol-1-yl | $X^2$ | G-2 | J-29 (3/5) | 4-Me | H |
| 5-bromo-3-(trifluoromethyl)pyrazol-1-yl | $X^2$ | G-2 | J-29 (3/5) | 4-Me | H |
| 5-ethyl-3-(trifluoromethyl)pyrazol-1-yl | $X^2$ | G-2 | J-29 (3/5) | 4-Me | H |
| 3,5-bis-(trifluoromethyl)pyrazol-1-yl | $X^2$ | G-2 | J-29 (3/5) | 4-Me | H |
| 1-methyl-3-(trifluoromethyl)pyrazol-5-yl | $X^2$ | G-2 | J-29 (3/5) | 4-Me | H |
| 1-methyl-4-(trifluoromethyl)imidazol-2-yl | $X^2$ | G-2 | J-29 (3/5) | 4-Me | H |
| 2,5-dichlorophenyl | $X^2$ | G-2 | J-29 (3/5) | 4,4-di-Me | H |
| 2-chloro-5-(trifluoromethyl)phenyl | $X^2$ | G-2 | J-29 (3/5) | 4,4-di-Me | H |
| 2,5-dimethylphenyl | $X^2$ | G-2 | J-29 (3/5) | 4,4-di-Me | H |
| 2-methyl-5-(trifluoromethyl)phenyl | $X^2$ | G-2 | J-29 (3/5) | 4,4-di-Me | H |
| 3,5-dimethylpyrazol-1-yl | $X^2$ | G-2 | J-29 (3/5) | 4,4-di-Me | H |
| 5-methyl-3-(trifluoromethyl)pyrazol-1-yl | $X^2$ | G-2 | J-29 (3/5) | 4,4-di-Me | H |
| 5-chloro-3-(trifluoromethyl)pyrazol-1-yl | $X^2$ | G-2 | J-29 (3/5) | 4,4-di-Me | H |
| 5-bromo-3-(trifluoromethyl)pyrazol-1-yl | $X^2$ | G-2 | J-29 (3/5) | 4,4-di-Me | H |
| 5-ethyl-3-(trifluoromethyl)pyrazol-1-yl | $X^2$ | G-2 | J-29 (3/5) | 4,4-di-Me | H |
| 3,5-bis-(trifluoromethyl)pyrazol-1-yl | $X^2$ | G-2 | J-29 (3/5) | 4,4-di-Me | H |
| 1-methyl-3-(trifluoromethyl)pyrazol-5-yl | $X^2$ | G-2 | J-29 (3/5) | 4,4-di-Me | H |
| 1-methyl-4-(trifluoromethyl)imidazol-2-yl | $X^2$ | G-2 | J-29 (3/5) | 4,4-di-Me | H |

*The definitions of G and J in the compounds of this table are as defined in Exhibits 2 and 3 in the above Embodiments. The $(R^5)_y$ column refers the substituents $(R^5)_x$ shown on J groups in Exhibit 3 other than the phenyl ring substituted by $R^{7a}$ shown in the structure heading this table. $R^{7a}$ may be selected from H (to indicate no substitution on the phenyl ring) as well as the substituents defined for $R^7$. A dash "—" in the $(R^5)_y$ column indicates no substitution on J besides the phenyl ring substituted by $R^{7a}$.

** $R^{3a}$ substituent in G is H.

*** Numbers in parentheses refer to the attachment points on ring J. The first number is the attachment point for ring G; the second number is the attachment point for the phenyl ring.

TABLE 5

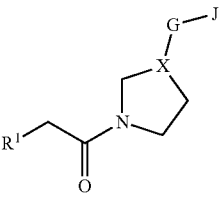

wherein J is one of J-29-1 through J-29-57 (as depicted in Exhibit A above).

| J |
|---|
| $R^1$ is 2,5-dichlorophenyl; X is $X^1$; G* is G-1. |
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |
| $R^1$ is 2,5-dichlorophenyl; X is $X^2$; G* is G-1. |
| J-29-1 |
| J-29-2 |
| J-29-3 |
| J-29-4 |
| J-29-5 |

TABLE 5-continued

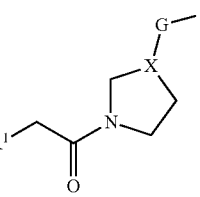

wherein J is one of J-29-1 through J-29-57 (as depicted in Exhibit A above).

| J |
|---|
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |
| $R^1$ is 2,5-dichlorophenyl; X is $X^1$; G* is G-2. |
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |

TABLE 5-continued

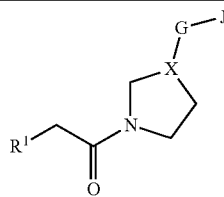

wherein J is one of J-29-1 through J-29-57 (as depicted in Exhibit A above).

| J |
|---|
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 2,5-dichlorophenyl; X is $X^2$; $G^*$ is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |

TABLE 5-continued

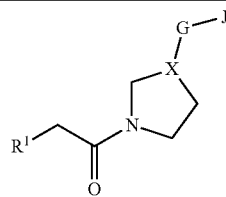

wherein J is one of J-29-1 through J-29-57 (as depicted in Exhibit A above).

| J |
|---|
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 2-chloro-5-(trifluoromethyl)phenyl; X is $X^1$; $G^*$ is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |

TABLE 5-continued

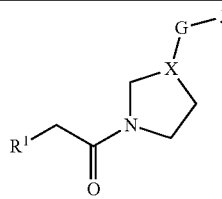

wherein J is one of J-29-1 through J-29-57 (as depicted in Exhibit A above).

| J |
|---|
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 2-chloro-5-(trifluoromethyl)phenyl; X is $X^2$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 2-chloro-5-(trifluoromethyl)phenyl; X is $X^1$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |

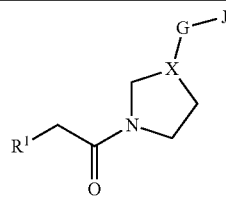

wherein J is one of J-29-1 through J-29-57 (as depicted in Exhibit A above).

TABLE 5-continued

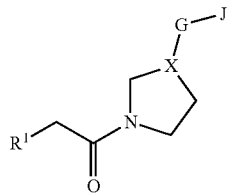

wherein J is one of J-29-1 through J-29-57 (as depicted in Exhibit A above).

| J |
|---|
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 2-chloro-5-(trifluoromethyl)phenyl; X is $X^2$; G* is G-2.

| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |

TABLE 5-continued

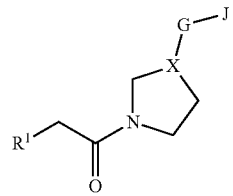

wherein J is one of J-29-1 through J-29-57 (as depicted in Exhibit A above).

| J |
|---|
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 2,5-dimethylphenyl; X is $X^1$; G* is G-1.

| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |

TABLE 5-continued

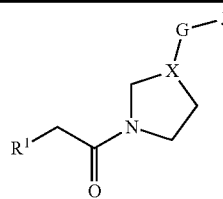

wherein J is one of J-29-1 through J-29-57 (as depicted in Exhibit A above).

| J |
|---|
| J-29-55 |
| J-29-56 |
| J-29-57 |

$R^1$ is 2,5-dimethylphenyl; X is $X^2$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 2,5-dimethylphenyl; X is $X^1$; G* is G-2.

| J |
|---|
| J-29-1 |
| J-29-2 |

TABLE 5-continued

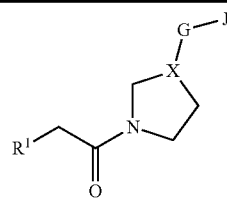

wherein J is one of J-29-1 through J-29-57 (as depicted in Exhibit A above).

| J |
|---|
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 2,5-dimethylphenyl; X is $X^2$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |

TABLE 5-continued

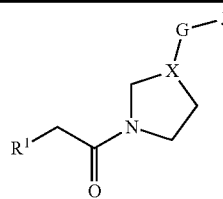

wherein J is one of J-29-1 through J-29-57 (as depicted in Exhibit A above).

| J |
|---|
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 2-methyl-5-(trifluoromethyl)phenyl; X is $X^1$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |

TABLE 5-continued

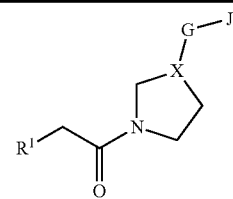

wherein J is one of J-29-1 through J-29-57 (as depicted in Exhibit A above).

| J |
|---|
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 2-methyl-5-(trifluoromethyl)phenyl; X is $X^2$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |

TABLE 5-continued

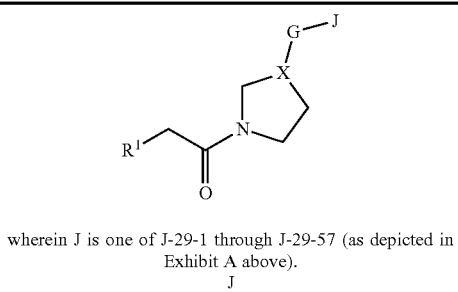

wherein J is one of J-29-1 through J-29-57 (as depicted in Exhibit A above).

| J |
|---|
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 2-methyl-5-(trifluoromethyl)phenyl; X is $X^1$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |

TABLE 5-continued

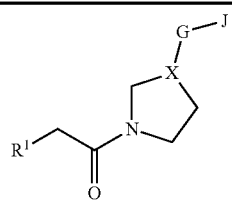

wherein J is one of J-29-1 through J-29-57 (as depicted in Exhibit A above).

| J |
|---|
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 2-methyl-5-(trifluoromethyl)phenyl; X is $X^2$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |

TABLE 5-continued

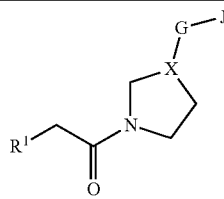

wherein J is one of J-29-1 through J-29-57 (as depicted in Exhibit A above).

| J |
|---|
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 3,5-dimethylpyrazol-1-yl; X is $X^1$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |

TABLE 5-continued

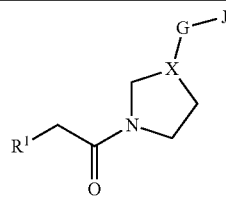

wherein J is one of J-29-1 through J-29-57 (as depicted in Exhibit A above).

| J |
|---|
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 3,5-dimethylpyrazol-1-yl; X is $X^2$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |

TABLE 5-continued

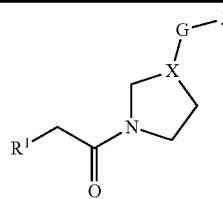

wherein J is one of J-29-1 through J-29-57 (as depicted in Exhibit A above).

| J |
|---|
| J-29-52 |
| J-29-53 |
| J-29-54 |
| J-29-55 |
| J-29-56 |
| J-29-57 |

$R^1$ is 3,5-dimethylpyrazol-1-yl; X is $X^1$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |

TABLE 5-continued

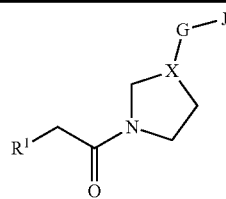

wherein J is one of J-29-1 through J-29-57 (as depicted in Exhibit A above).

| J |
|---|
| J-29-56 |
| J-29-57 |

$R^1$ is 3,5-dimethylpyrazol-1-yl; X is $X^2$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 3,5-dichloropyrazol-1-yl; X is $X^1$; G* is G-1.

| J |
|---|
| J-29-1 |
| J-29-2 |
| J-29-3 |

TABLE 5-continued

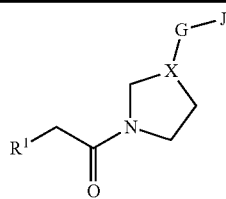

wherein J is one of J-29-1 through J-29-57 (as depicted in Exhibit A above).

| J |
|---|
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 3,5-dichloropyrazol-1-yl; X is $X^2$; G* is G-1.

| J-29-1 |
| J-29-2 |
| J-29-3 |
| J-29-4 |
| J-29-5 |
| J-29-6 |
| J-29-7 |
| J-29-8 |
| J-29-9 |
| J-29-10 |

TABLE 5-continued

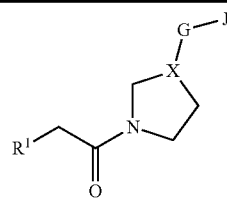

wherein J is one of J-29-1 through J-29-57 (as depicted in Exhibit A above).

| J |
|---|
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 3,5-dichloropyrazol-1-yl; X is $X^1$; G* is G-2.

| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |

TABLE 5-continued

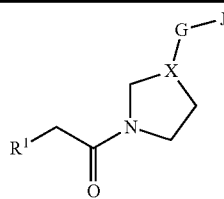

wherein J is one of J-29-1 through J-29-57 (as depicted in Exhibit A above).

| J |
|---|
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 3,5-dichloropyrazol-1-yl; X is $X^2$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |

TABLE 5-continued

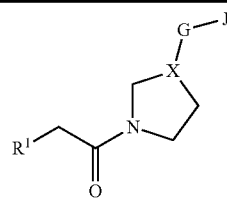

wherein J is one of J-29-1 through J-29-57 (as depicted in Exhibit A above).

| J |
|---|
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 3,5-dibromopyrazol-1-yl; X is $X^1$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |

TABLE 5-continued wherein J is one of J-29-1 through J-29-57 (as depicted in Exhibit A above).

| J |
|---|
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 3,5-dibromopyrazol-1-yl; X is $X^2$; $G^*$ is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 3,5-dibromopyrazol-1-yl; X is $X^1$; $G^*$ is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |

TABLE 5-continued

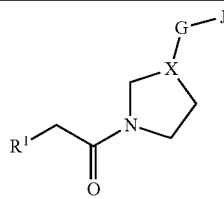

wherein J is one of J-29-1 through J-29-57 (as depicted in Exhibit A above).

| J |
|---|
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 3,5-dibromopyrazol-1-yl; X is $X^2$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |

TABLE 5-continued

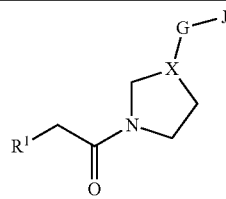

wherein J is one of J-29-1 through J-29-57 (as depicted in Exhibit A above).

| J |
|---|
| J-29-53 |
| J-29-54 |
| J-29-55 |
| J-29-56 |
| J-29-57 |

$R^1$ is 5-methyl-3-(trifluoromethyl)pyrazol-1-yl; X is $X^1$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |

TABLE 5-continued

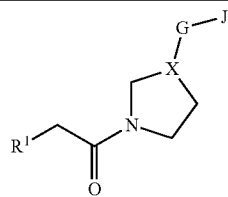

wherein J is one of J-29-1 through J-29-57 (as depicted in Exhibit A above).

| J |
|---|
| J-29-56 |
| J-29-57 |

$R^1$ is 5-methyl-3-(trifluoromethyl)pyrazol-1-yl; X is $X^2$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 5-methyl-3-(trifluoromethyl)pyrazol-1-yl; X is $X^1$; G* is G-2.

| J |
|---|
| J-29-1 |
| J-29-2 |
| J-29-3 |

TABLE 5-continued

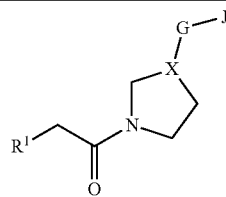

wherein J is one of J-29-1 through J-29-57 (as depicted in Exhibit A above).

| J |
|---|
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 5-methyl-3-(trifluoromethyl)pyrazol-1-yl; X is $X^2$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |

TABLE 5-continued

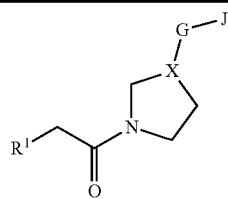

wherein J is one of J-29-1 through J-29-57 (as depicted in Exhibit A above).

| J |
|---|
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 5-chloro-3-(trifluoromethyl)pyrazol-1-yl; X is $X^1$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |

TABLE 5-continued

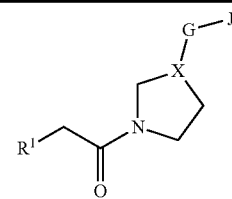

wherein J is one of J-29-1 through J-29-57 (as depicted in Exhibit A above).

| J |
|---|
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 5-chloro-3-(trifluoromethyl)pyrazol-1-yl; X is $X^2$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |

TABLE 5-continued

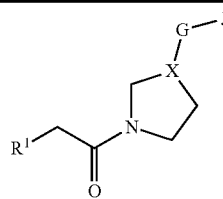

wherein J is one of J-29-1 through J-29-57 (as depicted in Exhibit A above).

| J |
|---|
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 5-chloro-3-(trifluoromethyl)pyrazol-1-yl; X is $X^1$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |

TABLE 5-continued

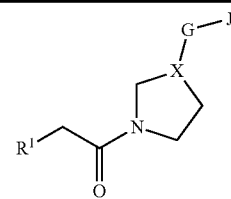

wherein J is one of J-29-1 through J-29-57 (as depicted in Exhibit A above).

| J |
|---|
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 5-chloro-3-(trifluoromethyl)pyrazol-1-yl; X is $X^2$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |

TABLE 5-continued

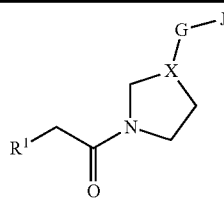

wherein J is one of J-29-1 through J-29-57 (as depicted in Exhibit A above).

| J |
|---|
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 5-bromo-3-(trifluoromethyl)pyrazol-1-yl; X is $X^1$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |

TABLE 5-continued

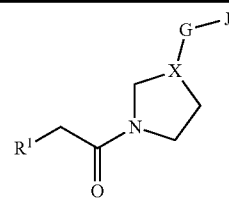

wherein J is one of J-29-1 through J-29-57 (as depicted in Exhibit A above).

| J |
|---|
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 5-bromo-3-(trifluoromethyl)pyrazol-1-yl; X is $X^2$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |

TABLE 5-continued

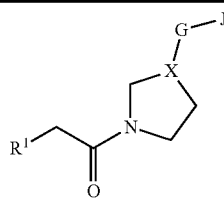

wherein J is one of J-29-1 through J-29-57 (as depicted in Exhibit A above).

| J |
|---|
| J-29-53 |
| J-29-54 |
| J-29-55 |
| J-29-56 |
| J-29-57 |
| $R^1$ is 5-bromo-3-(trifluoromethyl)pyrazol-1-yl; X is $X^1$; G* is G-2. |
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |

TABLE 5-continued

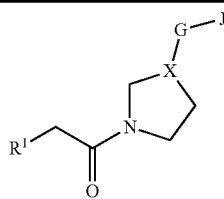

wherein J is one of J-29-1 through J-29-57 (as depicted in Exhibit A above).

| J |
|---|
| J-29-56 |
| J-29-57 |
| $R^1$ is 5-bromo-3-(trifluoromethyl)pyrazol-1-yl; X is $X^2$; G* is G-2. |
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |
| $R^1$ is 5-ethyl-3-(trifluoromethyl)pyrazol-1-yl; X is $X^1$; G* is G-1. |
| J-29-1 |
| J-29-2 |
| J-29-3 |

TABLE 5-continued

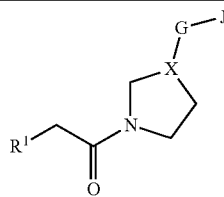

wherein J is one of J-29-1 through J-29-57 (as depicted in Exhibit A above).

| J |
|---|
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 5-ethyl-3-(trifluoromethyl)pyrazol-1-yl; X is $X^2$; G* is G-1.

| J-29-1 |
| J-29-2 |
| J-29-3 |
| J-29-4 |
| J-29-5 |
| J-29-6 |
| J-29-7 |
| J-29-8 |
| J-29-9 |
| J-29-10 |

TABLE 5-continued

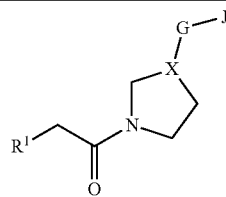

wherein J is one of J-29-1 through J-29-57 (as depicted in Exhibit A above).

| J |
|---|
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 5-ethyl-3-(trifluoromethyl)pyrazol-1-yl; X is $X^1$; G* is G-2.

| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |

TABLE 5-continued

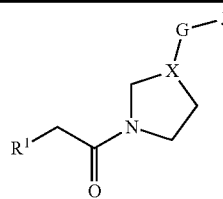

wherein J is one of J-29-1 through J-29-57 (as depicted in Exhibit A above).

| J |
|---|
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 5-ethyl-3-(trifluoromethyl)pyrazol-1-yl; X is $X^2$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |

TABLE 5-continued

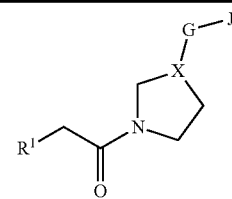

wherein J is one of J-29-1 through J-29-57 (as depicted in Exhibit A above).

| J |
|---|
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 3,5-bis-(trifluoromethyl)pyrazol-1-yl; X is $X^1$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |

TABLE 5-continued

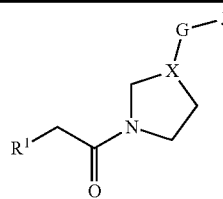

wherein J is one of J-29-1 through J-29-57 (as depicted in Exhibit A above).

J

J-29-32
J-29-33
J-29-34
J-29-35
J-29-36
J-29-37
J-29-38
J-29-39
J-29-40
J-29-41
J-29-42
J-29-43
J-29-44
J-29-45
J-29-46
J-29-47
J-29-48
J-29-49
J-29-50
J-29-51
J-29-52
J-29-53
J-29-54
J-29-55
J-29-56
J-29-57

$R^1$ is 3,5-bis-(trifluoromethyl)pyrazol-1-yl; X is $X^2$; G* is G-1.

J-29-1
J-29-2
J-29-3
J-29-4
J-29-5
J-29-6
J-29-7
J-29-8
J-29-9
J-29-10
J-29-11
J-29-12
J-29-13
J-29-14
J-29-15
J-29-16
J-29-17
J-29-18
J-29-19
J-29-20
J-29-21
J-29-22
J-29-23
J-29-24
J-29-25
J-29-26
J-29-27
J-29-28
J-29-29
J-29-30
J-29-31
J-29-32
J-29-33
J-29-34
J-29-35
J-29-36
J-29-37
J-29-38

TABLE 5-continued

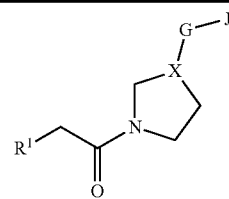

wherein J is one of J-29-1 through J-29-57 (as depicted in Exhibit A above).

J

J-29-39
J-29-40
J-29-41
J-29-42
J-29-43
J-29-44
J-29-45
J-29-46
J-29-47
J-29-48
J-29-49
J-29-50
J-29-51
J-29-52
J-29-53
J-29-54
J-29-55
J-29-56
J-29-57

$R^1$ is 3,5-bis-(trifluoromethyl)pyrazol-1-yl; X is $X^1$; G* is G-2.

J-29-1
J-29-2
J-29-3
J-29-4
J-29-5
J-29-6
J-29-7
J-29-8
J-29-9
J-29-10
J-29-11
J-29-12
J-29-13
J-29-14
J-29-15
J-29-16
J-29-17
J-29-18
J-29-19
J-29-20
J-29-21
J-29-22
J-29-23
J-29-24
J-29-25
J-29-26
J-29-27
J-29-28
J-29-29
J-29-30
J-29-31
J-29-32
J-29-33
J-29-34
J-29-35
J-29-36
J-29-37
J-29-38
J-29-39
J-29-40
J-29-41
J-29-42
J-29-43
J-29-44
J-29-45

TABLE 5-continued

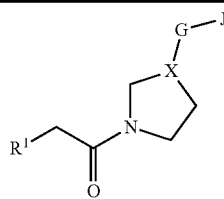

wherein J is one of J-29-1 through J-29-57 (as depicted in Exhibit A above).

| J |
|---|
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 3,5-bis-(trifluoromethyl)pyrazol-1-yl; X is $X^2$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |

TABLE 5-continued

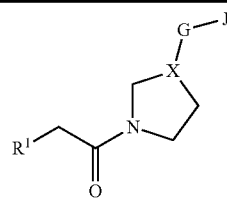

wherein J is one of J-29-1 through J-29-57 (as depicted in Exhibit A above).

| J |
|---|
| J-29-53 |
| J-29-54 |
| J-29-55 |
| J-29-56 |
| J-29-57 |

$R^1$ is 3-methyl-5-(trifluoromethyl)pyrazol-1-yl; X is $X^1$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |

TABLE 5-continued

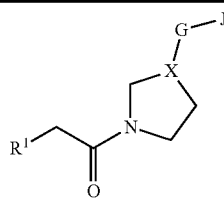

wherein J is one of J-29-1 through J-29-57 (as depicted in Exhibit A above).

| J |
|---|
| J-29-56 |
| J-29-57 |

R¹ is 3-methyl-5-(trifluoromethyl)pyrazol-1-yl; X is $X^2$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

R¹ is 3-methyl-5-(trifluoromethyl)pyrazol-1-yl; X is $X^1$; G* is G-2.

| J |
|---|
| J-29-1 |
| J-29-2 |
| J-29-3 |

TABLE 5-continued

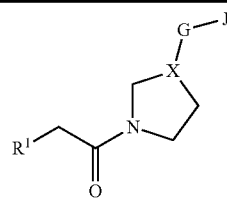

wherein J is one of J-29-1 through J-29-57 (as depicted in Exhibit A above).

| J |
|---|
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

R¹ is 3-methyl-5-(trifluoromethyl)pyrazol-1-yl; X is $X^2$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |

TABLE 5-continued
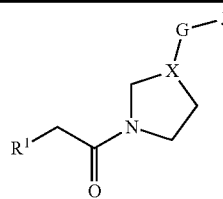
wherein J is one of J-29-1 through J-29-57 (as depicted in Exhibit A above).
| J |
|---|
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |
$R^1$ is 3-chloro-5-(trifluoromethyl)pyrazol-1-yl; X is $X^1$; G* is G-1.
| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |
$R^1$ is 3-chloro-5-(trifluoromethyl)pyrazol-1-yl; X is $X^2$; G* is G-1.
| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |

TABLE 5-continued

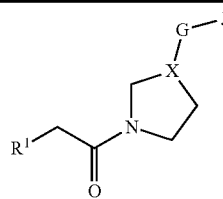

wherein J is one of J-29-1 through J-29-57 (as depicted in Exhibit A above).

| J |
|---|
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 3-chloro-5-(trifluoromethyl)pyrazol-1-yl; X is $X^1$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |

TABLE 5-continued

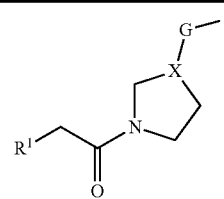

wherein J is one of J-29-1 through J-29-57 (as depicted in Exhibit A above).

| J |
|---|
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 3-chloro-5-(trifluoromethyl)pyrazol-1-yl; X is $X^2$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |

TABLE 5-continued

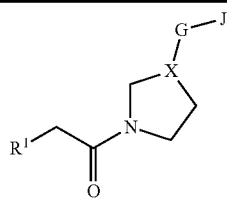

wherein J is one of J-29-1 through J-29-57 (as depicted in Exhibit A above).

| J |
|---|
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 3-bromo-5-(trifluoromethyl)pyrazol-1-yl; X is $X^1$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |

TABLE 5-continued

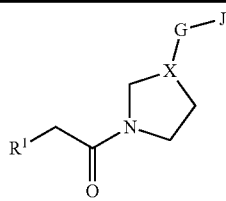

wherein J is one of J-29-1 through J-29-57 (as depicted in Exhibit A above).

| J |
|---|
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 3-bromo-5-(trifluoromethyl)pyrazol-1-yl; X is $X^2$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |

TABLE 5-continued

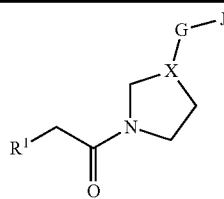

wherein J is one of J-29-1 through J-29-57 (as depicted in Exhibit A above).

| J |
|---|
| J-29-53 |
| J-29-54 |
| J-29-55 |
| J-29-56 |
| J-29-57 |

$R^1$ is 3-bromo-5-(trifluoromethyl)pyrazol-1-yl; X is $X^1$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |

TABLE 5-continued

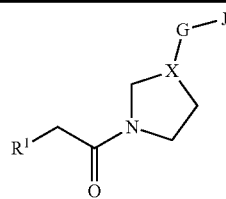

wherein J is one of J-29-1 through J-29-57 (as depicted in Exhibit A above).

| J |
|---|
| J-29-56 |
| J-29-57 |

$R^1$ is 3-bromo-5-(trifluoromethyl)pyrazol-1-yl; X is $X^2$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 5-methoxy-3-(trifluoromethyl)pyrazol-1-yl; X is $X^1$; G* is G-1.

| J |
|---|
| J-29-1 |
| J-29-2 |
| J-29-3 |

TABLE 5-continued

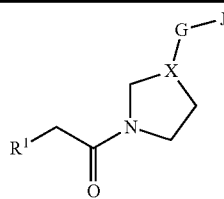

wherein J is one of J-29-1 through J-29-57 (as depicted in Exhibit A above).

| J |
|---|
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 5-methoxy-3-(trifluoromethyl)pyrazol-1-yl; X is $X^2$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |

TABLE 5-continued

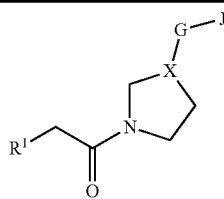

wherein J is one of J-29-1 through J-29-57 (as depicted in Exhibit A above).

| J |
|---|
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 5-methoxy-3-(trifluoromethyl)pyrazol-1-yl; X is $X^1$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |

TABLE 5-continued

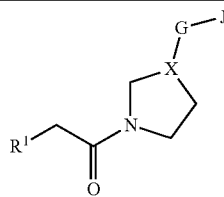

wherein J is one of J-29-1 through J-29-57 (as depicted in Exhibit A above).

| J |
|---|
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 5-methoxy-3-(trifluoromethyl)pyrazol-1-yl; X is $X^2$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |

TABLE 5-continued

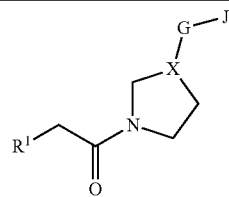

wherein J is one of J-29-1 through J-29-57 (as depicted in Exhibit A above).

| J |
|---|
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 5-difluoromethoxy-3-(trifluoromethyl)pyrazol-1-yl; X is $X^1$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |

TABLE 5-continued

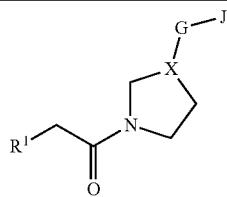

wherein J is one of J-29-1 through J-29-57 (as depicted in Exhibit A above).

| J |
|---|
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 5-difluoromethoxy-3-(trifluoromethyl)pyrazol-1-yl; X is $X^2$; G* is G-1.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |

TABLE 5-continued

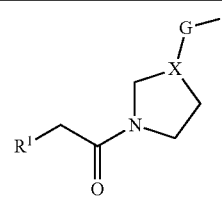

wherein J is one of J-29-1 through J-29-57 (as depicted in Exhibit A above).

| J |
|---|
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 5-difluoromethoxy-3-(trifluoromethyl)pyrazol-1-yl; X is $X^1$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |

TABLE 5-continued

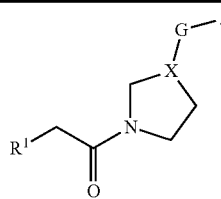

wherein J is one of J-29-1 through J-29-57 (as depicted in Exhibit A above).

| J |
|---|
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |

$R^1$ is 5-difluoromethoxy-3-(trifluoromethyl)pyrazol-1-yl; X is $X^2$; G* is G-2.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |

TABLE 5-continued

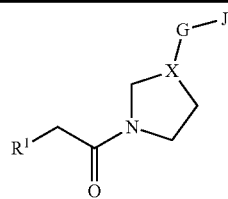

wherein J is one of J-29-1 through J-29-57 (as depicted in Exhibit A above).

| J |
|---|
| J-29-53 |
| J-29-54 |
| J-29-55 |
| J-29-56 |
| J-29-57 |

Table 5 above identifies particular compounds comprising a J group selected from J-29-1 through J-29-57 (i.e. particular examples of J-29). As many J-29-1 to J-29-57 include a chiral center, these J groups are illustrated in a particular enantiomeric configuration, which in some instances may provide the greatest fungicidal activity. One skilled in the art immediately recognizes the antipode (i.e. opposite enantiomer) for each of the compounds listed, and furthermore understands that the enantiomers can be present as pure enantiomers or in mixtures enriched in one enantiomer or in racemic mixtures.

** $R^{3a}$ substituent in G is H.

TABLE 6

| $R^{4a1}$ | $R^{4a2}$ | $A^a$ | $R^{4a1}$ | $R^{4a2}$ | $A^a$ |
|---|---|---|---|---|---|
| Me | Me | H | Me | Me | $CH_2CO_2Et$ |
| Me | Et | H | Me | Et | $CH_2CO_2Et$ |
| Me | Cl | H | Me | Cl | $CH_2CO_2Et$ |
| Me | Br | H | Me | Br | $CH_2CO_2Et$ |
| Me | I | H | Me | I | $CH_2CO_2Et$ |
| Me | $CF_2H$ | H | Me | $CF_2H$ | $CH_2CO_2Et$ |
| Me | $CF_3$ | H | Me | $CF_3$ | $CH_2CO_2Et$ |
| Me | $CF_3CH_2$ | H | Me | $CF_3CH_2$ | $CH_2CO_2Et$ |
| Me | $CF_3CF_2$ | H | Me | $CF_3CF_2$ | $CH_2CO_2Et$ |
| Me | $CCl_3$ | H | Me | $CCl_3$ | $CH_2CO_2Et$ |
| Me | MeO | H | Me | MeO | $CH_2CO_2Et$ |
| Et | Me | H | Et | Me | $CH_2CO_2Et$ |
| Et | Et | H | Et | Et | $CH_2CO_2Et$ |
| Et | Cl | H | Et | Cl | $CH_2CO_2Et$ |
| Et | Br | H | Et | Br | $CH_2CO_2Et$ |
| Et | I | H | Et | I | $CH_2CO_2Et$ |
| Et | $CF_2H$ | H | Et | $CF_2H$ | $CH_2CO_2Et$ |
| Et | $CF_3$ | H | Et | $CF_3$ | $CH_2CO_2Et$ |
| Et | $CF_3CH_2$ | H | Et | $CF_3CH_2$ | $CH_2CO_2Et$ |
| Et | $CF_3CF_2$ | H | Et | $CF_3CF_2$ | $CH_2CO_2Et$ |
| Et | $CCl_3$ | H | Et | $CCl_3$ | $CH_2CO_2Et$ |
| Et | MeO | H | Et | MeO | $CH_2CO_2Et$ |
| Cl | Me | H | Cl | Me | $CH_2CO_2Et$ |
| Cl | Et | H | Cl | Et | $CH_2CO_2Et$ |
| Cl | Cl | H | Cl | Cl | $CH_2CO_2Et$ |
| Cl | Br | H | Cl | Br | $CH_2CO_2Et$ |
| Cl | I | H | Cl | I | $CH_2CO_2Et$ |
| Cl | $CF_2H$ | H | Cl | $CF_2H$ | $CH_2CO_2Et$ |
| Cl | $CF_3$ | H | Cl | $CF_3$ | $CH_2CO_2Et$ |
| Cl | $CF_3CH_2$ | H | Cl | $CF_3CH_2$ | $CH_2CO_2Et$ |

TABLE 6-continued

| $R^{4a1}$ | $R^{4a2}$ | $A^a$ | $R^{4a1}$ | $R^{4a2}$ | $A^a$ |
|---|---|---|---|---|---|
| Cl | CF3CF2 | H | Cl | CF3CF2 | CH2CO2Et |
| Cl | CCl3 | H | Cl | CCl3 | CH2CO2Et |
| Cl | MeO | H | Cl | MeO | CH2CO2Et |
| Br | Me | H | Br | Me | CH2CO2Et |
| Br | Et | H | Br | Et | CH2CO2Et |
| Br | Cl | H | Br | Cl | CH2CO2Et |
| Br | Br | H | Br | Br | CH2CO2Et |
| Br | I | H | Br | I | CH2CO2Et |
| Br | CF2H | H | Br | CF2H | CH2CO2Et |
| Br | CF3 | H | Br | CF3 | CH2CO2Et |
| Br | CF3CH2 | H | Br | CF3CH2 | CH2CO2Et |
| Br | CF3CF2 | H | Br | CF3CF2 | CH2CO2Et |
| Br | CCl3 | H | Br | CCl3 | CH2CO2Et |
| Br | MeO | H | Br | MeO | CH2CO2Et |
| I | Me | H | I | Me | CH2CO2Et |
| I | Et | H | I | Et | CH2CO2Et |
| I | Cl | H | I | Cl | CH2CO2Et |
| I | Br | H | I | Br | CH2CO2Et |
| I | I | H | I | I | CH2CO2Et |
| I | CF2H | H | I | CF2H | CH2CO2Et |
| I | CF3 | H | I | CF3 | CH2CO2Et |
| I | CF3CH2 | H | I | CF3CH2 | CH2CO2Et |
| I | CF3CF2 | H | I | CF3CF2 | CH2CO2Et |
| I | CCl3 | H | I | CCl3 | CH2CO2Et |
| I | MeO | H | I | MeO | CH2CO2Et |
| CF2H | Me | H | CF2H | Me | CH2CO2Et |
| CF2H | Et | H | CF2H | Et | CH2CO2Et |
| CF2H | Cl | H | CF2H | Cl | CH2CO2Et |
| CF2H | Br | H | CF2H | Br | CH2CO2Et |
| CF2H | I | H | CF2H | I | CH2CO2Et |
| CF2H | CF2H | H | CF2H | CF2H | CH2CO2Et |
| CF2H | CF3 | H | CF2H | CF3 | CH2CO2Et |
| CF2H | CF3CH2 | H | CF2H | CF3CH2 | CH2CO2Et |
| CF2H | CF3CF2 | H | CF2H | CF3CF2 | CH2CO2Et |
| CF2H | CCl3 | H | CF2H | CCl3 | CH2CO2Et |
| CF2H | MeO | H | CF2H | MeO | CH2CO2Et |
| CF3 | Me | H | CF3 | Me | CH2CO2Et |
| CF3 | Et | H | CF3 | Et | CH2CO2Et |
| CF3 | Cl | H | CF3 | Cl | CH2CO2Et |
| CF3 | Br | H | CF3 | Br | CH2CO2Et |
| CF3 | I | H | CF3 | I | CH2CO2Et |
| CF3 | CF2H | H | CF3 | CF2H | CH2CO2Et |
| CF3 | CF3 | H | CF3 | CF3 | CH2CO2Et |
| CF3 | CF3CH2 | H | CF3 | CF3CH2 | CH2CO2Et |
| CF3 | CF3CF2 | H | CF3 | CF3CF2 | CH2CO2Et |
| CF3 | CCl3 | H | CF3 | CCl3 | CH2CO2Et |
| CF3 | MeO | H | CF3 | MeO | CH2CO2Et |
| CF3CH2 | Me | H | CF3CH2 | Me | CH2CO2Et |
| CF3CH2 | Et | H | CF3CH2 | Et | CH2CO2Et |
| CF3CH2 | Cl | H | CF3CH2 | Cl | CH2CO2Et |
| CF3CH2 | Br | H | CF3CH2 | Br | CH2CO2Et |
| CF3CH2 | I | H | CF3CH2 | I | CH2CO2Et |
| CF3CH2 | CF2H | H | CF3CH2 | CF2H | CH2CO2Et |
| CF3CH2 | CF3 | H | CF3CH2 | CF3 | CH2CO2Et |
| CF3CH2 | CF3CH2 | H | CF3CH2 | CF3CH2 | CH2CO2Et |
| CF3CH2 | CF3CF2 | H | CF3CH2 | CF3CF2 | CH2CO2Et |
| CF3CH2 | CCl3 | H | CF3CH2 | CCl3 | CH2CO2Et |
| CF3CH2 | MeO | H | CF3CH2 | MeO | CH2CO2Et |
| CF3CF2 | Me | H | CF3CF2 | Me | CH2CO2Et |
| CF3CF2 | Et | H | CF3CF2 | Et | CH2CO2Et |
| CF3CF2 | Cl | H | CF3CF2 | Cl | CH2CO2Et |
| CF3CF2 | Br | H | CF3CF2 | Br | CH2CO2Et |
| CF3CF2 | I | H | CF3CF2 | I | CH2CO2Et |
| CF3CF2 | CF2H | H | CF3CF2 | CF2H | CH2CO2Et |
| CF3CF2 | CF3 | H | CF3CF2 | CF3 | CH2CO2Et |
| CF3CF2 | CF3CH2 | H | CF3CF2 | CF3CH2 | CH2CO2Et |
| CF3CF2 | CF3CF2 | H | CF3CF2 | CF3CF2 | CH2CO2Et |
| CF3CF2 | CCl3 | H | CF3CF2 | CCl3 | CH2CO2Et |
| CF3CF2 | MeO | H | CF3CF2 | MeO | CH2CO2Et |
| CCl3 | Me | H | CCl3 | Me | CH2CO2Et |
| CCl3 | Et | H | CCl3 | Et | CH2CO2Et |
| CCl3 | Cl | H | CCl3 | Cl | CH2CO2Et |
| CCl3 | Br | H | CCl3 | Br | CH2CO2Et |
| CCl3 | I | H | CCl3 | I | CH2CO2Et |
| CCl3 | CF2H | H | CCl3 | CF2H | CH2CO2Et |
| CCl3 | CF3 | H | CCl3 | CF3 | CH2CO2Et |
| CCl3 | CF3CH2 | H | CCl3 | CF3CH2 | CH2CO2Et |
| CCl3 | CF3CF2 | H | CCl3 | CF3CF2 | CH2CO2Et |
| CCl3 | CCl3 | H | CCl3 | CCl3 | CH2CO2Et |
| CCl3 | MeO | H | CCl3 | MeO | CH2CO2Et |
| MeO | Me | H | MeO | Me | CH2CO2Et |
| MeO | Et | H | MeO | Et | CH2CO2Et |
| MeO | Cl | H | MeO | Cl | CH2CO2Et |
| MeO | Br | H | MeO | Br | CH2CO2Et |
| MeO | I | H | MeO | I | CH2CO2Et |
| MeO | CF2H | H | MeO | CF2H | CH2CO2Et |
| MeO | CF3 | H | MeO | CF3 | CH2CO2Et |
| MeO | CF3CH2 | H | MeO | CF3CH2 | CH2CO2Et |
| MeO | CF3CF2 | H | MeO | CF3CF2 | CH2CO2Et |
| MeO | CCl3 | H | MeO | CCl3 | CH2CO2Et |
| MeO | MeO | H | MeO | MeO | CH2CO2Et |
| Me | Me | CH2CO2H | Me | Me | CH2C(=O)Cl |
| Me | Et | CH2CO2H | Me | Et | CH2C(=O)Cl |
| Me | Cl | CH2CO2H | Me | Cl | CH2C(=O)Cl |
| Me | Br | CH2CO2H | Me | Br | CH2C(=O)Cl |
| Me | I | CH2CO2H | Me | I | CH2C(=O)Cl |
| Me | CF2H | CH2CO2H | Me | CF2H | CH2C(=O)Cl |
| Me | CF3 | CH2CO2H | Me | CF3 | CH2C(=O)Cl |
| Me | CF3CH2 | CH2CO2H | Me | CF3CH2 | CH2C(=O)Cl |
| Me | CF3CF2 | CH2CO2H | Me | CF3CF2 | CH2C(=O)Cl |
| Me | CCl3 | CH2CO2H | Me | CCl3 | CH2C(=O)Cl |
| Me | MeO | CH2CO2H | Me | MeO | CH2C(=O)Cl |
| Et | Me | CH2CO2H | Et | Me | CH2C(=O)Cl |
| Et | Et | CH2CO2H | Et | Et | CH2C(=O)Cl |
| Et | Cl | CH2CO2H | Et | Cl | CH2C(=O)Cl |
| Et | Br | CH2CO2H | Et | Br | CH2C(=O)Cl |
| Et | I | CH2CO2H | Et | I | CH2C(=O)Cl |
| Et | CF2H | CH2CO2H | Et | CF2H | CH2C(=O)Cl |
| Et | CF3 | CH2CO2H | Et | CF3 | CH2C(=O)Cl |
| Et | CF3CH2 | CH2CO2H | Et | CF3CH2 | CH2C(=O)Cl |
| Et | CF3CF2 | CH2CO2H | Et | CF3CF2 | CH2C(=O)Cl |
| Et | CCl3 | CH2CO2H | Et | CCl3 | CH2C(=O)Cl |
| Et | MeO | CH2CO2H | Et | MeO | CH2C(=O)Cl |
| Cl | Me | CH2CO2H | Cl | Me | CH2C(=O)Cl |
| Cl | Et | CH2CO2H | Cl | Et | CH2C(=O)Cl |
| Cl | Cl | CH2CO2H | Cl | Cl | CH2C(=O)Cl |
| Cl | Br | CH2CO2H | Cl | Br | CH2C(=O)Cl |
| Cl | I | CH2CO2H | Cl | I | CH2C(=O)Cl |
| Cl | CF2H | CH2CO2H | Cl | CF2H | CH2C(=O)Cl |
| Cl | CF3 | CH2CO2H | Cl | CF3 | CH2C(=O)Cl |
| Cl | CF3CH2 | CH2CO2H | Cl | CF3CH2 | CH2C(=O)Cl |
| Cl | CF3CF2 | CH2CO2H | Cl | CF3CF2 | CH2C(=O)Cl |
| Cl | CCl3 | CH2CO2H | Cl | CCl3 | CH2C(=O)Cl |
| Cl | MeO | CH2CO2H | Cl | MeO | CH2C(=O)Cl |
| Br | Me | CH2CO2H | Br | Me | CH2C(=O)Cl |
| Br | Et | CH2CO2H | Br | Et | CH2C(=O)Cl |
| Br | Cl | CH2CO2H | Br | Cl | CH2C(=O)Cl |
| Br | Br | CH2CO2H | Br | Br | CH2C(=O)Cl |
| Br | I | CH2CO2H | Br | I | CH2C(=O)Cl |
| Br | CF2H | CH2CO2H | Br | CF2H | CH2C(=O)Cl |
| Br | CF3 | CH2CO2H | Br | CF3 | CH2C(=O)Cl |
| Br | CF3CH2 | CH2CO2H | Br | CF3CH2 | CH2C(=O)Cl |
| Br | CF3CF2 | CH2CO2H | Br | CF3CF2 | CH2C(=O)Cl |
| Br | CCl3 | CH2CO2H | Br | CCl3 | CH2C(=O)Cl |
| Br | MeO | CH2CO2H | Br | MeO | CH2C(=O)Cl |
| I | Me | CH2CO2H | I | Me | CH2C(=O)Cl |
| I | Et | CH2CO2H | I | Et | CH2C(=O)Cl |
| I | Cl | CH2CO2H | I | Cl | CH2C(=O)Cl |

TABLE 6-continued

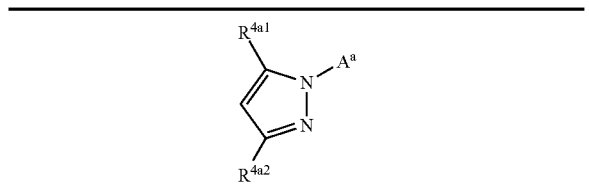

| $R^{4a1}$ | $R^{4a2}$ | $A^a$ | $R^{4a1}$ | $R^{4a2}$ | $A^a$ |
|---|---|---|---|---|---|
| I | Br | CH$_2$CO$_2$H | I | Br | CH$_2$C(=O)Cl |
| I | I | CH$_2$CO$_2$H | I | I | CH$_2$C(=O)Cl |
| I | CF$_2$H | CH$_2$CO$_2$H | I | CF$_2$H | CH$_2$C(=O)Cl |
| I | CF$_3$ | CH$_2$CO$_2$H | I | CF$_3$ | CH$_2$C(=O)Cl |
| I | CF$_3$CH$_2$ | CH$_2$CO$_2$H | I | CF$_3$CH$_2$ | CH$_2$C(=O)Cl |
| I | CF$_3$CF$_2$ | CH$_2$CO$_2$H | I | CF$_3$CF$_2$ | CH$_2$C(=O)Cl |
| I | CCl$_3$ | CH$_2$CO$_2$H | I | CCl$_3$ | CH$_2$C(=O)Cl |
| I | MeO | CH$_2$CO$_2$H | I | MeO | CH$_2$C(=O)Cl |
| CF$_2$H | Me | CH$_2$CO$_2$H | CF$_2$H | Me | CH$_2$C(=O)Cl |
| CF$_2$H | Et | CH$_2$CO$_2$H | CF$_2$H | Et | CH$_2$C(=O)Cl |
| CF$_2$H | Cl | CH$_2$CO$_2$H | CF$_2$H | Cl | CH$_2$C(=O)Cl |
| CF$_2$H | Br | CH$_2$CO$_2$H | CF$_2$H | Br | CH$_2$C(=O)Cl |
| CF$_2$H | I | CH$_2$CO$_2$H | CF$_2$H | I | CH$_2$C(=O)Cl |
| CF$_2$H | CF$_2$H | CH$_2$CO$_2$H | CF$_2$H | CF$_2$H | CH$_2$C(=O)Cl |
| CF$_2$H | CF$_3$ | CH$_2$CO$_2$H | CF$_2$H | CF$_3$ | CH$_2$C(=O)Cl |
| CF$_2$H | CF$_3$CH$_2$ | CH$_2$CO$_2$H | CF$_2$H | CF$_3$CH$_2$ | CH$_2$C(=O)Cl |
| CF$_2$H | CF$_3$CF$_2$ | CH$_2$CO$_2$H | CF$_2$H | CF$_3$CF$_2$ | CH$_2$C(=O)Cl |
| CF$_2$H | CCl$_3$ | CH$_2$CO$_2$H | CF$_2$H | CCl$_3$ | CH$_2$C(=O)Cl |
| CF$_2$H | MeO | CH$_2$CO$_2$H | CF$_2$H | MeO | CH$_2$C(=O)Cl |
| CF$_3$ | Me | CH$_2$CO$_2$H | CF$_3$ | Me | CH$_2$C(=O)Cl |
| CF$_3$ | Et | CH$_2$CO$_2$H | CF$_3$ | Et | CH$_2$C(=O)Cl |
| CF$_3$ | Cl | CH$_2$CO$_2$H | CF$_3$ | Cl | CH$_2$C(=O)Cl |
| CF$_3$ | Br | CH$_2$CO$_2$H | CF$_3$ | Br | CH$_2$C(=O)Cl |
| CF$_3$ | I | CH$_2$CO$_2$H | CF$_3$ | I | CH$_2$C(=O)Cl |
| CF$_3$ | CF$_2$H | CH$_2$CO$_2$H | CF$_3$ | CF$_2$H | CH$_2$C(=O)Cl |
| CF$_3$ | CF$_3$ | CH$_2$CO$_2$H | CF$_3$ | CF$_3$ | CH$_2$C(=O)Cl |
| CF$_3$ | CF$_3$CH$_2$ | CH$_2$CO$_2$H | CF$_3$ | CF$_3$CH$_2$ | CH$_2$C(=O)Cl |
| CF$_3$ | CF$_3$CF$_2$ | CH$_2$CO$_2$H | CF$_3$ | CF$_3$CF$_2$ | CH$_2$C(=O)Cl |
| CF$_3$ | CCl$_3$ | CH$_2$CO$_2$H | CF$_3$ | CCl$_3$ | CH$_2$C(=O)Cl |
| CF$_3$ | MeO | CH$_2$CO$_2$H | CF$_3$ | MeO | CH$_2$C(=O)Cl |
| CF$_3$CH$_2$ | Me | CH$_2$CO$_2$H | CF$_3$CH$_2$ | Me | CH$_2$C(=O)Cl |
| CF$_3$CH$_2$ | Et | CH$_2$CO$_2$H | CF$_3$CH$_2$ | Et | CH$_2$C(=O)Cl |
| CF$_3$CH$_2$ | Cl | CH$_2$CO$_2$H | CF$_3$CH$_2$ | Cl | CH$_2$C(=O)Cl |
| CF$_3$CH$_2$ | Br | CH$_2$CO$_2$H | CF$_3$CH$_2$ | Br | CH$_2$C(=O)Cl |
| CF$_3$CH$_2$ | I | CH$_2$CO$_2$H | CF$_3$CH$_2$ | I | CH$_2$C(=O)Cl |
| CF$_3$CH$_2$ | CF$_2$H | CH$_2$CO$_2$H | CF$_3$CH$_2$ | CF$_2$H | CH$_2$C(=O)Cl |
| CF$_3$CH$_2$ | CF$_3$ | CH$_2$CO$_2$H | CF$_3$CH$_2$ | CF$_3$ | CH$_2$C(=O)Cl |
| CF$_3$CH$_2$ | CF$_3$CH$_2$ | CH$_2$CO$_2$H | CF$_3$CH$_2$ | CF$_3$CH$_2$ | CH$_2$C(=O)Cl |
| CF$_3$CH$_2$ | CF$_3$CF$_2$ | CH$_2$CO$_2$H | CF$_3$CH$_2$ | CF$_3$CF$_2$ | CH$_2$C(=O)Cl |
| CF$_3$CH$_2$ | CCl$_3$ | CH$_2$CO$_2$H | CF$_3$CH$_2$ | CCl$_3$ | CH$_2$C(=O)Cl |
| CF$_3$CH$_2$ | MeO | CH$_2$CO$_2$H | CF$_3$CH$_2$ | MeO | CH$_2$C(=O)Cl |
| CF$_3$CF$_2$ | Me | CH$_2$CO$_2$H | CF$_3$CF$_2$ | Me | CH$_2$C(=O)Cl |
| CF$_3$CF$_2$ | Et | CH$_2$CO$_2$H | CF$_3$CF$_2$ | Et | CH$_2$C(=O)Cl |
| CF$_3$CF$_2$ | Cl | CH$_2$CO$_2$H | CF$_3$CF$_2$ | Cl | CH$_2$C(=O)Cl |
| CF$_3$CF$_2$ | Br | CH$_2$CO$_2$H | CF$_3$CF$_2$ | Br | CH$_2$C(=O)Cl |
| CF$_3$CF$_2$ | I | CH$_2$CO$_2$H | CF$_3$CF$_2$ | I | CH$_2$C(=O)Cl |
| CF$_3$CF$_2$ | CF$_2$H | CH$_2$CO$_2$H | CF$_3$CF$_2$ | CF$_2$H | CH$_2$C(=O)Cl |
| CF$_3$CF$_2$ | CF$_3$ | CH$_2$CO$_2$H | CF$_3$CF$_2$ | CF$_3$ | CH$_2$C(=O)Cl |
| CF$_3$CF$_2$ | CF$_3$CH$_2$ | CH$_2$CO$_2$H | CF$_3$CF$_2$ | CF$_3$CH$_2$ | CH$_2$C(=O)Cl |
| CF$_3$CF$_2$ | CF$_3$CF$_2$ | CH$_2$CO$_2$H | CF$_3$CF$_2$ | CF$_3$CF$_2$ | CH$_2$C(=O)Cl |
| CF$_3$CF$_2$ | CCl$_3$ | CH$_2$CO$_2$H | CF$_3$CF$_2$ | CCl$_3$ | CH$_2$C(=O)Cl |
| CF$_3$CF$_2$ | MeO | CH$_2$CO$_2$H | CF$_3$CF$_2$ | MeO | CH$_2$C(=O)Cl |
| CCl$_3$ | Me | CH$_2$CO$_2$H | CCl$_3$ | Me | CH$_2$C(=O)Cl |
| CCl$_3$ | Et | CH$_2$CO$_2$H | CCl$_3$ | Et | CH$_2$C(=O)Cl |
| CCl$_3$ | Cl | CH$_2$CO$_2$H | CCl$_3$ | Cl | CH$_2$C(=O)Cl |
| CCl$_3$ | Br | CH$_2$CO$_2$H | CCl$_3$ | Br | CH$_2$C(=O)Cl |
| CCl$_3$ | I | CH$_2$CO$_2$H | CCl$_3$ | I | CH$_2$C(=O)Cl |
| CCl$_3$ | CF$_2$H | CH$_2$CO$_2$H | CCl$_3$ | CF$_2$H | CH$_2$C(=O)Cl |
| CCl$_3$ | CF$_3$ | CH$_2$CO$_2$H | CCl$_3$ | CF$_3$ | CH$_2$C(=O)Cl |
| CCl$_3$ | CF$_3$CH$_2$ | CH$_2$CO$_2$H | CCl$_3$ | CF$_3$CH$_2$ | CH$_2$C(=O)Cl |
| CCl$_3$ | CF$_3$CF$_2$ | CH$_2$CO$_2$H | CCl$_3$ | CF$_3$CF$_2$ | CH$_2$C(=O)Cl |
| CCl$_3$ | CCl$_3$ | CH$_2$CO$_2$H | CCl$_3$ | CCl$_3$ | CH$_2$C(=O)Cl |
| CCl$_3$ | MeO | CH$_2$CO$_2$H | CCl$_3$ | MeO | CH$_2$C(=O)Cl |
| MeO | Me | CH$_2$CO$_2$H | MeO | Me | CH$_2$C(=O)Cl |
| MeO | Et | CH$_2$CO$_2$H | MeO | Et | CH$_2$C(=O)Cl |
| MeO | Cl | CH$_2$CO$_2$H | MeO | Cl | CH$_2$C(=O)Cl |
| MeO | Br | CH$_2$CO$_2$H | MeO | Br | CH$_2$C(=O)Cl |
| MeO | I | CH$_2$CO$_2$H | MeO | I | CH$_2$C(=O)Cl |
| MeO | CF$_2$H | CH$_2$CO$_2$H | MeO | CF$_2$H | CH$_2$C(=O)Cl |
| MeO | CF$_3$ | CH$_2$CO$_2$H | MeO | CF$_3$ | CH$_2$C(=O)Cl |
| MeO | CF$_3$CH$_2$ | CH$_2$CO$_2$H | MeO | CF$_3$CH$_2$ | CH$_2$C(=O)Cl |
| MeO | CF$_3$CF$_2$ | CH$_2$CO$_2$H | MeO | CF$_3$CF$_2$ | CH$_2$C(=O)Cl |
| MeO | CCl$_3$ | CH$_2$CO$_2$H | MeO | CCl$_3$ | CH$_2$C(=O)Cl |
| MeO | MeO | CH$_2$CO$_2$H | MeO | MeO | CH$_2$C(=O)Cl |
| OCF$_2$H | Me | CH$_2$CO$_2$H | OCF$_2$H | Me | CH$_2$C(=O)Cl |
| OCF$_2$H | Et | CH$_2$CO$_2$H | OCF$_2$H | Et | CH$_2$C(=O)Cl |
| OCF$_2$H | Cl | CH$_2$CO$_2$H | OCF$_2$H | Cl | CH$_2$C(=O)Cl |
| OCF$_2$H | Br | CH$_2$CO$_2$H | OCF$_2$H | Br | CH$_2$C(=O)Cl |
| OCF$_2$H | I | CH$_2$CO$_2$H | OCF$_2$H | I | CH$_2$C(=O)Cl |
| OCF$_2$H | CF$_2$H | CH$_2$CO$_2$H | OCF$_2$H | CF$_2$H | CH$_2$C(=O)Cl |
| OCF$_2$H | CF$_3$ | CH$_2$CO$_2$H | OCF$_2$H | CF$_3$ | CH$_2$C(=O)Cl |
| OCF$_2$H | CF$_3$CH$_2$ | CH$_2$CO$_2$H | OCF$_2$H | CF$_3$CH$_2$ | CH$_2$C(=O)Cl |
| OCF$_2$H | CF$_3$CF$_2$ | CH$_2$CO$_2$H | OCF$_2$H | CF$_3$CF$_2$ | CH$_2$C(=O)Cl |
| OCF$_2$H | CCl$_3$ | CH$_2$CO$_2$H | OCF$_2$H | CCl$_3$ | CH$_2$C(=O)Cl |
| OCF$_2$H | MeO | CH$_2$CO$_2$H | OCF$_2$H | MeO | CH$_2$C(=O)Cl |

TABLE 7

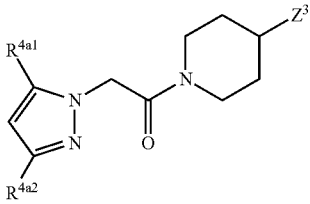

| $R^{4a1}$ | $R^{4a2}$ | $Z^3$ | $R^{4a1}$ | $R^{4a2}$ | $Z^3$ |
|---|---|---|---|---|---|
| Me | Me | CN | Me | Me | C(=S)NH$_2$ |
| Me | Et | CN | Me | Et | C(=S)NH$_2$ |
| Me | Cl | CN | Me | Cl | C(=S)NH$_2$ |
| Me | Br | CN | Me | Br | C(=S)NH$_2$ |
| Me | I | CN | Me | I | C(=S)NH$_2$ |
| Me | CF$_2$H | CN | Me | CF$_2$H | C(=S)NH$_2$ |
| Me | CF$_3$ | CN | Me | CF$_3$ | C(=S)NH$_2$ |
| Me | CF$_3$CH$_2$ | CN | Me | CF$_3$CH$_2$ | C(=S)NH$_2$ |
| Me | CF$_3$CF$_2$ | CN | Me | CF$_3$CF$_2$ | C(=S)NH$_2$ |
| Me | CCl$_3$ | CN | Me | CCl$_3$ | C(=S)NH$_2$ |
| Me | MeO | CN | Me | MeO | C(=S)NH$_2$ |
| Et | Me | CN | Et | Me | C(=S)NH$_2$ |
| Et | Et | CN | Et | Et | C(=S)NH$_2$ |
| Et | Cl | CN | Et | Cl | C(=S)NH$_2$ |
| Et | Br | CN | Et | Br | C(=S)NH$_2$ |
| Et | I | CN | Et | I | C(=S)NH$_2$ |
| Et | CF$_2$H | CN | Et | CF$_2$H | C(=S)NH$_2$ |
| Et | CF$_3$ | CN | Et | CF$_3$ | C(=S)NH$_2$ |
| Et | CF$_3$CH$_2$ | CN | Et | CF$_3$CH$_2$ | C(=S)NH$_2$ |
| Et | CF$_3$CF$_2$ | CN | Et | CF$_3$CF$_2$ | C(=S)NH$_2$ |
| Et | CCl$_3$ | CN | Et | CCl$_3$ | C(=S)NH$_2$ |
| Et | MeO | CN | Et | MeO | C(=S)NH$_2$ |
| Cl | Me | CN | Cl | Me | C(=S)NH$_2$ |
| Cl | Et | CN | Cl | Et | C(=S)NH$_2$ |
| Cl | Cl | CN | Cl | Cl | C(=S)NH$_2$ |
| Cl | Br | CN | Cl | Br | C(=S)NH$_2$ |
| Cl | I | CN | Cl | I | C(=S)NH$_2$ |
| Cl | CF$_2$H | CN | Cl | CF$_2$H | C(=S)NH$_2$ |
| Cl | CF$_3$ | CN | Cl | CF$_3$ | C(=S)NH$_2$ |
| Cl | CF$_3$CH$_2$ | CN | Cl | CF$_3$CH$_2$ | C(=S)NH$_2$ |
| Cl | CF$_3$CF$_2$ | CN | Cl | CF$_3$CF$_2$ | C(=S)NH$_2$ |
| Cl | CCl$_3$ | CN | Cl | CCl$_3$ | C(=S)NH$_2$ |
| Cl | MeO | CN | Cl | MeO | C(=S)NH$_2$ |
| Br | Me | CN | Br | Me | C(=S)NH$_2$ |
| Br | Et | CN | Br | Et | C(=S)NH$_2$ |

TABLE 7-continued

| $R^{4a1}$ | $R^{4a2}$ | $Z^3$ | $R^{4a1}$ | $R^{4a2}$ | $Z^3$ |
|---|---|---|---|---|---|
| Br | Cl | CN | Br | Cl | C(=S)NH$_2$ |
| Br | Br | CN | Br | Br | C(=S)NH$_2$ |
| Br | I | CN | Br | I | C(=S)NH$_2$ |
| Br | CF$_2$H | CN | Br | CF$_2$H | C(=S)NH$_2$ |
| Br | CF$_3$ | CN | Br | CF$_3$ | C(=S)NH$_2$ |
| Br | CF$_3$CH$_2$ | CN | Br | CF$_3$CH$_2$ | C(=S)NH$_2$ |
| Br | CF$_3$CF$_2$ | CN | Br | CF$_3$CF$_2$ | C(=S)NH$_2$ |
| Br | CCl$_3$ | CN | Br | CCl$_3$ | C(=S)NH$_2$ |
| Br | MeO | CN | Br | MeO | C(=S)NH$_2$ |
| I | Me | CN | I | Me | C(=S)NH$_2$ |
| I | Et | CN | I | Et | C(=S)NH$_2$ |
| I | Cl | CN | I | Cl | C(=S)NH$_2$ |
| I | Br | CN | I | Br | C(=S)NH$_2$ |
| I | I | CN | I | I | C(=S)NH$_2$ |
| I | CF$_2$H | CN | I | CF$_2$H | C(=S)NH$_2$ |
| I | CF$_3$ | CN | I | CF$_3$ | C(=S)NH$_2$ |
| I | CF$_3$CH$_2$ | CN | I | CF$_3$CH$_2$ | C(=S)NH$_2$ |
| I | CF$_3$CF$_2$ | CN | I | CF$_3$CF$_2$ | C(=S)NH$_2$ |
| I | CCl$_3$ | CN | I | CCl$_3$ | C(=S)NH$_2$ |
| I | MeO | CN | I | MeO | C(=S)NH$_2$ |
| CF$_2$H | Me | CN | CF$_2$H | Me | C(=S)NH$_2$ |
| CF$_2$H | Et | CN | CF$_2$H | Et | C(=S)NH$_2$ |
| CF$_2$H | Cl | CN | CF$_2$H | Cl | C(=S)NH$_2$ |
| CF$_2$H | Br | CN | CF$_2$H | Br | C(=S)NH$_2$ |
| CF$_2$H | I | CN | CF$_2$H | I | C(=S)NH$_2$ |
| CF$_2$H | CF$_2$H | CN | CF$_2$H | CF$_2$H | C(=S)NH$_2$ |
| CF$_2$H | CF$_3$ | CN | CF$_2$H | CF$_3$ | C(=S)NH$_2$ |
| CF$_2$H | CF$_3$CH$_2$ | CN | CF$_2$H | CF$_3$CH$_2$ | C(=S)NH$_2$ |
| CF$_2$H | CF$_3$CF$_2$ | CN | CF$_2$H | CF$_3$CF$_2$ | C(=S)NH$_2$ |
| CF$_2$H | CCl$_3$ | CN | CF$_2$H | CCl$_3$ | C(=S)NH$_2$ |
| CF$_2$H | MeO | CN | CF$_2$H | MeO | C(=S)NH$_2$ |
| CF$_3$ | Me | CN | CF$_3$ | Me | C(=S)NH$_2$ |
| CF$_3$ | Et | CN | CF$_3$ | Et | C(=S)NH$_2$ |
| CF$_3$ | Cl | CN | CF$_3$ | Cl | C(=S)NH$_2$ |
| CF$_3$ | Br | CN | CF$_3$ | Br | C(=S)NH$_2$ |
| CF$_3$ | I | CN | CF$_3$ | I | C(=S)NH$_2$ |
| CF$_3$ | CF$_2$H | CN | CF$_3$ | CF$_2$H | C(=S)NH$_2$ |
| CF$_3$ | CF$_3$ | CN | CF$_3$ | CF$_3$ | C(=S)NH$_2$ |
| CF$_3$ | CF$_3$CH$_2$ | CN | CF$_3$ | CF$_3$CH$_2$ | C(=S)NH$_2$ |
| CF$_3$ | CF$_3$CF$_2$ | CN | CF$_3$ | CF$_3$CF$_2$ | C(=S)NH$_2$ |
| CF$_3$ | CCl$_3$ | CN | CF$_3$ | CCl$_3$ | C(=S)NH$_2$ |
| CF$_3$ | MeO | CN | CF$_3$ | MeO | C(=S)NH$_2$ |
| CF$_3$CH$_2$ | Me | CN | CF$_3$CH$_2$ | Me | C(=S)NH$_2$ |
| CF$_3$CH$_2$ | Et | CN | CF$_3$CH$_2$ | Et | C(=S)NH$_2$ |
| CF$_3$CH$_2$ | Cl | CN | CF$_3$CH$_2$ | Cl | C(=S)NH$_2$ |
| CF$_3$CH$_2$ | Br | CN | CF$_3$CH$_2$ | Br | C(=S)NH$_2$ |
| CF$_3$CH$_2$ | I | CN | CF$_3$CH$_2$ | I | C(=S)NH$_2$ |
| CF$_3$CH$_2$ | CF$_2$H | CN | CF$_3$CH$_2$ | CF$_2$H | C(=S)NH$_2$ |
| CF$_3$CH$_2$ | CF$_3$ | CN | CF$_3$CH$_2$ | CF$_3$ | C(=S)NH$_2$ |
| CF$_3$CH$_2$ | CF$_3$CH$_2$ | CN | CF$_3$CH$_2$ | CF$_3$CH$_2$ | C(=S)NH$_2$ |
| CF$_3$CH$_2$ | CF$_3$CF$_2$ | CN | CF$_3$CH$_2$ | CF$_3$CF$_2$ | C(=S)NH$_2$ |
| CF$_3$CH$_2$ | CCl$_3$ | CN | CF$_3$CH$_2$ | CCl$_3$ | C(=S)NH$_2$ |
| CF$_3$CH$_2$ | MeO | CN | CF$_3$CH$_2$ | MeO | C(=S)NH$_2$ |
| CF$_3$CF$_2$ | Me | CN | CF$_3$CF$_2$ | Me | C(=S)NH$_2$ |
| CF$_3$CF$_2$ | Et | CN | CF$_3$CF$_2$ | Et | C(=S)NH$_2$ |
| CF$_3$CF$_2$ | Cl | CN | CF$_3$CF$_2$ | Cl | C(=S)NH$_2$ |
| CF$_3$CF$_2$ | Br | CN | CF$_3$CF$_2$ | Br | C(=S)NH$_2$ |
| CF$_3$CF$_2$ | I | CN | CF$_3$CF$_2$ | I | C(=S)NH$_2$ |
| CF$_3$CF$_2$ | CF$_2$H | CN | CF$_3$CF$_2$ | CF$_2$H | C(=S)NH$_2$ |
| CF$_3$CF$_2$ | CF$_3$ | CN | CF$_3$CF$_2$ | CF$_3$ | C(=S)NH$_2$ |
| CF$_3$CF$_2$ | CF$_3$CH$_2$ | CN | CF$_3$CF$_2$ | CF$_3$CH$_2$ | C(=S)NH$_2$ |
| CF$_3$CF$_2$ | CF$_3$CF$_2$ | CN | CF$_3$CF$_2$ | CF$_3$CF$_2$ | C(=S)NH$_2$ |
| CF$_3$CF$_2$ | CCl$_3$ | CN | CF$_3$CF$_2$ | CCl$_3$ | C(=S)NH$_2$ |
| CF$_3$CF$_2$ | MeO | CN | CF$_3$CF$_2$ | MeO | C(=S)NH$_2$ |
| CCl$_3$ | Me | CN | CCl$_3$ | Me | C(=S)NH$_2$ |
| CCl$_3$ | Et | CN | CCl$_3$ | Et | C(=S)NH$_2$ |
| CCl$_3$ | Cl | CN | CCl$_3$ | Cl | C(=S)NH$_2$ |
| CCl$_3$ | Br | CN | CCl$_3$ | Br | C(=S)NH$_2$ |
| CCl$_3$ | I | CN | CCl$_3$ | I | C(=S)NH$_2$ |
| CCl$_3$ | CF$_2$H | CN | CCl$_3$ | CF$_2$H | C(=S)NH$_2$ |
| CCl$_3$ | CF$_3$ | CN | CCl$_3$ | CF$_3$ | C(=S)NH$_2$ |
| CCl$_3$ | CF$_3$CH$_2$ | CN | CCl$_3$ | CF$_3$CH$_2$ | C(=S)NH$_2$ |
| CCl$_3$ | CF$_3$CF$_2$ | CN | CCl$_3$ | CF$_3$CF$_2$ | C(=S)NH$_2$ |
| CCl$_3$ | CCl$_3$ | CN | CCl$_3$ | CCl$_3$ | C(=S)NH$_2$ |
| CCl$_3$ | MeO | CN | CCl$_3$ | MeO | C(=S)NH$_2$ |
| MeO | Me | CN | MeO | Me | C(=S)NH$_2$ |
| MeO | Et | CN | MeO | Et | C(=S)NH$_2$ |
| MeO | Cl | CN | MeO | Cl | C(=S)NH$_2$ |
| MeO | Br | CN | MeO | Br | C(=S)NH$_2$ |
| MeO | I | CN | MeO | I | C(=S)NH$_2$ |
| MeO | CF$_2$H | CN | MeO | CF$_2$H | C(=S)NH$_2$ |
| MeO | CF$_3$ | CN | MeO | CF$_3$ | C(=S)NH$_2$ |
| MeO | CF$_3$CH$_2$ | CN | MeO | CF$_3$CH$_2$ | C(=S)NH$_2$ |
| MeO | CF$_3$CF$_2$ | CN | MeO | CF$_3$CF$_2$ | C(=S)NH$_2$ |
| MeO | CCl$_3$ | CN | MeO | CCl$_3$ | C(=S)NH$_2$ |
| MeO | MeO | CN | MeO | MeO | C(=S)NH$_2$ |
| OCF$_2$H | Me | CN | OCF$_2$H | Me | C(=S)NH$_2$ |
| OCF$_2$H | Et | CN | OCF$_2$H | Et | C(=S)NH$_2$ |
| OCF$_2$H | Cl | CN | OCF$_2$H | Cl | C(=S)NH$_2$ |
| OCF$_2$H | Br | CN | OCF$_2$H | Br | C(=S)NH$_2$ |
| OCF$_2$H | I | CN | OCF$_2$H | I | C(=S)NH$_2$ |
| OCF$_2$H | CF$_2$H | CN | OCF$_2$H | CF$_2$H | C(=S)NH$_2$ |
| OCF$_2$H | CF$_3$ | CN | OCF$_2$H | CF$_3$ | C(=S)NH$_2$ |
| OCF$_2$H | CF$_3$CH$_2$ | CN | OCF$_2$H | CF$_3$CH$_2$ | C(=S)NH$_2$ |
| OCF$_2$H | CF$_3$CF$_2$ | CN | OCF$_2$H | CF$_3$CF$_2$ | C(=S)NH$_2$ |
| OCF$_2$H | CCl$_3$ | CN | OCF$_2$H | CCl$_3$ | C(=S)NH$_2$ |
| OCF$_2$H | MeO | CN | OCF$_2$H | MeO | C(=S)NH$_2$ |

TABLE 8 wherein $J^1$ is one of J-29-1 through J-29-58 (as depicted in Exhibit A above).

| M | $J^1$ |
|---|---|
| CH$_3$ | J-29-1 |
| CH$_2$Cl | J-29-1 |
| CH$_2$Br | J-29-1 |
| CH$_2$I | J-29-1 |
| OH | J-29-1 |
| OMe | J-29-1 |
| OEt | J-29-1 |
| OPr | J-29-1 |
| O-i-Pr | J-29-1 |
| O-n-Bu | J-29-1 |
| O-t-Bu | J-29-1 |
| NMe$_2$ | J-29-1 |
| NEt$_2$ | J-29-1 |
| N(n-Pr)$_2$ | J-29-1 |
| 1-piperdinyl | J-29-1 |
| 1-pyrrolidinyl | J-29-1 |
| 4-morpholinyl | J-29-1 |
| CH$_3$ | J-29-2 |
| CH$_2$Cl | J-29-2 |
| CH$_2$Br | J-29-2 |
| CH$_2$I | J-29-2 |
| OH | J-29-2 |
| OMe | J-29-2 |
| OEt | J-29-2 |

TABLE 8-continued

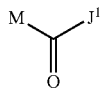

wherein J¹ is one of J-29-1 through J-29-58 (as depicted in Exhibit A above).

| M | J¹ |
|---|---|
| OPr | J-29-2 |
| O-i-Pr | J-29-2 |
| O-n-Bu | J-29-2 |
| O-t-Bu | J-29-2 |
| NMe₂ | J-29-2 |
| NEt₂ | J-29-2 |
| N(n-Pr)₂ | J-29-2 |
| 1-piperdinyl | J-29-2 |
| 1-pyrrolidinyl | J-29-2 |
| 4-morpholinyl | J-29-2 |
| CH₃ | J-29-3 |
| CH₂Cl | J-29-3 |
| CH₂Br | J-29-3 |
| CH₂I | J-29-3 |
| OH | J-29-3 |
| OMe | J-29-3 |
| OEt | J-29-3 |
| OPr | J-29-3 |
| O-i-Pr | J-29-3 |
| O-n-Bu | J-29-3 |
| O-t-Bu | J-29-3 |
| NMe₂ | J-29-3 |
| NEt₂ | J-29-3 |
| N(n-Pr)₂ | J-29-3 |
| 1-piperdinyl | J-29-3 |
| 1-pyrrolidinyl | J-29-3 |
| 4-morpholinyl | J-29-3 |
| CH₃ | J-29-4 |
| CH₂Cl | J-29-4 |
| CH₂Br | J-29-4 |
| CH₂I | J-29-4 |
| OH | J-29-4 |
| OMe | J-29-4 |
| OEt | J-29-4 |
| OPr | J-29-4 |
| O-i-Pr | J-29-4 |
| O-n-Bu | J-29-4 |
| O-t-Bu | J-29-4 |
| NMe₂ | J-29-4 |
| NEt₂ | J-29-4 |
| N(n-Pr)₂ | J-29-4 |
| 1-piperdinyl | J-29-4 |
| 1-pyrrolidinyl | J-29-4 |
| 4-morpholinyl | J-29-4 |
| CH₃ | J-29-5 |
| CH₂Cl | J-29-5 |
| CH₂Br | J-29-5 |
| CH₂I | J-29-5 |
| OH | J-29-5 |
| OMe | J-29-5 |
| OEt | J-29-5 |
| OPr | J-29-5 |
| O-i-Pr | J-29-5 |
| O-n-Bu | J-29-5 |
| O-t-Bu | J-29-5 |
| NMe₂ | J-29-5 |
| NEt₂ | J-29-5 |
| N(n-Pr)₂ | J-29-5 |
| 1-piperdinyl | J-29-5 |
| 1-pyrrolidinyl | J-29-5 |
| 4-morpholinyl | J-29-5 |
| CH₃ | J-29-6 |
| CH₂Cl | J-29-6 |
| CH₂Br | J-29-6 |
| CH₂I | J-29-6 |
| OH | J-29-6 |
| OMe | J-29-6 |
| OEt | J-29-6 |
| OPr | J-29-6 |
| O-i-Pr | J-29-6 |
| O-n-Bu | J-29-6 |
| O-t-Bu | J-29-6 |
| NMe₂ | J-29-6 |
| NEt₂ | J-29-6 |
| N(n-Pr)₂ | J-29-6 |
| 1-piperdinyl | J-29-6 |
| 1-pyrrolidinyl | J-29-6 |
| 4-morpholinyl | J-29-6 |
| CH₃ | J-29-7 |
| CH₂Cl | J-29-7 |
| CH₂Br | J-29-7 |
| CH₂I | J-29-7 |
| OH | J-29-7 |
| OMe | J-29-7 |
| OEt | J-29-7 |
| OPr | J-29-7 |
| O-i-Pr | J-29-7 |
| O-n-Bu | J-29-7 |
| O-t-Bu | J-29-7 |
| NMe₂ | J-29-7 |
| NEt₂ | J-29-7 |
| N(n-Pr)₂ | J-29-7 |
| 1-piperdinyl | J-29-7 |
| 1-pyrrolidinyl | J-29-7 |
| 4-morpholinyl | J-29-7 |
| CH₃ | J-29-8 |
| CH₂Cl | J-29-8 |
| CH₂Br | J-29-8 |
| CH₂I | J-29-8 |
| OH | J-29-8 |
| OMe | J-29-8 |
| OEt | J-29-8 |
| OPr | J-29-8 |
| O-i-Pr | J-29-8 |
| O-n-Bu | J-29-8 |
| O-t-Bu | J-29-8 |
| NMe₂ | J-29-8 |
| NEt₂ | J-29-8 |
| N(n-Pr)₂ | J-29-8 |
| 1-piperdinyl | J-29-8 |
| 1-pyrrolidinyl | J-29-8 |
| 4-morpholinyl | J-29-8 |
| CH₃ | J-29-9 |
| CH₂Cl | J-29-9 |
| CH₂Br | J-29-9 |
| CH₂I | J-29-9 |
| OH | J-29-9 |
| OMe | J-29-9 |
| OEt | J-29-9 |
| OPr | J-29-9 |
| O-i-Pr | J-29-9 |
| O-n-Bu | J-29-9 |
| O-t-Bu | J-29-9 |
| NMe₂ | J-29-9 |
| NEt₂ | J-29-9 |
| N(n-Pr)₂ | J-29-9 |
| 1-piperdinyl | J-29-9 |
| 1-pyrrolidinyl | J-29-9 |
| 4-morpholinyl | J-29-9 |
| CH₃ | J-29-10 |
| CH₂Cl | J-29-10 |
| CH₂Br | J-29-10 |
| CH₂I | J-29-10 |
| OH | J-29-10 |
| OMe | J-29-10 |
| OEt | J-29-10 |
| OPr | J-29-10 |
| O-i-Pr | J-29-10 |
| O-n-Bu | J-29-10 |
| O-t-Bu | J-29-10 |
| NMe₂ | J-29-10 |
| NEt₂ | J-29-10 |

TABLE 8-continued

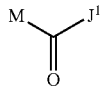

wherein $J^1$ is one of J-29-1 through J-29-58 (as depicted in Exhibit A above).

| M | $J^1$ |
|---|---|
| N(n-Pr)$_2$ | J-29-10 |
| 1-piperdinyl | J-29-10 |
| 1-pyrrolidinyl | J-29-10 |
| 4-morpholinyl | J-29-10 |
| CH$_3$ | J-29-11 |
| CH$_2$Cl | J-29-11 |
| CH$_2$Br | J-29-11 |
| CH$_2$I | J-29-11 |
| OH | J-29-11 |
| OMe | J-29-11 |
| OEt | J-29-11 |
| OPr | J-29-11 |
| O-i-Pr | J-29-11 |
| O-n-Bu | J-29-11 |
| O-t-Bu | J-29-11 |
| NMe$_2$ | J-29-11 |
| NEt$_2$ | J-29-11 |
| N(n-Pr)$_2$ | J-29-11 |
| 1-piperdinyl | J-29-11 |
| 1-pyrrolidinyl | J-29-11 |
| 4-morpholinyl | J-29-11 |
| CH$_3$ | J-29-12 |
| CH$_2$Cl | J-29-12 |
| CH$_2$Br | J-29-12 |
| CH$_2$I | J-29-12 |
| OH | J-29-12 |
| OMe | J-29-12 |
| OEt | J-29-12 |
| OPr | J-29-12 |
| O-i-Pr | J-29-12 |
| O-n-Bu | J-29-12 |
| O-t-Bu | J-29-12 |
| NMe$_2$ | J-29-12 |
| NEt$_2$ | J-29-12 |
| N(n-Pr)$_2$ | J-29-12 |
| 1-piperdinyl | J-29-12 |
| 1-pyrrolidinyl | J-29-12 |
| 4-morpholinyl | J-29-12 |
| CH$_3$ | J-29-13 |
| CH$_2$Cl | J-29-13 |
| CH$_2$Br | J-29-13 |
| CH$_2$I | J-29-13 |
| OH | J-29-13 |
| OMe | J-29-13 |
| OEt | J-29-13 |
| OPr | J-29-13 |
| O-i-Pr | J-29-13 |
| O-n-Bu | J-29-13 |
| O-t-Bu | J-29-13 |
| NMe$_2$ | J-29-13 |
| NEt$_2$ | J-29-13 |
| N(n-Pr)$_2$ | J-29-13 |
| 1-piperdinyl | J-29-13 |
| 1-pyrrolidinyl | J-29-13 |
| 4-morpholinyl | J-29-13 |
| CH$_3$ | J-29-14 |
| CH$_2$Cl | J-29-14 |
| CH$_2$Br | J-29-14 |
| CH$_2$I | J-29-14 |
| OH | J-29-14 |
| OMe | J-29-14 |
| OEt | J-29-14 |
| OPr | J-29-14 |
| O-i-Pr | J-29-14 |
| O-n-Bu | J-29-14 |
| O-t-Bu | J-29-14 |
| NMe$_2$ | J-29-14 |
| NEt$_2$ | J-29-14 |
| N(n-Pr)$_2$ | J-29-14 |
| 1-piperdinyl | J-29-14 |
| 1-pyrrolidinyl | J-29-14 |
| 4-morpholinyl | J-29-14 |

TABLE 8-continued

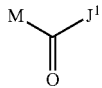

wherein $J^1$ is one of J-29-1 through J-29-58 (as depicted in Exhibit A above).

| M | $J^1$ |
|---|---|
| CH$_3$ | J-29-15 |
| CH$_2$Cl | J-29-15 |
| CH$_2$Br | J-29-15 |
| CH$_2$I | J-29-15 |
| OH | J-29-15 |
| OMe | J-29-15 |
| OEt | J-29-15 |
| OPr | J-29-15 |
| O-i-Pr | J-29-15 |
| O-n-Bu | J-29-15 |
| O-t-Bu | J-29-15 |
| NMe$_2$ | J-29-15 |
| NEt$_2$ | J-29-15 |
| N(n-Pr)$_2$ | J-29-15 |
| 1-piperdinyl | J-29-15 |
| 1-pyrrolidinyl | J-29-15 |
| 4-morpholinyl | J-29-15 |
| CH$_3$ | J-29-16 |
| CH$_2$Cl | J-29-16 |
| CH$_2$Br | J-29-16 |
| CH$_2$I | J-29-16 |
| OH | J-29-16 |
| OMe | J-29-16 |
| OEt | J-29-16 |
| OPr | J-29-16 |
| O-i-Pr | J-29-16 |
| O-n-Bu | J-29-16 |
| O-t-Bu | J-29-16 |
| NMe$_2$ | J-29-16 |
| NEt$_2$ | J-29-16 |
| N(n-Pr)$_2$ | J-29-16 |
| 1-piperdinyl | J-29-16 |
| 1-pyrrolidinyl | J-29-16 |
| 4-morpholinyl | J-29-16 |
| CH$_3$ | J-29-17 |
| CH$_2$Cl | J-29-17 |
| CH$_2$Br | J-29-17 |
| CH$_2$I | J-29-17 |
| OH | J-29-17 |
| OMe | J-29-17 |
| OEt | J-29-17 |
| OPr | J-29-17 |
| O-i-Pr | J-29-17 |
| O-n-Bu | J-29-17 |
| O-t-Bu | J-29-17 |
| NMe$_2$ | J-29-17 |
| NEt$_2$ | J-29-17 |
| N(n-Pr)$_2$ | J-29-17 |
| 1-piperdinyl | J-29-17 |
| 1-pyrrolidinyl | J-29-17 |
| 4-morpholinyl | J-29-17 |
| CH$_3$ | J-29-18 |
| CH$_2$Cl | J-29-18 |
| CH$_2$Br | J-29-18 |
| CH$_2$I | J-29-18 |
| OH | J-29-18 |
| OMe | J-29-18 |
| OEt | J-29-18 |
| OPr | J-29-18 |
| O-i-Pr | J-29-18 |
| O-n-Bu | J-29-18 |
| O-t-Bu | J-29-18 |
| NMe$_2$ | J-29-18 |
| NEt$_2$ | J-29-18 |
| N(n-Pr)$_2$ | J-29-18 |
| 1-piperdinyl | J-29-18 |
| 1-pyrrolidinyl | J-29-18 |
| 4-morpholinyl | J-29-18 |
| CH$_3$ | J-29-19 |
| CH$_2$Cl | J-29-19 |
| CH$_2$Br | J-29-19 |
| CH$_2$I | J-29-19 |

TABLE 8-continued

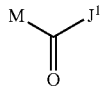

wherein J¹ is one of J-29-1 through J-29-58 (as depicted in Exhibit A above).

| M | J¹ |
|---|---|
| OH | J-29-19 |
| OMe | J-29-19 |
| OEt | J-29-19 |
| OPr | J-29-19 |
| O-i-Pr | J-29-19 |
| O-n-Bu | J-29-19 |
| O-t-Bu | J-29-19 |
| $NMe_2$ | J-29-19 |
| $NEt_2$ | J-29-19 |
| $N(n-Pr)_2$ | J-29-19 |
| 1-piperdinyl | J-29-19 |
| 1-pyrrolidinyl | J-29-19 |
| 4-morpholinyl | J-29-19 |
| $CH_3$ | J-29-20 |
| $CH_2Cl$ | J-29-20 |
| $CH_2Br$ | J-29-20 |
| $CH_2I$ | J-29-20 |
| OH | J-29-20 |
| OMe | J-29-20 |
| OEt | J-29-20 |
| OPr | J-29-20 |
| O-i-Pr | J-29-20 |
| O-n-Bu | J-29-20 |
| O-t-Bu | J-29-20 |
| $NMe_2$ | J-29-20 |
| $NEt_2$ | J-29-20 |
| $N(n-Pr)_2$ | J-29-20 |
| 1-piperdinyl | J-29-20 |
| 1-pyrrolidinyl | J-29-20 |
| 4-morpholinyl | J-29-20 |
| $CH_3$ | J-29-21 |
| $CH_2Cl$ | J-29-21 |
| $CH_2Br$ | J-29-21 |
| $CH_2I$ | J-29-21 |
| OH | J-29-21 |
| OMe | J-29-21 |
| OEt | J-29-21 |
| OPr | J-29-21 |
| O-i-Pr | J-29-21 |
| O-n-Bu | J-29-21 |
| O-t-Bu | J-29-21 |
| $NMe_2$ | J-29-21 |
| $NEt_2$ | J-29-21 |
| $N(n-Pr)_2$ | J-29-21 |
| 1-piperdinyl | J-29-21 |
| 1-pyrrolidinyl | J-29-21 |
| 4-morpholinyl | J-29-21 |
| $CH_3$ | J-29-22 |
| $CH_2Cl$ | J-29-22 |
| $CH_2Br$ | J-29-22 |
| $CH_2I$ | J-29-22 |
| OH | J-29-22 |
| OMe | J-29-22 |
| OEt | J-29-22 |
| OPr | J-29-22 |
| O-i-Pr | J-29-22 |
| O-n-Bu | J-29-22 |
| O-t-Bu | J-29-22 |
| $NMe_2$ | J-29-22 |
| $NEt_2$ | J-29-22 |
| $N(n-Pr)_2$ | J-29-22 |
| 1-piperdinyl | J-29-22 |
| 1-pyrrolidinyl | J-29-22 |
| 4-morpholinyl | J-29-22 |
| $CH_3$ | J-29-23 |
| $CH_2Cl$ | J-29-23 |
| $CH_2Br$ | J-29-23 |
| $CH_2I$ | J-29-23 |
| OH | J-29-23 |
| OMe | J-29-23 |
| OEt | J-29-23 |
| OPr | J-29-23 |
| O-i-Pr | J-29-23 |
| O-n-Bu | J-29-23 |
| O-t-Bu | J-29-23 |
| $NMe_2$ | J-29-23 |
| $NEt_2$ | J-29-23 |
| $N(n-Pr)_2$ | J-29-23 |
| 1-piperdinyl | J-29-23 |
| 1-pyrrolidinyl | J-29-23 |
| 4-morpholinyl | J-29-23 |
| $CH_3$ | J-29-24 |
| $CH_2Cl$ | J-29-24 |
| $CH_2Br$ | J-29-24 |
| $CH_2I$ | J-29-24 |
| OH | J-29-24 |
| OMe | J-29-24 |
| OEt | J-29-24 |
| OPr | J-29-24 |
| O-i-Pr | J-29-24 |
| O-n-Bu | J-29-24 |
| O-t-Bu | J-29-24 |
| $NMe_2$ | J-29-24 |
| $NEt_2$ | J-29-24 |
| $N(n-Pr)_2$ | J-29-24 |
| 1-piperdinyl | J-29-24 |
| 1-pyrrolidinyl | J-29-24 |
| 4-morpholinyl | J-29-24 |
| $CH_3$ | J-29-25 |
| $CH_2Cl$ | J-29-25 |
| $CH_2Br$ | J-29-25 |
| $CH_2I$ | J-29-25 |
| OH | J-29-25 |
| OMe | J-29-25 |
| OEt | J-29-25 |
| OPr | J-29-25 |
| O-i-Pr | J-29-25 |
| O-n-Bu | J-29-25 |
| O-t-Bu | J-29-25 |
| $NMe_2$ | J-29-25 |
| $NEt_2$ | J-29-25 |
| $N(n-Pr)_2$ | J-29-25 |
| 1-piperdinyl | J-29-25 |
| 1-pyrrolidinyl | J-29-25 |
| 4-morpholinyl | J-29-25 |
| $CH_3$ | J-29-26 |
| $CH_2Cl$ | J-29-26 |
| $CH_2Br$ | J-29-26 |
| $CH_2I$ | J-29-26 |
| OH | J-29-26 |
| OMe | J-29-26 |
| OEt | J-29-26 |
| OPr | J-29-26 |
| O-i-Pr | J-29-26 |
| O-n-Bu | J-29-26 |
| O-t-Bu | J-29-26 |
| $NMe_2$ | J-29-26 |
| $NEt_2$ | J-29-26 |
| $N(n-Pr)_2$ | J-29-26 |
| 1-piperdinyl | J-29-26 |
| 1-pyrrolidinyl | J-29-26 |
| 4-morpholinyl | J-29-26 |
| $CH_3$ | J-29-27 |
| $CH_2Cl$ | J-29-27 |
| $CH_2Br$ | J-29-27 |
| $CH_2I$ | J-29-27 |
| OH | J-29-27 |
| OMe | J-29-27 |
| OEt | J-29-27 |
| OPr | J-29-27 |
| O-i-Pr | J-29-27 |
| O-n-Bu | J-29-27 |
| O-t-Bu | J-29-27 |
| $NMe_2$ | J-29-27 |

TABLE 8-continued

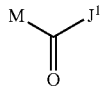

wherein J¹ is one of J-29-1 through J-29-58 (as depicted in Exhibit A above).

| M | J¹ |
|---|---|
| NEt$_2$ | J-29-27 |
| N(n-Pr)$_2$ | J-29-27 |
| 1-piperdinyl | J-29-27 |
| 1-pyrrolidinyl | J-29-27 |
| 4-morpholinyl | J-29-27 |
| CH$_3$ | J-29-28 |
| CH$_2$Cl | J-29-28 |
| CH$_2$Br | J-29-28 |
| CH$_2$I | J-29-28 |
| OH | J-29-28 |
| OMe | J-29-28 |
| OEt | J-29-28 |
| OPr | J-29-28 |
| O-i-Pr | J-29-28 |
| O-n-Bu | J-29-28 |
| O-t-Bu | J-29-28 |
| NMe$_2$ | J-29-28 |
| NEt$_2$ | J-29-28 |
| N(n-Pr)$_2$ | J-29-28 |
| 1-piperdinyl | J-29-28 |
| 1-pyrrolidinyl | J-29-28 |
| 4-morpholinyl | J-29-28 |
| CH$_3$ | J-29-29 |
| CH$_2$Cl | J-29-29 |
| CH$_2$Br | J-29-29 |
| CH$_2$I | J-29-29 |
| OH | J-29-29 |
| OMe | J-29-29 |
| OEt | J-29-29 |
| OPr | J-29-29 |
| O-i-Pr | J-29-29 |
| O-n-Bu | J-29-29 |
| O-t-Bu | J-29-29 |
| NMe$_2$ | J-29-29 |
| NEt$_2$ | J-29-29 |
| N(n-Pr)$_2$ | J-29-29 |
| 1-piperdinyl | J-29-29 |
| 1-pyrrolidinyl | J-29-29 |
| 4-morpholinyl | J-29-29 |
| CH$_3$ | J-29-30 |
| CH$_2$Cl | J-29-30 |
| CH$_2$Br | J-29-30 |
| CH$_2$I | J-29-30 |
| OH | J-29-30 |
| OMe | J-29-30 |
| OEt | J-29-30 |
| OPr | J-29-30 |
| O-i-Pr | J-29-30 |
| O-n-Bu | J-29-30 |
| O-t-Bu | J-29-30 |
| NMe$_2$ | J-29-30 |
| NEt$_2$ | J-29-30 |
| N(n-Pr)$_2$ | J-29-30 |
| 1-piperdinyl | J-29-30 |
| 1-pyrrolidinyl | J-29-30 |
| 4-morpholinyl | J-29-30 |
| CH$_3$ | J-29-31 |
| CH$_2$Cl | J-29-31 |
| CH$_2$Br | J-29-31 |
| CH$_2$I | J-29-31 |
| OH | J-29-31 |
| OMe | J-29-31 |
| OEt | J-29-31 |
| OPr | J-29-31 |
| O-i-Pr | J-29-31 |
| O-n-Bu | J-29-31 |
| O-t-Bu | J-29-31 |
| NMe$_2$ | J-29-31 |
| NEt$_2$ | J-29-31 |
| N(n-Pr)$_2$ | J-29-31 |
| 1-piperdinyl | J-29-31 |
| 1-pyrrolidinyl | J-29-31 |
| 4-morpholinyl | J-29-31 |
| CH$_3$ | J-29-32 |
| CH$_2$Cl | J-29-32 |
| CH$_2$Br | J-29-32 |
| CH$_2$I | J-29-32 |
| OH | J-29-32 |
| OMe | J-29-32 |
| OEt | J-29-32 |
| OPr | J-29-32 |
| O-i-Pr | J-29-32 |
| O-n-Bu | J-29-32 |
| O-t-Bu | J-29-32 |
| NMe$_2$ | J-29-32 |
| NEt$_2$ | J-29-32 |
| N(n-Pr)$_2$ | J-29-32 |
| 1-piperdinyl | J-29-32 |
| 1-pyrrolidinyl | J-29-32 |
| 4-morpholinyl | J-29-32 |
| CH$_3$ | J-29-33 |
| CH$_2$Cl | J-29-33 |
| CH$_2$Br | J-29-33 |
| CH$_2$I | J-29-33 |
| OH | J-29-33 |
| OMe | J-29-33 |
| OEt | J-29-33 |
| OPr | J-29-33 |
| O-i-Pr | J-29-33 |
| O-n-Bu | J-29-33 |
| O-t-Bu | J-29-33 |
| NMe$_2$ | J-29-33 |
| NEt$_2$ | J-29-33 |
| N(n-Pr)$_2$ | J-29-33 |
| 1-piperdinyl | J-29-33 |
| 1-pyrrolidinyl | J-29-33 |
| 4-morpholinyl | J-29-33 |
| CH$_3$ | J-29-34 |
| CH$_2$Cl | J-29-34 |
| CH$_2$Br | J-29-34 |
| CH$_2$I | J-29-34 |
| OH | J-29-34 |
| OMe | J-29-34 |
| OEt | J-29-34 |
| OPr | J-29-34 |
| O-i-Pr | J-29-34 |
| O-n-Bu | J-29-34 |
| O-t-Bu | J-29-34 |
| NMe$_2$ | J-29-34 |
| NEt$_2$ | J-29-34 |
| N(n-Pr)$_2$ | J-29-34 |
| 1-piperdinyl | J-29-34 |
| 1-pyrrolidinyl | J-29-34 |
| 4-morpholinyl | J-29-34 |
| CH$_3$ | J-29-35 |
| CH$_2$Cl | J-29-35 |
| CH$_2$Br | J-29-35 |
| CH$_2$I | J-29-35 |
| OH | J-29-35 |
| OMe | J-29-35 |
| OEt | J-29-35 |
| OPr | J-29-35 |
| O-i-Pr | J-29-35 |
| O-n-Bu | J-29-35 |
| O-t-Bu | J-29-35 |
| NMe$_2$ | J-29-35 |
| NEt$_2$ | J-29-35 |
| N(n-Pr)$_2$ | J-29-35 |
| 1-piperdinyl | J-29-35 |
| 1-pyrrolidinyl | J-29-35 |
| 4-morpholinyl | J-29-35 |
| CH$_3$ | J-29-36 |
| CH$_2$Cl | J-29-36 |
| CH$_2$Br | J-29-36 |

TABLE 8-continued

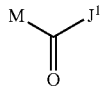

wherein J¹ is one of J-29-1 through J-29-58 (as depicted in Exhibit A above).

| M | J¹ |
|---|---|
| $CH_2I$ | J-29-36 |
| OH | J-29-36 |
| OMe | J-29-36 |
| OEt | J-29-36 |
| OPr | J-29-36 |
| O-i-Pr | J-29-36 |
| O-n-Bu | J-29-36 |
| O-t-Bu | J-29-36 |
| $NMe_2$ | J-29-36 |
| $NEt_2$ | J-29-36 |
| $N(n-Pr)_2$ | J-29-36 |
| 1-piperdinyl | J-29-36 |
| 1-pyrrolidinyl | J-29-36 |
| 4-morpholinyl | J-29-36 |
| $CH_3$ | J-29-37 |
| $CH_2Cl$ | J-29-37 |
| $CH_2Br$ | J-29-37 |
| $CH_2I$ | J-29-37 |
| OH | J-29-37 |
| OMe | J-29-37 |
| OEt | J-29-37 |
| OPr | J-29-37 |
| O-i-Pr | J-29-37 |
| O-n-Bu | J-29-37 |
| O-t-Bu | J-29-37 |
| $NMe_2$ | J-29-37 |
| $NEt_2$ | J-29-37 |
| $N(n-Pr)_2$ | J-29-37 |
| 1-piperdinyl | J-29-37 |
| 1-pyrrolidinyl | J-29-37 |
| 4-morpholinyl | J-29-37 |
| $CH_3$ | J-29-38 |
| $CH_2Cl$ | J-29-38 |
| $CH_2Br$ | J-29-38 |
| $CH_2I$ | J-29-38 |
| OH | J-29-38 |
| OMe | J-29-38 |
| OEt | J-29-38 |
| OPr | J-29-38 |
| O-i-Pr | J-29-38 |
| O-n-Bu | J-29-38 |
| O-t-Bu | J-29-38 |
| $NMe_2$ | J-29-38 |
| $NEt_2$ | J-29-38 |
| $N(n-Pr)_2$ | J-29-38 |
| 1-piperdinyl | J-29-38 |
| 1-pyrrolidinyl | J-29-38 |
| 4-morpholinyl | J-29-38 |
| $CH_3$ | J-29-39 |
| $CH_2Cl$ | J-29-39 |
| $CH_2Br$ | J-29-39 |
| $CH_2I$ | J-29-39 |
| OH | J-29-39 |
| OMe | J-29-39 |
| OEt | J-29-39 |
| OPr | J-29-39 |
| O-i-Pr | J-29-39 |
| O-n-Bu | J-29-39 |
| O-t-Bu | J-29-39 |
| $NMe_2$ | J-29-39 |
| $NEt_2$ | J-29-39 |
| $N(n-Pr)_2$ | J-29-39 |
| 1-piperdinyl | J-29-39 |
| 1-pyrrolidinyl | J-29-39 |
| 4-morpholinyl | J-29-39 |
| $CH_3$ | J-29-40 |
| $CH_2Cl$ | J-29-40 |
| $CH_2Br$ | J-29-40 |
| $CH_2I$ | J-29-40 |
| OH | J-29-40 |
| OMe | J-29-40 |
| OEt | J-29-40 |
| OPr | J-29-40 |
| O-i-Pr | J-29-40 |
| O-n-Bu | J-29-40 |
| O-t-Bu | J-29-40 |
| $NMe_2$ | J-29-40 |
| $NEt_2$ | J-29-40 |
| $N(n-Pr)_2$ | J-29-40 |
| 1-piperdinyl | J-29-40 |
| 1-pyrrolidinyl | J-29-40 |
| 4-morpholinyl | J-29-40 |
| $CH_3$ | J-29-41 |
| $CH_2Cl$ | J-29-41 |
| $CH_2Br$ | J-29-41 |
| $CH_2I$ | J-29-41 |
| OH | J-29-41 |
| OMe | J-29-41 |
| OEt | J-29-41 |
| OPr | J-29-41 |
| O-i-Pr | J-29-41 |
| O-n-Bu | J-29-41 |
| O-t-Bu | J-29-41 |
| $NMe_2$ | J-29-41 |
| $NEt_2$ | J-29-41 |
| $N(n-Pr)_2$ | J-29-41 |
| 1-piperdinyl | J-29-41 |
| 1-pyrrolidinyl | J-29-41 |
| 4-morpholinyl | J-29-41 |
| $CH_3$ | J-29-42 |
| $CH_2Cl$ | J-29-42 |
| $CH_2Br$ | J-29-42 |
| $CH_2I$ | J-29-42 |
| OH | J-29-42 |
| OMe | J-29-42 |
| OEt | J-29-42 |
| OPr | J-29-42 |
| O-i-Pr | J-29-42 |
| O-n-Bu | J-29-42 |
| O-t-Bu | J-29-42 |
| $NMe_2$ | J-29-42 |
| $NEt_2$ | J-29-42 |
| $N(n-Pr)_2$ | J-29-42 |
| 1-piperdinyl | J-29-42 |
| 1-pyrrolidinyl | J-29-42 |
| 4-morpholinyl | J-29-42 |
| $CH_3$ | J-29-43 |
| $CH_2Cl$ | J-29-43 |
| $CH_2Br$ | J-29-43 |
| $CH_2I$ | J-29-43 |
| OH | J-29-43 |
| OMe | J-29-43 |
| OEt | J-29-43 |
| OPr | J-29-43 |
| O-i-Pr | J-29-43 |
| O-n-Bu | J-29-43 |
| O-t-Bu | J-29-43 |
| $NMe_2$ | J-29-43 |
| $NEt_2$ | J-29-43 |
| $N(n-Pr)_2$ | J-29-43 |
| 1-piperdinyl | J-29-43 |
| 1-pyrrolidinyl | J-29-43 |
| 4-morpholinyl | J-29-43 |
| $CH_3$ | J-29-44 |
| $CH_2Cl$ | J-29-44 |
| $CH_2Br$ | J-29-44 |
| $CH_2I$ | J-29-44 |
| OH | J-29-44 |
| OMe | J-29-44 |
| OEt | J-29-44 |
| OPr | J-29-44 |
| O-i-Pr | J-29-44 |
| O-n-Bu | J-29-44 |
| O-t-Bu | J-29-44 |

TABLE 8-continued

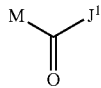

wherein J¹ is one of J-29-1 through J-29-58 (as depicted in Exhibit A above).

| M | J¹ |
|---|---|
| NMe$_2$ | J-29-44 |
| NEt$_2$ | J-29-44 |
| N(n-Pr)$_2$ | J-29-44 |
| 1-piperdinyl | J-29-44 |
| 1-pyrrolidinyl | J-29-44 |
| 4-morpholinyl | J-29-44 |
| CH$_3$ | J-29-45 |
| CH$_2$Cl | J-29-45 |
| CH$_2$Br | J-29-45 |
| CH$_2$I | J-29-45 |
| OH | J-29-45 |
| OMe | J-29-45 |
| OEt | J-29-45 |
| OPr | J-29-45 |
| O-i-Pr | J-29-45 |
| O-n-Bu | J-29-45 |
| O-t-Bu | J-29-45 |
| NMe$_2$ | J-29-45 |
| NEt$_2$ | J-29-45 |
| N(n-Pr)$_2$ | J-29-45 |
| 1-piperdinyl | J-29-45 |
| 1-pyrrolidinyl | J-29-45 |
| 4-morpholinyl | J-29-45 |
| CH$_3$ | J-29-46 |
| CH$_2$Cl | J-29-46 |
| CH$_2$Br | J-29-46 |
| CH$_2$I | J-29-46 |
| OH | J-29-46 |
| OMe | J-29-46 |
| OEt | J-29-46 |
| OPr | J-29-46 |
| O-i-Pr | J-29-46 |
| O-n-Bu | J-29-46 |
| O-t-Bu | J-29-46 |
| NMe$_2$ | J-29-46 |
| NEt$_2$ | J-29-46 |
| N(n-Pr)$_2$ | J-29-46 |
| 1-piperdinyl | J-29-46 |
| 1-pyrrolidinyl | J-29-46 |
| 4-morpholinyl | J-29-46 |
| CH$_3$ | J-29-47 |
| CH$_2$Cl | J-29-47 |
| CH$_2$Br | J-29-47 |
| CH$_2$I | J-29-47 |
| OH | J-29-47 |
| OMe | J-29-47 |
| OEt | J-29-47 |
| OPr | J-29-47 |
| O-i-Pr | J-29-47 |
| O-n-Bu | J-29-47 |
| O-t-Bu | J-29-47 |
| NMe$_2$ | J-29-47 |
| NEt$_2$ | J-29-47 |
| N(n-Pr)$_2$ | J-29-47 |
| 1-piperdinyl | J-29-47 |
| 1-pyrrolidinyl | J-29-47 |
| 4-morpholinyl | J-29-47 |
| CH$_3$ | J-29-48 |
| CH$_2$Cl | J-29-48 |
| CH$_2$Br | J-29-48 |
| CH$_2$I | J-29-48 |
| OH | J-29-48 |
| OMe | J-29-48 |
| OEt | J-29-48 |
| OPr | J-29-48 |
| O-i-Pr | J-29-48 |
| O-n-Bu | J-29-48 |
| O-t-Bu | J-29-48 |
| NMe$_2$ | J-29-48 |
| NEt$_2$ | J-29-48 |
| N(n-Pr)$_2$ | J-29-48 |
| 1-piperdinyl | J-29-48 |
| 1-pyrrolidinyl | J-29-48 |
| 4-morpholinyl | J-29-48 |
| CH$_3$ | J-29-49 |
| CH$_2$Cl | J-29-49 |
| CH$_2$Br | J-29-49 |
| CH$_2$I | J-29-49 |
| OH | J-29-49 |
| OMe | J-29-49 |
| OEt | J-29-49 |
| OPr | J-29-49 |
| O-i-Pr | J-29-49 |
| O-n-Bu | J-29-49 |
| O-t-Bu | J-29-49 |
| NMe$_2$ | J-29-49 |
| NEt$_2$ | J-29-49 |
| N(n-Pr)$_2$ | J-29-49 |
| 1-piperdinyl | J-29-49 |
| 1-pyrrolidinyl | J-29-49 |
| 4-morpholinyl | J-29-49 |
| CH$_3$ | J-29-50 |
| CH$_2$Cl | J-29-50 |
| CH$_2$Br | J-29-50 |
| CH$_2$I | J-29-50 |
| OH | J-29-50 |
| OMe | J-29-50 |
| OEt | J-29-50 |
| OPr | J-29-50 |
| O-i-Pr | J-29-50 |
| O-n-Bu | J-29-50 |
| O-t-Bu | J-29-50 |
| NMe$_2$ | J-29-50 |
| NEt$_2$ | J-29-50 |
| N(n-Pr)$_2$ | J-29-50 |
| 1-piperdinyl | J-29-50 |
| 1-pyrrolidinyl | J-29-50 |
| 4-morpholinyl | J-29-50 |
| CH$_3$ | J-29-51 |
| CH$_2$Cl | J-29-51 |
| CH$_2$Br | J-29-51 |
| CH$_2$I | J-29-51 |
| OH | J-29-51 |
| OMe | J-29-51 |
| OEt | J-29-51 |
| OPr | J-29-51 |
| O-i-Pr | J-29-51 |
| O-n-Bu | J-29-51 |
| O-t-Bu | J-29-51 |
| NMe$_2$ | J-29-51 |
| NEt$_2$ | J-29-51 |
| N(n-Pr)$_2$ | J-29-51 |
| 1-piperdinyl | J-29-51 |
| 1-pyrrolidinyl | J-29-51 |
| 4-morpholinyl | J-29-51 |
| CH$_3$ | J-29-52 |
| CH$_2$Cl | J-29-52 |
| CH$_2$Br | J-29-52 |
| CH$_2$I | J-29-52 |
| OH | J-29-52 |
| OMe | J-29-52 |
| OEt | J-29-52 |
| OPr | J-29-52 |
| O-i-Pr | J-29-52 |
| O-n-Bu | J-29-52 |
| O-t-Bu | J-29-52 |
| NMe$_2$ | J-29-52 |
| NEt$_2$ | J-29-52 |
| N(n-Pr)$_2$ | J-29-52 |

TABLE 8-continued

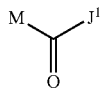

wherein J¹ is one of J-29-1 through J-29-58 (as depicted in Exhibit A above).

| M | J¹ |
|---|---|
| 1-piperdinyl | J-29-52 |
| 1-pyrrolidinyl | J-29-52 |
| 4-morpholinyl | J-29-52 |
| CH₃ | J-29-53 |
| CH₂Cl | J-29-53 |
| CH₂Br | J-29-53 |
| CH₂I | J-29-53 |
| OH | J-29-53 |
| OMe | J-29-53 |
| OEt | J-29-53 |
| OPr | J-29-53 |
| O-i-Pr | J-29-53 |
| O-n-Bu | J-29-53 |
| O-t-Bu | J-29-53 |
| NMe₂ | J-29-53 |
| NEt₂ | J-29-53 |
| N(n-Pr)₂ | J-29-53 |
| 1-piperdinyl | J-29-53 |
| 1-pyrrolidinyl | J-29-53 |
| 4-morpholinyl | J-29-53 |
| CH₃ | J-29-54 |
| CH₂Cl | J-29-54 |
| CH₂Br | J-29-54 |
| CH₂I | J-29-54 |
| OH | J-29-54 |
| OMe | J-29-54 |
| OEt | J-29-54 |
| OPr | J-29-54 |
| O-i-Pr | J-29-54 |
| O-n-Bu | J-29-54 |
| O-t-Bu | J-29-54 |
| NMe₂ | J-29-54 |
| NEt₂ | J-29-54 |
| N(n-Pr)₂ | J-29-54 |
| 1-piperdinyl | J-29-54 |
| 1-pyrrolidinyl | J-29-54 |
| 4-morpholinyl | J-29-54 |
| CH₃ | J-29-55 |
| CH₂Cl | J-29-55 |
| CH₂Br | J-29-55 |
| CH₂I | J-29-55 |
| OH | J-29-55 |
| OMe | J-29-55 |
| OEt | J-29-55 |
| OPr | J-29-55 |
| O-i-Pr | J-29-55 |
| O-n-Bu | J-29-55 |
| O-t-Bu | J-29-55 |
| NMe₂ | J-29-55 |
| NEt₂ | J-29-55 |
| N(n-Pr)₂ | J-29-55 |
| 1-piperdinyl | J-29-55 |
| 1-pyrrolidinyl | J-29-55 |
| 4-morpholinyl | J-29-55 |
| CH₃ | J-29-56 |
| CH₂Cl | J-29-56 |
| CH₂Br | J-29-56 |
| CH₂I | J-29-56 |
| OH | J-29-56 |
| OMe | J-29-56 |
| OEt | J-29-56 |
| OPr | J-29-56 |
| O-i-Pr | J-29-56 |
| O-n-Bu | J-29-56 |
| O-t-Bu | J-29-56 |
| NMe₂ | J-29-56 |
| NEt₂ | J-29-56 |
| N(n-Pr)₂ | J-29-56 |
| 1-piperdinyl | J-29-56 |

TABLE 8-continued

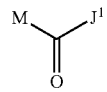

wherein J¹ is one of J-29-1 through J-29-58 (as depicted in Exhibit A above).

| M | J¹ |
|---|---|
| 1-pyrrolidinyl | J-29-56 |
| 4-morpholinyl | J-29-56 |
| CH₃ | J-29-57 |
| CH₂Cl | J-29-57 |
| CH₂Br | J-29-57 |
| CH₂I | J-29-57 |
| OH | J-29-57 |
| OMe | J-29-57 |
| OEt | J-29-57 |
| OPr | J-29-57 |
| O-i-Pr | J-29-57 |
| O-n-Bu | J-29-57 |
| O-t-Bu | J-29-57 |
| NMe₂ | J-29-57 |
| NEt₂ | J-29-57 |
| N(n-Pr)₂ | J-29-57 |
| 1-piperdinyl | J-29-57 |
| 1-pyrrolidinyl | J-29-57 |
| 4-morpholinyl | J-29-57 |
| CH₃ | J-29-58 |
| CH₂Cl | J-29-58 |
| CH₂Br | J-29-58 |
| CH₂I | J-29-58 |
| OH | J-29-58 |
| OMe | J-29-58 |
| OEt | J-29-58 |
| OPr | J-29-58 |
| O-i-Pr | J-29-58 |
| O-n-Bu | J-29-58 |
| O-t-Bu | J-29-58 |
| NMe₂ | J-29-58 |
| NEt₂ | J-29-58 |
| N(n-Pr)₂ | J-29-58 |
| 1-piperdinyl | J-29-58 |
| 1-pyrrolidinyl | J-29-58 |
| 4-morpholinyl | J-29-58 |

Table 8 above identifies particular compounds comprising a J¹ group selected from J-29-1 through J-29-58. As many J-29-1 through J-29-58 include a chiral center, these J¹ groups are illustrated in a particular enantiomeric configuration, which in some instances may provide the greatest fungicidal activity for compounds of Formula 1. One skilled in the art immediately recognizes the antipode (i.e. opposite enantiomer) for each of the compounds listed, and furthermore understands that the enantiomers can be present as pure enantiomers or in mixtures enriched in one enantiomer or in racemic mixtures.

Formulation/Utility

A compound of Formula 1 of this invention will generally be used as a fungicidal active ingredient in a composition, i.e. formulation, with at least one additional component selected from the group consisting of surfactants, solid diluents and liquid diluents, which serve as a carrier. Compounds within the scope of exclusion of proviso (a) of Formula 1 can also be used. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, pills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto vegetable seeds as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders. | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books. Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents arm described in Marsden, *Solvents Guide,* 2nd Ed., Interscience, New York, 1950.

The solid and liquid compositions of the present invention often include one or more surfactants. Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyl peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids. Such formulation auxiliaries and additives may control: pH (buffers), foaming during processing (antifoams such polyorganosiloxanes (e.g., Rhodorsil®) 416)), sedimentation of active ingredients (suspending agents), viscosity (thixotropic thickeners), in-container microbial growth (antimicrobials), product freezing (antifreezes), color (dyes/pigment dispersions (e.g., Pro-Ized® Colorant Red)), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and, usually, grinding as in a hammer mill or fluid-energy mill. Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry. The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Table A.

Example A

High Strength Concentrate

| | |
|---|---|
| Compound 1 | 98.5% |
| silica aerogel | 0.5% |
| synthetic amorphous fine silica | 1.0%. |

Example B

Wettable Powder

| | |
|---|---|
| Compound 2 | 65.0% |
| dodecylphenol polyethylene glycol ether | 2.0% |

-continued

| | |
|---|---|
| sodium ligninsulfonate | 4.0% |
| sodium silicoaluminate | 6.0% |
| montmorillonite (calcined) | 23.0%. |

Example C

Granule

| | |
|---|---|
| Compound 16 | 10.0% |
| attapulgite granules (low volatile matter, 0.71/0.30 mm; U.S.S. No. 25-50 sieves) | 90.0%. |

Example D

Aqueous Suspension

| | |
|---|---|
| Compound 37 | 25.0% |
| hydrated attapulgite | 3.0% |
| crude calcium ligninsulfonate | 10.0% |
| sodium dihydrogen phosphate | 0.5% |
| water | 61.5%. |

Example E

Extruded Pellet

| | |
|---|---|
| Compound 107 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example F

Microemulsion

| | |
|---|---|
| Compound 44 | 1.0% |
| triacetine | 30.0% |
| $C_8$-$C_{10}$ alkylpolyglycoside | 30.0% |
| glyceryl monooleate | 19.0% |
| water | 20.0%. |

Example G

Emulsifiable Concentrate

| | |
|---|---|
| Compound 1 | 10.0% |
| $C_8$-$C_{10}$ fatty acid methyl ester | 70.0% |
| polyoxyethylene sorbitol hexoleate | 20.0%. |

The compounds of Formula 1 of this invention are useful as plant disease control agents. The present invention therefore further comprises a method for controlling plant diseases caused by fungal plant pathogens comprising applying to the plant or portion thereof to be protected, or to the plant seed to be protected, an effective amount of a compound of the invention or a fungicidal composition containing said compound. Compounds within the scope of exclusion of proviso (a) of Formula 1 and fungicidal compositions containing them can also be used to control plant diseases in accordance with this invention. The compounds and/or compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, turf, vegetable, field, cereal, and fruit crops. These pathogens include: Oomycetes, including *Phytophthora* diseases such as *Phytophthora infestans, Phytophthora megasperma, Phytophthora parasitica, Phytophthora cinnamomi* and *Phytophthora capsici, Pythium* diseases such as *Pythium aphanidermatum*, and diseases in the Peronosporaceae family such as *Plasmopara viticola, Peronospora* spp. (including *Peronospora tabacina* and *Peronospora parasitica*), *Pseudoperonospora* spp. (including *Pseudoperonospora cubensis*) and *Bremia lactucae*; Ascomycetes, including *Alternaria* diseases such as *Altermaria solani* and *Alternaria brassicae, Guignardia* diseases such as *Guignardia bidwell, Venturia* diseases such as *Venturia inaequalis, Septoria* diseases such as *Septoria nodorum* and *Septoria tritici*, powdery mildew diseases such as *Erysiphe* spp. (including *Erysiphe graminis* and *Erysiphe polygoni*), *Uncinula necatur, Sphaerotheca fuligena* and *Podosphaera leucotricha, Pseudocercosporella herpotrichoides, Botrytis* diseases such as *Botrytis cinerea, Monilinia fructicola, Sclerotinia* diseases such as *Sclerotinia sclerotiorum, Magnaporthe grisea, Phomopsis viticola, Helminthosporium* diseases such as *Helminthosporium tritici repentis, Pyrenophora teres*, anthracnose diseases such as *Glomerella* or *Colletotrichum* spp. (such as *Colletotrichum graminicola* and *Colletotrichum orbiculare*), and *Gaeumannomyces graminis*; Basidiomycetes, including rust diseases caused by *Puccinia* spp. (such as *Puccinia recondita, Puccinia striiformis, Puccinia hordei, Puccinia graminis* and *Puccinia arachidis*), *Hemileia vastatrix* and *Phakopsora pachvrhizi*; other pathogens including *Rhizoctonia* spp. (such as *Rhizoctonia solani*); *Fusarium* diseases such as *Fusarium roseum, Fusarium graminearum* and *Fusarium oxysporum; Verticillium dahliae; Sclerotium rolfsii; Rynchosporium secalis; Cercosporidium personatum, Cercospora arachidicola* and *Cercospora beticola*; and other genera and species closely related to these pathogens. In addition to their fungicidal activity, the compositions or combinations also have activity against bacteria such as *Erwinia amylovora, Xanthomonas campestris, Pseudomonas syringae*, and other related species. Of note is control provided of disease caused by the Ascomycete and Oomycete classes. Of particular note is control provided of disease caused by the Oomycete class.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to seeds to protect the seeds and seedlings developing from the seeds. The compounds can also be applied through irrigation water to treat plants.

Rates of application for these compounds can be influenced by many factors of the environment and should be determined under actual use conditions. Foliage can normally be protected when treated at a rate of from less than about 1 g/ha to about 5,000 g/ha of active ingredient. Seed and seedlings can normally be protected when seed is treated at a rate of from about 0.1 to about 10 g per kilogram of seed.

Compounds of this invention can also be mixed with one or more other insecticides, fungicides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection. Examples of such agricultural protectants with which compounds of this invention can be formulated are: insecticides such as abamectin, acephate, acetamiprid, amidoflumet (S-1955), avermectin, azadirachtin, azinphos-methyl, bifenthrin, bifenazate, buprofezin, carbofuran, cartap, chlorantraniliprole (DPX-E2Y45), chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron; fungicides such as acibenzolar, aldimorph, amisulbrom, anilazine, azaconazole, azoxystrobin, benalaxyl, benodanil, benomyl, benthiavalicarb, benthiavalicarb-isopropyl, binapacryl, biphenyl, bitertanol, bixafen, blasticidin-S, Bordeaux mixture (tribasic copper sulfate), boscalid/nicobifen, bromuconazole, bupirimate, buthiobate, carboxin, carpropamid, captafol, captan, carbendazim, chloroneb, chlorothalonil, 5-chloro-6-(2,4,6-trifluorophenyl)-7-(4-methylpiperidin-1-yl)[1,2,4]triazolo[1,5-a]pyrimidine, chlozolinate, clotrimazole, copper oxychloride, copper salts such as copper sulfate and copper hydroxide, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, N-[2-(1,3-dimethylbutyl)phenyl]-5-fluoro-1,3-dimethyl-1H-pyrazol-4-carboxamide, dimethomorph, dimoxystrobin, diniconazole, diniconazole-M, dinocap, discostrobin, dithianon, dodemorph, dodine, econazole, edifenphos, enestroburin, epoxiconazole, etaconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin chloride, fentin hydroxide, ferbam, ferfurazoate, ferimzone, fluazinam, fludioxonil, flumetover, flumorph, fluopicolide, fluopyram, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, isotianil, kasugamycin, kresoxim-methyl, mancozeb, mandipropamid, maneb, mapanipyrin, mefenoxam, mepronil, meptyldinocap, metalaxyl, metconazole, methasulfocarb, metiram, metominostrobin, mepanipyrim, metiram, metrafenone, miconazole, myclobutanil, naftifine, neoasozin (ferric methanearsonate), nuarimol, octhilinone, ofurace, orysastrobin, oxadixyl, oxolinic acid, oxpoconazole, oxycarboxin, oxytetracycline, paclobutrazol, penconazole, pencycuron, penthiopyrad, perfurazoate, phosphonic acid, phthalide, picobenzamid, picoxystrobin, piperalin, polyoxin, probenazole, prochloraz, procymidone, propamocarb, propamocarb-hydrochloride, propiconazole, propineb, proquinazid, prothiocarb, prothioconazole, pyraclostrobin, pryazophos, pyribencarb, pyrifenox, pyrimethanil, pyrifenox, pyrolnitrine, pyroquilon, quinconazole, quinoxyfen, quintozene, silthiofam, simeconazole, spiroxamine, streptomycin, sulfur, tebuconazole, techrazene, tecloftalam, tecnazene, terbinafine, tetraconazole, thiabendazole, thiflluzamide, thiophanate, thiophanate-methyl, thiram, tiadinil, tolclofos-methyl, tolyfluanid, triadimefon, triadimenol, triarimol, triazoxide, tricyclazole, tridemorph, triflumizole, trimoprhamide tricyclazole, trifloxystrobin, triforine, triticonazole, uniconazole, validamycin, vinclozolin, zineb, ziram and zoxamide; nematocides such as aldicarb, aldoxycarb, fenamiphos, imicyafos and oxamyl; bactericides such as streptomycin; acaricides such as amitraz, chinomethionat, chlorobenzilate, cyenopyrafen, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis, Bacillus thuringiensis* delta endotoxin, baculovirus, and entomopathogenic bacteria, virus and fungi. Descriptions of various commercially available compounds listed above may be found in *The Pesticide Manual, Thirteenth Edition*, C. D. S. Thomlin, ed., British Crop Protection Council, 2003. For embodiments where one or more of these various mixing partners are used, the weight ratio of these various mixing partners (in total) to the compound of Formula 1 is typically between about 1:100 and about 3000:1. Of note are weight ratios between about 1:30 and about 300:1 (for example ratios between about 1:1 and about 30:1). It will be evident that including these additional components may expand the spectrum of diseases controlled beyond the spectrum controlled by the compound of Formula 1 alone.

In one mixture embodiment, granules of a solid composition comprising a compound of Formula 1 is mixed with granules of a solid composition comprising another agricultural protectant. These granule mixtures can be in accordance with the general granule mixture disclosure of PCT Patent Publication WO 94/24861 or more preferably the homogenous granule mixture teaching of U.S. Pat. No. 6,022,552.

Of note are combinations (e.g., in the form of compositions) of a compound of Formula 1 with at least one other fungicide. Of particular note are such combinations where the other fungicide has different site of action from the compound of Formula 1. In certain instances, combinations with other fungicides having a similar spectrum of control but a different site of action will be particularly advantageous for resistance management. Of particular note are compositions which in addition to compound of Formula 1 include at least one compound selected from the group consisting of (1) alkylenebis(dithiocarbamate) fungicides; (2) cymoxanil; (3) phenylamide fungicides; (4) pyrimidinone fungicides; (5) chlorothalonil; (6) carboxamides acting at complex II of the fungal mitochondrial respiratory electron transfer site; (7) quinoxyfen; (8) metrafenone; (9) cyflufenamid; (10) cyprodinil; (11) copper compounds; (12) phthalimide fungicides; (13) fosetyl-aluminum; (14) benzimidazole fungicides; (15) cyazofamid; (16) fluazinam; (17) iprovalicarb; (18) propamocarb; (19) validomycin; (20) dichlorophenyl dicarboximide fungicides; (21) zoxamide; (22) fluopicolide; (23) mandipropamid; (24) carboxylic acid amides acting on phospholipid biosynthesis and cell wall deposition; (25) dimethomorph; (26) non-DMI sterol biosynthesis inhibitors; (27) inhibitors of demethylase in sterol biosynthesis; (28) $bc_1$ complex fungicides; and salts of compounds of (1) through (28).

Further descriptions of classes of fungicidal compounds are provided below.

Pyrimidinone fungicides (group (4)) include compounds of Formula A1

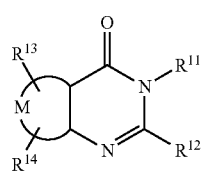

wherein M forms a fused phenyl, thiophene or pyridine ring; $R^{11}$ is $C_1$-$C_6$ alkyl; $R^{12}$ is $C_1$-$C_6$ alkyl or $C_1$-$C_6$ alkoxy; $R^{13}$ is halogen; and $R^{14}$ is hydrogen or halogen.

Pyrimidinone fungicides are described in PCT Patent Application Publication WO 94/26722 and U.S. Pat. Nos. 6,066,638, 6,245,770, 6,262,058 and 6,277,858. Of note are pyrimidinone fungicides selected from the group: 6-bromo-3-propyl-2-propyloxy-4(3H)-quinazolinone, 6,8-diiodo-3-propyl-2-propyloxy-4(31H)-quinazolinone, 6-iodo-3-propyl-2-propyloxy-4(3H)-quinazolinone (proquinazid), 6-chloro-2-propoxy-3-propylthieno[2,3-d]pyrimidin-4(3H)-one, 6-bromo-2-propoxy-3-propylthieno[2,3-d]pyrimidin-4(3H)-one, 7-bromo-2-propoxy-3-propylthieno[3,2-d]pyrimidin-4(3H)-one, 6-bromo-2-propoxy-3-propylpyrido[2,3-d]pyrimidin-4(3H)-one, 6,7-dibromo-2-propoxy-3-propylthieno[3,2-d]pyrimidin-4(3H)-one, and 3-(cyclopropylmethyl)-6-iodo-2-(propylthio)pyrido-[2,3-d]pyrimidin-4(3H)-one.

Sterol biosynthesis inhibitors (group (27)) control fungi by inhibiting enzymes in the sterol biosynthesis pathway. Demethylase-inhibiting fungicides have a common site of action within the fungal sterol biosynthesis pathway, involving inhibition of demethylation at position 14 of lanosterol or 24-methylene dihydrolanosterol, which are precursors to sterols in fungi. Compounds acting at this site are often referred to as demethylase inhibitors, DMI fungicides, or DMIs. The demethylase enzyme is sometimes referred to by other names in the biochemical literature, including cytochrome P-450 (14DM). The demethylase enzyme is described in, for example, *J. Biol. Chem.* 1992, 267, 13175-79 and references cited therein. DMI fungicides are divided between several chemical classes: azoles (including triazoles and imidazoles), pyrimidines, piperazines and pyridines. The triazoles include azaconazole, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole and uniconazole. The imidazoles include clotrimazole, econazole, imazalil, isoconazole, miconazole, oxpoconazole, prochloraz and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

$bc_1$ Complex Fungicides (group 28) have a fungicidal mode of action which inhibits the $bc_1$ complex in the mitochondrial respiration chain. The $bc_1$ complex is sometimes referred to by other names in the biochemical literature, including complex III of the electron transfer chain, and ubihydroquinone:cytochrome c oxidoreductase. This complex is uniquely identified by Enzyme Commission number EC1.10.2.2. The $bc_1$ complex is described in, for example, *J. Biol. Chem.* 1989, 264, 14543-48; *Methods Enzymol.* 1986, 126, 253-71; and references cited therein. Strobilurin fungicides such as azoxystrobin, dimoxystrobin, enestroburin (SYP-Z071), fluoxastrobin, kresoxim-methyl, metominostrobin, orysastrobin, picoxystrobin, pyraclostrobin and trifloxystrobin are known to have this mode of action (H. Sauter et al., *Angew. Chem. Int. Ed.* 1999, 38, 1328-1349). Other fungicidal compounds that inhibit the $bc_1$ complex in the mitochondrial respiration chain include famoxadone and fenamidone.

Alkylenebis(dithiocarbamate) fungicides (group (1)) include compounds such as mancozeb, maneb, propineb and zineb. Phenylamide fungicides (group (3)) include compounds such as metalaxyl, benalaxyl, furalaxyl and oxadixyl. Carboxamides (group (6)) include compounds such as boscalid, carboxin, fenfuram, flutolanil, furametpyr, mepronil, oxycarboxin, thifluzamide, penthiopyrad and N-[2-(1,3-dimethylbutyl)phenyl]-5-fluoro-1,3-dimethyl-1H-pyrazole-4-carboxamide (PCT Patent Publication WO 2003/010149), and are known to inhibit mitochondrial function by disrupting complex II (succinate dehydrogenase) in the respiratory electron transport chain. Copper compounds (group (11)) include compounds such as copper oxychloride, copper sulfate and copper hydroxide, including compositions such as Bordeaux mixture (tribasic copper sulfate). Phthalimide fungicides (group (12)) include compounds such as folpet and captan. Benzimidazole fungicides (group (14)) include benomyl and carbendazim. Dichlorophenyl dicarboximide fungicides (group (20)) include chlozolinate, dichlozoline, iprodione, isovaledione, myclozolin, procymidone and vinclozolin.

Non-DMI sterol biosynthesis inhibitors (group (26)) include morpholine and piperidine fungicides. The morpholines and piperidines are sterol biosynthesis inhibitors that have been shown to inhibit steps in the sterol biosynthesis pathway at a point later than the inhibitions achieved by the DMI sterol biosynthesis (group (27)). The morpholines include aldimorph, dodemorph, fenpropimorph, tridemorph and trimorphamide. The piperidines include fenpropidin.

Of note are these methods where plant diseases caused by Oomycete fungal plant pathogens are controlled.

The discussion above relating to the use of compounds of Formula 1 in compositions (e.g., certain compositions comprising surfactants, solid diluents, liquid diluents and/or biologically active compounds) and in methods for controlling plant diseases (e.g., controlling plant diseases caused by Oomycete fungal plant pathogens) also applies to compounds within the scope of exclusion of proviso (a) of Formula 1.

The following Tests demonstrate the control efficacy of compounds of this invention on specific pathogens. The pathogen control protection afforded by the compounds is not limited, however, to these species. See Index Tables A for compound descriptions. The stereocenters labeled as "R" (rectus) and "S" (sinister) are based on the Cahn-Ingold-Prelog system as used by Chemical Abstracts; a stereocenter label followed by an asterisks "**" means the stereochemical description is relative to other stereocenters, and the compound is racemic. The abbreviation "Ex." stands for "Example" and is followed by a number indicating in which example the compound is prepared. Index Table A lists the molecular weight of the highest isotopic abundance parent ion (M+1) formed by addition of $H^+$ (molecular weight of 1) to the molecule, observed by mass spectrometry using atmospheric pressure chemical ionization ($AP^+$). Chiral separation of Compound 1 into Compounds 3 and 4 was accomplished using a preparative CHIRALPAK® AD-RH column (Chiral Technologies, Inc., West Chester, Pa., U.S.A.) containing silica gel coated with amylose-tris(3,5-dimethylphenyl carbamate) and eluted with a water-methanol gradient. Specific rotation ($[\alpha]_D$) was measured in ethanol solution at 25° C. using a 100-mm path cell.

INDEX TABLE A

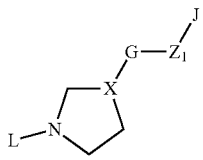

G is as defined in Exhibit 2; $R^{3a}$ in G is H. L groups are defined as illustrated below.

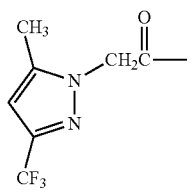

L-1

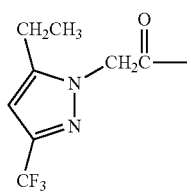

L-2

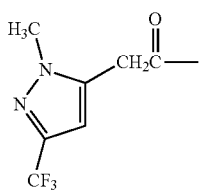

L-3

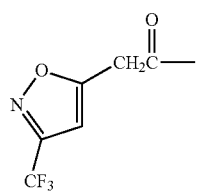

L-4

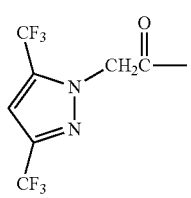

L-5

INDEX TABLE A-continued
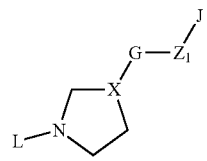
G is as defined in Exhibit 2; $R^{3a}$ in G is H. L groups are defined as illustrated below.
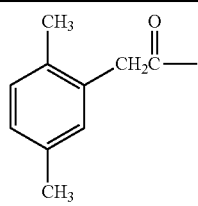
L-6
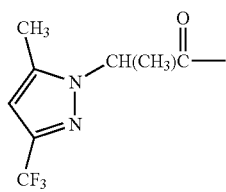
L-7
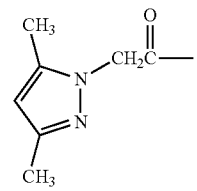
L-8
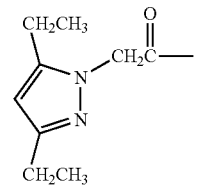
L-9
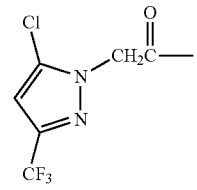
L-10
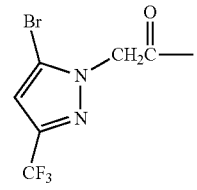
L-11
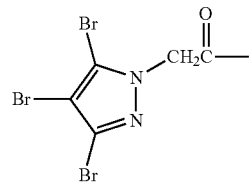
L-12

INDEX TABLE A-continued
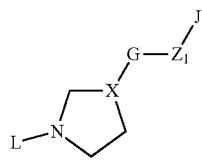
G is as defined in Exhibit 2; $R^{3a}$ in G is H. L groups are defined as illustrated below.
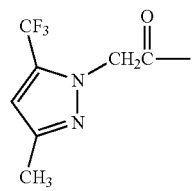 L-13
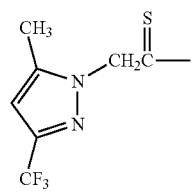 L-14
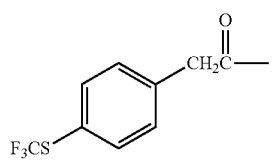 L-15
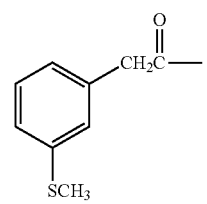 L-16
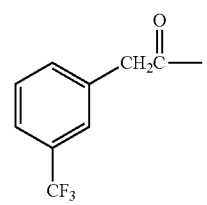 L-17
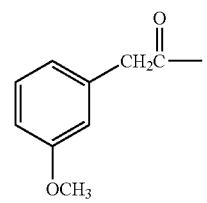 L-18
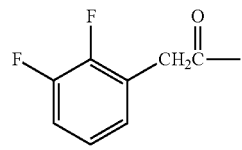 L-19

INDEX TABLE A-continued
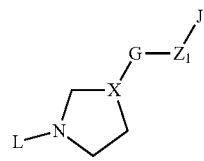
G is as defined in Exhibit 2; $R^{3a}$ in G is H. L groups are defined as illustrated below.
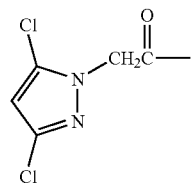
L-20
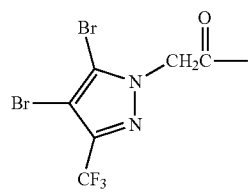
L-21
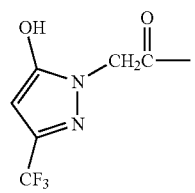
L-22
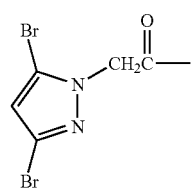
L-23
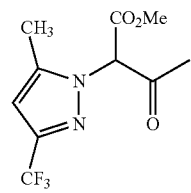 [SMILES: COC(=O)C(C(C)=O)n1nc(C(F)(F)F)cc1C]
L-24
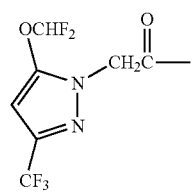
L-25
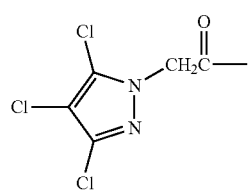
L-26

INDEX TABLE A-continued
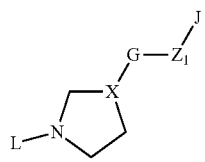
G is as defined in Exhibit 2; $R^{3a}$ in G is H. L groups are defined as illustrated below.
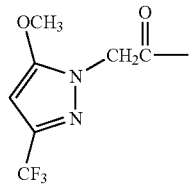 L-27
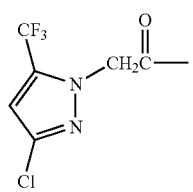 L-28
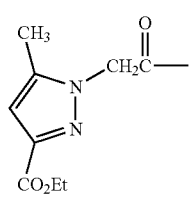 L-29
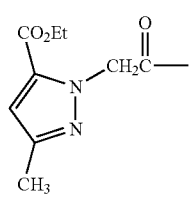 L-30
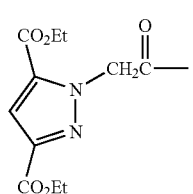 L-31
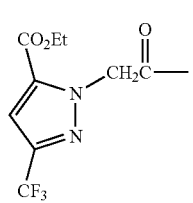 L-32

INDEX TABLE A-continued

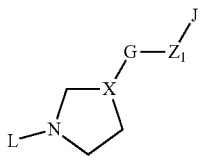

G is as defined in Exhibit 2; $R^{3a}$ in G is H. L groups are defined as illustrated below.

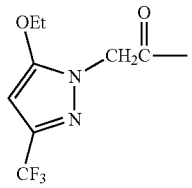

L-33

| Cmpd. | L | X | G | $Z_1$—J | AP+ (M + 1) |
|---|---|---|---|---|---|
| 1 (Ex. 1) | L-1 | $X^1$ | G-1 | 4,5-dihydro-5-phenyl-3-isoxazolyl | 504 |
| 2 (Ex. 2) | L-1 | $X^1$ | G-1 | 5-phenyl-3-isoxazolyl | 502 |
| 3 (Ex. 12) | L-1 | $X^1$ | G-1 | 4,5-dihydro-5-phenyl-3-isoxazolyl [Note 1] | 504 |
| 4 | L-1 | $X^1$ | G-1 | 4,5-dihydro-5-phenyl-3-isoxazolyl [Note 2] | 504 |
| 5 | L-1 | $X^1$ | G-1 | 5,6-dihydro-6-phenyl-4H-1,2-oxazin-3-yl | 518 |
| 6 (Ex. 4) | L-1 | $X^1$ | G-1 | 4,5-dihydro-3-phenyl-5-isoxazolyl | 504 |
| 7 (Ex. 3) | L-1 | $X^1$ | G-1 | (5S)-4,5-dihydro-1-methyl-5-phenyl-1H-imidazol-2-yl | 517 |
| 8 (Ex. 5) | L-1 | $X^1$ | G-1 | 5-(2-chlorophenyl)-4,5-dihydro-3-isoxazolyl | 538 |
| 9 | L-1 | $X^1$ | G-1 | 5-(4-chlorophenyl)-4,5-dihydro-3-isoxazolyl | 538 |
| 10 | L-1 | $X^1$ | G-1 | 4,5-dihydro-5-(4-methylphenyl)-3-isoxazolyl | 518 |
| 11 | L-1 | $X^1$ | G-1 | (4R**,5R**)-4,5-dihydro-4-methyl-5-phenyl-3-isoxazolyl | 518 |
| 12 | L-1 | $X^1$ | G-27 | 3-phenyl-1H-pyrazol-1-yl | 483 |
| 13 | L-1 | $X^1$ | G-1 | 4-phenyl-2-oxazolidinyl | 506 |
| 14 | L-1 | $X^1$ | G-1 | 3-acetyl-4-phenyl-2-oxazolidinyl | 548 |
| 15 (Ex. 8) | L-1 | $X^1$ | G-1 | 4,5-dihydro-5-methyl-5-phenyl-3-isoxazolyl | 518 |
| 16 (Ex. 8) | L-1 | $X^1$ | G-1 | 3a,4,5,9b-tetrahydronaphth[2,1-d]isoxazol-3-yl | 530 |
| 17 | L-1 | $X^1$ | G-1 | 5-(3-chlorophenyl)-4,5-dihydro-3-isoxazolyl | 538 |
| 18 (Ex. 8) | L-1 | $X^1$ | G-1 | 4,5-dihydro-5-(4-methoxyphenyl)-3-isoxazolyl | 534 |
| 19 (Ex. 1) | L-2 | $X^1$ | G-1 | 4,5-dihydro-5-phenyl-3-isoxazolyl | 518 |
| 20 | L-3 | $X^1$ | G-1 | 4,5-dihydro-5-phenyl-3-isoxazolyl | 504 |
| 21 | L-4 | $X^1$ | G-1 | 4,5-dihydro-5-phenyl-3-isoxazolyl | 491 |
| 22 (Ex. 1) | L-5 | $X^1$ | G-1 | 4,5-dihydro-5-phenyl-3-isoxazolyl | 558 |
| 23 | L-6 | $X^1$ | G-1 | 4,5-dihydro-5-phenyl-3-isoxazolyl | 460 |
| 24 | L-1 | $X^1$ | G-1 | 4,5-dihydro-5-(phenylmethyl)-3-isoxazolyl | 518 |
| 25 | L-1 | $X^1$ | G-1 | (4R**,5S**)-4,5-dihydro-4-methyl-5-phenyl-3-isoxazolyl | 518 |
| 26 | L-1 | $X^1$ | G-1 | 4-biphenyl | 511 |
| 27 | L-1 | $X^1$ | G-1 | 4,5-dihydro-5-(3-methylbutyl)-3-isoxazolyl | 498 |
| 28 | L-1 | $X^1$ | G-1 | 4,5-dihydro-5-(2,2-dimethylpropyl)-3-isoxazolyl | 498 |
| 29 | L-1 | $X^1$ | G-1 | 5,6-dihydro-6-methyl-6-phenyl-4H-1,2-oxazin-3-yl | 532 |
| 30 | L-1 | $X^1$ | G-1 | 3-phenyl-5-isoxazolyl | 502 |
| 31 | L-1 | $X^1$ | G-1 | 4,5-dihydro-4-phenyl-2-oxazolyl | 504 |
| 32 | L-1 | $X^1$ | G-1 | 4,5-dihydro-1-(phenylmethyl)-1H-imidazol-2-yl | 517 |
| 33 | L-1 | $X^1$ | G-27 | 3-biphenyl | 494 |
| 34 | L-1 | $X^1$ | G-27 | 6-phenyl-2-pyridyl | 495 |
| 35 | L-1 | $X^1$ | G-1 | 4,5-dihydro-5-phenyl-5-(trifluoromethyl)-3-isoxazolyl | 572 |
| 36 | L-1 | $X^1$ | G-1 | 5-[3-(trifluoromethyl)phenyl]-3-isoxazolyl | 570 |
| 37 (Ex. 8) | L-1 | $X^1$ | G-1 | 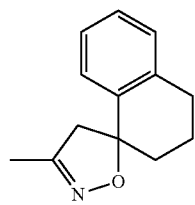 | 544 |
| 38 | L-1 | $X^1$ | G-1 | 5-(4-biphenyl)-3-isoxazolyl | 578 |
| 39 | L-1 | $X^1$ | G-1 | 4,5-dihydro-5-(3,5-dichlorophenyl)-5-(trifluoromethyl)-3-isoxazolyl | 640 |
| 40 | L-1 | $X^1$ | G-1 | 5-phenyl-1,3,4-oxadiazol-2-yl | 503 |
| 41 | L-1 | $X^1$ | G-1 | 4,5-dihydro-5-phenyl-2-oxazolyl | 504 |
| 42 | L-1 | $X^1$ | G-1 | 5-phenyl-2-oxazolyl | 502 |
| 43 | L-1 | $X^1$ | G-1 | 2-benzothiazolyl | 492 |

INDEX TABLE A-continued

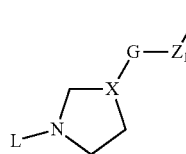

G is as defined in Exhibit 2; $R^{3a}$ in G is H. L groups are defined as illustrated below.

| | | | | | |
|---|---|---|---|---|---|
| 44 (Ex. 8) | L-1 | $X^1$ | G-1 | 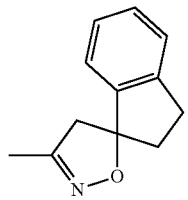 | 530 |
| 45 | L-1 | $X^1$ | G-1 | 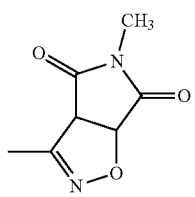 | 511 |
| 46 | L-1 | $X^1$ | G-1 | (4R)-4,5-dihydro-4-phenyl-2-oxazolyl | 504 |
| 47 | L-1 | $X^1$ | G-1 | (5S)-4,5-dihydro-5-phenyl-2-oxazolyl | 504 |
| 48 | L-1 | $X^1$ | G-1 | 5,6-dihydro-6-phenyl-4H-1,3-oxazin-2-yl | 518 |
| 49 | L-1 | $X^1$ | G-1 | (4S)-4,5-dihydro-4-phenyl-2-oxazolyl | 504 |
| 50 | L-1 | $X^1$ | G-1 | (5R)-4,5-dihydro-5-phenyl-2-oxazolyl | 504 |
| 51 | L-1 | $X^1$ | G-1 | 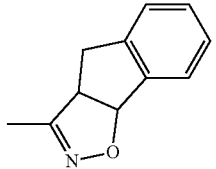 | 516 |
| 52 | L-1 | $X^1$ | G-1 | 2-benzoxazolyl | 475 |
| 53 | L-1 | $X^1$ | G-1 | 5,6-dihydro-5-phenyl-4H-1,3-oxazin-2-yl | 518 |
| 54 | L-1 | $X^1$ | G-1 | 5,6-dihydro-4-phenyl-4H-1,3-oxazin-2-yl | 518 |
| 55 | L-1 | $X^1$ | G-1 | 4,5-dihydro-5-(methoxycarbonyl)-3-isoxazolyl | 486 |
| 56 | L-1 | $X^1$ | G-1 | 4,5-dihydro-5-(1,1-dimethylethyl)-3-isoxazolyl | 484 |
| 57 | L-1 | $X^1$ | G-1 | 4,5-dihydro-5-(2-bromoethyl)-3-isoxazolyl | 534 |
| 58 | L-1 | $X^1$ | G-1 | 2-benzimidazolyl | 475 |
| 59 | L-1 | $X^1$ | G-1 | 5-(2-fluorophenyl)-3-isoxazolyl | 520 |
| 60 | L-1 | $X^1$ | G-1 | 5-(2-trifluoromethylphenyl)-3-isoxazolyl | 570 |
| 61 | L-1 | $X^1$ | G-1 | 2-naphthalenyl | 485 |
| 62 | L-1 | $X^1$ | G-1 | phenyl | 435 |
| 63 | L-7 | $X^1$ | G-1 | 4,5-dihydro-5-phenyl-3-isoxazolyl | 518 |
| 64 | L-1 | $X^1$ | G-1 | 5-(2,4-difluorophenyl)-3-isoxazolyl | 538 |
| 65 | L-1 | $X^1$ | G-1 | 1-phenyl-2-pyrrolidon-4-yl | 518 |
| 66 | L-1 | $X^1$ | G-1 | 4,5-dihydro-5-cyano-3-isoxazolyl | 453 |
| 67 | L-1 | $X^1$ | G-1 | 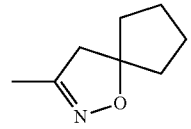 | 482 |
| 68 | L-1 | $X^1$ | G-1 | 3-phenyl-1,2,4-oxadiazol-5-yl | 503 |
| 69 | L-15 | $X^1$ | G-1 | 4,5-dihydro-5-phenyl-3-isoxazolyl | 532 |
| 70 | L-16 | $X^1$ | G-1 | 4,5-dihydro-5-phenyl-3-isoxazolyl | 478 |
| 71 | L-17 | $X^1$ | G-1 | 4,5-dihydro-5-phenyl-3-isoxazolyl | 500 |
| 72 | L-1 | $X^1$ | G-1 | 4-phenoxyphenyl | 577 |
| 73 | L-1 | $X^1$ | G-1 | 1-naphthalenyl | 485 |
| 74 | L-1 | $X^1$ | G-1 | 3-biphenyl | 511 |
| 75 | L-1 | $X^1$ | G-1 | 3-phenoxyphenyl | 527 |
| 76 | L-1 | $X^1$ | G-1 | 1-phenylpyrazol-3-yl | 501 |
| 77 | L-1 | $X^1$ | G-1 | 1-(4-methylphenyl)-1,2,3-triazol-4-yl | 516 |
| 78 | L-1 | $X^1$ | G-1 | 1-phenylpyrazol-5-yl | 501 |

INDEX TABLE A-continued

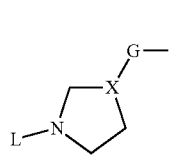

G is as defined in Exhibit 2; $R^{3a}$ in G is H. L groups are defined as illustrated below.

| | | | | | |
|---|---|---|---|---|---|
| 79 | L-1 | $X^1$ | G-1 | 4,5-dihydro-5-(2-fluorophenyl)-3-isoxazolyl | 522 |
| 80 | L-17 | $X^1$ | G-1 | 4,5-dihydro-5-(2-fluorophenyl)-3-isoxazolyl | 518 |
| 81 | L-1 | $X^1$ | G-1 | 5,6-dihydro-5-phenyl-6-methoxy-4H-1,2-oxazin-3-yl | 548 |
| 82 | L-1 | $X^1$ | G-1 | 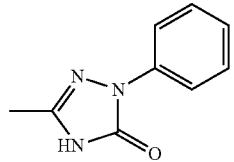 | 518 |
| 83 | L-1 | $X^1$ | G-1 | 5-phenyl-2-furanyl | 501 |
| 84 | L-1 | $X^1$ | G-1 | 2-phenyl-4-thiazoyl | 518 |
| 85 | L-1 | $X^1$ | G-1 | 5-phenyl-2-thienyl | 517 |
| 86 | L-1 | $X^1$ | G-1 | 3-(2,4-dichlorophenyl)-5-isoxazoyl | 570 |
| 87 | L-1 | $X^1$ | G-1 | 3-(3,4-dichlorophenyl)-5-isoxazoyl | 570 |
| 88 | L-1 | $X^1$ | G-1 | 4,5-dihydro-5-(naphthalen-2-yl)-3-isoxazolyl | 554 |
| 89 | L-18 | $X^1$ | G-1 | 4,5-dihydro-5-phenyl-3-isoxazolyl | 462 |
| 90 | L-19 | $X^1$ | G-1 | 4,5-dihydro-5-phenyl-3-isoxazolyl | 468 |
| 91 | L-1 | $X^1$ | G-1 | 4,5-dihydro-5-(4-t-butylphenyl)-3-isoxazolyl | 560 |
| 92 | L-1 | $X^1$ | G-1 | (5R)-4,5-dihydro-5-phenyl-1H-imidazol-2-yl | 503 |
| 93 | L-8 | $X^1$ | G-1 | 4,5-dihydro-5-phenyl-3-isoxazolyl | 450 |
| 94 | L-9 | $X^1$ | G-1 | 4,5-dihydro-5-phenyl-3-isoxazolyl | 478 |
| 95 | L-1 | $X^1$ | G-1 | 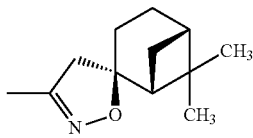 | 536 |
| 96 | L-1 | $X^1$ | G-1 | 4,5-dihydro-5-(4-fluorophenyl)-3-isoxazolyl | 522 |
| 97 | L-1 | $X^1$ | G-1 | 4,5-dihydro-5-(4-trifluoromethylphenyl)-3-isoxazolyl | 572 |
| 98 (Ex. 9) | L-1 | $X^1$ | G-1 | 4,5-dihydro-5-(2-pyridyl)-3-isoxazolyl | 505 |
| 99 | L-1 | $X^1$ | G-1 | 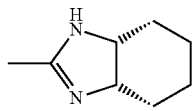 | 481 |
| 100 | L-1 | $X^1$ | G-1 | 4,5-dihydro-5-isopropyl-5-phenyl-3-isoxazolyl | 546 |
| 101 | L-1 | $X^1$ | G-1 | 4,5-dilhydro-5-propyl-5-phenyl-3-isoxazolyl | 546 |
| 102 (Ex. 1) | L-1 | $X^1$ | G-1 | 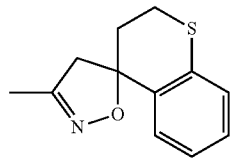 | 562 |
| 103 | L-1 | $X^1$ | G-1 | 4,5-dihydro-5-cyclopropyl-5-phenyl-3-isoxazolyl | 544 |
| 104 | L-1 | $X^1$ | G-1 | 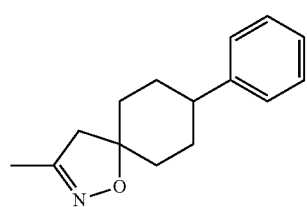 | 572 |

INDEX TABLE A-continued

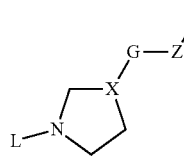

G is as defined in Exhibit 2; $R^{3a}$ in G is H. L groups are defined as illustrated below.

| | | | | | |
|---|---|---|---|---|---|
| 105 | L-1 | $X^1$ | G-1 | 4,5-dihydro-5-ethyl-5-phenyl-3-isoxazolyl | 532 |
| 106 | L-1 | $X^1$ | G-1 | 4,5-dihydro-5-(4-biphenyl)-3-isoxazolyl | 580 |
| 107 (Ex. 10) | L-10 | $X^1$ | G-1 | 4,5-dihydro-5-phenyl-3-isoxazolyl | 524 |
| 108 | L-1 | $X^1$ | G-1 | (4R,5R)-4,5-dihydro-4,5-diphenyl-1H-imidazol-2-yl | 579 |
| 109 | L-1 | $X^1$ | G-1 | 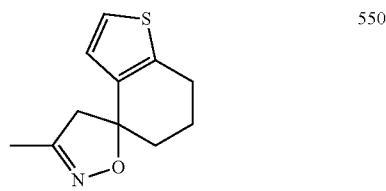 | 550 |
| 110 | L-1 | $X^1$ | G-1 | 4,5-dihydro-5-(4-hydroxyphenyl)-3-isoxazolyl | 520 |
| 111 | L-1 | $X^1$ | G-1 | 4,5-dihydro-5-(2-pyrazinyl)-3-isoxazolyl | 506 |
| 112 | L-1 | $X^1$ | G-1 | 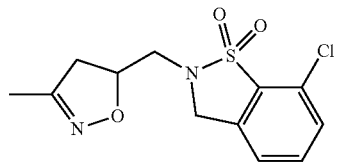 | 643 |
| 113 | L-1 | $X^1$ | G-1 | 4,5-dihydro-5-(4-acetoxyphenyl)-3-isoxazolyl | 562 |
| 114 | L-1 | $X^1$ | G-1 | 4,5-dihydro-5-(2-trifluoromethylphenyl)-3-isoxazolyl | 572 |
| 115 | L-1 | $X^1$ | G-1 | 4,5-dihydro-5-(3-trifluoromethylphenyl)-3-isoxazolyl | 572 |
| 116 | L-1 | $X^1$ | G-1 | 4,5-dihydro-5-(methoxycarbonylmethyl)-3-isoxazolyl | 500 |
| 117 | L-1 | $X^1$ | G-1 | 4,5-dihydro-5-(phenylsulfonyl)-3-isoxazolyl | 568 |
| 118 | L-1 | $X^1$ | G-1 | (5R)-4,5-dihydro-1-methyl-5-phenyl-1H-imidazol-2-yl | 517 |
| 119 | L-1 | $X^1$ | G-1 | (4S,5R)-4,5-dihydro-4,5-diphenyl-1H-imidazol-2-yl | 579 |
| 120 | L-1 | $X^1$ | G-1 | 4-chlorophenyl | 469 |
| 121 | L-1 | $X^1$ | G-1 | 2-chlorophenyl | 469 |
| 122 | L-1 | $X^1$ | G-1 | 4-(trifluoromethyl)phenyl | 503 |
| 123 | L-1 | $X^1$ | G-1 | 3-chlorophenyl | 469 |
| 124 | L-1 | $X^1$ | G-1 | 3-pyridyl | 436 |
| 125 | L-1 | $X^1$ | G-1 | 4,5-dihydro-5-(3,4-dihydroxyphenyl)-3-isoxazolyl | 536 |
| 126 (Ex. 11) | L-11 | $X^1$ | G-1 | 4,5-dihydro-5-phenyl-3-isoxazolyl | 568 |
| 127 | L-12 | $X^1$ | G-1 | 4,5-dihydro-5-phenyl-3-isoxazolyl | 658 |
| 128 (Ex. 1) | L-13 | $X^1$ | G-1 | 4,5-dihydro-5-phenyl-3-isoxazolyl | 504 |
| 129 | L-1 | $X^1$ | G-1 | 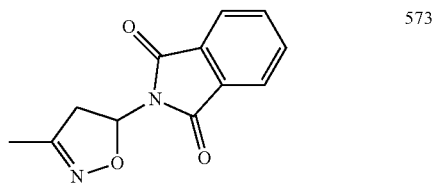 | 573 |
| 130 (Ex. 6) | L-14 | $X^1$ | G-1 | 4,5-dihydro-5-phenyl-3-isoxazolyl | 520 |
| 131 | L-1 | $X^1$ | G-1 | 4,5-dihydro-5-(2-methoxyphenyl)-3-isoxazolyl | 534 |
| 132 | L-1 | $X^1$ | G-1 | 4,5-dihydro-5-methyl-5-(2,5-dichloro-3-thienyl)-3-isoxazolyl | 592 |
| 133 | L-1 | $X^1$ | G-1 | 4,5-dihydro-5-(2,5-dimethylphenyl)-3-isoxazolyl | 532 |
| 134 | L-1 | $X^1$ | G-1 | 4,5-dihydro-5-(4-methoxycarbonylphenyl)-3-isoxazolyl | 562 |
| 135 | L-1 | $X^1$ | G-1 | 4,5-dihydro-5-(2,6-dichlorophenyl)-3-isoxazolyl | 572 |
| 136 | L-1 | $X^1$ | G-1 | 4,5-dihydro-5-(2,4-dimethylphenyl)-3-isoxazolyl | 532 |
| 137 (Ex. 1) | L-1 | $X^1$ | G-1 | 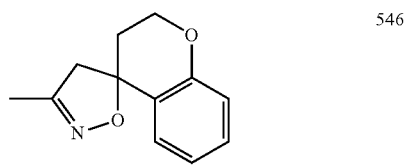 | 546 |

INDEX TABLE A-continued

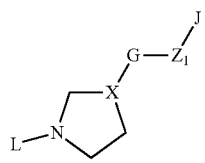

G is as defined in Exhibit 2; $R^{3a}$ in G is H. L groups are defined as illustrated below.

| | | | | | |
|---|---|---|---|---|---|
| 138 | L-1 | $X^1$ | G-1 | 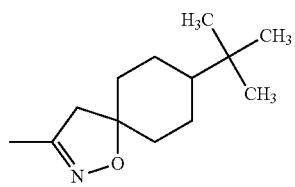 | 552 |
| 139 | L-1 | $X^1$ | G-1 | 4,5-dihydro-5,5-diphenyl-3-isoxazolyl | 580 |
| 140 | L-1 | $X^1$ | G-1 | 4,5-dihydro-5-(2-methoxyphenyl)-5-methyl-3-isoxazolyl | 548 |
| 141 | L-1 | $X^1$ | G-1 | 4,5-dihydro-5-(methoxymethyl)-5-phenyl-3-isoxazolyl | 548 |
| 142 | L-1 | $X^1$ | G-1 | 4,5-dihydro-5-(methylthiomethyl)-5-phenyl-3-isoxazolyl | 564 |
| 143 | L-1 | $X^1$ | G-1 | 4,5-dihydro-5-(methylsulfonylmethyl)-5-phenyl-3-isoxazolyl | 596 |
| 144 | L-1 | $X^1$ | G-1 | 4,5-dihydro-5-(methylsulfinylmethyl)-5-phenyl-3-isoxazolyl | 580 |
| 145 | L-1 | $X^1$ | G-1 | 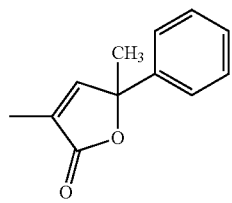 | 531 |
| 146 | L-1 | $X^1$ | G-1 | 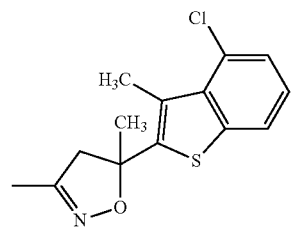 | 622 |
| 147 | L-1 | $X^1$ | G-1 | 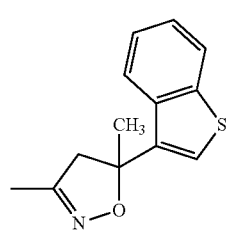 | 574 |
| 148 | L-1 | $X^1$ | G-1 | 4,5-dihydro-5-(3-thienyl)-3-isoxazolyl | 510 |
| 149 | L-1 | $X^1$ | G-1 | 3-methylphenyl | 449 |
| 150 | L-1 | $X^1$ | G-1 | 4-methoxyphenyl | 465 |
| 151 | L-1 | $X^1$ | G-1 | 4-methylphenyl | 449 |
| 152 | L-1 | $X^1$ | G-1 | 3-methoxyphenyl | 465 |
| 153 | L-1 | $X^1$ | G-1 | 2-methoxyphenyl | 465 |
| 154 (Ex. 7) | L-1 | $X^2$ | G-1 | 4,5-dihydro-5-phenyl-3-isoxazolyl | 505 |
| 155 | L-1 | $X^1$ | G-1 | 4,5-dihydro-5-(2,4,6-trimethoxyphenyl)-3-isoxazolyl | 594 |
| 156 | L-1 | $X^1$ | G-1 | 4,5-dihydro-5-acetoxymethyl-5-phenyl-3-isoxazolyl | 576 |

INDEX TABLE A-continued

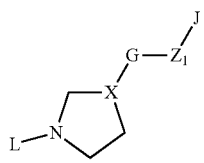

G is as defined in Exhibit 2; R³ᵃ in G is H. L groups are defined as illustrated below.

| 157 | L-1 | X¹ | G-1 | 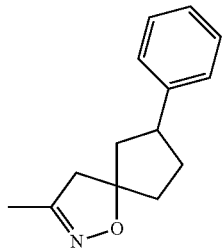 [Note 3] | 558 |
| 158 | L-1 | X¹ | G-1 | 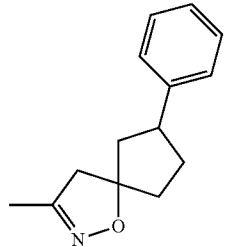 [Note 4] | 558 |
| 159 | L-1 | X¹ | G-1 | 4,5-dihydro-5-hydroxymethyl-5-phenyl-3-isoxazolyl | 534 |
| 160 | L-1 | X¹ | G-1 | 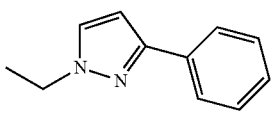 | 515 |
| 161 | L-1 | X¹ | G-1 | 4,5-dihydro-5-(2-methylphenyl)-3-isoxazolyl | 518 |
| 162 | L-1 | X¹ | G-1 | 4,5-dihydro-5-thien-2-yl-3-isoxazolyl | 510 |
| 163 | L-8 | X¹ | G-1 | 4,5-dihydro-5-methyl-5-phenyl-3-isoxazolyl | 464 |
| 164 | L-8 | X¹ | G-1 | 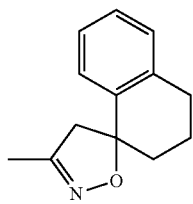 | 490 |
| 165 | L-8 | X¹ | G-1 | 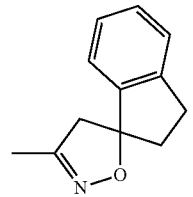 | 476 |
| 166 | L-20 | X¹ | G-1 | 4,5-dihydro-5-phenyl-3-isoxazolyl | 490 |
| 167 | L-21 | X¹ | G-1 | 4,5-dihydro-5-phenyl-3-isoxazolyl | 647 |

INDEX TABLE A-continued
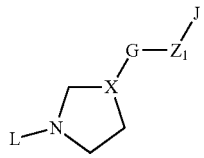
G is as defined in Exhibit 2; R³ᵃ in G is H. L groups are defined as illustrated below.
| 168 | L-23 | X¹ | G-1 | 4,5-dihydro-5-phenyl-3-isoxazolyl | 579 |
| 169 | L-1 | X¹ | G-1 | | 496 |
| 170 | L-1 | X¹ | G-1 | [Note 5] | 572 |
| 171 | L-1 | X¹ | G-1 | [Note 5] | 572 |
| 172 | L-24 | X¹ | G-1 | 4,5-dihydro-5-phenyl-3-isoxazolyl | 562 |
| 173 | L-1 | X¹ | G-1 | | 498 |
| 174 | L-1 | X¹ | G-1 | | 510 |
| 175 | L-1 | X¹ | G-1 | [Note 3] | 576 |

INDEX TABLE A-continued
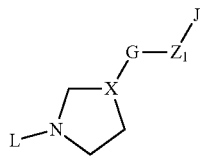
G is as defined in Exhibit 2; $R^{3a}$ in G is H. L groups are defined as illustrated below.
| | | | | | |
|---|---|---|---|---|---|
| 176 | L-1 | $X^1$ | G-1 | 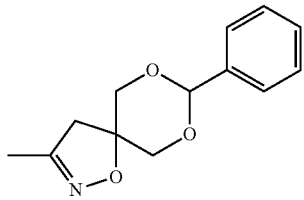 [Note 4] | 576 |
| 177 | L-1 | $X^1$ | G-1 | 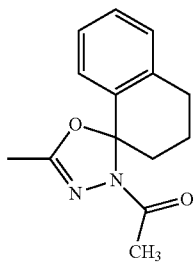 [SMILES: CC(=O)N1N=C(C)OC12CCCc1ccccc12] | 587 |
| 178 | L-1 | $X^1$ | G-1 | 4,5-dihydro-5-(2,6-dimethylphenyl)-3-isoxazolyl | 532 |
| 179 | L-1 | $X^1$ | G-1 | 4,5-dihydro-5-(2,4,6-trimethylphenyl)-3-isoxazolyl | 546 |
| 180 | L-1 | $X^1$ | G-1 | 4,5-dihydro-5-pyridin-4-yl-3-isoxazolyl | 505 |
| 181 | L-1 | $X^1$ | G-1 | 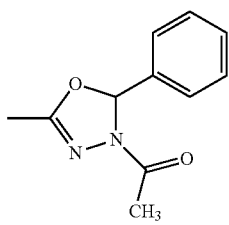 | 547 |
| 182 | L-1 | $X^1$ | G-1 | 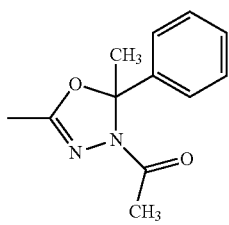 [SMILES: CC(=O)N1N=C(C)OC1(C)c1ccccc1] | 561 |
| 183 | L-1 | $X^1$ | G-1 | 4,5-dihydro-5-phenyl-1H-pyrazol-3-yl | 503 |
| 184 | L-1 | $X^1$ | G-1 | 4,5-dihydro-5-phenyl-(1-methyl-1H-pyrazol-3-yl) | 517 |
| 185 | L-1 | $X^1$ | G-1 | 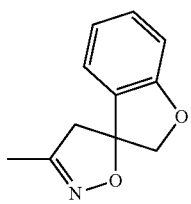 | 532 |

INDEX TABLE A-continued
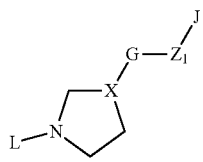
G is as defined in Exhibit 2; R³ᵃ in G is H. L groups are defined as illustrated below.
| | | | | | |
|---|---|---|---|---|---|
| 186 | L-1 | X¹ | G-1 | 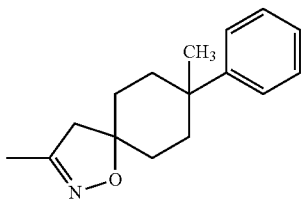 [Note 3] | 586 |
| 187 | L-1 | X¹ | G-1 | 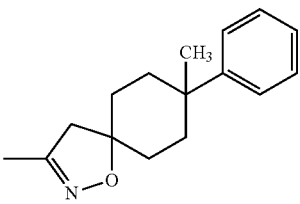 [Note 4] | 586 |
| 188 | L-1 | X¹ | G-1 | 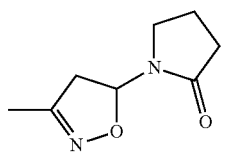 | 511 |
| 189 | L-1 | X¹ | G-1 | 4,5-dihydro-5-(2-bromo-phenyl)-3-isoxazolyl | 582 |
| 190 | L-26 | X¹ | G-1 | 4,5-dihydro-5-phenyl-3-isoxazolyl | 524 |
| 191 | L-1 | X¹ | G-1 | 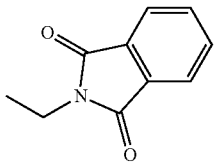 | 518 |
| 192 | L-1 | X¹ | G-1 | 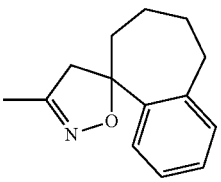 [SMILES: CC1=NOC2(CCCCc3ccccc32)C1] | 558 |
| 193 | L-1 | X¹ | G-1 | 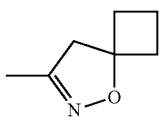 | 468 |
| 194 | L-1 | X¹ | G-1 | 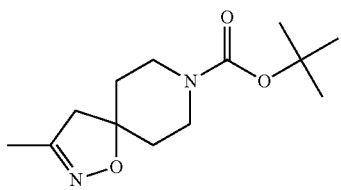 [SMILES: CC1=NOC2(CCN(C(=O)OC(C)(C)C)CC2)C1] | 597 |

INDEX TABLE A-continued

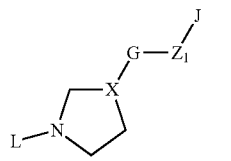

G is as defined in Exhibit 2; $R^{3a}$ in G is H. L groups are defined as illustrated below.

| | | | | | |
|---|---|---|---|---|---|
| 195 | L-1 | $X^1$ | G-1 | | 497 |
| 196 | L-1 | $X^1$ | G-1 | | 539 |
| 197 | L-1 | $X^1$ | G-1 | 4,5-dihydro-5-phenyl-(1-acetyl-1H-pyrazol-3-yl) | 545 |
| 198 | L-28 | $X^1$ | G-1 | 4,5-dihydro-5-phenyl-3-isoxazolyl | 524 |
| 199 | L-1 | $X^1$ | G-1 | | 500 |
| 200 | L-1 | $X^1$ | G-1 | | 484 |
| 201 | L-1 | $X^1$ | G-1 | 4,5-dihydro-5-(4-methylthiazol-5-yl)-3-isoxazolyl | 525 |
| 202 | L-1 | $X^1$ | G-1 | | 566 |
| 203 | L-1 | $X^1$ | G-1 | 3-isoxazolyl | 425 |
| 204 | L-1 | $X^1$ | G-1 | 4,5-dihydro-5-phenoxy-3-isoxazolyl | 520 |
| 205 | L-1 | $X^1$ | G-1 | 4,5-dihydro-5-methyl-5-(2-methylphenyl)-3-isoxazolyl | 532 |
| 206 | L-1 | $X^1$ | G-1 | 4,5-dihydro-5-(2,6-dimethoxyphenyl)-3-isoxazolyl | 564 |
| 207 | L-1 | $X^1$ | G-1 | | 469 |
| 208 | L-1 | $X^1$ | G-1 | | 500 |

INDEX TABLE A-continued

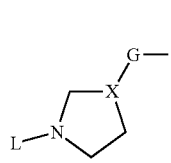

G is as defined in Exhibit 2; $R^{3a}$ in G is H. L groups are defined as illustrated below.

| # | L | X | G | J | MW |
|---|---|---|---|---|---|
| 209 | L-1 | $X^1$ | G-1 | 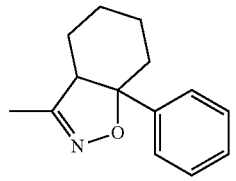 | 558 |
| 210 | L-1 | $X^1$ | G-1 | 5-(2-hydroxycarbonylphenyl)-3-isoxazolyl | 546 |
| 211 | L-1 | $X^1$ | G-1 | 4,5-dihydro-5-(1,1-dimethylethoxy)-3-isoxazolyl | 500 |
| 212 | L-1 | $X^1$ | G-1 | 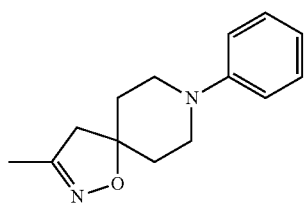 | 573 |
| 213 | L-1 | $X^1$ | G-1 | 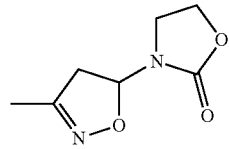 | 513 |
| 214 | L-1 | $X^1$ | G-1 | 4,5-dihydro-5-(2,6-difluorophenyl-3-isoxazolyl | 540 |
| 215 | L-1 | $X^1$ | G-1 | 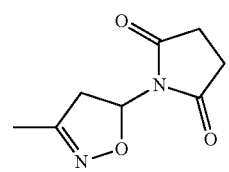 | 525 |
| 216 | L-1 | $X^1$ | G-1 | 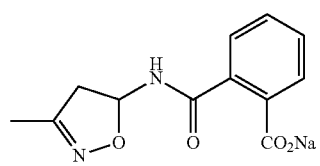 | 613 |
| 217 (Ex. 13) | L-1 | $X^3$ | G-1 | 4,5-dihydro-5-phenyl-3-isoxazolyl | 502 |
| 218 | L-1 | $X^1$ | G-1 | 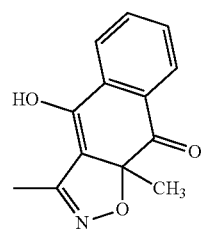 | 572 |
| 219 | L-1 | $X^1$ | G-1 | 4,5-dihydro-5-(1-methylbenzimidazol-2-yl)-3-isoxazolyl | 58 |
| 220 | L-1 | $X^1$ | G-1 | 4,5-dihydro-5-(2-cyanophenyl)-3-isoxazolyl | 529 |
| 221 | L-1 | $X^1$ | G-1 | 4,5-dihydro-5-2-methoxycarbonylphenyl)-3-isoxazolyl | 562 |

INDEX TABLE A-continued
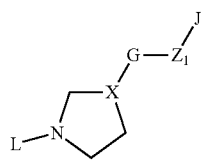
G is as defined in Exhibit 2; $R^{3a}$ in G is H. L groups are defined as illustrated below.
| 222 | L-1 | $X^1$ | G-1 | 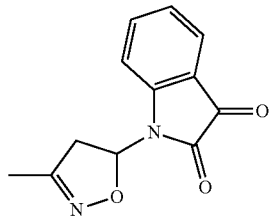 | 573 |
| 223 | L-1 | $X^1$ | G-1 | 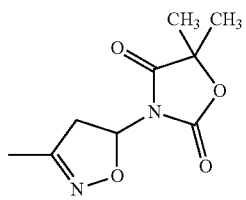 | 555 |
| 224 | L-1 | $X^1$ | G-1 | 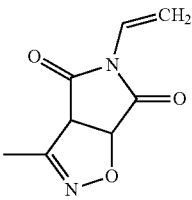 | 523 |
| 225 | L-1 | $X^1$ | G-1 | 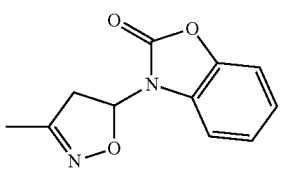 | 561 |
| 226 | L-1 | $X^1$ | G-1 | 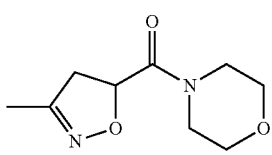 | 541 |
| 227 | L-1 | $X^1$ | G-1 | 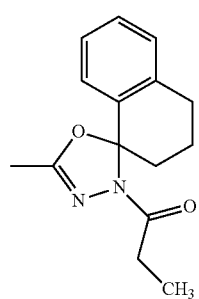 | 601 |

INDEX TABLE A-continued
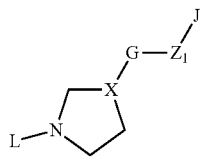
G is as defined in Exhibit 2; $R^{3a}$ in G is H. L groups are defined as illustrated below.
| | | | | | |
|---|---|---|---|---|---|
| 228 | L-1 | $X^1$ | G-1 | 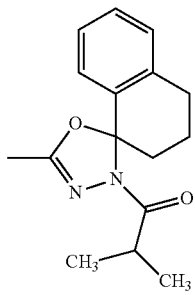 | 615 |
| 229 | L-5 | $X^1$ | G-1 | 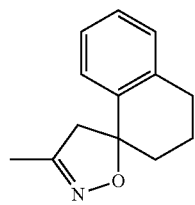 | 598 |
| 230 | L-10 | $X^1$ | G-1 | 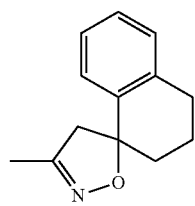 | 564 |
| 231 | L-5 | $X^1$ | G-1 | 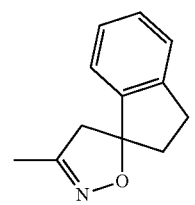 | 584 |
| 232 | L-10 | $X^1$ | G-1 | 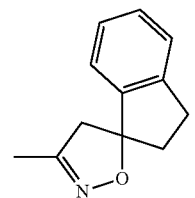 | 550 |
| 233 | L-1 | $X^1$ | G-1 | 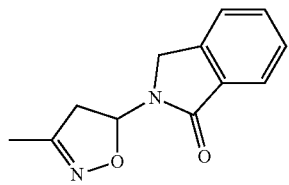 | 559 |

INDEX TABLE A-continued

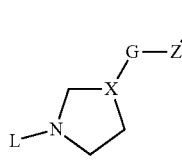

G is as defined in Exhibit 2; R³ᵃ in G is H. L groups are defined as illustrated below.

| | | | | | |
|---|---|---|---|---|---|
| 234 | L-1 | X¹ | G-1 | 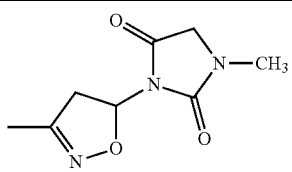 | 540 |
| 235 | L-1 | X¹ | G-1 | 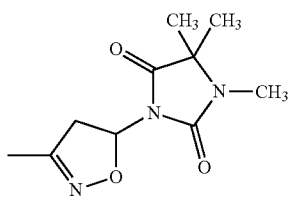 | 568 |
| 236 | L-1 | X¹ | G-1 | 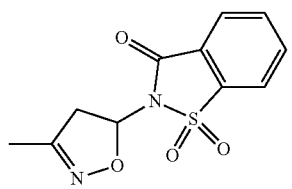 | 609 |
| 237 | L-29 | X¹ | G-1 | 4,5-dihydro-5-phenyl-3-isoxazolyl | 508 |
| 238 | L-30 | X¹ | G-1 | 4,5-dihydro-5-phenyl-3-isoxazolyl | 508 |
| 239 | L-31 | X¹ | G-1 | 4,5-dihydro-5-phenyl-3-isoxazolyl | 566 |
| 240 | L-32 | X¹ | G-1 | 4,5-dihydro-5-phenyl-3-isoxazolyl | 562 |
| 241 | L-33 | X¹ | G-1 | 4,5-dihydro-5-phenyl-3-isoxazolyl | 534 |
| 242 | L-1 | X¹ | G-1 | 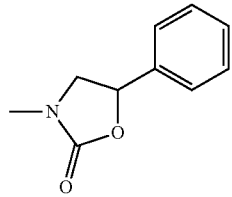 | 520 |
| 243 | L-1 | X¹ | G-1 | 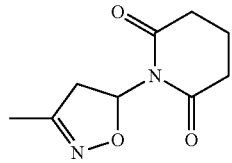 | 539 |
| 244 | L-1 | X¹ | G-1 | 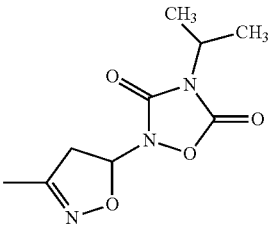 | 570 |
| 245 | L-1 | X¹ | G-1 | 4-fluorophenyl | 453 |
| 246 | L-1 | X¹ | G-1 | 4-t-butylphenyl | 491 |
| 247 | L-1 | X¹ | G-1 | 4-cyanophenyl | 460 |
| 248 | L-1 | X¹ | G-1 | 4-nitrophenyl | 480 |
| 249 | L-1 | X¹ | G-1 | 4-bromophenyl | 513 |

INDEX TABLE A-continued

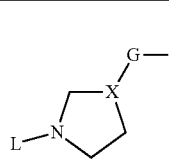

G is as defined in Exhibit 2; $R^{3a}$ in G is H. L groups are defined as illustrated below.

| | | | | | |
|---|---|---|---|---|---|
| 250 | L-1 | $X^1$ | G-1 | 4-iodophenyl | 561 |
| 251 | L-1 | $X^1$ | G-1 | | 569 |
| 252 | L-1 | $X^1$ | G-1 | | 587 |
| 253 | L-1 | $X^1$ | G-1 | [Note 3] | 521 |
| 254 | L-1 | $X^1$ | G-1 | [Note 4] | 521 |
| 255 | L-1 | $X^1$ | G-1 | [Note 3] | 521 |
| 256 | L-1 | $X^1$ | G-1 | [Note 4] | 521 |
| 257 | L-22 | $X^1$ | G-1 | 4,5-dihydro-5-phenyl-3-isoxazolyl | 506 |
| 258 | L-25 | $X^1$ | G-1 | 4,5-dihydro-5-phenyl-3-isoxazolyl | 556 |
| 259 | L-27 | $X^1$ | G-1 | 4,5-dihydro-5-phenyl-3-isoxazolyl | 520 |
| 260 | L-5 | $X^1$ | G-1 | 4,5-dihydro-5-methyl-5-phenyl-3-isoxazolyl | 572 |
| 261 | L-10 | $X^1$ | G-1 | 4,5-dihydro-5-methyl-5-phenyl-3-isoxazolyl | 538 |
| 262 | L-1 | $X^1$ | G-1 | 4,5-dihydro-5-(2-aminosulfonylbenzyl)-3-isoxazolyl | 597 |
| 263 | L-1 | $X^1$ | G-1 | 4,5-dihydro-5-(2-acetoxyphenyl)-3-isoxazolyl | 562 |
| 264 | L-1 | $X^1$ | G-1 | 4,5-dihydro-5-(N-methyl-N-phenylcarbonylamino)-3-isoxazolyl | 561 |
| 265 | L-1 | $X^1$ | G-1 | 4,5-dihydro-5-cyano-5-phenyl-3-isoxazolyl | 529 |
| 266 | L-8 | $X^1$ | G-1 | | 478 |

INDEX TABLE A-continued

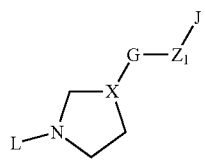

G is as defined in Exhibit 2; $R^{3a}$ in G is H. L groups are defined as illustrated below.

| | | | | | |
|---|---|---|---|---|---|
| 267 | L-1 | $X^1$ | G-1 | 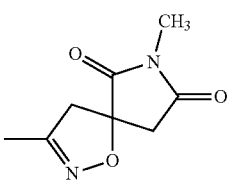 | 525 |
| 268 | L-1 | $X^1$ | G-1 | 4-ethylphenyl | 463 |
| 769 | L-1 | $X^1$ | G-1 | 4-trifluoromethoxyphenyl | 519 |
| 270 | L-1 | $X^1$ | G-1 | 4-methoxycarbonylphenyl | 493 |
| 271 | L-1 | $X^1$ | G-1 | 4-propylphenyl | 477 |
| 272 | L-1 | $X^1$ | G-1 | 4-methylthiophenyl | 481 |
| 273 | L-1 | $X^1$ | G-1 | 4-isopropylphenyl | 477 |
| 274 | L-1 | $X^1$ | G-1 | 4-isobutylphenyl | 491 |
| 275 | L-1 | $X^1$ | G-1 | 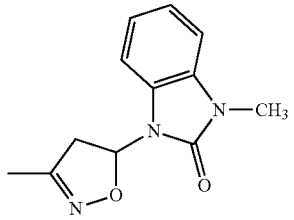 | 574 |
| 276 | L-5 | $X^1$ | G-1 | 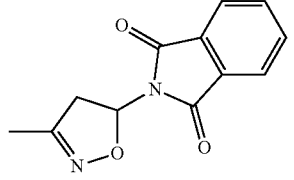 | 677 |
| 277 | L-8 | $X^1$ | G-1 | 4,5-dihydro-5-(2,4,6-trimethoxyphenyl)-3-isoxazolyl | 540 |
| 278 | L-1 | $X^1$ | G-1 | 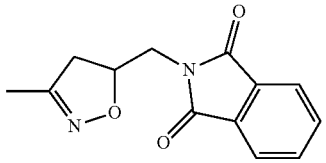 | 587 |
| 279 | L-1 | $X^1$ | G-1 | 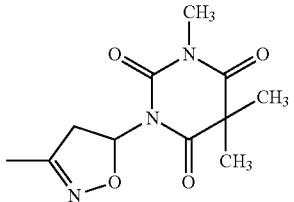 | 596 |

INDEX TABLE A-continued

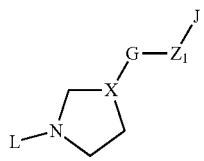

G is as defined in Exhibit 2; $R^{3a}$ in G is H. L groups are defined as illustrated below.

| | | | | | | |
|---|---|---|---|---|---|---|
| 280 | L-1 | $X^1$ | G-1 | 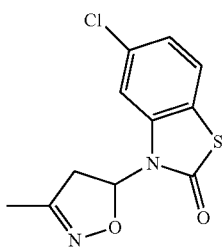 [SMILES: CC1=NOC(n2c(=O)sc3ccc(Cl)cc32)C1] | | 611 |
| 281 | L-1 | $X^1$ | G-1 | 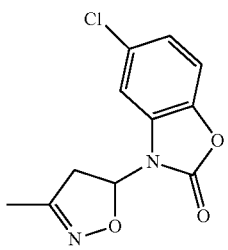 [SMILES: CC1=NOC(n2c(=O)oc3ccc(Cl)cc32)C1] | | 595 |
| 282 | L-1 | $X^1$ | G-1 | 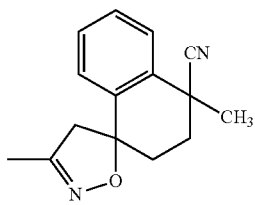 | [Note 3] | 583 |
| 283 | L-1 | $X^1$ | G-1 | 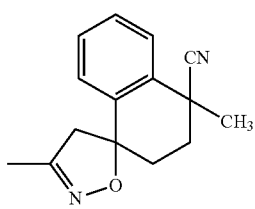 | [Note 4] | 583 |
| 284 | L-8 | $X^1$ | G-1 | 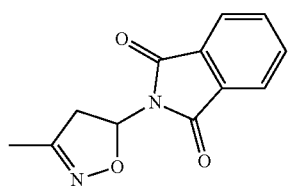 [SMILES: CC1=NOC(N2C(=O)c3ccccc3C2=O)C1] | | 519 |

[Note 1]:
Faster eluting enantiomer from the CHIRALPAK ® AD-RH column using methanol in water as eluant, specific rotation = −98.8°. Analysis using analytical CHIRALPAK ® AD-RH column indicated about 100% optical purity.

[Note 2]:
Slower eluting enantiomer from the CHIRALPAK ® AD-RH reverse phase column using methanol in water as eluant, specific rotation = +88°. Analysis using analytical CHIRALPAK ® AD-RH column indicated about 93% optical purity.

[Note 3]:
Diastereomer A.

[Note 4]:
Diastereomer B.

[Note 5]:
Mixture of isomers.

Biological Examples of the Invention

General protocol for preparing test suspensions for Test A-C: The test compounds were first dissolved in acetone in an amount equal to 3% of the final volume and then suspended at the desired concentration (in ppm) in acetone and purified water (50/50 mix by volume) containing 250 ppm of the surfactant Trem® 014 (polyhydric alcohol esters). The resulting test suspensions were then used in Tests A-C. Spraying a 200 ppm test suspension to the point of run-off on the test plants was equivalent to a rate of 500 g/ha.

Test A

Grape seedlings were inoculated with a spore suspension of *Plasmopara vilicola* (the causal agent of grape downy mildew) and incubated in a saturated atmosphere at 20° C. for 24 h. After a short drying period, the test suspension was sprayed to the point of run-off on the grape seedlings, which were then moved to a growth chamber at 20° C. for 5 days, after which time the grape seedling were placed back into a saturated atmosphere at 20° C. for 24 h. Upon removal, visual disease ratings were made.

Test B

The test suspension was sprayed to the point of run-off on tomato seedlings. The following day the seedlings were inoculated with a spore suspension of *Phytophthora infestans* (the causal agent of tomato late blight) and incubated in a saturated atmosphere at 20° C. for 24 h, and then moved to a growth chamber at 20° C. for 5 days, after which time visual disease ratings were made.

Test C

Tomato seedlings were inoculated with a spore suspension of *Phytophthora infestans* (the causal agent of tomato late blight) and incubated in a saturated atmosphere at 20° C. for 17 h. After a short drying period, the test suspension was sprayed to the point of run-off on the tomato seedlings, which were then moved to a growth chamber at 20° C. for 4 days, after which time visual disease ratings were made.

In addition to Tests A-C, the compounds were also sprayed on 2 separate sets of tomato plants, which were inoculated with *Botrytis cinerea* or *Alternaria solani* 24 h after treatment, bluegrass plants, which were inoculated with *Pythium aphanidermatum* 24 h after treatment and 3 separate sets of wheat plants, which were inoculated with *Erysiphe graminis* f. sp. *tritici*, *Puccinia recondita* or *Septoria nodorum* 24 h after treatment. Test compounds did not show noticeable activity against these additional pathogens under the test conditions at the application rates tested.

Results for Tests A-C are given in Table A. In the table, a rating of 100 indicates 100% disease control and a rating of 0 indicates no disease control (relative to the controls). A dash (-) indicates no test results.

TABLE A

RESULTS OF BIOLOGICAL TESTS

| Compound | Percent Disease Control | | |
|---|---|---|---|
| | Test A | Test B | Test C |
| 1 | 100 | 100 | 99 |
| 2 | 100 | 99 | 99 |
| 3** | 100 | 100 | 99 |
| 4** | 100 | 100 | 99 |
| 5 | 96 | 100 | 99 |
| 6* | 95 | 100 | 99 |
| 7 | 0 | 93 | 59 |
| 8 | 100 | 100 | 99 |
| 9 | 99 | 100 | 99 |
| 10 | 97 | 100 | 99 |
| 11 | 99 | 100 | 99 |
| 12 | 52 | 47 | 0 |
| 13 | 0 | 95 | 86 |
| 14 | 25 | 99 | 99 |
| 15 | 100 | 100 | 98 |
| 16 | 99 | 100 | 99 |
| 17* | 100 | 99 | 99 |
| 18* | 100 | 100 | 99 |
| 19* | 100 | 100 | 99 |
| 20* | 96 | 99 | 99 |
| 21* | 46 | 50 | 7 |
| 22* | 100 | 100 | 99 |
| 23* | 99 | 100 | 99 |
| 24 | 99 | 100 | 93 |
| 25* | 100 | 100 | 99 |
| 26 | 76 | 83 | 33 |
| 27 | 100 | 100 | 98 |
| 28 | 99 | 100 | 94 |
| 29 | 99 | 100 | 99 |
| 30** | 31 | 57 | 50 |
| 31** | 84 | 83 | 60 |
| 32 | 0 | 26 | 0 |
| 33 | 15 | 9 | 0 |
| 34 | 0 | 40 | 0 |
| * | 100 | 100 | 96 |
| 36 | 58 | 57 | 24 |
| 37* | 100 | 100 | 99 |
| 38 | 0 | 9 | 0 |
| 39 | 8 | 67 | 0 |
| 40 | 47 | 100 | 99 |
| 41 | 0 | 100 | 99 |
| 42 | 62 | 100 | 96 |
| 43 | 0 | 43 | 0 |
| 44* | 100 | 100 | 99 |
| 45 | 30 | 26 | 0 |
| 46 | 0 | 99 | 53 |
| 47 | 0 | 85 | 47 |
| 48 | 0 | 85 | 0 |
| 49 | 0 | 100 | 96 |
| 50 | 0 | 100 | 99 |
| 51 | 99 | 100 | 99 |
| 52 | 85 | 100 | 67 |
| 53* | 24 | 68 | 26 |
| 54 | 16 | 73 | 0 |
| 55 | 17 | 26 | 0 |
| 56 | 99 | 100 | 99 |
| 57 | 99 | 100 | 99 |
| 58 | 0 | 99 | 0 |
| 59* | 97 | 100 | 91 |
| 60 | 100 | 95 | 94 |
| 61 | 80 | 77 | 0 |
| 62 | 73 | 73 | 26 |
| 63 | 80 | 100 | 98 |
| 64 | 90 | 99 | 88 |
| 65 | 46 | 100 | 83 |
| 66 | 48 | 63 | 73 |
| 67* | 100 | 100 | 99 |
| 68 | 96 | 95 | 88 |
| 69 | 40 | 9 | 0 |
| 70 | 8 | 24 | 0 |
| 71 | — | 99 | 33 |
| 72 | 72 | 100 | 52 |
| 73 | 27 | 40 | 0 |
| 74 | 50 | 40 | 0 |
| 75 | 72 | 24 | 0 |
| 76 | 72 | 92 | 67 |

TABLE A-continued

RESULTS OF BIOLOGICAL TESTS

| Compound | Percent Disease Control | | |
|---|---|---|---|
| | Test A | Test B | Test C |
| 77 | 87 | 100 | 99 |
| 78 | 0 | 0 | 0 |
| 79 | 100 | 100 | 66 |
| 80 | 99 | 100 | 57 |
| 81 | 93 | 92 | 77 |
| 82 | 0 | 88 | 26 |
| 83 | 46 | 92 | 0 |
| 84 | 67 | 33 | 0 |
| 85 | 85 | 70 | 0 |
| 86 | 83 | 79 | 14 |
| 87 | 76 | 44 | 0 |
| 88* | 99 | 100 | 99 |
| 89 | 49 | 73 | 0 |
| 90 | 66 | 57 | 0 |
| 91* | 99 | 100 | 91 |
| 92* | 13 | 33 | 9 |
| 93* | 78 | 100 | 99 |
| 94* | 99 | 100 | 99 |
| 95* | 100 | 100 | 95 |
| 96* | 100 | 100 | 99 |
| 97* | 99 | 100 | 95 |
| 98* | 77 | 100 | 99 |
| 99 | 31 | 33 | 0 |
| 100* | 100 | 100 | 99 |
| 101* | 100 | 100 | 99 |
| 102* | 100 | 100 | 99 |
| 103* | 100 | 100 | 99 |
| 104 | 100 | 100 | 99 |
| 105* | 100 | 100 | 99 |
| 106* | 80 | 85 | 24 |
| 107* | 100 | 100 | 99 |
| 108 | 0 | 58 | 0 |
| 109* | 100 | 100 | 98 |
| 110* | 97 | 100 | 99 |
| 111* | 97 | 100 | 97 |
| 112* | 76 | 100 | 68 |
| 113* | 99 | 100 | 99 |
| 114* | 100 | 100 | 99 |
| 115* | 100 | 100 | 99 |
| 116 | 46 | 100 | 79 |
| 117* | 93 | 100 | 99 |
| 118* | 0 | 87 | 16 |
| 119 | 0 | 82 | 0 |
| 120 | 99 | 88 | 0 |
| 121 | 83 | 47 | 0 |
| 122 | 99 | 46 | 0 |
| 123 | 95 | 68 | 0 |
| 124 | 8 | 98 | 26 |
| 125 | 31 | 53 | 0 |
| 126 | 100 | 100 | 99 |
| 127 | 73 | 40 | 0 |
| 128* | 100 | 100 | 99 |
| 129* | 99 | 100 | 99 |
| 130** | 100 | 100 | 99 |
| 131* | 100 | 100 | 99 |
| 132* | 85 | 100 | 91 |
| 133* | 100 | 100 | 99 |
| 134* | 90 | 100 | 66 |
| 135* | 100 | 100 | 99 |
| 136* | 99 | 100 | 99 |
| 137* | 100 | 100 | 99 |
| 138* | 93 | 100 | 99 |
| 139* | 87 | 98 | 87 |
| 140* | 98 | 100 | 57 |
| 141* | 99 | 100 | 99 |
| 142* | 97 | 100 | 98 |
| 143* | 99 | 100 | 99 |
| 144* | 99 | 100 | 93 |
| 145 | 17 | 58 | 0 |
| 146 | 83 | 100 | 53 |
| 147* | 100 | 100 | 95 |
| 148** | 100 | 100 | 99 |
| 149 | 99 | 97 | — |
| 150 | 99 | 100 | — |
| 151 | 100 | 99 | — |
| 152 | 91 | 89 | — |
| 153 | 73 | 0 | — |
| 154* | 90 | 100 | 99 |
| 155* | 100 | 100 | 99 |
| 156* | 100 | 100 | 99 |
| 157* | 100 | 100 | 94 |
| 158 | 96 | 100 | 99 |
| 159 | 94 | 100 | 99 |
| 160 | 68 | 80 | 17 |
| 161* | 100 | 100 | 99 |
| 162* | 100 | 100 | 99 |
| 163** | 99 | 100 | 98 |
| 164** | 99 | 100 | 99 |
| 165** | 99 | 100 | 99 |
| 166** | 100 | 100 | 98 |
| 167 | 67 | 64 | 24 |
| 168** | 100 | 100 | 99 |
| 169 | 100 | 100 | 99 |
| 170* | 99 | 100 | 93 |
| 171* | 99 | 100 | 98 |
| 172* | 91 | 63 | 0 |
| 173* | 100 | 100 | 99 |
| 174* | 100 | 100 | 99 |
| 175 | 68 | 100 | 33 |
| 176 | 68 | 100 | 63 |
| 177* | 93 | 100 | 99 |
| 178* | 100 | 100 | 99 |
| 179* | 99 | 100 | 98 |
| 180 | 50 | 100 | 99 |
| 181 | 80 | 100 | 97 |
| 182 | 99 | 100 | 97 |
| 183* | 92 | 92 | 33 |
| 184* | 99 | 95 | 73 |
| 185* | 100 | 100 | 98 |
| 186* | 95 | 100 | 86 |
| 187* | 99 | 100 | 93 |
| 188* | 99 | 100 | 99 |
| 189* | 100 | 100 | 99 |
| 190 | 80 | 68 | 17 |
| 191 | 99 | 100 | 99 |
| 192* | 99 | 100 | 99 |
| 193* | 100 | 100 | 99 |
| 194* | 94 | 100 | 99 |
| 195 | 48 | 92 | 80 |
| 196* | 99 | 100 | 99 |
| 197* | 89 | 100 | 90 |
| 198* | 100 | 100 | 99 |
| 199 | 91 | 99 | 98 |
| 200 | 80 | 100 | 90 |
| 201* | 99 | 100 | 99 |
| 202 | 95 | 100 | 98 |
| 203* | 99 | 100 | 92 |
| 204* | 99 | 100 | 99 |
| 205* | 99 | 100 | 99 |
| 206* | 99 | 100 | 99 |
| 207 | 40 | 83 | 0 |
| 208 | 79 | 64 | 0 |
| 209* | 99 | 100 | 90 |
| 210 | 91 | 100 | 83 |
| 211* | 100 | 100 | 99 |
| 212* | 98 | 100 | 99 |
| 213* | 94 | 100 | 98 |
| 214* | 100 | 100 | 99 |
| 215* | 99 | 100 | 99 |
| 216* | 100 | 100 | 99 |
| 217* | 95 | 100 | 99 |
| 218* | 73 | 63 | 47 |
| 219 | 100 | 100 | 99 |
| 220 | 100 | 100 | 99 |
| 221 | 100 | 100 | 99 |
| 222 | 100 | 100 | 100 |
| 223 | 100 | 100 | 100 |
| 224 | 0 | 63 | 0 |

TABLE A-continued

RESULTS OF BIOLOGICAL TESTS

| Compound | Test A | Test B | Test C |
|---|---|---|---|
| 225 | 100 | 100 | 100 |
| 226 | 83 | 100 | 99 |
| 227 | 100 | 100 | 100 |
| 228 | 99 | 100 | 100 |
| 229** | 100 | 100 | 100 |
| 230** | 100 | 100 | 100 |
| 231** | 100 | 100 | 100 |
| 232** | 100 | 100 | 100 |
| 233* | 100 | 100 | 100 |
| 234* | 99 | 100 | 100 |
| 235* | 99 | 100 | 100 |
| 236* | 100 | 100 | 100 |
| 237* | 22 | 47 | 16 |
| 238* | 100 | 100 | 100 |
| 239* | 14 | 0 | 0 |
| 240* | 100 | 100 | 100 |
| 241* | 100 | 100 | 100 |
| 242* | 99 | 100 | 85 |
| 243** | 99 | 100 | 100 |
| 244* | 98 | 100 | 99 |
| 245* | 99 | 74 | 0 |
| 246* | 99 | 79 | 40 |
| 247* | 99 | 100 | 88 |
| 248* | 90 | 73 | 26 |
| 249* | 99 | 64 | 0 |
| 250* | 86 | 58 | 0 |
| 251* | 99 | 100 | 99 |
| 252* | 88 | 91 | 97 |
| 253* | 100 | 100 | 95 |
| 254* | 100 | 100 | 93 |
| 255* | 95 | 100 | 93 |
| 256* | 100 | 100 | 99 |
| 257* | 17 | 0 | 0 |
| 258** | 100 | 100 | 98 |
| 259* | 100 | 100 | 99 |
| 260** | 100 | 100 | 96 |
| 261** | 100 | 100 | 93 |
| 262* | 79 | 100 | 91 |
| 263* | 99 | 84 | 83 |
| 264* | 99 | 100 | 88 |
| 265** | 100 | 100 | 98 |
| 266* | 100 | 100 | 100 |
| 267 | 100 | 100 | 100 |
| 268 | 100 | 100 | 88 |
| 269 | 100 | 100 | 0 |
| 270 | 99 | 83 | 0 |
| 271 | 100 | 100 | 72 |
| 272 | 100 | 100 | 100 |
| 273 | 100 | 100 | 90 |
| 274 | 99 | 100 | 100 |
| 275** | 99 | 100 | 98 |
| 276** | 100 | 100 | 97 |
| 277* | 86 | 100 | 99 |
| 278* | 94 | 100 | 99 |
| 279* | 100 | 100 | 99 |
| 280** | 92 | 100 | 98 |
| 281** | 100 | 100 | 99 |
| 282 | — | — | — |
| 283 | — | — | — |
| 284 | — | — | — |

*indicates compounds tested at 40 ppm.
**indicates compounds tested at 10 ppm.

What is claimed is:

1. A compound selected from Formula 1B, an N-oxide and salt thereof

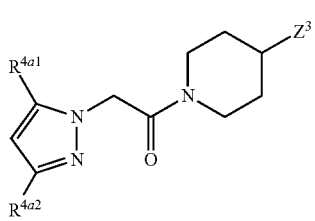

wherein
each $R^{4a1}$ and $R^{4a2}$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy, $C_1$-$C_2$ haloalkoxy, $C_1$-$C_2$ alkylthio, $C_1$-$C_2$ haloalkylthio, $C_2$-$C_3$ alkoxyalkyl, $C_2$-$C_3$ alkylcarbonyl, $C_2$-$C_3$ alkoxycarbonyl, $C_2$-$C_3$ alkylaminocarbonyl or $C_3$-$C_4$ dialkylaminocarbonyl; and
$Z^3$ is CN or C(=S)NH$_2$.

2. A compound of claim 1 wherein
each $R^{4a1}$ and $R^{4a2}$ is independently $C_1$-$C_3$ alkyl, $C_1$-$C_3$ haloalkyl, halogen, cyano, $C_1$-$C_2$ alkoxy or $C_1$-$C_2$ haloalkoxy.

3. A compound of claim 1 selected from the group consisting of:
1-[2-[5-methyl-3-(trifluoromethyl)-1H-pyrazol-1-yl]acetyl]-4-piperidinecarbothioamide,
1-[2-[3,5-bis(trifluoromethyl)-1H-pyrazol-1-yl]acetyl]-4-piperidinecarbothioamide,
1-[2-[5-methyl-3-(trifluoromethyl)-1H-pyrazol-1-yl]acetyl]-4-piperidinecarbonitrile, and
1-[2-[3,5-bis(trifluoromethyl)-1H-pyrazol-1-yl]acetyl]-4-piperidinecarbonitrile.

4. A compound selected from:
1-(2-chloroacetyl)-4-piperidinecarbonitrile and
1-(2-chloroacetyl)-N-(1,1-dimethylethyl)-4-piperidinecarboxamide.

* * * * *